(12) United States Patent
Johnson et al.

(10) Patent No.: US 11,897,905 B2
(45) Date of Patent: Feb. 13, 2024

(54) DEGRADABLE POLYMERS OF A CYCLIC SILYL ETHER AND USES THEREOF

(71) Applicant: Massachusetts Institute of Technology, Cambridge, MA (US)

(72) Inventors: Jeremiah A. Johnson, Boston, MA (US); Peyton Shieh, Cambridge, MA (US); Wenxu Zhang, Belmont, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 119 days.

(21) Appl. No.: 17/204,462

(22) Filed: Mar. 17, 2021

(65) Prior Publication Data

US 2021/0284664 A1  Sep. 16, 2021

Related U.S. Application Data

(62) Division of application No. 16/542,824, filed on Aug. 16, 2019, now Pat. No. 10,988,491.

(60) Provisional application No. 62/872,696, filed on Jul. 10, 2019, provisional application No. 62/872,679, filed on Jul. 10, 2019, provisional application No. 62/765,142, filed on Aug. 17, 2018.

(51) Int. Cl.
| | | |
|---|---|---|
| *C07F 7/08* | (2006.01) |
| *A61K 31/787* | (2006.01) |
| *C08G 61/06* | (2006.01) |
| *C08L 79/08* | (2006.01) |
| *C08L 83/04* | (2006.01) |
| *A61K 45/06* | (2006.01) |

(52) U.S. Cl.
CPC .......... *C07F 7/0834* (2013.01); *A61K 31/787* (2013.01); *C08G 61/06* (2013.01); *C08L 79/08* (2013.01); *C08L 83/04* (2013.01); *A61K 45/06* (2013.01); *C08G 2261/126* (2013.01); *C08G 2261/3324* (2013.01); *C08G 2261/418* (2013.01); *C08L 2201/06* (2013.01)

(58) Field of Classification Search
CPC ....... C07F 7/0834; C08G 61/06; C08L 79/08; C08L 83/04
See application file for complete search history.

(56) References Cited

U.S. PATENT DOCUMENTS

| | | | |
|---|---|---|---|
| 2,482,276 A | 9/1949 | Hyde et al. | |
| 2,676,182 A | 4/1954 | Daudt et al. | |
| 3,256,308 A * | 6/1966 | Sterling | C08F 236/06 |
| | | | 556/464 |
| 3,337,598 A | 8/1967 | Pawloski et al. | |
| 4,359,425 A | 11/1982 | Totani et al. | |
| 4,510,136 A | 4/1985 | Moberg et al. | |
| 5,811,515 A * | 9/1998 | Grubbs | C07K 7/64 |
| | | | 530/331 |
| 7,183,059 B2 * | 2/2007 | Verdine | C07D 207/16 |
| | | | 435/7.1 |
| 8,067,505 B2 | 11/2011 | Harris et al. | |
| 8,829,206 B2 | 9/2014 | Terrill et al. | |
| 8,829,207 B2 | 9/2014 | Billodeaux et al. | |
| 8,968,920 B2 * | 3/2015 | Lee | H01M 10/0567 |
| | | | 429/188 |
| 8,969,598 B2 | 3/2015 | Terrill et al. | |
| 9,381,253 B2 | 7/2016 | Johnson et al. | |
| 9,447,129 B2 | 9/2016 | Johnson et al. | |
| 9,822,216 B2 | 11/2017 | Mahanthappa et al. | |
| 9,944,730 B2 | 4/2018 | Rhodes et al. | |
| 10,023,536 B2 | 7/2018 | Johnson et al. | |
| 10,105,449 B2 | 10/2018 | Johnson et al. | |
| 10,153,513 B2 | 12/2018 | Grubbs et al. | |
| 10,159,749 B2 | 12/2018 | Johnson et al. | |
| 10,591,818 B2 | 3/2020 | Knapp et al. | |

(Continued)

FOREIGN PATENT DOCUMENTS

| | | |
|---|---|---|
| CN | 101412792 A | 4/2009 |
| CN | 103819486 A | 5/2014 |

(Continued)

OTHER PUBLICATIONS

J. Ebdon, New Methods of Polymer Synthesis, Chapter 3 (1991) (Year: 1991).*

(Continued)

*Primary Examiner* — Alexander R Pagano
(74) *Attorney, Agent, or Firm* — Wolf, Greenfield & Sacks, P.C.

(57) ABSTRACT

The present disclosure provides cyclic silyl ethers of the formula:

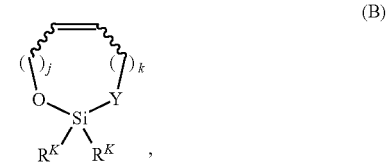

and salts thereof. The cyclic silyl ethers may be useful as monomers for preparing polymers. Also described herein are polymers prepared by polymerizing a cyclic silyl ether and optionally one or more additional monomers. The polymers may be degradable (e.g., biodegradable). One or more O—Si bonds of the polymers may be the degradation sites. Also described herein are compositions and kits including the cyclic silyl ethers or polymers; methods of preparing the polymers; and methods of using the polymers, compositions, and kits.

35 Claims, 113 Drawing Sheets

(56) References Cited

U.S. PATENT DOCUMENTS

| | | |
|---|---|---|
| 10,683,387 B2 | 6/2020 | Johnson et al. |
| 10,716,858 B2 | 7/2020 | Johnson et al. |
| 10,961,338 B2 | 3/2021 | Johnson et al. |
| 10,973,847 B2 | 4/2021 | Johnson et al. |
| 10,988,491 B2* | 4/2021 | Johnson ............... A61K 31/787 |
| 2001/0006988 A1 | 7/2001 | Kuhnle et al. |
| 2002/0183473 A1 | 12/2002 | Matyjaszewski et al. |
| 2002/0198328 A1 | 12/2002 | L'Alloret |
| 2003/0004364 A1 | 1/2003 | Yaghi et al. |
| 2003/0065023 A1 | 4/2003 | Swindell et al. |
| 2005/0109976 A1 | 5/2005 | Fuchs et al. |
| 2008/0063937 A1 | 3/2008 | Lee et al. |
| 2011/0166128 A1 | 7/2011 | Remenar et al. |
| 2011/0243848 A1 | 10/2011 | Appel et al. |
| 2011/0300219 A1 | 12/2011 | Lippard et al. |
| 2013/0296491 A1 | 11/2013 | Xia et al. |
| 2013/0324666 A1 | 12/2013 | Yan et al. |
| 2014/0024137 A1 | 1/2014 | Arya et al. |
| 2014/0308234 A1 | 4/2014 | Johnson et al. |
| 2014/0142249 A1 | 5/2014 | Cho et al. |
| 2015/0225438 A1 | 8/2015 | Johnson et al. |
| 2016/0024246 A1 | 1/2016 | Mahanthappa et al. |
| 2016/0289392 A1 | 10/2016 | Grubbs et al. |
| 2016/0296631 A1 | 10/2016 | Johnson et al. |
| 2016/0361702 A1 | 12/2016 | Cohen et al. |
| 2017/0000909 A1 | 1/2017 | Gianneschi et al. |
| 2017/0073311 A1 | 3/2017 | Johnson et al. |
| 2017/0348431 A1 | 12/2017 | Johnson et al. |
| 2018/0030213 A1 | 2/2018 | Johnson et al. |
| 2018/0036415 A9 | 2/2018 | Johnson et al. |
| 2018/0094099 A1 | 4/2018 | Johnson et al. |
| 2018/0312634 A1* | 11/2018 | Chung ................. C08F 291/12 |
| 2019/0030067 A1 | 1/2019 | Johnson et al. |
| 2019/0038751 A1 | 2/2019 | Johnson et al. |
| 2019/0038782 A1 | 2/2019 | Johnson et al. |
| 2019/0039617 A1 | 2/2019 | Miura et al. |
| 2019/0054187 A1 | 2/2019 | Johnson et al. |
| 2019/0192672 A1 | 6/2019 | Johnson et al. |
| 2020/0055879 A1 | 2/2020 | Johnson et al. |
| 2020/0123297 A1 | 4/2020 | Johnson et al. |
| 2020/0239626 A1* | 7/2020 | Miyake ................. C08G 61/124 |
| 2020/0261596 A1 | 8/2020 | Ali et al. |
| 2020/0362095 A1 | 11/2020 | Johnson et al. |
| 2020/0369685 A1 | 11/2020 | Johnson et al. |
| 2021/0023224 A1 | 1/2021 | Johnson et al. |
| 2021/0113701 A1* | 4/2021 | Johnson .................. C08L 65/00 |
| 2021/0147598 A1* | 5/2021 | Johnson .................. C08L 65/00 |
| 2021/0220391 A1 | 7/2021 | Johnson et al. |
| 2021/0317143 A9 | 10/2021 | Johnson et al. |
| 2021/0386861 A1* | 12/2021 | Johnson ................. C08G 61/08 |
| 2022/0251288 A1 | 8/2022 | Johnson et al. |
| 2022/0370628 A9 | 11/2022 | Johnson et al. |
| 2023/0068959 A1 | 3/2023 | Johnson et al. |
| 2023/0192610 A1 | 6/2023 | Johnson et al. |

FOREIGN PATENT DOCUMENTS

| | | | |
|---|---|---|---|
| DE | 2263509 A1 | | 7/1974 |
| EP | 3315126 A1 | | 5/2018 |
| EP | 3584245 A1 | | 12/2019 |
| JP | 05112739 A | * | 5/1993 |
| KR | 20120113694 A | | 10/2012 |
| WO | WO 2001/032652 A2 | | 5/2001 |
| WO | WO 2010/047765 A1 | | 4/2010 |
| WO | WO 2011/084846 A1 | | 7/2011 |
| WO | WO 2013/010676 A2 | | 2/2013 |
| WO | WO 2013/169739 A1 | | 11/2013 |
| WO | WO 2014/004884 A1 | | 1/2014 |
| WO | WO 2014/169073 A1 | | 10/2014 |
| WO | WO 2016/023036 A1 | | 2/2016 |
| WO | WO 2016/172386 A1 | | 10/2016 |
| WO | WO 2017/208209 A1 | | 12/2017 |
| WO | WO 2018/106738 A1 | | 6/2018 |
| WO | WO 2018/149359 A1 | | 8/2018 |
| WO | WO 2019/006426 A2 | | 1/2019 |
| WO | WO 2019/200367 A1 | | 10/2019 |
| WO | WO 2020/037236 A1 | | 2/2020 |
| WO | WO 2022/099210 A1 | | 5/2022 |
| WO | WO 2022/212752 A1 | | 10/2022 |

OTHER PUBLICATIONS

S. Dutta et al., 15 Soft Matter, 2928-2941 (2019) (Year: 2019).*
X. Li et al., 10 Soft Matter, 2008-2015 (2014) (Year: 2014).*
G. Qiu et al., 128 Reactive and Functional Polymers, 1-15 (2018) (Year: 2018).*
Ekladious et al., 18 Nature Reviews Drug Discovery, 273-294 (2019) (Year: 2019).*
S. Tue et al., 23 Current Opinion in Solid State & Materials Science, 50-61 (2019) (Year: 2019).*
G. Alvaradejo et al., 8 ACS Macro Letters, 473-478 (2019) (Year: 2019).*
J. Foster et al., 141 Journal of the American Chemical Society, 2742-2753 (2019) (Year: 2019).*
P. Shieh et al., 11 Nature Chemistry, 1124-1131 (2019) (Year: 2019).*
Y. Shibuya et al., 6 ACS Macro Letters, 963-968 (2017) (Year: 2017).*
T. Kodger, Mechanical Failure in Colloidal Gels (2014) (Year: 2014).*
M Sowers et al., Nature Communications (2014) (Year: 2014).*
CAS Abstract of S. Masuoka et al., JP 05112739 (1993) (Year: 1993).*
U.S. Appl. No. 14/249,254, filed Apr. 9, 2014, Johnson et al.
U.S. Appl. No. 15/190,018, filed Jun. 22, 2016, Johnson et al.
U.S. Appl. No. 15/616,498, filed Jun. 7, 2017, Johnson et al.
U.S. Appl. No. 15/662,239, filed Jul. 27, 2017, Johnson et al.
U.S. Appl. No. 15/725,036, filed Oct. 4, 2017, Johnson et al.
U.S. Appl. No. 16/024,665, filed Jun. 29, 2018, Johnson et al.
U.S. Appl. No. 16/024,643, filed Jun. 29, 2018, Johnson et al.
U.S. Appl. No. 16/024,662, filed Jun. 29, 2018, Johnson et al.
U.S. Appl. No. 16/080,503, filed Aug. 28, 2018, Johnson et al.
U.S. Appl. No. 16/167,412, filed Oct. 22, 2018, Johnson et al.
U.S. Appl. No. 16/231,166, filed Dec. 21, 2018, Johnson et al.
U.S. Appl. No. 16/825,269, filed Mar. 20, 2020, Johnson et al.
U.S. Appl. No. 16/887,427, filed May 29, 2020 Johnson et al.
U.S. Appl. No. 16/898,331, filed Jun. 10, 2020, Johnson et al.
Extended European Search Report for EP 14782253.0, dated Nov. 11, 2016.
International Preliminary Report on Patentability for PCT/US2014/033554, dated Oct. 22, 2015.
International Search Report and Written Opinion for PCT/US2014/033554, dated Aug. 29, 2014.
International Search Report for PCT/US2017/036447, dated Sep. 7, 2017.
International Preliminary Report on Patentability for Application No. PCT/US2017/036447 dated Dec. 20, 2018.
International Search Report and Written Opinion for PCT/US2017/064784, dated Mar. 1, 2018.
International Search Report and Written Opinion for PCT/US2018/040488, dated Oct. 15, 2018.
International Search Report and Written Opinion for PCT/US2018/040494, dated Oct. 10, 2018.
Invitation to Pay Additional Fees for PCT/US2018/040496, dated Nov. 21, 2018.
International Search Report and Written Opinion for PCT/US2017/055145, dated Jan. 23, 2018.
International Preliminary Report on Patentability for PCT/US2017/055145, dated Apr. 18, 2019.
International Preliminary Report on Patentability for PCT/US2017/064784, dated Jun. 20, 2019.
International Search Report for PCT/US2017/48641, dated Nov. 9, 2017.
International Preliminary Report on Patentability for Application No. PCT/US2017/48641 dated Mar. 7, 2019.
International Search Report and Written Opinion for Application No. PCT/US2018/040496 dated Jan. 14, 2019.

(56) References Cited

OTHER PUBLICATIONS

International Preliminary Report on Patentability for PCT/US2018/040488, dated Jan. 9, 2020.
International Preliminary Report on Patentability for PCT/US2018/040494, dated Jan. 9, 2020.
International Preliminary Report on Patentability for PCT/US2018/040496, dated Jan. 9, 2020.
International Search Report and Written Opinion for PCT/US2019/046872, dated Oct. 29, 2019.
Ahn et al., Two-photon fluorescence microscopy imaging of cellular oxidative stress using profluorescent nitroxides. J Am Chem Soc. Mar. 14, 2012;134(10):4721-30. doi: 10.1021/ja210315x. Epub Mar. 1, 2012.
Aime et al., Lanthanide(III) chelates for NMR biomedical applications. Chem. Soc. Rev., 1998;27:19-29.
Aime et al., Pushing the sensitivity envelope of lanthanide-based magnetic resonance imaging (MRI) contrast agents for molecular imaging applications. Acc Chem Res. Jul. 21, 2009;42(7):822-31. doi: 10.1021/ar800192p.
Alge et al., Synthetically tractable click hydrogels for three-dimensional cell culture formed using tetrazine-norbornene chemistry. Biomacromolecules. Apr. 8, 2013;14(4):949-53. doi: 10.1021/bm4000508. Epub Mar. 8, 2013.
Altintas et al., Constructing star polymersvia modular ligation strategies. Polym. Chem., 2012;3:34-45. DOI: 10.1039/C1PY00249J.
Amouri et al., Host-guest interactions: design strategy and structure of an unusual cobalt cage that encapsulates a tetrafluoroborate anion. Angew Chem Int Ed Engl. Jul. 18, 2005;44(29):4543-6.
Anderson, Late Transition Metal Complexes of Pentafluorophenylphosphino-Pincer Ligands. Doctoral Thesis. Victoria University of Wellington. 2012:ii, iii, 32.
Angelov et al., EPR and rheological study of hybrid interfaces in gold-clay-epoxy nanocomposites. Langmuir. Nov. 11, 2014;30(44):13411-21. doi: 10.1021/la503361k. Epub Oct. 30, 2014.
Angot et al., Living Radical Polymerization Immobilized on Wang Resins: Synthesis and Harvest of Narrow Polydispersity Poly(methacrylate)s. Macromolecules, 2001;34(4):768-774. DOI: 10.1021/ma0011690.
Anraku et al., Size-controlled long-circulating PICsome as a ruler to measure critical cut-off disposition size into normal and tumor tissues. Chem Commun (Camb). Jun. 7, 2011;47(21):6054-6. doi: 10.1039/c1cc11465d. Epub Apr. 26, 2011.
Arvizo et al., Modulating pharmacokinetics, tumor uptake and biodistribution by engineered nanoparticles. PLoS One. 2011;6(9):e24374. doi: 10.1371/journal.pone.0024374. Epub Sep. 13, 2011.
Aryal et al., Polymeric nanoparticles with precise ratiometric control over drug loading for combination therapy. Mol Pharm. Aug. 1, 2011;8(4):1401-7. doi: 10.1021/mp200243k. Epub Jul. 6, 2011.
Bapat et al., Dynamic-covalent nanostructures prepared by Diels-Alder reactions of styrene-maleic anhydride-derived copolymers obtained by one-step cascade block copolymerization. Polym. Chem., 2012;3:3112-3120. DOI: 10.1039/C2PY20351K.
Bapat et al., Redox-Responsive Dynamic-Covalent Assemblies: Stars and Miktoarm Stars. Macromolecules, 2013;46(6):2188-2198. DOI: 10.1021/ma400169m.
Barbour et al., An intermolecular (H2O)10 cluster in a solid-state supramolecular complex. Nature. 1998;393(6686): 671-673.
Barner et al., Synthesis of core-shell poly(divinylbenzene) microspheres via reversible addition fragmentation chain transfer graft polymerization of styrene. J. Polym. Sci. A Polym. Chem., 42: 5067-5076. doi:10.1002/pola.20328.
Barnes et al., Using an RNAi Signature Assay to Guide the Design of Three-Drug-Conjugated Nanoparticles with Validated Mechanisms, In Vivo Efficacy, and Low Toxicity. J Am Chem Soc. Sep. 28, 2016;138(38):12494-501. doi: 10.1021/jacs.6b06321. Epub Sep. 14, 2016.
Barrett et al., pH-Based Regulation of Hydrogel Mechanical Properties Through Mussel-Inspired Chemistry and Processing. Advanced Functional Materials. Mar. 6, 2013;23(9):1111-1119.
Bar-Shir et al., Single 19F Probe for Simultaneous Detection of Multiple Metal Ions Using miCEST MRI. J. Am. Chem. Soc., 2015;137(1):78-81. DOI: 10.1021/ja511313k.
Bates et al., Polarity-switching top coats enable orientation of sub-10-nm block copolymer domains. Science. Nov. 9, 2012;338(6108):775-9. doi: 10.1126/science.1226046.
Beck et al., Multistimuli, multiresponsive metallo-supramolecular polymers. J Am Chem Soc. Nov. 19, 2003;125(46):13922-3.
Bender et al., Site-isolated luminescent europium complexes with polyester macroligands: metal-centered heteroarm stars and nanoscale assemblies with labile block junctions. J Am Chem Soc. Jul. 24, 2002;124(29):8526-7.
Blencowe et al., Core cross-linked star polymers via controlled radical polymerisation. Polymer Jan. 2009;50(1):5-32.
Blinco et al., Profluorescent Nitroxides as Sensitive Probes of Oxidative Change and Free Radical Reactions. Australian Journal of Chemistry 2010;64(4):373-389. https://doi.org/10.1071/CH10442.
Boase et al., Molecular imaging with polymers. Polym. Chem., 2012,3, 1384-1389. DOI: 10.1039/C2PY20132A.
Bobko et al., Reversible reduction of nitroxides to hydroxylamines: roles for ascorbate and glutathione. Free Radic Biol Med. Feb. 1, 2007;42(3):404-12. Epub Nov. 10, 2006.
Bohbot-Raviv et al., Discovering new ordered phases of block copolymers. Phys Rev Lett. Oct. 16, 2000;85(16):3428.
Bolton et al., Synthesis and Melt Self-Assembly of PS-PMMA-PLA Triblock Bottlebrush Copolymers. Macromolecules, 2014;47(9):2864-74. DOI: 10.1021/ma500625k.
Brasch et al., Work in progress: nuclear magnetic resonance study of a paramagnetic nitroxide contrast agent for enhancement of renal structures in experimental animals. Radiology. Jun. 1983;147(3):773-9.
Brasch, Work in progress: methods of contrast enhancement for NMR imaging and potential applications. A subject review. Radiology. Jun. 1983; 147(3):781-8.
Brummelhuis et al., Stimuli-responsive star polymers through thiol-yne core functionalization/crosslinking of block copolymer micelles. Polym. Chem., 2011;2:1180-1184. DOI: 10.1039/C1PY00002K.
Budil et al., Nonlinear-Least-Squares Analysis of Slow-Motion EPR Spectra in One and Two Dimensions Using a Modified Levenberg-Marquardt Algorithm. Elsevier. Journal of Magnetic Resonance, Series A. Jun. 1996; 120(2):155-189.
Buerkle et al., Supramolecular gels formed from multi-component low molecular weight species. Chem Soc Rev. Sep. 21, 2012;41(18):6089-102. doi: 10.1039/c2cs35106d. Epub Jun. 7, 2012.
Bunzen et al., Self-assembly of M24L48 polyhedra based on empirical prediction. Angew Chem Int Ed Engl. Mar. 26, 2012;51(13):3161-3. doi: 10.1002/anie.201108731.
Burdynska et al., Synthesis of Star Polymers Using ARGET ATRP. Macromolecules, 2010;43(22):9227-9229. DOI: 10.1021/ma101971z.
Burnworth et al., Decoupling Optical Properties in Metallo-Supramolecular Poly (p-phenylene ethynylene)s. Macromolecules. 2008;41(6):2157-2163.
Burts et al., Brush-first and click: efficient synthesis of nanoparticles that degrade and release doxorubicin in response to light. Photochem Photobiol. Mar.-Apr. 2014;90(2):380-5. doi: 10.1111/php.12182. Epub Nov. 25, 2013.
Burts et al., Brush-first synthesis of core-photodegradable miktoarm star polymers via ROMP: towards photoresponsive self-assemblies. Macromol Rapid Commun. Jan. 2014;35(2):168-173. doi: 10.1002/marc.201300618. Epub Nov. 22, 2013.
Burts et al., Using EPR to Compare PEG-branch-nitroxide "Bivalent-Brush Polymers" and Traditional PEG Bottle-Brush Polymers: Branching Makes a Difference. Macromolecules. 2012;45(20):8310-18.
Cabral et al., Accumulation of sub-100 nm polymeric micelles in poorly permeable tumours depends on size. Nat Nanotechnol. Oct. 23, 2011;6(12):815-23. doi: 10.1038/nnano.2011.166.

(56) References Cited

OTHER PUBLICATIONS

Caiolfa et al., Polymer-bound camptothecin: initial biodistribution and antitumour activity studies. J Control Release. Mar. 1, 2000;65(1-2):105-19.

Campos-Fernández et al., A One-Pot, High-Yield Synthesis of a Paramagnetic Nickel Square from Divergent Precursors by Anion Template Assembly. Angewandte Chemie International Edition. Dec. 3, 1999;38(23):3477-3479.

Campos-Fernández et al., Fine-tuning the ring-size of metallacyclophanes: a rational approach to molecular pentagons. J Am Chem Soc. Jan. 31, 2001;123(4):773-4.

Caravan et al., Gadolinium(III) Chelates as MRI Contrast Agents: Structure, Dynamics, and Applications. Chem Rev. Sep. 8, 1999;99(9):2293-352.

Castilla et al., Stereochemistry in subcomponent self-assembly. Acc Chem Res. Jul. 15, 2014;47(7):2063-73. doi: 10.1021/ar5000924. Epub May 2, 2014.

Chambron et al., Topologically complex molecules obtained by transition metal templation: it is the presentation that determines the synthesis strategy. New Journal of Chemistry. 2013;37(1):49-57.

Chand et al., Self-assembly of a novel macrotricyclic Pd(II) metal-locage encapsulating a nitrate ion. Chem Commun (Camb). Sep. 7, 2001;(17):1652-3.

Chang et al., Dose-dense chemotherapy improves mechanisms of antitumor immune response. Cancer Res. Jan. 1, 2013;73(1):119-27. doi: 10.1158/0008-5472.CAN-12-2225. Epub Oct. 29, 2012.

Chen et al., Polymeric phosphorylcholine-camptothecin conjugates prepared by controlled free radical polymerization and click chemistry. Bioconjug Chem. Dec. 2009;20(12):2331-41. doi: 10.1021/bc900339x.

Chen et al., Synthesis of superporous hydrogels: hydrogels with fast swelling and superabsorbent properties. J Biomed Mater Res. Jan. 1999;44(1):53-62.

Cheng et al., Well-defined diblock macromonomer with a norbornene group at block junction: anionic living linking synthesis and ring-opening metathesis polymerization. Macromol. Mar. 4, 2010;43(7):3153-5.

Cheon et al., Synergistically integrated nanoparticles as multimodal probes for nanobiotechnology.Acc Chem Res. Dec. 2008;41(12):1630-40. doi: 10.1021/ar800045c.

Chiang et al., Vitamin D for the prevention and treatment of pancreatic cancer. World J Gastroenterol. Jul. 21, 2009;15(27):3349-54.

Chifotides et al., Anion-π interactions in supramolecular architectures. Acc Chem Res. Apr. 16, 2013;46(4):894-906. doi: 10.1021/ar300251k. Epub Mar. 11, 2013.

Choi et al., Self-confirming "AND" logic nanoparticles for fault-free MRI. J Am Chem Soc. Aug. 18, 2010;132(32):11015-7. doi: 10.1021/ja104503g.

Chou et al., In vitro and in vivo studies of FePt nanoparticles for dual modal CT/MRI molecular imaging. J Am Chem Soc. Sep. 29, 2010;132(38):13270-8. doi: 10.1021/ja1035013.

Clever et al., Inclusion of anionic guests inside a molecular cage with palladium(II) centers as electrostatic anchors. Angew Chem Int Ed Engl. 2009;48(38):7010-2. doi: 10.1002/anie.200902717.

Cok et al., Synthesis of Model Network Hydrogels via Tetrazine-Olefin Inverse Electron Demand Diels-Alder Cycloaddition. Macromolecular Symposia. Jul. 2013;329(1):108-112.

Conrad et al., Tunable, temperature-responsive polynorbornenes with side chains based on an elastin peptide sequence. Angew Chem Int Ed Engl. 2009;48(44):8328-30. doi: 10.1002/anie.200903888.

Cordier et al., Self-healing and thermoreversible rubber from supramolecular assembly. Nature. Feb. 21, 2008;451(7181):977-80. doi: 10.1038/nature06669.

Corey et al., Diisopropylsilyl ditriflate and di-tert-butylsilyl ditriflate: new reagents for the protection of diols. Tetrahedron Letters. 1982;23(47):4871-4874.

Dag et al., Three-arm star ring opening metathesis polymers via alkyne-azide click reaction. J. Polym. Sci. A Polym. Chem., 47: 2344-2351. doi: 10.1002/pola.23324.

Dalsin et al., Bottlebrush block polymers: Quantitative theory and experiments. ACS Nano. Nov. 6, 2015;9(12):12233-45.

Davies et al., Environmentally responsive MRI contrast agents. Chem Commun (Camb). Oct. 28, 2013;49(84):9704-21. doi: 10.1039/c3cc44268c.

Davis et al., A novel nitroxide is an effective brain redox imaging contrast agent and in vivo radioprotector. Free Radic Biol Med. Aug. 1, 2011;51(3):780-90. doi: 10.1016/j.freeradbiomed.2011.05.019. Epub May 25, 2011.

Davis et al., Atom transfer radical polymerization of tert-butyl acrylate and preparation of block copolymers. Macromol. May 30, 2000;33(11):4039-47.

Davis et al., Nanoparticle therapeutics: an emerging treatment modality for cancer. Nat Rev Drug Discov. Sep. 2008;7(9):771-82. doi: 10.1038/nrd2614.

Desmarets et al., Design, Self-Assembly, and Molecular Structures of 3D Copper(II) Capsules Templated by BF4—Guest Anions. European Journal of Inorganic Chemistry. Oct. 2009;(29-30):4396-4400. doi: 10.1002/ejic.200900606.

Detappe et al., Advanced multimodal nanoparticles delay tumor progression with clinical radiation therapy. J Control Release. Sep. 28, 2016;238:103-113. doi: 10.1016/j.jconrel.2016.07.021. Epub Jul. 14, 2016.

Dhar et al., Polyvalent oligonucleotide gold nanoparticle conjugates as delivery vehicles for platinum(IV) warheads. J Am Chem Soc. Oct. 21, 2009;131(41):14652-3. doi: 10.1021/ja9071282.

Dhar et al., Targeted delivery of a cisplatin prodrug for safer and more effective prostate cancer therapy in vivo. Proc Natl Acad Sci U S A. Feb. 1, 2011;108(5):1850-5. doi: 10.1073/pnas.1011379108. Epub Jan. 13, 2011.

Dhar et al., Targeted delivery of cisplatin to prostate cancer cells by aptamer functionalized Pt(IV) prodrug-PLGA-PEG nanoparticles. Proc Natl Acad Sci U S A. Nov. 11, 2008;105(45):17356-61. doi: 10.1073/pnas.0809154105. Epub Oct. 31, 2008.

Doane et al., The unique role of nanoparticles in nanomedicine: imaging, drug delivery and therapy. Chem Soc Rev. Apr. 7, 2012;41(7):2885-911. doi: 10.1039/c2cs15260f. Epub Jan. 27, 2012.

Duncan, The dawning era of polymer therapeutics. Nat Rev Drug Discov. May 2003;2(5):347-60.

Durr et al., Mild and Efficient Modular Synthesis of Poly(acrylonitrile-co-butadiene) Block and Miktoarm Star Copolymer Architectures. Macromolecules, 2013;46(1):49-62. DOI: 10.1021/ma302017c.

Eryazici et al., Two Large-Pore Metal-Organic Frameworks Derived from a Single Polytopic Strut. Crystal Growth & Design. Mar. 7, 2012;12(3):1075-1080.

Feng et al., A metabonomic analysis of organ specific response to USPIO administration. Biomaterials. Sep. 2011;32(27):6558-69. doi: 10.1016/j.biomaterials.2011.05.035.

Fenlon et al., The Thread & Cut Method: Syntheses of Molecular Knot Precursors. Eur J Org Chem. Jun. 2008;2008(18):3065-3068.

Ferrauto et al., Frequency-encoded MRI-CEST agents based on paramagnetic liposomes/RBC aggregates. Nano Lett. Dec. 10, 2014;14(12):6857-62. doi: 10.1021/nl5026612. Epub Nov. 10, 2014.

Ferrauto et al., Lanthanide-loaded erythrocytes as highly sensitive chemical exchange saturation transfer MRI contrast agents. J Am Chem Soc. Jan. 15, 2014;136(2):638-41. doi: 10.1021/ja411793u. Epub Dec. 30, 2013.

Forgan et al., Chemical topology: complex molecular knots, links, and entanglements. Chem Rev. Sep. 14, 2011;111(9):5434-64. doi: 10.1021/cr200034u. Epub Jun. 21, 2011.

Foster et al., Differentially Addressable Cavities within Metal-Organic Cage-Cross-Linked Polymeric Hydrogels. J Am Chem Soc. Aug. 5, 2015;137(30):9722-9. doi: 10.1021/jacs.5b05507. Epub Jul. 23, 2015.

Fox et al., Soluble polymer carriers for the treatment of cancer: the importance of molecular architecture. Acc Chem Res. Aug. 18, 2009;42(8):1141-51. doi: 10.1021/ar900035f.

Frechet. Functional polymers and dendrimers: reactivity, molecular architecture, and interfacial energy. Science. Mar. 25, 1994;263(5154):1710-5.

Fullenkamp et al., Mussel-Inspired Histidine-Based Transient Network Metal Coordination Hydrogels. Macromolecules. Jan. 18, 2013;46(3):1167-1174.

(56) References Cited

OTHER PUBLICATIONS

Gao et al., Development of star polymers as unimolecular containers for nanomaterials. Macromol Rapid Commun. May 14, 2012;33(9):722-34. doi: 10.1002/marc.201200005. Epub Mar. 14, 2012.
Gao et al., Modular Approaches to Star and Miktoarm Star Polymers by ATRP of Cross-Linkers. Macromol. Symp., 291-292: 12-16. doi: 10.1002/masy.201050502.
Gao et al., Synthesis of Acid-Labile PEG and PEG-Doxorubicin-Conjugate Nanoparticles via Brush-First ROMP. ACS Macro Lett. Sep. 16, 2014;3(9):854-857. Epub Aug. 13, 2014.
Gao et al., Synthesis of functional polymers with controlled architecture by CRP of monomers in the presence of cross-linkers: From stars to gels. Progress in Polymer Science Apr. 2009;34(4):317-350.
Gao et al., Synthesis of Star Polymers by a New "Core-First" Method: Sequential Polymerization of Cross-Linker and Monomer. Macromolecules, 2008;41(4):1118-1125.
Ge et al., A Pyrene-functionalized Polynorbornene for Ratiometric Fluorescence Sensing of Pyrophosphate. Chem. Asian J. 2016;11:687.
Gestwicki et al., Influencing receptor-ligand binding mechanisms with multivalent ligand architecture. J Am Chem Soc. Dec. 18, 2002;124(50):14922-33.
Gilgorich et al., Palladium-catalyzed reductive coupling of styrenes and organostannanes under aerobic conditions. J Am Chem Soc. Nov. 21, 2007;129(46):14193-5. Epub Oct. 27, 2007.
Glunde et al., Magnetic resonance spectroscopy in metabolic and molecular imaging and diagnosis of cancer. Chem Rev. May 1, 20102;110(5):3043-59. doi: 10.1021/cr9004007.
Godugu et al., Abstract 2139: Effect of telmisartan on triple negative breast cancer (TNBC) and lung cancer tumor progression and intratumoral distribution of nanoparticles. Cancer Res. 2013;73(8).
Goh et al., Highly efficient synthesis of low polydispersity core cross-linked star polymers by Ru-catalyzed living radical polymerization. Macromol Rapid Commun. Mar. 2, 2011;32(5):456-61. doi: 10.1002/marc.201000641. Epub Jan. 7, 2011.
Grahovac et al., Abstract B41: The angiotensin receptor blocker telmisartan inhibits the growth of pancreatic ductal adenocarcinoma and improves survival. Cancer Res. 2016;76(24).
Grason et al., Geometric theory of diblock copolymer phases. Phys Rev Lett. Jul. 31, 2003;91(5):058304.
Greenwald et al., Effective drug delivery by PEGylated drug conjugates. Adv Drug Deliv Rev. Feb. 10, 2003;55(2):217-50.
Gumbley et al., Photoresponsive Polymers Containing Nitrobenzyl Esters via Ring-Opening Metathesis Polymerization. Macromolecules. 2011;44(20):7956-61.
Hackelbusch et al., Chain Dynamics in Supramolecular Polymer Networks. Macromolecules. 2013;46(15):6273-6286.
Hackelbusch et al., Multiresponsive Polymer Hydrogels by Orthogonal Supramolecular Chain Cross-Linking. Macromolecules. 2014;47(12):4028-4036.
Haddleton et al., Well-defined oligosaccharide-terminated polymers from living radical polymerization. Biomacromolecules. 2000 Summer; 1(2):152-6.
Hafkamp et al., Organogel formation and molecular imprinting by functionalized gluconamides and their metal complexes. Chemical Communications. 1997;6:545-546. doi: 10.1039/A608266A.
Hall et al., Platinum(IV) antitumour compounds: their bioinorganic chemistry. Coord Chem Rev. 2002;232:49-67.
Hall et al., The cellular distribution and oxidation state of platinum(II) and platinum(IV) antitumour complexes in cancer cells. J Biol Inorg Chem. Sep. 2003;8(7):726-32. Epub Jul. 12, 2003.
Han et al., Recent Development of Peptide Coupling Reagents in Organic Synthesis. Tetrahedron, 2004;60:2447-2467.
Hansell et al., Additive-free clicking for polymer functionalization and coupling by tetrazine-norbornene chemistry. J Am Chem Soc. Sep. 7, 2011;133(35):13828-31. doi: 10.1021/ja203957h. Epub Aug. 11, 2011.
Hao et al., Dendrimers as scaffolds for multifunctional reversible addition—fragmentation chain transfer agents: Syntheses and polymerization. J. Polym. Sci. A Polym. Chem., 2004;42:5877-5890. doi: 10.1002/pola.20434.
Harrington et al., Iron-clad fibers: a metal-based biological strategy for hard flexible coatings. Science. Apr. 9, 2010;328(5975):216-20. doi: 10.1126/science.1181044. Epub Mar. 4, 2010.
Harris et al., Giant hollow M(n)L(2n) spherical complexes: structure, functionalisation and applications. Chem Commun (Camb). Aug. 4, 2013;49(60):6703-12. doi: 10.1039/c3cc43191f.
Harrison et al., A multimeric MR-optical contrast agent for multimodal imaging. Chem Commun (Camb). Oct. 9, 2014;50(78):11469-71. doi: 10.1039/c4cc05651e.
Harrison et al., Multimeric Near IR-MR Contrast Agent for Multimodal in Vivo Imaging. J Am Chem Soc. Jul. 22, 2015;137(28):9108-16. doi: 10.1021/jacs.5b04509. Epub Jul. 14, 2015.
Harvey et al., Lanthanide Complexes as Paramagnetic Probes for 19F Magnetic Resonance. Eur. J. Inorg. Chem., 2012: 2015-2022. doi:10.1002/ejic.201100894.
Hawker et al., Preparation of polymers with controlled molecular architecture. A new convergent approach to dendritic macromolecules. J Am Chem Soc. Oct. 1990; 112(21):7638-47.
Hedrick et al., Dendrimer-like Star Block and Amphiphilic Copolymers by Combination of Ring Opening and Atom Transfer Radical Polymerization. Macromolecules, 1998;31(25):8691-8705. DOI: 10.1021/ma980932b.
Hein et al., Copper-catalyzed azide-alkyne cycloaddition (CuAAC) and beyond: new reactivity of copper(I) acetylides. Chem Soc Rev. Apr. 2010;39(4):1302-15. doi: 10.1039/b904091a. Epub Mar. 4, 2010.
Helms et al., One-Pot Reaction Cascades Using Star Polymers with Core-Confined Catalysts. Angewandte Chemie, 2005;44:6384-6387. doi:10.1002/ange.200502095.
Heroguez et al., Novel Styrene—Butadiene Copolymers by Ring-Opening Metathesis Polymerization. Macromol. Oct. 3, 2000;33(20):7241-8.
Hirakawa et al., Removal of Perchlorate Anion from an Aqueous Solution by Encapsulation in an Anion-templated Self-assembled Molecular Capsule. Chemistry Letters. 2009;38(3):290-291.
Holbrook et al., Gd(III)-Dithiolane Gold Nanoparticles for T1-Weighted Magnetic Resonance Imaging of the Pancreas. Nano Lett. May 11, 2016;16(5):3202-9. doi: 10.1021/acs.nanolett.6b00599. Epub Apr. 20, 2016.
Holliday et al., Strategies for the Construction of Supramolecular Compounds through Coordination Chemistry. Angew Chem Int Ed Engl. Jun. 1, 2001;40(11):2022-2043.
Holten-Andersen et al., Metal-coordination: using one of nature's tricks to control soft material mechanics. J. Mater. Chem. B. 2014;2:2467-2472.
Holten-Andersen et al., pH-induced metal-ligand cross-links inspired by mussel yield self-healing polymer networks with near-covalent elastic moduli. PNAS. Feb. 15, 2011;108:2651-2655.
Hoogenboom et al., 1-Lactide Polymerization Utilizing a Hydroxy-Functionalized 3,6-Bis(2-pyridyl)pyridazine as Supramolecular (Co)initiator: Construction of Polymeric [2×2] Grids. Macromolecules, 2003;36(13):4743-9. DOI: 10.1021/ma034119e.
Hoye et al., Silicon tethered ring-closing metathesis reactions for self- and cross-coupling of alkenols. Tetrahedron Letters. Feb. 19, 1999;40(8):1429-1432.
Hu et al., Enhancing Gelation of Doubly Thermosensitive Hydrophilic ABC Linear Triblock Copolymers in Water by Thermoresponsive Hairy Nanoparticles. Macromolecules, 2016;49(15):5502-13. DOI: 10.1021/acs.macromol.6b01156.
Hu et al., Nanoparticle-based combination therapy toward overcoming drug resistance in cancer. Biochem Pharmacol. Apr. 15, 2012;83(8):1104-11. doi: 10.1016/j.bcp.2012.01.008. Epub Jan. 18, 2012.
Huang et al., Polymer-Stabilized Perfluorobutane Nanodroplets for Ultrasound Imaging Agents. J Am Chem Soc. Jan. 11, 2017;139(1):15-18. doi: 10.1021/jacs.6b08800. Epub Dec. 29, 2016.
Huynh, Novel Polymeric Micelles via RAFT Polymerization for Platinum Drug Delivery. Doctoral Thesis. The University of New South Wales. 2012:i, 57-58.

(56) References Cited

OTHER PUBLICATIONS

Hyodo et al., Assessment of tissue redox status using metabolic responsive contrast agents and magnetic resonance imaging. J Pharm Pharmacol. Aug. 2008;60(8):1049-60. doi: 10.1211/jpp.60.8.0011.

Hyodo et al., Brain redox imaging using blood-brain barrier-permeable nitroxide MRI contrast agent. J Cereb Blood Flow Metab. Jun. 2008;28(6):1165-74. doi: 10.1038/jcbfm.2008.5. Epub Feb. 13, 2008.

Hyodo et al., Probing the intracellular redox status of tumors with magnetic resonance imaging and redox-sensitive contrast agents. Cancer Res. Oct. 15, 2006;66(20):9921-8.

Iha et al., Applications of Orthogonal "Click" Chemistries in the Synthesis of Functional Soft Materials. Chem. Rev., 2009;109(11):5620-5686. DOI: 10.1021/cr900138t.

Inglis et al., Well-defined star shaped polymer-fullerene hybrids via click chemistry. Soft Matter, 2010;6:82-84. DOI: 10.1039/B920806M.

Jackson et al., pH triggered self-assembly of core cross-linked star polymers possessing thermoresponsive cores. Chem. Commun., 2011;47:6807-6809. DOI: 10.1039/C1CC11785H.

Jakubowski et al., Activators regenerated by electron transfer for atom transfer radical polymerization of styrene. Macromol. Jan. 10, 2006;39(1):39-45.

Jamieson et al., Structure, Recognition, and Processing of Cisplatin-DNA Adducts. Chem Rev. Sep. 8, 1999;99(9):2467-98.

Jeong et al., Highly tunable self-assembled nanostructures from a poly (2-vinylpyridine-b-dimethylsiloxane) block copolymer. Nano Lett. Sep. 27, 2011;11(10):4095-101.

Jesberger et al., Hyperbranched polymers as scaffolds for multi-functional reversible addition-fragmentation chain-transfer agents: A route to polystyrene-core-polyesters and polystyrene-block-poly(butyl acrylate)-core-polyesters. J. Polym. Sci. A Polym. Chem., 2003;41:3847-3861. doi:10.1002/pola.10976.

Jiang et al., Morphology and Phase Diagram of Comb Block Copolymer A m+ 1 (BC) m. J Phys Chem B. May 7, 2009;113(21):7462-7.

Johnson et al., Core-clickable PEG-branch-azide bivalent-bottle-brush polymers by ROMP: grafting-through and clicking-to. J Am Chem Soc. Jan. 26, 2011;133(3):559-66. doi: 10.1021/ja108441d. Epub Dec. 13, 2010.

Johnson et al., Drug-loaded, bivalent-bottle-brush polymers by graft-through ROMP. Macromolecules. Dec. 28, 2010;43(24):10326-10335.

Johnson et al., Efficient Synthesis of Doxorubicin Releasing Brush Polymers by Graft—Through Romp. Polymer Preprints. 2010;51(2):96-97.

Jokerst et al., Molecular imaging with theranostic nanoparticles. Acc Chem Res. Oct. 18, 2011;44(10):1050-60. doi: 10.1021/ar200106e. Epub Sep. 15, 2011.

Jokerst et al., Nanoparticle PEGylation for imaging and therapy. Nanomedicine (Lond). Jun. 2011;6(4):715-28. doi: 10.2217/nnm.11.19.

Joralemon et al., PEGylated polymers for medicine: from conjugation to self-assembled systems. Chem Commun (Camb). Mar. 7, 2010;46(9):1377-93. doi: 10.1039/b920570p. Epub Jan. 28, 2010.

Jung et al., Orientation-controlled self-assembled nanolithography using a polystyrene-polydimethylsiloxane block copolymer. Nano Lett. Jul. 11, 2007;7(7):2046-50.

Kale et al., Supramolecular assemblies of amphiphilic homopolymers. Langmuir. May 19, 2009;25(17):9660-70.

Kalyani et al., Oxidatively intercepting Heck intermediates: Pd-catalyzed 1,2- and 1,1-arylhalogenation of alkenes. J Am Chem Soc. Feb. 20, 2008;130(7):2150-1. doi: 10.1021/ja0782798. Epub Jan. 30, 2008.

Kawamoto et al., Graft-through Synthesis and Assembly of Janus Bottlebrush Polymers from A-Branch-B Diblock Macromonomers. J Am Chem Soc. Sep. 14, 2016;138(36):11501-4. doi: 10.1021/jacs.6b07670. Epub Sep. 1, 2016.

Kawamoto et al., Loops versus branch functionality in model click hydrogels. Macromol. Dec. 1, 2015;48(24):8980-8.

Kean et al., Increasing the maximum achievable strain of a covalent polymer gel through the addition of mechanically invisible cross-links. Adv Mater. Sep. 10, 2014;26(34):6013-8. doi: 10.1002/adma.201401570. Epub Jul. 17, 2014.

Keana et al., Nitroxides as potential contrast enhancing agents for MRI application: influence of structure on the rate of reduction by rat hepatocytes, whole liver homogenate, subcellular fractions, and ascorbate. Magn Reson Med. Dec. 1987;5(6):525-36.

Khanna et al., Designing Miktoarm Polymers Using a Combination of "Click" Reactions in Sequence with Ring-Opening Polymerization. Macromolecules, 2010;43(13):5688-5698. DOI: 10.1021/ma100845a.

Kim et al., Anion-directed self-assembly of coordination polymer into tunable secondary structure. J Am Chem Soc. Jun. 9, 2004;126(22):7009-14.

Kim et al., Supporting Information Experimental Section. J Am Chem Soc. Jun. 9, 2004;126(22):7009-14. Available at: http://pubs.acs.org/doi/suppl/10.1021/ja049799v/suppl_file/ja049799vsi20040219_113203.pdf Retrieved Apr. 24, 2015.

Kirchhoff et al., Boronic acids: new coupling partners in room-temperature Suzuki reactions of alkyl bromides. Crystallographic characterization of an oxidative-addition adduct generated under remarkably mild conditions. J Am Chem Soc. Nov. 20, 2002;124(46):13662-3.

Kishi et al., An M2L4 molecular capsule with an anthracene shell: encapsulation of large guests up to 1 nm. J Am Chem Soc. Aug. 3, 2011;133(30):11438-41. doi: 10.1021/ja2037029. Epub Jul. 8, 2011.

Kokuryo et al., SPIO-PICsome: development of a highly sensitive and stealth-capable MRI nano-agent for tumor detection using SPIO-loaded unilamellar polyion complex vesicles (PICsomes). J Control Release. Aug. 10, 2013;169(3):220-7. doi: 10.1016/j.jconrel.2013.03.016. Epub Mar. 29, 2013.

Kolishetti et al., Engineering of self-assembled nanoparticle platform for precisely controlled combination drug therapy. Proc Natl Acad Sci U S A. Oct. 19, 2010;107(42):17939-44. doi: 10.1073/pnas.1011368107. Epub Oct. 4, 2010.

Kreutzer et al., Water-Soluble, Unimolecular Containers Based on Amphiphilic Multiarm Star Block Copolymers. Macromolecules, 2006;39(13):4507-4516. DOI: 10.1021/ma060548b.

Kwon et al., Block copolymer micelles as long-circulating drug vehicles. Adv Drug Delivery Rev. 1995;16:295-309.

Lammers et al., Simultaneous delivery of doxorubicin and gemcitabine to tumors in vivo using prototypic polymeric drug carriers. Biomaterials. Jul. 2009;30(20):3466-75. doi: 10.1016/j.biomaterials.2009.02.040. Epub Mar. 21, 2009.

Lee et al., Multifunctional nanoparticles for multimodal imaging and theragnosis. Chem Soc Rev. Apr. 7, 2012;41(7):2656-72. doi: 10.1039/c2cs15261d. Epub Dec. 21, 2011.

Lee et al., Mussel-Inspired Adhesives and Coatings. Annu Rev Mater Res. Aug. 1, 2011;41:99-132.

Lee et al., Novel phase morphologies in a microphase-separated dendritic polymer melt. Macromol. Jan. 12, 2009;42(3):849-59.

Lee et al., Single-molecule mechanics of mussel adhesion. Proc Natl Acad Sci U S A. Aug. 29, 2006;103(35):12999-3003. Epub Aug. 18, 2006.

Lee et al., Stimuli-responsive molecular brushes. Progress in Polymer Science (Oxford), 35(1-2), 24-44. DOI: 10.1016/j.progpolymsci.2009.11.002.

Leininger et al., Self-assembly of discrete cyclic nanostructures mediated by transition metals. Chem Rev. Mar. 8, 2000;100(3):853-908.

Li et al., Polycatechol Nanoparticle MRI Contrast Agents. Small, 2016;12(5):668-677. https://doi.org/10.1002/smll.201502754.

Li et al., A magnetic switch for spin-catalyzed interconversion of nuclear spin isomers. J Am Chem Soc. Mar. 31, 2010;132(12):4042-3. doi: 10.1021/ja910282p.

Li et al., Crosslinking-induced morphology change of latex nanoparticles: A study of RAFT-mediated polymerization in aqueous dispersed media using amphiphilic double-brush copolymers as reactive surfactants. J Polym Sci Part A: Polym Chem. Nov. 15, 2014;52(22):3250-9.

(56) References Cited

OTHER PUBLICATIONS

Li et al., Distance-Dependent Paramagnet-Enhanced Nuclear Spin Relaxation of H2@C60 Derivatives Covalently Linked to a Nitroxide Radical. J. Phys. Chem. Lett., 2010;1(14):2135-2138. DOI: 10.1021/jz100645w.

Li et al., Dynamic cylindrical assembly of triblock copolymers by a hierarchical process of covalent and supramolecular interactions. J Am Chem Soc. Jan. 4, 2011;133(5):1228-31.

Li et al., Efficient synthesis of narrowly dispersed amphiphilic double-brush copolymers through the polymerization reaction of macromonomer micelle emulsifiers at the oil-water interface. Polym Chem. 2016;7(27):4476-85.

Li et al., Facile syntheses of cylindrical molecular brushes by a sequential RAFT and ROMP "grafting-through" methodology. J Polym Sci A Polym Chem. Oct. 15, 2009;47(20):5557-5563.

Li et al., Highly fluorescent M2L4 molecular capsules with anthracene shells. Chem Commun (Camb). Aug. 14, 2011;47(30):8605-7. doi: 10.1039/c1cc12946e. Epub Jun. 28, 2011.

Li et al., Isostructural M2L4 molecular capsules with anthracene shells: synthesis, crystal structures, and fluorescent properties. Chemistry. Jul. 2, 2012;18(27):8358-65. doi: 10.1002/chem.201200155. Epub May 25, 2012.

Li et al., Pinpointing the extent of electronic delocalization in the Re(I)-to-tetrazine charge-separated excited state using time-resolved infrared spectroscopy. J Am Chem Soc. Aug. 26, 2009;131(33):11656-7. doi: 10.1021/ja903901n.

Li et al., Star Polymers via Cross-Linking Amphiphilic Macroinitiators by AGET ATRP in Aqueous Media. J. Am. Chem. Soc., 2009;131(30):10378-10379. DOI: 10.1021/ja904204g.

Li et al., Surface Properties of Bottlebrush Polymer Thin Films. Macromolecules. 2012;45(17):7118-7127.

Li et al., Synthesis of Hetero-Grafted Amphiphilic Diblock Molecular Brushes and Their Self-Assembly in Aqueous Medium. Macromolecules. 2010;43(3):1182-1184.

Li et al., Well-defined amphiphilic double-brush copolymers and their performance as emulsion surfactants. Macromol. May 18, 2012;45(11):4623-9.

Liang et al., The copper(I)-catalyzed alkyne-azide cycloaddition (CuAAC) "click" reaction and its applications. An overview. Coordination Chemistry Reviews Dec. 2011;255(23-24):2933-2945.

Liao et al., A convergent synthetic platform for single-nanoparticle combination cancer therapy: ratiometric loading and controlled release of cisplatin, doxorubicin, and camptothecin. J Am Chem Soc. Apr. 23, 2014;136(16):5896-9. doi: 10.1021/ja502011g. Epub Apr. 11, 2014.

Liao et al., A palladium-catalyzed three-component cross-coupling of conjugated dienes or terminal alkenes with vinyl triflates and boronic acids. J Am Chem Soc. Apr. 20, 2011;133(15):5784-7. doi: 10.1021/ja201358b. Epub Mar. 30, 2011.

Liao et al., Palladium-catalyzed hydroarylation of 1,3-dienes with boronic esters via reductive formation of pi-allyl palladium intermediates under oxidative conditions. J Am Chem Soc. Aug. 4, 2010;132(30):10209-11. doi: 10.1021/ja105010t.

Liao et al., Two-component control of guest binding in a self-assembled cage molecule. Chem Commun (Camb). Jul. 21, 2010;46(27):4932-4. doi: 10.1039/c0cc00234h. Epub Jun. 2010.

Lim et al., Multiplexed imaging of therapeutic cells with multispectrally encoded magnetofluorescent nanocomposite emulsions. J Am Chem Soc. Dec. 2, 2009;131(47):17145-54. doi: 10.1021/ja904472z.

Liu et al., "Brush-first" method for the parallel synthesis of photocleavable, nitroxide-labeled poly(ethylene glycol) star polymers. J Am Chem Soc. Oct. 3, 2012;134(39):16337-44. doi: 10.1021/ja3067176. Epub Sep. 24, 2012.

Liu et al., Aqueous Dispersion Polymerization of 2-Methoxyethyl Acrylate for the Synthesis of Biocompatible Nanoparticles Using a Hydrophilic RAFT Polymer and a Redox Initiator. Macromolecules, 2011;44(13):5237-5245. DOI: 10.1021/ma200984h.

Liu et al., Assembly of trigonal and tetragonal prismatic cages from octahedral metal ions and a flexible molecular clip. Inorg Chem. Jul. 23, 2007;46(15):5814-6. Epub Jan. 26, 2007.

Liu et al., Discrete M2L2 metallacycle and M2L4 cage frameworks and anion competitive reactions of Cu2L4 type receptor. Inorganic Chemistry Communications. Jun. 2009;12(6):457-460.

Liu et al., Nuts and bolts of chemical exchange saturation transfer MRI. NMR Biomed. Jul. 2013;26(7):810-28. doi: 10.1002/nbm.2899. Epub Jan. 10, 2013.

Liu et al., Particles without a Box: Brush-first Synthesis of Photodegradable PEG Star Polymers under Ambient Conditions. J Vis Exp. 2013;80:e50874, doi:10.3791/50874.

Liu et al., Synthesis of functional core, star polymers via RAFT polymerization for drug delivery applications. Macromol Rapid Commun. May 14, 2012;33(9):760-6. doi: 10.1002/marc.201200029. Epub Apr. 12, 2012.

Lock et al., One-Component Supramolecular Filament Hydrogels as Theranostic Label-Free Magnetic Resonance Imaging Agents. ACS Nano. Jan. 24, 2017;11(1):797-805.

Love et al., A practical and highly active ruthenium-based catalyst that effects the cross metathesis of acrylonitrile. Angew Chem Int Ed Engl. Nov. 4, 2002;41(21):4035-7.

Loveless et al., Chemoresponsive viscosity switching of a metallo-supramolecular polymer network near the percolation threshold. J. Mater Chem. 2007;17:56-61.

Loveless et al., Rational Control of Viscoelestic Properties in Multicomponent Associative Polymer Networks. Macromolecules. 2005;38(24):10171-10177.

Luo et al., Toroidal structures from brush amphiphiles. Chem Commun. 2014;50(5):536-8.

Ma et al., Nanoparticles for combination drug therapy. ACS Nano. Nov. 26, 2013;7(11):9518-25. doi: 10.1021/nn405674m.

Mackay et al., Self-assembling chimeric polypeptide-doxorubicin conjugate nanoparticles that abolish tumours after a single injection. Nat Mater. Dec. 2009;8(12):993-9. doi: 10.1038/nmat2569. Epub Nov. 8, 2009.

Macrenaris et al., Cell-Permeable Esterase-Activated Ca(II)-Sensitive MRI Contrast Agent. Bioconjug Chem. Feb. 17, 2016;27(2):465-73. doi: 10.1021/acs.bioconjchem.5b00561. Epub Jan. 6, 2016.

Maeda et al., Polymeric drugs for efficient tumor-targeted drug delivery based on EPR-effect. Eur J Pharm Biopharm. Mar. 2009;71(3):409-19. doi: 10.1016/j.ejpb.2008.11.010. Epub Dec. 3, 2008.

Mastarone et al., A modular system for the synthesis of multiplexed magnetic resonance probes. J Am Chem Soc. Apr. 13, 2011;133(14):5329-37. doi: 10.1021/ja1099616. Epub Mar. 17, 2011.

Matson et al., Synthesis of fluorine-18 functionalized nanoparticles for use as in vivo molecular imaging agents. J Am Chem Soc. May 28, 2008;130(21):6731-3. doi: 10.1021/ja802010d. Epub May 2, 2008.

Matsumoto et al., High-resolution mapping of tumor redox status by magnetic resonance imaging using nitroxides as redox-sensitive contrast agents. Clin Cancer Res. Apr. 15, 2006;12(8):2455-62.

Matsumura et al., A new concept for macromolecular therapeutics in cancer chemotherapy: mechanism of tumoritropic accumulation of proteins and the antitumor agent smancs. Cancer Res. Dec. 1986;46(12 Pt 1):6387-92.

McCammant et al., Palladium-catalyzed 1,4-difunctionalization of butadiene to form skipped polyenes. J Am Chem Soc. Mar. 20, 2013;135(11):4167-70. doi: 10.1021/ja3110544. Epub Mar. 12, 2013.

McKenzie et al., Highly Efficient and Versatile Formation of Biocompatible Star Polymers in Pure Water and Their Stimuli-Responsive Self-Assembly. Macromolecules, 2014;47(22):7869-7877. DOI: 10.1021/ma502008j.

McKenzie et al., Visible Light Mediated Controlled Radical Polymerization in the Absence of Exogenous Radical Sources or Catalysts. Macromolecules, 2015;48(12):3864-3872. DOI: 10.1021/acs.macromol.5b00965.

Medarova et al., In vivo imaging of siRNA delivery and silencing in tumors. Nat Med. Mar. 2007;13(3):372-7. Epub Feb. 25, 2007.

Mendichovszky et al., Gadolinium and nephrogenic systemic fibrosis: time to tighten practice. Pediatr Radiol. May 2008;38(5):489-96; quiz 602-3. Epub Oct. 18, 2007.

(56) References Cited

OTHER PUBLICATIONS

Menyo et al., Versatile tuning of supramolecular hydrogels through metal complexation of oxidation-resistant catechol-inspired ligands. Soft Matter. 2013;9:10314-10323.

Meyer et al., The dynamic chemistry of molecular borromean rings and Solomon knots. Chemistry. Nov. 8, 2010;16(42):12570-81. doi: 10.1002/chem.201001806.

Mi et al., A pH-activatable nanoparticle with signal-amplification capabilities for non-invasive imaging of tumour malignancy. Nat Nanotechnol. Aug. 2016;11(8):724-30. doi: 10.1038/nnano.2016.72. Epub May 16, 2016.

Mi et al., Hydrothermally synthesized PEGylated calcium phosphate nanoparticles incorporating Gd-DTPA for contrast enhanced MRI diagnosis of solid tumors. Journal of Controlled Release Jan. 2014;174(28):63-71.

Miyake et al., Precisely tunable photonic crystals from rapidly self-assembling brush block copolymer blends. Angew Chem Int Ed Engl. Nov. 5, 2012;51(45):11246-8. doi: 10.1002/anie.201205743. Epub Sep. 13, 2012.

Moghimi et al., Long-circulating and target-specific nanoparticles: theory to practice. Pharmacol Rev. Jun. 2001;53(2):283-318.

Mukherjee et al., pH-Sensitive Nanoaggregates for Site-Specific Drug-Delivery as Well as Cancer Cell Imaging. ACS Omega, 2016;1(5):755-764. DOI: 10.1021/acsomega.6b00167.

Mukherjee et al., Site-Specific Amphiphilic Magnetic Copolymer Nanoaggregates for Dual Imaging. Macromolecules, 2015;48(19):6791-6800. DOI: 10.1021/acs.macromol.5b01716.

Mukherjee et al., Oximes as reversible links in polymer chemistry: dynamic macromolecular stars. Polym. Chem., 2014;5:6923-6931. DOI: 10.1039/C4PY01282H.

Muthukrishnan et al., Synthesis and Characterization of Glycomethacrylate Hybrid Stars from Silsesquioxane Nanoparticles. Macromolecules, 2005;38(26):10631-10642. DOI: 10.1021/ma051949e.

Na et al., Development of a T1 contrast agent for magnetic resonance imaging using MnO nanoparticles. Angew Chem Int Ed Engl. 2007;46(28):5397-401.

Na et al., Inorganic Nanoparticles for MRI Contrast Agents. Adv. Mater., 21: 2133-2148. doi:10.1002/adma.200802366.

Nair et al., Modulating mechanical properties of self-assembled polymer networks by multi-functional complementary hydrogen bonding. Soft Matter. 2011;7(2):553-559.

Nair et al., Multiresponsive Reversible Polymer Networks Based on Hydrogen Bonding and Metal Coordination. Macromolecules. 2011;44(9):3346-3357.

Nardone et al., Pediatric nephrogenic systemic fibrosis is rarely reported: a RADAR report. Pediatr Radiol. Feb. 2014;44(2):173-80. doi: 10.1007/s00247-013-2795-x. Epub Sep. 21, 2013.

Nguyen et al., Nitroxide-Based Macromolecular Contrast Agents with Unprecedented Transverse Relaxivity and Stability for Magnetic Resonance Imaging of Tumors. ACS Cent. Sci., 2017;3(7):800-811. DOI: 10.1021/acscentsci.7b00253.

Nicholls et al., DNA-gadolinium-gold nanoparticles for in vivo T1 MR imaging of transplanted human neural stem cells. Biomaterials. Jan. 2016;77:291-306. doi: 10.1016/j.biomaterials.2015.11.021. Epub Nov. 14, 2015.

Nishiyama et al., Novel cisplatin-incorporated polymeric micelles can eradicate solid tumors in mice. Cancer Res. Dec. 15, 2003;63(24):8977-83.

Nomura et al., Facile Controlled Synthesis of Soluble Star Shape Polymers by Ring-Opening Metathesis Polymerization (ROMP). Macromolecules, 2009;42(4):899-901. DOI: 10.1021/ma8027529.

Nomura et al., Use of Pyridine-Coated Star-Shaped ROMP Polymer as the Supporting Ligand for Ruthenium-Catalyzed Chemoselective Hydrogen Transfer Reduction of Ketones. Organometallics, 2012;31(14):5074-5080. DOI: 10.1021/om300417v.

Ohno et al., Synthesis of well-defined cyclodextrin-core star polymers. J. Polym. Sci. A Polym. Chem., 39: 2206-2214. doi:10.1002/pola.1197.

Paletta et al., Synthesis and Reduction Kinetics of Sterically Shielded Pyrrolidine Nitroxides. Org. Lett., 2012;14(20):5322-5325. DOI: 10.1021/ol302506f.

Park et al., Star Synthesis Using Macroinitiators via Electrochemically Mediated Atom Transfer Radical Polymerization. Macromolecules, 2013;46(15):5856-5860 DOI: 10.1021/ma401308e.

Patel et al., Synthesis and cell adhesive properties of linear and cyclic RGD functionalized polynorbornene thin films. Biomacromolecules. Aug. 13, 2012;13(8):2546-53. doi: 10.1021/bm300795y. Epub Jul. 27, 2012.

Patrick et al., Intracellular pH measurements using perfluorocarbon nanoemulsions. J Am Chem Soc. Dec. 11, 2013;135(49):18445-57. doi: 10.1021/ja407573m. Epub Nov. 22, 2013.

Peer et al., Nanocarriers as an emerging platform for cancer therapy. Nat Nanotechnol. Dec. 2007;2(12):751-60. doi: 10.1038/nnano.2007.387.

Petros et al., Strategies in the design of nanoparticles for therapeutic applications. Nat Rev Drug Discov. Aug. 2010;9(8):615-27. doi: 10.1038/nrd2591. Epub Jul. 9, 2010.

Plummer et al., A Phase I clinical study of cisplatin-incorporated polymeric micelles (NC-6004) in patients with solid tumours. Br J Cancer. Feb. 15, 2011;104(4):593-8. doi: 10.1038/bjc.2011.6. Epub Feb. 1, 2011.

Prevost et al., Strained organosilacyclic compounds:synthesis of anti-Bredt olefins and trans-dioxasilacyclooctenes. Dalton Trans. Oct. 21, 2010;39(39):9275-81. doi: 10.1039/c003227a. Epub Jul. 8, 2010.

Qiu et al., Efficient and versatile synthesis of star polymers in water and their use as emulsifiers. Chem. Commun., 2011;47:12685-12687. DOI: 10.1039/C1CC15679A.

Rajca et al., Correction to organic radical contrast agents for magnetic resonance imaging. J Am Chem Soc. Feb. 26, 2014;136(8):3318. doi: 10.1021/ja413028d. Epub Feb. 17, 2014.

Rajca et al., Organic radical contrast agents for magnetic resonance imaging. J Am Chem Soc. Sep. 26, 2012;134(38):15724-7. Epub Sep. 17, 2012.

Rangadurai et al., Temporal and triggered evolution of host-guest characteristics in amphiphilic polymer assemblies. J Am Chem Soc. Jun. 10, 2016;138(24):7508-11.

Rasmussen et al., Improved numerical algorithm for exploring block copolymer mesophases. J Polym Sci Part B: Poly Phys. Aug. 15, 2002;40(16):1777-83.

Ratnakar et al., Modulation of CEST images in vivo by T1 relaxation: a new approach in the design of responsive PARACEST agents. J Am Chem Soc. Oct. 9, 2013;135(40):14904-7. doi: 10.1021/ja406738y. Epub Sep. 25, 2013.

Ren et al., Organic Catalyst-Mediated Ring-Opening Polymerization for the Highly Efficient Synthesis of Polyester-Based Star Polymers. ACS Macro Lett., 2012;1(6):681-686. DOI: 10.1021/mz300169m.

Ren et al., Star Polymers. Chem Rev. Jun. 22, 2016;116(12):6743-836. doi: 10.1021/acs.chemrev.6b00008. Epub Jun. 14, 2016.

Ren et al., Synthetic Strategies towards Well-Defined Complex Polymeric Architectures through Covalent Chemistry. Chemie Ingenieur Technik, 86: 2195-2214. doi:10.1002/cite.201400088.

Rizzo et al., In vivo nanotoxicity testing using the zebrafish embryo assay. J. Mater. Chem. B, 2013,1, 3918-3925. DOI: 10.1039/C3TB20528B.

Rolfe et al., Multimodal polymer nanoparticles with combined 19F magnetic resonance and optical detection for tunable, targeted, multimodal imaging in vivo. J Am Chem Soc. Feb. 12, 2014;136(6):2413-9. doi: 10.1021/ja410351h. Epub Jan. 29, 2014.

Ronson et al., Metal-organic container molecules through subcomponent self-assembly. Chem Commun (Camb). Mar. 28, 2013;49(25):2476-90. doi: 10.1039/c2cc36363a.

Rowan et al., Metal-ligand induced supramolecular polymerization: a route to responsive materials. Faraday Discuss. 2005;128:43-53.

Roy et al., Cyclic β-Peptoids. Org. Lett., 2008;10(5):921-924. DOI: 10.1021/ol7030763.

Runge et al., "Synthesis and Self-Assembly of Bottlebrush Block Copolymers" PMSEPreprints, 2005, 92, 5-6.

(56) References Cited

OTHER PUBLICATIONS

Rzayev et al., Molecular Bottlebrushes: New Opportunities in Nanomaterials Fabrication. ACS Macro Lett., 2012;1(9):1146-1149. DOI: 10.1021/mz300402x.

Rzayev, Synthesis of polystyrene-polylactide bottlebrush block copolymers and their melt self-assembly into large domain nanostructures. Macromol. Feb. 20, 2009;42(6):2135-41.

Saini et al., Pd(0)-catalyzed 1,1-diarylation of ethylene and allylic carbonates. Org Lett. Oct. 4, 2013;15(19):5008-11. doi: 10.1021/ol4023358. Epub Sep. 18, 2013.

Samuni et al., Factors influencing nitroxide reduction and cytotoxicity in vitro. Antioxid Redox Signal. Jun. 2004;6(3):587-95.

Sancey et al., Long-term in vivo clearance of gadolinium-based AGuIX nanoparticles and their biocompatibility after systemic injection. ACS Nano. Mar. 24, 2015;9(3):2477-88. doi: 10.1021/acsnano.5b00552. Epub Feb. 26, 2015.

Sanders et al., Metal-free sequential [3+2]-dipolar cycloadditions using cyclooctynes and 1,3-dipoles of different reactivity. J Am Chem Soc. Feb. 2, 2011;133(4):949-57. doi: 10.1021/ja1081519. Epub Dec. 23, 2010.

Sartori et al., Nitroxide paramagnet-induced para-ortho conversion and nuclear spin relaxation of H2 in organic solvents. J Am Chem Soc. Sep. 24, 2008;130(38):12752-6. doi: 10.1021/ja8037195. Epub Aug. 20, 2008.

Saunders et al., Synthesis of amphiphilic star block copolymers using ring-opening metathesis polymerization. Macromolecules, 1992;25(7):2055-2057. DOI: 10.1021/ma00033a035.

Schmidt et al., Supramolecular three-armed star polymers via cyclodextrin host-guest self-assembly. Polym. Chem., 2012;3:3139-3145. DOI: 10.1039/C2PY20293J.

Sengupta et al., Temporal targeting of tumour cells and neovasculature with a nanoscale delivery system. Nature. Jul. 28, 2005;436(7050):568-72.

Sheiko et al., Cylindrical molecular brushes: Synthesis, characterization, and properties. Progress in Polymer Science (Oxford), 33(7), 759-785. DOI: 10.1016/j.progpolymsci.2008.05.001.

Shi et al., Core cross-linked star (CCS) polymers with tunable polarity: synthesis by RAFT dispersion polymerization, self-assembly and emulsification. Polym. Chem., 2013;4:1950-1959. DOI: 10.1039/C3PY21120G.

Shibata et al., Quantitative Synthesis of Star-Shaped Poly(vinyl ether)s with a Narrow Molecular Weight Distribution by Living Cationic Polymerization. J. Am. Chem. Soc., 2006;128(23):7497-7504. DOI: 10.1021/ja057611h.

Shin et al., Recent advances in magnetic nanoparticle-based multimodal imaging. Chem Soc Rev. Jul. 21, 2015;44(14):4501-16. doi: 10.1039/c4cs00345d.

Sides et al., Parallel algorithm for numerical self-consistent field theory simulations of block copolymer structure. Polymer. Sep. 1, 2003;44(19):5859-66.

Sinturel et al., High χ-low N block polymers: how far can we go ?. ACS Macro Lett. Sep. 2, 2015;4:1044-50.

Skomski et al., Redox-active on-surface assembly of metal-organic chains with single-site Pt(II). J Am Chem Soc. Jul. 16, 2014;136(28):9862-5. doi: 10.1021/ja504850f. Epub Jul. 1, 2014.

Smith et al., Nanomaterials for in Vivo Imaging. Chem Rev. Feb. 8, 2017;117(3):901-986. doi: 10.1021/acs.chemrev.6b00073. Epub Jan. 3, 2017.

Smulders et al., Building on architectural principles for three-dimensional metallosupramolecular construction. Chem Soc Rev. Feb. 21, 2013;42(4):1728-54. doi: 10.1039/c2cs35254k. Epub Oct. 2, 2012.

Sowers et al., Redox-responsive branched-bottlebrush polymers for in vivo MRI and fluorescence imaging. Nature Communications. 2014;5:Article No. 5460.

Spiniello et al., Synthesis and characterization of fluorescently labeled core cross-linked star polymers. J. Polym. Sci. A Polym. Chem., 2008;46:2422-2432. doi:10.1002/pola.22576.

Stenzel-Rosenbaum et al., Synthesis of Poly(styrene) Star Polymers Grown from Sucrose, Glucose, and Cyclodextrin Cores via Living Radical Polymerization Mediated by a Half-Metallocene Iron Carbonyl Complex. Macromolecules, 2001;34(16):5433-5438. DOI: 10.1021/ma0021803.

Su et al., Coordination-directed assembly of trigonal and tetragonal molecular boxes encapsulating anionic guests. Journal of the Chemical Society, Dalton Transactions. 2001:359-361. doi: 10.1039/B010118O.

Sulistio et al., Star polymers composed entirely of amino acid building blocks: a route towards stereospecific, biodegradable and hierarchically functionalized stars. Chem. Commun., 2011;47:1151-1153. DOI: 10.1039/C0CC03541F.

Sun et al., Multicomponent metal-ligand self-assembly. Curr Opin Chem Biol. Dec. 2002;6(6):757-64.

Sun et al., Self-assembled M24L48 polyhedra and their sharp structural switch upon subtle ligand variation. Science. May 28, 2010;328(5982):1144-7. doi:10.1126/science.1188605. Epub Apr. 29, 2010.

Sveinbjornsson et al., Rapid self-assembly of brush block copolymers to photonic crystals. Proc Natl Acad Sci U S A. Sep. 4, 2012;109(36):14332-6. doi: 10.1073/pnas.1213055109. Epub Aug. 21, 2012.

Swaminathan et al., Nephrogenic systemic fibrosis, gadolinium, and iron mobilization. N Engl J Med. Aug. 16, 2007;357(7):720-2.

Takamizu et al., Synthesis of oligo(thiophene)-coated star-shaped ROMP polymers: unique emission properties by the precise integration of functionality. Journal of the American Chemical Society 2012;134(18):7892-7895.

Tam et al., Recent advances in metallogels. Chem Soc Rev. Feb. 21, 2013;42(4):1540-67. doi: 10.1039/c2cs35354g. Epub Jan. 8, 2013.

Tanino et al., Control of Stereochemistry by sigma-Participation of a Silyl Group. A Novel Method for Diastereoselective Polyol Synthesis. J Org Chem. Jun. 27, 1997;62(13):4206-4207. doi: 10.1021/jo9703515. PMID: 11671736.

Terashima et al., Star-Polymer-Catalyzed Living Radical Polymerization: Microgel-Core Reaction Vessel by Tandem Catalyst Interchange. Angew. Chem., 2011;50:7892-7895. doi:10.1002/anie.201101381.

Terreno et al., Challenges for molecular magnetic resonance imaging. Chem Rev. May 12, 2010;110(5):3019-42. doi: 10.1021/cr100025t.

Theodorakis et al., Interplay between chain collapse and microphase separation in bottle-brush polymers with two types of side chains. Macromol. May 4, 2010;43(11):5137-48.

Thompson et al., Labelling polymers and micellar nanoparticles via initiation, propagation and termination with ROMP. Polym. Chem., 2014;5:1954-1964.

Tirotta et al., (19)F magnetic resonance imaging (MRI): from design of materials to clinical applications. Chem Rev. Jan. 28, 2015;115(2):1106-29. doi: 10.1021/cr500286d. Epub Oct. 20, 2014.

Tominaga et al., Finite, spherical coordination networks that self-organize from 36 small components. Angew Chem Int Ed Engl. Oct. 25, 2004;43(42):5621-5.

Tomooka et al., Planar chiral dialkoxysilane:introduction of inherent chirality and high reactivity in conventional achiral alkene. Chemistry. Jun. 16, 2014;20(25):7598-602. doi: 10.1002/chem.201402434. Epub May 6, 2014.

Torchilin, Tumor delivery of macromolecular drugs based on the EPR effect. Adv Drug Deliv Rev. Mar. 18, 2011;63(3):131-5. doi: 10.1016/j.addr.2010.03.011. Epub Mar. 18, 2010.

Tsuji et al., Facile Palladium catalyzed decarboxylative allylation of active methylene compounds under neutral conditions using allylic carbonates. Tetrahedron Letters. 1982;23(46):4809-12.

Tu et al., Multimodal magnetic-resonance/optical-imaging contrast agent sensitive to NADH. Angew Chem Int Ed Engl. 2009;48(35):6547-51. doi: 10.1002/anie.200900984.

Tunca et al., Novel miktofunctional initiator for the preparation of an ABC-type miktoarm star polymer via a combination of controlled polymerization techniques. J. Polym. Sci. A Polym. Chem., 42: 4228-4236. doi:10.1002/pola.20284.

Valeur et al., Amide bond formation: beyond the myth of coupling reagents. Chem. Soc. Rev., 2009;38:606-631. DOI: 10.1039/B701677H.

(56) References Cited

OTHER PUBLICATIONS

Verduzco et al., Correction: Structure, function, self-assembly, and applications of bottlebrush copolymers. Chem Soc Rev. Nov. 7, 2015;44(21):7916. doi: 10.1039/c5cs90099a.

Verduzco et al., Structure, function, self-assembly, and applications of bottlebrush copolymers. Chem. Soc. Rev., 2015;44:2405-20.

Verwilst et al., Recent advances in Gd-chelate based bimodal optical/MRI contrast agents. Chem Soc Rev. Apr. 7, 2015;44(7):1791-806. doi: 10.1039/c4cs00336e. Epub Jan. 27, 2015.

Villaraza et al., Macromolecules, dendrimers, and nanomaterials in magnetic resonance imaging: the interplay between size, function, and pharmacokinetics. Chem Rev. May 12, 2010;110(5):2921-59. doi: 10.1021/cr900232t.

Wang et al., Advances of cancer therapy by nanotechnology. Cancer Res Treat. Mar. 2009;41(1):1-11. doi: 10.4143/crt.2009.41.1.1. Epub Mar. 31, 2009.

Wang et al., Synthesis of Unnatural Amino Acids Functionalized with Sterically Shielded Pyrroline Nitroxides. Org Lett. Oct. 17, 2014;16(20): 5298-5300. Published online Sep. 16, 2014. doi: [10.1021/ol502449r].

Wei et al., Exceedingly small iron oxide nanoparticles as positive MRI contrast agents. Proc. Natl. Acad. Sci. USA 2017;114(9):2325-2330.

Weng et al., Control of Gel Morphology and Properties of a Class of Metallo-Supramolecular Polyers by Good/Poor Solvent Environments. Macromolecules. 2009;42(1):236-246.

Weng et al., Effect of monomer structure on the gelation of a class of metallo-supramolecular polymers. Soft Matter. 2009;5(23):4647-4657.

Weng et al., Structural origin of the thixotropic behavior of a class of metallosupramolecular gels. Tetrahedron. Jul. 30, 2007;63(31):7419-7431.

Weng et al., Understanding the mechanism of gelation and stimuli-responsive nature of a class of metallo-supramolecular gels. J Am Chem Soc. Sep. 6, 2006;128(35):11663-72.

Westhaus et al., Triggered release of calcium from lipid vesicles: a bioinspired strategy for rapid gelation of polysaccharide and protein hydrogels. Biomaterials. Mar. 2001;22(5):453-62.

Wollinsky et al., Therapeutic and diagnostic applications of dendrimers for cancer treatment. Adv Drug Deliv Rev. Jun. 10, 2008;60(9):1037-55. doi: 10.1016/j.addr.2008.02.012. Epub Mar. 4, 2008.

Wong et al., Quantitative formation of core cross-linked star polymers via a one-pot two-step single electron transfer-living radical polymerization. Polym. Chem., 2013;4:4562-4565. DOI: 10.1039/C3PY00726J.

Worrell et al., Direct evidence of a dinuclear copper intermediate in Cu(I)-catalyzed azide-alkyne cycloadditions. Science. Apr. 26, 2013;340(6131):457-60. doi: 10.1126/science.1229506. Epub Apr. 4, 2013.

Xia et al., Efficient synthesis of narrowly dispersed brush copolymers and study of their assemblies: the importance of side chain arrangement. J Am Chem Soc. Dec. 30, 2009;131(51):18525-32. doi: 10.1021/ja908379q.

Xia et al., Efficient Synthesis of Narrowly Dispersed Brush Polymers via Living Ring-Opening Metathesis Polymerization of Macromonomers. Macromolecules, 2009;42(11):3761-3766. DOI: 10.1021/ma900280c.

Xia et al., EPR study of spin labeled brush polymers in organic solvents. J Am Chem Soc. Dec. 14, 2011;133(49):19953-9. doi: 10.1021/ja2085349. Epub Nov. 21, 2011.

Xiao et al., The use of polymeric platinum(IV) prodrugs to deliver multinuclear platinum(II) drugs with reduced systemic toxicity and enhanced antitumor efficacy. Biomaterials. Nov. 2012;33(33):8657-69. doi: 10.1016/j.biomaterials.2012.08.015. Epub Aug. 28, 2012.

Xing et al., A stable metal coordination polymer gel based on a calix[4]arene and its 'uptake' of non-ionic organic molecules from the aqueous phase. Chem Commun (Camb). Feb. 21, 2002;(4):362-3.

Xing et al., Design of coordination polymer as stable catalytic systems. Chemistry. Nov. 4, 2002;8(21):5028-32.

Xing et al., Spontaneous Enrichment of Organic Molecules from Aqueous and Gas Phases into a Stable Metallogel. Langmuir. 2002;18:9654-9658.

Xu et al., Mechanism of Shear Thickening in Reversibly Cross-linked Supramolecular Polymer Networks. Macromolecules. Apr. 13, 2010;43(7):3556-3565.

Xu et al., Scaling Laws in Supramolecular Polymer Networks. Macromolecules. 2011;44(13):5465-5472.

Xu et al., Strain Hardening and Strain Softening of Reversibly Cross-linked Supramolecular Polymer Networks. Macromolecules. Sep. 27, 2011;44(18):7478-7488.

Yan et al., Hierarchical self-assembly: well-defined supramolecular nanostructures and metallohydrogels via amphiphilic discrete organoplatinum(II) metallacycles. J Am Chem Soc. Sep. 25, 2013;135(38):14036-9. doi: 10.1021/ja406877b. Epub Aug. 8, 2013.

Yan et al., Particle carriers for combating multidrug-resistant cancer. ACS Nano. Nov. 26, 2013;7(11):9512-7. doi: 10.1021/nn405632s. Epub Nov. 11, 2013.

Yan et al., Responsive supramolecular polymer metallogel constructed by orthogonal coordination-driven self-assembly and host/guest interactions. J Am Chem Soc. Mar. 26, 2014;136(12):4460-3. doi: 10.1021/ja412249k. Epub Mar. 12, 2014.

Yan et al., Supramolecular polymers with tunable topologies via hierarchical coordination-driven self-assembly and hydrogen bonding interfaces. Proc Natl Acad Sci U S A. Sep. 24, 2013;110(39):15585-90. doi: 10.1073/pnas.1307472110. Epub Sep. 9, 2013.

Yang et al., Luminescent chemodosimeters for bioimaging. Chem Rev. Jan. 9, 2013;113(1):192-270. doi: 10.1021/cr2004103. Epub Jun. 18, 2012.

Yi et al., Telmisartan attenuates hepatic fibrosis in bile ductligated rats. Acta Pharmacol Sin. Dec. 2012;33(12):1518-24. doi: 10.1038/aps.2012.115. Epub Oct. 29, 2012.

Yoneya et al., Coordination-directed self-assembly of M12L24 nanocage: effects of kinetic trapping on the assembly process. ACS Nano. Feb. 25, 2014;8(2):1290-6. doi: 10.1021/nn404595j. Epub Jan. 31, 2014.

Yoneya et al., Simulation of metal-ligand self-assembly into spherical complex M6L8. J Am Chem Soc. Sep. 5, 2012;134(35):14401-7. doi: 10.1021/ja303542r. Epub Aug. 22, 2012.

Yoshizawa et al., Molecular architectures of multi-anthracene assemblies. Chem Soc Rev. Mar. 21, 2014;43(6):1885-98. doi: 10.1039/c3cs60315f.

You et al., Manganese displacement from Zinpyr-1 allows zinc detection by fluorescence microscopy and magnetic resonance imaging. Chem Commun (Camb). Jun. 21, 2010;46(23):4139-41. doi: 10.1039/c0cc00179a. Epub May 10, 2010.

Yount et al., Small-molecule dynamics and mechanisms underlying the macroscopic mechanical properties of coordinatively cross-linked polymer networks. J Am Chem Soc. Oct. 19, 2005;127(41):14488-96.

Yount et al., Strong means slow: dynamic contributions to the bulk mechanical properties of supramolecular networks. Angew Chem Int Ed Engl. Apr. 29, 2005;44(18):2746-8.

Yuan et al., One-pot syntheses of amphiphilic centipede-like brush copolymers via combination of ring-opening polymerization and "click" chemistry. Macromol. Jan. 27, 2010;43(4):1739-46.

Yue et al., Macrocyclic and lantern complexes of palladium(II) with bis(amidopyridine) ligands: synthesis, structure, and host-guest chemistry. Inorg Chem. Nov. 29, 2004;43(24):7671-81.

Zhang et al., Active cross-linkers that lead to active gels. Angew Chem Int Ed Engl. Oct. 25, 2013;52(44):11494-8. doi: 10.1002/anie.201304437. Epub Sep. 12, 2013.

Zhang et al., Cyclodextrin-centred star polymers synthesized via a combination of thiol-ene click and ring opening polymerization. Chem Commun (Camb). Aug. 21, 2012;48(65):8063-5. doi: 10.1039/c2cc33742h. Epub Jul. 6, 2012.

Zhang et al., Dual-functional gadolinium-based copper(II) probe for selective magnetic resonance imaging and fluorescence sensing. Inorg Chem. Feb. 20, 2012;51(4):2325-31. doi: 10.1021/ic202322f. Epub Feb. 8, 2012.

(56) References Cited

OTHER PUBLICATIONS

Zhang et al., One-pot RAFT synthesis of core cross-linked star polymers of polyPEGMA in water by sequential homogeneous and heterogeneous polymerizations. Polym. Chem., 2012;3:2656-2664. DOI: 10.1039/C2PY20442H.

Zhang et al., polyMOFs: A Class of Interconvertible Polymer-Metal-Organic-Framework Hybrid Materials. Angew Chem Int Ed Engl. May 18, 2015;54(21):6152-7. doi: 10.1002/anie.201502733. Epub Apr. 29, 2015.

Zhang et al., Redox-Responsive, Core Cross-Linked Polyester Micelles. ACS Macro Lett., 2013;2(1):40-44. DOI: 10.1021/mz300522n.

Zhao et al., Polystyrene—Polylactide Bottlebrush Block Copolymer at the Air/Water Interface. Macromol. Sep. 28, 2009;42(22):9027-33.

Zhao et al., Rheological Behavoir of Shear-Responsive Metallo-Supramolecular Gels. Macromolecules. 2004;37(10):3529-3531.

Zhelev et al., Imaging of superoxide generation in the dopaminergic area of the brain in Parkinson's disease, using mito-TEMPO. ACS Chem Neurosci. Nov. 20, 2013;4(11):1439-45. doi: 10.1021/cn400159h. Epub Sep. 16, 2013.

Zhelev et al., Nitroxyl radicals as low toxic spin-labels for non-invasive magnetic resonance imaging of blood-brain barrier permeability for conventional therapeutics. Chem Commun (Camb). Jan. 7, 2009;(1):53-5. doi: 10.1039/b816878d. Epub Nov. 13, 2008.

Zhelev et al., Nitroxyl radicals for labeling of conventional therapeutics and noninvasive magnetic resonance imaging of their permeability for blood-brain barrier: relationship between structure, blood clearance, and MRI signal dynamic in the brain. Mol Pharm. Mar.-Apr. 2009;6(2):504-12. doi: 10.1021/mp800175k.

Zheng et al., Construction of Smart Supramolecular Polymeric Hydrogels Cross-linked by Discrete Organoplatinum(II) Metallacycles via Post-Assembly Polymerization. J. Am. Chem. Soc., 2016;138(14):4927-37. DOI: 10.1021/jacs.6b01089.

Zheng et al., Morphology of ABC triblock copolymers. Macromol. Oct. 1995;28(21):7215-23.

Zhou et al., Counting primary loops in polymer gels. Proc Natl Acad Sci U S A. Nov. 20, 2012;109(47):19119-24. doi: 10.1073/pnas.1213169109. Epub Nov. 6, 2012.

Zhou et al., Efficient formation of multicompartment hydrogels by stepwise self-assembly of thermoresponsive ABC triblock terpolymers. J Am Chem Soc. Jun. 27, 2012;134(25):10365-8. doi: 10.1021/ja303841f. Epub Jun. 13, 2012.

Zhou et al., Photo-controlled growth of telechelic polymers and end-linked polymer gels. Angew Chem Int Ed Engl. Feb. 18, 2013;52(8):2235-8. doi: 10.1002/anie.201207966. Epub Jan. 17, 2013.

International Search Report and Written Opinion for PCT/US2019/027414, dated Sep. 12, 2019.

International Preliminary Report on Patentability for PCT/US2019/027414, dated Oct. 22, 2020.

International Preliminary Report on Patentability for PCT/US2019/046872, dated Mar. 4, 2021.

International Search Report and Written Opinion for PCT/US2020/023836, dated Jul. 7, 2020.

International Preliminary Report on Patentability for PCT/US2020/023836, dated Dec. 2, 2021.

Invitation to Pay Additional Fees for PCT/US2020/059827 dated Feb. 4, 2021.

International Search Report and Written Opinion for PCT/US2020/059827 dated Mar. 15, 2021.

International Preliminary Report on Patentability for PCT/US2020/059827 dated Jul. 21, 2022.

Invitation to Pay Additional Fees for PCT/US2020/055862, dated Feb. 12, 2021.

International Search Report and Written Opinion for PCT/US2020/055862 dated May 6, 2021.

International Preliminary Report on Patentability for PCT/US2020/055862 dated Apr. 28, 2022.

International Search Report and Written Opinion for Application No. PCT/US2020/050927 dated Jan. 21, 2021.

International Preliminary Report on Patentability for PCT/US2020/050927, dated May 27, 2022.

International Search Report and Written Opinion for Application No. PCT/US2021/061135 dated Apr. 28, 2022.

Invitation to Pay Additional Fees for Application No. PCT/US2021/058668 dated Jan. 10, 2022.

International Search Report and Written Opinion for Application No. PCT/US2021/058668 dated Mar. 10, 2022.

Invitation to Pay Additional Fees for Application No. PCT/US2022/31759 dated Aug. 16, 2022.

International Search Report and Written Opinion for Application No. PCT/US2022/31759 dated Aug. 8, 2022.

[No Author Listed], Dimethyl-[(1R)-1-naphthalen-1-yl-2-[(2-naphthalen-2-yloxyacetyl)amino]ethyl]azanium. PubChem CID No. 8701426. Feb. 12, 2015. Retrieved from <https://pubchem.ncbi.nlm.nih.gov/compound/8701426> on Nov. 4, 2022. 7 pages.

Alvaredo et al., Polyoxazoline-Based Bottlebrush and Brush-Arm Star Polymers via ROMP: Syntheses and Applications as Organic Radical Contrast Agents. ACS Macro Lett. Apr. 16, 2019;8(4):473-478. doi: 10.1021/acsmacrolett.9b00016. Epub Apr. 4, 2019.

Blackmore, P.M., Synthesis and properties of stereoregular fluoropolymers. Doctoral thesis at Durham University. 1986. pp. i-iii, 46, 62. Accessed from <http://etheses.dur.ac.uk/6795/>.

Blencowe et al., Ring-opening metathesis polymerization with the second generation Hoveyda-Grubbs catalyst: an efficient approach toward high-purity functionalized macrocyclic oligo(cyclooctene)s. J Am Chem Soc. Apr. 17, 2013;135(15):5717-25. doi: 10.1021/ja312418z. Epub Apr. 8, 2013.

Boadi et al., Alternating Ring-Opening Metathesis Polymerization Provides Easy Access to Functional and Fully Degradable Polymers. Macromolecules. Jul. 28, 2020;53(14):5857-5868. doi: 10.1021/acs.macromol.0c01051. Epub Jul. 16, 2020.

Borke et al., Poly(glyceryl glycerol): A multi-functional hydrophilic polymer for labeling with boronic acids. Polym Chem. Jun. 1, 2017;55(11):1822-30. doi: 10.1002/pola.28497.

Cannon, J.G., Analog Design. In: Burger's Medicinal Chemistry and Drug Discovery, Fifth Edition, vol. I: Principles and Practice. 1995. Burger, Ed. Wiley Interscience. Chapter 19:783-802.

Collins et al., Chemical approaches to targeted protein degradation through modulation of the ubiquitin-proteasome pathway. Biochem J. Mar. 15, 2017;474(7):1127-1147. doi: 10.1042/BCJ20160762.

Fedorenko et al., Facial selectivity in the reaction of dihalocarbenes with 2-substituted 4,7-dihydro-1,3-dioxepines. Mendeleev Comm. May 29, 2007;17:170-1. doi: 10.1016/J.MENCOM.2007.05.013.

Feist et al., Enol Ethers Are Effective Monomers for Ring-Opening Metathesis Polymerization: Synthesis of Degradable and Depolymerizable Poly(2,3-dihydrofuran). J Am Chem Soc. Dec. 27, 2019;142(3):1186-9. doi: 10.1021/jacs.9b11834.

Fiers et al., Orthogonal Synthesis of Xeno Nucleic Acids. Chemistry. Dec. 12, 2016;22(50):17945-17948. doi: 10.1002/chem.201604386. Epub Nov. 3, 2016.

Fraser et al., Degradable Cyclooctadiene/Acetal Copolymers: versatile Precursors to 1,4-Hydroxytelechelic Polybutadiene and Hydroytelechelic Polyethylene. Macromolecules. Oct. 9, 1995;28(21):7256-61. doi: 10.1021/ma00125a031.

Frauenrath et al., Synthesis of 2,3-substituted tetrahydropyrans by rearrangement of 5,6-dihydro-4H-1,3-dioxocins. Tetrahedron Lett. Jan. 1, 1990;31(5):649-50. doi: 10.1016/S0040-4039(00)94591-X.

Gupta et al., Cell protective, ABC triblock polymer-based thermoresponsive hydrogels with ROS-triggered degradation and drug release. J Am Chem Soc. Oct. 22, 2014;136(42):14896-902. doi: 10.1021/ja507626y. Epub Oct. 7, 2014.

Herges et al., Synthesis and Fragmentation of 2,2-Diazido-1,3,2-dioxasila-5-cycloheptenes. The Chemical Vapor Deposition of SiO2. J Am Chem Soc. Dec. 18, 1996;18(50):12752-7. doi: 10.1021/ja9615886.

Hilf et al., End Capping Ring-Opening Olefin Metathesis Polymerization Polymers with Vinyl Lactones. J Am Chem Soc. Jul. 23, 2008;130(33):11040-8. doi: 10.1021/ja8022863.

(56) References Cited

OTHER PUBLICATIONS

Hilf et al., Monofunctional metathesis polymers via sacrificial diblock copolymers. Angew Chem Int Ed Engl. Dec. 4, 2006;45(47):8045-8. doi: 10.1002/anie.200602323.
Hilf et al., Sacrificial Synthesis of Hydroxy-Telechelic Metathesis Polymers via Multiblock-Copolymers. Macromolecules. Feb. 24, 2009;42(4):1099-106. doi: 10.1021/ma802440k.
Klimovitskii et al., Conformational isomerism in 3,5,8-trioxabicyclo[5.1.0]octane and its diastereomeric 4-methyl derivatives. A combined IR, X-ray and ab initio study. J Mol Struc. Feb. 28, 2007;828(1-3):147-53. doi: 10.1016/j.molstruc.2006.05.045.
Kumar et al., Multivalency in the recognition and antagonism of a HIV TAR RNA-TAT assembly using an aminoglycoside benzimidazole scaffold. Org Biomol Chem. Feb. 14, 2016;14(6):2052-6. doi: 10.1039/c5ob02016f.
Lexer et al., Acrylates as termination reagent for the preparation of semi-telechelic polymers made by ring opening metathesis polymerization. J Polym Sci Part A: Polym Chem. Jan. 1, 2009;47(1):299-305. doi: 10.1002/pola.23137.
Moatsou et al., Degradable precision polynorbornenes via ring-opening metathesis polymerization. J Polym Sci Part A: Polym Chem. May 1, 2016;54(9):1236-42. doi: 10.1002/pola.27964.
Nagarkar et al., End functional ROMP polymers via degradation of a ruthenium Fischer type carbene. Chem Sci. Sep. 2, 2014;5(12):4687-92. doi: 10.1039/C4SC02242D.
Nguyen et al., Pro-organic radical contrast agents ("pro-ORCAs") for real-time MRI of pro-drug activation in biological systems. Polym Chem. Aug. 7, 2020;11(29):4768-4779. doi: 10.1039/d0py00558d. Epub Jun. 26, 2020.
Nguyen et al., Scalable Synthesis of Multivalent Macromonomers for ROMP. ACS Macro Lett. Apr. 17, 2018;7(4):472-476. doi: 10.1021/acsmacrolett.8b00201. Epub Mar. 26, 2018.
Nguyen et al., Triply Loaded Nitroxide Brush-Arm Star Polymers Enable Metal-Free Millimetric Tumor Detection by Magnetic Resonance Imaging. ACS Nano. Nov. 27, 2018;12(11):11343-11354. doi: 10.1021/acsnano.8b06160. Epub Nov. 2, 2018.
Ogata et al., Scissionable polymer resists for extreme ultraviolet lithography. Proceedings of the SPIE, Extreme Ultraviolet (EUV) Lithography. Mar. 22, 2010;7636:763634/1. doi: 10.1117/12.847320.
Ohwada et al., Design, synthesis and antifungal activity of a novel water soluble prodrug of antifungal triazole. Bioorg Med Chem Lett. Jan. 20, 2003;13(2):191-6. doi: 10.1016/s0960-894x(02)00892-2.
Shieh et al., Tailored silyl ether monomers enable backbone-degradable polynorbornene-based linear, bottlebrush and star copolymers through ROMP. Nat Chem. Dec. 2019; 11(12):1124-1132. doi: 10.1038/s41557-019-0352-4. Epub Oct. 28, 2019.
Smith et al., Modular synthesis of biologically active phosphatidic acid probes using click chemistry. Mol Biosyst. Sep. 2009;5(9):962-72. doi: 10.1039/b901420a. Epub May 7, 2009.
Tinworth et al., Small molecule-mediated protein knockdown as a new approach to drug discovery. Med Chem Commun. Jul. 26, 2016;7:2206-16. doi: 10.1039/C6MD00347H.
Tong et al., Copolymers of Functionalized and Nonfunctionalized Polydicyclopentadiene. ACS Applied Polymer Materials. Jan. 8, 2021;3(1):110-115.
Venkatesh et al., Role of the development scientist in compound lead selection and optimization. J Pharm Sci. Feb. 2000;89(2):145-54. doi: 10.1002/(SICI)1520-6017(200002)89:2<145::AID-JPS2>3.0.CO;2-6.
Wang et al., Readily recyclable carbon fiber reinforced composites based on degradable thermosets: a review. Green Chem. Sep. 19, 2019;21(21):5781-96. doi: 10.1039/C9GC01760G.
Wurz et al., A "Click Chemistry Platform" for the Rapid Synthesis of Bispecific Molecules for Inducing Protein Degradation. J Med Chem. Jan. 25, 2018;61(2):453-461. doi: 10.1021/acs.jmedchem.6b01781. Epub Apr. 17, 2017.
International Preliminary Report on Patentability for Application No. PCT/US2021/058668 dated May 19, 2023.
International Search Report and Written Opinion for PCT/US2022/047333 dated Jan. 25, 2023.
Invitation to Pay Additional Fees for Application No. PCT/US2023/062223 dated Apr. 20, 2023.
[No Author Listed], 2-Propen-1-amine, 3-(2-methoxyphenyl)-N-2-propyn-1-yl. CAS Registry File RN 1883141-01-2. STN Entry Date Mar. 10, 2016.
Altuna et al., Self-healable polymer networks based on the cross-linking of epoxidised soybean oil by an aqueous citric acid solution. Green Chem. Sep. 9, 2013;15(12):3360-6. doi: 10.1039/C3GC41384E.
Asaro et al., Recycling of rubber wastes by devulcanization. Res Conserv Rec. Jun. 2018;133:250-62. doi: 10.1016/j.resconrec.2018.02.016.
Autenrieth et al., Stereospecific Ring-Opening Metathesis Polymerization (ROMP) of endo-Dicyclopentadiene by Molybdenum and Tungsten Catalysts. Macromolecules. Apr. 2015;48(8):2480-92. doi: 10.1021/acs.macromol.5b00123.
Bang et al., Polydicyclopentadiene aerogels from first- versus second-generation Grubbs' catalysts: a molecular versus a nanoscopic perspective. J Sol-Gel Sci Technol. 2015;75(2):460-74. doi: 10.1007/s10971-015-3718-0.
Baslé et al., Protein chemical modification on endogenous amino acids. Chem Biol. Mar. 26, 2010;17(3):213-27. doi: 10.1016/j.chembiol.2010.02.008.
Beck et al., Strategies and challenges for the next generation of antibody-drug conjugates. Nat Rev Drug Discov. May 2017;16(5):315-337. doi: 10.1038/nrd.2016.268. Epub Mar. 17, 2017.
Bento et al., Nucleophilic substitution at silicon (SN2@Si) via a central reaction barrier. J Org Chem. Mar. 16, 2007;72(6):2201-7. doi: 10.1021/jo070076e. Epub Feb. 15, 2007.
Capelot et al., Catalytic Control of the Vitrimer Glass Transition. ACS Macro Lett. Jul. 17 2012;1(7):789-792. doi: 10.1021/mz300239f. Epub Jun. 11, 2012.
Chen et al., Characterization of thermally reworkable thermosets: materials for environmentally friendly processing and reuse. Polymer. Jan. 2002;43(1):131-9. doi: 10.1016/S0032-3861(01)00605-X.
Chen et al., Thermally Crosslinked Functionalized Polydicyclopentadiene with a High $T_g$ and Tunable Surface Energy. ACS Omega. Oct. 6, 2016;1(4):532-540. doi: 10.1021/acsomega.6b00193. Erratum in: ACS Omega. Jun. 9, 2017;2(6):2593.
Christensen et al., Closed-loop recycling of plastics enabled by dynamic covalent diketoenamine bonds. Nat Chem. May 2019; 11(5):442-448. doi: 10.1038/s41557-019-0249-2. Epub Apr. 22, 2019.
Clark et al., Dynamically Restructuring Hydrogel Networks Formed with Reversible Covalent Crosslinks. Advanced Materials. 2007;19:2503-2507. 10.1002/adma.200602649.
Cole et al., Microplastics as contaminants in the marine environment: A review. Mar Pol Bull. Dec. 2011;62(12):2588-97. doi: 10.1016/j.marpolbul.2011.09.025.
Corma et al., Formation and hydrolysis of acetals catalysed by acid Faujasites. Appl Catal. Mar. 12, 1990;59(1):333-40. doi: 10.1016/S0166-9834(00)82207-1.
Cuthbert et al., Structure of the Thermally Induced Cross-Link in C-Linked Methyl Ester-Functionalized Polydicyclopentadiene (fPDCPD). Macromolecules. Feb. 28, 2018;51(5):2038-47. doi: 10.1021/acs.macromol.7b02750.
Cypryk et al., Mechanism of the Acid-Catalyzed Si—O Bond Cleavage in Siloxanes and Siloxanols. A Theoretical Study. Organometallics. Apr. 24, 2002;21(11):2165-75. doi: 10.1021/om011055s.
Davidson et al., Polymerization of Dicyclopentadiene: A Tale of Two Mechanisms. Macromolecules. 1996;29:786-8.
Davies et al., Protection of hydroxy groups by silylation: use in peptide synthesis and as lipophilicity modifiers for peptides. J Chem Soc Perkin Trans. 1;1992:3043-8. doi: 10.1039/P19920003043.
Defauchy et al., Kinetic analysis of polydicyclopentadiene oxidation. Polym Degrad Stab. Aug. 2017;142:169-77. doi: 10.1016/j.polymdegradstab.2017.06.005.
Delancey et al., Controlling crosslinking in thermosets via chain transfer with monoterpenes. Polym Chem. Jun. 20, 2011;49(17):3719-27. doi: 10.1002/pola.24808.

(56) References Cited

OTHER PUBLICATIONS

Denissen et al., Chemical control of the viscoelastic properties of vinylogous urethane vitrimers. Nat Commun. Mar. 20, 2017;8:14857. doi: 10.1038/ncomms14857.

Dennler et al., Antibody Conjugates: From Heterogeneous Populations to Defined Reagents. Antibodies. Aug. 3, 2015;4(3):197-224. doi: 10.3390/antib4030197.

Dong et al., A Simple and Versatile Method for the Formation of Acetals/Ketals Using Trace Conventional Acids. ACS Omega. May 7, 2018;3(5):4974-4985. doi: 10.1021/acsomega.8b00159.

Elder et al., Nanovoid formation and mechanics: a comparison of poly(dicyclopentadiene) and epoxy networks from molecular dynamics simulations. Soft Matter. 2016;12:4418-34. doi: 10.1039/C6SM00691D.

Evans, R.A., The Rise of Azide-Alkyne 1,3-Dipolar 'Click' Cycloaddition and its Application to Polymer Science and Surface Modification. Aust J Chem. Jun. 18, 2007;60(6):384-95. doi: 10.1071/CH06457.

Flory, P.J., Molecular Size Distribution in Three Dimensional Polymers. I. Gelation. J Am Chem Soc. Nov. 1, 1941;63(11):3083-90. doi: 10.1021/ja01856a061.

Fortman et al., Approaches to Sustainable and Continually Recyclable Cross-Linked Polymers. ACS Sus Chem Eng. Aug. 26, 2018;6(9):11145-59. doi: 10.1021/acssuschemeng.8b02355.

Fortman et al., Mechanically activated, catalyst-free polyhydroxyurethane vitrimers. J Am Chem Soc. Nov. 11, 2015;137(44):14019-22. doi: 10.1021/jacs.5b08084. Epub Nov. 2, 2015.

Fu et al., Relay Conjugation of Living Metathesis Polymers. J Am Chem Soc. Sep. 26, 2018;140(38):12181-12188. doi: 10.1021/jacs.8b07315. Epub Sep. 11, 2018.

Furstner et al., Alkyne metathesis: development of a novel molybdenum-based catalyst system and its application to the total synthesis of epothilone A and C. Chem Eur J. Dec. 17, 2001;7(24):5299-317. doi: 10.1002/1521-3765(20011217)7:24<5299::aid-chem5299>3.0. co;2-x.

Furstner et al., Mo[N(t-Bu)(Ar)]$_3$ Complexes as Catalyst Precursors: In Situ Activation and Application to Metathesis Reactions of Alkynes and Diynes. J Am Chem Soc. Sep. 23, 1999;121(40):9453-4. doi: 10.1021/ja991340r.

Gallivan et al., A neutral, water-soluble olefin metathesis catalyst based on an N-heterocyclic carbene ligand. Tetrahedron Lett. Apr. 11, 2005;46(15):2577-80. doi: 10.1016/j.tetlet.2005.02.096.

Grubbs et al., Ring-Closing Metathesis and Related Processes in Organic Synthesis. Acc Chem Res. Nov. 1, 1995;28(11):446-52. doi: 10.1021/ar00059a002.

Gu et al., A (Macro)Molecular-Level Understanding of Polymer Network Topology. Trends Chem. Jun. 2019;1(3):318-34. doi: 10.1016/j.trechm.2019.02.017.

Gu et al., A unifying review of polymer networks: from rubbers and gels to porous frameworks. Angew Chemie Int Ed. Jul. 2019;59(13):5022-49. doi: 0.1002/anie.201902900. Author Manuscript, 66 pages.

Gu et al., Polymer Networks: From Plastics and Gels to Porous Frameworks. Angew Chem Int Ed Engl. Mar. 23, 2020;59(13):5022-5049. doi: 10.1002/anie.201902900. Epub Jan. 15, 2020.

Hamblett et al., Effects of drug loading on the antitumor activity of a monoclonal antibody drug conjugate. Clin Cancer Res. Oct. 15, 2004;10(20):7063-70. doi: 10.1158/1078-0432.CCR-04-0789.

Hann et al., The impact of the use of "oxo-degradable" plastic on the environment. European Commission, Directorate-General for Environment. Sep. 20, 2016. doi: 10.2779/992559. 150 pages.

Hartley et al., Photochemistry of Ketone Polymers. II. Studies of Model Compounds. Macromolecules. Sep. 1, 1968;1(5):413-7. doi: 10.1021/ma60005a009.

Hilf et al., Heterotelechelic Ring-Opening Metathesis Polymers. Macromolecules. Nov. 16, 2009;43(1):208-12. doi: 10.1021/ma902074y.

Hine et al., Structure property relationships in linear and cross-linked poly(imidonorbornenes) prepared using ring opening metathesis polymerisation (ROMP). Polymer. Nov. 2001;42(23):9413-22. doi: 10.1016/S0032-3861(01)00488-8.

Ho et al., An overview on biodegradation of polystyrene and modified polystyrene: the microbial approach. Crit Rev Biotechnol. Mar. 2018;38(2):308-320. doi: 10.1080/07388551.2017.1355293. Epub Aug. 1, 2017.

Hu et al., Thermal oxidation aging of polydicyclopentadiene and composites. Polym Comp. Jun. 21, 2016;39(5):1742-51. doi: 10.1002/pc.24125.

Huang et al., Thermal oxidation of Poly(dicyclopentadiene)-kinetic modeling of double bond consumption. Polym Degrad Stab. Aug. 2019;166:258-71. doi: 10.1016/j.polymdegradstab.2019.06.003.

Kaburagi et al., Operationally simple and efficient workup procedure for TBAF-mediated desilylation: application to halichondrin synthesis. Org Lett. Feb. 15, 2007;9(4):723-6. doi: 10.1021/ol063113h.

Kantor et al., The Mechanism of the Acid- and Base-Catalyzed Equilibration of Siloxanes. J Am Chem Soc. Oct. 1, 1954;76(20):5190-7. doi: 10.1021/ja01649a076.

Kawamoto et al., Loops versus Branch Functionality in Model Click Hydrogels. Macromolecules. Dec. 1, 2015;48(24):8980-88. doi: 10.1021/acs.macromol.5b02243.

Kessler et al., Cure kinetics of the ring-opening metathesis polymerization of dicyclopentadiene. J Polym Sci Part A: Polym Chem. May 30, 2002;40:2373-83. doi: 10.1002/pola.10317.

Kloxin et al., Covalent Adaptable Networks (CANs): A Unique Paradigm in Crosslinked Polymers. Macromolecules. Mar. 23, 2010;43(6):2643-2653. doi: 10.1021/ma902596s.

Knall et al., Inverse electron demand Diels-Alder (iEDDA)-initiated conjugation: a (high) potential click chemistry scheme. Chem Soc Rev. Jun. 21, 2013;42(12):5131-42. doi: 10.1039/c3cs60049a.

Kolb et al., Click Chemistry: Diverse Chemical Function from a Few Good Reactions. Angew Chem Int Ed Engl. Jun. 1, 2001;40(11):2004-2021. doi: 10.1002/1521-3773(20010601)40:11<2004::AID-ANIE2004>3.0.CO;2-5.

Kovacic et al., Ring-opening Metathesis Polymerisation derived poly(dicyclopentadiene) based materials. Mater Chem Front. Jun. 4, 2020;4:2235-55. doi: 10.1039/D0QM00296H.

Lambert et al., Ado-trastuzumab Emtansine (T-DM1): an antibody-drug conjugate (ADC) for HER2-positive breast cancer. J Med Chem. Aug. 28, 2014;57(16):6949-64. doi: 10.1021/jm500766w. Epub Jul. 10, 2014.

Li et al., Reprocessable Polymer Networks via Thiourethane Dynamic Chemistry: Recovery of Cross-link Density after Recycling and Proof-of-Principle Solvolysis Leading to Monomer Recovery. Macromolecules. Oct. 22, 2019;52(21):8207-16. doi: 10.1021/acs.macromol.9b01359.

Li et al., Vitrimers Designed Both to Strongly Suppress Creep and to Recover Original Cross-Link Density after Reprocessing: Quantitative Theory and Experiments. Macromolecules. Jul. 17, 2018;51(15):5537-46. doi: 10.1021/acs.macromol.8b00922.

Liu et al., Dynamic transfer auto-catalysis of epoxy vitrimers enabled by the carboxylic acid/epoxy ratio based on facilely synthesized trifunctional monoesterified cyclic anhydrides. Eur Polym J. Jul. 15, 2020;135:109881. doi: 10.1016/j.eurpolymj.2020.109881.

Liu et al., Particles without a box: brush-first synthesis of photo-degradable PEG star polymers under ambient conditions. J Vis Exp. Oct. 10, 2013;(80):50874. doi: 10.3791/50874.

Long et al., Ballistic Response of Polydicyclopentadiene vs. Epoxy Resins and Effects of Crosslinking. In: Dynamic Behavior of Materials, vol. 1. Conference Proceedings of the Society for Experimental Mechanics. Chapter 37. 2017:285-90. Springer New York LLC. doi: 10.1007/978-3-319-41132-3_37.

Luginbuhl et al., One-week glucose control via zero-order release kinetics from an injectable depot of glucagon-like peptide-1 fused to a thermosensitive biopolymer. Nat Biomed Eng. 2017;1:0078. doi: 10.1038/s41551-017-0078. Epub Jun. 5, 2017.

Lyon et al., Reducing hydrophobicity of homogeneous antibody-drug conjugates improves pharmacokinetics and therapeutic index. Nat Biotechnol. Jul. 2015;33(7):733-5. doi: 10.1038/nbt.3212. Epub Jun. 15, 2015.

(56) References Cited

OTHER PUBLICATIONS

Ma et al., Degradable thermosets based on labile bonds or linkages: A review. Prog Polym Sci. Jan. 2018;76:65-110. doi: 10.1016/j.progpolymsci.2017.07.008.

Macosko et al., A new derivation of average molecular weights of nonlinear polymers. Macromolecules. Mar.-Apr. 1976;9(2):199-206. doi: 10.1021/ma60050a003.

Manyeruke et al., Synthesis and evaluation of 3-hydroxy-3-phenylpropanoate ester-AZT conjugates as potential dual-action HIV-1 Integrase and Reverse Transcriptase inhibitors. Bioorg Med Chem. Dec. 15, 2015;23(24):7521-8. doi: 10.1016/j.bmc.2015.10.039.

Mathers et al., Functional Hyperbranched Polymers Using Ring-Opening Metathesis Polymerization of Dicyclopentadiene with Monoterpenes. Macromolecules. Feb. 10, 2009;42(5):1512-8. doi: 10.1021/ma802441t.

Mohite et al., Polydicyclopentadiene aerogels grafted with PMMA: I. Molecular and interparticle crosslinking. Soft Matter. Dec. 6, 2012;9:1516-30. doi: 10.1039/C2SM26931G.

Montarnal et al., Silica-like malleable materials from permanent organic networks. Science. Nov. 18, 2011;334(6058):965-8. doi: 10.1126/science.1212648.

Nishimura et al., Rhodium-Catalyzed Asymmetric Cycloisomerization of 1,6-Ene-ynamides. Adv Synth Catal. May 3, 2013;355(7):1374-82. doi: 10.1002/adsc.201300148.

Nishimura et al., Silyl Ether as a Robust and Thermally Stable Dynamic Covalent Motif for Malleable Polymer Design. J Am Chem Soc. Oct. 25, 2017;139(42):14881-14884. doi: 10.1021/jacs.7b08826. Epub Oct. 16, 2017.

Osthoff et al., Chemical Stress-Relaxation of Polydimethylsiloxane Elastomers. J Am Chem Soc. Sep. 1, 1954;76(18):4659-63. doi: 10.1021/ja01647a052.

Panchamoorthy et al., Targeting the human MUC1-C oncoprotein with an antibody-drug conjugate. JCI Insight. Jun. 21, 2018;3(12):e99880. doi: 10.1172/jci.insight.99880.

Parker et al., Halogen radicals contribute to photooxidation in coastal and estuarine waters. Proc Natl Acad Sci U S A. May 24, 2016;113(21):5868-73. doi: 10.1073/pnas.1602595113. Epub May 9, 2016.

Parrott et al., Tunable bifunctional silyl ether cross-linkers for the design of acid-sensitive biomaterials. J Am Chem Soc. Dec. 22, 2010;132(50):17928-32. doi: 10.1021/ja108568g. Epub Nov. 24, 2010.

Perring et al., Epoxidation of the surface of polydicyclopentadiene for the self-assembly of organic monolayers. J Mater Chem. Sep. 8, 2010;20:8679-85. doi: 10.1039/COJM01999B.

Pesek et al., Synthesis of bottlebrush copolymers based on poly(dimethylsiloxane) for surface active additives. Polymer. Aug. 19, 2016;98(19):495-504.

Post et al., A Review on the Potential and Limitations of Recyclable Thermosets for Structural Applications. Polym Rev. Oct. 8, 2019;60(2):359-88. doi: 10.1080/15583724.2019.1673406.

Price, F.P., Freezing Point Depression of Sulfuric Acid by Siloxane. J Am Chem Soc. Feb. 1, 1948;70(2):871-2. doi: 10.1021/ja01182a516.

Qi et al., A brush-polymer conjugate of exendin-4 reduces blood glucose for up to five days and eliminates poly(ethylene glycol) antigenicity. Nat Biomed Eng. 2016;1:0002. doi: 10.1038/s41551-016-0002. Epub Nov. 28, 2016.

Reddy et al., Mechanism of cyclic acetal formation. Tetrahedron. 1982;38(12):1825-6. doi: 10.1016/0040-4020(82)80257-3.

Robertson et al., Alkyl Phosphite Inhibitors for Frontal Ring-Opening Metathesis Polymerization Greatly Increase Pot Life. ACS Macro Lett. Jun. 20, 2017;6(6):609-612. doi: 10.1021/acsmacrolett.7b00270. Epub May 24, 2017.

Robertson et al., Frontal Ring-Opening Metathesis Polymerization of Exo-Dicyclopentadiene for Low Catalyst Loadings. ACS Macro Lett. May 17, 2016;5(5):593-596. doi: 10.1021/acsmacrolett.6b00227. Epub Apr. 25, 2016.

Robertson et al., Rapid energy-efficient manufacturing of polymers and composites. Nature. May 9, 2018;557:223-7. doi: 10.1038/s41586-018-0054-x.

Rohde et al., Thermoset Blends of an Epoxy Resin and Polydicyclopentadiene. Macromolecules. Nov. 30, 2016;49(23):8960-70. doi: 10.1021/acs.macromol.6b01649.

Rule et al., ROMP Reactivity of endo- and exo-Dicyclopentadiene. Macromolecule. Sep. 6, 2002;35:7878-82. doi: 10.1021/MA0209489.

Röttger et al., High-performance vitrimers from commodity thermoplastics through dioxaborolane metathesis. Science. Apr. 7, 2017;356(6333):62-65. doi: 10.1126/science.aah5281.

Saed et al., Catalytic Control of Plastic Flow in Siloxane-Based Liquid Crystalline Elastomer Networks. ACS Macro Lett. May 19, 2020;9(5):749-755. doi: 10.1021/acsmacrolett.0c00265. Epub May 6, 2020.

Saed et al., Siloxane crosslinks with dynamic bond exchange enable shape programming in liquid-crystalline elastomers. Sci Rep. Apr. 20, 2020;10(1):6609. doi: 10.1038/s41598-020-63508-4.

Saha et al., Cross-linked ROMP polymers based on odourless dicyclopentadiene derivative. Polym Chem. Apr. 14, 2016;7:3071-5. doi: 10.1039/C6PY00378H.

Sakamoto et al., Protacs: chimeric molecules that target proteins to the Skp1-Cullin-F box complex for ubiquitination and degradation. Proc Natl Acad Sci U S A. Jul. 17, 2001;98(15):8554-9. doi: 10.1073/pnas.141230798. Epub Jul. 3, 2001.

Sanda et al., Vinylcyclopropanone Cyclic Acetal-Synthesis, Polymerization, Structure of the Polymer and Mechanism of the Polymerization. Macromolecules. Feb. 1994;27(5):1099-111. doi: 10.1021/ma00083a006.

Schrock et al., Tungsten(VI) neopentylidyne complexes. Organometallics. Dec. 1, 1982;1(12):1645-51. doi: 10.1021/om00072a018.

Scott, D.W., Equilibria between Linear and Cyclic Polymers in Methylpolysiloxanes. J Am Chem Soc. Nov. 1, 1946;68(11):2294-8. doi: 10.1021/ja01215a050.

Self et al., Brønsted-Acid-Catalyzed Exchange in Polyester Dynamic Covalent Networks. ACS Macro Lett. Jul. 17, 2018;7(7):817-821. doi: 10.1021/acsmacrolett.8b00370. Epub Jun. 22, 2018.

Sheng et al., The influence of cross-linking agents on ring-opening metathesis polymerized thermosets. J Thermal Analys Calorimet. Jul. 19, 2007;89(2):459-64. doi: 10.1007/s10973-006-8468-3.

Shieh et al., A Comonomer Strategy for Triggered Degradation and Re/Upcycling of High-Performance Thermoset Plastics. Dec. 13, 2019. 18 pages. Accessed Dec. 27, 2022 from <https://chemrxiv.org/engage/chemrxiv/article-details/60c7467bee301c7f63c79516>.

Shieh et al., Cleavable comonomers enable degradable, recyclable thermoset plastics. Nature. Jul. 2020;583(7817):542-547. doi: 10.1038/s41586-020-2495-2. Epub Jul. 22, 2020. Erratum in: Nature. Sep. 2020;585(7823):E4. Supplementary Information, 55 pages.

Snyder et al., Reprocessable Acid-Degradable Polycarbonate Vitrimers. Macromolecules. Jan. 4, 2018;51(2):389-97. doi: 10.1021/acs.macromol.7b02299.

Sommazzi et al., Olefin-carbon monoxide copolymers. Prog Polym Sci. 1997;22(8):1547-605. doi: 10.1016/S0079-6700(97)00009-9.

Stockmayer et al., Theory of Molecular Size Distribution and Gel Formation in Branched Polymers II. General Cross Linking. J Chem Phys. Apr. 1944;12(4):125-31. doi: 10.1063/1.1723922.

Takahashi et al., Degradable epoxy resins prepared from diepoxide monomer with dynamic covalent disulfide linkage. Polymer. Jan. 15, 2016;82:319-26. doi: 10.1016/J.POLYMER.2015.11.057.

Takayama et al., Topographical Micropatterning of Poly(dimethylsiloxane) Using Laminar Flows of Liquids in Capillaries. Adv Mater. Apr. 18, 2001;13(8):570-4. doi: 10.1002/1521-4095(200104)13:8<570::AID-ADMA570>3.0.CO;2-B.

Tolcher et al., Randomized phase II study of BR96-doxorubicin conjugate in patients with metastatic breast cancer. J Clin Oncol. Feb. 1999;17(2):478-84. doi: 10.1200/JCO.1999.17.2.478.

Tournier et al., An engineered PET depolymerase to break down and recycle plastic bottles. Nature. Apr. 2020;580(7802):216-219. doi: 10.1038/s41586-020-2149-4. Epub Apr. 8, 2020.

(56) References Cited

OTHER PUBLICATIONS

Trail et al., Cure of xenografted human carcinomas by BR96-doxorubicin immunoconjugates. Science. Jul. 9, 1993;261(5118):212-5. doi: 10.1126/science.8327892. Erratum in: Science Feb. 25, 1994;263(5150):1076.

Tretbar et al., Direct Silyl Ether Metathesis for Vitrimers with Exceptional Thermal Stability. J Am Chem Soc. Oct. 23, 2019;141(42):16595-16599. doi: 10.1021/jacs.9b08876. Epub Oct. 14, 2019.

Veysset et al., Dynamics of supersonic microparticle impact on elastomers revealed by real-time multi-frame imaging. Sci Rep. May 9, 2016;6:25577. doi: 10.1038/srep25577. Erratum in: Sci Rep. Feb. 16, 2018;8:46944.

Wang et al., Counting loops in sidechain-crosslinked polymers from elastic solids to single-chain nanoparticles. Chem Sci. May 1, 2019;10(20):5332-5337. doi: 10.1039/c9sc01297d.

Wang et al., Counting Secondary Loops Is Required for Accurate Prediction of End-Linked Polymer Network Elasticity. ACS Macro Lett. Feb. 6, 2018;7(2):244-9. doi: 10.1021/acsmacrolett.8b00008.

Wiles et al., Polyolefins with controlled environmental degradability. Polym Degrad Stab. Jul. 2006;91(7):1581-92. doi: 10.1016/j.polymdegradstab.2005.09.010.

Winne et al., Dynamic covalent chemistry in polymer networks: a mechanistic perspective. Polym Chem. Oct. 16, 2019;10:6091-108. doi: 10.1039/C9PY01260E.

Xiao et al., Precision glycocalyx editing as a strategy for cancer immunotherapy. Proc Natl Acad Sci U S A. Sep. 13, 2016;113(37):10304-9. doi: 10.1073/pnas.1608069113. Epub Aug. 22, 2016.

Xu et al., Site-specific labeling of an anti-MUC1 antibody: probing the effects of conjugation and linker chemistry on the internalization process. RSC Adv. Jan. 15, 2019;9(4):1909-1917. doi: 10.1039/c8ra09902b.

Yan et al., The relationship among pKa, pH, and binding constants in the interactions between boronic acids and diols-it is not as simple as it appears. Tetrahedron. Nov. 29, 2004;60(49):11205-11209.

Yang et al., Curing Kinetics and Mechanical Properties of endo-Dicyclopentadiene Synthesized Using Different Grubbs' Catalysts. Ind Eng Chem Res. Jan. 28, 2014;53(8):3001-11. doi: 10.1021/ie403285q.

Yang et al., Curing study of dicyclopentadiene resin and effect of elastomer on its polymer network. Polymer. Mar. 1997;38(5):1121-30. doi: 10.1016/S0032-3861(96)00599-X.

Yang et al., Reworkable Epoxies: Thermosets with Thermally Cleavable Groups for Controlled Network Breakdown. Chem Mater. Jun. 1998; 10(6):1475-82.

Yurkovetskiy et al., A Polymer-Based Antibody-Vinca Drug Conjugate Platform: Characterization and Preclinical Efficacy. Cancer Res. Aug. 15, 2015;75(16):3365-72. doi: 10.1158/0008-5472.CAN-15-0129. Epub Jun. 25, 2015.

Yurkovetskiy et al., Fully degradable hydrophilic polyals for protein modification. Biomacromolecules. Sep.-Oct. 2005;6(5):2648-58. doi: 10.1021/bm049210k.

Zhang et al., Convergent Synthesis of Branched Metathesis Polymers with Enyne Reagents. Macromolecules. Sep. 28, 2021;54(18):8435-8442. doi: 10.1021/acs.macromol.1c01051. Epub Sep. 8, 2021.

Zhang et al., Loading dependent swelling and release properties of novel biodegradable, elastic and environmental stimuli-sensitive polyurethanes. J Control Release. Oct. 21, 2008;131(2):128-36. doi: 10.1016/j.jconrel.2008.07.026. Epub Jul. 24, 2008.

Zhang et al., Practical Synthesis of Functional Metathesis Initiators Using Enynes. Macromol. Aug. 16, 2018;51(16):6497-503. doi: 10.1021/acs.macromol.8b00866.

Zheng et al., A Surprise from 1954: Siloxane Equilibration Is a Simple, Robust, and Obvious Polymer Self-Healing Mechanism. J Am Chem Soc. Jan. 18, 2012;134(4):2024-7. doi: 10.1021/ja2113257.

Zhong et al., Quantifying the impact of molecular defects on polymer network elasticity. Science. Sep. 16, 2016;353(6305):1264-8. doi: 10.1126/science.aag0184.

Zych et al., Polyethylene vitrimers via silyl ether exchange reaction. Polymer. Jun. 11, 2020;99:112567. doi: 10.1016/j.polymer.2020.122567.

\* cited by examiner

Ring Opening Metathesis Polymerization

Kiessling and coworkers

1998

α-D-methyl manno-
pyranoside(αMeMan)
2

α-D-methyl gluco-
pyranoside(αMeGlc)
3

α-mannose polymer
n = 10, 25, and 143
4 a,b,c

α-galactose polymer
5

Kiessling (2013)

Does not degrade above pH 4.5.

Kilbinger (2006)

Forms block copolymers, leaving polynorbornene fragment intact

Hawker, Gutekunst (2015)

Requires multi-step synthesis of new monomer for each polymer

Traditional ROMP Polymers

This application

Exo

Endo

6 Endo

Acetal XL

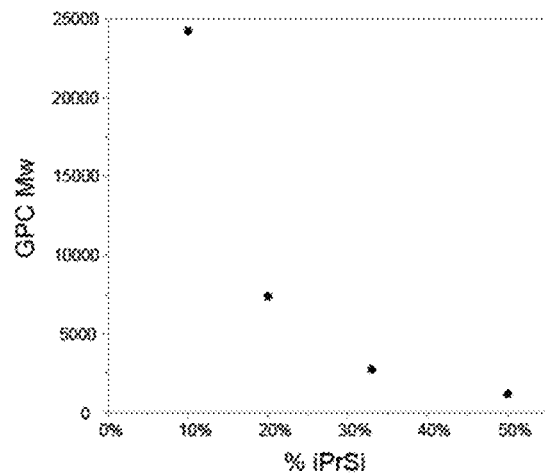
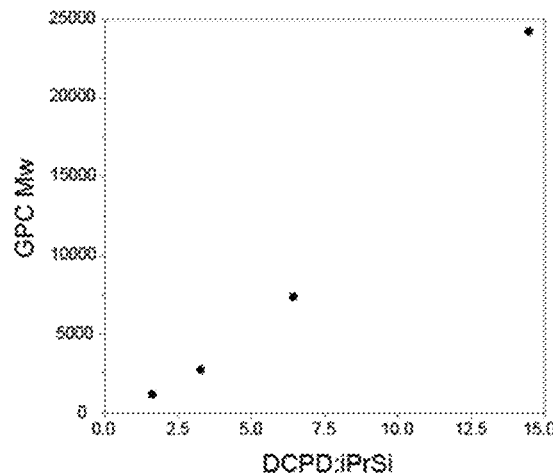
FIG. 81A
FIG. 81B
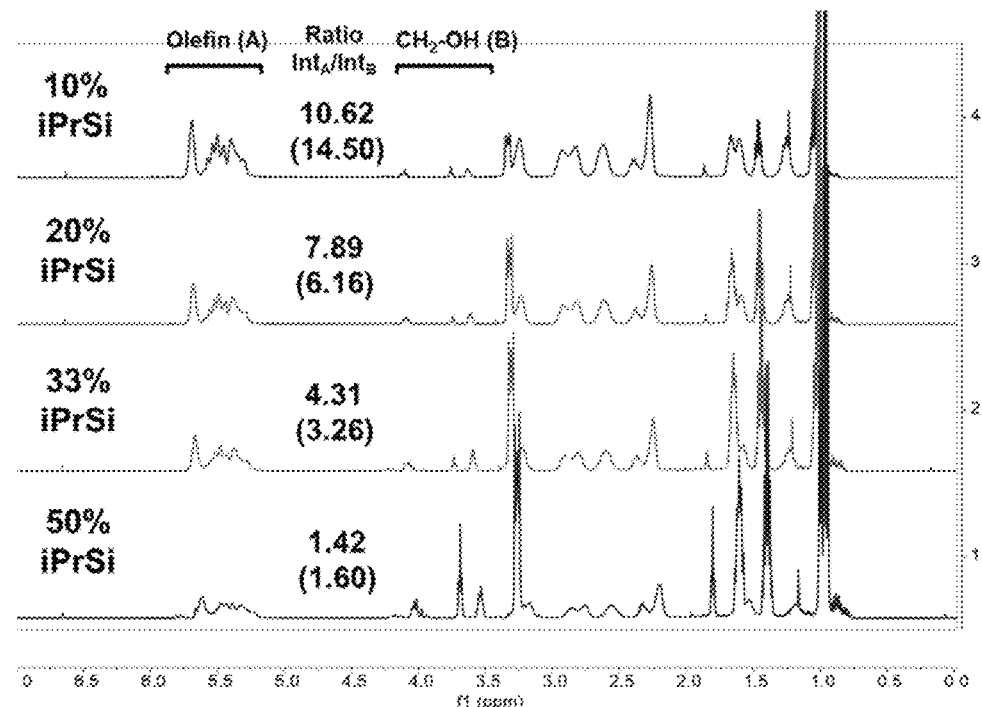
FIG. 82

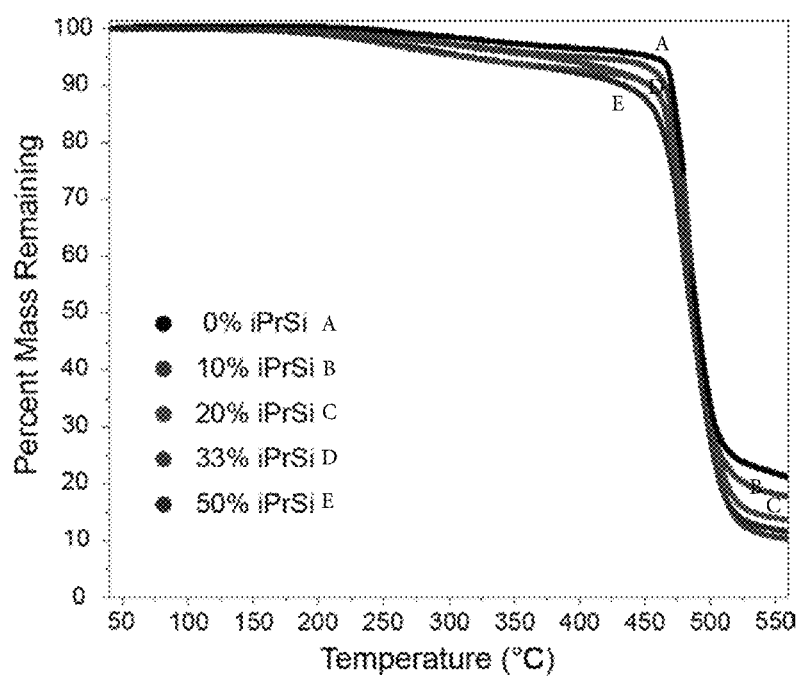
FIG. 98
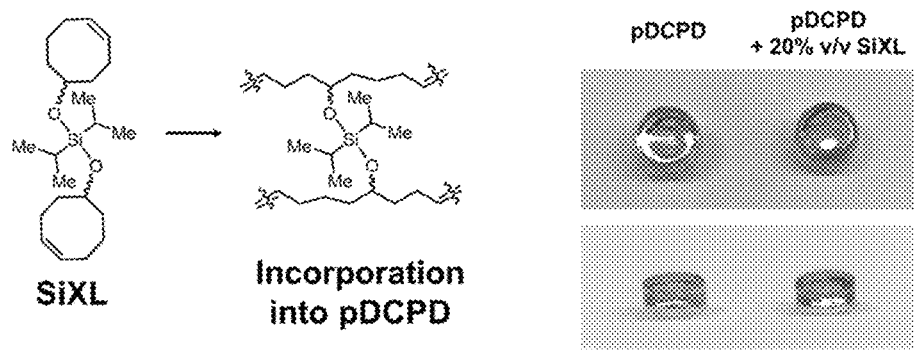
FIG. 99A
FIG. 99B

Initial     12 Hours

Initial     15 Minutes     60 Minutes     12 Hours

DEGRADABLE POLYMERS OF A CYCLIC SILYL ETHER AND USES THEREOF

RELATED APPLICATIONS

This application is a division of U.S. Application, U.S. Ser. No. 16/542,824, filed Aug. 16, 2019, which claims priority under 35 U.S.C. § 119(e) to U.S. Provisional Application, U.S. Ser. No. 62/765,142, filed Aug. 17, 2018; U.S. Provisional Application, U.S. Ser. No. 62/872,679, filed July 2019; and U.S. Provisional Application, U.S. Ser. No. 62/872,696, filed Jul. 10, 2019, each of which is incorporated herein by reference.

GOVERNMENT SUPPORT

This invention was made with Government support under Grant No. R01 CA220468 awarded by the National Institutes of Health. The Government has certain rights in the invention.

BACKGROUND OF THE INVENTION

Bottlebrush polymers have found widespread applications in fields ranging from drug delivery and molecular imaging to novel materials and stimuli responsive networks (*ACS Macro Letters* 2012, 1, 1146. *Progress in Polymer Science* 2008, 33, 759. *Progress in Polymer Science* 2010, 35, 24). Graft-through ring-opening metathesis polymerization (ROMP) offers distinct advantages over other bottlebrush synthesis methods (*Journal of the American Chemical Society* 2009, 131, 18525. *Macromolecules* 2009, 42, 3761). The fast-initiating Grubb's $3^{rd}$ generation catalyst has been shown to sustain propagation of polymer chain reactions with exceptionally high tolerance towards a wide range of sterically-hindered multivalent macromonomers, reaching high degrees of polymerization and low dispersity values, even at low millimolar concentrations (*Chemical Society Reviews* 2015, 44, 2405. *Angewandte Chemie International Edition* 2012, 51, 11246). Furthermore, it is possible to control composition, morphology, and size of final macromolecules, allowing the preparation of remarkable polymeric architectures, such as bottlebrush polymers and star polymers (*Angewandte Chemie International Edition* 2012, 51, 11246. *Journal of the American Chemical Society* 2016, 138, 12494. *Journal of the American Chemical Society* 2016, 138, 11501. *Chemical Reviews* 2016, 116, 6743. *Journal of the American Chemical Society* 2014, 136, 5896). Due to the high packing density of their side-chains, the backbones of bottlebrush polymers are very rigid and adopt extended morphologies with minimal side-chain entanglement (*Chemical Society Reviews* 2015, 44, 2405). Recently, self-assembly behaviors of bottlebrush block copolymers (BBCPs) have become an active area of research (*Chemical Society Reviews* 2015, 44, 2405. *Proceedings of the National Academy of Sciences* 2012, 109, 14332).

Polymeric star nanoarchitectures, on the other hand, offer several different valuable features, such as tunable nanoscale sizes and shapes that mimic globular biomacromolecules, allowing for extended blood circulation and efficient biodistribution and/or tumor accumulation (*Accounts of Chemical Research* 2009, 42, 1141. *Nat Nano* 2007, 2, 751. *European Journal of Pharmaceutics and Biopharmaceutics* 2009, 71, 409). These properties make star polymers particularly well-suited for biological applications (*Chemical Reviews* 2016, 116, 6743).

The development of bottlebrush and star polymeric structures (e.g., brush-arm star polymers (BASPs) (see FIG. 2)) is a growing field of research as these polymeric structures have broad applications. Previous work has reported preparation of multi-component MMs that can be used in graft-through ROMP; these MMs contain side-chains with a multitude of functions and properties, which can either be on different MMs, or branching off the same MM (*Journal of the American Chemical Society* 2016, 138, 11501. *Journal of the American Chemical Society* 2014, 136, 5896. *Proceedings of the National Academy of Sciences* 2012, 109, 14332. *Nat Nano* 2007, 2, 751. *ACS Macro Letters* 2014, 3, 854. *Nat Rev Drug Discov* 2003, 2, 347). In particular, the branched platform consists of a ROMP-compatible norbornene group on a molecule that also contains two orthogonally functionalizable sites: an alkyne, for which copper (I)-catalyzed alkyne-azide cycloaddition (CuAAC) can be applied (*Coordination Chemistry Reviews* 2011, 255, 2933. *Chemical Society Reviews* 2010, 39, 1302. *Science* 2013, 340, 457), and a carboxylic acid group, compatible with carbodiimide coupling chemistry (*Tetrahedron* 2004, 60, 2447. *Chemical Society Reviews* 2009, 38, 606. *Organic Process Research & Development* 2016, 20, 140. *Chemical Reviews* 2011, 111, 6557. *Angewandte Chemie International Edition* 978, 17, 522), both of which are efficient, and known modes of conjugations. The side-chains can be functionalized with two dissimilar polymers that self-assemble into various morphologies or a polymer chain containing an agent (e.g., a therapeutic agent (e.g., drug), a diagnostic agent (e.g., imaging agent), a prophylactic agent, or a biological ligand); resulting polymers are reported to demonstrate interesting characteristics across multiple applications, including self-assembly, drug delivery, and molecular imaging (*Journal of the American Chemical Society* 2016, 138, 12494. *Journal of the American Chemical Society* 2016, 138, 11501. *Journal of the American Chemical Society* 2014, 136, 5896. *Photochemistry and Photobiology* 2014, 90, 380. *Journal of the American Chemical Society* 2012, 134, 16337. *Nature Communications* 2014, 5, 5460).

Even though ROMP has found utility in many applications (*Journal of the American Chemical Society*, 1998, 120, 10579; *Journal of the American Chemical Society*, 2014, 136, 15422), one disadvantage of previous polymers synthesized from ROMP is their poor degradability, thus limiting their utility in certain fields. A reported polymer synthesized via ROMP was degradable only at a pH of 4.5 or less (*Angewandte Chemie International Edition*, 2013, 52, 5061). Another example required multi-step syntheses for each monomer in order to generate a polymer (*Journal of the American Chemical Society*, 2015, 137, 8038). Therefore, there is a need for degradable brush polymers and degradable BASPs.

Tough and highly crosslinked materials are typically associated with a lack of degradability. As an example, poly-dicyclopentadiene (pDCPD) is a produced on industrial scale and valued for its high impact resistance and compatibility with injection molding processes. Owing to its crosslinked all-carbon backbone, however, these materials are considered non degradable and thus cannot be reused or remolded after formation. Degradable versions of this material, which maintain all of their desirable mechanical properties but enable mild strategies to break down the material, may open the door to myriad applications for both this material and its degraded fragments.

SUMMARY OF THE INVENTION

Described herein, in one aspect, are cyclic silyl ethers of the formula:

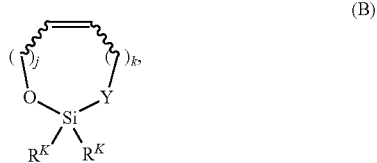

and salts thereof. The cyclic silyl ethers may be useful as monomers for preparing polymers.

In another aspect, described herein are polymers prepared by polymerizing a cyclic silyl ether. In certain embodiments, the polymers are homopolymers. In certain embodiments, the polymers are copolymers. In certain embodiments, the polymers are prepared by polymerizing a cyclic silyl ether and one or more additional monomers. The additional monomers are different from the cyclic silyl ether. The polymers may be degradable (e.g., biodegradable). In certain embodiments, one or more O—Si bonds of the polymers are the degradation sites.

Ring opening metathesis polymerization has provided access to new polymers with relative ease. Polymers derived from ROMP have found wide utility, notably their use for the generation of brush polymers (brushes) and BASPs. These polymers have been employed in vast applications including self-assembly, drug delivery, and molecular imaging. Further elaboration into various applications is limited by the overall poor degradability of polymers generated from ROMP.

The present disclosure provides polymers (e.g., brush polymers and brush-arm star polymers (BASPs)). The provided polymers are copolymers of one or more instances of a first monomer, which comprises a norbornene moiety; and a second monomer, which comprises a cyclic silyl ether moiety. Ring opening metathesis polymerization (ROMP) may be employed, in the presence of a metathesis catalyst, to prepare the polymers. The Si—O bonds in the backbone of the polymers may be cleaved under a first condition (e.g., hydrolysis). Therefore, under certain conditions (e.g., the first condition), the polymers may be degraded.

One or more instances of the first monomer may independently comprise one or more instances of a click-chemistry handle (e.g., —C≡CH). The polymers, which also comprise the one or more instances of the click-chemistry handle, may be useful for conjugating with one or more instances of—(a linker comprising a complementary click-chemistry handle (e.g., —N₃))—(an agent). In certain embodiments, at least one instance of the agent is a pharmaceutical agent. In certain embodiments, at least one instance of the agent is a cosmetic agent or nutraceutical agent. The linker comprising the complementary click-chemistry handle may also be cleavable under a second condition (e.g., ultraviolet irradiation, hydrolysis, reduction, oxidation, or contacting with an enzyme). In certain embodiments, the first and second conditions are the same. In certain embodiments, the first and second conditions are different from each other. Therefore, under certain conditions (e.g., a combination of the first and second conditions), the polymers may be degraded and may release the agent. Therefore, the polymers may be useful for delivering the agent. The increased degradability of the polymers may allow for improved biological applicability, such as higher bioavailability, higher tolerability, less toxicity, higher absorption, larger distribution, faster metabolism, faster excretion, higher subject compliance, larger therapeutic window, higher potency, or higher efficacy, or a combination thereof.

An instance of the first monomer may comprise one or more instances of the agent. The loading of the agent may be increased when an instance of the first monomer comprises two or more instances of the agent. In certain embodiments, all instances of the agent included in an instance of the first monomer are the same. In certain embodiments, at least two instances of the agent included in an instance of the first monomer are different from each other.

Each two instances of the first monomer may be the same or different. In certain embodiments, at least two instances of the first monomer are different (e.g., different at least in that at least one instance of the agent included in one instance of the first monomer is different from at least one instance of the agent included in the other instance of the first monomer. Therefore, the polymers may be useful for delivering two or more types of pharmaceutical agents. The linkers attaching the two or more types of pharmaceutical agents to the backbone of the polymers may be different. Therefore, such linkers may be cleaved at different rates under different conditions. Therefore, the polymers may be useful for controlled delivery of two or more types of pharmaceutical agents.

Also provided in the present disclosure are compositions (e.g., pharmaceutical compositions), kits, methods of preparation, and methods of use, each of which involve the polymers.

In one aspect, the present disclosure provides a brush polymer prepared by a method comprising polymerizing: (1) one or more instances of a first monomer, wherein each instance of the first monomer is independently of Formula (A1) or (A2) or a salt thereof; and (2) a second monomer, where the second monomer is of Formula (B) or a salt thereof, in the presence of a metathesis catalyst.

In another aspect, the present disclosure provides a method of preparing a brush polymer, the method comprises polymerizing one or more instances of the first monomer, and the second monomer in the presence of a metathesis catalyst.

In another aspect, the present disclosure provides a BASP prepared by a method comprising crosslinking one or more instances of the brush polymer in the presence of: (1) a crosslinker of Formula (C) or a salt thereof, and (2) a metathesis catalyst.

In another aspect, the present disclosure provides a method of preparing a BASP, the method comprises crosslinking one or more instances of the brush polymer in the presence of a crosslinker and a metathesis catalyst.

In another aspect, the present disclosure provides a pharmaceutical composition comprising: a brush polymer, or a BASP; and optionally a pharmaceutically acceptable excipient.

In another aspect, the present disclosure provides a kit comprising: a brush polymer, a BASP, or a pharmaceutical composition; and instructions for using the brush polymer, BASP, or pharmaceutical composition.

In another aspect, the present disclosure provides a method of delivering an agent to a subject in need thereof, the method comprising administering to the subject in need thereof a brush polymer, a BASP, or a pharmaceutical composition, wherein: each of the brush polymer and BASP comprises at least one instance of M; and at least one instance of M is an agent.

In another aspect, the present disclosure provides a method of delivering an agent to a cell, the method comprising contacting the cell with a brush polymer, a BASP, or a pharmaceutical composition, wherein: each of the brush polymer and BASP comprises at least one instance of M; and at least one instance of M is an agent.

In another aspect, the present disclosure provides a method of treating a disease in a subject in need thereof, the method comprising administering to the subject in need thereof a therapeutically effective amount of a brush polymer, a BASP, or a pharmaceutical composition, wherein each of the brush polymer and BASP comprises at least one instance of the agent, wherein: each of the brush polymer and BASP comprises at least one instance of M; and at least one instance of M is a therapeutic agent.

In another aspect, the present disclosure provides a method of preventing a disease in a subject in need thereof, the method comprising administering to the subject in need thereof a prophylactically effective amount of a brush polymer, a BASP, or a pharmaceutical composition, wherein each of the brush polymer and BASP comprises at least one instance of the agent, wherein: each of the brush polymer and BASP comprises at least one instance of M; and at least one instance of M is a prophylactic agent.

In another aspect, the present disclosure provides a method of diagnosing a disease in a subject in need thereof, the method comprising administering to the subject in need thereof a diagnostically effective amount of a brush polymer, a BASP, or a pharmaceutical composition, wherein each of the brush polymer and BASP comprises at least one instance of the agent, wherein: each of the brush polymer and BASP comprises at least one instance of M; and at least one instance of M is a diagnostic agent.

Also described herein is a strategy for generating degradable pDCPD through copolymerization with small amounts of a degradable monomer. Only a small amount of co-monomer is required to render pDCPD degradable, opening the door to the commercial implementation of this approach for generating tough yet degradable materials. Moreover, this degradable monomer approach was systemically utilized to characterize the network properties of this material in depth, enabling new insight to the network topology of this industrially important polymer. The discovery of a small molecule monomer with clevable moieties (e.g., silyl ethers) that copolymerize efficiently under ring-opening metathesis polymerization (ROMP) with the dicyclopentadiene monomer enabled this work, by incorporating functionalities which can be cleaved (e.g., by reaction with fluoride or through hydrolysis). Degradation of these materials may open the door to new ways to broaden the understanding of these important materials and open the door to new applications enabled by newly endowed recyclability and processability.

Ring opening metathesis polymerization has provided access to new polymers with relative ease. Polymers derived from ROMP have found wide utility, notably their use for the generation of polymers. These polymers have been employed in vast applications including self-assembly, drug delivery, molecular imaging, use as bulk materials, and in the manfacture of goods and resins. Further elaboration into various applications is limited by the overall poor degradability of polymers generated from ROMP.

The present disclosure provides polymers (e.g., polymers comprising dicyclopentadiene and derivatives thereof). The provided polymers are copolymers of one or more instances of a first monomer, which comprises a dicyclopentadiene moiety; and a second monomer, which comprises a cyclic silyl ether or. Ring opening metathesis polymerization (ROMP) may be employed, in the presence of a metathesis catalyst, to prepare the polymers. The Si—O bonds in the backbone of the polymers may be cleaved under a first condition (e.g., hydrolysis). Therefore, under certain conditions, the polymers may be degraded.

Also provided in the present disclosure are compositions, kits, methods of preparation, and methods of use, each of which involve the polymers.

In one aspect, the present disclosure provides a polymer prepared by a method comprising polymerizing: (1) one or more instances of a first monomer, wherein each instance of the first monomer is independently of Formula (A1) or (A2) or a salt thereof; and (2) a second monomer, where the second monomer is of Formula (B) or a salt thereof, in the presence of a metathesis catalyst.

In another aspect, the present disclosure provides a method of preparing a polymer, the method comprises polymerizing one or more instances of the first monomer, and the second monomer in the presence of a metathesis catalyst.

In another aspect, the present disclosure provides a kit comprising: a polymer or a composition; and instructions for using the polymer or composition. The details of certain embodiments of the invention are set forth in the Detailed Description of Certain Embodiments, as described below. Other features, objects, and advantages of the invention will be apparent from the Definitions, Figures, Examples, Clauses, and Claims.

BRIEF DESCRIPTION OF THE DRAWINGS

FIG. 42A shows a resulting chromatogram from GPC of iPrBrush as after 0 days, 2 days, 7 days, 14 days, and 35 days at pH 6.5, and after addition of HCl.

Figure 42A:
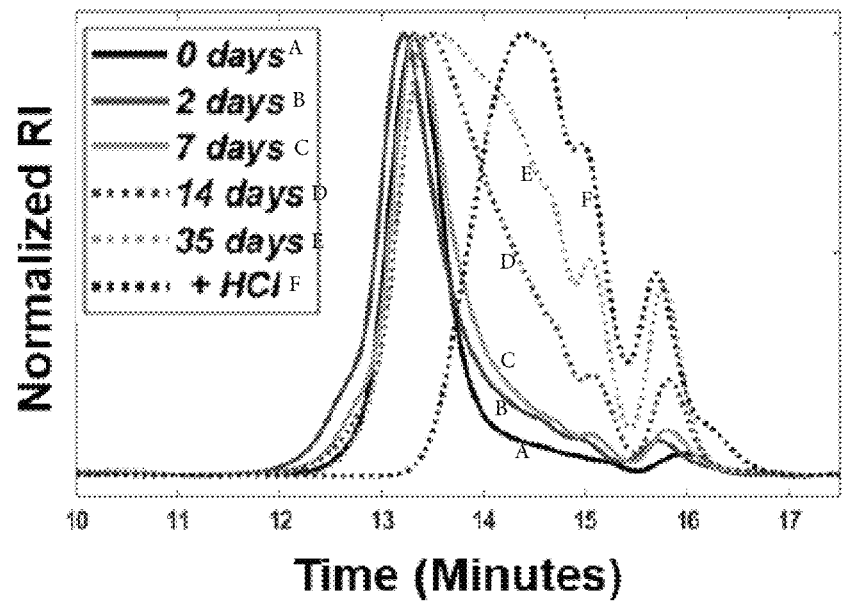
Figure 42B:
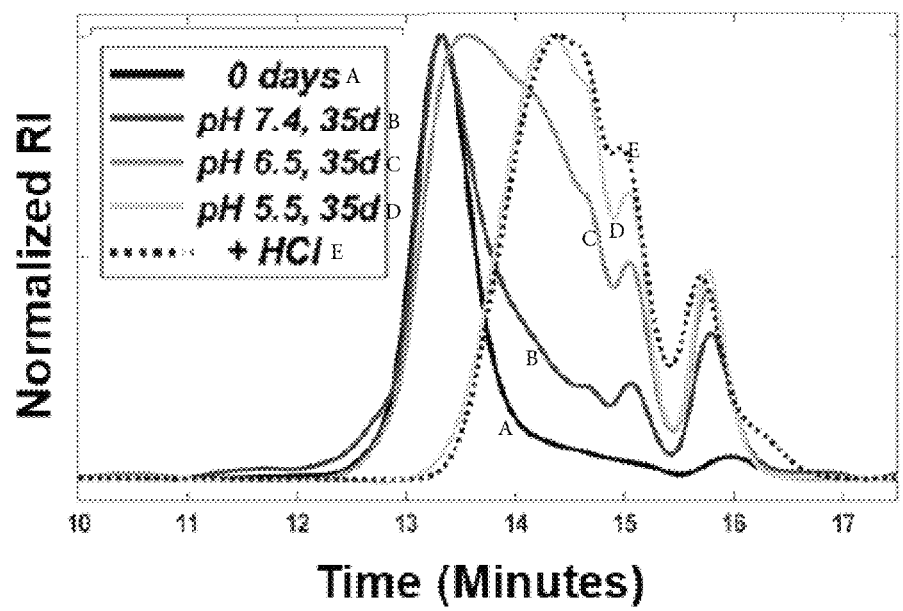

FIG. 42B shows a resulting chromatogram from GPC of iPrBrush after 0 days, after 35 days at pH 7.4, after 35 days at pH 6.5, after 35 days at pH 5.5, and after addition of HCl.

Figure 43A:
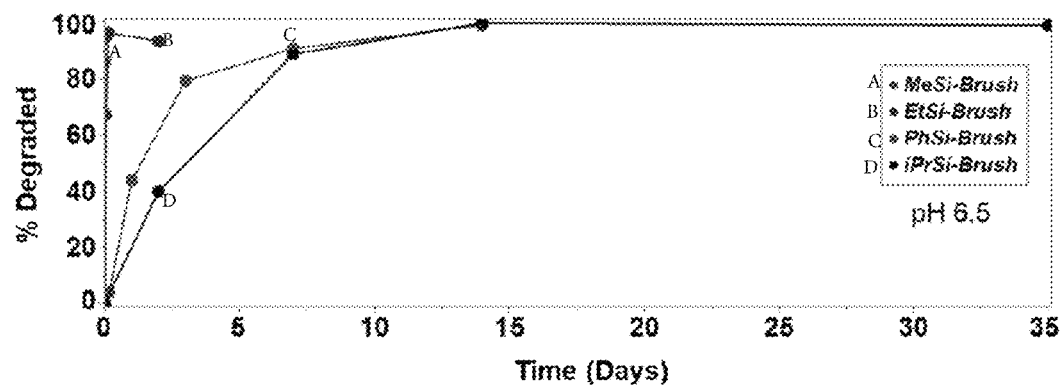

FIG. 43A shows a graph of time versus percent degraded of MeBrush, EtBrush, iPrBrush, and PhBrush to demonstrate the monomer-dependent degradation. Degradation is shown as a function of time for copolymers incubated at pH 6.5. The rate of degradation varies with the comonomer silyl ether substituents.

Figure 43B:
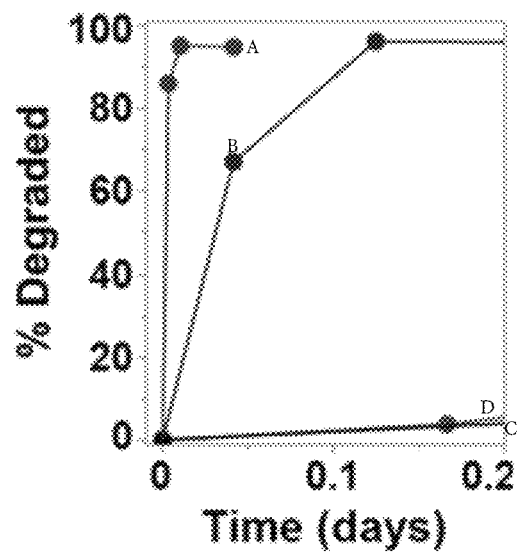

FIG. 43B shows a zoomed in region (0-0.2 days) of FIG. 43A.

Figure 44A:
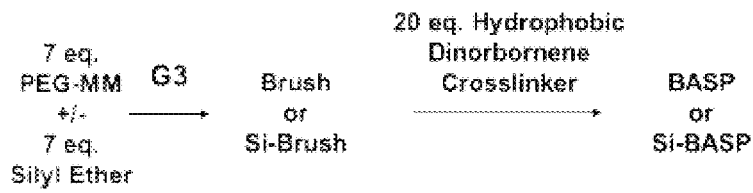

FIG. 44A shows a scheme of the incorporation of brushes (e.g., Brush, MeBrush, EtBrush, iPrBrush, PhBrush) into BASPs.

Figure 44B:
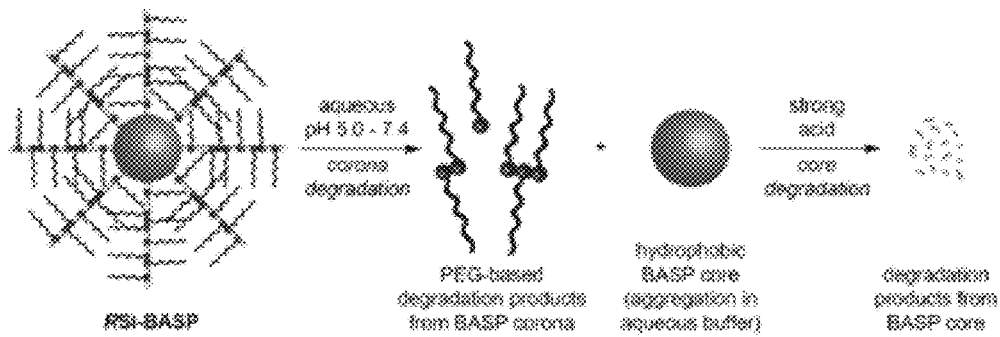

FIG. 44B shows a scheme of the degradation of BASPs via corona degradation followed by core degradation. The synthesis of BASPs via crosslinking of short (DP=7) PEG-based bottlebrush (co)polymers with AcXL is shown. When a silyl ether monomer is combined with PEG-MINI in the first step, the resulting BASPs (RSi-BASP) have silyl-ether linkages with substituents R in the backbones of their bottlebrush arms. In addition, they have acetal cores that can be independently degraded due to their different susceptibility to acid.

Figure 44C:
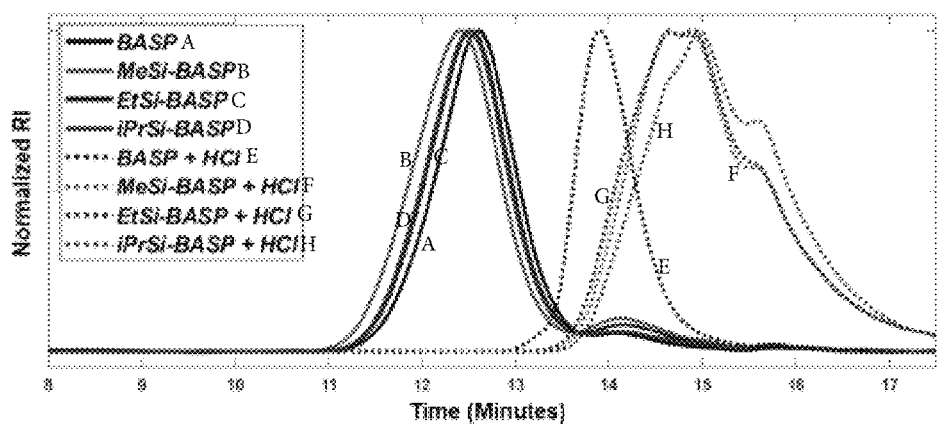

FIG. 44C shows a resulting chromatogram from GPC of BASPs (made from either Brush, MeBrush, iPrBrush, or EtBrush) and after degradation with HCl. GPC traces showing the successful formation of BASPs without silyl ethers (BASP, black curve) or with (RSi-BASP, all other solid curves) are shown. Forcing acidic hydrolysis only cleaves the core of the BASP (lacking silyl ethers) re-generating the DP=7 bottlebrush arms (black dashed line). In contrast, RSi-BASPs undergo both core and arm degradation yielding significantly smaller fragments. *indicates residual bottlebrush (left) and PEG-MM (right) following the ROMP reaction.

Figure 45A:
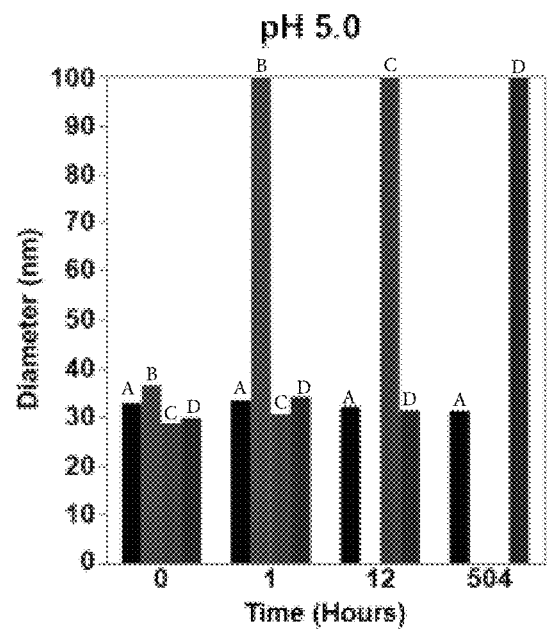

FIG. 45A shows the time dependence of nanoparticle aggregation. The legend is the same as the legend in FIG. 45B. Hydrodynamic diameters of MeSi-BASP, EtSi-BASP, and iPrSi-BASP as a function of time and pH as measured by dynamic light scattering. Aggregation of the RSi-BASPs is indicative of degradation of the silyl-ether bottlebrush shell, which exposes the hydrophobic acetal-based core that is not degradable under these mild conditions. As for the bottlebrush polymers described above, the silyl ether substituents affect the extent of degradation as a function of time at a given pH.

Figure 45B:
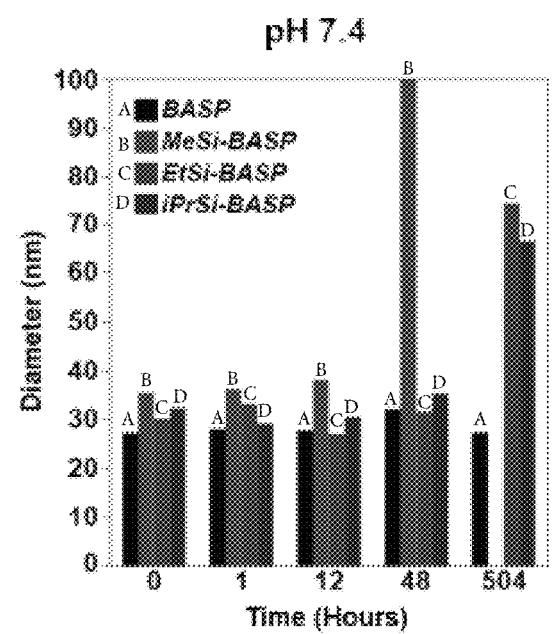

FIG. 45B shows the time dependence of nanoparticle aggregation.

Figure 46A:
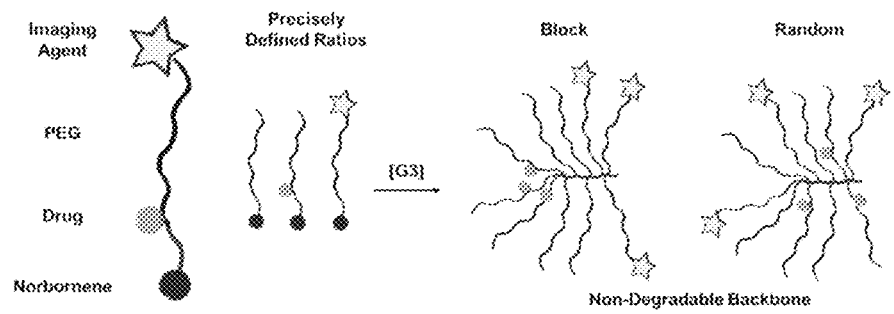

FIG. 46A shows a scheme of the incorporation of imaging agents and drugs into a brush via a bottom-up approach to drug delivery vehicles.

Figure 46B:
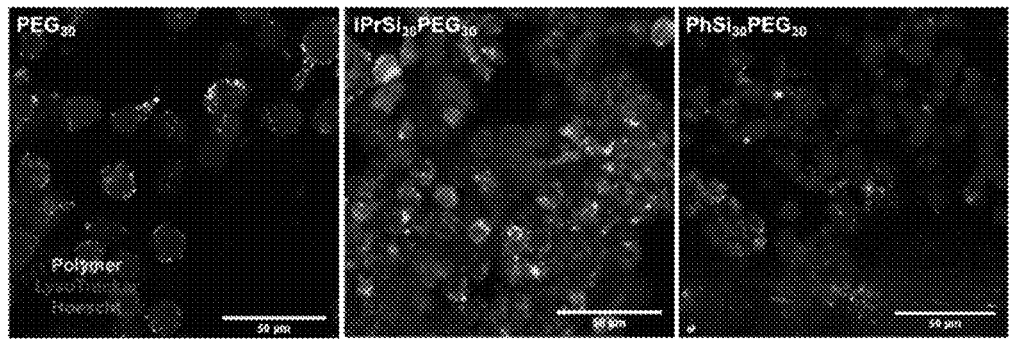

FIG. 46B shows images demonstrating that incorporation of iPr silyl or Ph silyl into the backbone of the brush showed minimal effect in vitro.

Figure 46C:
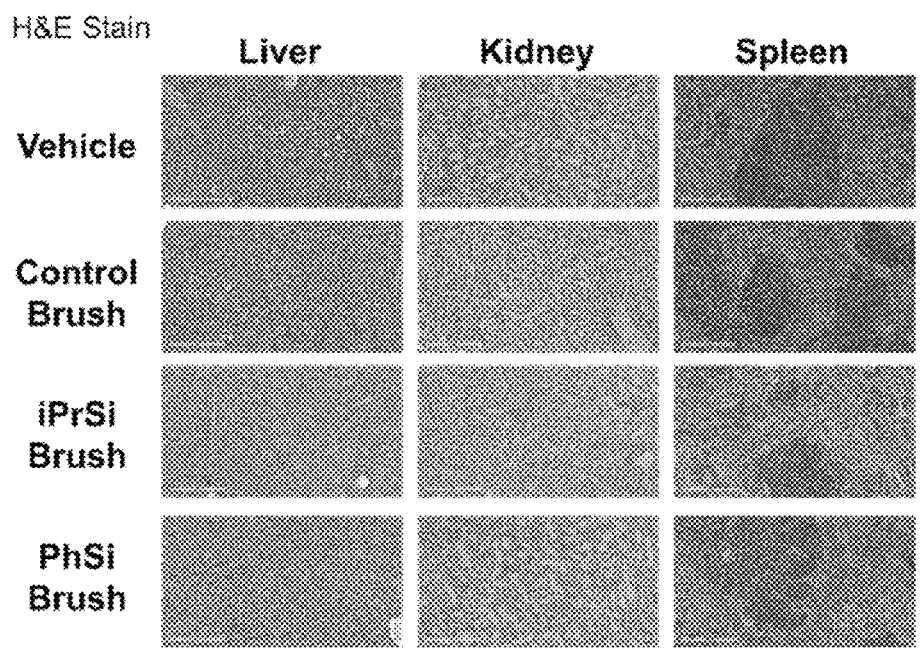

FIG. 46C shows the results of an H&E stain with a vehicle as a control, the brush without any silyl ether in the backbone, iPrBrush, and PhBrush in each of liver, kidney, and spleen tissues, demonstrating that silyl ether substitution in the backbone showed minimal toxicity in vivo.

Figure 46D:
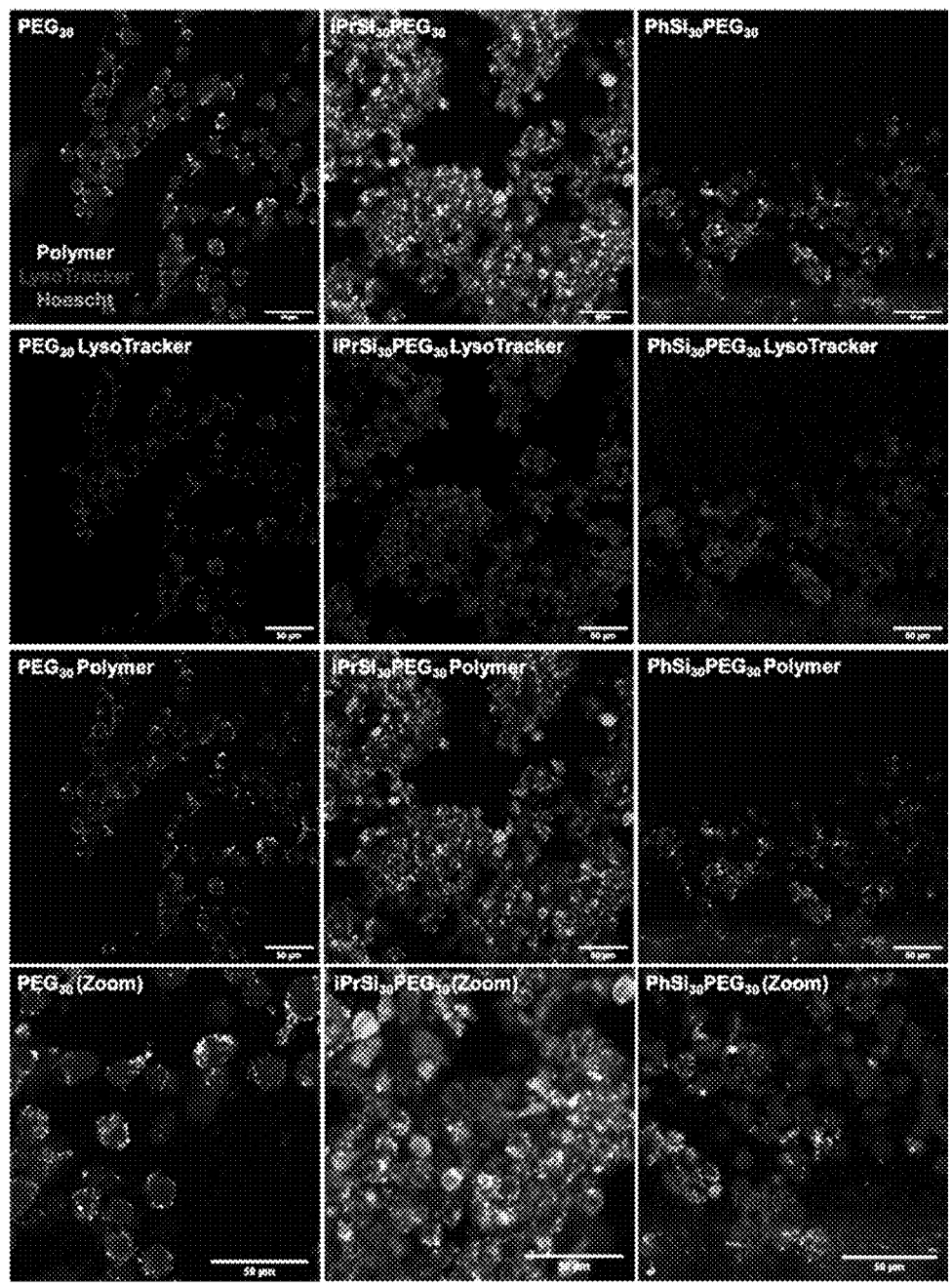

FIG. 46D shows observation of cell uptake of bottlebrush polymers in OVCAR8 cells by confocal microscopy. Cells were incubated with bottlebrush polymers, then stained with LysoTracker Deep Red and Hoescht 33342. The punctate fluorescence signal from the polymer, which colocalizes with the LysoTracker stain, suggests localization of all three polymers within acidic compartments after uptake.

Figure 47:
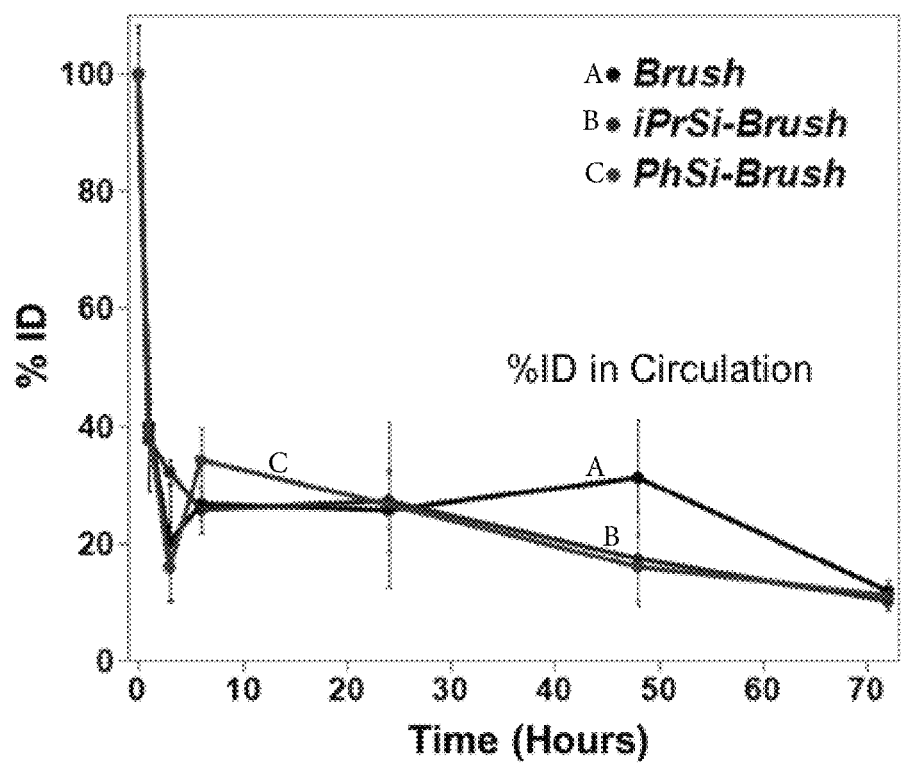

FIG. 47 shows a graph of percentage of infused dose over time for non-silyl containing brush (Brush), iPrBrush (iPrSi-Brush), and PhBrush (PhSi-Brush) demonstrating that silyl ether substitution maintained pharmacokinetics. 72 h pharmacokinetics (PK) are shown as determined by fluorescence analysis of blood samples. No significant differences between the silyl ether-containing bottlebrush copolymers and their homopolymer analogue are observed.

Figure 48B:
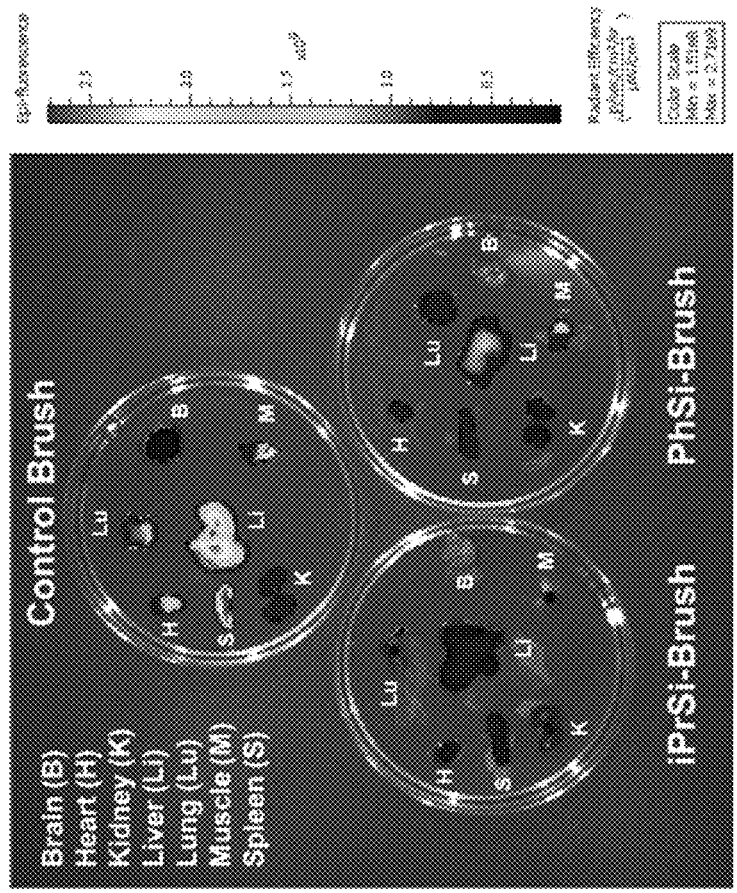
Figure 48A:
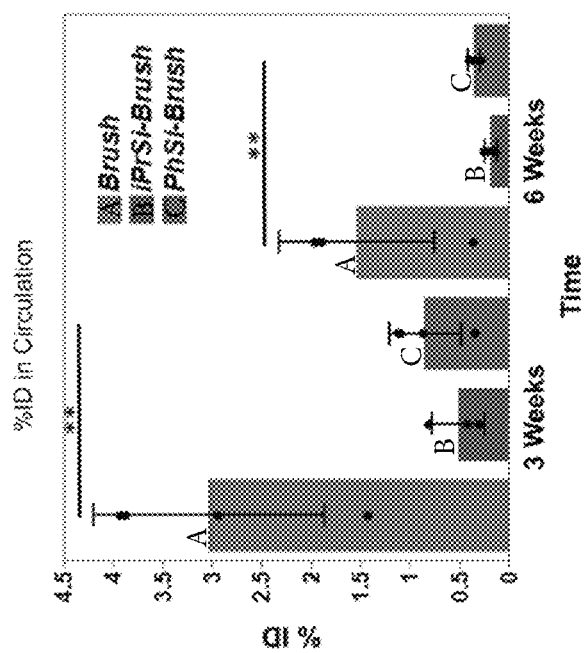

FIG. 48A shows a graph of percentage of infused dose at 3 and 6 weeks for non-silyl containing brush, iPrBrush, and PhBrush demonstrating that silyl ether subsitution in the brush promoted clearance of the brush. In contrast to short-term PK, significantly lower amounts of the silyl ether-containing bottlebrush copolymers are present in circulation after 3 weeks and 6 weeks. Statistical significance was assessed by a two-tailed t-test. Error bars represent the standard deviation for n=3 mice. **–p<0.01.

FIG. 48B shows residual fluorescence after 6 weeks in brain, heart, kidney, liver, lung, muscle, and spleen, demonstrating that silyl ether substitution in the brush promoted clearance of the brush.

Figure 48C:
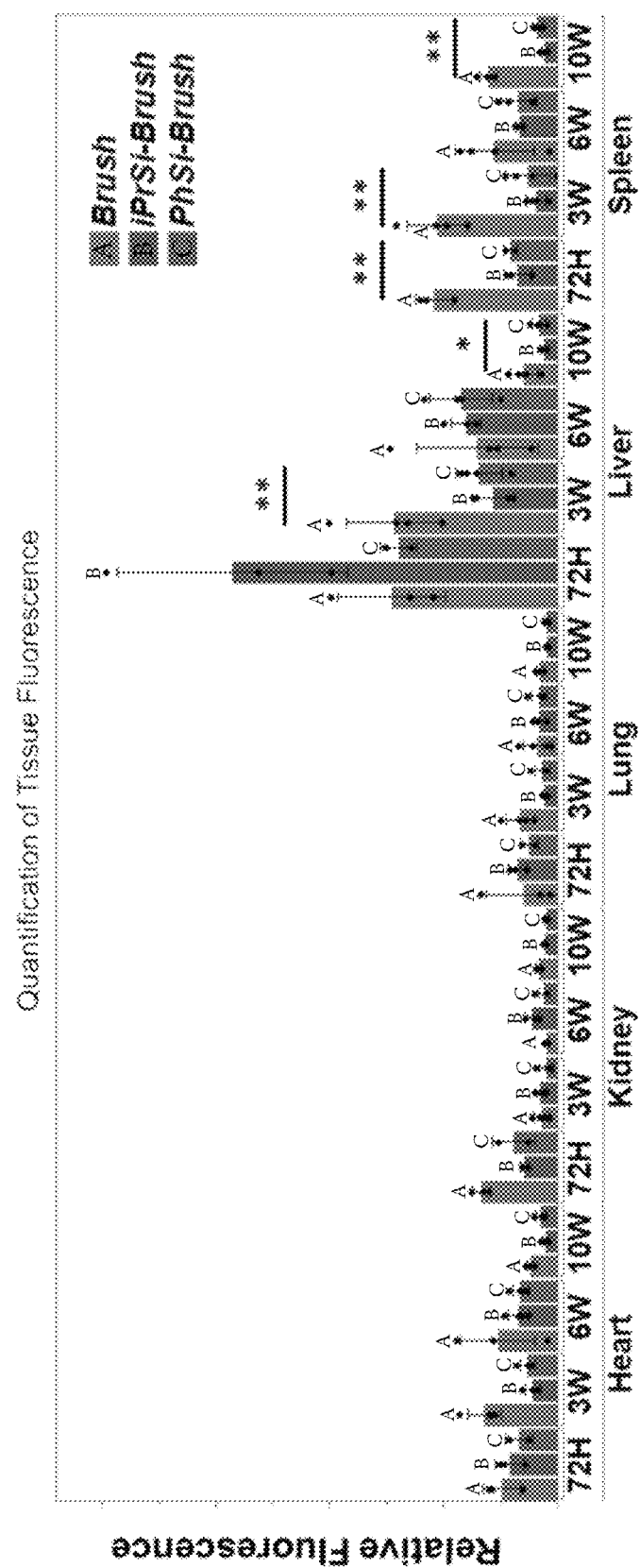

FIG. 48C shows the quantification of tissue fluoresence for non-silyl containing brush, iPrBrush, and PhBrush in heart, kidney, lung, liver, and spleen at 72 hours, 3 weeks, 6 weeks, and 10 weeks, demonstrating that silyl ether substitution in the brush promoted clearance of the brush. Concentrations of bottlebrush polymers with and without silyl ether comonomers in various organs as a function of time from three days to ten weeks after injection are shown. The silyl ether-containing bottlebrush polymers showed a lower signal in the liver and especially the spleen over the course of the experiment. Statistical significance was assessed by a two-tailed t-test. Error bars represent the standard deviation for n=3-4 mice. *–p<0.05, **–p<0.01.

Figure 48D:
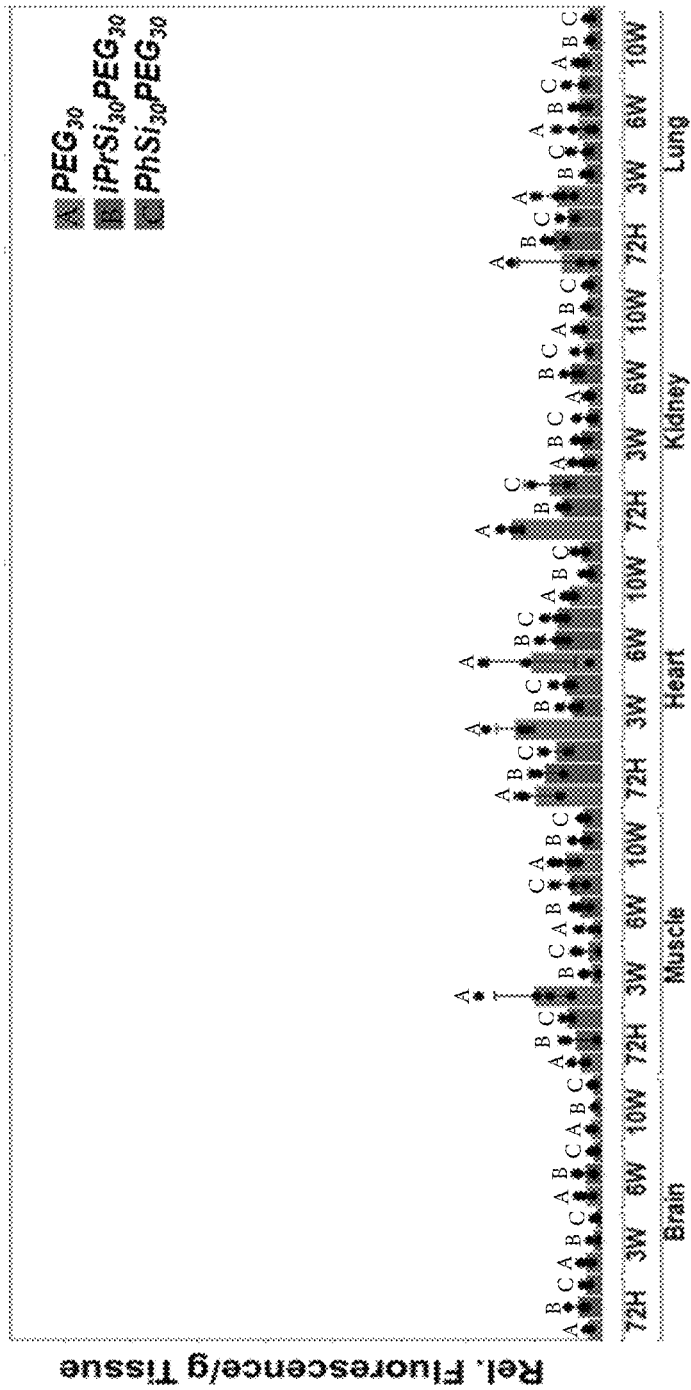

FIG. 48D shows additional data on the concentrations of bottlebrush polymers with or without silyl ether co-monomers in the brain and muscle. Minimal fluorescence signal is observed in all samples, suggesting little polymer accumulation at these sites.

Figure 49A:
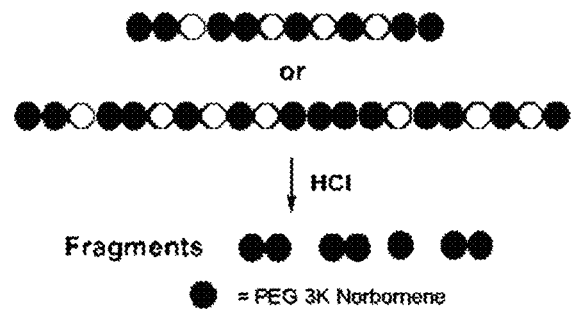

FIG. 49A shows a schematic showing polymers prepared by polymerizing iPrSi and PEG 3K norbornene

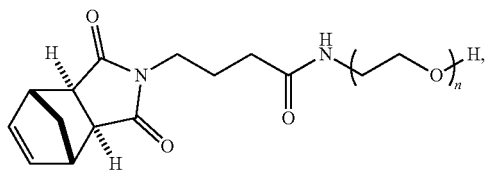

wherein the weight average molecular weight of

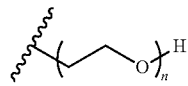

is about 3 kDa), and a schematic showing the degradation of the polymers by HCl.

Figure 49B:
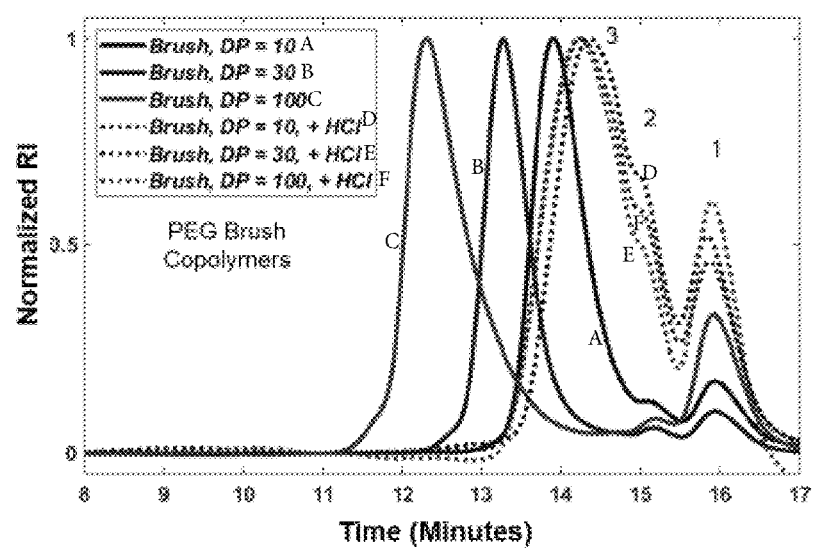

FIG. 49B shows a resulting chromatogram from GPC of copolymers described in FIG. 49A wherein DP was 10, 30, or 100 before and after treatment with HCl, demonstrating the degradation of the polymers into fragments. The resulting fragments after acidic hydrolysis are independent of polymer length. The star corresponds to unreacted monomer in the GPC traces prior to degradation.

Figure 49C:
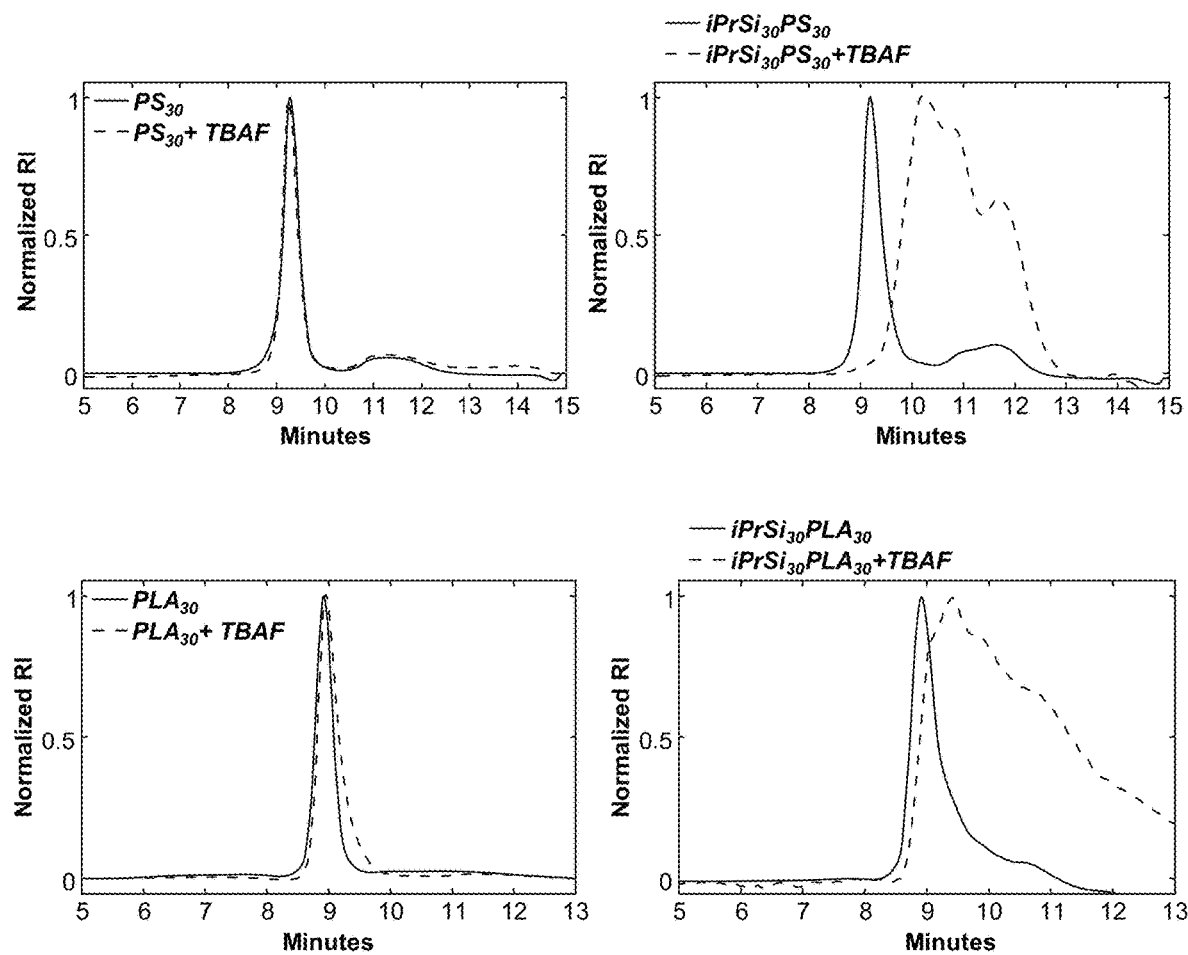

FIG. 49C shows GPC traces of PS or PLA bottlebrush polymers (target DP=30 macromonomer units) prepared in the presence of iPrSi and treated with TBAF.

Figure 50A:
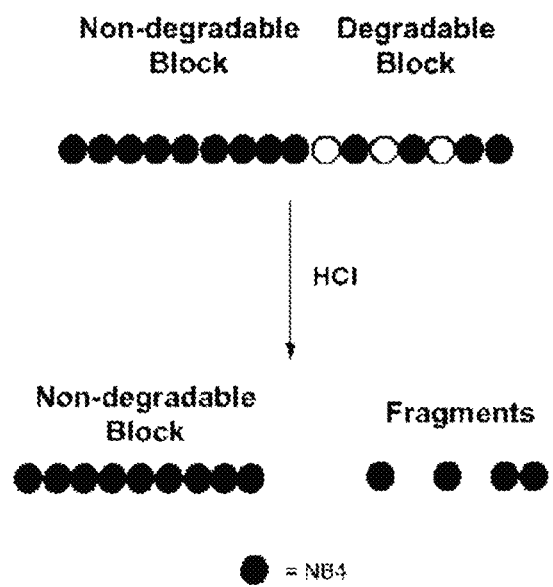

FIG. 50A shows a scheme of the selective degradation in block copolymers (e.g., NB4-p-SiNB4), which includes a NB4 block and a p-SiNB4 block.

Figure 50B:
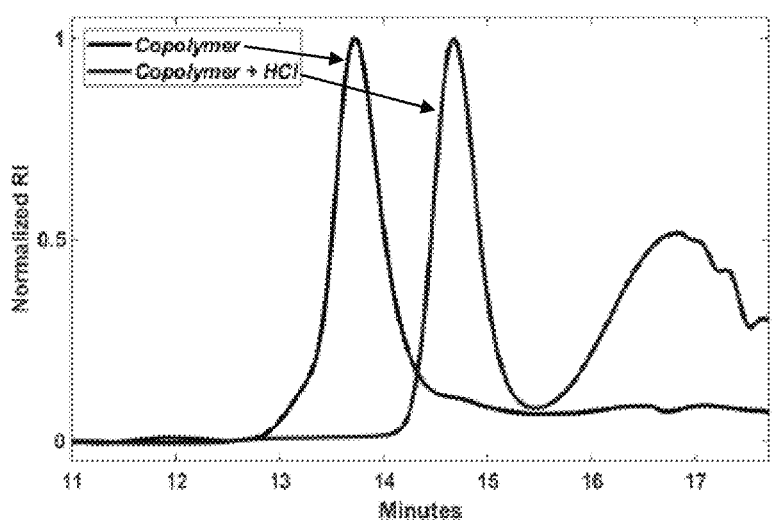

FIG. 50B shows a resulting chromatogram from GPC of block copolymer NB4-p-SiNB4 described in FIG. 50A (Copolymer) and upon treatment with HCl.

Figure 50C:
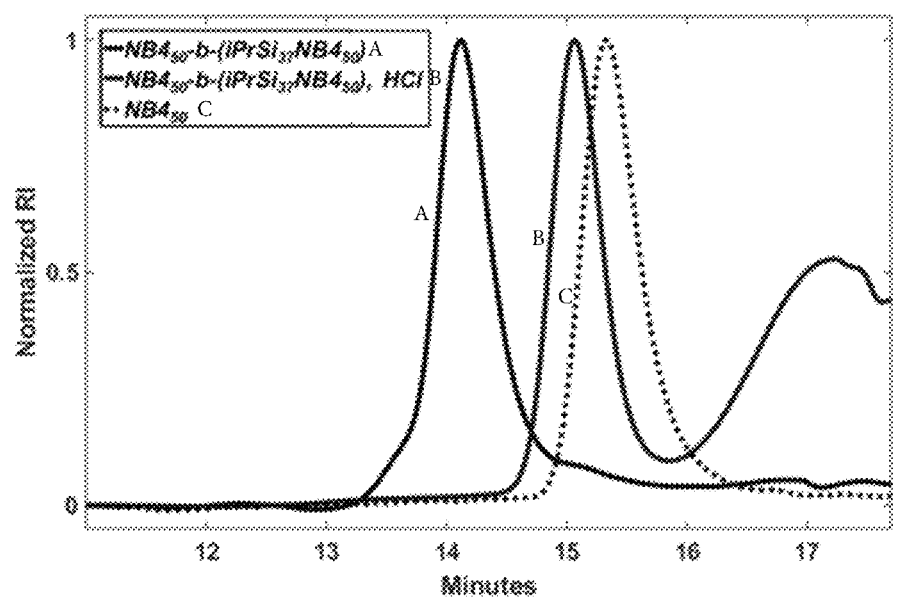

FIG. 50C shows GPC traces of linear NB4 polymer containing degradable and non degradable blocks, before and after acidic hydrolysis. After acidic hydrolysis, a primary peak with similar molecular weight to that of an NB4 homopolymer (target DP=50), along with additional smaller fragments, was observed. The slightly earlier retention time of the high molecular weight peak after degradation suggests the incorporation of additional NB4 units to the end of the initial polynorbornene block, which are not cleaved by acidic hydrolysis. The $M_n$ of the copolymer is $2.23 \times 10^4$ ($M_w/M_n$=1.04), which is then degraded to two sets of peaks: one with an $M_n$ of $8.50 \times 10^3$ ($M_w/M_n$=1.02) corresponding to the NB4 homopolymer and a broader set of fragments with $M_n$ of $7.07 \times 10^2$ ($M_w/M_n$=1.33).

Figure 51A:
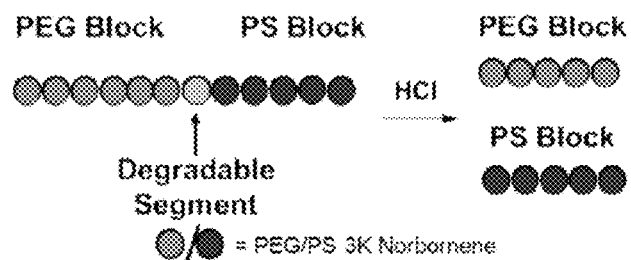

FIG. 51A shows a scheme of the use of degradable linkers in block brush copolymers including 1) a PEG Block (prepared by polymerizing PEG 3K norbornene), 2) a PS Block (prepared by polymerizing PS 3K norbornene

Figure 51B:
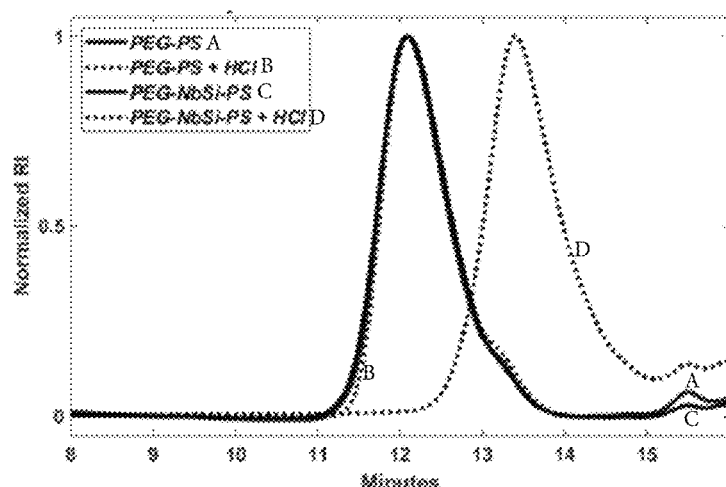

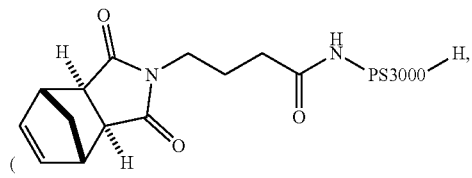

wherein PS3000 is polystyrene with weight average molecular weight of about 3 kDa)); and a silyl containing linker formed from iPrSi FIG. 51B shows a resulting chromatogram from GPC of a (PEG Block)-(PS Block) block copolymer (PEG-PS), PEG-PS after treatment with HCl, a (PEG Block)-iPrSi-(PS Block) block copolymer (PEG-NbSi-PS), and PEG-NbSi-PS after treatment with HCl. This demonstrates that the inclusion of a silyl ether in between the PEG Block and PS Block allowed for degradation into separate blocks.

Figure 51C:
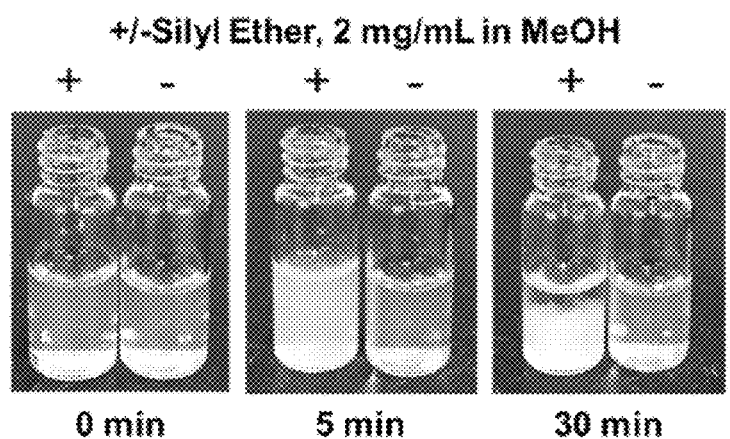

FIG. 51C shows PEG-PS (-Silyl Ether) or PEG-NbSi-PS (+Silyl Ether) in McOH over time.

Figure 51D:
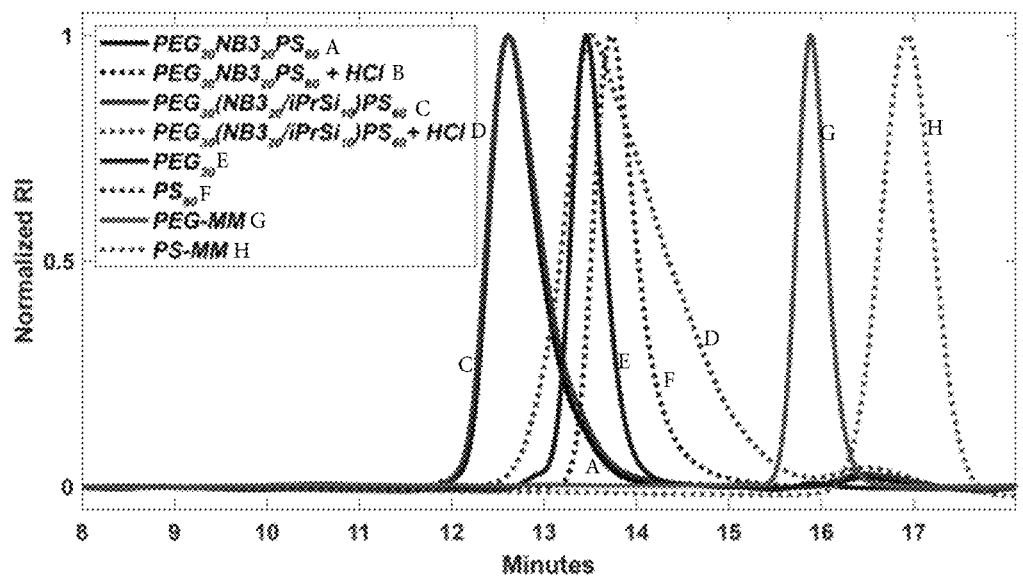

FIG. 51D shows GPC traces of PEG-PS copolymers before and after treatment with HCl, demonstrating degradation only with polymers containing a silyl ether-containing block.

Figures 52A, 52B:
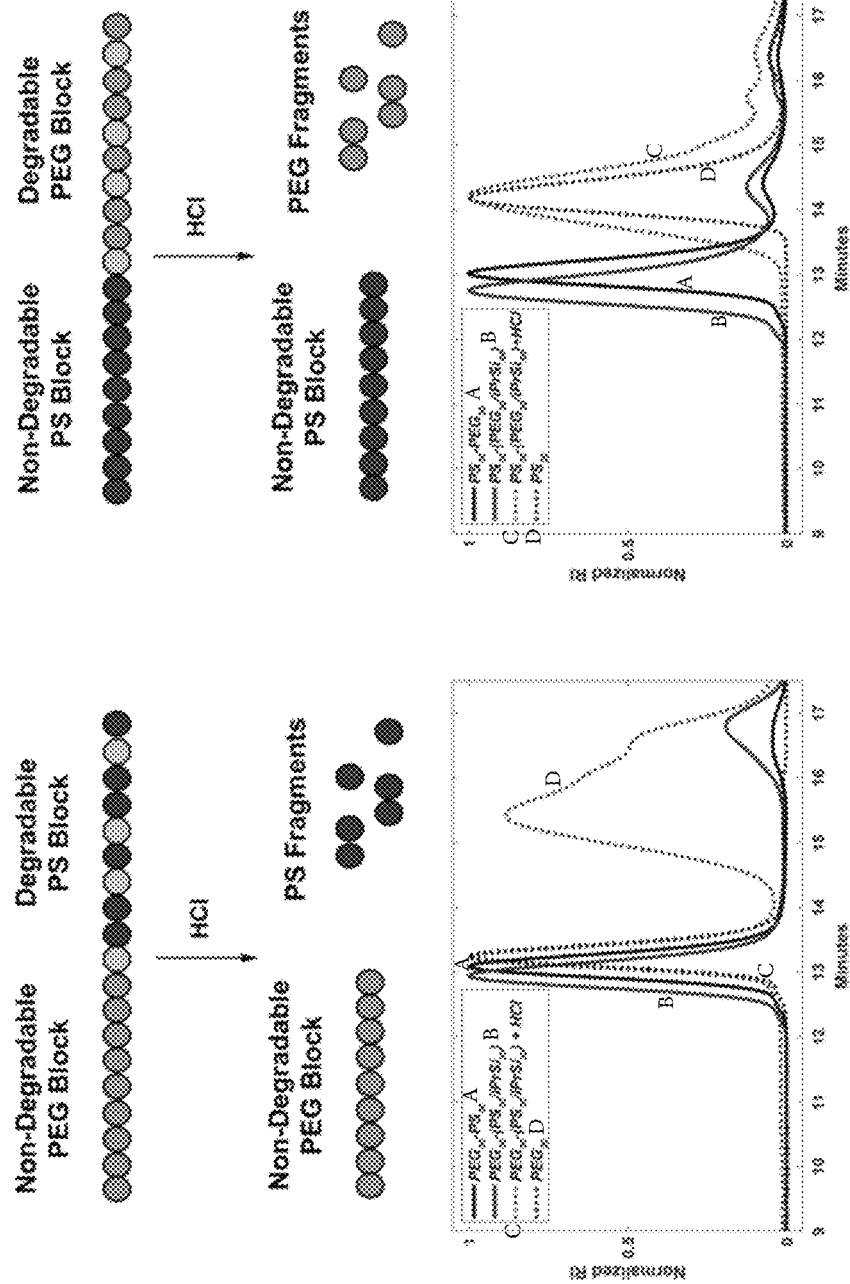

FIGS. 52A and 52B show GPC traces of either (FIG. 52A) PEG-PS or (FIG. 52B) PS-PEG bottlebrush polymers (target DP=30/30/30 PEG-MM/PS-MM/iPrSi), demonstrating that either the PS or PEG blocks can be selectively degraded depending on the location of the silyl ether monomer. Differences in refractive index traces between the two samples correspond to the different refractive indices of PS and PEG.

Figure 53:
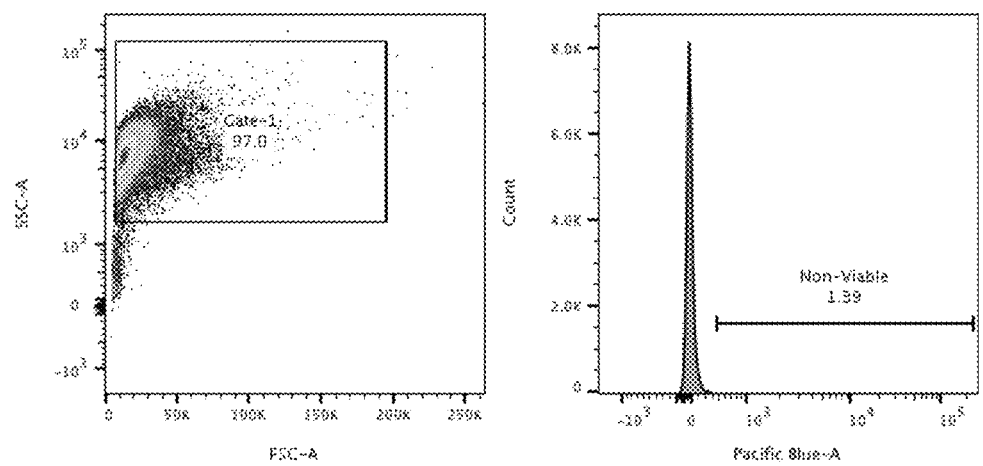

FIG. 53 shows an example of the gating used to assay Jurkat cell viability.

Figure 54:
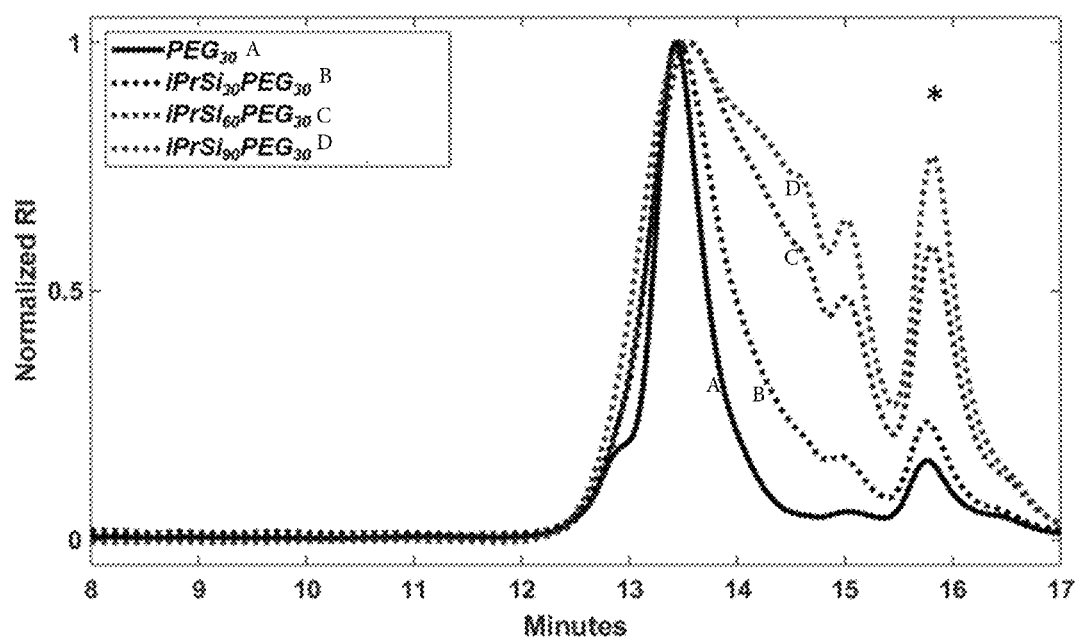

FIG. 54 shows GPC traces for PEG-MM-derived bottlebrush polymers (target DP=30 PEG-MINI units) copolymerized with different equivalents of iPrSi (1-3 equivalents relative to PEG-MM), demonstrating that excess iPrSi negatively impacts the resulting molar mass dispersity. The star indicates unreacted macromonomer.

Figure 55A:
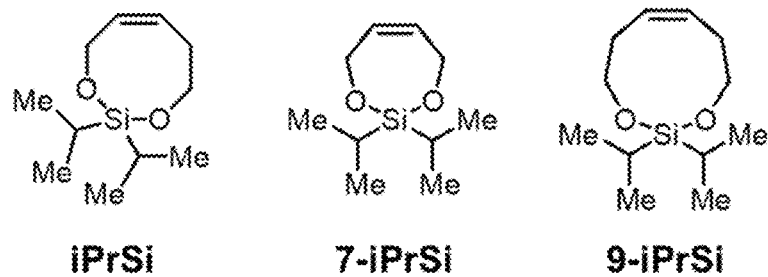
Figure 55B:
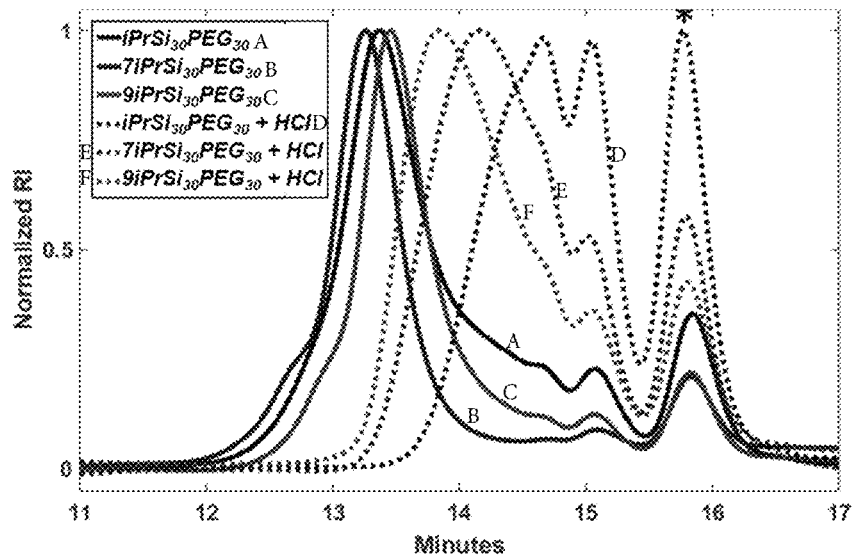

FIGS. 55A and 55B show a comparison of copolymerization reactions performed with seven-versus eight-versus nine-membered silyl ether monomers for synthesizing bottlebrush polymers (target DP=30 PEG-MINI units). The star indicates unreacted macromonomer in the solid GPC traces.

Figure 56A:
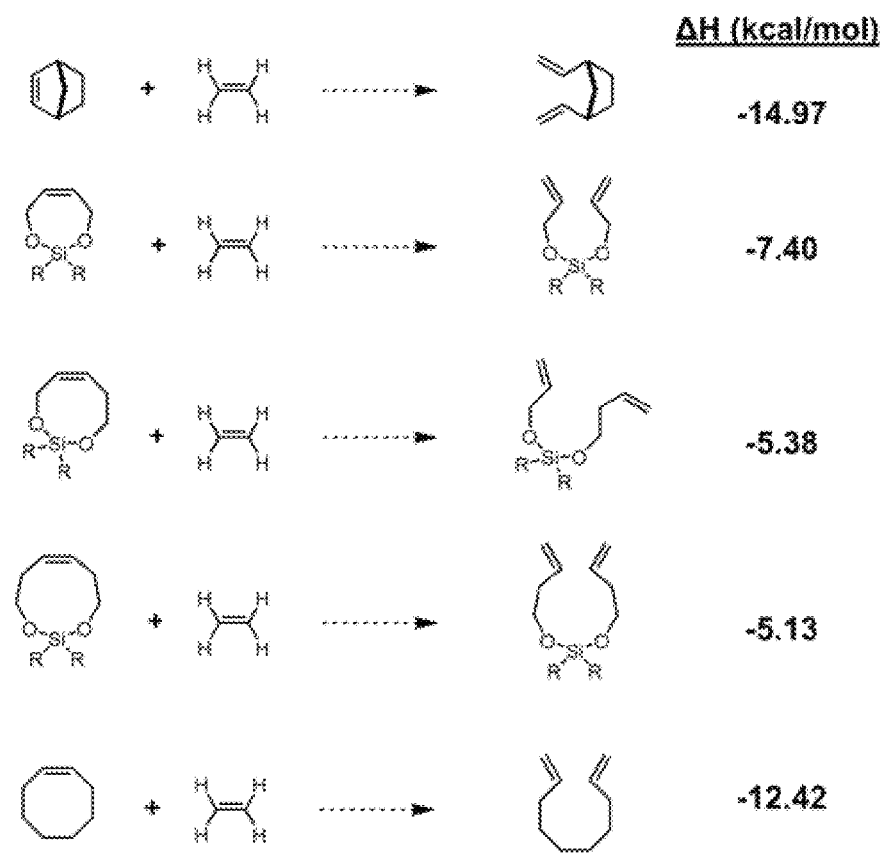

FIG. 56A shows DFT calculations of reaction enthalpy of hypothetical ring opening metathesis reactions for norbornene and silyl ether derivatives of different ring sizes.

Figure 56B:
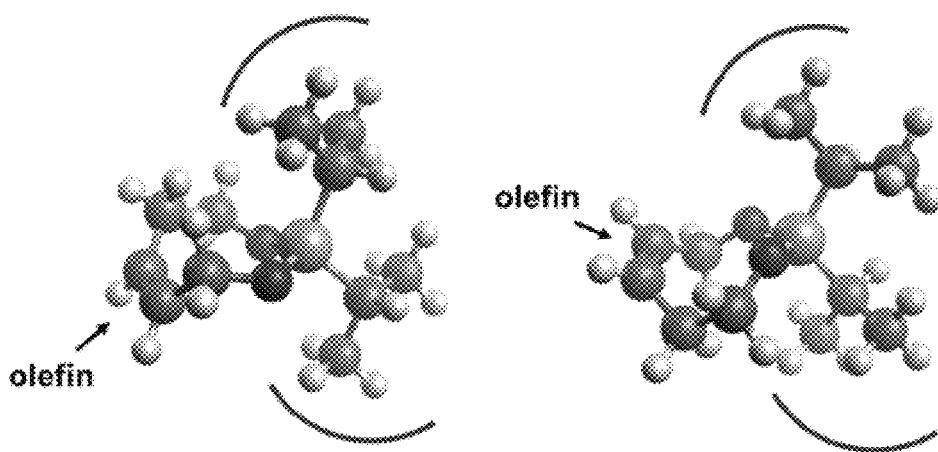

FIG. 56B shows 3D models of iPrSi, showing the potential role that silyl ether substituents may play in influencing the accessibility of backbone olefins.

Figure 57A:
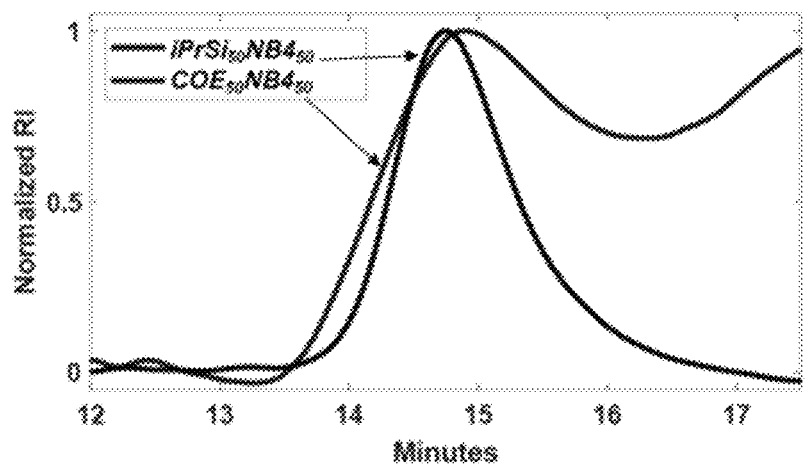
Figure 57B:
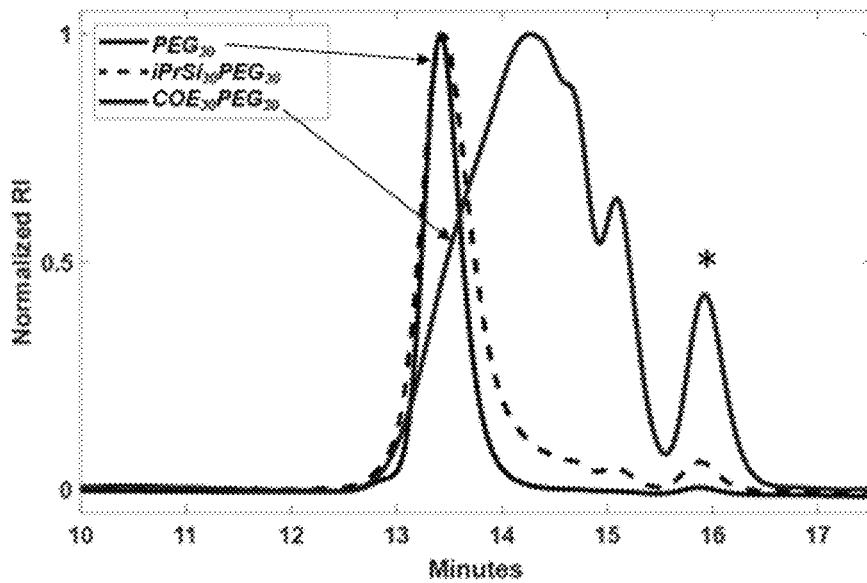

FIGS. 57A and 57B show GPC traces of linear and bottlebrush copolymers prepared by combining (FIG. 57A) NB4 or (FIG. 57B) PEG-MM with iPrSi or cyclooctene (COE) at a 1:1 molar ratio (target DP=50/50 for the linear polymer and DP=30/30 for the bottlebrush polymer). Dramatically higher dispersity and the formation of smaller fragments is observed in both cases, indicative of substantial chain transfer reactions. The star corresponds to unreacted monomer in the solid GPC traces.

Figure 58:
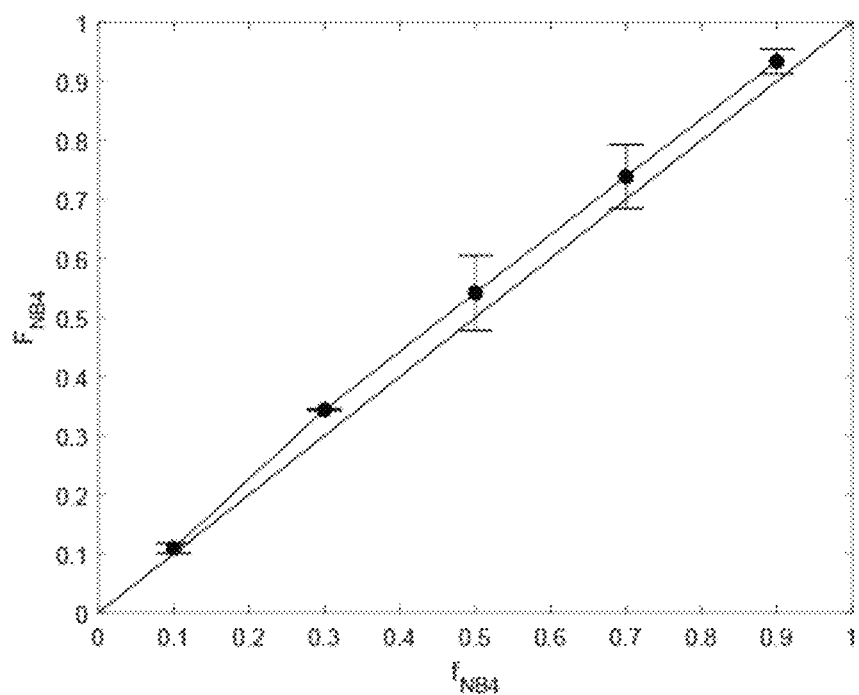

FIG. 58 shows a Mayo-Lewis plot of the copolymerization of NB4 and iPrSi, indicating statistical copolymerization of the two monomers.

Figure 59:
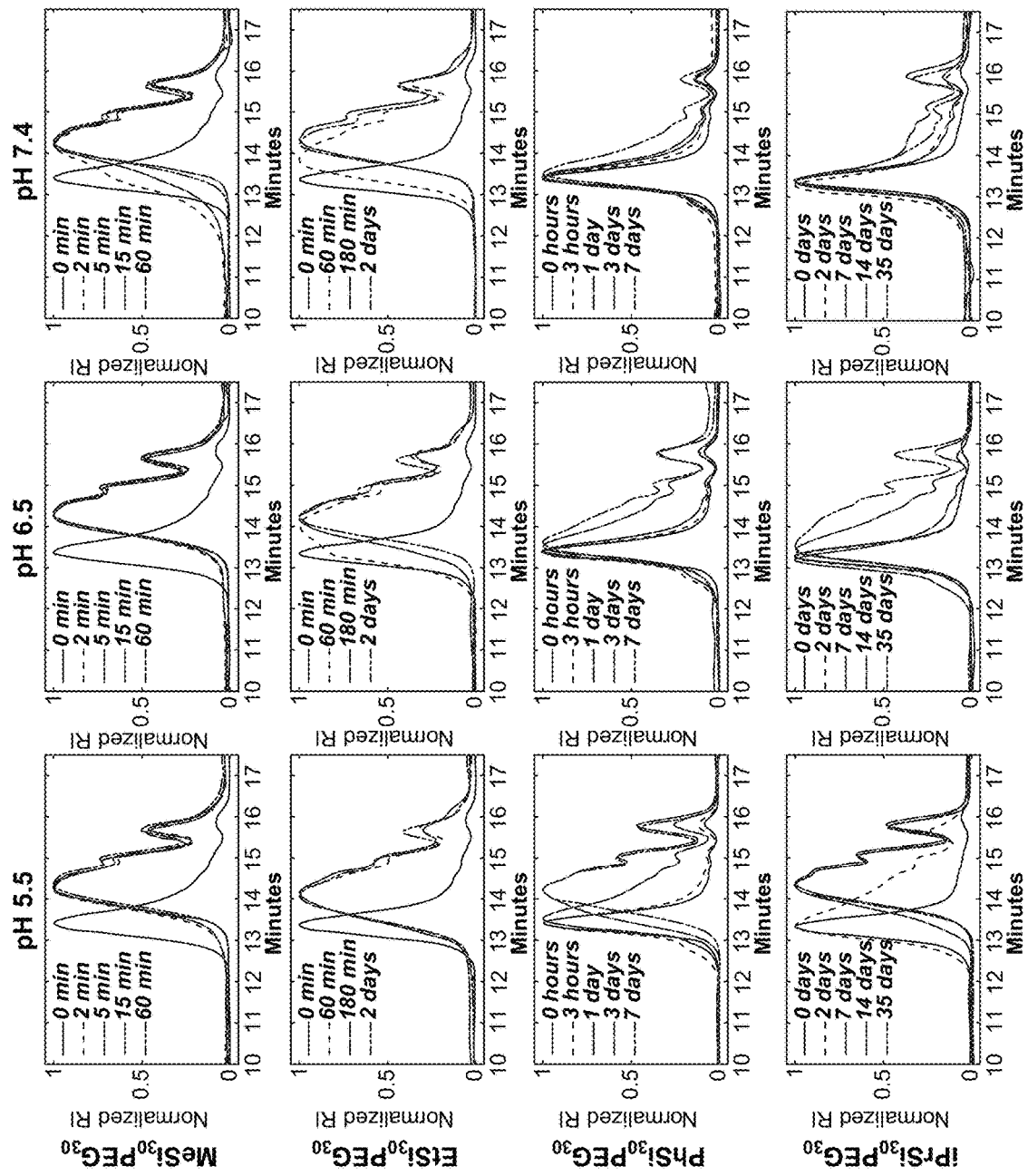

FIG. 59 shows GPC traces for silyl ether containing bottlebrush copolymers (target DP=30/30) after storage at different pH values (5.5, 6.5, 7.4) over time at 37° C.

Figure 60:
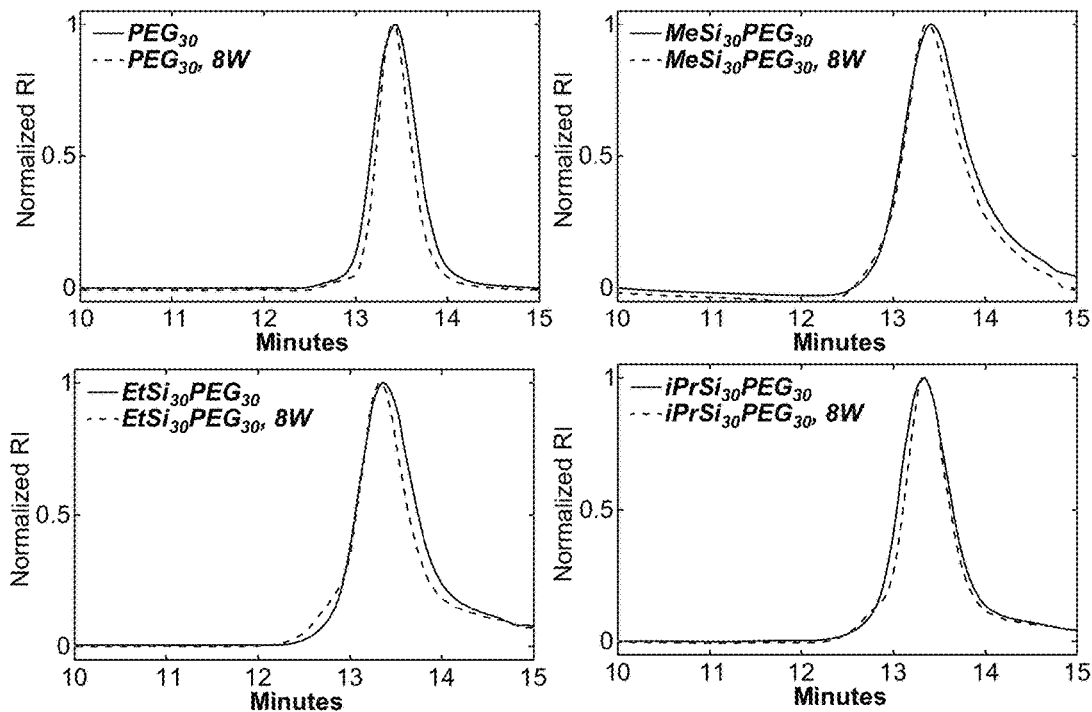

FIG. 60 shows GPC traces of bottlebrush copolymers (target DP=30/30) after storage for two months in solution at RT.

Figure 61:
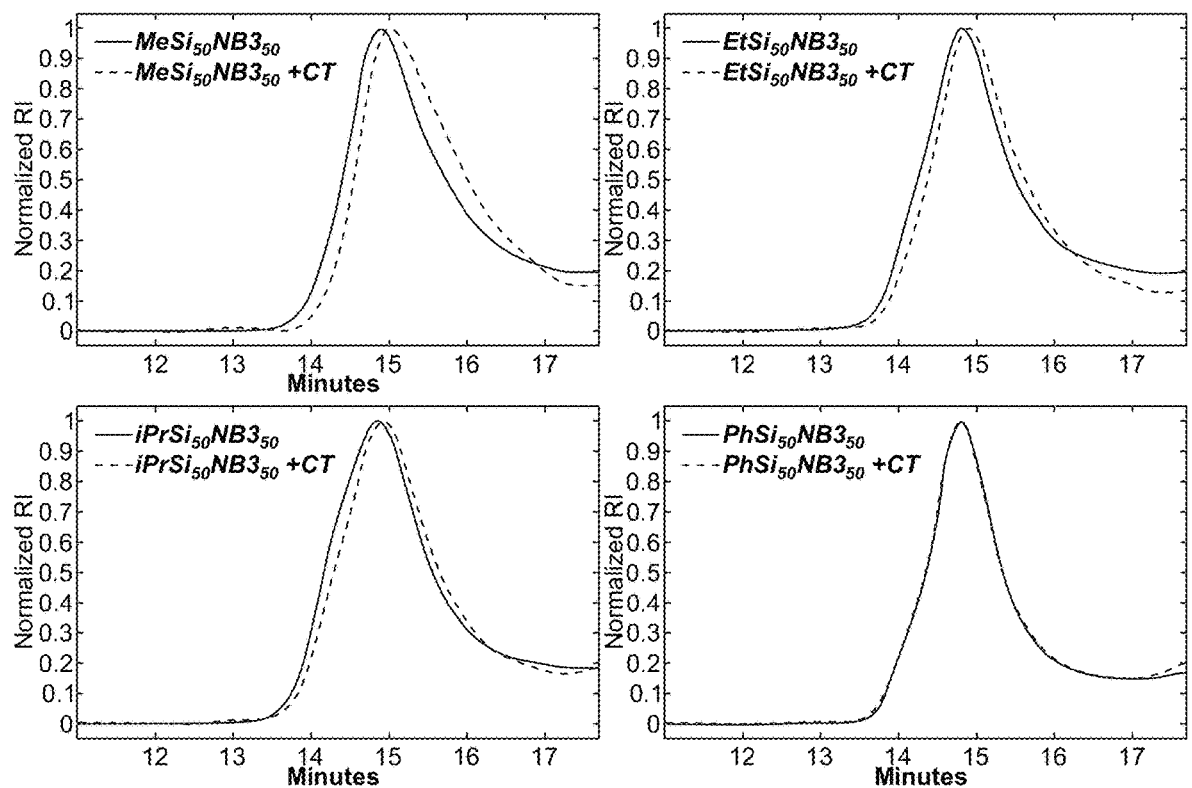

FIG. 61 shows GPC traces of NB3/silyl ether copolymers (target DP=50/50) before and after subjecting to forced chain-transfer reactions using chain-transfer agent cis-4-octene (CT) and additional Grubbs II catalyst, showing minimal conversion into smaller fragments. Overall, the amount of conversion appears to rank from Ph<iPr<Et<Me, which is consistent with the steric bulk of these substituents.

Figure 62A:
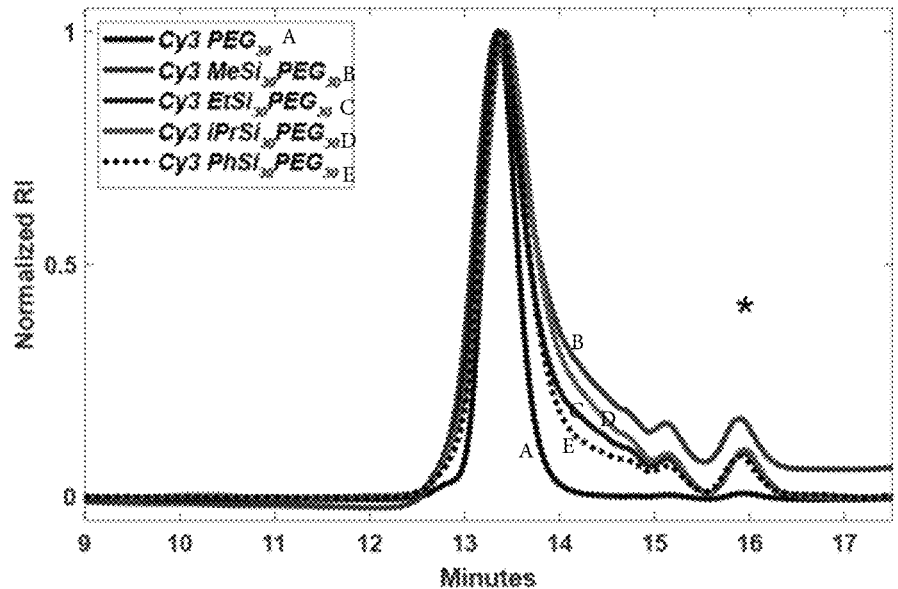
Figure 62B:
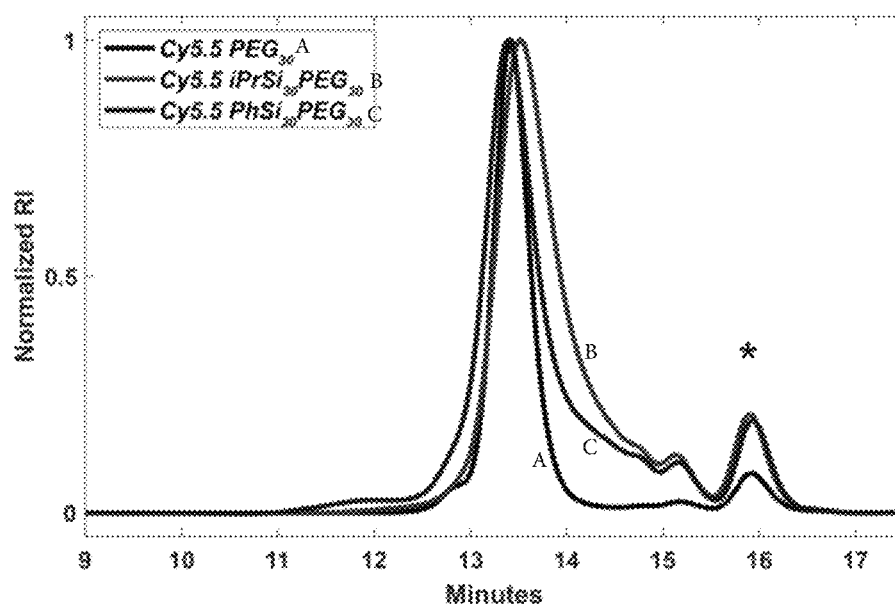

FIGS. 62A and 62B show GPC traces of Cy3 (FIG. 62A) and Cy5.5 (FIG. 62B) labeled bottlebrush polymers used for in vitro and in vivo experiments. The star corresponds to unreacted monomer.

Figure 62C:
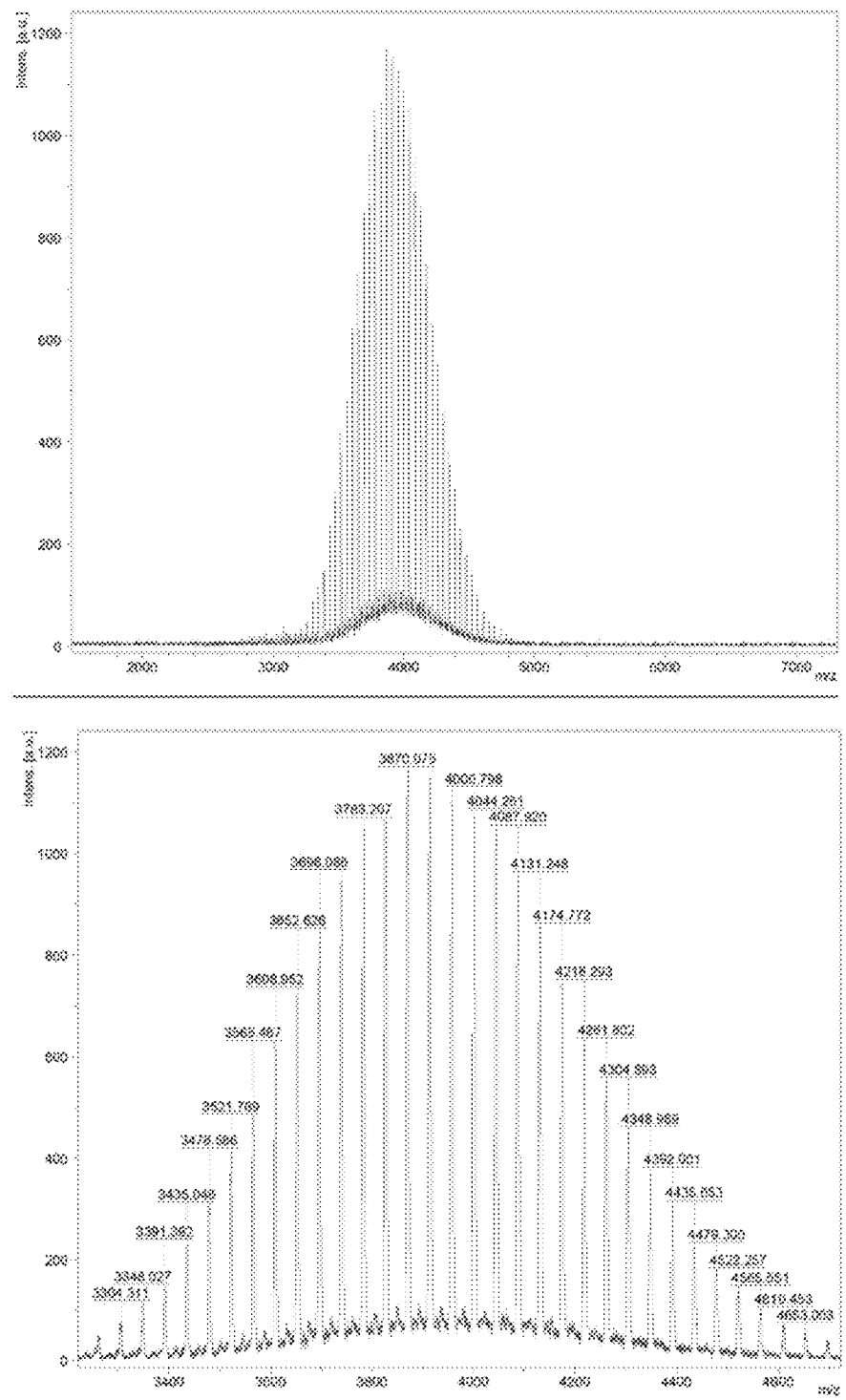

FIG. 62C shows MALDI-TOF spectra for Cy3-MM.

Figure 63A:
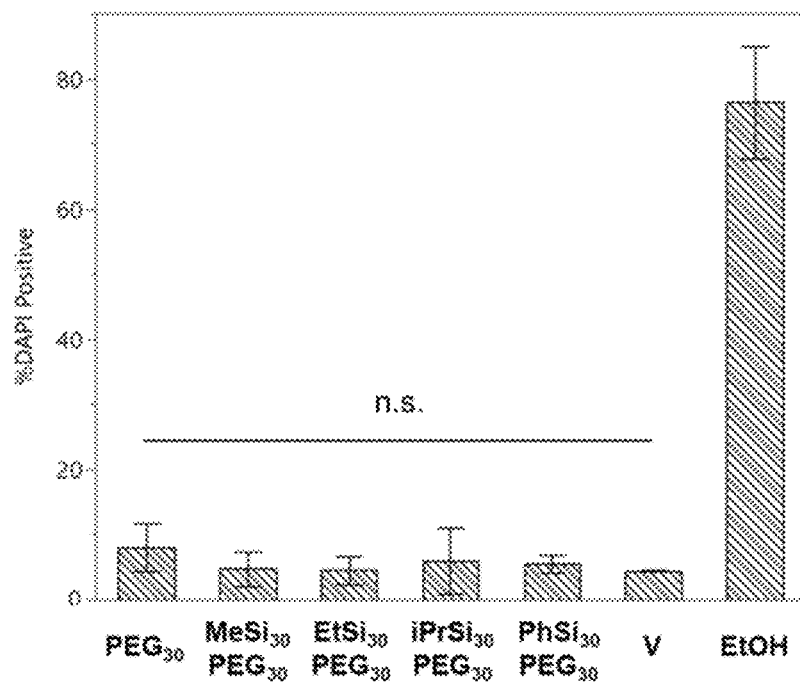
Figure 63B:
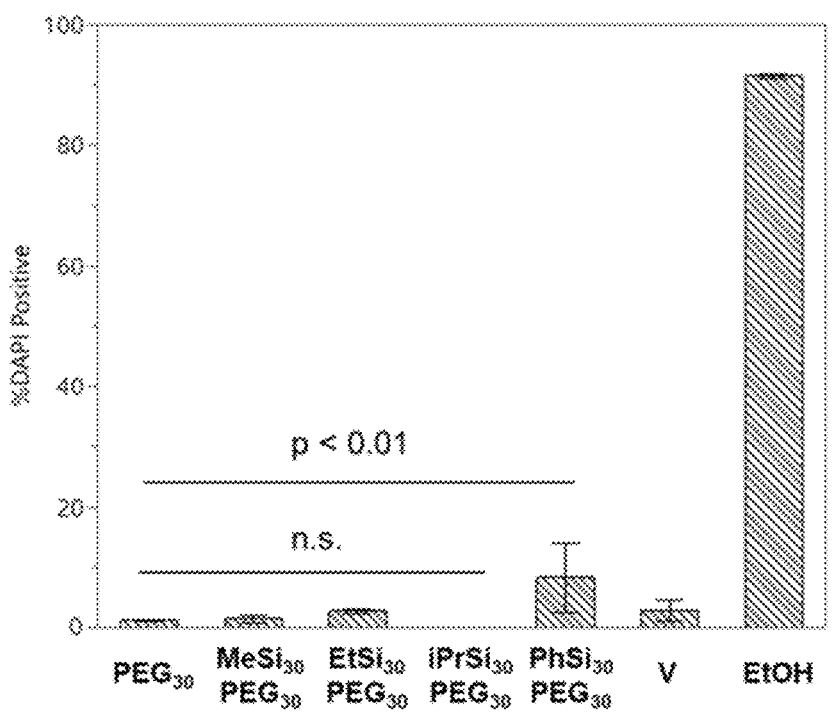

FIGS. 63A and 63B show viability of (FIG. 63A) Jurkat and (FIG. 63B) OVCAR8 cells treated with bottlebrush polymers (0.75 mg/mL, 36 h, Target DP=30/30) as assessed via flow cytometry. Excitation was performed with a 405 nm laser and emission was measured after passing through a 440/40 nm bandpass filter. V=vehicle.

Figure 64A:
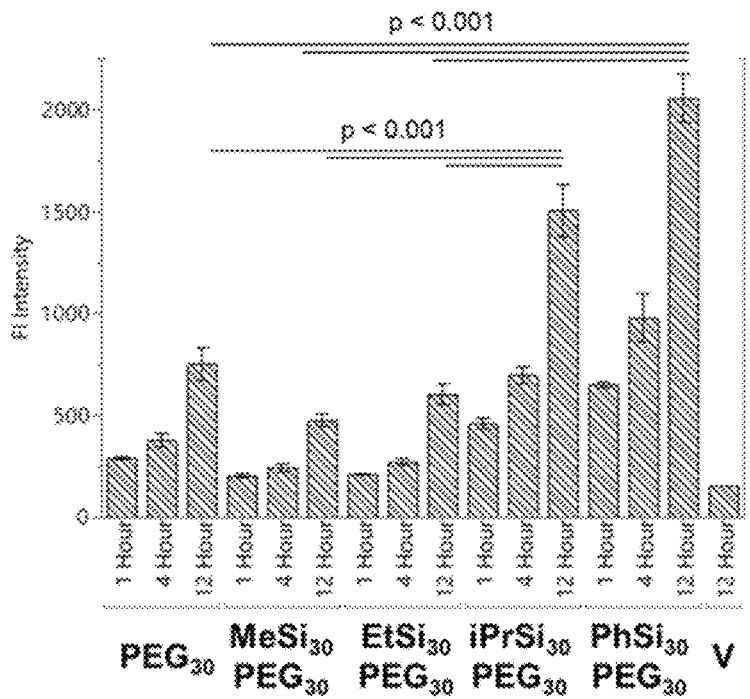
Figure 64B:
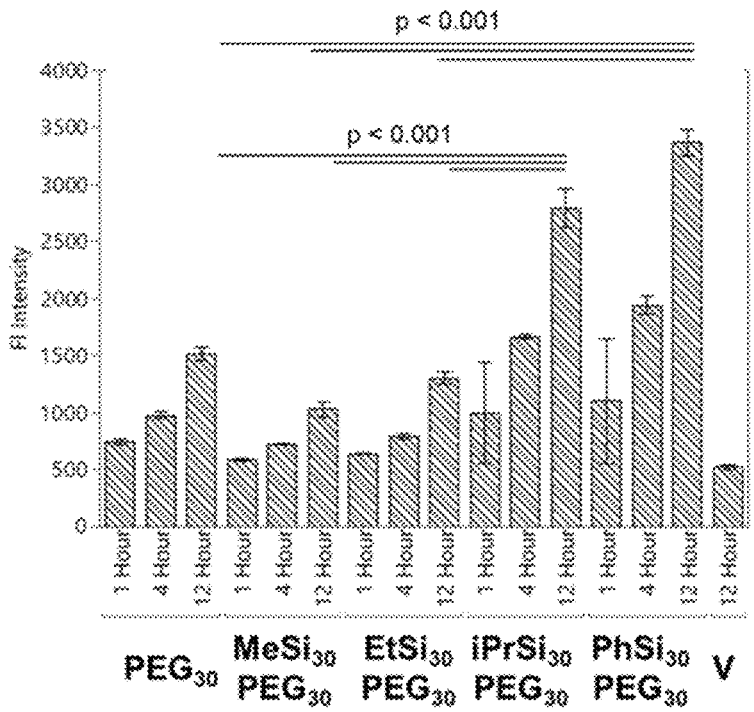

FIGS. 64A and 64B show quantification of cell uptake of bottlebrush polymers in (FIG. 64A) Jurkat and (FIG. 64B) OVCAR8 cells by flow cytometry. Cells were incubated with bottlebrush polymers (0.75 mg/mL, 36 h, Target DP=30/30) for the indicated time points and analyzed by flow cytometry. Excitation was performed with a 561 nm laser and emission was measured after passing through a 582/15 nm bandpass filter. V=vehicle.

Figure 65:
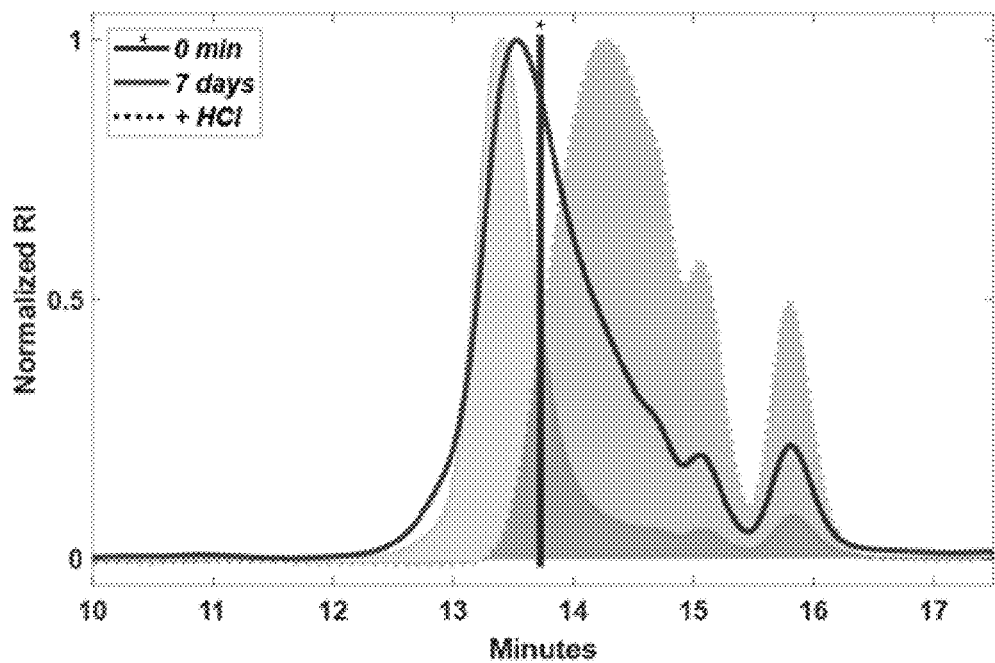

FIG. 65 is an example image of the fully intact, fully degraded, and an intermediate timepoint with the cutoff retention time.

Figure 66A:
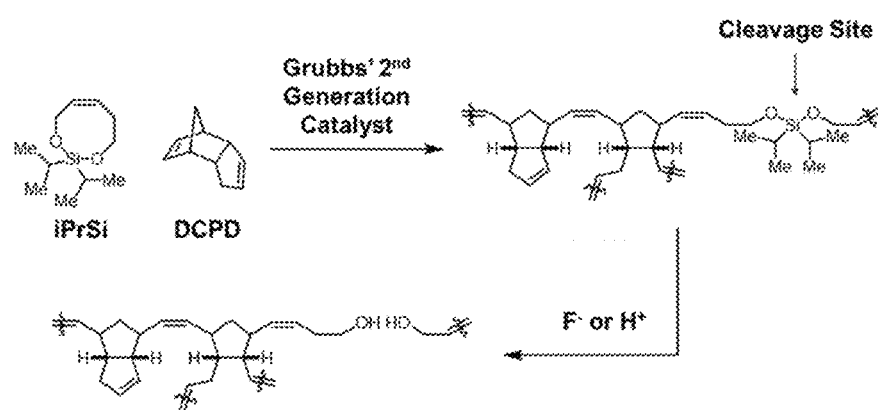

FIG. 66A shows the structure of monomers and protocol for synthesizing degradable pDCPD. The silane monomer iPrSi co-polymerizes efficiently with norbornenes under ring opening metathesis polymerization. The presence of silyl ether functionalities along the backbone opens the door to sites for degradation.

Figure 66B:
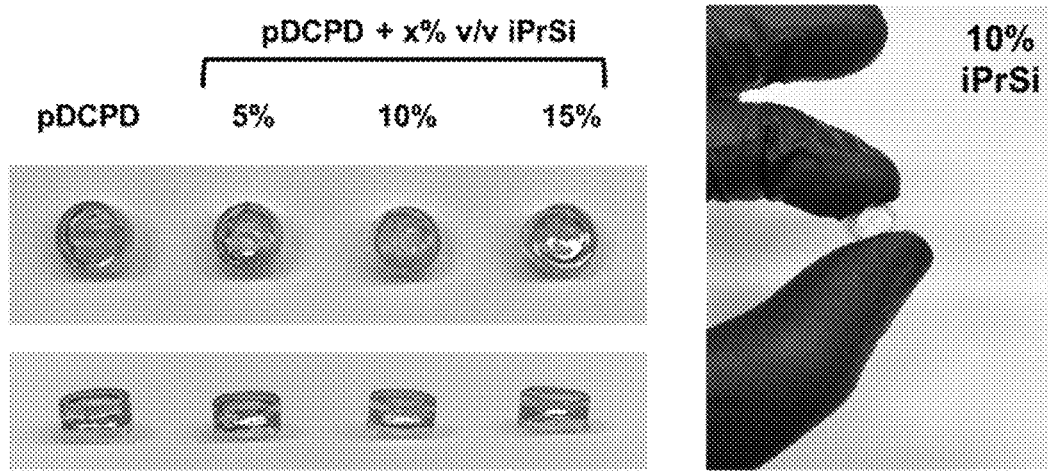

FIG. 66B shows images of pDCPD with or without iPrSi. Materials look qualitatively similar after synthesis. A sample containing 10% iPrSi is completely resistant to compression by hand.

Figure 66C:
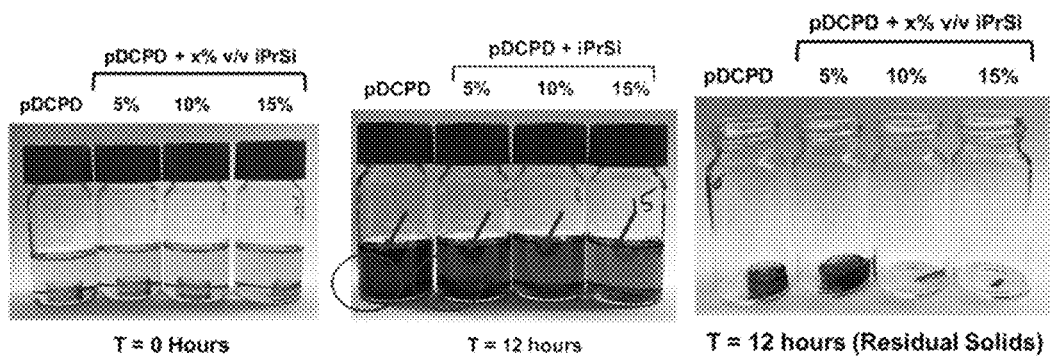

FIG. 66C demonstrates iPrSi containing pDCPD dissolves in 0.5 M TBAF in THF.

Samples containing different levels of iPrSi (5%, 10%, 15%) were incubated in 0.5 M TBAF in THF overnight. The 10% and 15% iPrSi samples showed virtually complete dissolution after this time, while the 5% iPrSi sample remained intact although significantly softer. This is consistent with the prediction that there is a threshold of iPrSi incorporation that should enable full dissolution, and suggests that 10% v/v of iPrSi is enough to render the resulting material degradable.

Figure 67:
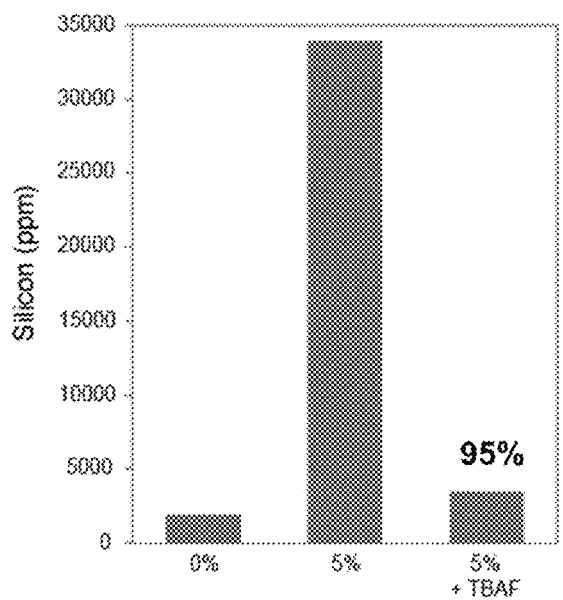

FIG. 67 shows ICP-OES data on solid 0% and 5% iPrSi doped pDCPD samples before and after TBAF treatment. These results demonstrate that at least 95% of the silyl ether groups in the material are cleaved under our conditions. The residual silicon signal in the 0% sample, which is expected to show no silicon in ICP-OES analysis, is likely derived from environmental sources of silicon such as the glass used to prepare and digest the material.

Figure 68A:
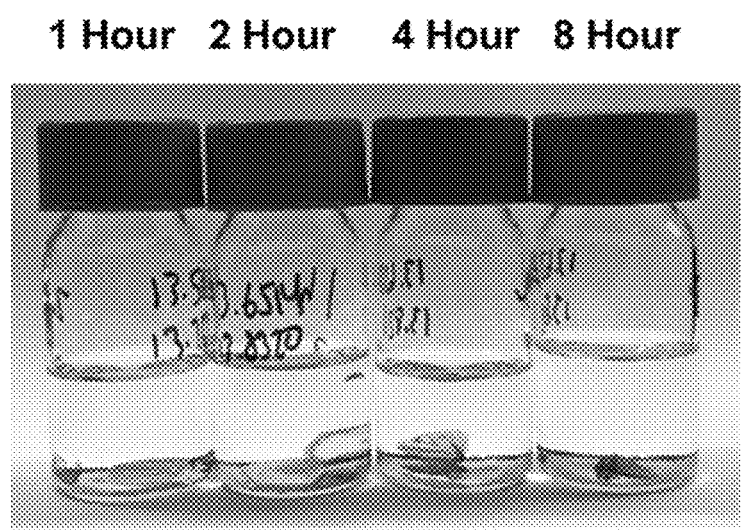
Figure 68B:
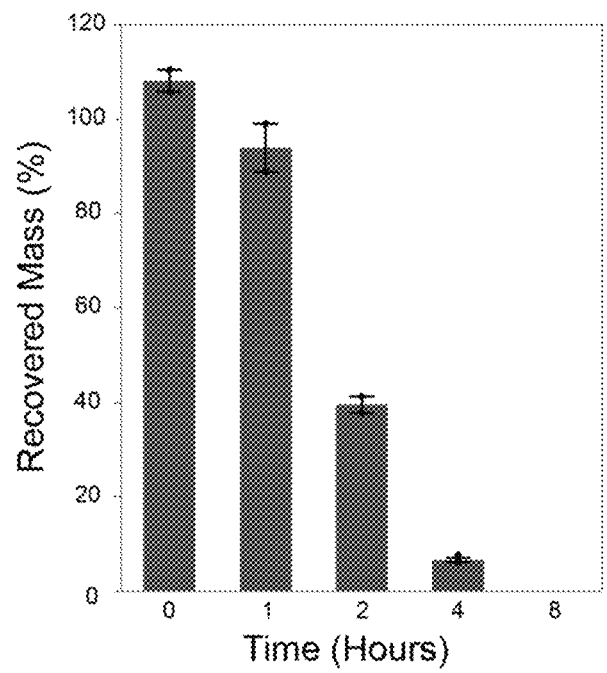

FIGS. 68A and 68B show the dissolution of iPrSi doped pDCPD is time-dependent. 10% iPrSi doped pDCPD was incubated with TBAF at 1, 2, 4, or 8 hours in the presence of 200 mol % TBAF. FIG. 68A shows images of samples after treatment with TBAF for various times, followed by washing with THF to remove unreacted TBAF and to stop the reaction. FIG. 68B shows quantification of residual solid mass as a percentage of initial sample mass. No apparent swelling of the material was observed, suggesting that degradation of the material proceeds via surface erosion and that diffusion of TBAF into the material is rate-limiting.

Figure 69A:
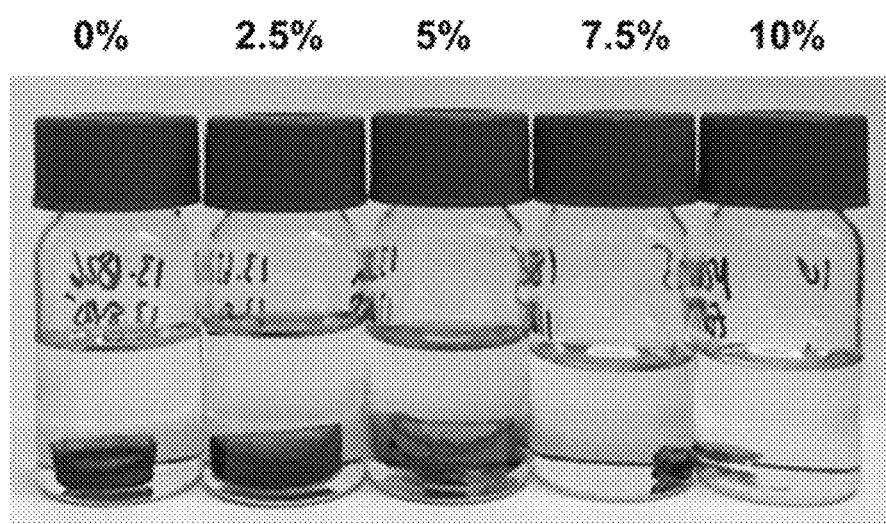

FIG. 69A shows samples containing different levels of iPrSi (0, 2.5, 5, 7.5, and 10%) were incubated in 0.5 M TBAF in THF overnight, showing iPrSi-dependent degradation.

Figure 69B:
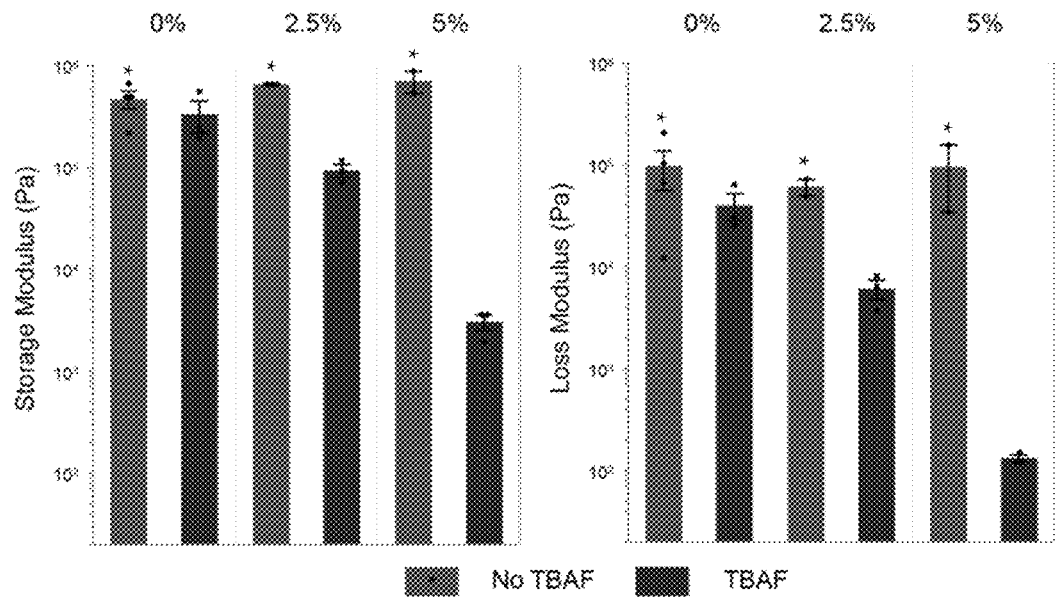

FIG. 69B shows rheological measurements on swollen samples, showing a significant loss in mechanical properties for the 5% iPrSi-doped pDCPD sample upon treatment with TBAF.

Figure 69C:
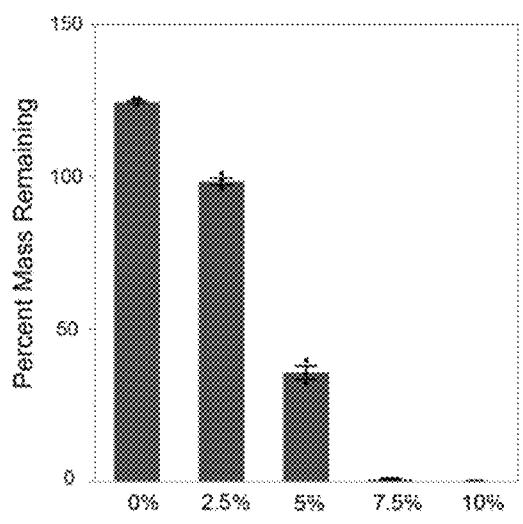

FIG. 69C shows quantification of remaining mass of the samples, showing how the residual mass of the material decreases as a function of silyl ether monomer incorporation.

Figure 69D:
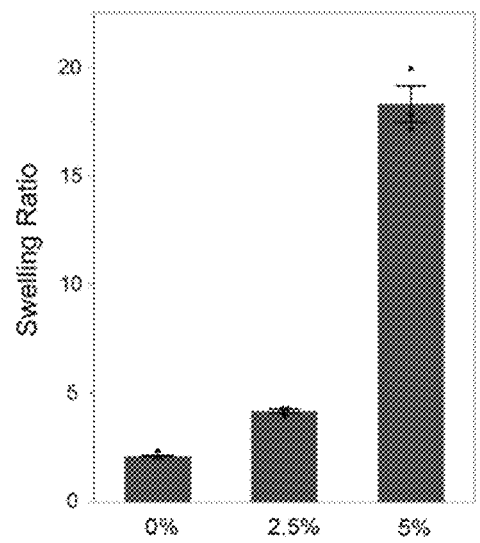

FIG. 69D shows quantification of swelling ratio of samples, showing a concomitant increase in swelling ratio with higher levels of silyl ether monomer incorporation.

Figure 70:
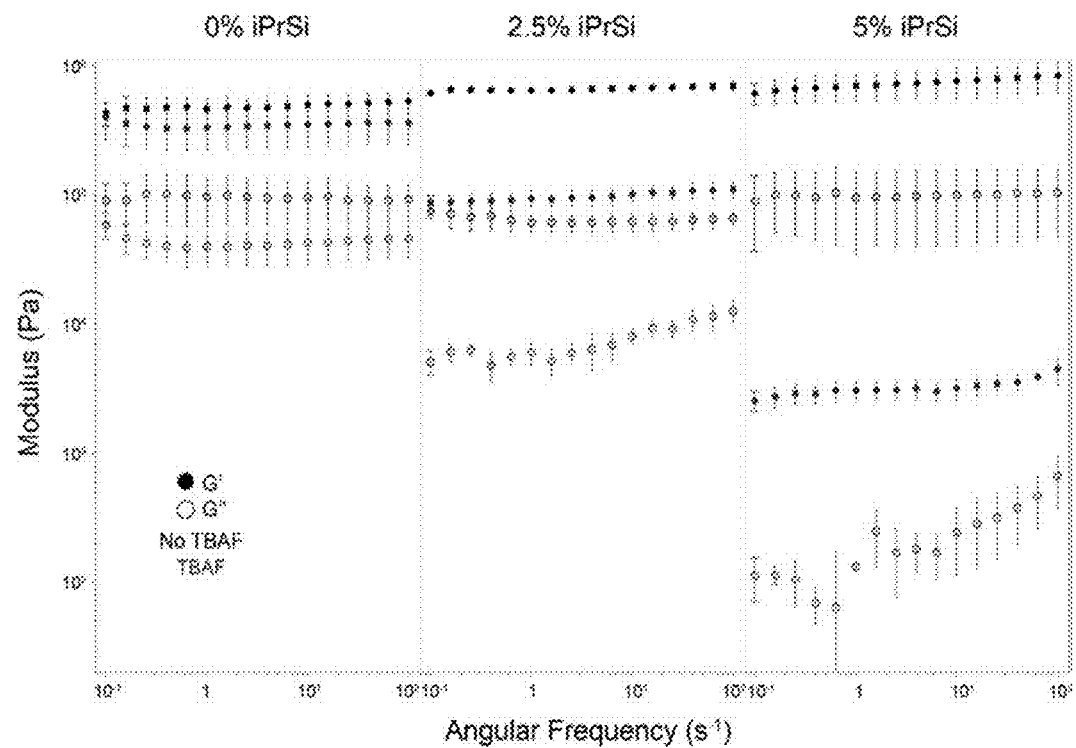

FIG. 70 shows rheological measurements of THF swollen samples of degraded pDCPD samples with different levels of crosslinking. Samples containing different levels of iPrSi show decreased levels of crosslinking after TBAF treatment. In contrast, all three samples show similar mechanical properties upon swelling in THF in the absence of TBAF.

Figure 71:
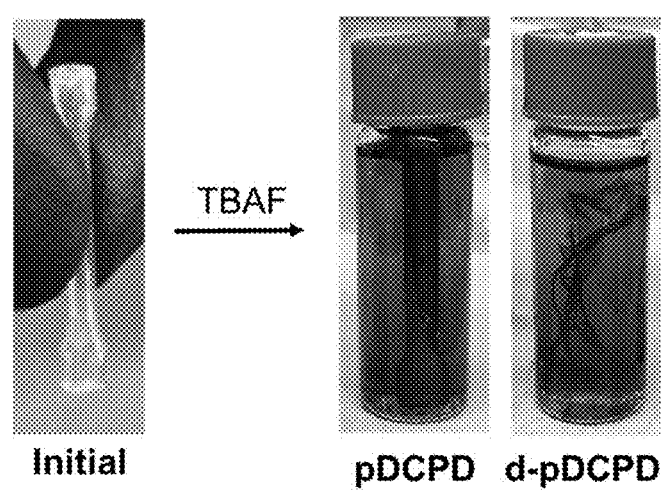

FIG. 71 shows images from the dissolution of a dogbone-shaped sample of either pDCPD or 10% iPrSi doped pDCPD by TBAF. While pDCPD remains intact under these conditions, it was observed that the bulk of the doped pDCPD material dissolves under these conditions. The remaining undissolved material takes on the shape of the parent material (dogbone), suggesting that it is derived from the material surface.

Figure 72A:
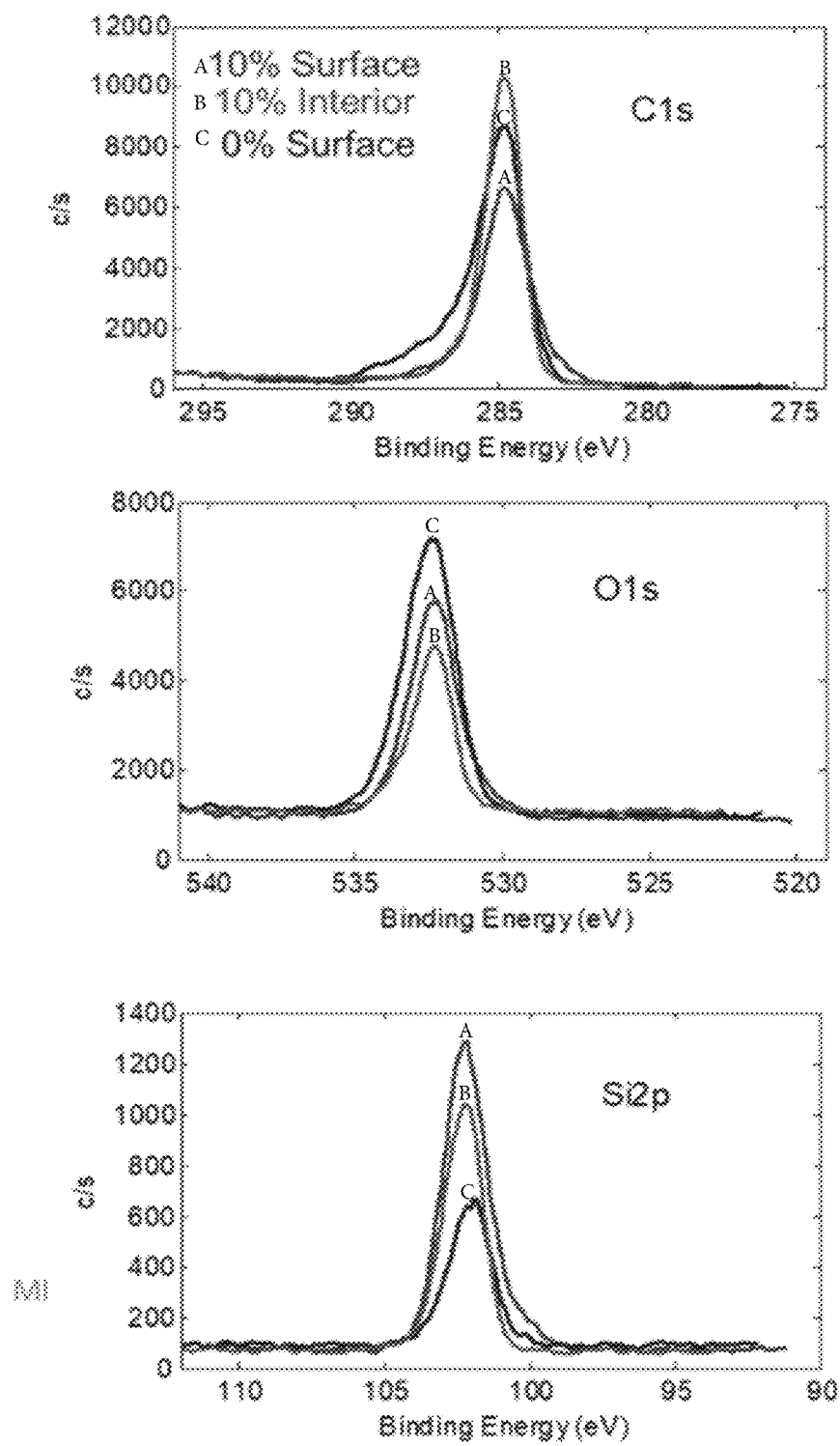
Figure 72B:
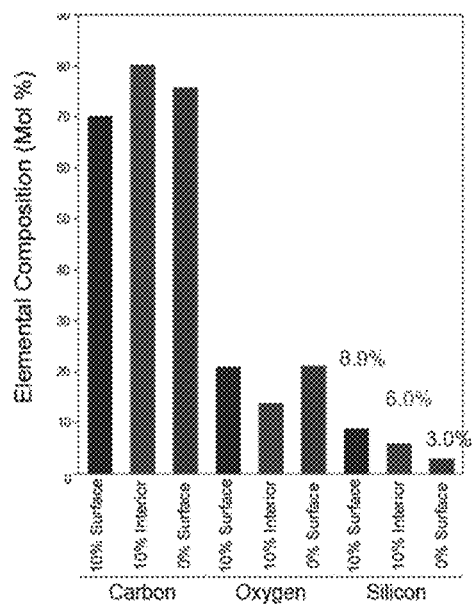

FIGS. 72A and 72B shows XPS characterization of surface silicon on pDCPD and doped 10% pDCPD, demonstrating that the silyl ether groups are present on the surface of 10% doped pDCPD. FIG. 72A shows raw XPS traces for C, O, and Si. The different binding energy on the Si2p peak from the 0% iPrSi containing pDCPD sample is consistent with the silicon signal being derived from a source other than our silyl ether monomer. FIG. 72B shows quantification of carbon, oxygen, and silicon on the surface and interior of pDCPD containing 10 or 0% iPrSi. The presence of large amounts of silicon on both the material surface suggests that iPrSi is present in both the interior and the surface of the material.

Figure 73:
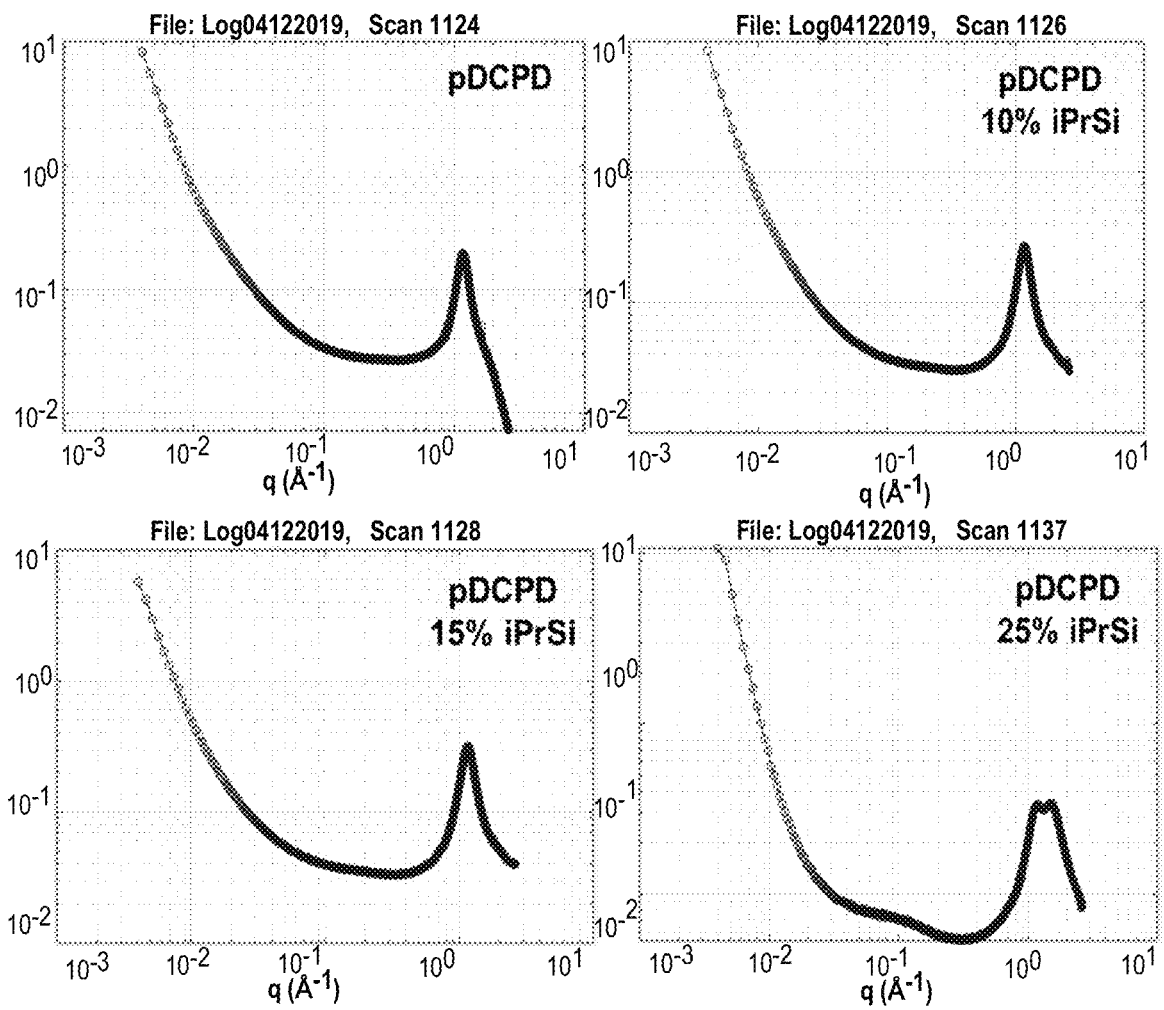
Figure 74:
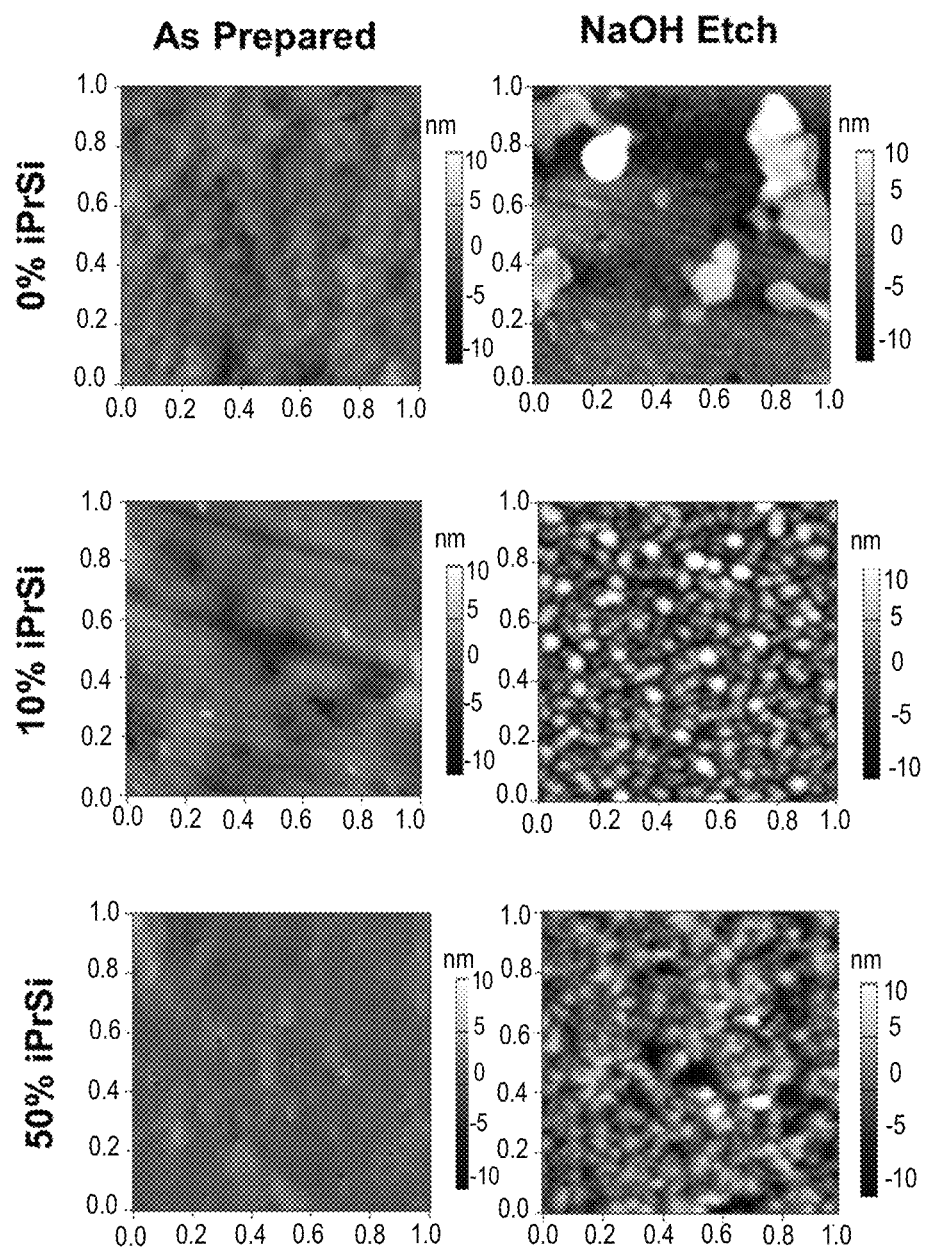

FIG. 73 shows SAXS data of pDCPD and 10% doped pDCPD containing different levels of silyl ethers. No additional features are observed until high levels of iPrSi are incorporated, consistent with the even distribution of the silyl ether functionalities within the material FIG. 74 shows AFM characterization of surface roughness for samples with 0, 10, 20, 33, and 50% iPrSi in pDCPD, before and after etching by NaOH. Noticeable etching is observed in samples containing 10% and 50% iPrSi, suggesting the presence of hydrolysable silyl ether units on the material surface.

Figure 75A:
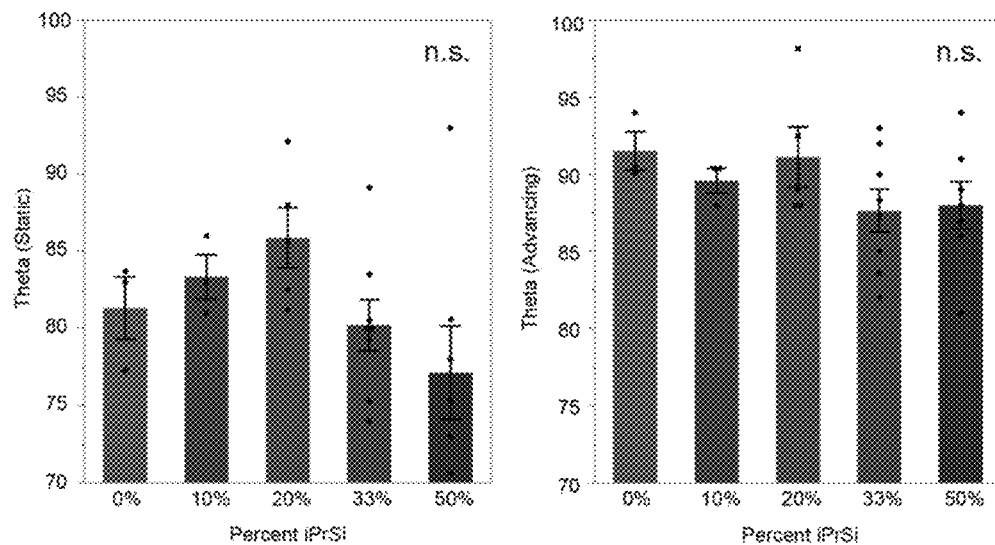
Figure 75B:
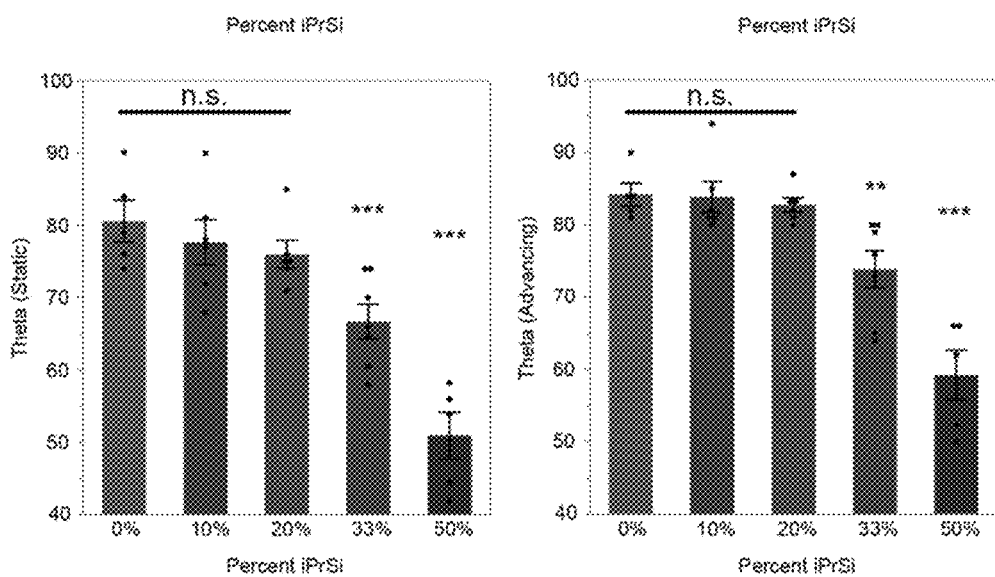

FIGS. 75A to 75B shows contact angle measurement of pDCPD and doped pDCPD, both freshly prepared and etched with 2M NaOH for 30 minutes for samples with 0, 10, 20, 33, and 50% iPrSi. FIG. 75A shows measurement of freshly prepared pDCPD samples containing different levels of silyl ether. FIG. 75B shows contact angle measurements from pDCPD samples etched with 2M NaOH for 30 minutes, showing a decrease in contact angle as a function of silyl ether incorporation. –p<0.01, *–p<0.001.

Figure 76:
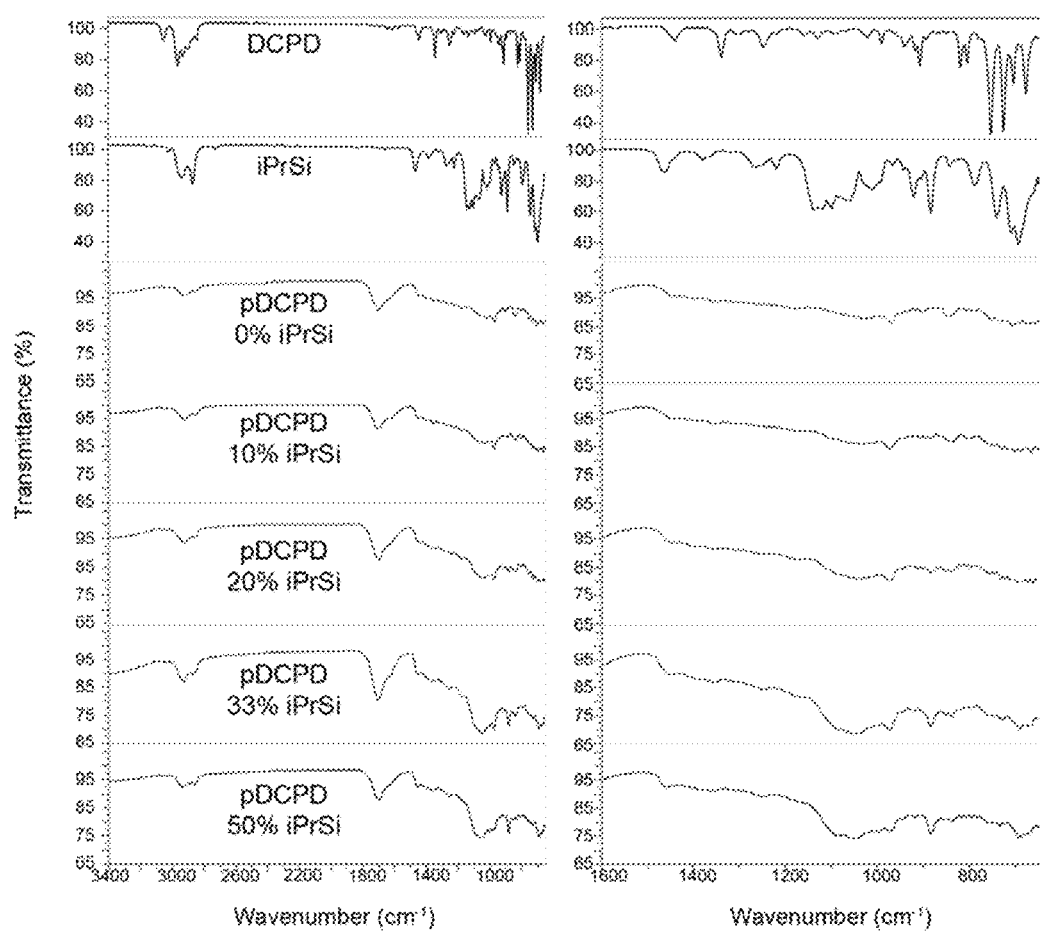

FIG. 76 shows ATR FTIR measurement of pDCPD samples. A new peak at around 890 $cm^{-1}$, which absorbs strongly in the FTIR spectra of the iPrSi monomer, also shows up in iPrSi-doped pDCPD, suggesting the presence of silyl ether functionalities within 1 μm of the surface.

Figure 77:
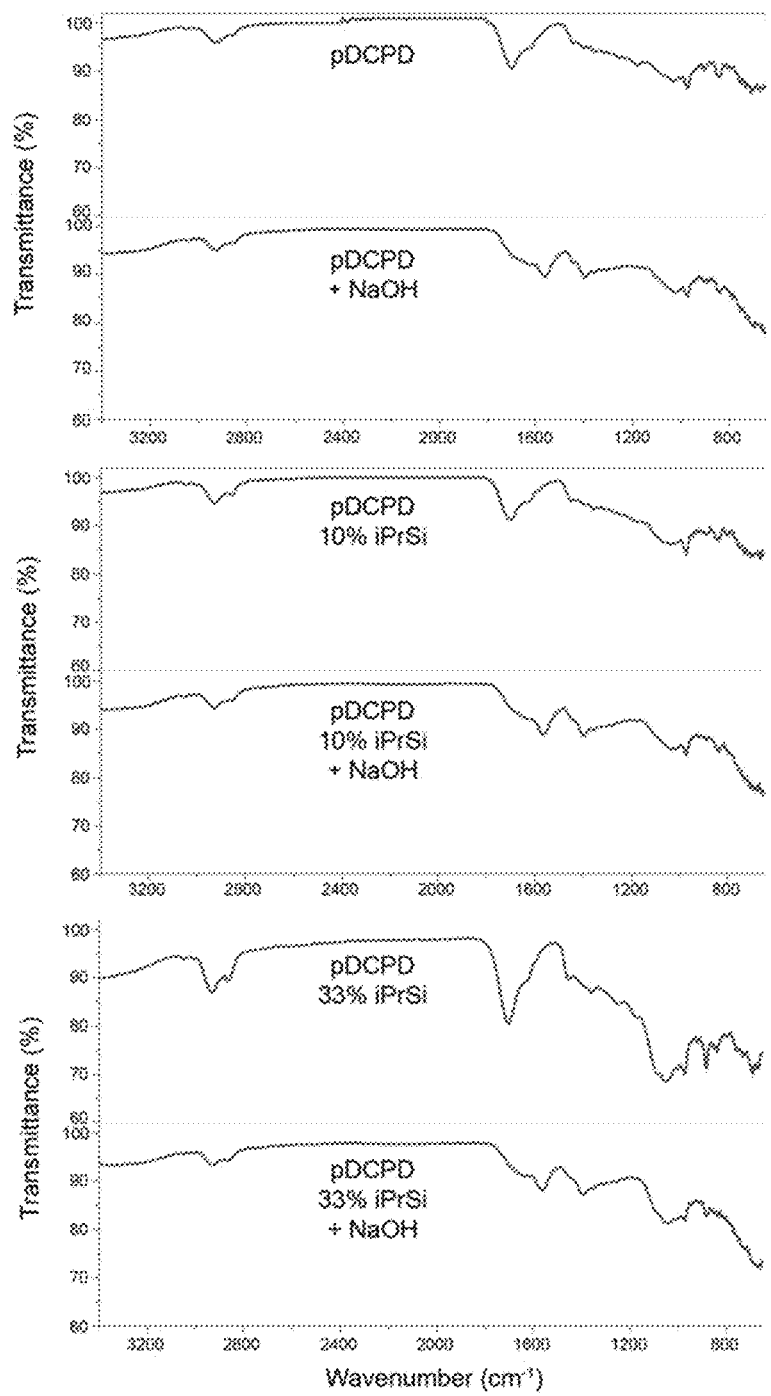

FIG. 77 shows ATR FTIR measurement of pDCPD samples after NaOH treatment. The 890 $cm^{-1}$ peak decreases in magnitude upon sodium hydroxide treatment, consistent with hydroxide mediated cleavage of the silyl ether groups on the material surface. Additional changes to the material, such as the loss of peaks around the 1700 $cm^{-1}$ range, likely correspond to oxidation products on the pDCPD surface.

Figure 78:
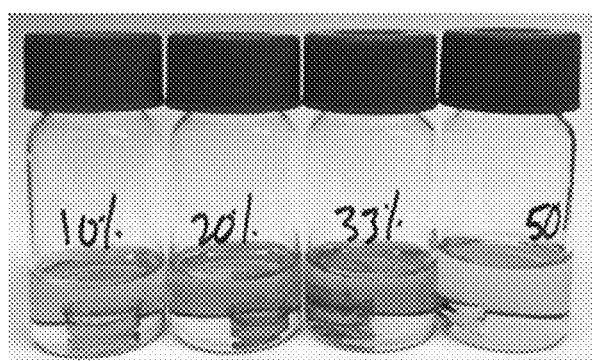
Figure 78:
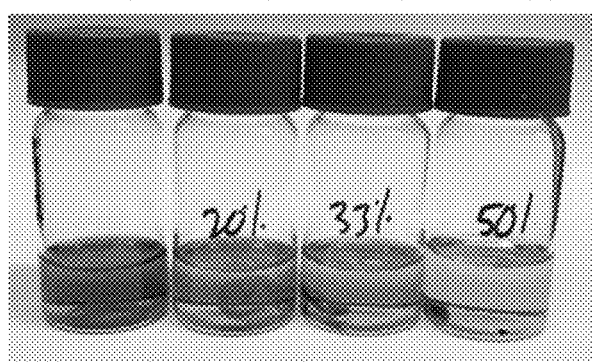

FIG. 78 shows samples containing higher levels of pDCPD dissolve in the presence of 2 equivalents of TBAF in THF.

Figure 79A:
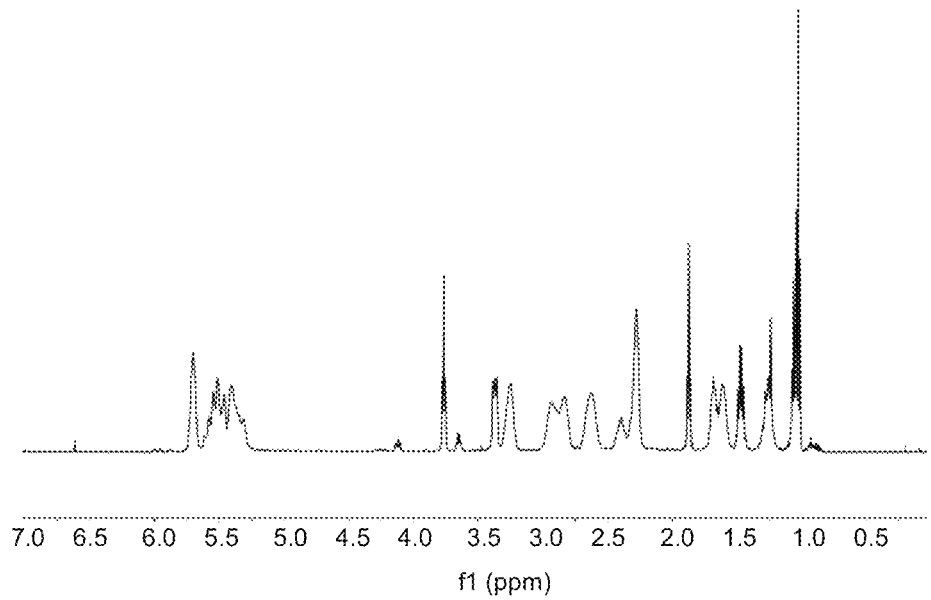
Figure 79B:
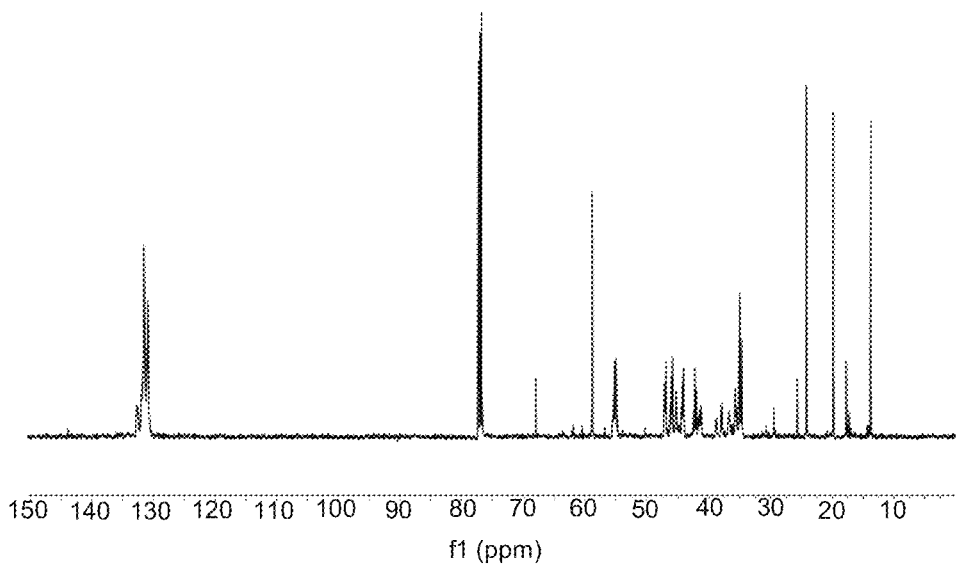
Figure 79C:
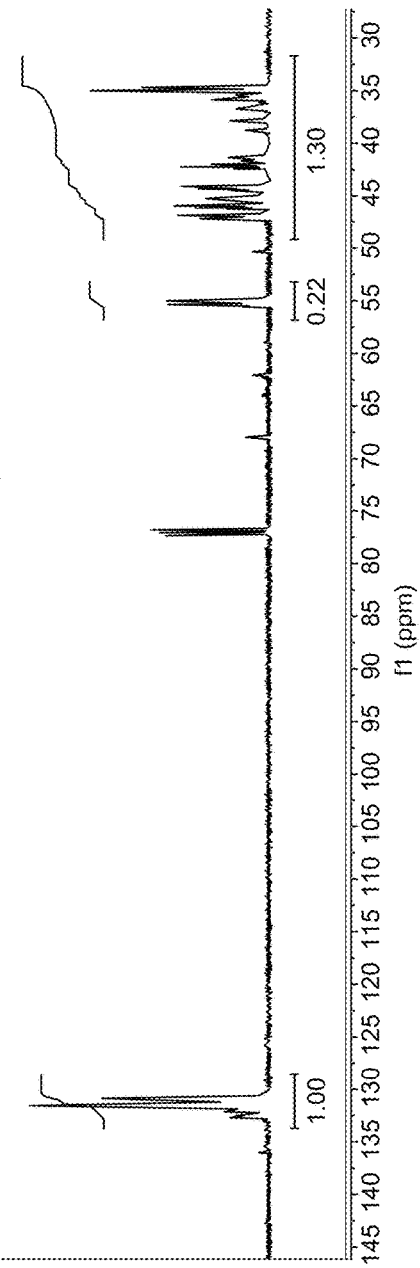
Figure 79C:
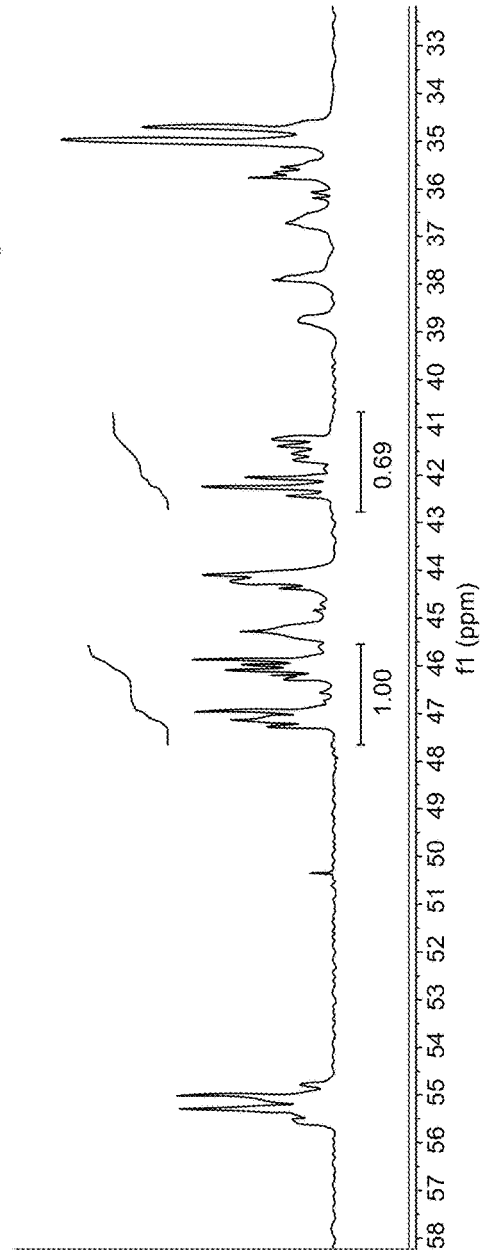

FIGS. 79A, 79B, and 79C show characterization of the pDCPD network enabled by degradation. FIGS. 79A and 79B show solution phase $^1H$ and $^{13}C$ NMR spectra of pDCPD fragments after dissolution in deuterated chloroform, respectively. FIG. 79C shows high-resolution analysis of the fragment enables identification of olefin geometry along material backbone.

Figure 80A:
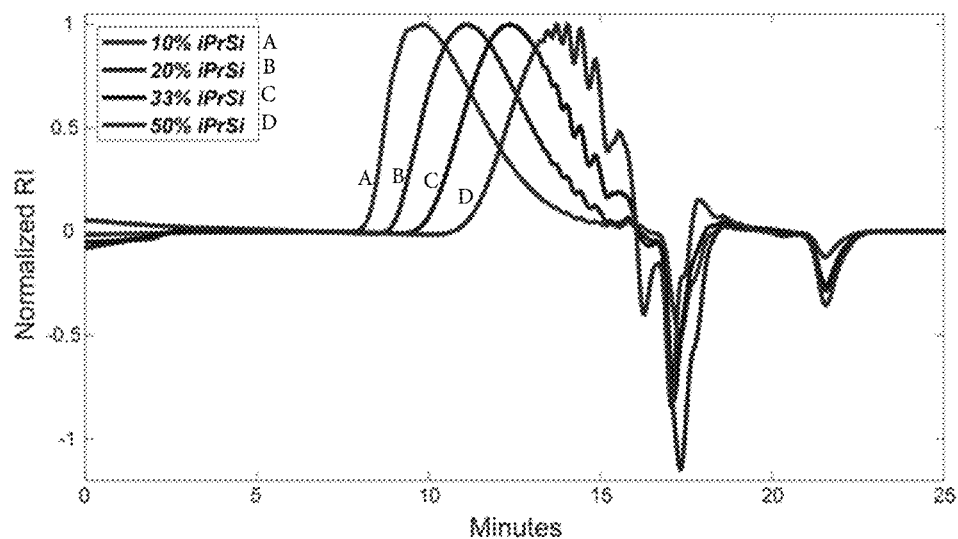
Figure 80B:
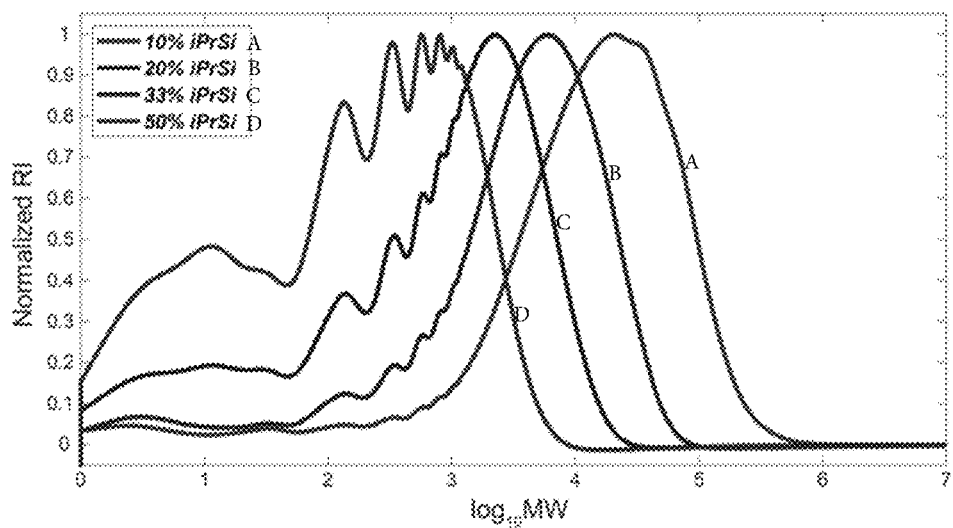

FIGS. 80A and 80B show a gel-permeation chromatograph of the degradation solution, confirming smaller fragments upon incorporation of more iPrSi monomer.

FIG. 81A shows a plot of calculated GPC Mw as a function of % iPrSi incorporation.

FIG. 81B shows a plot of calculated GPC Mw as a function of the molar ratio of DCPD to iPrSi monomers.

FIG. 82 shows an $^1H$ NMR of soluble fragments derived from materials with different amounts of hydroxyl groups, showing increased levels of silyl ether-derived fragments in the resulting material with higher levels of input. In parentheses are the theoretical integration values assuming equal addition of equal volumes of the two materials. Furthermore, these results indicate significant consumption of monomer under these conditions.

Figure 83:
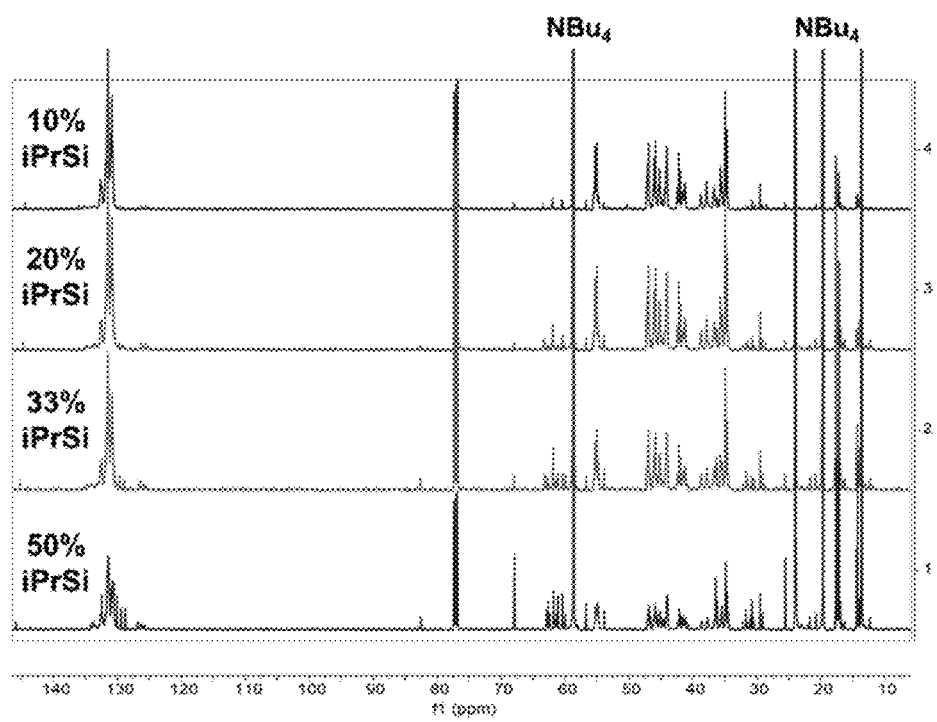

FIG. 83 shows a full solution-phase $^{13}C$ NMR spectra of the degradation solution, enabling characterization of crosslink density within the parent pDCPD material.

Figure 84A:
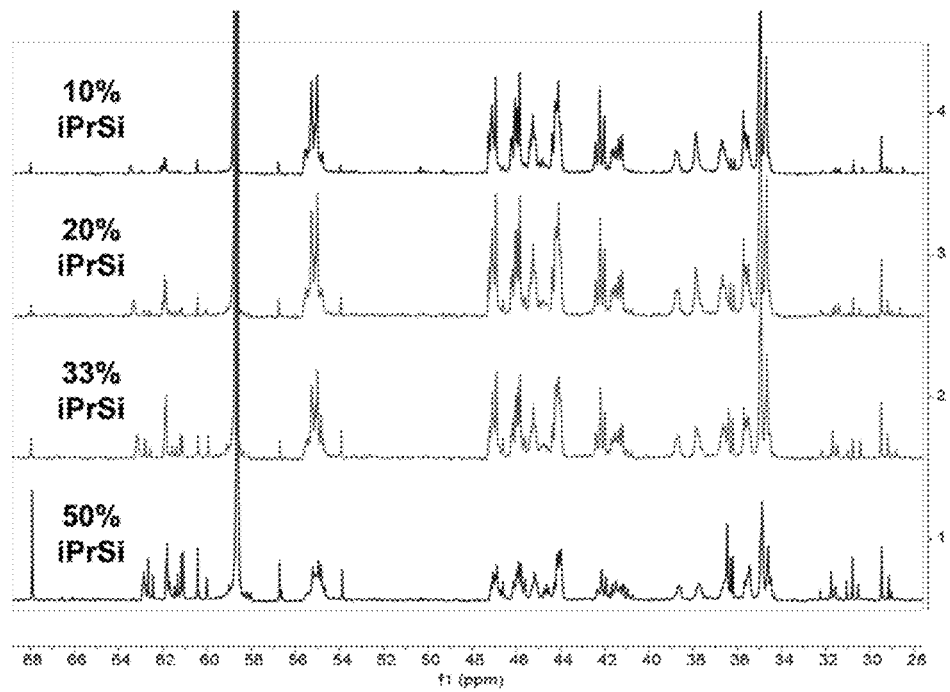

FIG. 84A shows from about 28-69 ppm of a $^{13}C$ NMR spectra of pDCPD fragments with different levels of iPrSi doping.

Figure 84B:
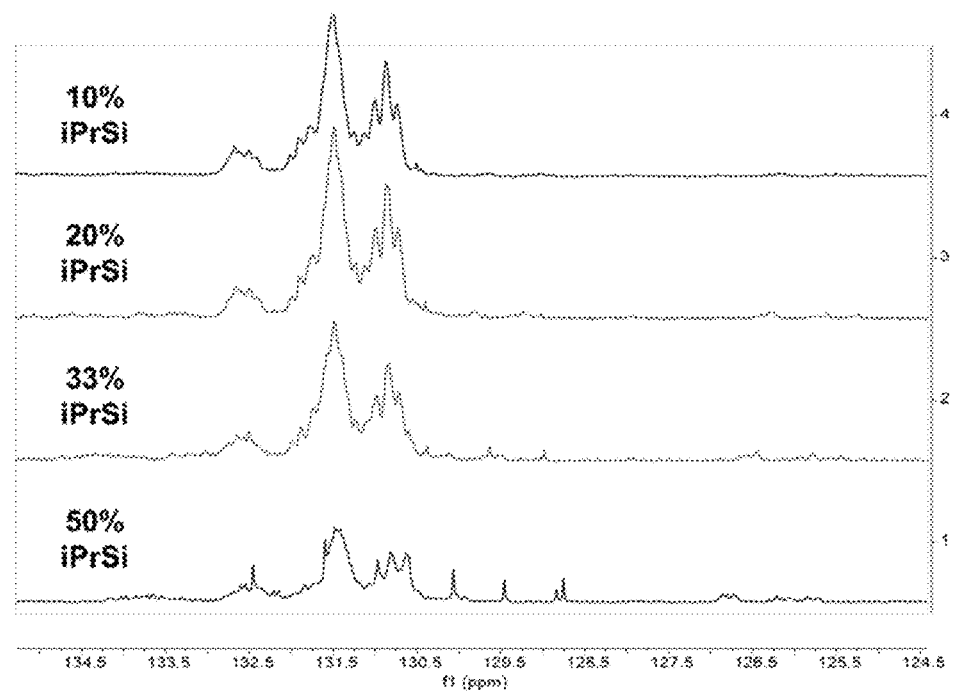

FIG. 84B shows from about 124.5-134 ppm of a $^{13}C$ NMR spectra of pDCPD fragments with different levels of iPrSi doping.

Figure 85A:
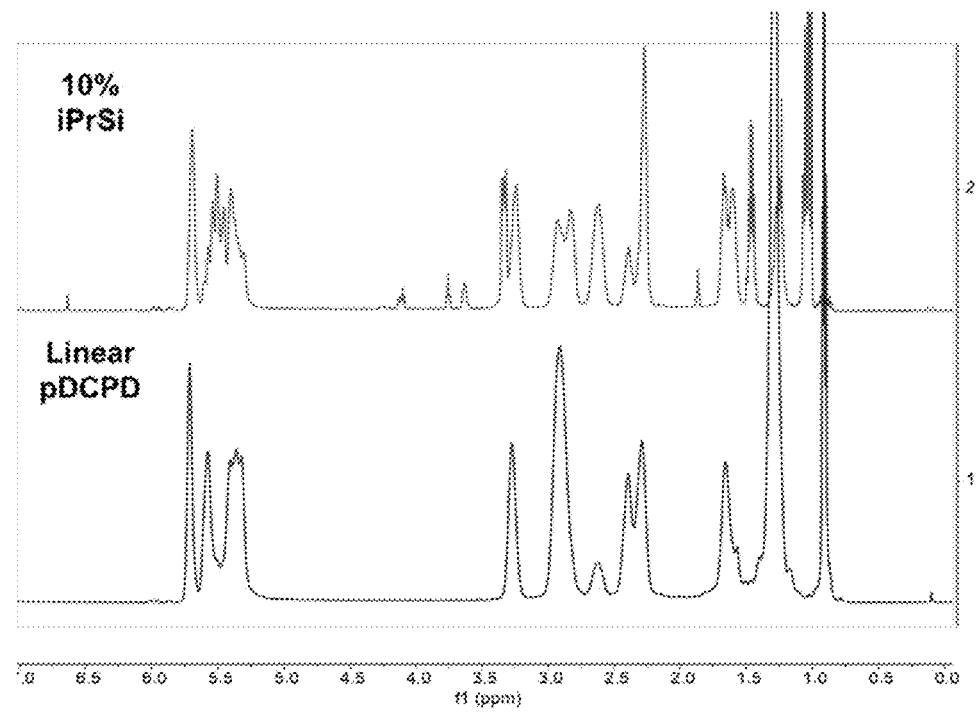
Figure 85B:
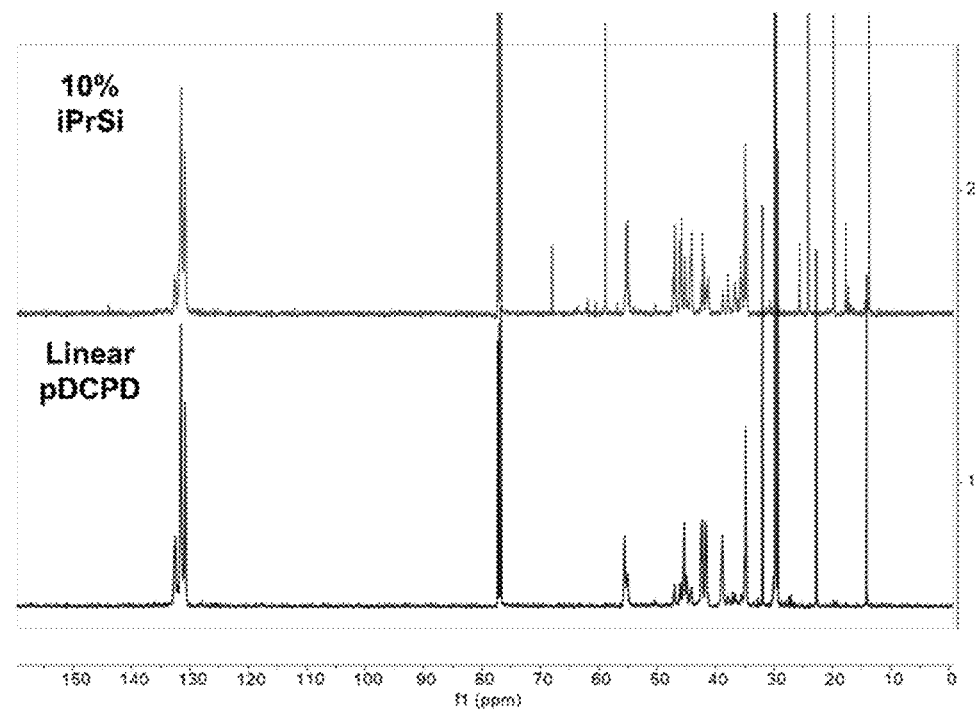

FIGS. 85A and 85B show a comparison to NMR spectra from pDCPD fragments described herein and independently synthesized linear pDCPD. Linear pDCPD was synthesized through the polymerization of DCPD with Schrock's catalyst, which has been shown to not participate in further crosslinking reactions. FIG. 85A shows from about 0-7 ppm and FIG. 85B shows from about 0-160 ppm.

Figure 86A:
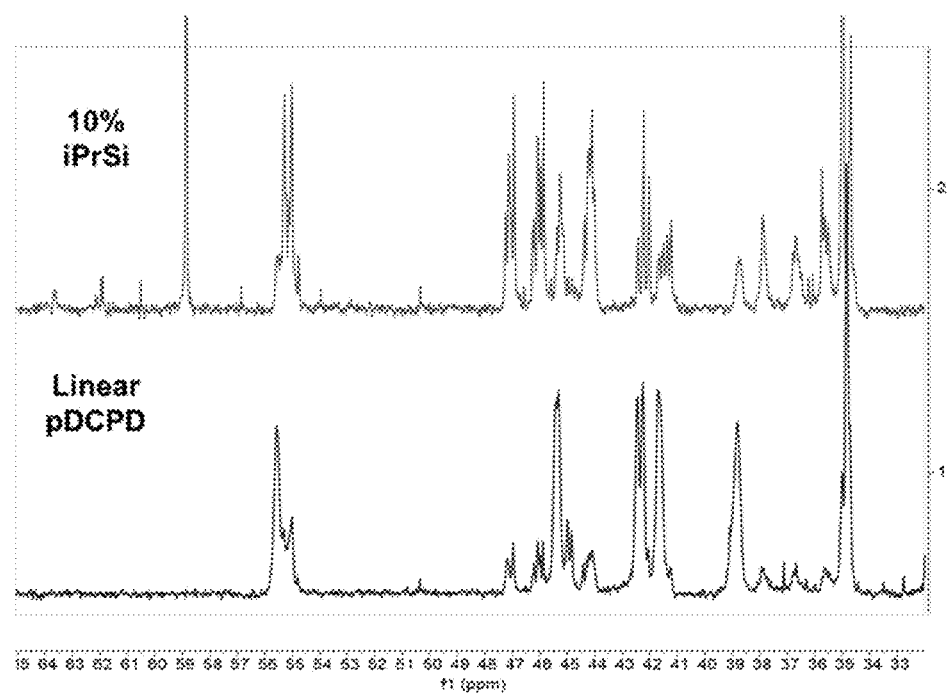
Figure 86B:
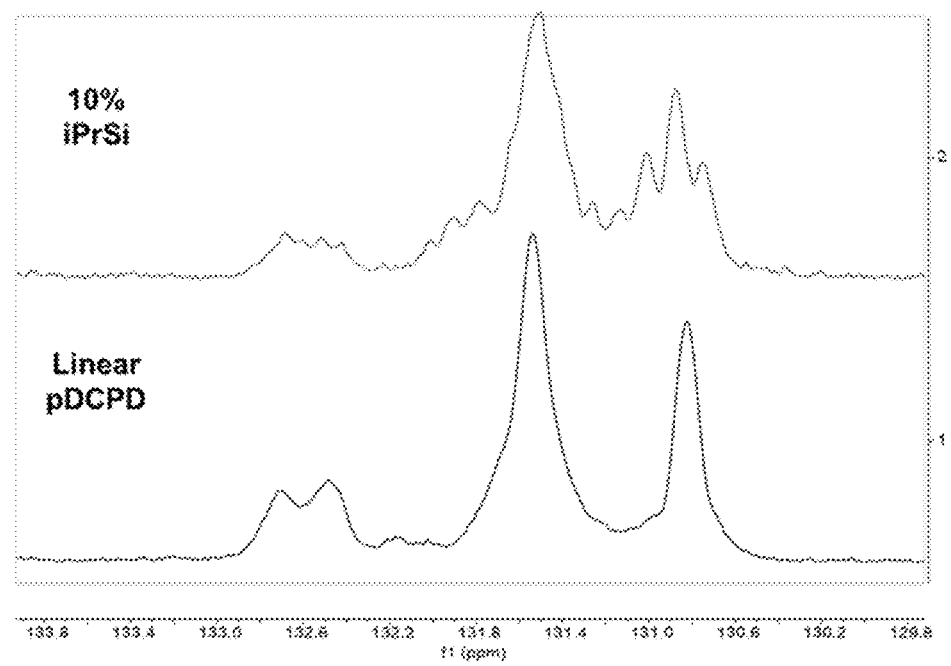

FIGS. 86A and 86B show an additional $^{13}C$ spectra comparing pDCPD fragments described herein to linear pDCPD. The differences in the olefin regions, as evidenced in B, are assigned to pDCPD crosslinks. FIG. 86A shows from about 32-65 ppm and FIG. 86B shows from about 129.8-133.8 ppm.

Figure 87:
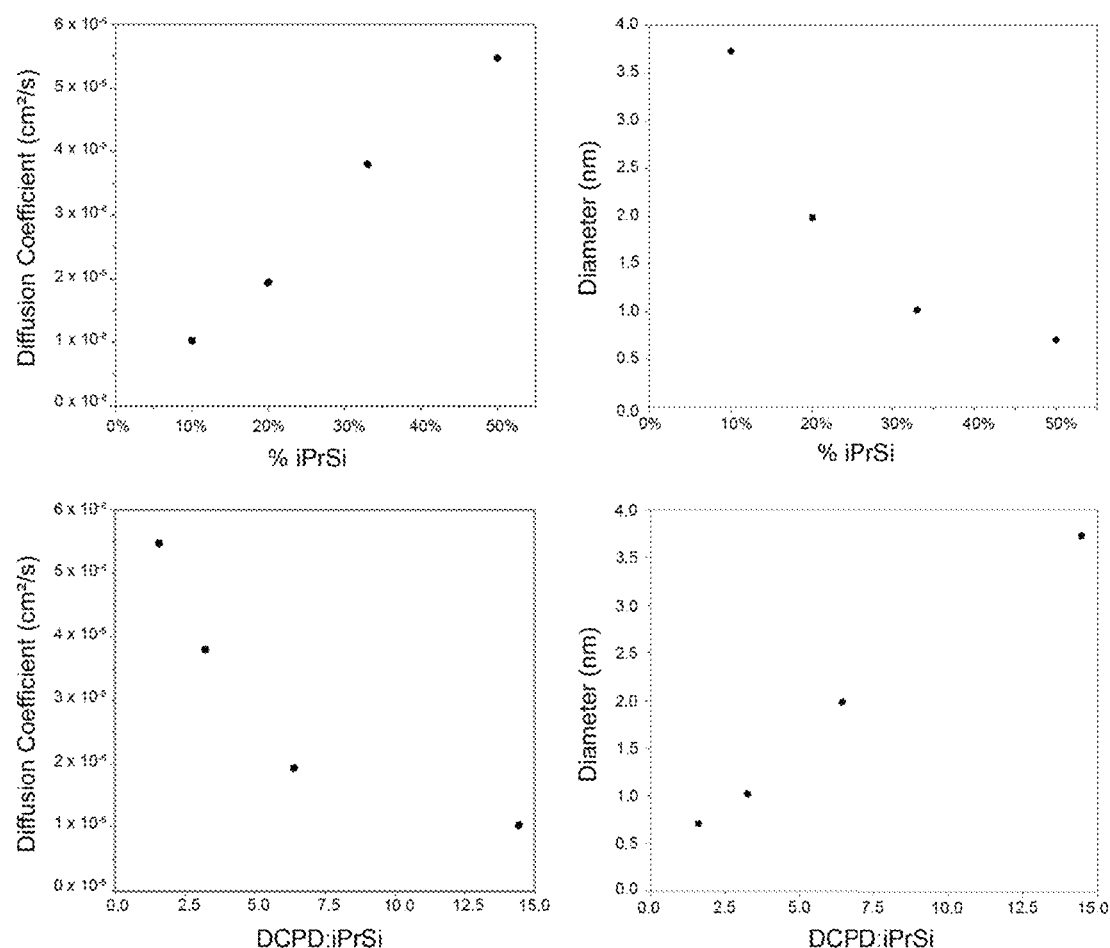

FIG. 87 shows a plot of diffusion rate and diameters (calculated from the Stokes-Einstein equation) as a function of % v/v iPrSi or the molar ratio of DCPD to iPrSi monomers. These results demonstrate that higher levels of iPrSi incorporation result in pDCPD result in fragments with a smaller diameter.

Figure 88:
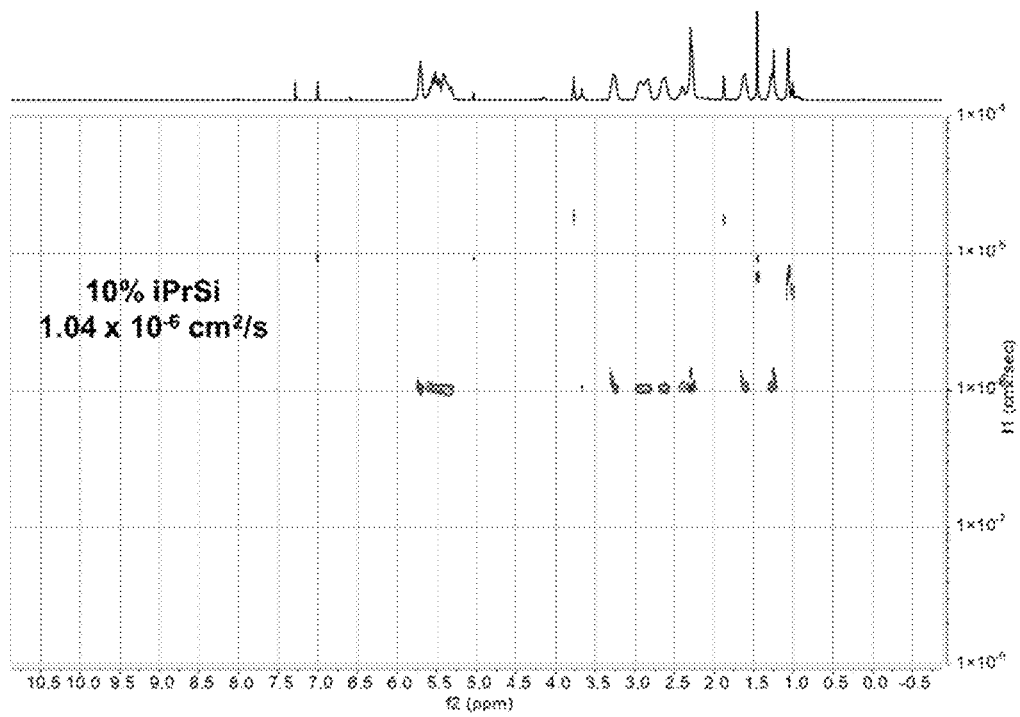

FIG. 88 shows a DOSY spectra of the degradation solution from pDCPD doped with 10% iPrSi.

Figure 89:
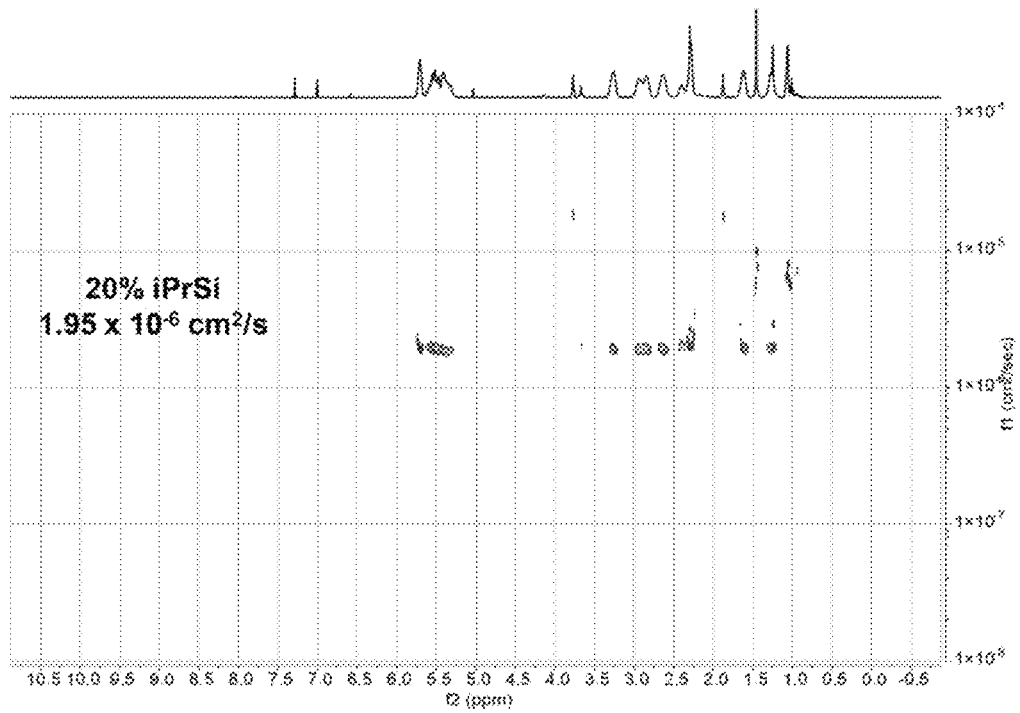

FIG. 89 shows a DOSY spectra of the degradation solution from pDCPD doped with 20% iPrSi.

Figure 90:
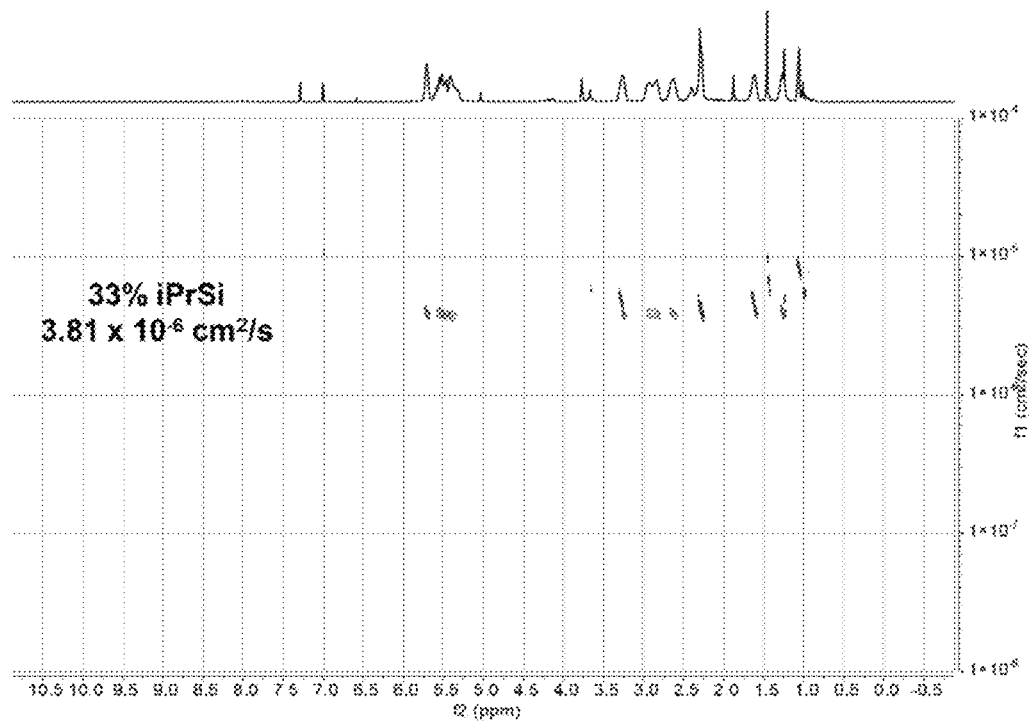

FIG. 90 shows a DOSY spectra of the degradation solution from pDCPD doped with 33% iPrSi.

Figure 91:
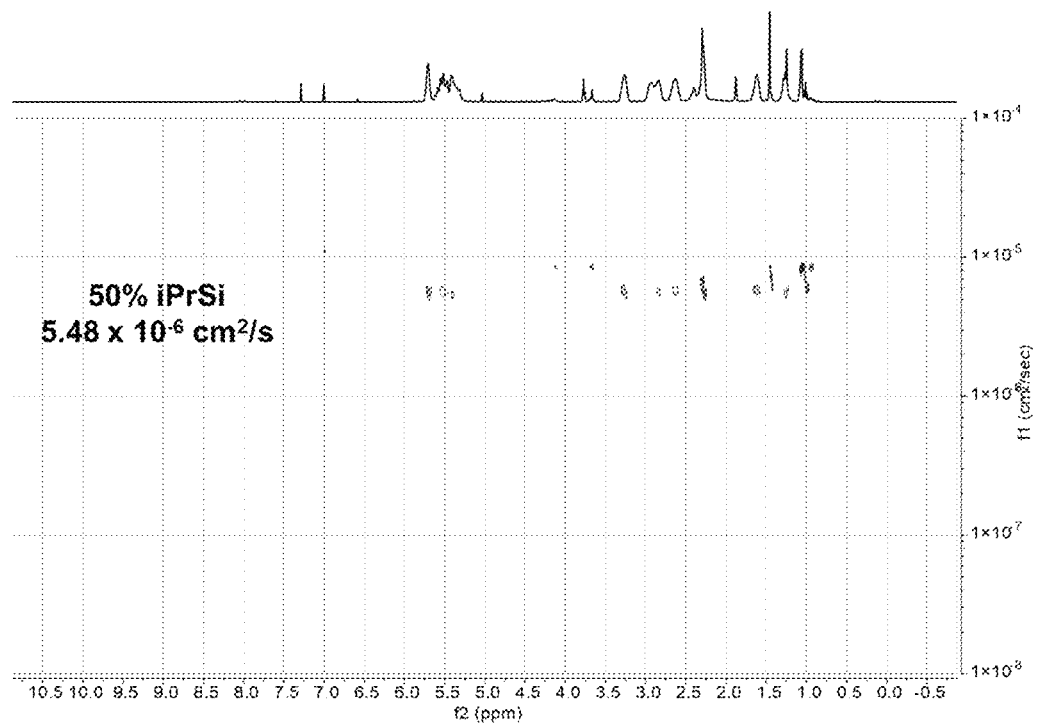

FIG. 91 shows a DOSY spectra of the degradation solution from pDCPD doped with 50% iPrSi.

Figure 92:
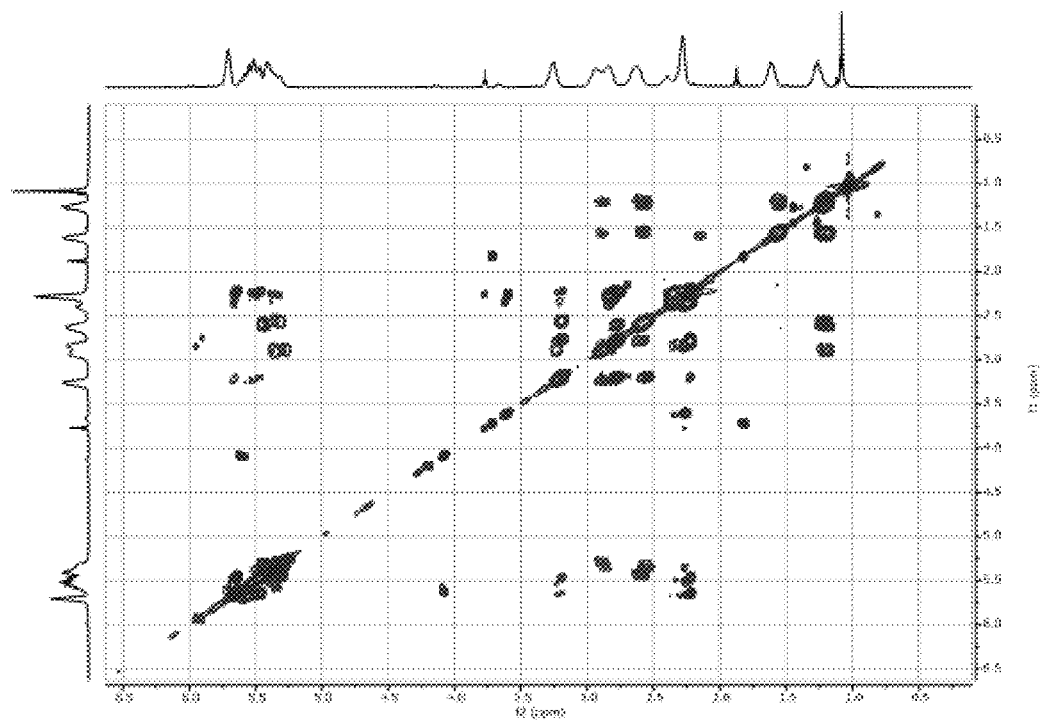

FIG. 92 shows a solution-phase COSY of the degradation solution derived from 10% iPrSi doped pDCPD.

Figure 93:
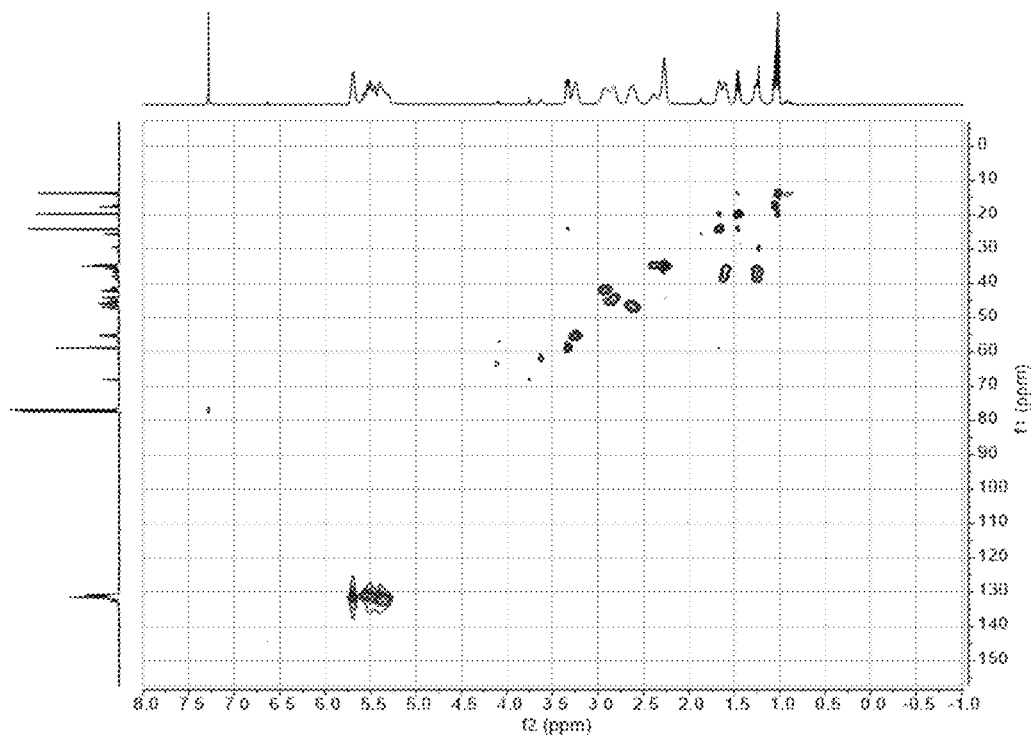

FIG. 93 shows a solution-phase HSQC of the degradation solution derived from 10% iPrSi doped pDCPD.

Figure 94:
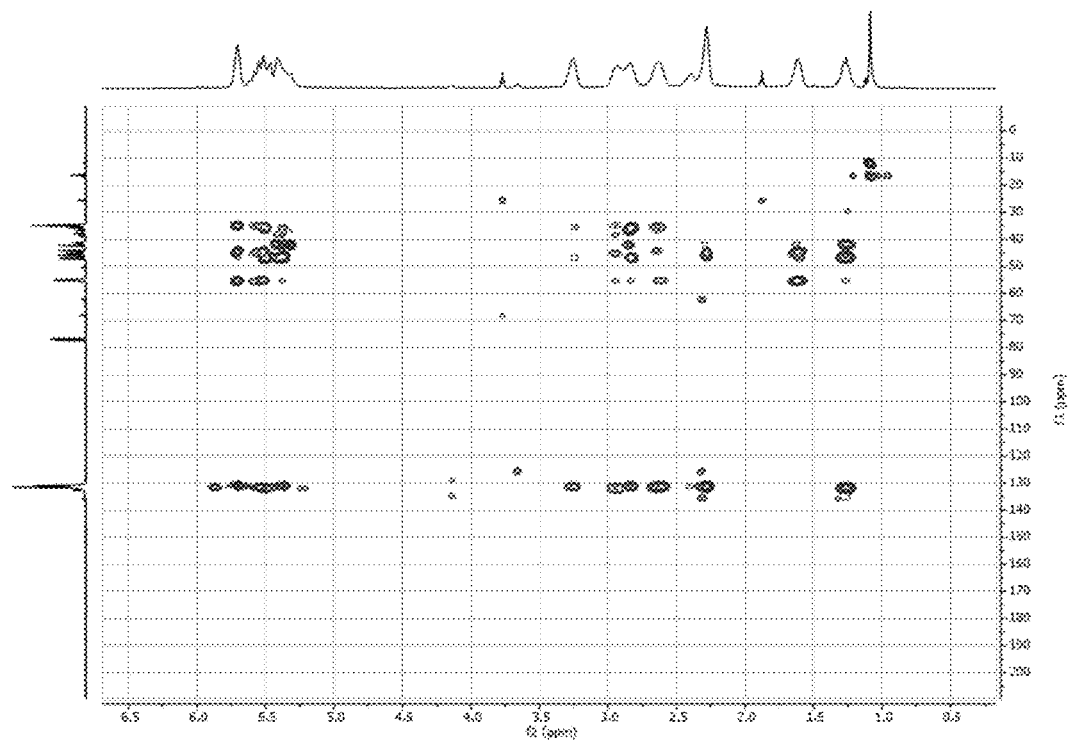

FIG. 94 shows a solution-phase HMBC of the degradation solution derived from 10% iPrSi doped pDCPD.

Figure 95:
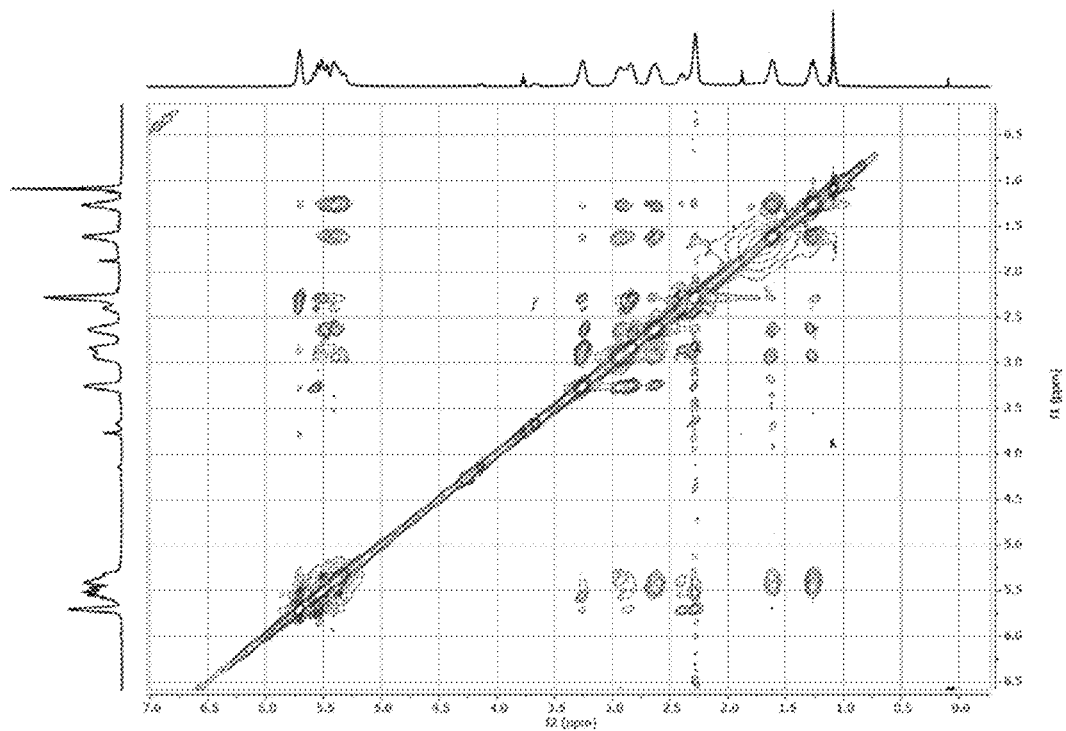

FIG. 95 shows a solution-phase NOESY of the degradation solution from 10% iPrSi-doped pDCPD.

Figure 96A:
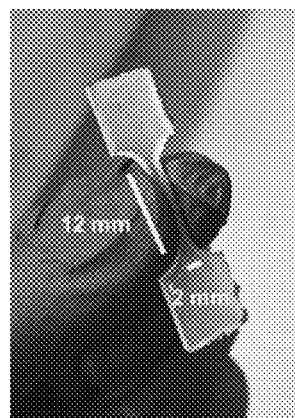
Figure 96B:
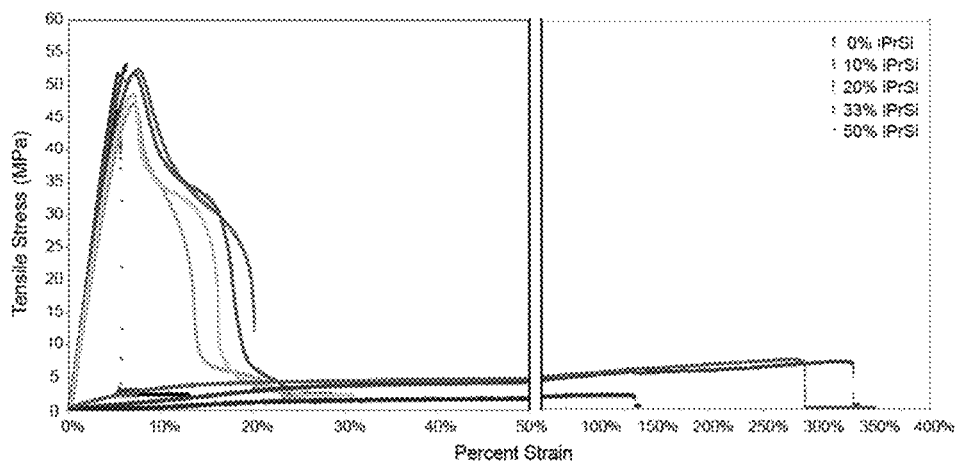
Figure 96C:
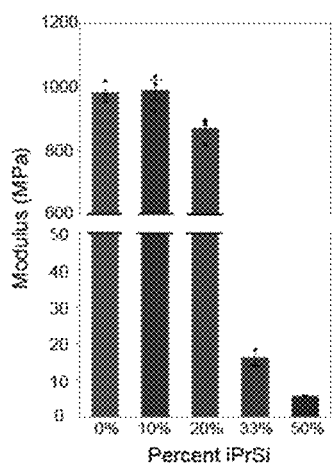
Figure 96D:
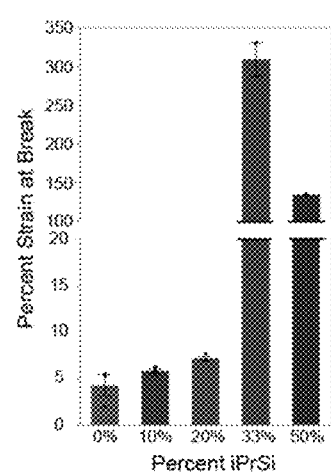
Figure 96E:
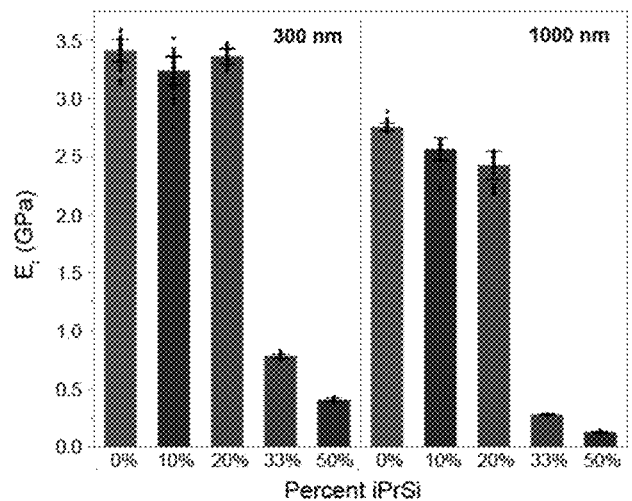

FIGS. 96A to 96E show a variety tensile testing results. FIG. 96A shows that a doped pDCPD can be molded into dogbones for tensile testing. FIG. 96B shows stress-stain curves for the pDCPD, demonstrating virtually identical curves for 0 and 10% iPrSi modified pDCPD. FIG. 96C shows a quantification of tensile modulus for all samples from tensile testing. FIG. 96D shows a quantification of percent strain at break for all samples from tensile testing. FIG. 96E shows a quantification of reduced modulus for all samples from nanoindentation experiments performed at two different depths.

Figure 97:
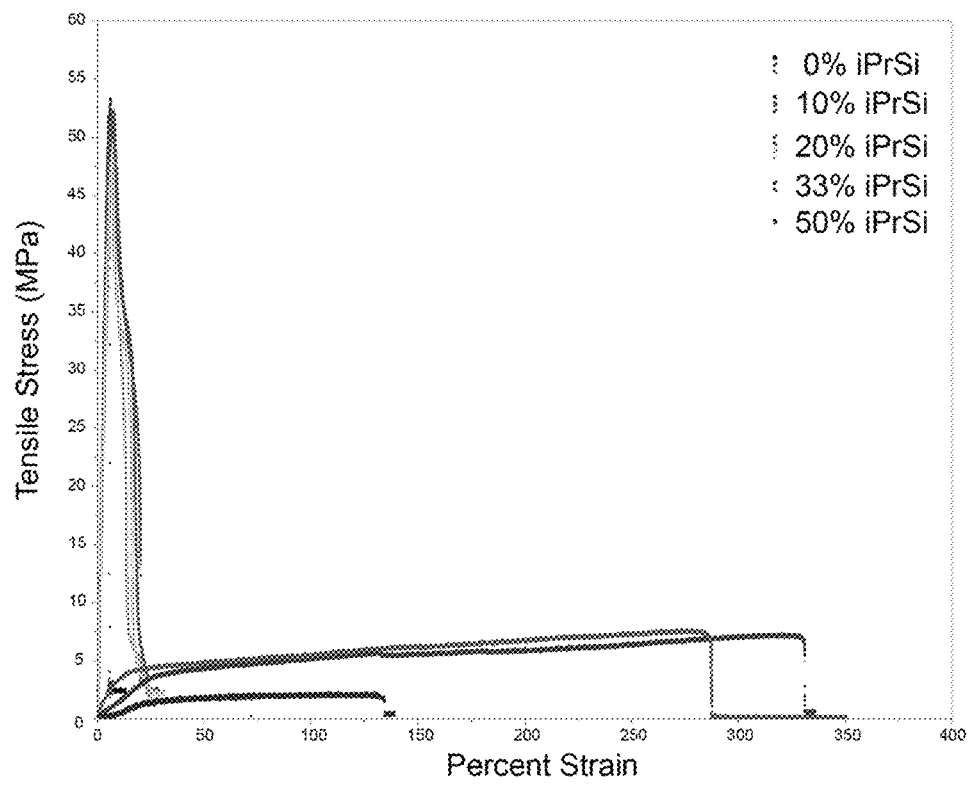

FIG. 97 shows an example of full stress-strain curves from pDCPD samples containing different levels of iPrSi as depicted in FIG. 69B.

FIG. 98 shows an example of thermogravimetric analysis of pDCPD samples containing different levels of iPrSi.

FIGS. 99A to 99D show an example evaluation of a silyl ether crosslinker in pDCPD.

Figure 99C:
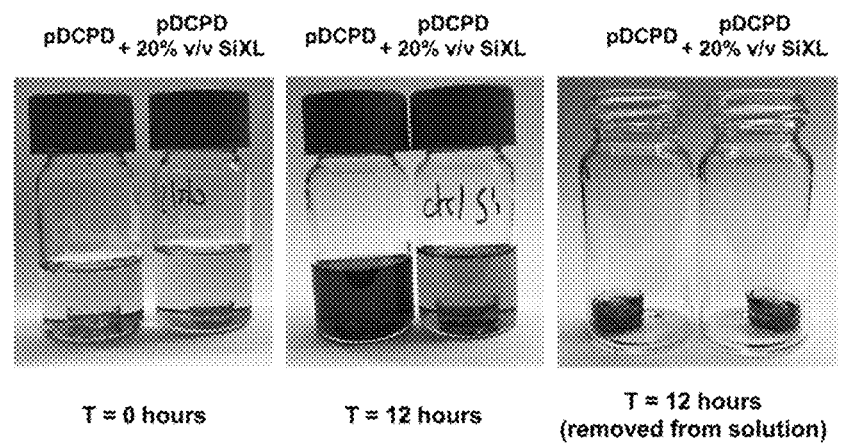

FIG. 99A shows proposed incorporation of SiXL into pDCPD. FIG. 99B shows images of pDCPD containing 0 or 20% SiXL. FIG. 99C shows images of the pDCPD containing 0 or 20% SiXL after treatment with TBAF. Both samples remain fully intact after treatment with TBAF.

Figure 99D:
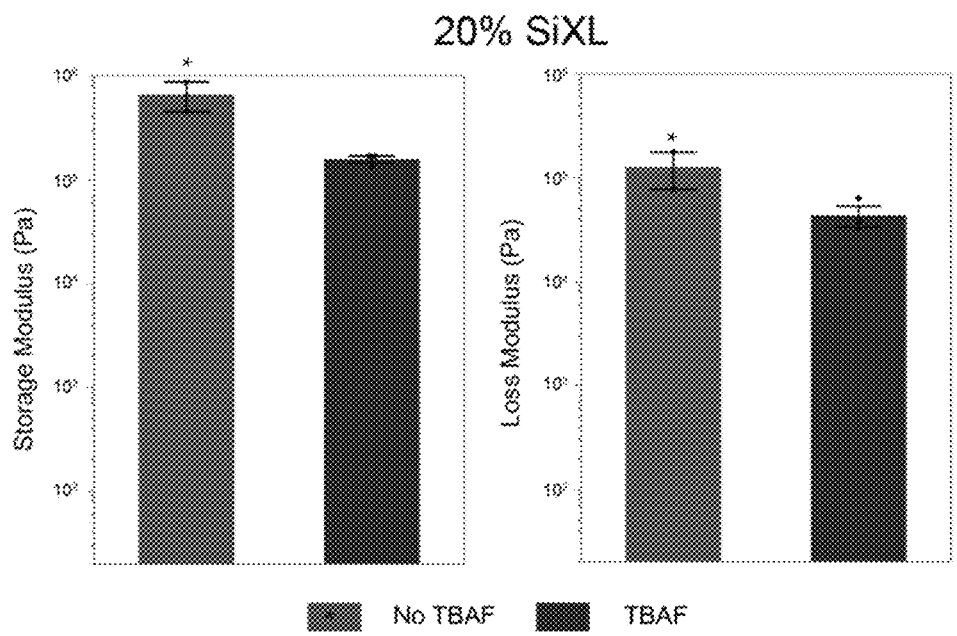

FIG. 99D shows storage and loss moduli of 20% SiXL doped pDCPD either swollen in THF or treated with TBAF. While some loss of mechanical properties in the TBAF-treated sample is apparent, consistent with a loss of crosslinks in the material, the material maintains a significant portion of its original mechanical properties.

Figure 100:
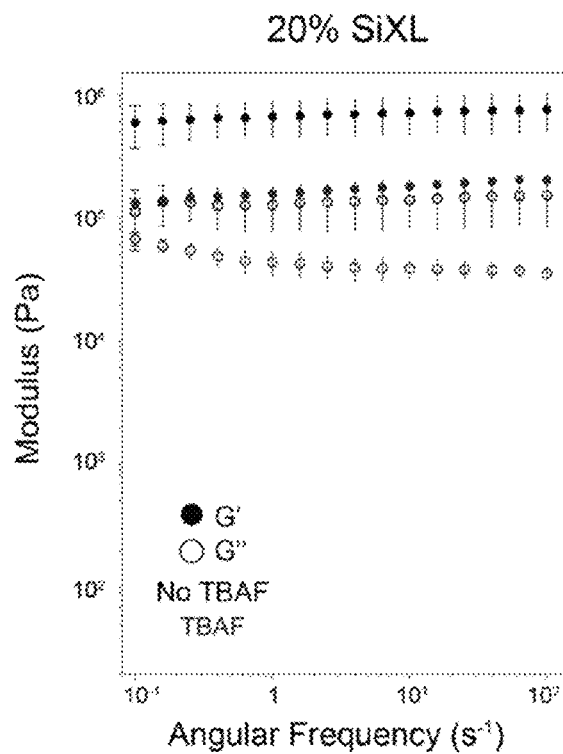

FIG. 100 shows an example of rheological measurements of THF swollen samples of degraded pDCPD samples with control samples with different levels of crosslinking. pDCPD doped with 20% SiXL shows significant mechanical strength even after treatment with TBAF, consistent with the presence of a large number of non-degradable crosslinks.

Figure 101:
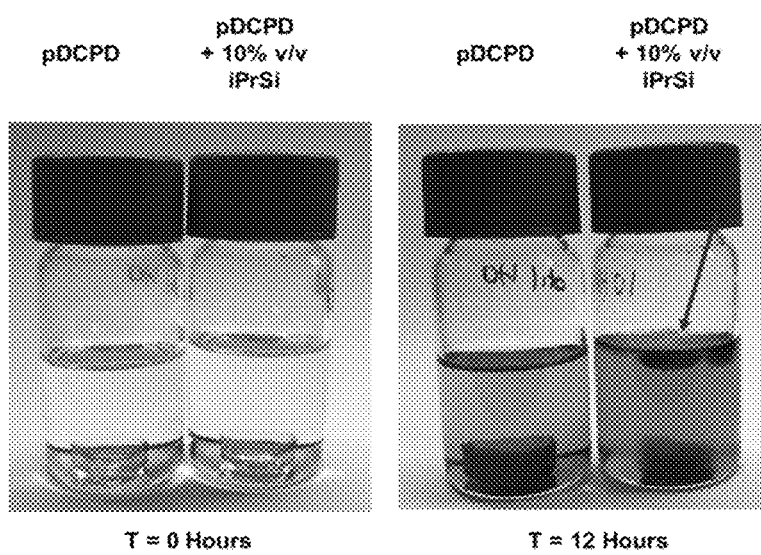

FIG. 101 shows an example of pDCPD containing 10% v/v iPrSi dissolves in 15% Conc. HCl in THF. Samples were incubated in 15% concentrated HCl in THF for 12 hours. After this time, the pDCPD remained intact whereas the pDCPD containing iPrSi showed significant levels of dissolution. The arrow indicates droplets consisting of soluble fragments derived from the parent material.

Figure 102A:
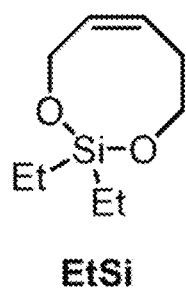
Figure 102B:
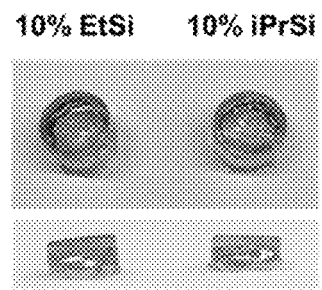

FIGS. 102A to 102D show a synthesis and degradation of EtSi or iPrSi doped pDCPD. FIG. 102A shows the structure of EtSi monomer, which differs from iPrSi in terms of the alkyl substituents on the silyl ether group. The less sterically hindered ethyl groups should render the silyl ether more susceptible to cleavage. FIG. 102B shows images of 10%

Figure 102C:
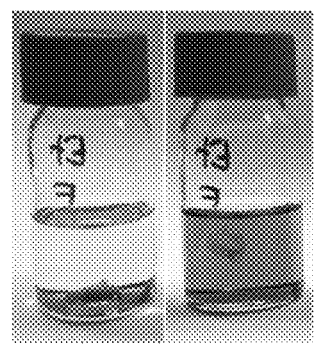
Figure 102D:
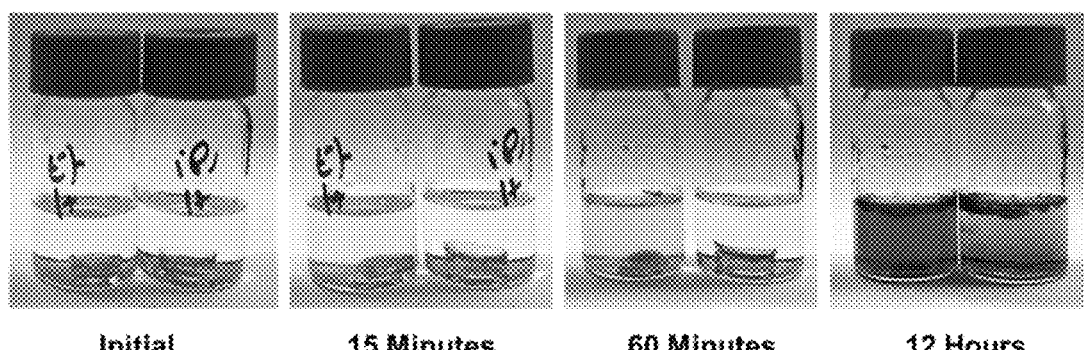

EtSi or iPrSi doped pDCPD. FIG. 102C shows 10% EtSi dissolves fully in 0.5 M TBAF in THF after 12 hours. FIG. 102D shows images of 10% EtSi or iPrSi doped pDCPD exposed to THF containing 15% concentrated aqueous HCl (12.1 N). The EtSi sample shows noticeably more rapid degradation under these conditions as compared to the iPrSi sample. Both samples are largely degraded by 12 hours.

Figure 103:
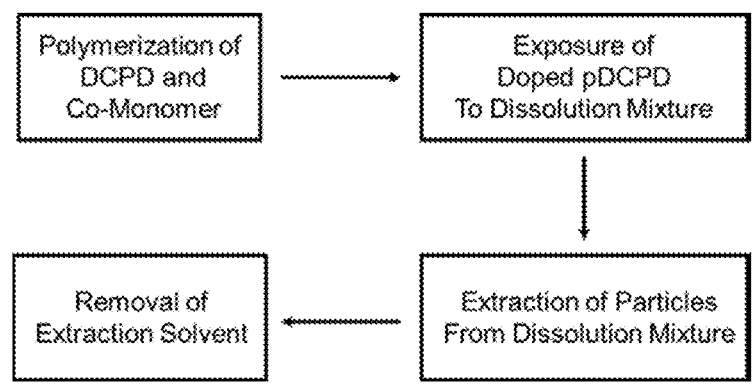

FIG. 103 shows the general workflow for pDCPD nanoparticle synthesis.

Figure 104A:

Figure 104B:
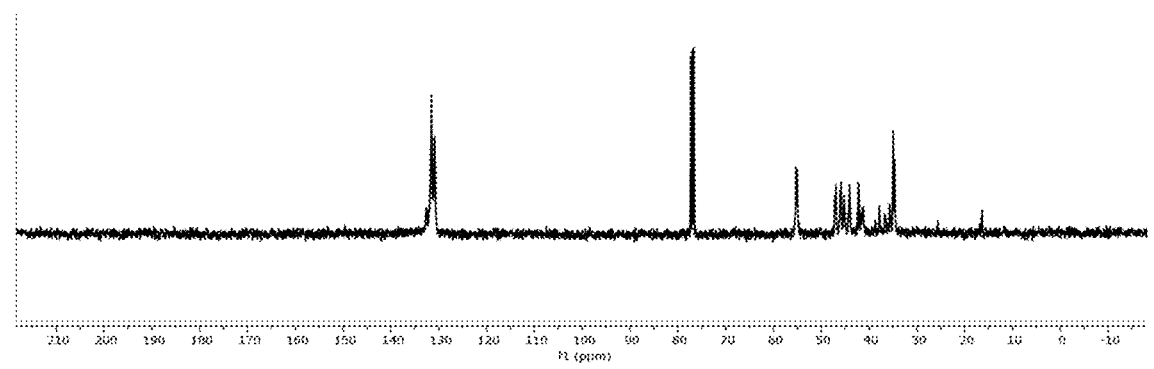

FIG. 104A and FIG. 104B show NMR spectroscopy of particles derived from 10% v/v incorporation of a degradable silyl ether monomer. FIG. 104A shows $^1$H NMR spectroscopy.

FIG. 104B shows $^{13}$C NMR spectroscopy.

Figure 105:
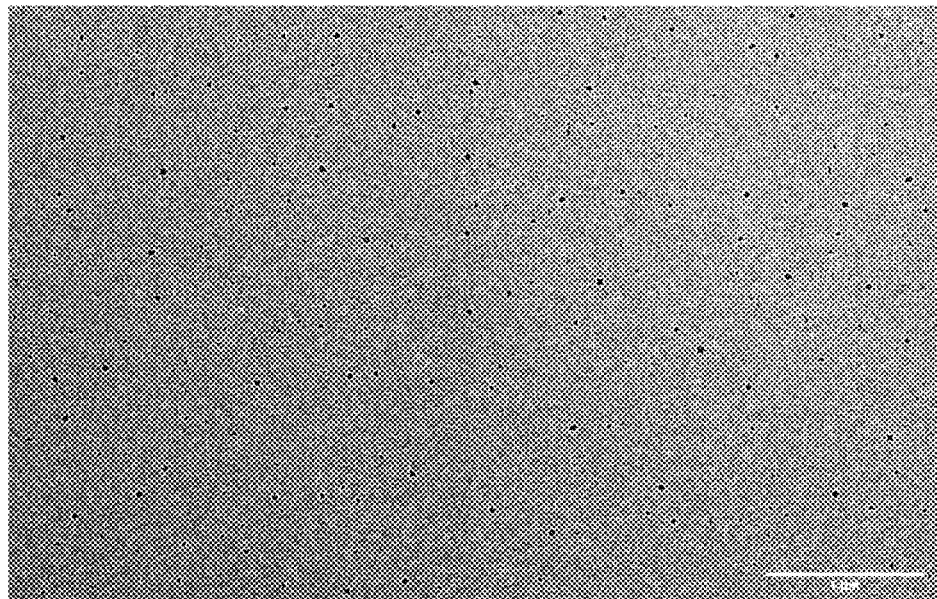

FIG. 105 shows TEM images of particles (stained with $RuO_4$) derived from 10% v/v incorporation of a degradable silyl ether monomer.

Figure 106:
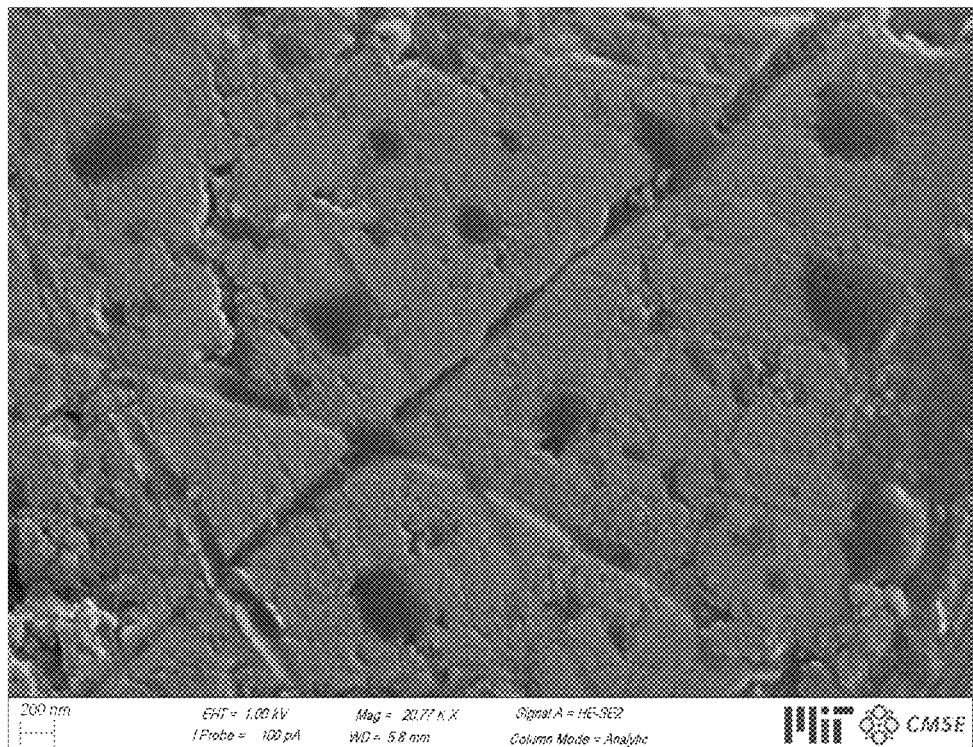

FIG. 106 shows SEM images of particles (dark) derived from 10% v/v incorporation of a degradable silyl ether monomer.

Figure 107A:
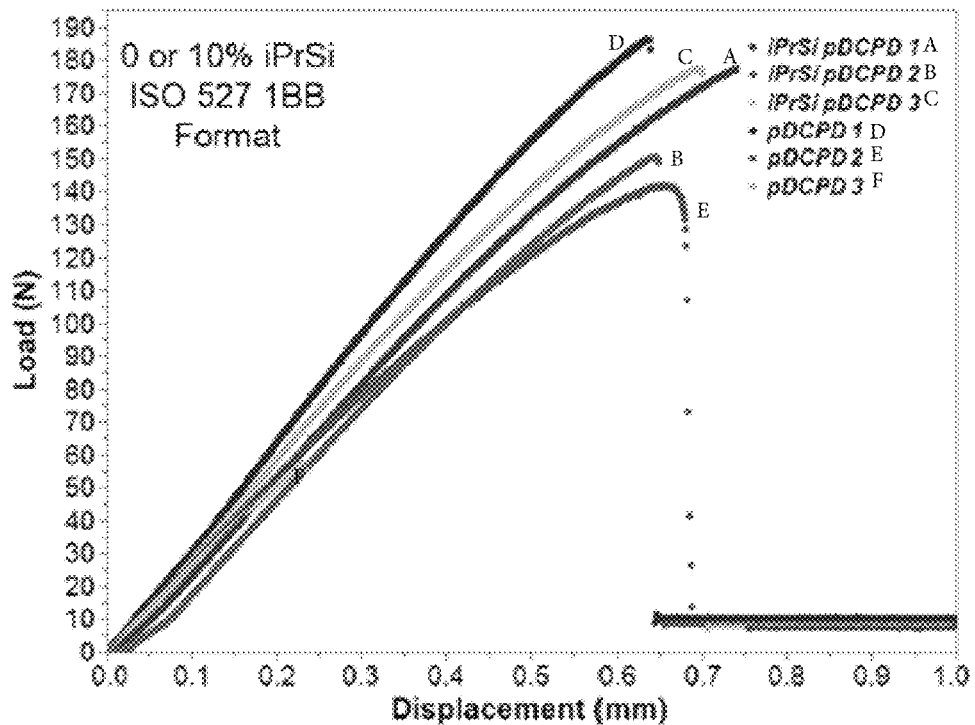
Figure 107B:
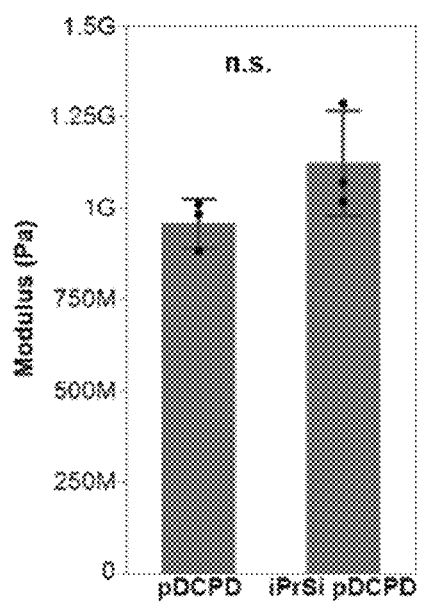

FIGS. 107A and 107B show silyl ether doping maintained appearance and mechanical properties of the polymer.

DEFINITIONS

Unless otherwise required by context, singular terms shall include pluralities, and plural terms shall include the singular.

Other than in the examples, or where otherwise indicated, all numbers expressing quantities of ingredients or reaction conditions used herein should be understood as modified in all instances by the term "about." "About" and "approximately" shall generally mean an acceptable degree of error for the quantity measured given the nature or precision of the measurements. Exemplary degrees of error are within 20 percent (%), typically, within 10%, or more typically, within 5%, 4%, 3%, 2% or 1% of a given value or range of values.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *Marchs Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can include one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The disclosure additionally encompasses compounds as individual isomers substantially free of other isomers, and alternatively, as mixtures of various isomers.

When a range of values is listed, it is intended to encompass each value (e.g., each of the two end values ("inclusive")) and sub-range within the range. For example "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

The term "alkyl" refers to a radical of a straight-chain or branched saturated hydrocarbon group. In some embodiments, an alkyl group has 1 to 1000 carbon atoms ("$C_1$-$C_{1000}$ alkyl"), 1 to 900 carbon atoms ("$C_1$-$C_{900}$ alkyl"), 1 to 800 carbon atoms ("$C_1$-$C_{800}$ alkyl"), 1 to 700 carbon atoms ("$C_1$-$C_{700}$ alkyl"), 1 to 600 carbon atoms ("$C_1$-$C_{600}$ alkyl"), 1 to 500 carbon atoms ("$C_1$-$C_{500}$ alkyl"), 1 to 400 carbon atoms ("$C_1$-$C_{400}$ alkyl"), 1 to 300 carbon atoms ("$C_1$-$C_{300}$ alkyl"), 1 to 200 carbon atoms ("$C_1$-$C_{200}$ alkyl"), 1 to 100 carbon atom ("$C_1$-$C_{100}$ alkyl"). In some embodiments, an alkyl group has 1 to 10 carbon atoms ("$C_1$-$C_{10}$ alkyl"), 1 to 9 carbon atoms ("$C_1$-$C_9$ alkyl"), 1 to 8 carbon atoms ("$C_1$-$C_8$ alkyl"), 1 to 7 carbon atoms ("$C_1$-$C_7$ alkyl"), 1 to 6 carbon atoms ("$C_1$-$C_6$ alkyl"), 1 to 5 carbon atoms ("$C_1$-$C_5$ alkyl"), 1 to 4 carbon atoms ("$C_1$-$C_4$ alkyl"), 1 to 3 carbon atoms ("$C_1$-$C_3$ alkyl"), 1 to 2 carbon atoms ("$C_1$-$C_2$ alkyl"), or 1 carbon atom ("$C_1$ alkyl"). Examples of $C_1$-$C_6$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents.

The term "alkenyl" refers to a radical of a straight-chain or branched hydrocarbon group having from 2 to 1000 carbon atoms and one or more carbon-carbon double bonds (e.g., 1, 2, 3, or 4 double bonds). In some embodiments, an alkenyl group has 2 to 1000 carbon atoms ("$C_2$-$C_{1000}$ alkenyl"), 2 to 900 carbon atoms ("$C_2$-$C_{900}$ alkenyl"), 2 to 800 carbon atoms ("$C_2$-$C_{800}$ alkenyl"), 2 to 700 carbon atoms ("$C_2$-$C_{700}$ alkenyl"), 2 to 600 carbon atoms ("$C_2$-$C_{600}$ alkenyl"), 2 to 500 carbon atoms ("$C_2$-$C_{500}$ alkenyl"), 2 to 400 carbon atoms ("$C_2$-$C_{400}$ alkenyl"), 2 to 300 carbon atoms ("$C_2$-$C_{300}$ alkenyl"), 2 to 200 carbon atoms ("$C_2$-$C_{200}$ alkenyl"), 2 to 100 carbon atom ("$C_2$-$C_{100}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Unless otherwise specified, each instance of an alkenyl group is independently unsubstituted (an "unsubstituted alkenyl") or substituted (a "substituted alkenyl") with one or more substituents. In an alkenyl group, a C=C double bond for which the stereochemistry is not specified (e.g., —CH=CHCH$_3$, 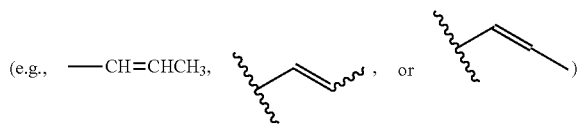 )

may be in the (E)- or (Z)-configuration.

The term "alkynyl" refers to a radical of a straight-chain or branched hydrocarbon group having from 2 to 1000 carbon atoms and one or more carbon-carbon triple bonds (e.g., 1, 2, 3, or 4 triple bonds). In some embodiments, an alkynyl group has 2 to 1000 carbon atoms ("$C_2$-$C_{1000}$ alkynyl"), 2 to 900 carbon atoms ("$C_2$-$C_{900}$ alkynyl"), 2 to 800 carbon atoms ("$C_2$-$C_{800}$ alkynyl"), 2 to 700 carbon atoms ("$C_2$-$C_{700}$ alkynyl"), 2 to 600 carbon atoms ("$C_2$-$C_{600}$ alkynyl"), 2 to 500 carbon atoms ("$C_2$-$C_{500}$ alkynyl"), 2 to 400 carbon atoms ("$C_2$-$C_{400}$ alkynyl"), 2 to 300 carbon atoms ("$C_2$-$C_{300}$ alkynyl"), 2 to 200 carbon atoms ("$C_2$-$C_{200}$ alkynyl"), 2 to 100 carbon atom ("$C_2$-$C_{100}$ alkynyl"). In some embodiments, an alkynyl group has 2 to 9 carbon atoms ("$C_{2-9}$ alkynyl"), 2 to 8 carbon atoms ("$C_{2-8}$ alkynyl"), 2 to 7 carbon atoms ("$C_{2-7}$ alkynyl"), 2 to 6 carbon atoms ("$C_{2-6}$ alkynyl"), 2 to 5 carbon atoms ("$C_{2-5}$ alkynyl"), 2 to 4 carbon atoms ("$C_{2-4}$ alkynyl"), 2 to 3 carbon atoms ("$C_{2-3}$ alkynyl"), or 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Unless otherwise specified, each instance of an alkynyl group is independently unsubstituted (an "unsubstituted alkynyl") or substituted (a "substituted alkynyl") with one or more substituents.

The term "heteroalkyl" refers to an alkyl group which further includes at least one heteroatom (e.g., 1, 2, 3, or 4 heteroatoms) selected from oxygen, nitrogen, phosphorus, or sulfur within (i.e., inserted between adjacent carbon atoms of) and/or placed at one or more terminal position(s) of the parent chain. In certain embodiments, a heteroalkyl group refers to a saturated group having from 1 to 1000 carbon atoms and 1 or more heteroatoms within the parent chain ("$C_1$-$C_{1000}$ heteroalkyl"), 1 to 900 carbon atoms and 1 or more heteroatoms within the parent chain ("$C_1$-$C_{900}$ heteroalkyl"), 1 to 800 carbon atoms and 1 or more heteroatoms within the parent chain ("$C_1$-$C_{800}$ heteroalkyl"), 1 to 700 carbon atoms and 1 or more heteroatoms within the parent chain ("$C_1$-$C_{700}$ heteroalkyl"), 1 to 600 carbon atoms and 1 or more heteroatoms within the parent chain ("$C_1$-$C_{600}$ heteroalkyl"), 1 to 500 carbon atoms and 1 or more heteroatoms within the parent chain ("$C_1$-$C_{500}$ heteroalkyl"), 1 to 400 carbon atoms and for more heteroatoms within the parent chain ("$C_1$-$C_{400}$ heteroalkyl"), 1 to 300 carbon atoms and 1 or more heteroatoms within the parent chain ("$C_1$-$C_{300}$ heteroalkyl"), 1 to 200 carbon atoms and 1 or more heteroatoms within the parent chain ("$C_1$-$C_{200}$ heteroalkyl"), or 1 to 100 carbon atoms and 1 or more heteroatoms within the parent chain ("$C_1$-$C_{100}$ heteroalkyl"). In certain embodiments, a heteroalkyl group refers to a saturated group having from 1 to 10 carbon atoms and 1 or more heteroatoms within the parent chain ("$C_1$-$C_{10}$ heteroalkyl"), 1 to 9 carbon atoms and 1 or more heteroatoms within the parent chain ("$C_1$-$C_9$ heteroalkyl"), 1 to 8 carbon atoms and 1 or more heteroatoms within the parent chain ("$C_1$-$C_8$ heteroalkyl"), 1 to 7 carbon atoms and 1 or more heteroatoms within the parent chain ("$C_1$-$C_7$ heteroalkyl"), 1 to 6 carbon atoms and 1 or more heteroatoms within the parent chain ("$C_1$-$C_6$ heteroalkyl"), 1 to 5 carbon atoms and 1 or more heteroatoms within the parent chain ("$C_1$-$C_5$ heteroalkyl"), 1 to 4 carbon atoms and for more heteroatoms within the parent chain ("$C_1$-$C_4$ heteroalkyl"), 1 to 3 carbon atoms and 1 or more heteroatoms within the parent chain ("$C_1$-$C_3$ heteroalkyl"), 1 to 2 carbon atoms and 1 heteroatom within the parent chain ("$C_1$-$C_2$ heteroalkyl"), or 1 carbon atom and 1 heteroatom ("$C_1$ heteroalkyl"). Unless otherwise specified, each instance of a heteroalkyl group is independently unsubstituted (an "unsubstituted heteroalkyl") or substituted (a "substituted heteroalkyl") with one or more substituents.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a saturated group having from 1 to 1000 carbon atoms and 1 or more heteroatoms within the parent chain ("heteroC$_1$-C$_{1000}$ alkenyl"), 1 to 900 carbon atoms and 1 or more heteroatoms within the parent chain ("heteroC$_1$-C$_{900}$ alkenyl"), 1 to 800 carbon atoms and 1 or more heteroatoms within the parent chain ("heteroC$_1$-C$_{800}$ alkenyl"), 1 to 700 carbon atoms and 1 or more heteroatoms within the parent chain ("heteroC$_1$-C$_{700}$ alkenyl"), 1 to 600 carbon atoms and 1 or more heteroatoms within the parent chain ("heteroC$_1$-C$_{600}$ alkenyl"), 1 to 500 carbon atoms and 1 or more heteroatoms within the parent chain ("heteroC$_1$-C$_{500}$ alkenyl"), 1 to 400 carbon atoms and for more heteroatoms within the parent chain ("heteroC$_1$-C$_{400}$ alkenyl"), 1 to 300 carbon atoms and 1 or more heteroatoms within the parent chain ("heteroC$_1$-C$_{300}$ alkenyl"), 1 to 200 carbon atoms and 1 or more heteroatoms within the parent chain ("heteroC$_1$-C$_{200}$ alkenyl"), or 1 to 100 carbon atoms and 1 or more heteroatoms within the parent chain ("heteroC$_1$-C$_{100}$ alkenyl"). In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and for 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a saturated group having from 1 to 1000 carbon atoms and 1 or more heteroatoms within the parent chain ("heteroC$_1$-C$_{1000}$ alkynyl"), 1 to 900 carbon atoms and 1 or more heteroatoms within the parent chain ("heteroC$_1$-C$_{900}$ alkynyl"), 1 to 800 carbon atoms and 1 or more heteroatoms within the parent chain ("heteroC$_1$-C$_{800}$ alkynyl"), 1 to 700 carbon atoms and 1 or more heteroatoms within the parent chain (heteroC$_1$-C$_{700}$ alkynyl), 1 to 600 carbon atoms and 1 or more heteroatoms within the parent chain ("heteroC$_1$-C$_{600}$ alkynyl"), 1 to 500 carbon atoms and 1 or more heteroatoms within the parent chain ("heteroC$_1$-C$_{500}$ alkynyl"), 1 to 400 carbon atoms and for more heteroatoms within the parent chain ("heteroC$_1$-C$_{400}$ alkynyl"), 1 to 300 carbon atoms and 1 or more heteroatoms within the parent chain ("heteroC$_1$-C$_{300}$ alkynyl"), 1 to 200 carbon atoms and 1 or more heteroatoms within the parent chain ("heteroC$_1$-C$_{200}$ alkynyl"), or 1 to 100 carbon atoms and 1 or more heteroatoms within the parent chain ("heteroC$_1$-C$_{100}$ alkynyl"). In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and for 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" or "cycloalkyl" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"), 3 to 7 ring carbon atoms ("C$_{3-7}$ carbocyclyl"), 3 to 6 ring carbon atoms ("C$_{3-6}$ carbocyclyl"), 4 to 6 ring carbon atoms ("C$_{4-6}$ carbocyclyl"), 5 to 6 ring carbon atoms ("C$_{5-6}$ carbocyclyl"), or 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3}$-8 carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, phosphorus, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents.

In some embodiments, a heterocyclyl group is a 5-10 membered non-aromatic ring system having ring carbon atoms and 1-4 ring heteroatoms, wherein each heteroatom is independently selected from nitrogen, oxygen, phosphorus, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, phosphorus, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, phosphorus, and sulfur ("5-6 membered heterocyclyl"). In some embodiments, the 5-6 membered heterocyclyl has 1-3 ring heteroatoms selected from nitrogen, oxygen, phosphorus, and sulfur. In some embodiments, the 5-6 membered heterocyclyl has 1-2 ring heteroatoms selected from nitrogen, oxygen, phosphorus, and sulfur. In some embodiments, the 5-6 membered heterocyclyl has 1 ring heteroatom selected from nitrogen, oxygen, phosphorus, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl, and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_6$-14 aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group be monovalent or may have more than one point of attachment to another moiety (e.g., it may be divalent, trivalent, etc), although the valency may be specified directly in the name of the group. For example, "triazoldiyl" refers to a divalent triazolyl moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

As understood from the above, alkyl, alkenyl, alkynyl, carbocyclyl, aryl, and heteroaryl groups are, in certain embodiments, optionally substituted. Optionally substituted refers to a group which may be substituted or unsubstituted (e.g., "substituted" or "unsubstituted" alkyl). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Affixing the suffix "ene" to a group indicates the group is a polyvalent (e.g., bivalent, trivalent, tetravalent, or pentavalent) moiety. In certain embodiments, affixing the suffix "ene" to a group indicates the group is a bivalent moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{CC}$)$_3^+$X$^-$, —P(OR$^{CC}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{CC}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{CC}$)N(R$^{CC}$)$_2$, —SO$_2$N(R$^{cc}$)$_2$, —SO$_2$R$^{cc}$, —SO$_2$OR$^{cc}$, —SOR$^{33}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

In certain embodiments, the carbon atom substituents are independently halogen, substituted or unsubstituted C$_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R$^{aa}$, or —NR$^{bb}$C(=O)N(R$^{bb}$)$_2$. In certain embodiments, the carbon atom substituents are independently halogen, substituted or unsubstituted C$_{1-6}$ alkyl, —OR$^{aa}$, —SR$^{33}$, —N(R$^{bb}$)$_2$, —CN, —SCN, or —NO$_2$.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{33}$, —N(R$^{cc}$)$_2$, —CN, —C(=O)R$^{33}$, —C(=O)N(R$^{cc}$)$_2$, —CO$_2$R$^{33}$, —SO$_2$R$^{33}$, —C(=NR$^{bb}$)R$^{33}$, —C(=NR$^{cc}$)OR$^{33}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{33}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{33}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{33}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{33}$, —N(R$^{cc}$)$_2$, —C(=O)R$^{33}$, —C(=O)N(R$^{cc}$)$_2$, —CO$_2$R$^{33}$, —SO$_2$R$^{33}$, —C(=NR$^{cc}$)R$^{33}$, —C(=NR$^{cc}$)OR$^{33}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{33}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{33}$, R$^{bb}$, R$^{cc}$ and R$^{dd}$ are as defined herein. Nitrogen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenoxyacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl- 2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenyl ethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenyl ethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethyl ammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethylbenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethyl silylethanesulfonamide (SES), 9-anthracenesulfonamide, 4-(4',8'-dimethoxynaphthylmethyl)benzenesulfonamide (DNMBS), benzylsulfonamide, trifluoromethyl sulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethyl silyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3^+$X$^-$, —P(OR$^{cc}$)$_2$, —P(OR$^{cc}$)$_3^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethyl silyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxido, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis (4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthhyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH.

The term "thiol" or "thio" refers to the group —SH.

The term "amine" or "amino" refers to the group —NH— or $NH_2$.

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this disclosure include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

"Biological half-life" refers to the time required for half of a substance to be removed by biological processes in a biological system, such as that of a subject (e.g., human). Typically, this refers to natural processes, such as the the body's cleansing through the function of kidneys and liver in addition to excretion functions to eliminate a substance from the body. In a medical context, half-life may also describe the time it takes for the blood plasma concentration of a substance to halve. A substance that leaves plasma may have any of several fates. It can be eliminated from the body, or it can be translocated to another body fluid compartment such as the intracellular fluid or it can be destroyed in the blood.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences,* 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

"Biological half-life" refers to the half-life under physiological conditions.

"Click chemistry" refers to a chemical approach to conjugation introduced by Sharpless in 2001 and describes chemistry tailored to generate substances quickly and reliably by joining units together. See, e.g., Kolb, Finn and Sharpless *Angewandte Chemie International Edition* 2001 40, 2004-2021; Evans, *Australian Journal of Chemistry* 2007 60, 384-395). Exemplary coupling reactions (some of which may be classified as "click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgen cycloaddition; thiol-yne addition; imine formation; Michael additions (e.g., maleimide addition reactions); and Diels-Alder reactions (e.g., tetrazine [4+2] cycloaddition). Examples of click chemistry reactions and click-chemistry handles can be found in, e.g., Kolb, H. C.; Finn, M. G. and Sharpless, K. B. *Angew. Chem. Int. Ed.* 2001, 40, 2004-2021. Kolb, H. C. and Sharless, K. B. *Drug Disc. Today,* 2003, 8, 112-1137; Rostovtsev, V. V.; Green L. G.; Fokin, V. V. and Shrapless, K. B. *Angew. Chem. Int. Ed.* 2002, 41, 2596-2599; Tomoe, C. W.; Christensen, C. and Meldal, M. *J. Org. Chem.* 2002, 67, 3057-3064. Wang, Q. et al. *J. Am. Chem. Soc.* 2003, 125, 3192-3193; Lee, L. V. et al. *J. Am. Chem. Soc.* 2003 125, 9588-9589; Lewis, W. G. et al. *Angew. Chem. Int. Ed.* 2002, 41, 1053-41057; Manetsch, R. et al., *J. Am. Chem. Soc.* 2004, 126, 12809-12818; Mocharla, V. P. et al. *Angew. Chem., Int. Ed.* 2005, 44, 116-120. Any methods known in the art of bioconjugation can be used (e.g., click chemistry reactions). For example, the nanoparticle may comprise a click chemistry handle on its outer shell, which can react with a click chemistry handle on a targeting agent, thereby covalently linking the nanoparticle with the targeting agent. In certain embodiments, the one or more nanoparticles are conjugated to the targeting agent via click chemistry, and therefore the linker comprises a moiety derived from a click chemistry reaction (e.g., triazole, diazole, diazine, sulfide bond, maleimide ring, succinimide ring, ester, amide).

"Bottlebrush", "brush", and "brush polymer" are used interchangably.

The term "average molecular weight" may encompass the number average molecular weight ($M_n$), weight average molecular weight ($M_w$), higher average molecular weight ($M_z$ or $M_z+1$), GPC/SEC (gel permeation chromatography/size-exclusion chromatography)-determined average molecular weight ($M_p$), and viscosity average molecular weight ($M_v$).

The term "polydispersity" (PDI) as used herein refers to a measure of the distribution of molecular size in a mixture, e.g., as determined by a chromatographic method, such as gel permeation chromatography or size exclusion chromatography, or through dynamic light scattering. Polydispersity (PDI) is a measure of the distribution of molecular mass in a given polymer. Polydispersity is calculated by: PDI=$M_w/M_n$ (Stepto, R. F. T., et al., *Pure Appl. Chem.,* 2009, 81, 351-353). $M_n$ is more sensitive to molecules of low molecular mass, while $M_w$ is more sensitive to molecules of high molecular mass. The dispersity indicates the distribution of individual molecular masses in a bath of polymers. Ð has a value equal to or greater than 1.

The term "degree of polymerization" (DP) refers to the number of repeating units in a polymer. In certain embodiments, the DP is determined by a chromatographic method, such as gel permeation chromatography. For a homopolymer, the DP refers to the number of repeating units included in the homopolymer. For a copolymer of two types of monomers (e.g., a first monomer and a second monomer) wherein the molar ratio of the two types of monomers is about 1:1, the DP refers to the number of repeating units of either one of the two type of monomers included in the copolymer. For a copolymer of two types of monomers (e.g., a first monomer and a second monomer) wherein the molar ratio of the two types of monomers is not about 1:1, two DPs may be used. A first DP refers to the number of repeating units of the first monomer included in the copolymer, and a second DP refers to the number of repeating units of the second monomer included in the copolymer. Unless provided otherwise, a DP of "xx", wherein xx is an integer, refers to the number of repeating units of either one of the two types of monomers of a copolymer of two types of monomers (e.g., a first monomer and a second monomer) wherein the molar ratio of the two types of monomers is about 1:1. Unless provided otherwise, a DP of "xx-yy", wherein xx and yy are integers, refers to xx being the number of repeating units of the first monomer, and yy being the number of repeating units of the second monomer, of a copolymer of two types of monomers (e.g., a first monomer and a second monomer) wherein the molar ratio of the two types of monomers is not about 1:1.

As used herein, the term "agent" means a molecule, group of molecules, complex or substance administered to an organism for diagnostic, therapeutic, preventative medical, or veterinary purposes. In certain embodiments, the agent is an agent (e.g., a therapeutic agent, a diagnostic agent, or a prophylactic agent). In certain embodiments, the monomers, conjugates, or particles disclosed herein comprise an agent(s), e.g., a first therapeutic agent (e.g., at least one (including, e.g., at least two, at least three). In some embodiments, the BASP-compositions (e.g., monomers, conjugates, or particles) can further comprise a second therapeutic agent, a targeting moiety, a diagnostic moiety, e.g., as described herein. The agent(s) can be coupled to the conjugate or particle. In other embodiments, the agent(s) can be associated with a conjugate or particle. In some embodiments, a first agent can be coupled to the conjugate or particle, and a second agent, targeting moiety, and/or diagnostic moiety can be non-covalently associated with the conjugate or particle. Any of the agents disclosed herein can be used in the monomers, conjugates, particles and other compositions and methods disclosed herein.

As used herein, the term "therapeutic agent" includes an agent that is capable of providing a local or systemic biological, physiological, or therapeutic effect in the biological system to which it is applied. For example, a therapeutic agent can act to control tumor growth, control infection or inflammation, act as an analgesic, promote anti-cell attachment, and enhance bone growth, among other functions. Other suitable therapeutic agents can include anti-viral agents, hormones, antibodies, or therapeutic proteins. Other therapeutic agents include prodrugs, which are agents that are not biologically active when administered but, upon administration to a subject are converted to biologically active agents through metabolism or some other mechanism.

An agent, e.g., a therapeutic agent, can include a wide variety of different compounds, including chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof.

In some embodiments, the agent is in the form of a prodrug. The term "prodrug" refer to a compound that becomes active, e.g., by solvolysis, reduction, oxidation, or under physiological conditions, to provide a pharmaceutically active compound, e.g., in vivo. A prodrug can include a derivative of a pharmaceutically active compound, such as, for example, to form an ester by reaction of the acid, or acid anhydride, or mixed anhydrides moieties of the prodrug moiety with the hydroxyl moiety of the pharmaceutical active compound, or to form an amide prepared by the acid, or acid anhydride, or mixed anhydrides moieties of the prodrug moiety with a substituted or unsubstituted amine of the pharmaceutically active compound. Simple aliphatic or aromatic esters, amides, and anhydrides derived from acidic groups may comprise prodrugs. In some embodiments, the conjugate or particle described herein incorporates one therapeutic agent or prodrug thereof. In some embodiments, the conjugate or particle described herein incorporates more than one therapeutic agents or prodrugs.

In some embodiments, the agent, e.g., a therapeutic agent, a small molecule. The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than 2,000 g/mol. In certain embodiments, the molecular weight of a small molecule is not more than 1,500 g/mol. In certain embodiments, the molecular weight of a small molecule is not more than 1,000 g/mol, not more than 900 g/mol, not more than 800 g/mol, not more than 700 g/mol, not more than 600 g/mol, not more than 500 g/mol, not more than 400 g/mol, not more than 300 g/mol, not more than 200 g/mol, or not more than 100 g/mol. In certain embodiments, the molecular weight of a small molecule is at least 100 g/mol, at least 200 g/mol, at least 300 g/mol, at least 400 g/mol, at least 500 g/mol, at least 600 g/mol, at least 700 g/mol, at least 800 g/mol, or at least 900 g/mol, or at least 1,000 g/mol. Combinations of the above ranges (e.g., at least 200 g/mol and not more than 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present disclosure.

Exemplary agents, e.g., a therapeutic agents, in the BASP-compositions include, but are not limited to, those found in *Harrison's Principles of Internal Medicine*, 13th Edition, Eds. T. R. Harrison et al. McGraw-Hill N.Y., NY; *Physicians' Desk Reference*, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

In some embodiments, exemplary therapeutic agents in the BASP-compositions include, but are not limited to, one or more of the agents listed in Paragraph [0148] of U.S. Pat. No. 9,381,253, incorporated by reference herein.

In other embodiments, exemplary therapeutic agents in the BASP-compositions include, but are not limited to, one or more of the therapeutic agents listed in WO 2013/169739, including the anti-hypertensive and/or a collagen modifying agents ("AHCM") disclosed, e.g., in Paragraphs 40-49, 283, 286-295; the microenviroment modulators disclosed, e.g., in Paragraphs 113-121, of WO 2013/169739, incorporated herein by reference. In some embodiments, the BASP-composition comprising the AHCM and/or the microenvironment modulator causes one or more of: reduces solid stress (e.g., growth-induced solid stress in tumors); decreases tumor fibrosis; reduces interstitial hypertension or interstitial fluid pressure (IFP); increases interstitial tumor transport; increases tumor or vessel perfusion; increases vascular diameters and/or enlarges compressed or collapsed blood vessels; reduces or depletes one or more of: cancer cells, or stromal cells (e.g., tumor associated fibroblasts or immune cells); decreases the level or production of extracellular matrix components, such as fibers (e.g., collagen, procollagen), and/or polysaccharides (e.g., glycosaminoglycans such as hyaluronan or hyaluronic acid); decreases the level or production of collagen or procollagen; decreases the level or production of hyaluronic acid; increases tumor oxygenation; decreases tumor hypoxia; decreases tumor acidosis; enables immune cell infiltration; decreases immunosuppression; increases antitumor immunity; decreases the production of cancer stem cells (also referred to herein as tumor-initiating cells); or enhances the efficacy (e.g., penetration or diffusion), of the therapy, e.g., the cancer therapy (e.g., radiation, photodynamic therapy, chemotherapeutics, and immunotherapies) in a tumor or tumor vasculature, in the subject.

Agents, e.g., therapeutic agents, include the herein disclosed categories and specific examples. It is not intended that the category be limited by the specific examples. Those of ordinary skill in the art will recognize also numerous other compounds that fall within the categories and that are useful according to the present disclosure.

Examples of therapeutic agents include, but are not limited to, antimicrobial agents, analgesics, antiinflammatory agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anti-cancer properties, or a combination thereof. Other suitable therapeutic agents include contraceptives and vitamins as well as micro- and macronutrients. Still other examples include antiinfectives such as antibiotics and antiviral agents; analgesics and analgesic combinations; anorexics; antiheimintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; anti-hypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

In certain instances, the diagnostic agent is an imaging agent or contrast agent. The terms "imaging agent" and "contrast agent" refer to a substance used to enhance the contrast of structures or fluids within the body in medical imaging. It is commonly used to enhance the visibility of blood vessels and the gastrointestinal tract in medical imaging.

The term "crosslinker" refers to a compound that allows for two or more polymers (e.g., brush polymers) to be joined by covalent bonds. In certain embodiments, the crosslinker results in a covalent attachment between two polymers.

The term "ring-opening metathesis polymerization (ROMP)" refers to a type of olefin metathesis chain-growth polymerization that is driven by the relief of ring strain in cyclic olefins (e.g. norbornene or cyclopentene). The catalysts used in the ROMP reaction ("metathesis catalyst") include $RuCl_3$/alcohol mixture, bis(cyclopentadienyl)dimethylzirconium(IV), dichloro[1,3-bis(2,6-isopropylphenyl)-2-imidazolidinylidene](benzylidene)(tricyclohexylphosphine)ruthenium(II), dichloro[1,3-Bis(2-methylphenyl)-2-imidazolidinylidene](benzylidene)(tricyclohexylphosphine)ruthenium(II), dichloro[1,3-bis(2,4,6-trimethylphenyl)-2-imidazolidinylidene][3-(2-pyridinyl)propylidene]ruthenium (II), dichloro(3-methyl-2-butenylidene)bis (tricyclopentylphosphine)ruthenium(II), dichloro[1,3-bis(2-methylphenyl)-2-imidazolidinylidene](2-isopropoxyphenylmethylene)ruthenium(II) (Grubbs C571), dichloro(benzylidene)bis(tricyclohexylphosphine)ruthenium(II) (Grubbs I), dichloro[1,3-bis(2,4,6-trimethylphenyl)-2-imidazolidinylidene](benzylidene)(tricyclohexylphosphine) ruthenium(II) (Grubbs II), and dichloro[1,3-bis(2,4,6-trimethylphenyl)-2-imidazolidinylidene](benzylidene)bis(3-bromopyridine)ruthenium(II) (Grubbs III).

A "protein," "peptide," or "polypeptide" comprises a polymer of amino acid residues linked together by peptide bonds. The term refers to proteins, polypeptides, and peptides of any size, structure, or function. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. One or more of the amino acids in a protein may be protected. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these. In certain embodiments, a protein comprises between 2 and 10, between 10 and 30, between 30 and 100, between 100 and 300, or between 300 and 1,000, inclusive, amino acids. In certain embodiments, the amino acids in a protein are natural amino acids. In certain embodiments, the amino acids in a protein are unnatural amino acids. In certain embodiments, the amino acids in a protein are a combination of natural amino acids and unnatural amino acids.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay and/or prevent recurrence.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population of subjects.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactically effective amount. In certain embodiments, an effective amount is the amount of a compound or pharmaceutical composition described herein in a single dose. In certain embodiments, an effective amount is the combined amounts of a compound or pharmaceutical composition described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "ratiometric" refers to the situation where $C_1^i$ is substantially equal to $C_0^i$, wherein $C_0^i$ refers to the ratio of the amount of a first agent before the first agent is delivered to a subject, tissue, or cell, to the total amount of two or more agents (including the first agent) before the two or more agents are delivered to the subject, tissue, or cell; and $C_1^i$ refers to the ratio of the amount of the first agent that is delivered to the subject, tissue, or cell, to the total amount of the two or more agents (including the first agent) that are delivered to the subject, tissue, or cell. In certain embodiments, the delivery of each one of the two or more agents is ratiometric.

The term "v/v" refers to volume per volume and is used herein to express concentrations of monomers. Unless otherwise provided, a percent concentration of a second monomer in a first monomer is expressed in v/v. For example, a mixture of a first monomer and 10% second monomer refers to a mixture of a first monomer and a second monomer, wherein the volume of the second monomer is 10% of the combined volumes of the first and second monomers.

The term "orthogonal" refers to the situation where a first agent and a second agent, each of which is included in a BASP described herein, is independently released from the BASP. In certain embodiments, under a first condition, the first agent, but not the second agent, is released from the BASP. For example, an orthogonal release or orthogonal delivery of the first and second agents includes: under a first condition, the first agent, but not the second agent, is released from the BASP; under a second condition, the second agent, but not the first agent, is released from the BASP. The release or delivery of the first and second agents is not orthogonal when, for example, under a third condition, both the first and second agents are released from the BASP.

The term "self-assembly" refers to a process in which a disordered system of pre-existing components forms an organized structure or pattern as a consequence of specific, local interactions among the components themselves, without external direction. When the constitutibe components are molecules, the process is termed molecular self-assembly. Self-assembly can be classified as either static or dynamic. In static self-assembly, the ordered state forms as a system approaches equilibrium, reducing its free energy. However, in dynamic self-assembly, patterns of pre-existing components organized by specific local interactions are not commonly described as "self-assembled" by scientists in the associated disciplines. These structures are better described as "self-organized", although these terms are often used interchangeably.

The disclosure is not intended to be limited in any manner by the above exemplary listing of substituents. Additional terms may be defined in other sections of this disclosure.

DETAILED DESCRIPTION OF CERTAIN EMBODIMENTS

The aspects described herein are not limited to specific embodiments, methods, apparati, or configurations, and as such can, of course, vary. The terminology used herein is for the purpose of describing particular aspects only and, unless specifically defined herein, is not intended to be limiting.

The present disclosure provides cyclic silyl ethers of Formula (B), or salts thereof. The present disclosure also provides polymers, methods of preparing the polymers, compositions comprising the cyclic silyl ethers, polymers, and kits comprising the polymers. The present disclosure also provides methods of using the polymers, compositions, or kits.

The present disclosure provides brush polymers, BASPs, methods of preparing the brush polymers, methods of preparing the BASPs, compositions comprising the brush polymers or BASPs, and kits comprising the brush polymers or BASPs. The present disclosure also provides methods of using the brush polymers, BASPs, compositions, or kits (e.g., methods of delivering an agent to a subject in need thereof, methods of delivering an agent to a cell, methods of treating a disease in a subject in need thereof, methods of preventing a disease in a subject in need thereof, and methods of diagnosing a disease in a subject in need thereof).

Cyclic Silyl Ethers

In certain aspects, the present disclosure provides compounds of Formula (B):

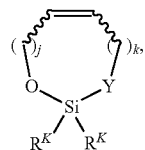

(B)

or a salt thereof wherein

Y is O or $C(R^Q)_2$;

each instance of $R^Q$ is independently hydrogen, halogen, or substituted or unsubstituted, $C_{1-6}$ alkyl;

each instance of $R^K$ is independently hydrogen, halogen, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or —$OR^N$;

each instance of $R^N$ is independently hydrogen, substituted or unsubstituted acyl, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or an oxygen protecting group;

j is 1, 2, or 3; and k is 0, 1, 2, or 3.

In some aspects, the compound is the second monomer.

In certain embodiments, the compound of Formula (B) or second monomer is of the formula:

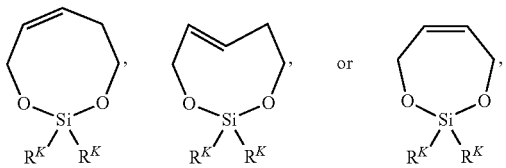

or a salt thereof. In certain embodiments, the compound of Formula (B) or second monomer is of the formula:

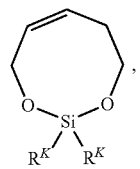

or a salt thereof. In some embodiments, the compound of Formula (B) or second monomer is of the formula:

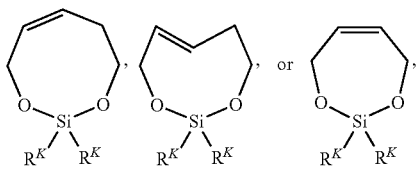

or a salt thereof, wherein $R^K$ is unsubstituted methyl, unsubstituted ethyl, unsubstituted isopropyl, or unsubstituted phenyl. In certain embodiments, the compound of Formula (B) or second monomer is of the formula:

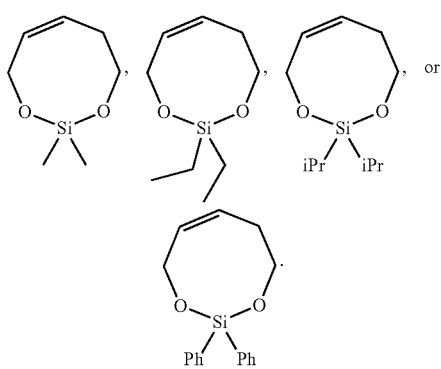

In certain embodiments, the compound of Formula (B) or second monomer is of the formula:

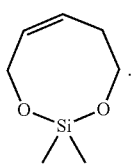

In certain embodiments, the compound of Formula (B) or second monomer is of the formula:

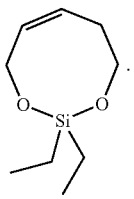

In certain embodiments, the compound of Formula (B) or second monomer is of the formula:

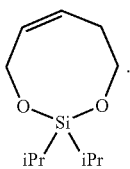

In certain embodiments, the compound of Formula (B) or second monomer is of the formula:

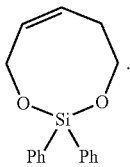

In certain embodiments, the compound of Formula (B) or second monomer is of the formula

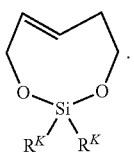

In certain embodiments, the compound of Formula (B) or second monomer is of the formula:

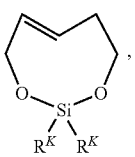

wherein $R^K$ is unsubstituted isopropyl. In certain embodiments, the compound of Formula (B) or second monomer is of the formula:

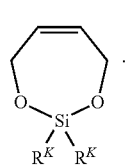

In certain embodiments, the compound of Formula (B) or second monomer is of the formula:

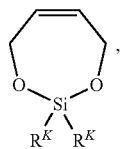

wherein $R^K$ is unsubstituted isopropyl. In certain embodiments, the compound of Formula (B) or second monomer is of the formula:

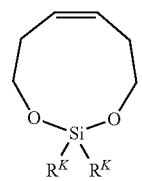

In certain embodiments, the compound of Formula (B) or second monomer is of the formula:

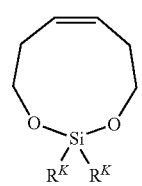

wherein $R^K$ is unsubstituted isopropyl.

In some embodiments, the compound of Formula (B) or second monomer has a molecular weight of about 110 g/mol up to about 320 g/mol. In some embodiments, the compound of Formula (B) or second monomer is of the formula

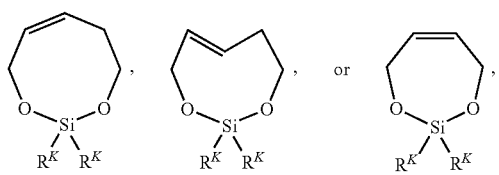

or salt thereof, wherein the molecular weight of the compound of Formula (B) or second monomer is about 130 g/mol to about 320 g/mol. In some embodiments, the compound of Formula (B) or second monomer is of the formula

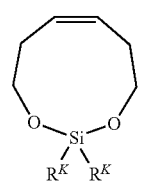

or salt thereof, wherein the molecular weight of the compound of Formula (B) or second monomer is about 130 g/mol to about 320 g/mol.

In certain embodiments, Y is O. In certain embodiments, Y is $C(R^Q)_2$ (e.g., —$CH_2$— or —$C(CH_3)_2$—).

In certain embodiments, at least one instance of $R^Q$ is hydrogen. In certain embodiments, each instance of $R^Q$ is hydrogen. In certain embodiments, at least one instance of $R^Q$ is halogen (e.g., F). In certain embodiments, at least one instance of $R^Q$ is substituted or unsubstituted, $C_{1-6}$ alkyl (e.g., —$CH_3$).

In certain embodiments, at least one instance of $R^K$ is substituted or unsubstituted, $C_{1-6}$ alkyl, or substituted or unsubstituted phenyl. In certain embodiments, each instance of $R^K$ is independently substituted or unsubstituted, $C_{1-6}$ alkyl, or substituted or unsubstituted phenyl. In certain embodiments, each instance of $R^K$ is unsubstituted $C_{1-3}$ alkyl or unsubstituted phenyl. In certain embodiments, each instance of $R^K$ is unsubstituted methyl. In certain embodiments, each instance of $R^K$ is unsubstituted ethyl. In certain embodiments, each instance of $R^K$ is unsubstituted propyl (e.g., isopropyl). In certain embodiments, each instance of $R^K$ is substituted isopropyl. In certain embodiments, each instance of $R^K$ is unsubstituted isopropyl. In certain embodiments, each instance of $R^K$ is unsubstituted phenyl. In certain embodiments, each instance of $R^K$ is substituted phenyl. In certain embodiments, at least one instance of $R^K$ is hydrogen. In certain embodiments, at least one instance of $R^K$ is halogen. In certain embodiments, at least one instance of $R^K$ is substituted or unsubstituted, $C_{1-10}$ alkyl or —$OR^N$. In certain embodiments, at least one instance of $R^K$ is substituted or unsubstituted carbocyclyl, substituted or unsubstituted heterocyclyl, substituted or unsubstituted aryl, or substituted or unsubstituted heteroaryl. In certain embodiments, each instance of $R^K$ is —$OR^N$ (e.g., —O(unsubstituted $C_{1-6}$ alkyl)).

In certain embodiments, at least one instance of $R^N$ is substituted or unsubstituted, $C_{1-6}$ alkyl, or substituted or unsubstituted phenyl. In certain embodiments, each instance of $R^N$ is independently substituted or unsubstituted, $C_{1-6}$ alkyl, or substituted or unsubstituted phenyl. In certain embodiments, each instance of $R^N$ is unsubstituted $C_{1-3}$ alkyl or unsubstituted phenyl. In certain embodiments, each instance of $R^N$ is unsubstituted methyl. In certain embodiments, each instance of $R^N$ is unsubstituted ethyl. In certain embodiments, each instance of $R^N$ is unsubstituted propyl (e.g., isopropyl). In certain embodiments, each instance of $R^N$ is unsubstituted phenyl. In certain embodiments, at least one instance of $R^N$ is hydrogen. In certain embodiments, at least one instance of $R^N$ is halogen. In certain embodiments, at least one instance of $R^N$ is substituted or unsubstituted, $C_{1-10}$ alkyl. In certain embodiments, at least one instance of $R^N$ is an oxygen protecting group. In certain embodiments, at least one instance of $R^N$ is substituted or unsubstituted carbocyclyl, substituted or unsubstituted heterocyclyl, substituted or unsubstituted aryl, or substituted or unsubstituted heteroaryl.

In certain embodiments, j is 1. In certain embodiments, j is 2. In certain embodiments, j is 3.

In certain embodiments, k is 1. In certain embodiments, k is 2. In certain embodiments, k is 3. In certain embodiments, k is 0.

In certain embodiments, j is 1, and k is 1. In certain embodiments, j is 1, and k is 2. In certain embodiments, j is 2, and k is 1.

Polymers

Provided herein are polymers (e.g., polymers and subclasses thereof including block polymers, brush polymers, BASPs). In some aspects, the present disclosure provides a polymer prepared by a method comprising polymerizing (1) one or more instances of a first monomer, or a salt thereof and (2) a second monomer, wherein the second monomer is of Formula (B), or a salt thereof, wherein any two instances of the first monomer are the same as or different from each other, and the second monomer is the same as or different from any instance of the first monomer; in the presence of a metathesis catalyst. In some embodiments, the first monomer is different than the second monomer. In some embodiments, the polymer is prepared by polymerizing a single instance of a first monomer (i.e., all instances of the first monomer are the same) and a single instance of a second monomer (i.e., all instances of the second monomer are the same). In certain embodiments, the polymer comprises more than one instances of a first monomer (i.e., all instances of the first monomer are not the same, the first monomer is represented by two different and distinct chemical formulae) and a single instance of a second monomer (i.e., all instances of the second monomer are the same). In some embodiments, the polymer comprises more than one instance of a first monomer, wherein any two instances of the first monomer are the same as or different from each other, and the second monomer is the same as or different from any instance of the first monomer.

In some embodiments, the polymer is a block copolymer. In certain embodiments, the block copolymer comprises two different types of blocks, wherein the blocks are composed of homopolymers (e.g., one or multiple blocks of a first monomer and one or multiple blocks of a second monomer). In some embodiments, the block copolymer comprises two different types of blocks, wherein the blocks are composed of homopolymers or copolymers (e.g., the polymer comprises either (1) one or multiple blocks of a first monomer with a different first monomer and (2) one or multiple blocks of a second monomer, or (1') one or multiple blocks of a first monomer and (2') one or multiple blocks of a first monomer with a second monomer).

In certain embodiments, the block copolymer comprises blocks of one or more instances of a first monomer; and blocks of one or more instances of a first monomer and a second monomer, wherein the second monomer is a compound of Formula (B); wherein any two instances of the first monomer are the same as or different from each other, and the second monomer is the same as or different from any instance of the first monomer. In some embodiments, the block copolymer comprises one or multiple blocks of a homopolymer consisting of a first monomer and one or multiple blocks of a copolymer consisting of a first monomer and a second monomer. For example, the block copolymer is of the form AAAAAAA-ABABABABA, wherein A represents a first monomer and B represents a second monomer.

In certain embodiments, the block copolymer comprises blocks of one or more instances of a first monomer; blocks comprising one or more instances of a second monomer, wherein the second monomer is a compound of Formula (B); and blocks of one or more instances of a first monomer, wherein any two instances of the first monomer are the same as or different from each other, and the second monomer is the same as or different from any instance of the first monomer. In some embodiments, the block copolymers comprises one or multiple blocks of a homopolymer consisting of a first monomer, one or multiple blocks of a homopolymer consisting of a second monomer, and one or multiple blocks of a homopolymer consisting of a same or different first monomer. For examples, the block copolymer is of the form AAAAA-BBBBB-AAAAA, wherein A represents a first monomer and B represents a second monomer. For example, the block copolymer is of the form AAAAA-BBBBB-A*A*A*A*, wherein A represents a first monomer, B represents a second monomer, and A* represents either a first monomer which is different than A.

In some aspects, the first monomer comprises a partially unsaturated bond. In certain embodiments, the first monomer comprises an alkene. In some embodiments, the first monomer comprises a substituted or unsubstituted partially unsaturated monocyclic carbocyclic ring or a substituted or unsubstituted partially unsaturated monocyclic heterocyclic ring. In some embodiments, the first monomer comprises an unsubstituted partially unsaturated monocyclic carbocyclic ring. In certain embodiments, the first monomer comprises an unsubstituted partially unsaturated monocyclic heterocyclic ring.

In certain aspects, the present disclosure relates to a polymer comprising:
n2 instances of a first block, wherein the each instance of the first block independently is of Formula (A1') or (A2"):

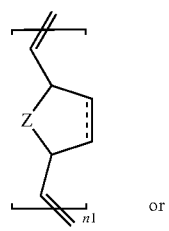

(A1')

or

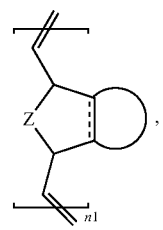

(A2")

or a salt thereof; and
n3 instances of a second block, wherein the each instance of the second block independently comprises Formula (A1') or (A2"):

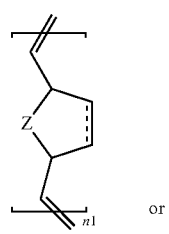

(A1')

or

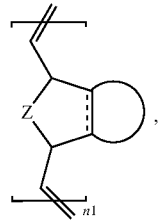

(A2")

or a salt thereof, and Formula (B1):

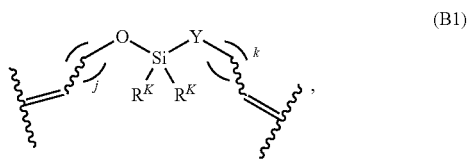

(B1)

or a salt thereof;
wherein:
each instance of n1 is independently an integer between 2 and 1,000, inclusive;
n2 is an integer between 2 and 100, inclusive;
n3 is an integer between 1 and 101, inclusive;
each instance of

is Ring B, wherein each instance of Ring B is independently a substituted or unsubstituted, monocyclic carbocyclic ring, substituted or unsubstituted, monocyclic heterocyclic ring, substituted or unsubstituted, monocyclic aryl ring, or substituted or unsubstituted, monocyclic heteroaryl ring;
each instance of Z is independently $C(R^P)_2$ or O;
each instance of $R^1$ is independently hydrogen, halogen, or substituted or unsubstituted, $C_{1-6}$ alkyl;
each instance of ==== is independently a single bond or double bond;
Y is O or $C(R^Q)_2$;
each instance of $R^Q$ is independently hydrogen, halogen, or substituted or unsubstituted, $C_{1-6}$ alkyl;
each instance of $R^K$ is independently hydrogen, halogen, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or —$OR^N$;
each instance of $R^N$ is independently hydrogen, substituted or unsubstituted acyl, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or an oxygen protecting group;
j is 1, 2, or 3; and
k is 0, 1, 2, or 3.
In certain embodiments, the first block is of the Formula (A1') and the second block comprises Formula (A1') and Formula (B1). In certain embodiments, the first block is of the Formula (A1') and the second block comprises Formula (A2') and Formula (B1). In certain embodiments, the first block is of the Formula (A2') and the second block comprises Formula (A1') and Formula (B1). In certain embodiments, the first block is of the Formula (A2') and the second block comprises Formula (A2') and Formula (B1).

In certain aspects, the present disclosure includes polymers comprising:

n2 instances of a first block, wherein the each instance of the first block is independently of Formula (A1') or (A2''):

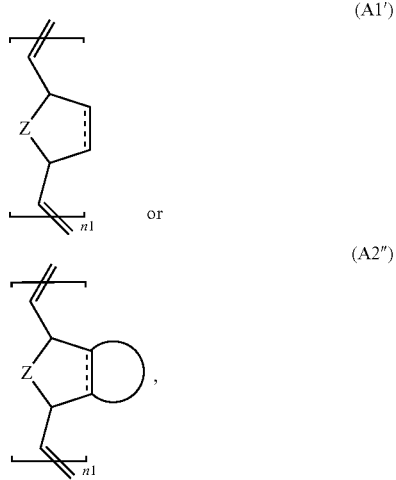

or a salt thereof; and
n3 instances of a linker of the formula:

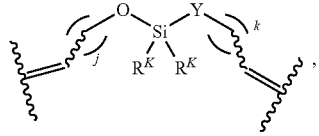

or a salt thereof;
wherein:
at least two instances of the first block are immediately separated by one or more instances of the linker;
each instance of n1 is independently an integer between 2 and 1,000, inclusive;
n2 is an integer between 2 and 100, inclusive;
n3 is an integer between 1 and 101, inclusive;
each instance of

is Ring B, wherein each instance of Ring B is independently a substituted or unsubstituted, monocyclic carbocyclic ring, substituted or unsubstituted, monocyclic heterocyclic ring, substituted or unsubstituted, monocyclic aryl ring, or substituted or unsubstituted, monocyclic heteroaryl ring;
each instance of Z is independently $C(R^P)_2$ or O;
each instance of $R^P$ is independently hydrogen, halogen, or substituted or unsubstituted, $C_{1-6}$ alkyl;

each instance of ==== is independently a single bond or double bond;
Y is O or $C(R^Q)_2$;
each instance of $R^Q$ is independently hydrogen, halogen, or substituted or unsubstituted, $C_{1-6}$ alkyl;
each instance of $R^K$ is independently hydrogen, halogen, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or —$OR^N$;
each instance of $R^N$ is independently hydrogen, substituted or unsubstituted acyl, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or an oxygen protecting group;
j is 1, 2, or 3; and
k is 0, 1, 2, or 3.

In certain embodiments, the first instance of the first block is of the Formula (A1') and the second block instance of the first block is of the Formula (A1'), wherein the two instances of A1' are the same (e.g., a polymer of the formula $(A1')_{n1}$-$(B1)$-$(A1')_{n1}$). In certain embodiments, the first instance of the first block is of the Formula (A1') and the second block instance of the first block is of the Formula (A1'), wherein the two instances of A1' are different (e.g., a polymer of the formula $(A1')_{n1}$-$(B1)$-$(A1'^*)_{n1}$). In certain embodiments, the first instance of the first block is of the Formula (A2') and the second block instance of the first block is of the Formula (A2'), wherein the two instances of A2' are the same (e.g., a polymer of the formula $(A2')_{n1}$). In certain embodiments, the first instance of the first block is of the Formula (A2') and the second block instance of the first block is of the Formula (A2'), wherein the two instances of A2' are different (e.g., a polymer of the formula $(A2')_{n1}$-$(B1)$-$(A2'^*)_{n1}$).

In certain embodiments, the first instance of the first block is of the Formula (A1') and the second block instance of the first block is of the Formula (A2'), (e.g., a polymer of the formula $(A1')_{n1}$-$(B1)$-$(A2')_{n1}$). In certain embodiments, the first instance of the first block is of the Formula (A2') and the second block instance of the first block is of the Formula (A1') (e.g., a polymer of the formula $(A2')_{n1}$-$(B1)$-$(A1')_{n1}$).

In some embodiments, at least one instance of n1 is an integer between 10 and 100, inclusive. In certain embodiments, at least one instance of n1 is an integer between 10 and 300, inclusive. In some embodiments, n2 is an integer between 2 and 80 inclusive. In certain embodiments, n2 is 2. In certain embodiments, n3 is an integer between 1 and 50, inclusive. In certain embodiments, n3 is 1.

In certain embodiments, Formula (B1) or the linker is of the formula

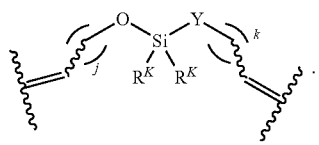

In certain embodiments, Formula (B1) or the linker is of the formula

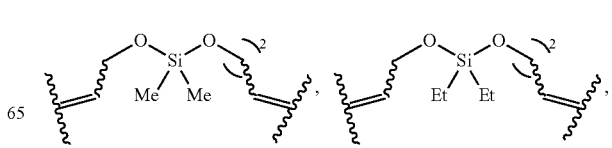

-continued

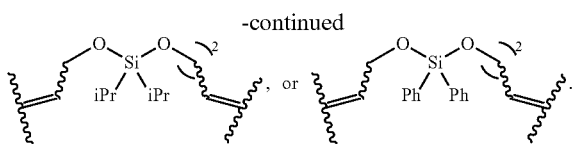

In some embodiments, the first monomer is of Formula (A') or (A"):

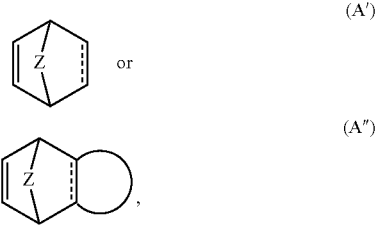

or salt thereof, wherein
each instance of

is Ring B, wherein each instance of Ring B is independently a substituted or unsubstituted, monocyclic carbocyclic ring, substituted or unsubstituted, monocyclic heterocyclic ring, substituted or unsubstituted, monocyclic aryl ring, or substituted or unsubstituted, monocyclic heteroaryl ring;
each instance of Z is independently $C(R^P)_2$ or O;
each instance of $R^P$ is independently hydrogen, halogen, or substituted or unsubstituted, $C_{1-6}$ alkyl; and
each instance of ═══ is independently a single bond or double bond.

In certain embodiments, each instance of

is Ring B, wherein each instance of Ring B is independently unsubstituted, monocyclic aryl ring, or substituted or unsubstituted, monocyclic heteroaryl ring. In certain embodiments, at least one instance of Ring B is a substituted or unsubstituted, monocyclic heterocyclic ring. In certain embodiments, at least one instances of Ring B is a substituted or unsubstituted, 5-membered monocyclic heterocyclic ring.

In certain embodiments, at least one instance of Z is $C(R^P)_2$. In certain embodiments at least one instance of Z is $CH_2$. In certain embodiments, at least one instance of Z is O.

In certain embodiments, each instance of $R^P$ is hydrogen. In certain embodiments, at least one instance of $R^P$ is hydrogen. In certain embodiments, at least one instance of $R^P$ is halogen. In certain embodiments, at least one instance of $R^1$ is unsubstituted, $C_{1-6}$ alkyl or $C_{1-6}$ alkyl substituted with one or more halogen. In certain embodiments, at least one instance of $R^1$ is unsubstituted methyl.

As reported herein, the silane monomer iPrSi co-polymerizes efficiently with norbornenes under ring opening metathesis polymerization. The presence of silyl ether functionalities along the backbone opens the door to sites for degradation.

Poly-dicyclopentadiene ("poly-DCPD" or "pDCPD") is a mechanically tough and commercially important material but lacks inherent degradability owing to its highly crosslinked all-carbon backbone. The ability to generate degradable versions of this material that maintain its ease of synthesis and desirable mechanical properties may open the door to many applications for this material. Reported herein is a strategy for generating degradable poly-dicyclopentadiene through copolymerization with a silyl ether monomer.

In earlier work, it was demonstrated how tailored monomers can be used to generate backbone degradable linear and bottlebrush polymers. For example, one monomer, iPrSi, was found to be broadly useful in the generation of a wide variety of degradable polynorbornene derived materials. We determined if it would also be useful for highly crosslinked networks. By introducing sites of degradation along the polymer backbone, it was thought to be able to degrade the resulting material into soluble fragments through either fluoride or acid treatment. Importantly, it was hypothesized that on only a small amount of silane-based monomer may be needed in order to enable full degradation, thus leading to a hypothesized minimal impact on the overall mechanical properties of the final material.

Earlier results on copolymerization of iPrSi with other small molecule norbornenes suggested that silane monomers most efficiently copolymerize with endo-functionalized norbornenes. Based on this, it was expected that the monomer would copolymerize efficiently with dicyclopentadiene, an important factor for obtaining even incorporation of degradation sites along the polynorbornene backbone.

In certain embodiments, a polymer is prepared by a method comprising polymerizing: (1) one or more instances of a first monomer, wherein each instance of the first monomer is independently of Formula (D1) or (D2):

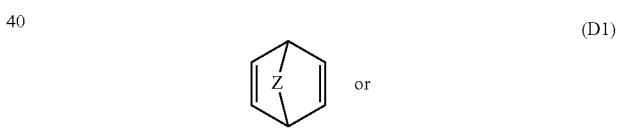

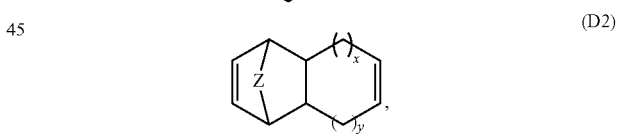

or a salt thereof; and (2) a second monomer, where the second monomer is of Formula (B):

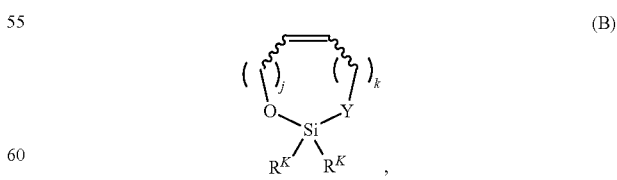

or a salt thereof; in the presence of a metathesis catalyst;
wherein:
each instance of Z is independently $C(R^P)_2$ or;
each instance of $R^P$ is independently hydrogen, halogen, or substituted or unsubstituted, $C_{1-6}$ alkyl;

each instance of x is independently 0, 1, or 2;

each instance of y is independently 0, 1, or 2;

Y is O or C(R$^Q$)$_2$;

each instance of R$^Q$ is independently hydrogen, halogen, or substituted or unsubstituted, C$_{1-6}$ alkyl;

each instance of R$^K$ is independently hydrogen, halogen, substituted or unsubstituted, C$_{1-10}$ alkyl, substituted or unsubstituted carbocyclyl, substituted or unsubstituted heterocyclyl, substituted or unsubstituted aryl, substituted or unsubstituted heteroaryl, or —OR$^N$;

each instance of R$^N$ is independently hydrogen, substituted or unsubstituted acyl, substituted or unsubstituted, C$_{1-10}$ alkyl, substituted or unsubstituted carbocyclyl, substituted or unsubstituted heterocyclyl, substituted or unsubstituted aryl, substituted or unsubstituted heteroaryl, or an oxygen protecting group;

j is 1, 2, or 3; and k is 0, 1, 2, or 3.

Also described herein are cyclic olefin silane monomers (e.g., second monomers of Formula (B)) that copolymerized efficiently with cyclic dienes. When mixed with cyclic diene monomers (e.g., first monomers of Formula (D1) or (D2)) before polymerization, the resulting polymers are shown to degrade under, e.g., aqueous acidic conditions. The cyclic olefin monomers may have a low molecular weight and may be easily prepared (e.g., purified by distillation), which may open the door to many opportunities for backbone degradable materials.

In certain embodiments, each instance of the first monomer is of Formula (D1). In certain embodiments, at least one instance of the first monomer is of the formula:

or a salt thereof.

In certain embodiments, each instance of the first monomer is of Formula (D2).

In certain embodiments, at least one instance of the first monomer is of the formula:

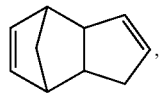

or a salt thereof.

In some embodiments, at least one instance of the first monomer is of the formula:

or salt thereof.

In some embodiments, a polymer as described herein comprises a first monomer of the formula:

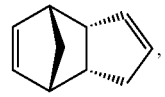

or salt thereof, and second monomer of the formula:

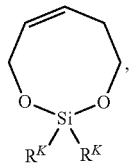

or salt thereof.

In certain embodiments, at least two instances of a variable are different from each other. In certain embodiments, all instances of a variable are different from each other. In certain embodiments, all instances of a variable are the same.

In certain embodiments, at least one instance of Z is C(R$^P$)$_2$. In certain embodiments at least one instance of Z is CH$_2$. In certain embodiments, at least one instance of Z is O.

In certain embodiments, each instance of R$^P$ is hydrogen. In certain embodiments, at least one instance of R$^P$ is hydrogen. In certain embodiments, at least one instance of R$^P$ is halogen. In certain embodiments, at least one instance of R$^P$ is unsubstituted, C$_{1-6}$ alkyl or C$_{1-6}$ alkyl substituted with one or more halogen. In certain embodiments, at least one instance of R$^1$ is unsubstituted methyl.

In certain embodiments, x is 1. In certain embodiments, x is 2. In certain embodiments, x is 0.

In certain embodiments, y is 1. In certain embodiments, y is 2. In certain embodiments, y is 0.

In certain embodiments, x is 1, and y is 1. In certain embodiments, x is 1, and y is 0. In certain embodiments, x is 0, and y is 1.

In certain embodiments, the step of polymerizing comprises polymerizing a first instance of the first monomer, or a salt thereof; a second instance of the first monomer, or a salt thereof; and the second monomer, or a salt thereof, in the presence of the metathesis catalyst.

In some embodiments, the molar ratio of the one or more instances of the first monomer to the second monomer is between 4.5:1 and 6:1, between 6:1 and 9.5:1, between 9.5:1 and 14:1, between 14:1 and 19:1, or between 19:1 and 29:1, inclusive. In some embodiments, the molar ratio of the one or more instances of the first monomer to the second monomer is between 6:1 and 19:1, inclusive. In some embodiments, the molar ratio of the one or more instances of the first monomer to the second monomer is between 4.5:1 and 19:1, inclusive. In some embodiments, the molar ratio of the one or more instances of the first monomer to the second monomer is between 6:1 and 29:1, inclusive. In some embodiments, the molar ratio of the one or more instances of the first monomer to the second monomer is between 4.5:1 and 29:1, inclusive.

In certain embodiments, the average molecular weight of the polymer is between 10 kDa and 10,000 kDa, inclusive. In certain embodiments, the average molecular weight of the polymer is between 10 kDa and 30 kDa, between 30 kDa and 100 kDa, between 100 kDa and 1,000 kDa, between 1,000 kDa and 10,000 kDa, or between 10,000 kDa and 100,000 kDa, inclusive. In certain embodiments, the average molecular weight of the polymer is between 10 kDa and 100 kDa, inclusive. In certain embodiments, the average molecular weight is as determined by gel permeation chromatography.

In some embodiments, the polymer may be crosslinked via ROMP of more than one of the cyclic dienes present in the first monomer. In certain embodiments, the crosslink density is 5%-20%, inclusive. In some embodiments, the crosslink density is 10%-15%, inclusive. In certain embodiments, the crosslink density is about 12%, inclusive.

In certain embodiments, the PDI of the polymer is between 1 and 2, between 1.1 and 2, between 1.3 and 2, between 1.5 and 2, between 1.1 and 1.5, between 1.1 and 1.3, between 1.3 and 2, between 1.3 and 1.5, between 1.5 and 2, inclusive. In certain embodiments, the PDI of the polymer is between 1 and 2, between 1.1 and 2, between 1.3 and 2, between 1.5 and 2, between 1.1 and 1.5, between 1.1 and 1.3, between 1.3 and 2, between 1.3 and 1.5, between 1.5 and 2, inclusive.

In some cases, the polymers are in the form of particles (e.g., nanoparticles, i.e., the particle have a characteristic dimension of less than about 1 micrometer). Provided herein is a strategy for generating poly-dicyclopentatdiene nanoparticles. In some embodiments, these particles can find use as reinforcements for composite materials and offer opportunities for upcycling polydicyclopentadiene derived materials. In some embodiments, after polymerization, a polymer is subjected to conditions that result in dissolution. In certain embodiments, after dissolution, the dissolution mixture/solution is extracted with solvent. In some embodiments, after extraction, the solvent is removed by dissolution, leaving only particles. In certain embodiments, the characteristic dimension of a particle is the diameter of a perfect sphere having the same volume as the particle. In certain embodiments, the polymer particle has a characteristic dimension of less than about 300 nm. In certain embodiments, the polymer particle has a characteristic dimension of less than about 200 nm. In certain embodiments, the polymer particle has a characteristic dimension of less than about 150 nm. In certain embodiments, the polymer particle has a characteristic dimension of less than about 100 nm. In certain embodiments, the polymer particle has a characteristic dimension of less than about 50 nm. In certain embodiments, the polymer particle has a characteristic dimension of less than about 30 nm. In certain embodiments, the polymer particle has a characteristic dimension of less than about 20 nm. In certain embodiments, the polymer particle has a characteristic dimension of less than about 10 nm. In certain embodiments, the polymer particle has a characteristic dimension between 6 and 250 nm, inclusive. In certain embodiments, the polymer particle has a characteristic dimension between 8 and 200 nm, inclusive. In certain embodiments, the polymer particle has a characteristic dimension between 12 and 200 nm, inclusive. In certain embodiments, the polymer particle has a characteristic dimension between 50 and 200 nm, inclusive. In certain embodiments, the particle has a characteristic dimension of less than about 300 nm. In certain embodiments, the particle has a characteristic dimension of less than about 200 nm. In certain embodiments, the particle has a characteristic dimension of less than about 150 nm. In certain embodiments, the particle has a characteristic dimension of less than about 100 nm. In certain embodiments, the particle has a characteristic dimension of less than about 50 nm. In certain embodiments, the particle has a characteristic dimension of less than about 30 nm. In certain embodiments, the particle has a characteristic dimension of less than about 20 nm. In certain embodiments, the particle has a characteristic dimension of less than about 10 nm. In certain embodiments, the particle has a characteristic dimension between 6 and 250 nm, inclusive. In certain embodiments, the particle has a characteristic dimension between 8 and 200 nm, inclusive. In certain embodiments, the particle has a characteristic dimension between 12 and 200 nm, inclusive. In certain embodiments, the particle has a characteristic dimension between 50 and 200 nm, inclusive.

Brush Polymers

In certain embodiments, a brush polymer is prepared by a method comprising polymerizing: (1) one or more instances of a first monomer, wherein each instance of the first monomer is independently of Formula (A1) or (A2):

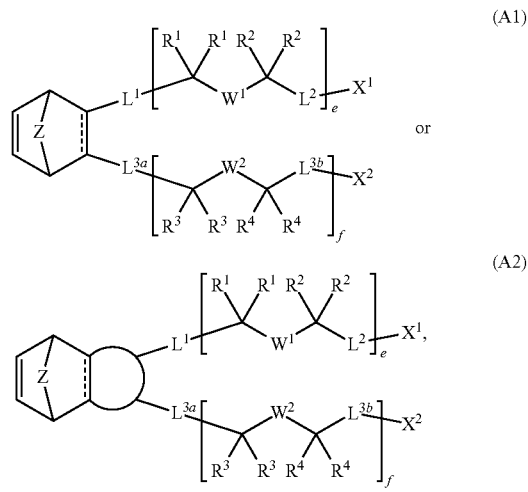

or a salt thereof; and (2) a second monomer, where the second monomer is of Formula (B):

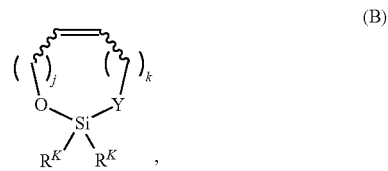

or a salt thereof; in the presence of a metathesis catalyst; wherein:

each instance of

is Ring B, wherein each instance of Ring B is independently a substituted or unsubstituted, monocyclic carbocyclic ring, substituted or unsubstituted, monocyclic heterocyclic ring, substituted or unsubstituted, monocyclic aryl ring, or substituted or unsubstituted, monocyclic heteroaryl ring;

each instance of Z is independently $C(R^P)_2$ or O;

each instance of $R^P$ is independently hydrogen, halogen, or substituted or unsubstituted, $C_{1-6}$ alkyl;

each instance of ⚌ is independently a single bond or double bond;

each instance of $L^1$, $L^2$, $L^{3a}$, and $L^{3b}$ is independently a single bond, substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or $C_{2-200}$ heteroalkynylene;

each instance of $R^1$, $R^2$, $R^3$, and $R^4$ is independently hydrogen, halogen, or substituted or unsubstituted, $C_{1-6}$ alkyl, or two instances of $R^1$ attached to the same carbon atom are taken together to form oxo, or two instances of $R^2$ attached to the same carbon atom are taken together to form oxo, or two instances of $R^3$ attached to the same carbon atom are taken together to form oxo, or two instances of $R^4$ attached to the same carbon atom are taken together to form oxo;

each instance of $W^1$ and $W^2$ is independently a single bond,

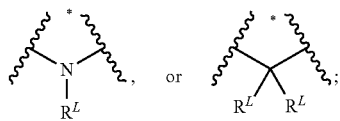

each instance of $R^L$ is independently hydrogen, a nitrogen protecting group when attached to a nitrogen atom, or $-L(M)_m$;

each instance of M is independently hydrogen or an agent;

each instance of m is independently an integer between 1 and 10, inclusive;

each instance of L is independently substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or substituted or unsubstituted, $C_{2-200}$ heteroalkynylene;

optionally one or more carbon atoms in each instance of the substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;

optionally one or more heteroatoms in each instance of the substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;

each instance of e and f is independently an integer between 0 and 10, inclusive;

each instance of $X^1$ and $X^2$ is independently hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, $-OR^C$, $-N(R^C)_2$, $-C(=O)R^C$, $-C(=O)OR^C$, $-C(=O)N(R^C)_2$, $-NR^CC(=O)R^C$, $-NR^CC(=O)OR^C$, $NR^CC(=O)N(R^C)_2$, $-OC(=O)R^C$, $-OC(=O)OR^C$, or $-OC(=O)N(R^C)_2$;

each instance of $R^C$ is independently hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, a leaving group, an oxygen protecting group when attached to an oxygen atom, a nitrogen protecting group when attached to a nitrogen atom,

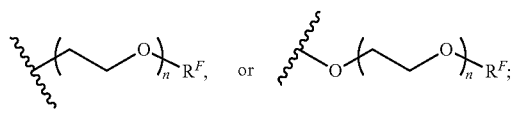

each instance of n is independently an integer between 1 and 300, inclusive; and each instance of $R^F$ is independently hydrogen, substituted or unsubstituted, $C_{1-6}$ alkyl, or an oxygen protecting group;

or

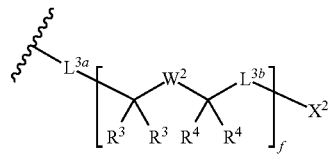

is hydrogen or absent, as valency permits;

Y is O or $C(R^Q)_2$;

each instance of $R^Q$ is independently hydrogen, halogen, or substituted or unsubstituted, $C_{1-6}$ alkyl;

each instance of $R^K$ is independently hydrogen, halogen, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or $-OR^N$;

each instance of 10 is independently hydrogen, substituted or unsubstituted acyl, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or an oxygen protecting group;

j is 1, 2, or 3; and k is 0, 1, 2, or 3.

In certain embodiments, each instance of the first monomer is of Formula (A1), or a salt thereof.

In certain embodiments, at least one instance of the first monomer is of the formula:

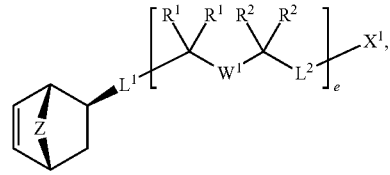

or a salt thereof.

In certain embodiments, each instance of the first monomer is of Formula (A2), or a salt thereof.

In certain embodiments, at least one instance of the first monomer is of the formula:

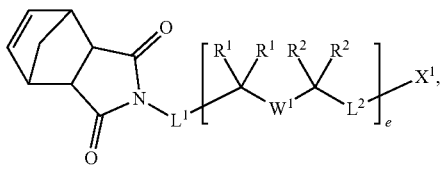

or a salt thereof.

In certain embodiments, at least one instance of the first monomer is of the formula:

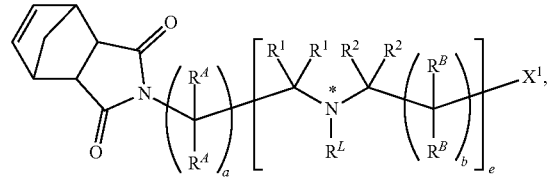

(A2a)

or a salt thereof, wherein:

each instance of $R^A$ is independently hydrogen, halogen, or substituted or unsubstituted, $C_{1-6}$ alkyl; a is an integer from 1 to 20, inclusive; each instance of $R^B$ is independently hydrogen, halogen, or substituted or unsubstituted, $C_{1-6}$ alkyl; each instance of b is independently an integer from 1 to 20, inclusive; and e is an integer from 1 to 10, inclusive.

In certain embodiments, at least one instance of the first monomer is of the formula:

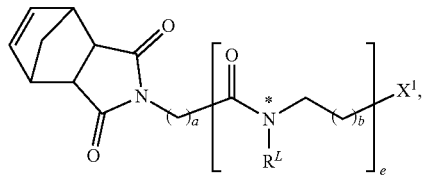

or a salt thereof, wherein e is an integer from 1 to 10, inclusive.

In certain embodiments, at least one instance of the first monomer is of the formula:

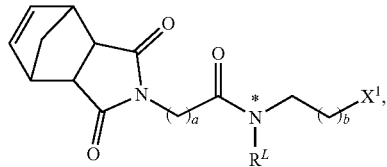

or a salt thereof.

In certain embodiments, at least one instance of the first monomer is of the formula:

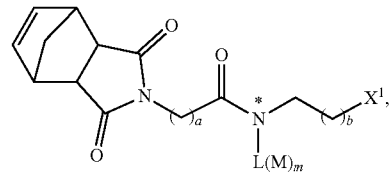

or a salt thereof, wherein -L(M)$_m$ comprises one or more instances of —C≡CH.

In certain embodiments, at least one instance of the first monomer is of the formula:

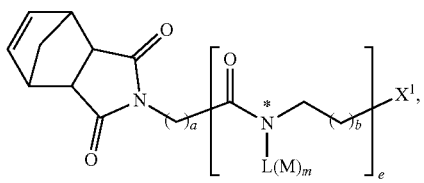

or a salt thereof, wherein: e is an integer from 1 to 10, inclusive; and at least one instance of -L(M)$_m$ comprises one or more instances of —C≡CH.

In certain embodiments, at least one instance of the first monomer is of the formula:

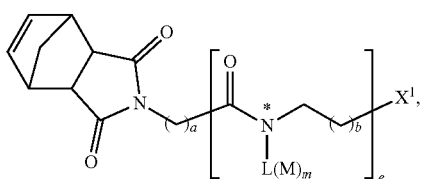

or a salt thereof, wherein: e is an integer from 1 to 10, inclusive; and at least one instance of M is an agent.

In certain embodiments, at least one instance of the first monomer is of the formula:

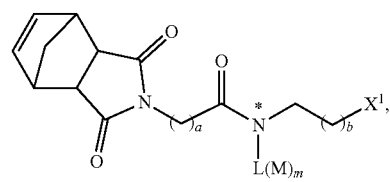

or a salt thereof, wherein at least one instance of M is an agent.

A brush polymer comprising: n2 instances of a block, wherein the each instance of the block is independently of Formula (A3) or (A4):

(A3)

[structural formula A3]

or (A4)

[structural formula A4]

or a salt thereof; and
n3 instances of a linker of the formula:

(B1)

[structural formula B1]

or a salt thereof;
wherein:
each instance of n1 is independently an integer between 2 and 1,000, inclusive;
n2 is an integer between 2 and 100, inclusive;
n3 is an integer between 1 and 101, inclusive;
at least two instances of the block are immediately separated by one or more instances of the linker;
each instance of

[ring symbol]

is Ring B, wherein each instance of Ring B is independently a substituted or unsubstituted, monocyclic carbocyclic ring, substituted or unsubstituted, monocyclic heterocyclic ring, substituted or unsubstituted, monocyclic aryl ring, or substituted or unsubstituted, monocyclic heteroaryl ring;
each instance of Z is independently $C(R^P)_2$ or O;
each instance of $R^P$ is independently hydrogen, halogen, or substituted or unsubstituted, $C_{1-6}$ alkyl;
each instance of ==== is independently a single bond or double bond;
each instance of $L^1$, $L^2$, $L^{3a}$, and $L^{3b}$ is independently a single bond, substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or $C_{2-200}$ heteroalkynylene;

each instance of $R^1$, $R^2$, $R^3$, and $R^4$ is independently hydrogen, halogen, or substituted or unsubstituted, $C_{1-6}$ alkyl, or two instances of $R^1$ attached to the same carbon atom are taken together to form oxo, or two instances of $R^2$ attached to the same carbon atom are taken together to form oxo, or two instances of $R^3$ attached to the same carbon atom are taken together to form oxo, or two instances of $R^4$ attached to the same carbon atom are taken together to form oxo;
each instance of $W^1$ and $W^2$ is independently a single bond,

[structural fragment with N–$R^L$]    or    [structural fragment with C($R^L$)$_2$];

each instance of $R^L$ is independently hydrogen, a nitrogen protecting group when attached to a nitrogen atom, or -L(M)$_m$;
each instance of M is independently hydrogen or an agent;
each instance of m is independently an integer between 1 and 10, inclusive;
each instance of L is independently substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or substituted or unsubstituted, $C_{2-200}$ heteroalkynylene;
optionally one or more carbon atoms in each instance of the substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;
optionally one or more heteroatoms in each instance of the substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;
each instance of e and f is independently an integer between 0 and 10, inclusive;
each instance of $X^1$ and $X^2$ is independently hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, —$OR^C$, —$N(R^C)_2$, —C(=O)$R^C$, —C(=O)$OR^C$, —C(=O)N($R^C$)$_2$, —$NR^C$C(=O)$R^C$, —$NR^C$C(=O)$OR^C$, $NR^C$C(=O)N($R^C$)$_2$, —OC(=O)$R^C$, —OC(=O)$OR^C$, or —OC(=O)N($R^C$)$_2$;
each instance of $R^C$ is independently hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, a leaving group, an oxygen protecting group when attached to an oxygen atom, a nitrogen protecting group when attached to a nitrogen atom,

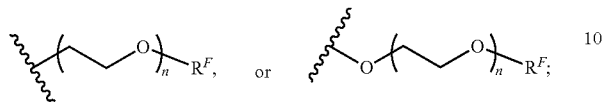

each instance of n is independently an integer between 1 and 300, inclusive; and each instance of $R^F$ is independently hydrogen, substituted or unsubstituted, $C_{1-6}$ alkyl, or an oxygen protecting group;

or

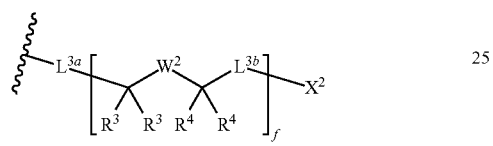

is hydrogen or absent, as valency permits;

Y is O or $C(R^Q)_2$;

each instance of $R^Q$ is independently hydrogen, halogen, or substituted or unsubstituted, $C_{1-6}$ alkyl;

each instance of $R^K$ is independently hydrogen, halogen, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or —$OR^N$;

each instance of $R^N$ is independently hydrogen, substituted or unsubstituted acyl, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or an oxygen protecting group;

j is 1, 2, or 3; and k is 0, 1, 2, or 3.

In some embodiments, at least one instance of n1 is an integer between 10 and 100, inclusive. In certain embodiments, at least one instance of n1 is an integer between 10 and 300, inclusive. In some embodiments, n2 is an integer between 2 and 80 inclusive. In certain embodiments, n2 is 2. In certain embodiments, n3 is an integer between 1 and 50, inclusive. In certain embodiments, n3 is 1.

In some embodiments, the brush polymer is a block copolymer comprising: (1) a block comprising homo-Formula (A3) or (A4) and (2) a block comprising copolymerized Formula (B1) with Formula (A3) or (A4). In certain embodiments, the brush polymer is a block copolymer comprising: (1) a block comprising homo-Formula (A3) or (A4), (2) a block comprising Formula (B1), and (3) a block comprising homo-Formula (A3) or (A4).

In some embodiments, Formula (A4) is of the formula:

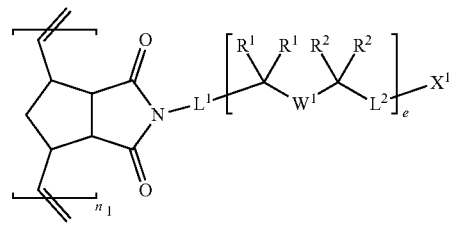

(e.g.,

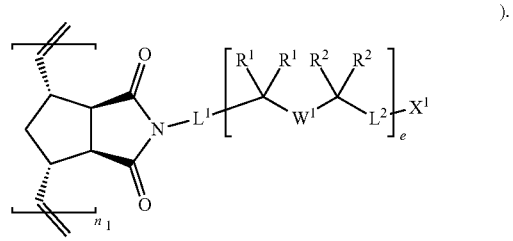

).

In some embodiments, Formula (A4) is of the formula:

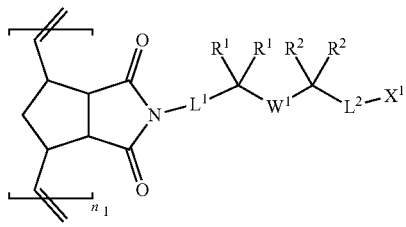

(e.g.,

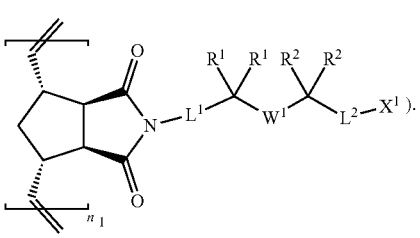

).

In certain embodiments, the linker is of the formula

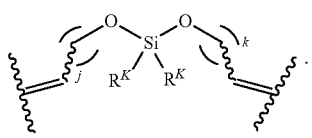

In some embodiments, the linker is of the formula

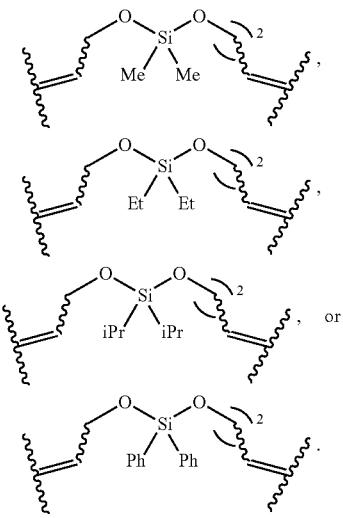

In certain embodiments, at least two instances of a variable are different from each other. In certain embodiments, all instances of a variable are different from each other. In certain embodiments, all instances of a variable are the same.

In certain embodiments, each instance of

is Ring B, wherein each instance of Ring B is independently unsubstituted, monocyclic aryl ring, or substituted or unsubstituted, monocyclic heteroaryl ring. In certain embodiments, at least one instance of Ring B is a substituted or unsubstituted, monocyclic heterocyclic ring. In certain embodiments, at least one instances of Ring B is a substituted or unsubstituted, 5-membered monocyclic heterocyclic ring. In certain embodiments, at least one instance of Ring B is

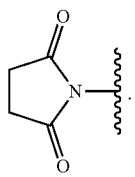

In certain embodiments, at least one instance of

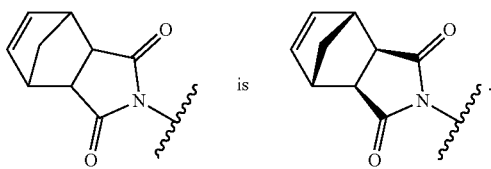 [SMILES: *N1C(=O)C2C3C=CC(C3)C2C1=O ; *N1C(=O)[C@@H]2[C@H](C1=O)[C@H]1C=C[C@@H]2C1]

In certain embodiments, at least one instance of Ring B is a substituted or unsubstituted, monocyclic carbocyclic ring. In certain embodiments, at least one instances of Ring B is a substituted or unsubstituted, 5-membered monocyclic carbocyclic ring.

In certain embodiments, each instance of

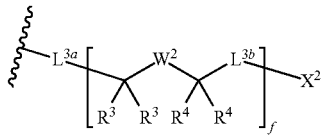

is hydrogen or absent, as valency permits.

In certain embodiments, at least one instance of Z is $C(R^P)_2$. In certain embodiments at least one instance of Z is $CH_2$. In certain embodiments, at least one instance of Z is O.

In certain embodiments, each instance of $R^P$ is hydrogen. In certain embodiments, at least one instance of $R^P$ is hydrogen. In certain embodiments, at least one instance of $R^P$ is halogen. In certain embodiments, at least one instance of $R^P$ is unsubstituted, $C_{1-6}$ alkyl or $C_{1-6}$ alkyl substituted with one or more halogen. In certain embodiments, at least one instance of $R^P$ is unsubstituted methyl.

In certain embodiments, at least one instance of ═══ is a single bond. In certain embodiments, at least one instance of ═══ is a double Pond.

In certain embodiments, at least one instance of $L^1$, $L^2$, $L^{3a}$, and $L^{3b}$ is a single bond. In certain embodiments, at least one instance of $L^1$ is substituted or unsubstituted, $C_{1-20}$ alkylene. In certain embodiments, at least one instance of $L^2$ is substituted or unsubstituted, $C_{1-20}$ alkylene. In certain embodiments, at least one instance of $L^1$ is substituted or unsubstituted, $C_{2-20}$ heteroalkylene. In certain embodiments, at least one instance of $L^2$ is substituted or unsubstituted, $C_{2-20}$ heteroalkylene. In certain embodiments, at least one instance of $L^{3a}$ is hydrogen. In certain embodiments, at least one instance of $L^{3b}$ is hydrogen. In some embodiments, at least one instance of $L^{3a}$ is a single bond. In some embodiments, at least one instance of $L^1$ is a single bond.

In certain embodiments, at least one instance of $L^{3a}$ is a single bond, and at least one instance of $L^1$ is a single bond. In some embodiments, each instance of $L^{3a}$ is a single bond, and each instance of $L^1$ is a single bond.

In certain embodiments, each instance of $R^1$, $R^2$, $R^3$, and $R^4$ is hydrogen. In certain embodiments, at least two instances of $R^1$ attached to the same carbon atom are taken together to form oxo. In certain embodiments, at least two instances of $R^2$ attached to the same carbon atom are taken together to form oxo. In certain embodiments, at least two instances of $R^3$ attached to the same carbon atom are taken together to form oxo. In certain embodiments, at least two instances of $R^4$ attached to the same carbon atom are taken together to form oxo. In certain embodiments, at least one instance of $R^1$, $R^2$, $R^3$, and $R^4$ is hydrogen. In certain embodiments, at least two instances of $R^1$ attached to the same carbon atom are each hydrogen. In certain embodiments, at least two instances of $R^2$ attached to the same carbon atom are each hydrogen. In certain embodiments, at least two instances of $R^1$ attached to the same carbon atom are taken together to form oxo, and at least two instances of $R^2$ attached to the same carbon atom are each hydrogen. In certain embodiments, at least two instances of $R^2$ attached to the same carbon atom are taken together to form oxo, and at least two instances of $R^1$ attached to the same carbon atom are each hydrogen. In certain embodiments, at least one instance of $R^1$, $R^2$, $R^3$, and $R^4$ is halogen (e.g. F). In certain embodiments, at least one instance of $R^1$, $R^2$, $R^3$, and $R^4$ is unsubstituted $C_{1-6}$ alkyl. In certain embodiments, at least one instance of $R^1$, $R^2$, $R^3$, and $R^4$ is substituted $C_{1-6}$ alkyl.

In certain embodiments, at least one instance of $W^1$ or $W^2$ is a single bond. In certain embodiments, at least one instance of $W^1$ or $W^2$ is

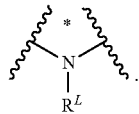

In certain embodiments, each instance of $W^1$ is

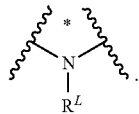

In certain embodiments, at least one instance of $W^1$ or $W^2$ is

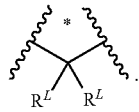

In certain embodiments, at least one instance of $R^L$ is hydrogen. In certain embodiments, at least one instance of $R^L$ is a nitrogen protecting group when attached to a nitrogen atom. In certain embodiments, at least one instance of $R^L$ is -L(M)$_m$. In certain embodiments, each instance of $R^L$ is -L(M)$_m$.

In certain embodiments, wherein at least one instance of -L(M)$_m$ comprises one or more click-chemistry handles. In certain embodiments, wherein at least one instance of -L(M)$_m$ comprises one or more instances of —C≡CH. In certain embodiments, wherein each instance of -L(M)$_m$ comprises one or more (e.g., 2 or 3) instances of —C≡CH. In certain embodiments, wherein each instance of M is hydrogen. In certain embodiments, wherein at least one instance of M is an agent. In certain embodiments, wherein at least one instance of L comprises an amino acid or a peptide. In certain embodiments, wherein at least one instance of L is cleavable by ultraviolet irradiation, hydrolysis, reduction, oxidation, or contacting with an enzyme. In certain embodiments, wherein each instance of L is cleavable by hydrolysis or contacting with an enzyme.

In certain embodiments, wherein at least one instance of L is substituted or unsubstituted, $C_{2-50}$ heteroalkylene, wherein:

one or more carbon atoms and/or one or more heteroatoms, of the substituted or unsubstituted, $C_{2-50}$ heteroalkylene are replaced with

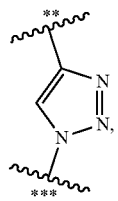

wherein the atom labeled with "*" is closer to the attachment point labeled with "" than the attachment point labeled with "*"; and optionally one or more carbon atoms and/or one or more heteroatoms, of the $C_{2-50}$ heteroalkylene are independently replaced with substituted or unsubstituted phenylene.

In certain embodiments, wherein at least one instance of L is $C_{2-50}$ heteroalkylene, wherein:

the $C_{2-50}$ heteroalkylene is unsubstituted or substituted with one or more substituents independently selected from the group consisting of halogen, unsubstituted $C_{1-6}$ alkyl, and oxo; one or more carbon atoms and/or one or more heteroatoms, of the $C_{2-50}$ heteroalkylene are replaced with

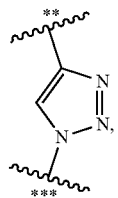 [SMILES: *c1cn(*)nn1]

wherein the atom labeled with "*" is closer to the attachment point labeled with "" than the attachment point labeled with "*"; and optionally one or more carbon atoms and/or one or more heteroatoms, of the $C_{2-50}$ heteroalkylene are independently replaced with substituted or unsubstituted phenylene.

In certain embodiments, at least one instance of -L(M)$_m$ comprises 1, 2, 3, 4, or 5 click-chemistry handles. In certain embodiments, each instance of -L(M)$_m$ comprises independently a click-chemistry handle. In certain embodiments, at least one instance of the click-chemistry handle comprises an alkenylene group or alkynylene group. In certain embodiments, at least one instance of the click-chemistry handle comprises an internal alkenylene group or alkynylene group. In certain embodiments, at least one instance of the click-chemistry handle comprises an terminal alkenylene group or alkynylene group. In certain embodiments, at least one instance of the click-chemistry handle is —C≡CH, substituted or unsubstituted cyclooctynyl optionally fused independently with one or more instances of substituted or unsubstituted phenyl, substituted or unsubstituted cyclopropenyl, substituted or unsubstituted cyclobutenyl, substituted or unsubstituted trans-cyclooctenyl optionally fused independently with one or more instances of substituted or unsubstituted phenyl, or substituted or unsubstituted

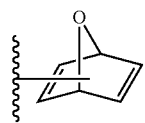

In certain embodiments, each instance of the click-chemistry handle is —C≡CH. In certain embodiments, at least one instance of -L(M)$_m$ is —(CH$_2$)$_g$—C≡CH, wherein each instance of g is independently an integer from 1 to 10, inclusive. In certain embodiments, at least one instance of -L(M)$_m$ comprises 2, 3, 4, or 5 instances of —(CH$_2$)$_g$—C≡H, wherein each instance of g is independently an integer from 1 to 10, inclusive. Each instance of g is independently an integer selected from the group consisting of 1, 2, 3, 4, 5, 6, 7, 8, 9, and 10.

In certain embodiments, at least one instance of -L(M)$_m$ comprises:

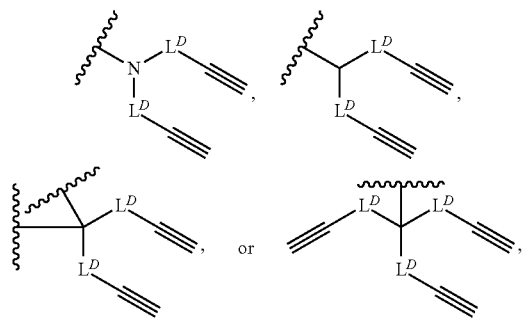

wherein each instance of L$^D$ is independently substituted or unsubstituted, C$_{1-10}$ alkylene, or substituted or unsubstituted, C$_{2-10}$ heteroalkylene. In certain embodiments, at least one instance of -L(M)$_m$ comprises:

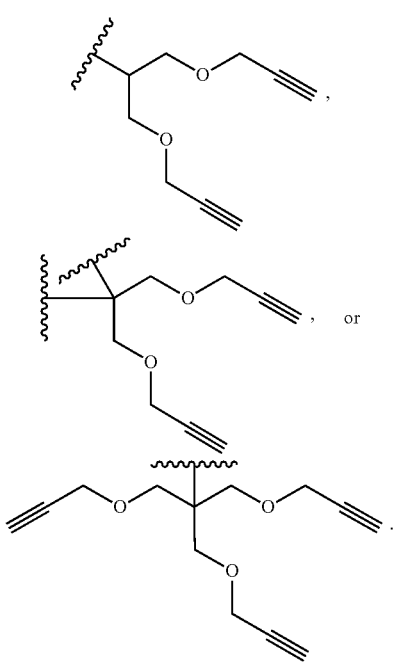

In certain embodiments, at least one instance of -L(M)$_m$ comprises:

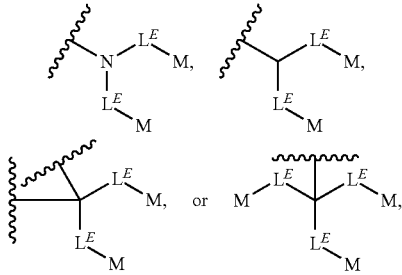

wherein each instance of L$^E$ is independently substituted or unsubstituted, C$_{1-50}$ alkylene, substituted or unsubstituted, C$_{2-50}$ alkenylene, substituted or unsubstituted, C$_{2-50}$ alkynylene, substituted or unsubstituted, C$_{2-50}$ heteroalkylene, substituted or unsubstituted, C$_{2-50}$ heteroalkenylene, or substituted or unsubstituted, C$_{2-50}$ heteroalkynylene, wherein: optionally one or more carbons of each instance of the substituted or unsubstituted, C$_{1-50}$ alkylene, substituted or unsubstituted, C$_{2-50}$ alkenylene, substituted or unsubstituted, C$_{2-50}$ alkynylene, substituted or unsubstituted, C$_{2-50}$ heteroalkylene, substituted or unsubstituted, C$_{2-50}$ heteroalkenylene, and substituted or unsubstituted, C$_{2-50}$ heteroalkynylene are independently replaced with substituted or unsubstituted carbocyclylene, substituted or unsubstituted heterocyclylene, substituted or unsubstituted aryl ene, or substituted or unsubstituted heteroarylene; and optionally one or more heteroatoms of each instance of the substituted or unsubstituted, C$_{2-50}$ heteroalkylene, substituted or unsubstituted, C$_{2-50}$ heteroalkenylene, and substituted or unsubstituted, C$_{2-50}$ heteroalkynylene are independently replaced with substituted or unsubstituted carbocyclylene, substituted or unsubstituted heterocyclylene, substituted or unsubstituted arylene, or substituted or unsubstituted heteroaryl ene.

In certain embodiments, at least one instance of L is substituted or unsubstituted, C$_{2-200}$ alkynylene. In certain embodiments, at least one instance of L is substituted or unsubstituted, C$_{2-200}$ heteroalkynylene. In certain embodiments, at least one instance of L is substituted or unsubstituted, C$_{2-200}$ heteroalkylene, wherein one or more carbons and/or one or more heteroatoms, of the substituted or unsubstituted, C$_{2-200}$ heteroalkylene, are independently replaced with substituted or unsubstituted heteroarylene. In certain embodiments, at least one instance of L is substituted or unsubstituted, C$_{2-200}$ heteroalkylene, wherein one or more carbons and/or one or more heteroatoms, of the substituted or unsubstituted, C$_{2-200}$ heteroalkylene, are independently replaced with

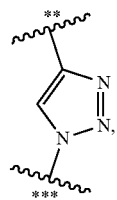 [SMILES: *c1cn(*)nn1]

wherein the nitrogen atom labeled with "*" is closer to the attachment point labeled with "" than the attachment point labeled with "*". In certain embodiments, at least one instance of L is substituted or unsubstituted, $C_{2\text{-}200}$ heteroalkylene, wherein one carbon or one heteroatom, of the substituted or unsubstituted, $C_{2\text{-}200}$ heteroalkylene, is replaced with

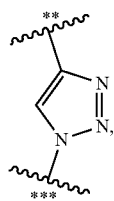

wherein the nitrogen atom labeled with "*" is closer to the attachment point labeled with "" than the attachment point labeled with "*".

In certain embodiments, at least one instance of L comprises

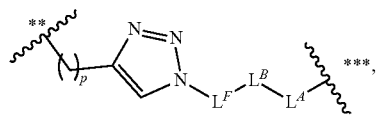

wherein: each instance of p is independently an integer from 1 to 10, inclusive; each instance of $L^F$ is independently substituted or unsubstituted, $C_{2\text{-}180}$ heteroalkylene; each instance of -$L^B$-$L^A$- is independently —C(=O)O—, —OC(=O)—, —C(=O)NR$^E$—, or —NR$^E$C(=O)—, wherein each instance of R$^E$ is independently hydrogen, substituted or unsubstituted, $C_{1\text{-}6}$ alkyl, or a nitrogen protecting group; and the nitrogen atom labeled with "*" is closer to the attachment point labeled with "" than the attachment point labeled with "*". In certain embodiments, L is

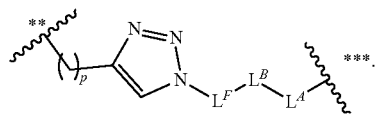

In certain embodiments, at least one instance of L comprises

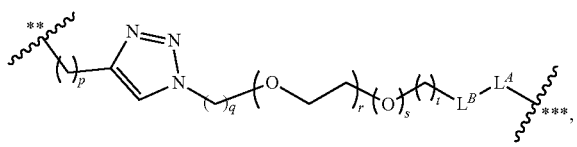

wherein: each instance of p is independently an integer from 1 to 10, inclusive; each instance of q is independently an integer from 1 to 10, inclusive; each instance of r is independently an integer from 0 to 10, inclusive; each instance of s is independently 0 or 1; each instance of t is independently an integer from 0 to 10, inclusive; each instance of -$L^B$-$L^A$- is independently —C(=O)O—, —OC(=O)—, —C(=O)NR$^E$—, or —NR$^E$C(=O)—, wherein each instance of R$^E$ is independently hydrogen, substituted or unsubstituted, $C_{1\text{-}6}$ alkyl, or a nitrogen protecting group; and the nitrogen atom labeled with "*" is closer to the attachment point labeled with "" than the attachment point labeled with "*". In certain embodiments, L is

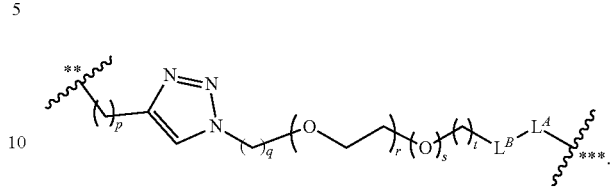

In certain embodiments, at least one instance of L comprises wherein: each instance of p is independently an integer from 1 to

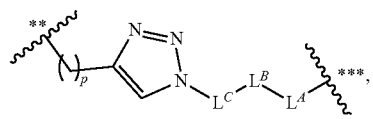

wherein: each instance of p is independently an integer from 1 to 10, inclusive; each instance of $L^C$ is independently substituted or unsubstituted, $C_{1\text{-}180}$ alkylene; each instance of -$L^B$-$L^A$- is independently —C(=O)O—, —OC(=O)—, —C(=O)NR$^E$—, or —NR$^E$C(=O)—, wherein each instance of R$^E$ is independently hydrogen, substituted or unsubstituted, $C_{1\text{-}6}$ alkyl, or a nitrogen protecting group; and the nitrogen atom labeled with "*" is closer to the attachment point labeled with "" than the attachment point labeled with "*". In certain embodiments, L is

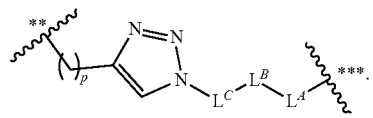

In certain embodiments, $L^C$ is independently $C_{1\text{-}180}$ alkylene substituted with one or more instances of: substituted or unsubstituted phenyl and/or substituted or unsubstituted, $C_{1\text{-}6}$ alkyl.

In certain embodiments, at least two instances of L are different from each other. In certain embodiments, all instances of L are different from each other. In certain embodiments, all instances of L are the same.

In certain embodiments, at least one instance of L comprises a polymer chain. In some embodiments, at least one instance of the polymer chain is a polyethylene glycol (PEG), a polyethylene oxide (PEO), a polypropylene glycol (PPG), a polyglycerol (PG), a poloxamine (PDX), a polybutylene oxide (PBO), polylactic acid (PLA), polyglycolic acid (PGA), poly(lactic-co-glycolic acid) (PLGA), polycaprolactone (PCL), polydioxanone (PDO), a polyanhydride, a polyacrylide, a polyvinyl, or a polyorthoester. In some embodiments, at least one instance of the polymer chain is polyethylene glycol (PEG). In some embodiments, the PEG has a molecular weight of between about 100 and about 6000 g/mol (e.g., $PEG_{100}$, $PEG_{200}$, $PEG_{400}$, $PEG_{600}$, $PEG_{800}$, $PEG_{1000}$, $PEG_{1500}$, $PEG_{2000}$, $PEG_{3000}$, $PEG_{4000}$, or $PEG_{6000}$). In some embodiments, the PEG is $PEG_{100}$. In some embodiments, the PEG is $PEG_{200}$. In some embodiments, the PEG is $PEG_{400}$. In some embodiments, the PEG is PEG$_{600}$. In some embodiments, the PEG is PEG$_{800}$. In some embodiments, the PEG is PEG$_{1000}$. In some embodiments, the PEG is PEG$_{2000}$. In some embodiments, the PEG is PEG$_{3000}$. In some embodiments, the PEG is PEG$_{4000}$. In some embodiments, the PEG is PEG$_{6000}$.

In certain embodiments, the polymer chain is in the form of a conjugate, BASP, or particle (e.g., nanoparticle or microparticle). The agent is covalently bound to the polymer chain, through a cleavable linker (which can also be referred to herein as a "sensitive linker"). In certain embodiments, at least one instance (e.g., each instance) of L comprises a cleavable linker. In certain embodiments, at least one instance (e.g., each instance) of L is a cleavable linker. A cleavable linker is "cleaved" or "degraded" when one or more bonds of the cleavable linker are broken, e.g., resulting in release of an agent, e.g., from the conjugate or particle. Linker cleavage or agent release need not be 100%, e.g., a cleavage or release of at least 10%, 20%, 30%, 40%, 50%, 60%, 70%, 80%, 90%, 95%, or higher, e.g., over a period of 1 minute, 10 minute, 1 hour, 6 hours, 12 hours, 24 hours, 2 days, 4 days, 7 days, 2 weeks, or 4 weeks is encompassed by this term.

In some embodiments, the cleavable linker is cleavable by or is sensitive to an enzyme (e.g., an esterase or a protease), pH (e.g., acidic pH, basic pH), light (e.g., ultraviolet light), a nucleophile, reduction, or oxidation. In some embodiments, the cleavable linker is cleavable by or is sensitive to an enzyme (e.g., an esterase or a protease) or pH (e.g., acidic pH, basic pH). In some embodiments, the cleavable linker is not cleavable by light (e.g., ultraviolet light).

In some embodiments, the cleavable linker comprises an ester, an acetal, a ketal, a phosphoramidite, a hydrazone, an imine, an oxime, a disulfide, or a silyl moiety, a combination of acetal or ketal with ester group, an oligo-acetal or oligo-ketal group, a combination of the oligo-ketal and silyl ether group, or a combination of the oligo-ketal and vinyl ether group. In some embodiments, the cleavable linker comprises an ester. In some embodiments, the cleavable linker comprises an acetal. In some embodiments, the cleavable linker comprises a phosphoramidite. In some embodiments, the cleavable linker comprises a hydrazine. In some embodiments, the cleavable linker comprises an imine. In some embodiments, the cleavable linker comprises an oxime. In some embodiments, the cleavable linker comprises a silyl moiety. In some embodiments, the cleavable linker comprises a disulfide.

In other embodiments, the cleavable linker is chosen from a combination of acetal or ketal with cis-aconityl, hydrazine, oxime, imidazole, or trityl groups. Any of the aforesaid groups or combination of groups can modified to enhance the pH sensitivity of the cleavable linker, e.g., as described herein.

In some embodiments, the cleavable linker is an amide, urea, carbamate, carbonate, or disulfide.

In some embodiments, the cleavable linker comprises: —OC(O)—, —C(O)O—,

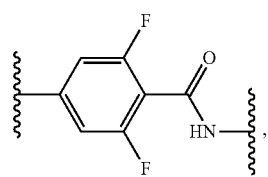

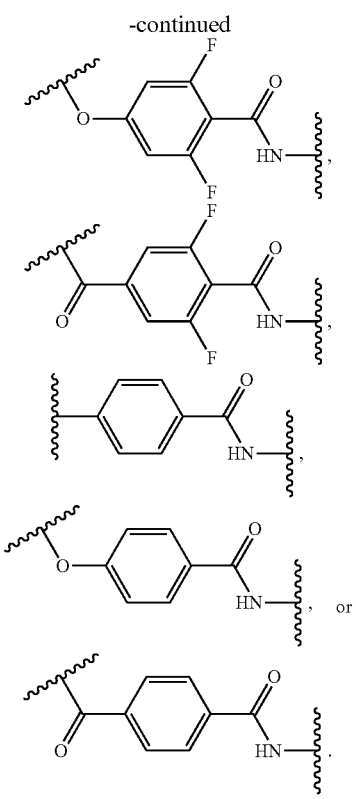

The cleavable linker may include an atom or a part of a moiety that is derived in part from the agent (e.g., a therapeutic agent).

In some embodiments, the cleavable linker is cleaved or degraded, e.g., preferentially cleaved or degraded, upon exposure to a first set of conditions relative to a second set of conditions. For example, the cleavable linker can be "preferentially cleaved" or "preferentially degraded" in a first set of conditions relative to a second set of conditions if at least 10%, 20%, 30%, 40%, 50%, 60%, 70%, 80%, 90%, 95%, or more of a bond or bonds of the cleavable linker are broken, or the agent is released, in the first set of conditions relative to the second set of conditions.

In some embodiments, the cleavable linker is degraded or hydrolyzed at physiological conditions. In some embodiments, the linker is pH sensitive or cleaved at a certain pH. In some embodiments, the linker is degraded or hydrolyzed through the action of an enzyme (e.g., a protease or esterase). For example, in some embodiments, the cleavable linker is preferentially cleaved in a tissue microenvironment, e.g., a tumor microenvironment, which is referred to herein as a "tissue microenvironment cleavable linker." In embodiments, the tissue (e.g., tumor) microenvironment cleavable linker is preferentially cleaved or degraded upon exposure to a first desired tissue or tumor microenvironment relative to a second tissue or non-tumor tissue. A tissue (e.g., tumor) microenvironment cleavable linker can be preferentially cleaved if at least 10%, 20%, 30%, 40%, 50%, 60%, 70%, 80%, 90%, 95% or more of a bond or bonds of the linker are broken, or the agent is released, in a desired tissue or tumor microenvironment relative to another tissue or non-tumor tissue. In one embodiments, the tissue (e.g., tumor) microenvironment cleavable linker is preferentially cleaved or degraded if one or more of the bonds of the linker are broken, or the agent is released, at least 2, 5, 10, 20, 30, 40, 50, 60, 70, 80, or 100 times faster upon exposure to a first desired tissue or tumor microenvironment relative to a second tissue or non-tumor tissue. The tissue (e.g., tumor) microenvironment can have a particular set of conditions, e.g., pH, enzymes, that cause the cleavage or degradation of the linker.

In some embodiments, the cleavable linker is a peptide. In some embodiments, the linker is a peptide, and the peptide sequence is comprised of naturally occurring amino acids. In some embodiments, the linker is a peptide, and the peptide sequence comprises at least one synthetically derived amino acids, e.g., at least 2, at least 3, at least 4, at least 5, at least 8, at least 10, at least 15, at least 20, or more synthetically derived amino acids (unnatural amino acid). In some embodiments, the peptide has a linear structure. In some embodiments, the peptide has a branched structure. In some embodiments, the peptide has a branched structure with, e.g., at least 2, at least 3, at least 4, at least 5, at least 6, at least 7, or at least 8 branching points. In some embodiments, the peptide has a cyclic structure.

In some embodiments, the cleavable linker is a peptide, and the peptide sequence comprises at least 2 amino acid residues. In some embodiments, the peptide sequence comprises at least 3, at least 4, at least 5, at least 6, at least 7, at least 8, at least 9, or at least 10 amino acid residues. In some embodiments, the peptide sequence is from about 1 to about 10 amino acid residues. In some embodiments, the peptide sequence is from about 1 to about 15, about 20, about 25, about 30, about 40, about 50, about 60, about 70, about 80, about 90, or about 100 amino acid residues. In some embodiments, the peptide sequence is from about 10 to about 100 amino acid residues. In some embodiments, the peptide sequence is from about 25 to about 100 amino acid residues. In some embodiments, the peptide sequence is from about 50 to about 100 amino acid residues.

In some embodiments, the cleavable linker comprises a substrate peptide that is cleaved, e.g., activated, by a matrix metalloprotease (MMP) selected from a sequence disclosed in U.S. Patent Application No. 2015/0087810 with a publication date of Mar. 26, 2015. In some embodiments, the substrate peptide comprises a protease substrate comprising an amino acid sequence selected from the group consisting of SEQ ID NOs: 353-363, 372-375, 376-378, 395-401, 411-419, 426-433, 437-449, 454-456, 459-469, 475-482, 487-495, 318-323, 325-327, 330-335, 341-347, 14-33, and 159, e.g., as described in U.S. Patent Application No. 2015/0087810. In some embodiments, the linker comprises a substrate peptide derived from a sequence disclosed in U.S. Pat. No. 8,541,203, e.g., a substrate peptide chosen from an enzyme selected from the group consisting of MMP-1, MMP-2, MMP-3, MMP-8, MMP-9, MMP-14, plasmin, PSA, PSMA, CATHEPSIN D, CATHEPSIN K, CATHEPSIN S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE. In some embodiments, the linker comprises a sequence disclosed in U.S. Pat. No. 8,513,390. In some embodiments, the linker comprises a sequence disclosed in International Patent Publication No. WO2003/079972. In some embodiments, the linker comprises a sequence disclosed in U.S. Pat. No. 7,495,099. In some embodiments, the linker comprises a sequence disclosed in U.S. Pat. No. 8,580,244. In some embodiments, the linker comprises a sequence disclosed in one of the following articles: van Kempen, et al. *Eur Cancer* (2006) 42:728-734; Desnoyers, L. R. et al. *Sci Transl Med* (2013) 5:207ra144; Rice, J. J. et al. *Protein Sci* (2006) 15:825-836; Boulware, K. T. and Daugherty, P. S. *Proc Natl Acad Sci USA* (2006) 103:7583-7588; Deperthes, D. *Biol Chem* (2002) 383:1107-1112; Harris, J. L. *Proc Natl Acad Sci USA* (2000) 97:7754-7759; Salmaso S. and Caliceti, P. J *Drug Deliv* (2013) 2013:1-19; and Eckhard, U et al. *Matrix Biol* (2015) doi: 10.1016/j.matbio.2015.09.003 (epub ahead of print). The contents of any of the publications referenced herein are hereby expressly incorporated by reference.

In some embodiments, the cleavable linker comprises a substrate peptide that is cleaved, e.g., activated, by a protease, e.g., a protease present in a tumor or fibrotic microenvironment (e.g, a matrix metalloprotease (MMP), e.g., as described by Desnoyers, L. R. et al. *Sci Transl Med* (2013) 5:207ra144; Eckhard, U et al *Matrix Biol* (2015) doi: 10.1016/j.matbio.2015.09.003 (epub ahead of print); and van Kempen, et al. *Eur Cancer* (2006) 42:728-734. In one embodiments, the linker includes the amino acid sequence of a substrate for uPA, e.g., comprises the amino acid sequence LSGRSDNH (SEQ ID NO:1), e.g., as described in U.S. Pat. No. 8,513,390. In some embodiments, the linker sequence further includes a Gly-Ser-containing peptide linker, at either end, or both ends to the substrate peptide. Additional exemplary proteases that may be upregulated in a tumor microenvironment include, but are not limited to, urokinase-type plasminogen activator (uPA), which is upregulated in human carcinomas (S. Ulisse, et al. *Curr. Cancer Drug Targets* 9, 32-71 (2009)), membrane-type serine protease 1 (MT-SP1/matriptase) (K. Uhland *Cell. Mol. Life Sci.* 63, 2968-2978 (2006); A. M. LeBeau, et al. *Proc. Natl. Acad. Sci.* U.S.A. 110, 93-98 (2013)), and legumain, a lysosomal protease found to be released and active in the acidic extracellular tumor microenvironment (C. Liu, et al. *Cancer Res.* 63, 2957-2964 (2003)). In some embodiments, the protease is produced by an inflammatory cell, e.g., a tumor infiltrating leukocyte (e.g., a leukocyte-derived MMP), e.g., as described by van Kempen, et al. *Eur Cancer* (2006) 42:728-734. In other embodiments, the MMP is chosen from MMP1, MMP2, MMP3, MMP7, MMP8, MMP9, MMP12, MMP13 or MMP14, e.g., as described by Eckhard, U et al. supra.

In some embodiments, the substrate peptide is derived from a CLiPS library (as described in, e.g., K. T. Boulware, P. S. Daugherty, *Proc. Natl. Acad Sci*. U.S.A. 103, 7583-7588 (2006)).

In other embodiments, the substrate peptide specificity is evaluated using combinatorial fluorogenic substrate libraries, e.g., as described by Harris, J. L. *Proc Natl Acad Sci USA* (2000) 97:7754-7759. In other embodiments, the substrate peptide is derived from a phage display library (e.g., it is a phase display substrate), e.g., as described by Deperthes, D. *Biol Chem* (2002) 383:1107-1112. For example, a phage display substrate is exposed to a plurality of proteases; peptides released through specific cleavage can be amplified in an expression system. In other embodiments, the substrate peptide is derived from a bacterial display library, e.g., as described by Rice, J. J. et al. *Protein Sci* (2006) 15:825-836.

In one embodiments, the tissue (e.g., tumor) microenvironment cleavable linker is cleavable by an enzyme. In some embodiments, the enzyme comprises an esterase or a protease. Exemplary proteases include MMP-1, MMP-2, MMP-3, MMP-8, MMP-9, MMP-14, plasmin, PSA, PSMA, CATHEPSIN D, CATHEPSIN K, CATHEPSIN S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, or TACE.

In other embodiments, the tissue microenvironment cleavable linker is cleavable at a particular pH. In some embodiments, the tissue microenvironment cleavable linker is cleavable at a pH between about 5.0 and about 7.4, between 5.0 and 7.0, between 5.0 and 6.5, between 5.0 and 5.5, or between 5.9 and 6.2. In one embodiment, the tissue microenvironment cleavable linker is cleavable at a pH between about 6.0 and about 7.0, between about 6.2 and about 6.9, between about 6.5 and about 6.8, or between about 6.5 and about 6.7. In one embodiment, the tissue microenvironment cleavable linker is cleavable at a pH between about 5.5 and about 6.5, e.g., between 5.9 and 6.2. In one embodiment, the tissue microenvironment cleavable linker is cleavable at a hypoxic pH, e.g., a pH about 6.7 to 6.9, e.g., compared to a physiological pH of about 7.4.

In some embodiments, the tissue microenvironment cleavable linker is cleavable is cleaved at a pH of no more than 7.4, no more than 7.0, no more than 6.9, no more than 6.8, no more than 6.7, no more than 6.6, no more than 6.5, no more than 6.4, no more than 6.3, no more than 6.2, no more than 6.1, no more than 6.0, no more than 5.5 or lower.

In one embodiment, the tissue microenvironment cleavable linker is preferentially cleaved or degraded upon exposure to a first pH relative to a second pH. In one embodiment, the tissue microenvironment cleavable linker is cleaved or degraded at least 2, 5, 10, 20, 30, 40, 50, 60, 70, 80, or 100 times faster upon exposure to a first pH relative to a second pH. In other embodiments, the tissue microenvironment cleavable linker shows a greater release or degradation rate at a first acidic pH (e.g., pH=6.7) relative to a second more basic pH (e.g., pH=7.4). In one embodiment, ratio of release or degradation rate of the tissue microenvironment cleavable linker at pH=6.7 relative to pH=7.4 is greater than 1, 1.2, 1.4, 1.6, 1.8, 2, 2.2, 2.4, 2.6, 2.8, 3 or higher. In one embodiment, ratio of release or degradation rate of the tissue microenvironment cleavable linker at pH=6.7 relative to pH=7.4 is greater than 2.

In one embodiment, the tissue microenvironment cleavable linker shows increased pH-sensitivity in a hypoxic microenvironment, e.g., in a tumor, or fibrotic tissue.

In some embodiments, the tissue microenvironment cleavable linker exhibits an increased release rate or increased release yield of the agent at a desired site (e.g., a tumor), e.g., relative to the release rate or release yield at another site. In one embodiment, the tissue microenvironment cleavable linker comprises an electron withdrawing group (e.g., an electron withdrawing group that enhances the cleavage rate or yield.

In certain embodiments, the rate of cleavage of at least one instance of Si—O bond in the backbone of the polymer is slower (e.g., at least 3-fold, at least 10-fold, at least 30-fold, at least 100-fold, at least 300-fold, at least 1,000-fold, or at least 10,000-fold slower) than that of at least one instance of L under the same conditions. In certain embodiments, the rate of cleavage of at least one instance of Si—O bond in the backbone of the polymer is faster (e.g., at least 3-fold, at least 10-fold, at least 30-fold, at least 100-fold, at least 300-fold, at least 1,000-fold, or at least 10,000-fold faster) than that of at least one instance of L under the same conditions.

In certain embodiments, at least one instance of M is hydrogen. In certain embodiments, each instance of M is hydrogen. In certain embodiments, each instance of M is an agent. In certain embodiments, at least one instance of M is an agent. An agent can be a molecule, group of molecules, complex or substance administered to an organism for diagnostic, therapeutic, preventative medical, or veterinary purposes. In certain embodiments, at least one instance of the agent is a pharmaceutical agent. In certain embodiments, at least one instance of the agent is a therapeutic agent. In certain embodiments, at least one instance of the agent is a diagnostic agent or a prophylactic agent. In certain embodiments, at least one instance of the agent or therapeutic agent is an anti-cancer agent. Anti-cancer agents encompass biotherapeutic anti-cancer agents as well as chemotherapeutic agents. Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF), and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents include, but are not limited to, anti-estrogens (e.g. tamoxifen, raloxifene, and megestrol), LHRH agonists (e.g. goscrelin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent) docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonucleotide reductase inhibitors (e.g. hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g. 1-methyl-4-phenylpyridinium ion), cell cycle inhibitors (e.g., staurosporine), actinomycin (e.g. actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe), and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine. In certain embodiments, the anti-cancer agent is paclitaxel. In certain embodiments, the agent is an anti-hypertension agent. Exemplary anti-hypertension agents include, but are not limited to, amiloride, amlodipine, atenolol, azilsartan, benazepril, bendroflumethiazide, betaxolol, bisoprolol, bucindolol, bumetanide, candesartan, captopril, carteolol, carvedilol, chlorothiazide, chlorthalidone, cilnidipine, clevidipine, diltiazem, doxazosin, enalapril, epitizide, eplerenone, eprosartan, ethacrynic acid, felodipine, Fimasartan, fosinopril, furosemide, hydrochlorothiazide, indapamide, indoramin, irbesartan, isradipine, labetalol, lercanidipine, levamlodipine, lisinopril, losartan, methyclothiazide, metolazone, metoprolol, moexipril, nadolol, nebivolol, nicardipine, nifedipine, nimodipine, nisoldipine, nitrendipine, olmesartan, oxprenolol, penbutolol, perindopril, pindolol, phenoxybenzamine, phentolamine, polythiazide, prazosin, propranolol, quinapril, ramipril, spironolactone, telmisartan, terazosin, timolol, tolazoline, torsemide, trandolapril, triamterene, valsartan, and verapamil. In certain embodiments, the agent is telmisartan.

Exemplary diagnostic agents include, but are not limited to, fluorescent molecules; gases; metals; imaging agents, such as commercially available imaging agents used in positron emissions tomography (PET), computer assisted tomography (CAT), single photon emission computerized tomography, x-ray, fluoroscopy, and magnetic resonance imaging (MRI); and contrast agents, such as magnetic-resonance signal enhancing agents, X-ray attenuating agents, ultrasound scattering agent, and ultrasound frequency shifting agents. Examples of suitable materials for use as contrast agents in MRI include gadolinium chelates, as well as iron, magnesium, manganese, copper, and chromium. Examples of materials useful for CAT and x-ray imaging include iodine-based materials. In certain embodiments, the diagnostic agent is used in magnetic resonance imaging (MRI), such as iron oxide particles or gadolinium complexes. Gadolinium complexes that have been approved for clinical use include gadolinium chelates with DTPA, DTPA-BMA, DOTA and HP-DO3A which are reviewed in Aime, et al. (Chemical Society Reviews (1998), 27:19-29), the entire teachings of which are incorporated herein by reference.

In certain embodiments, the diagnostic agent is a metal, inorganic compound, organometallic compound, organic compound, or salt thereof. In certain embodiments, the imaging agent contains a metal selected from the group consisting of scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, meitnerium, gadolinium, gallium, thallium, and barium. In certain embodiments, the diagnostic agent is an organic compound. In certain embodiments, the diagnostic agent is metal-free. In certain embodiments, the diagnostic agent is a metal-free organic compound.

In certain embodiments, the imaging agent is a magnetic resonance imaging (MRI) agent.

In certain embodiments, the MRI agent is gadolinium. In certain embodiments, the MRI agent is a nitroxide radical-containing compound.

In certain embodiments, the imaging agent is a nuclear medicine imaging agent. In certain embodiments, the nuclear medicine imaging agent is selected from the group consisting of $^{64}$Cu diacetyl-bis(N$^4$-methylthiosemicarbazone) ($^{64}$Cu-ASTM), $^{18}$F-fluorodeoxyglucose (FDG), $^{18}$F-fluoride, 3'-deoxy-3'-[$^{18}$F]fluorothymidine (FLT), $^{18}$F-fluoromisonidazole (FMIS0), gallium, technetium-99m, and thallium.

In certain embodiments, the imaging agent is radiographic imaging agent. In certain embodiments, the radiographic imaging agent is selected from the group consisting of barium, gastrografin, and iodine contrast agent.

In certain embodiments, the imaging agent is a radical-containing compound. In certain embodiments, the imaging agent is a nitroxide radical-containing compound. In certain embodiments, the imaging agent or diagnostic agent is of the formula:

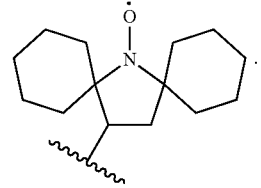

In certain embodiments, the imaging agent or diagnostic agent is an organic compound.

In certain embodiments, the imaging agent is a salt of an organic compound. In certain embodiments, the imaging agent or diagnostic agent is of the formula:

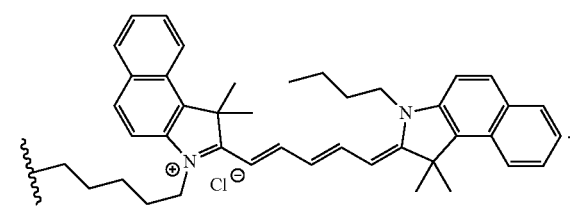 [SMILES: *CCCCC[N+]1=C(/C=C/C=C/C=C2\N(CCCC)c3ccc4ccccc4c3C2(C)C)C(C)(C)c2c1ccc1ccccc21 ; [Cl-]]

In certain embodiments, the diagnostic agent may comprise a fluorescent molecule, a metal chelate, a contrast agent, a radionuclide, or a positron emission tomography (PET) imaging agent, an infrared imaging agent, a near-IR imaging agent, a computer assisted tomography (CAT) imaging agent, a photon emission computerized tomography imaging agent, an X-ray imaging agent, or a magnetic resonance imaging (MRI) agent.

In some embodiments, the diagnostic agent is a fluorescent molecule. In some embodiments, the fluorescent molecule comprises an acridine dye, a cyanine dye, a rhodamine dye, a BODIPY dye, a fluorescein dye, a dansyl dye, an Alexa dye, an atto dye, a quantum dot, or a fluorescent protein. In some embodiments, the fluorescent molecule is a cyanine dye (e.g., Cy3, Cy 3.5, Cy5, Cy5.5, Cy7, or Cy7.5).

In some embodiments, the diagnostic agent is an MRI agent (e.g., a contrast agent).

Examples of suitable materials for use as MRI agents (e.g., contrast agents) include gadolinium chelates, as well as iron, magnesium, manganese, copper, and chromium.

In some embodiments, the diagnostic agent is a CAT imaging agent or an X-ray imaging agent. Examples of materials useful for CAT and X-ray imaging include iodine-based materials.

In some embodiments, the diagnostic agent is a PET imaging agent. Examples of suitable PET imaging agents include compounds and compositions comprising the positron emitting radioisotopoes $^{18}$F, $^{15}$O, $^{13}$N, $^{11}$C, $^{82}$Rb, $^{64}$Cu, and $^{68}$Ga, e.g., fludeoxyglucose ($^{18}$F-FDG), $^{68}$Ga-DOTA-psuedopeptides (e.g., $^{68}$Ga-DOTA-TOC), $^{11}$C-metomidate, $^{11}$C-acetate, $^{11}$C-methionine, $^{11}$C-choline, $^{18}$F-fluciclovine, $^{18}$F-fluorocholine, $^{18}$F-fluorodeoxysorbitol, $^{18}$F-3'-fluoro-3'-deoxythymidine, $^{11}$C-raclopride, and $^{18}$F-desmethoxyfallypride.

In some embodiments, the diagnostic agent is a near-IR imaging agent. Examples of near-IR imaging agents include Pz 247, DyLight 750, DyLight 800, cyanine dyes (e.g., Cy5, Cy5.5, Cy7), AlexaFluor 680, AlexaFluor 750, IRDye 680, IRDye 800CW, and Kodak X-SIGHT dyes.

In some embodiments, the agent can be a radionuclide, e.g., for use as a therapeutic, diagnostic, or prognostic agents. Among the radionuclides used, gamma-emitters, positron-emitters, and X-ray emitters are suitable for diagnostic and/or therapy, while beta emitters and alpha-emitters may also be used for therapy. Suitable radionuclides for forming use with various embodiments of the present disclosure include, but are not limited to, $^{123}$I, $^{125}$I, $^{130}$I, $^{131}$I, $^{133}$I, $^{135}$I, $^{47}$Sc, $^{72}$As, $^{72}$Sc, $^{90}$Y, $^{88}$Y, $^{97}$Ru, $^{100}$Pd, $^{101m}$Rh, $^{119}$Sb, $^{128}$Ba $^{197}$Hg, $^{211}$At, $^{212}$Bi, $^{212}$Pb $^{109}$Pd, $^{111}$In, $^{67}$Ga $^{68}$Ga, $^{67}$Cu, $^{75}$Br, $^{77}$Br, $^{99m}$TC, $^{14}$C, $^{13}$N, $^{15}$O, $^{32}$P, $^{33}$P, or $^{18}$F.

Prophylactic agents that can be included in the conjugates or particles of the disclosure include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Prophylactic agents may be combined with interleukins, interferon, cytokines, and adjuvants such as cholera toxin, alum, Freund's adjuvant.

In certain embodiments, at least one instance of the agent is a cosmetic agent. In certain embodiments, at least one instance of the agent is a nutraceutical agent. In certain embodiments, at least one instance of the agent is a small molecule. In certain embodiments, at least one instance of the agent is a peptide or protein.

In certain embodiments, at least one instance of m is 1. In certain embodiments, each instance of m is 1. In certain embodiments, at least one instance of m is 2 or 3. In certain embodiments, at least one instance of m is 4, 5, 6, 7, 8, 9, or 10.

In certain embodiments, at least one instance of e is 0. In certain embodiments, each instance of e is 0. In certain embodiments, at least one instance of e is 1, 2, 3, 4, 5, 6, 7, 8, 9, and 10. In certain embodiments, each instance of e is 1, 2, 3, 4, 5, 6, 7, 8, 9, and 10. In certain embodiments, at least one instance of e is 1. In certain embodiments, each instance of e is 1. In certain embodiments, at least one instance of e is 2, 3, or 4. In certain embodiments, at least one instance of e is 5, 6, 7, 8, 9, or 10.

In certain embodiments, at least one instance of f is 0. In certain embodiments, each instance of f is 0. In certain embodiments, at least one instance of f is 1, 2, 3, 4, 5, 6, 7, 8, 9, and 10. In certain embodiments, each instance of f is 1, 2, 3, 4, 5, 6, 7, 8, 9, and 10. In certain embodiments, at least one instance of f is 1. In certain embodiments, each instance of f is 1. In certain embodiments, at least one instance of f is 2, 3, or 4. In certain embodiments, at least one instance of f is 5, 6, 7, 8, 9, or 10.

In certain embodiments at least one instance of $X^1$ and $X^2$ is —OH, C(=O)$R^C$, —C(=O)O$R^C$, or —C(=O)N($R^C$)$_2$. In certain embodiments at least one instance of $X^1$ and $X^2$ is —O$R^C$, —N($R^C$)$_2$, —N$R^C$C(=O)$R^C$, —N$R^C$C(=O)O$R^C$, —N$R^C$C(=O)N($R^C$)$_2$, —OC(=O)$R^C$, —OC(=O)O$R^C$, or —OC(=O)N($R^C$)$_2$. In certain embodiments, at least one instance of $X^1$ and $X^2$ is O$R^C$ or N($R^C$)$_2$. In certain embodiments, at least one instance of $X^1$ and $X^2$ is hydrogen or $C_{1-6}$ alkyl. In certain embodiments, at least one instance of $X^1$ and $X^2$ is substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl.

In certain embodiments, at least one instance of $X^1$ is —O$R^C$, —N($R^C$)$_2$, —C(=O)$R^C$, —C(=O)O$R^C$, —C(=O)N($R^C$)$_2$. In certain embodiments at least one instance of $X^1$ and $X^2$ is —O$R^C$, —N($R^C$)$_2$, —N$R^C$C(=O)$R^C$, —N$R^C$C(=O)O$R^C$, —N$R^C$C(=O)N($R^C$)$_2$, —OC(=O)$R^C$, —OC(=O)O$R^C$, or —OC(=O)N($R^C$)$_2$. In certain embodiments, at least one instance of $X^1$ and $X^2$ is O$R^C$ or N($R^C$)$_2$.

In certain embodiments, at least one instance of $X^1$ and $X^2$ is hydrogen or $C_{1-6}$ alkyl. In certain embodiments, at least one instance of $X^1$ and $X^2$ is substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl.

In certain embodiments, at least one instance of $X^1$ is —O$R^C$, —N($R^C$)$_2$, —C(=O)$R^C$, —C(=O)O$R^C$, —C(=O)N($R^C$)$_2$, —N$R^C$C(=O)$R^C$, —N$R^C$C(=O)O$R^C$, —N$R^C$C(=O)N($R^C$)$_2$, —OC(=O)$R^C$, —OC(=O)O$R^C$, or —OC(=O)N($R^C$)$_2$. In certain embodiments, each instance of $X^1$ is independently —O$R^C$, —N($R^C$)$_2$, —C(=O)$R^C$, —C(=O)O$R^C$, —C(=O)N($R^C$)$_2$, —N$R^C$C(=O)$R^C$, —N$R^C$C(=O)O$R^C$, —N$R^C$C(=O)N($R^C$)$_2$, —OC(=O)$R^C$, —OC(=O)O$R^C$, or —OC(=O)N($R^C$)$_2$. In certain embodiments, at least one instance of $X^1$ is —O$R^C$ N($R^C$)$_2$, —C(=O)$R^C$, —C(=O)N($R^C$)$_2$, —N$R^C$C(=O)$R^C$, or —N$R^C$C(=O)N($R^C$)$_2$. In certain embodiments, each instance of $X^1$ is —O$R^C$, —N($R^C$)$_2$, —C(=O)$R^C$, —C(=O)N($R^C$)$_2$, —N$R^C$C(=O)$R^C$, or —N$R^C$C(=O)N($R^C$)$_2$.

In some embodiments, at least one instance of $X^1$ is hydrogen, and at least one $X^2$ is hydrogen. In some embodiments, each instance of $X^1$ and $X^2$ is hydrogen.

In certain embodiments, at least one instance of $R^C$ is hydrogen, substituted or unsubstituted, $C_{1-6}$ alkyl, an oxygen protecting group, or a leaving group. In certain embodiments, at least one instance of $R^C$ is substituted or unsubstituted, $C_{50-1000}$ heteroalkyl. In certain embodiments, at least one instance of $R^C$ is substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl. In certain embodiments, at least one instance of $R^C$ is

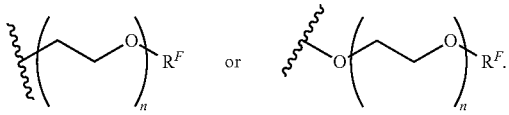

In certain embodiments, each instance of $R^C$ is independently

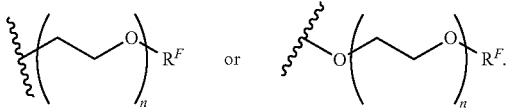

In certain embodiments, at least one instance of $R^C$ is

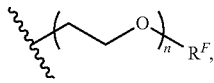

wherein: n is an integer from 1 to 300 (e.g., from 10 to 200, or from 20 to 100), inclusive; and $R^F$ is hydrogen, substituted or unsubstituted, $C_{1-6}$ alkyl (e.g., —$CH_3$), or an oxygen protecting group. In certain embodiments, $R^C$ is

wherein: n is an integer from 1 to 300 (e.g., from 10 to 200, or from 20 to 100), inclusive; and $R^F$ is hydrogen, substituted or unsubstituted, $C_{1-6}$ alkyl (e.g., —$CH_3$), or an oxygen protecting group. In certain embodiments, wherein at least one instance of $R^C$ is

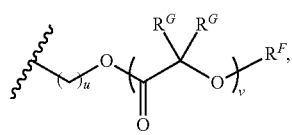

wherein: u is 1, 2, 3, 4, 5, or 6; each instance of $R^G$ is independently hydrogen, halogen, or substituted or unsubstituted, $C_{1-6}$ alkyl (e.g., —$CH_3$); v is an integer from 1 to 300 (e.g., from 10 to 200, or from 20 to 100), inclusive; and $R^F$ is hydrogen, substituted or unsubstituted, $C_{1-6}$ alkyl (e.g., —$CH_3$), or an oxygen protecting group. In certain embodiments, the first monomer does not comprise —O—O—. In certain embodiments, at least one instance of $R^C$ is a polystyrene radical (e.g., polystyrene radical having a weight average molecular weight of between 1 and 3, between 3 and 10, between 10 and 30, between 30 and 100, kDa, inclusive). In certain embodiments, at least one instance of $R^C$ is a polystyrene radical having a weight average molecular weight of between 1 and 10, kDa, inclusive. In certain embodiments, provided that each instance of $R^C$ is the same type of polymer radical (e.g., PEG, e.g.,

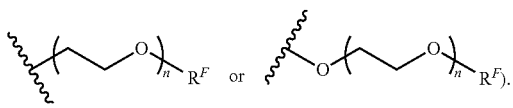

In certain embodiments, provided that at least two instances of $R^C$ are two different types of polymer radicals (e.g., PEG, e.g.,

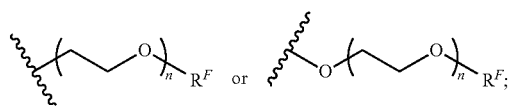

and a polystyrene radical, respectively). In certain embodiments, provided that each instance of $R^C$ in one instance of the block is the same type of polymer radical (e.g., PEG, e.g.,

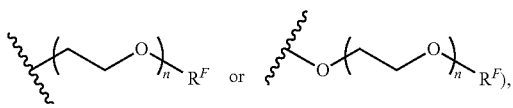

each instance of $R^C$ in another instance of the block is the same type of polymer radical (e.g., a polystyrene radical), each instance of $R^C$ in one instance of the block and each instance of $R^C$ in another instance of the block are different types of polymer radicals.

In some embodiments, the molecular weight of at least one instance of the first monomer is between about 1 kDa and about 10 kDa, e.g., between about 2 kDa and about 8 kDa or about 3 kDa and about 6 kDa, e.g., as detected by mass spectrometry. In some embodiments, the molecular weight of at least one instance of the first monomer is between about 3 kDa and about 6 kDa. In some embodiments, the molecular weight of at least one instance of the first monomer is about 2 kDa, about 3 kDa, about 4 kDa, about 5 kDa, or about 6 kDa. In some embodiments, the hydrodynamic diameter of at least one instance of the first monomer is between about 0.5 nm and about 3 nm, e.g., about 1 nm and about 2 nm, e.g., as detected by dynamic light scattering.

In certain embodiments, each instance of $R^A$ is hydrogen. In certain embodiments, at least one instance of $R^A$ is hydrogen. In certain embodiments, each instance of $R^A$ is halogen. In certain embodiments, at least one instance of $R^A$ is halogen. In certain embodiments, each instance of $R^A$ is unsubstituted $C_{1-6}$ alkyl. In certain embodiments, at least one instance of $R^A$ is unsubstituted $C_{1-6}$ alkyl. In certain embodiments, each instance of $R^A$ is substituted $C_{1-6}$ alkyl. In certain embodiments, at least one instance of $R^A$ is substituted $C_{1-6}$ alkyl.

In certain embodiments, at least one instance of a is 2, 3, 4, 5, or 6. In certain embodiments, each instance of a is independently 2, 3, 4, 5, or 6. In certain embodiments, at least one instance of a is 3, 4, or 5. In certain embodiments, each instance of a is independently 3, 4, or 5.

In certain embodiments, each instance of $R^B$ is hydrogen. In certain embodiments, at least one instance of $R^B$ is hydrogen. In certain embodiments, each instance of $R^B$ is halogen. In certain embodiments, at least one instance of $R^B$ is halogen. In certain embodiments, each instance of $R^B$ is unsubstituted $C_{1-6}$ alkyl. In certain embodiments, at least one instance of $R^B$ is unsubstituted $C_{1-6}$ alkyl. In certain embodiments, each instance of $R^B$ is substituted $C_{1-6}$ alkyl. In certain embodiments, at least one instance of $R^B$ is substituted $C_{1-6}$ alkyl.

In certain embodiments, at least one instance of b is 1, 2, 3, 4, 5, or 6. In certain embodiments, each instance of b is independently 1, 2, 3, 4, 5, or 6. In certain embodiments, at least one instance of b is 1, 2, or 3. In certain embodiments, each instance of b is independently 1, 2, or 3.

In certain embodiments, the step of polymerizing comprises polymerizing a first instance of the first monomer, or a salt thereof; a second instance of the first monomer, or a salt thereof; and the second monomer, or a salt thereof, in the presence of the metathesis catalyst; the first instance of the first monomer comprises a first instance of the agent; the second instance of the first monomer comprises a second instance of the agent; and the first and second instances of the agent are the same or different from each other.

In certain embodiments, the molar ratio of the one or more instances of the first monomer to the second monomer is between 1:2 and 2:1, inclusive. In certain embodiments, the molar ratio of the one or more instances of the first monomer to the second monomer is between 1:10 and 10:1 (e.g., between 1:5 and 5:1), inclusive. In some embodiments, the molar ratio of the one or more instances of the first monomer to the second monomer is between 1:35 and 35:1, inclusive. In some embodiments, the molar ratio of the second monomer to the one or more instances of the first monomer is between 1:33 and 1:27, inclusive. In some embodiments, the molar ratio of the second monomer to the one or more instances of the first monomer is between 1:17 and 1:11, inclusive. In some embodiments, the molar ratio of the second monomer to the one or more instances of the first monomer is between 1:11 and 1:6, inclusive. In certain embodiments, the molar ratio of the one or more instances of the first monomer to the second monomer is about 1:1.

In certain embodiments, the number average polymerization degree is between 2 and 1,000, inclusive, with respect to the first monomer; and between 2 and 1,000, inclusive, with respect to the second monomer. In certain embodiments, the number average polymerization degree is between 10 and 200, inclusive, with respect to the first monomer; and between 10 and 200, inclusive, with respect to the second monomer. In certain embodiments, the number average polymerization degree is between 15 and 100, inclusive, with respect to the first monomer; and between 15 and 100, inclusive, with respect to the second monomer. In certain embodiments, the number average polymerization degree is between 2 and 1,000, between 10 and 1,000, between 100 and 1,000, between 2 and 100, between 10 and 100, between 2 and 10, inclusive, with respect to the first monomer. In certain embodiments, the number average polymerization degree is between 2 and 1,000, between 10 and 1,000, between 100 and 1,000, between 2 and 100, between 10 and 100, between 2 and 10, inclusive, with respect to the second monomer.

In certain embodiments, the PDI of the brush polymer is between 1 and 2, between 1.1 and 2, between 1.3 and 2, between 1.5 and 2, between 1.1 and 1.5, between 1.1 and 1.3, between 1.3 and 2, between 1.3 and 1.5, between 1.5 and 2, inclusive.

Brush Arm Star Polymers (BASPs)

In another aspect, the present disclosure provides BASPs prepared by a method comprising crosslinking one or more instances of the brush polymer described herein, in the presence of:

a crosslinker of Formula (C):

or a salt thereof; and

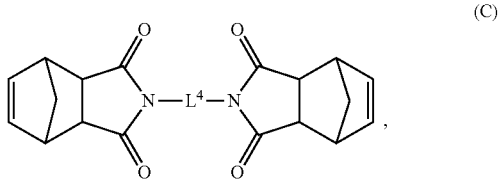

(C)

a metathesis catalyst;

wherein:

$L^4$ is substituted or unsubstituted, $C_{1-100}$ alkylene, substituted or unsubstituted, $C_{2-100}$ heteroalkylene, substituted or unsubstituted, $C_{2-100}$ alkenylene, substituted or unsubstituted, $C_{2-100}$ heteroalkenylene, substituted or unsubstituted, $C_{2-100}$ alkynylene, substituted or unsubstituted, $C_{2-100}$ heteroalkynylene, substituted or unsubstituted carbocyclylene, substituted or unsubstituted heterocyclylene, substituted or unsubstituted arylene, or substituted or unsubstituted heteroarylene, or a combination thereof.

In certain embodiments, $L^4$ is -(substituted or unsubstituted phenylene)-(substituted or unsubstituted, $C_{2-20}$ heteroalkylene)-(substituted or unsubstituted phenylene)-. In certain embodiments, $L^4$ comprises —O—C($R^M$)$_2$—O— in the backbone of $L^4$; and each instance of $R^M$ is independently hydrogen, halogen, or substituted or unsubstituted, $C_{1-6}$ alkyl. In certain embodiments, $L^4$ comprises —O—C(CH$_3$)$_2$—O— in the backbone of $L^4$. In certain embodiments, the crosslinker is of the formula:

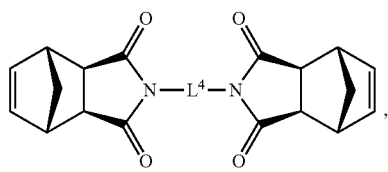

or a salt thereof.

In certain embodiments, the crosslinker is of the formula:

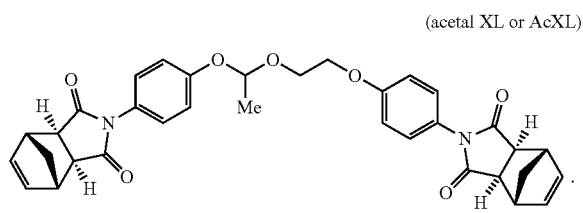 [SMILES: CC(OCCOc1ccc(N2C(=O)[C@@H]3[C@H](C2=O)[C@H]2C=C[C@@H]3C2)cc1)Oc1ccc(N2C(=O)[C@@H]3[C@H](C2=O)[C@H]2C=C[C@@H]3C2)cc1]

(acetal XL or AcXL)

In certain embodiments, the step of crosslinking comprises crosslinking a first and second instances of the brush polymer in the presence of the crosslinker, or a salt thereof;

In certain embodiments, the first instance of the brush polymer comprises a first instance of the agent; the second instance of the brush polymer comprises a second instance of the agent; and the first and second instances of the agent are the same or different from each other.

In certain embodiments, the terms "BASP", "conjugate", and "particle" are used interchangeably. Exemplary conjugates or particles may be described by a number of properties, including, $M_n$=average molecular weight (kDa), $D_H$=average hydrodynamic diameter (nm), and PDI=polydispersity.

In certain embodiments, the molar ratio of crosslinker to the polymer is between 1:2 and 1:20, inclusive. In certain embodiments, the molar ratio of crosslinker to the polymer is between 1:8 and 1:14, inclusive.

In certain embodiments, the $M_n$ is determined with gel permeation chromatography, viscometry via the (Mark-Houwink equation), colligative methods (such as vapor pressure osmometry), end-group determination, or proton NMR. In certain embodiments, the $M_w$ is determined with static light scattering, small angle neutron scattering, X-ray scattering, and sedimentation velocity. In some embodiments, the average molecular weight of the conjugate, or particle is between about 10 kDa and about 100 kDa, e.g., between about 15 kDa and about 85 kDa, about 20 kDa and about 60 kDa, or about 30 kDa and about 50 kDa, e.g., as determined by gel permeation chromatography. In one embodiment, the average molecular weight of the conjugate, or particle is between about 20 kDa and about 60 kDa. In one embodiment, the average molecular weight of the conjugate, or particle is between about 30 kDa and about 50 kDa.

In some embodiments, the average molecular weight of the conjugate, or particle is less than about 100 kDa (e.g., less than about 95 kDa, about 90 kDa, about 85 kDa, about 80 kDa, about 75 kDa, about 70 kDa, about 65 kDa, about 60 kDa, about 55 kDa, or about 50 kDa), e.g., as determined by gel permeation chromatography. In some embodiments, the average molecular weight of the conjugate, or particle is less than about 75 kDa (e.g., less than about 70 kDa, about 65 kDa, about 60 kDa, about 55 kDa, or about 50 kDa).

In some embodiments, the average molecular weight of the particle is between about 100 kDa and about 1,000 kDa, e.g., between about 200 kDa and about 700 kDa or about 300 kDa and about 500 kDa, e.g., as determined by gel permeation chromatography. In one embodiment, the average molecular weight of the particle is between about 2000 kDa and about 70 kDa. In one embodiment, the average molecular weight of the particle is between about 300 kDa and about 500 kDa.

In some embodiments, the average molecular weight of the particle is less than about 1,000 kDa (e.g., less than about 950 kDa, about 900 kDa, about 850 kDa, about 800 kDa, about 750 kDa, about 700 kDa, about 650 kDa, about 600 kDa, about 550 kDa, or about 500 kDa), e.g., as determined by gel permeation chromatography. In some embodiments, the average molecular weight of the particle is less than about 750 kDa (e.g., less than about 700 kDa, about 650 kDa, about 600 kDa, about 550 kDa, or about 500 kDa). In some embodiments, the average molecular weight of the particle is less than about 500 kDa (e.g., less than about 450 kDa, about 400 kDa, about 350 kDa, or 300 kDa).

In certain embodiments, the PDI of the BASP is between 1 and 2, between 1.1 and 2, between 1.3 and 2, between 1.5 and 2, between 1.1 and 1.5, between 1.1 and 1.3, between 1.3 and 2, between 1.3 and 1.5, between 1.5 and 2, inclusive.

In some embodiments, the average hydrodynamic diameter of the conjugate, or particle is less than 50 nm (e.g., less than about 45 nm, about 40 nm, about 35 nm, about 25 nm, about 20 nm, about 15 nm, about 10 nm, about 7.5 nm, or less), e.g., as determined by dynamic light scattering. In some embodiments, the average hydrodynamic diameter of the conjugate, or particle is between about 1 nm and about 20 nm (e.g., between about 2.5 nm and about 17.5 nm, or about 5 nm and about 15 nm). In some embodiments, the average hydrodynamic diameter of the conjugate, or particle is between about 5 nm and about 15 nm.

In some embodiments, the average hydrodynamic diameter of the particle is less than 100 nm (e.g., less than about 90 nm, about 80 nm, about 75 nm, about 70 nm, about 65 nm, about 60 nm, about 55 nm, about 50 nm, about 45 nm, about 40 nm, about 35 nm, about 25 nm, or less), e.g., as determined by dynamic light scattering. In some embodiments, the average hydrodynamic diameter of the particle is between about 5 nm and about 100 nm (e.g., between about 7.5 nm and about 75 nm, about 10 nm and about 50 nm, about 12.5 nm and about 40 nm, or about 15 nm and about 30 nm). In some embodiments, the average hydrodynamic diameter of the particle is between about 10 nm and about 50 nm. In some embodiments, the average hydrodynamic diameter of the particle is between about 15 nm and about 30 nm.

In some embodiments, the average polydispersity of the conjugate or particle is less than about 0.5 (e.g., less than about 0.4, about 0.35, about 0.3, about 0.25, about 0.2, about 0.15, or less). In some embodiments, the average polydispersity of the conjugate or particle is less than about 0.3. In some embodiments, the average polydispersity of the conjugate or particle is less than about 0.2. In some embodiments, the conjugate or particle is monodisperse. In some embodiments, the conjugate or particle is about 50% monodisperse (e.g., about 55%, about 60%, about 65%, about 70%, about 75%, about 80%, about 85%, about 90%, about 95%, about 99%, or about 99.9% monodisperse).

In some embodiments, the conjugate or particle is substantially soluble in water (e.g., hydrophilic). In some embodiments, the conjugate or particle is substantially insoluble in water (e.g., hydrophobic). In some embodiments, the conjugate or particle is substantially insoluble in water and greater than about 10,000 parts water are required to dissolve 1 part polymer. In one embodiment, the conjugate or particle is amphiphilic. In one embodiment, the conjugate or particle comprises a segment that is hydrophobic and a segment that is hydrophilic.

In some cases, the polymers (i.e., BASPs) are in the form of particles (e.g., nanoparticles, i.e., the particle have a characteristic dimension of less than about 1 micrometer). In certain embodiments, the characteristic dimension of a particle is the diameter of a perfect sphere having the same volume as the particle. In certain embodiments, the BASP particle has a characteristic dimension of less than about 300 nm. In certain embodiments, the BASP particle has a characteristic dimension of less than about 200 nm. In certain embodiments, the BASP particle has a characteristic dimension of less than about 150 nm. In certain embodiments, the BASP particle has a characteristic dimension of less than about 100 nm. In certain embodiments, the BASP particle has a characteristic dimension of less than about 50 nm. In certain embodiments, the BASP particle has a characteristic dimension of less than about 30 nm. In certain embodiments, the BASP particle has a characteristic dimension of less than about 20 nm. In certain embodiments, the BASP particle has a characteristic dimension of less than about 10 nm. In certain embodiments, the BASP particle has a characteristic dimension between 6 and 250 nm, inclusive. In certain embodiments, the BASP particle has a characteristic dimension between 8 and 200 nm, inclusive. In certain embodiments, the BASP particle has a characteristic dimension between 12 and 200 nm, inclusive. In certain embodiments, the BASP particle has a characteristic dimension between 50 and 200 nm, inclusive.

The BASPs described herein may be able to deliver multiple agents ratiometrically and/or orthogonally. Different chemical and/or physical conditions may be employed to individually release the multiple agents upon delivery. The convergent synthesis of BASPs allow the attachment of different agents to the BASPs through different linkers (e.g., linkers cleavable by reduction, hydrolysis (such as esters), oxidation, and UV irradiation (such as the moiety

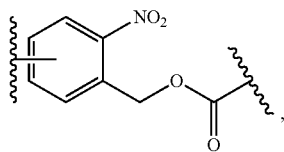

wherein the moiety may be further substituted)). The hydrolyzation, oxidation, UV irradiation, and reduction may be performed in any order and at the same time or different times. The BASPs described herein may be able to deliver multiple agents ratiometrically and/or orthogonally. Different chemical and/or physical conditions may be employed to individually release the multiple agents upon delivery. The convergent synthesis of BASPs allow the attachment of different agents to the BASPs through different linkers (e.g., linkers cleavable by reduction, hydrolysis (such as esters), oxidation, and UV irradiation (such as the moiety

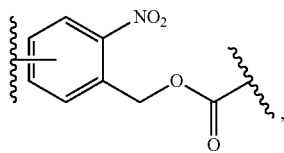

wherein the moiety may be further substituted)). The hydrolyzation, oxidation, UV irradiation, and reduction may be performed in any order and at the same time or different times.

Methods of Preparing the Polymers

In another aspect, the present disclosure provides methods of preparing a polymer, the method comprises polymerizing one or more instances of the first monomer, and the second monomer in the presence of the metathesis catalyst. In certain embodiments, the molar ratio of the first monomer to the metathesis catalyst is 1000-4000 to 1. In certain embodiments, the molar ratio of the first monomer to the metathesis catalyst is 2000-3000 to 1. In certain embodiments, the molar ratio of the first monomer to the metathesis catalyst is 2250-2750 to 1.

In certain embodiments, the present disclosure provides methods of preparing a polymer, the method comprises polymerizing a first monomer of the formula:

or salt thereof, and second monomer of the formula:

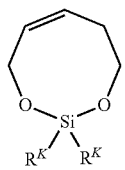

or salt thereof. In some embodiments, $R^K$ is unsubstituted $C_{1-3}$ alkyl (e.g., unsubstituted isopropyl).

In certain embodiments, the method of preparing a polymer further comprises (b) exposing the polymer to a solvent.

In certain embodiments, the method of preparing a polymer further comprises (c) solid-liquid phase separation. In certain embodiments, Step (c) is subsequent to Step (b).

In certain embodiments, the method of preparing a polymer further comprises curing. In some embodiments, curing forms a resin. In certain embodiments, curing is carried out at 70 to 150° C., inclusive. In certain embodiments, curing is carried out at 100 to 150° C., inclusive. In certain embodiments, curing is carried out at 100 to 130° C., inclusive. In certain embodiments, curing is carried out at 110 to 120° C., inclusive. In some embodiments, curing is carried out at about 110° C. In some embodiments, curing is carried out at about 120° C. In some embodiments, curing is carried out for 1 minute to 3 hours, inclusive. In some embodiments, curing is carried out for 15 minutes to 1 hour, inclusive. In some embodiments, curing is carried out for 15 minutes. In certain embodiments, curing is carried out for 30 minutes. In some embodiments, curing is carried out for 1 hour. In certain embodiments, curing is carried out at ambient pressure. In some embodiments, curing is carried out at lower-than-ambient pressure. In some embodiments, curing is carried out at higher-than-ambient pressure.

The preparation of the polymers may involve a metathesis reaction. In certain embodiments, the metathesis reaction is a ring-opening metathesis polymerization (ROMP) (see, e.g., Liu et al. *J. Am. Chem. Soc.* 2012, 134, 16337; Liu, J.; Gao, A. X.; Johnson, J. A. *J Vis Exp* 2013, e50874).

In certain embodiments, the metathesis catalyst (e.g., ROMP catalyst) is a tungsten (W), molybdenum (Mo), or ruthenium (Ru) catalyst. In certain embodiments, the metathesis catalyst is a ruthenium catalyst. Metathesis catalysts useful in the synthetic methods described herein include catalysts as depicted below, and as described in Grubbs et al., *Acc. Chem. Res.* 1995, 28, 446-452; U.S. Pat. No. 5,811,515; Schrock et al., *Organometallics* (1982) 1 1645; Gallivan et al., *Tetrahedron Letters* (2005) 46:2577-2580; Furstner et al., *J. Am. Chem. Soc.* (1999) 121:9453;

and *Chem. Eur. J.* (2001) 7:5299; the entire contents of each of which are incorporated herein by reference.

In certain embodiments, the metathesis catalyst is a Grubbs catalyst. In certain embodiments, the Grubbs catalyst is selected from the group consisting of:

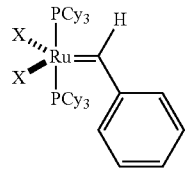

X = Cl; Br; I
Cy = cyclohexyl

Benzylidenebis-(tricyclohexylphosphine)-dichlororuthenium (X=Cl); Benzylidenebis-(tricyclohexylphosphine)-dibromoruthenium (X=Br); Benzylidenebis-(tricyclohexylphosphine)-diiodoruthenium (X=I);

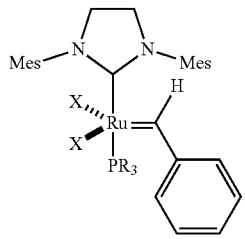

X = Cl; Br; I
R = cyclohexyl (Cy);
phenyl (Ph); benzyl (Bn)

1,3-(Bis(mesityl)-2-imidazolidinylidene)dichloro-(phenylmethylene) (tricyclohexyl-phosphine)ruthenium (X=Cl; R=cyclohexyl); 1,3-(Bis(mesityl)-2-imidazolidinylidene)dibromo-(phenylmethylene) (tricyclohexyl-phosphine)ruthenium (X=Br; R=cyclohexyl); 1,3-(Bis(mesityl)-2-imidazolidinylidene)diiodo-(phenylmethylene) (tricyclohexyl-phosphine)ruthenium (X=I; R=cyclohexyl); 1,3-(Bis(mesityl)-2-imidazolidinylidene)dichloro-(phenylmethylene) (triphenylphosphine)ruthenium (X=Cl; R=phenyl); 1,3-(Bis(mesityl)-2-imidazolidinylidene)dichloro-(phenylmethylene) (tribenzylphosphine)ruthenium (X=Cl; R=benzyl);

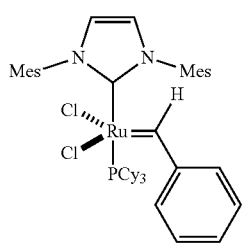

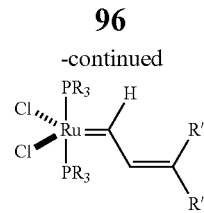

R = cyclohexyl (Cy);
phenyl (Ph)
R' = methyl; phenyl

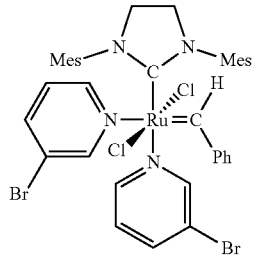

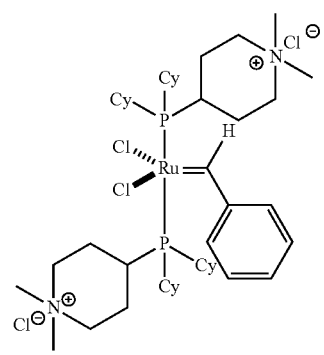

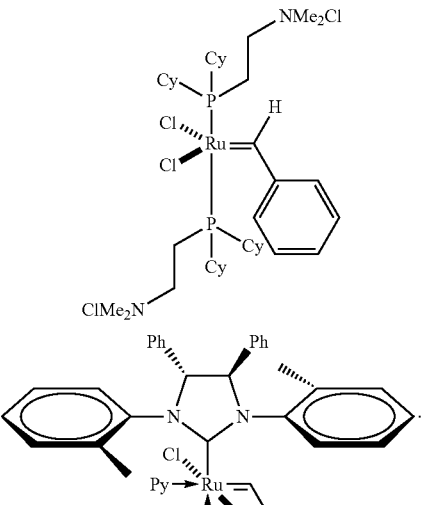

Py = pyridine
Ph = phenyl

In certain embodiments, the metathesis catalyst is a Grubbs-Hoveyda catalyst. In certain embodiments, the Grubbs-Hoveyda catalyst is selected from the group consisting of:

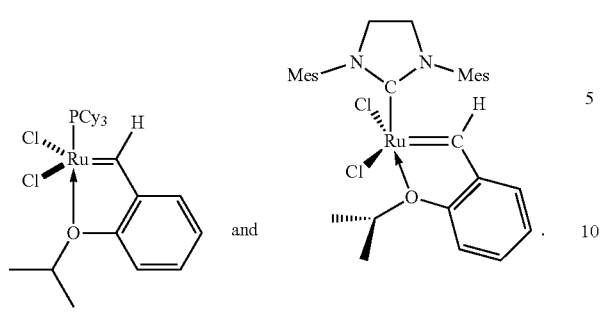

In certain embodiments, the metathesis catalyst is of the formula:

Blechart Catalyst

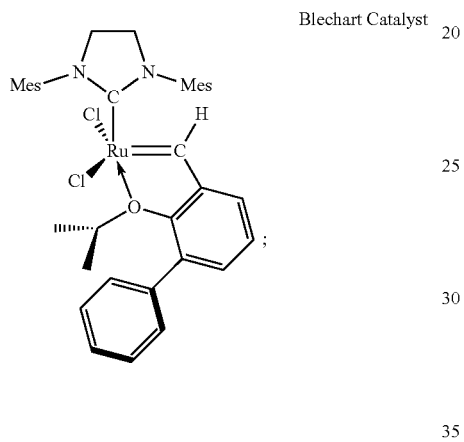

Neolyst™ M1

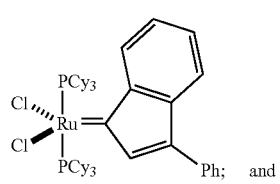

Furstner Catalyst

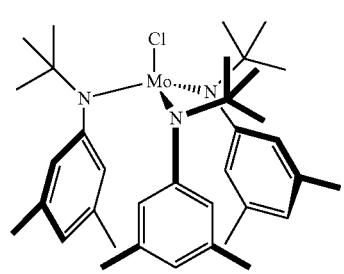

In certain embodiments, the metathesis catalyst is selected from the group consisting of:

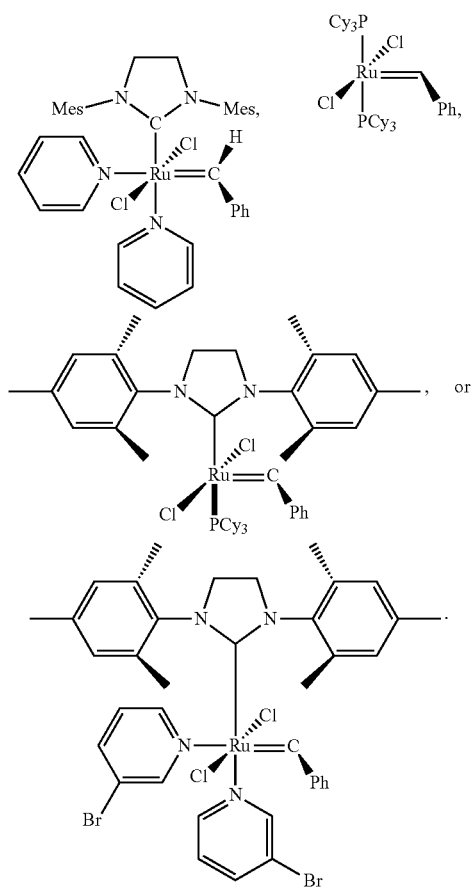

, or

.

The ROMP can be conducted in one or more aprotic solvents. The term "aprotic solvent" means a non-nucleophilic solvent having a boiling point range above ambient temperature, preferably from about 25° C. to about 190° C. at atmospheric pressure. In certain embodiments, the aprotic solvent has a boiling point from about 80° C. to about 160° C. at atmospheric pressure. In certain embodiments, the aprotic solvent has a boiling point from about 80° C. to about 150° C. at atmospheric pressure. Examples of such solvents are methylene chloride, acetonitrile, toluene, DMF, diglyme, THF, and DMSO.

The ROMP can be quenched with a vinyl ether of the formula

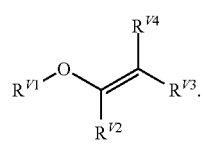

Each of $R^{V1}$, $R^{V2}$, $R^{V3}$ and $R^{V4}$ is independently optionally substituted alkyl, optionally substituted alkenyl, optionally substituted alkynyl, optionally substituted carbocyclyl, optionally substituted phenyl, optionally substituted heterocyclyl, or optionally substituted heteroaryl. In certain embodiments, $R^{V1}$ is optionally substituted alkyl, and $R^{V2}$, $R^{V3}$, and $R^{V4}$ are hydrogen. In certain embodiments, $R^{V1}$ is unsubstituted alkyl, and $R^{V2}$, $R^{V3}$, and $R^{V4}$ are hydrogen. In certain embodiments, $R^{V1}$ is substituted alkyl, and $R^{V2}$, $R^{V3}$, and $R^{V4}$ are hydrogen. In certain embodiments, $R^{V1}$ is methyl, and $R^{V2}$, $R^{V3}$, and $R^{V4}$ are hydrogen. In certain embodiments, $R^{V1}$ is ethyl, and $R^{V2}$, $R^{V3}$, and $R^{V4}$ are hydrogen. In certain embodiments, $R^{V1}$ is propyl, and $R^{V2}$, $R^{V3}$, and $R^{V4}$ are hydrogen. In certain embodiments, $R^{V1}$ is optionally substituted alkenyl, and $R^{V2}$, $R^{V3}$, and $R^{V4}$ are hydrogen. In certain embodiments, $R^{V1}$ is unsubstituted alkenyl, and $R^{V2}$, $R^{V3}$, and $R^{V4}$ are hydrogen. In certain embodiments, $R^{V1}$ is vinyl, and $R^{V2}$, $R^{V3}$, and $R^{V4}$ are hydrogen. In certain embodiments, at least one of $R^{V1}$, $R^{V2}$, $R^{V3}$ and $R^{V4}$ is conjugated with a diagnostic agent as defined above. In certain embodiments, the ROMP is quenched by ethyl vinyl ether. Excess ethyl vinyl ether can be removed from the polymer by vacuum.

Methods of Preparing the Brush Polymers or BASPs

In another aspect, the present disclosure provides methods of preparing a brush polymer, the method comprises polymerizing one or more instances of the first monomer, and the second monomer in the presence of the metathesis catalyst.

In another aspect, the present disclosure provides methods of preparing a BASP, the method comprises crosslinking one or more instances of the brush polymer in the presence of the crosslinker and the metathesis catalyst.

The preparation of the polymers may involve a metathesis reaction. In certain embodiments, the metathesis reaction is a ring-opening metathesis polymerization (ROMP) (see, e.g., Liu et al. *J. Am. Chem. Soc.* 2012, 134, 16337; Liu, J.; Gao, A. X.; Johnson, J. A. *J Vis Exp* 2013, e50874).

In certain embodiments, the metathesis catalyst (e.g., ROMP catalyst) is a tungsten (W), molybdenum (Mo), or ruthenium (Ru) catalyst. In certain embodiments, the metathesis catalyst is a ruthenium catalyst. Metathesis catalysts useful in the synthetic methods described herein include catalysts as depicted below, and as described in Grubbs et al., *Acc. Chem. Res.* 1995, 28, 446-452; U.S. Pat. No. 5,811,515; Schrock et al., *Organometallics* (1982) 1 1645; Gallivan et al., *Tetrahedron Letters* (2005) 46:2577-2580; Furstner et al., *J Am. Chem. Soc.* (1999) 121:9453; and *Chem. Eur. J.* (2001) 7:5299; the entire contents of each of which are incorporated herein by reference.

In certain embodiments, the metathesis catalyst is a Grubbs catalyst. In certain embodiments, the Grubbs catalyst is selected from the group consisting of:

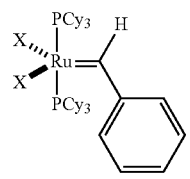

X = Cl; Br; I
Cy = cyclohexyl

Benzylidenebis-(tricyclohexylphosphine)-dichlororuthenium (X═Cl); Benzylidenebis-(tricyclohexylphosphine)-dibromoruthenium (X═Br); Benzylidenebis-(tricyclohexylphosphine)-diiodoruthenium (X═I);

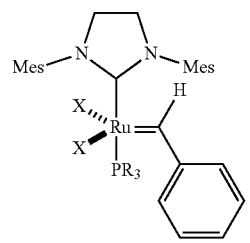

X = Cl; Br; I
R = cyclohexyl (Cy);
phenyl (Ph); benzyl (Bn)

1,3-(Bis(mesityl)-2-imidazolidinylidene)dichloro-(phenylmethylene) (tricyclohexyl-phosphine)ruthenium (X═Cl; R═cyclohexyl); 1,3-(Bis(mesityl)-2-imidazolidinylidene)dibromo-(phenylmethylene) (tricyclohexyl-phosphine)ruthenium (X═Br; R═cyclohexyl); 1,3-(Bis(mesityl)-2-imidazolidinylidene)diiodo-(phenylmethylene) (tricyclohexyl-phosphine)ruthenium (X═I; R═cyclohexyl); 1,3-(Bis(mesityl)-2-imidazolidinylidene)dichloro-(phenylmethylene) (triphenylphosphine)ruthenium (X═Cl; R═phenyl); 1,3-(Bis(mesityl)-2-imidazolidinylidene)dichloro-(phenylmethylene) (tribenzylphosphine)ruthenium (X═Cl; R═benzyl);

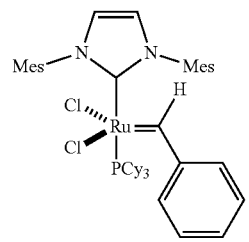

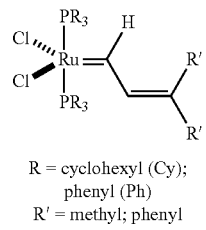

R = cyclohexyl (Cy);
phenyl (Ph)
R' = methyl; phenyl

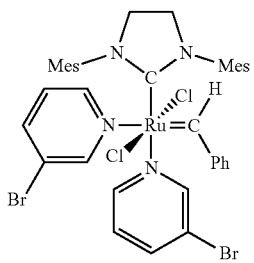

-continued

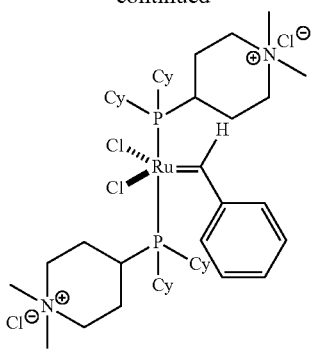

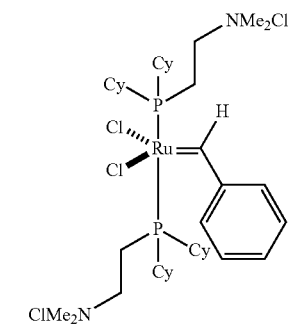

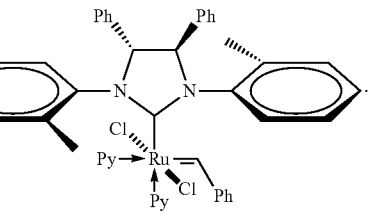

Py = pyridine
Ph = phenyl

In certain embodiments, the metathesis catalyst is a Grubbs-Hoveyda catalyst. In certain embodiments, the Grubbs-Hoveyda catalyst is selected from the group consisting of:

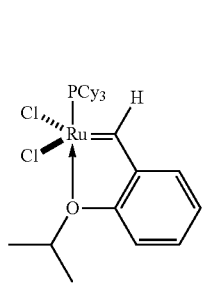 and 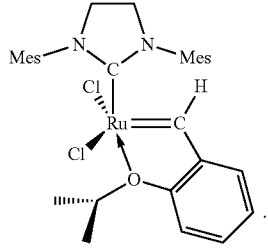.

In certain embodiments, the metathesis catalyst is of the formula:

Blechart Catalyst

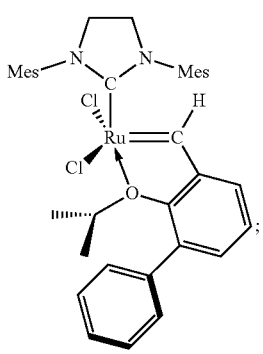;

Neolyst™ M1

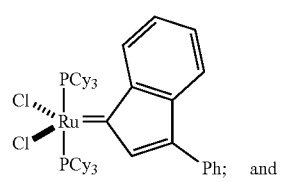; and

Furstner Catalyst

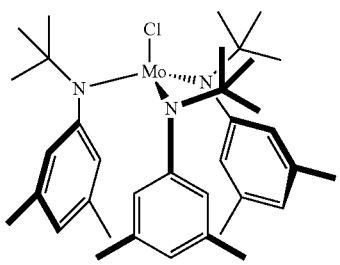.

In certain embodiments, the metathesis catalyst is selected from the group consisting of:

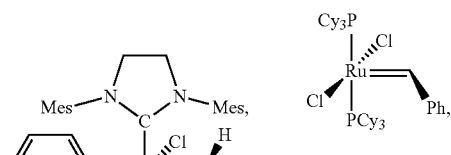

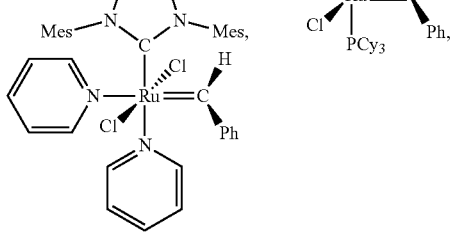

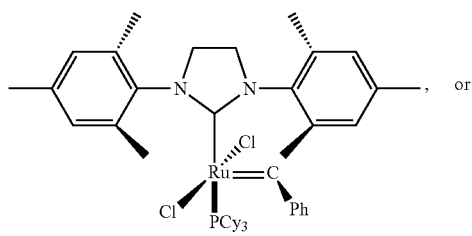, or

-continued

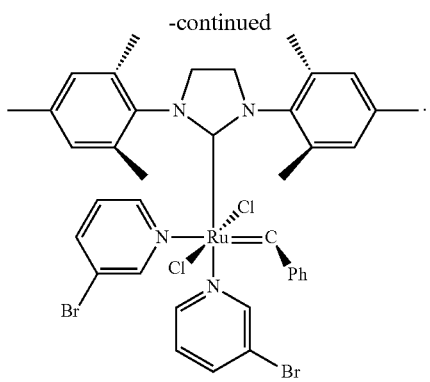

The ROMP can be conducted in one or more aprotic solvents. The term "aprotic solvent" means a non-nucleophilic solvent having a boiling point range above ambient temperature, preferably from about 25° C. to about 190° C. at atmospheric pressure. In certain embodiments, the aprotic solvent has a boiling point from about 80° C. to about 160° C. at atmospheric pressure. In certain embodiments, the aprotic solvent has a boiling point from about 80° C. to about 150° C. at atmospheric pressure. Examples of such solvents are methylene chloride, acetonitrile, toluene, DMF, diglyme, THF, and DMSO.

The ROMP can be quenched with a vinyl ether of the formula

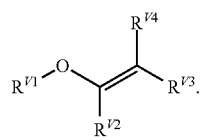

Each of $R^{V1}$, $R^{V2}$, $R^{V3}$ and $R^{V4}$ is independently optionally substituted alkyl, optionally substituted alkenyl, optionally substituted alkynyl, optionally substituted carbocyclyl, optionally substituted phenyl, optionally substituted heterocyclyl, or optionally substituted heteroaryl. In certain embodiments, $R^{V1}$ is optionally substituted alkyl, and $R^{V2}$, $R^{V3}$, and $R^{V4}$ are hydrogen. In certain embodiments, $R^{V1}$ is unsubstituted alkyl, and $R^{V2}$, $R^{V3}$, and $R^{V4}$ are hydrogen. In certain embodiments, $R^{V1}$ is substituted alkyl, and $R^{V2}$, $R^{V3}$, and $R^{V4}$ are hydrogen. In certain embodiments, $R^{V1}$ is methyl, and $R^{V2}$, $R^{V3}$, and $R^{V4}$ are hydrogen. In certain embodiments, $R^{V1}$ is ethyl, and $R^{V2}$, $R^{V3}$ and $R^{V4}$ are hydrogen. In certain embodiments, $R^{V1}$ is propyl, and $R^{V2}$, $R^{V3}$, and $R^{V4}$ are hydrogen. In certain embodiments, $R^{V1}$ is optionally substituted alkenyl, and $R^{V2}$, $R^{V3}$, and $R^{V4}$ are hydrogen. In certain embodiments, $R^{V1}$ is unsubstituted alkenyl, and $R^{V2}$, $R^{V3}$, and $R^{V4}$ are hydrogen. In certain embodiments, $R^{V1}$ is vinyl, and $R^{V2}$, $R^{V3}$, and $R^{V4}$ are hydrogen. In certain embodiments, at least one of $R^{V1}$, $R^{V2}$, $R^{V3}$ and $R^{V4}$ is conjugated with a diagnostic agent as defined above. In certain embodiments, the ROMP is quenched by ethyl vinyl ether. Excess ethyl vinyl ether can be removed from the BASPs by vacuum.

Compositions and Kits Comprising the Monomers

The present disclosure provides compositions comprising a compound or monomer described herein (e.g., a compound of Formula (B)), and optionally an excipient. In certain embodiments, the excipient is a solvent.

Compositions described herein can be prepared by any method known in the art. In general, such preparatory methods include bringing the compound or monomer described herein into association with a carrier or excipient, and/or one or more other accessory ingredients, and then, if necessary and/or desirable, shaping, and/or packaging the product into a desired unit.

Also encompassed by the disclosure are kits (e.g., commercial packs, reagent packs). The kits provided may comprise a composition or a compound or monomer described herein (e.g., a compound of Formula (B)) and instructions for use. The kits provided may comprise a compound or monomer described herein (e.g., a compound of Formula (B)), or composition thereof as described herein and instructions for use. The kits may further comprise a container (e.g., a vial, ampule, bottle, syringe, and/or dispenser package, or other suitable container). The kits may comprises a compound or monomer described herein (e.g., a compound of Formula (B)) and a metathesis catalyst. The kits may comprise a suitable container comprising a monomer as described herein (e.g., a compound of Formula (B)) and a second container comprising a metathesis catalyst. The kits may comprise a compound or monomer described herein (e.g., a compound of Formula (B)), a metathesis catalyst, and a second, different monomer.

In certain embodiments, a kit described herein further includes instructions for using the kit (e.g., for preparing a polymer).

Compositions and Kits Comprising the Polymers

The present disclosure provides compositions comprising a polymer described herein, and optionally an excipient. In certain embodiments, the composition is a pharmaceutical composition. In certain embodiments, the composition is a cosmetic composition. In certain embodiments, the composition is a nutraceutical composition. In certain embodiments, the excipient is a pharmaceutically acceptable excipient. In certain embodiments, the excipient is a cosmetically acceptable excipient. In certain embodiments, the excipient is a nutraceutically acceptable excipient.

Compositions described herein can be prepared by any method known in the art. In general, such preparatory methods include bringing the polymer described herein into association with a carrier or excipient, and/or one or more other accessory ingredients, and then, if necessary and/or desirable, shaping, and/or packaging the product into a desired unit.

Also encompassed by the disclosure are kits (e.g., pharmaceutical packs). The kits provided may comprise a composition or polymer described herein and instructions for use. The kits provided may comprise a polymer, or composition thereof as described herein and instructions for use. The kits may further comprise a container (e.g., a vial, ampule, bottle, syringe, and/or dispenser package, or other suitable container).

In certain embodiments, a kit described herein further includes instructions for using the kit. A kit described herein may also include information as required by a regulatory agency such as the U.S. Food and Drug Administration (FDA).

Compositions and Kits Comprising the Brush Polymers or BASPs

The present disclosure provides compositions comprising a polymer described herein, and optionally an excipient. In certain embodiments, the polymer is a brush polymer described herein. In certain embodiments, the polymer is a BASP described herein. In certain embodiments, the composition is a pharmaceutical composition. In certain embodiments, the composition is a cosmetic composition. In certain embodiments, the composition is a nutraceutical composition. In certain embodiments, the excipient is a pharmaceutically acceptable excipient. In certain embodiments, the excipient is a cosmetically acceptable excipient. In certain embodiments, the excipient is a nutraceutically acceptable excipient.

In certain embodiments, the pharmaceutical compositions are useful for delivering an agent (e.g., to a subject or cell). In certain embodiments, the pharmaceutical compositions are useful for treating a disease in a subject in need thereof. In certain embodiments, the pharmaceutical compositions are useful for preventing a disease in a subject. In certain embodiments, the pharmaceutical compositions are useful for diagnosing a disease in a subject.

In certain embodiments, the polymer described herein is provided in an effective amount in the composition. In certain embodiments, the effective amount is a therapeutically effective amount. In certain embodiments, the effective amount is a prophylactically effective amount. In certain embodiments, the effective amount is an amount effective for treating a proliferative disease in a subject in need thereof. In certain embodiments, the effective amount is an amount effective for preventing a proliferative disease in a subject in need thereof. In certain embodiments, the effective amount is an amount effective for treating a hematological disease in a subject in need thereof. In certain embodiments, the effective amount is an amount effective for preventing a hematological disease in a subject in need thereof. In certain embodiments, the effective amount is an amount effective for treating a neurological disease in a subject in need thereof. In certain embodiments, the effective amount is an amount effective for preventing a neurological disease in a subject in need thereof. In certain embodiments, the effective amount is an amount effective for treating a in a painful condition subject in need thereof. In certain embodiments, the effective amount is an amount effective for preventing a painful condition in a subject in need thereof. In certain embodiments, the effective amount is an amount effective for treating a psychiatric disorder in a subject in need thereof. In certain embodiments, the effective amount is an amount effective for preventing a psychiatric disorder in a subject in need thereof. In certain embodiments, the effective amount is an amount effective for treating a metabolic disorder in a subject in need thereof. In certain embodiments, the effective amount is an amount effective for preventing a metabolic disorder in a subject in need thereof. In certain embodiments, the effective amount is an amount effective for reducing the risk of developing a disease (e.g., proliferative disease, hematological disease, neurological disease, painful condition, psychiatric disorder, or metabolic disorder) in a subject in need thereof. In certain embodiments, the effective amount is an amount effective for inhibiting the activity (e.g., aberrant activity, such as increased activity) of a protein kinase in a subject or cell.

In certain embodiments, the cell is in vitro. In certain embodiments, the cell is in vivo.

Pharmaceutical compositions described herein can be prepared by any method known in the art of pharmacology. In general, such preparatory methods include bringing the polymer described herein (which may includes a therapeutic agent (the "active ingredient")) into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients, such as cocoa butter and suppository waxes, coloring agents, coating agents, sweetening, flavoring, and perfuming agents, may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methyl cellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan monostearate (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methyl cellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates or particles described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates or particles described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a polymer described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the polymer in powder form through the outer layers of the skin to the dermis are suitable.

Formulations suitable for topical administration include liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including a flavoring agent such as saccharin sodium, a volatile oil, a buffering agent, a surface active agent, and/or a preservative such as methylhydroxybenzoate.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Polymers provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The polymers and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the polymer or pharmaceutical composition described herein is suitable for topical administration to the eye of a subject.

The exact amount of a polymer required to achieve an effective amount will vary from subject to subject, depending, for example, on species, age, and general condition of a subject, severity of the side effects or disorder, identity of the particular polymer, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a polymer described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a polymer described herein. In certain embodiments, a dose described herein includes independently between 1 mg and 3 mg, inclusive, of a polymer described herein. In certain embodiments, a dose described herein includes independently between 3 mg and 10 mg, inclusive, of a polymer described herein. In certain embodiments, a dose described herein includes independently between 10 mg and 30 mg, inclusive, of a polymer described herein. In certain embodiments, a dose described herein includes independently between 30 mg and 100 mg, inclusive, of a polymer described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

A polymer or composition, as described herein, can be administered in combination with one or more additional pharmaceutical agents (e.g., therapeutically and/or prophylactically active agents). The polymers or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof, and/or in inhibiting the activity of a protein kinase in a subject or cell), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a polymer described herein and an additional pharmaceutical agent shows a synergistic effect that is absent in a pharmaceutical composition including one of the polymer and the additional pharmaceutical agent, but not both.

The polymer or composition can be administered concurrently with, prior to, or subsequent to one or more additional pharmaceutical agents, which are different from the polymer or composition and may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is an agent useful for treating and/or preventing a disease (e.g., proliferative disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the polymer or composition described herein in a single dose or administered separately in different doses. The particular combination to employ in a regimen will take into account compatibility of the polymer described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include anti-proliferative agents, anti-cancer agents, cytotoxic agents, anti-angiogenesis agents, anti-inflammatory agents, immunosuppressants, anti bacterial agents, anti-viral agents, cardiovascular agents, cholesterol-lowering agents, antidiabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In certain embodiments, the additional pharmaceutical agent is a binder or inhibitor of a protein kinase. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the polymers described herein or pharmaceutical compositions can be administered in combination with an anti-cancer therapy including surgery, radiation therapy, transplantation (e.g., stem cell transplantation, bone marrow transplantation), immunotherapy, and chemotherapy.

Also encompassed by the disclosure are kits (e.g., pharmaceutical packs). The kits provided may comprise a pharmaceutical composition or polymer described herein (e.g., brush polymer or BASP) and instructions for use. The kits may further comprise a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or polymer described herein. In some embodiments, the pharmaceutical composition or polymer described herein provided in the first container and the second container are combined to form one unit dosage form.

In some embodiments, the percentage of the conjugates or particles that comprise an agent is between about 1 and about 100% (e.g., about 1%, about 2%, about 3%, about 4%, about 5%, about 10%, about 15%, about 20%, about 30%, about 40%, about 50%, about 60%, about 70%, about 80%, about 90%, or about 100%). In some embodiments, the percentage of the conjugates or particles that comprise an agent is less than about 50%, e.g., less than about 40%, less than about 35%, less than about 30%, less than about 25%, less than about 20%, less than about 15%, or less than about 10%. In some embodiments, the percentage of the conjugates (e.g., in a particle) that comprise an agent is between about 5% and about 50%, about 5% and about 40%, about 5% and about 30%, about 5% and about 25%, or about 5% and about 20%. In some embodiments, the percentage of the conjugates (e.g., in a particle) that comprise an agent is between about 5% and about 90%. In some embodiments, the percentage of the conjugates (e.g., in a particle) that comprise an agent is between about 5% and about 75%. In the some embodiments, the conjugates (e.g., in a particle) that comprise an agent is between about 5% and about 50%. In the some embodiments, the percentage of the conjugates (e.g., in a particle) that comprise an agent is between about 10% and about 25%.

In some embodiments, the total amount of the agent present in the conjugate or particle is greater than about 5% (e.g., about 6%, about 7%, about 8%, about 9%, about 10%, about 12%, about 15%, about 20%, about 25%, about 30%, or more) of the total size or weight of the conjugate or particle. In some embodiments, the total amount of the agent present in the conjugate or particle is greater than about 10% (e.g., about 12%, about 15%, about 20%, about 25%, about 30%, or more) of the total size or weight of the conjugate or particle.

Without being bound by theory, the conjugates or particles disclosed herein may improve the efficiency of an agent by one or more of increasing the localization and/or release (e.g., preferential release) of the agent to a target cell (e.g., a cancer or a fibrotic cell; a cell associated with a hypoxic environment), or increasing the half life of the agent, thus resulting in a significantly higher amount of a released agent at a target site (e.g., a tumor or liver (e.g., cirrhotic cell). According, the conjugates and particles disclosed herein can be more effective therapeutically than the free agent (e.g., due to enhanced drug uptake in the target tissue) and/or allow for a lower therapeutic dose of the agent, e.g., without substantially compromising the resulting drug concentration at a target tissue. In some embodiments, the conjugates and particles disclosed herein can reduce the adverse effect associated with systemic administration of an agent in free form (e.g., not coupled to a polymer, conjugate or particle described herein).

Without being bound by theory, due to the localized delivery of the compositions described herein (e.g., the agent-containing particles), a lower dose or amount of the agent in the particles can be administered (e.g., through local sustained delivery) compared to the agent in free form. In other embodiments, the agent-containing particles are administered at a dose or amount of the agent that is less than the dose or amount of said agent in free form to have a desired effect (e.g., a desired therapeutic effect).

In some embodiments, the agent is incorporated into a particle at a dose that is less than the dose or amount of said agent in free form to have a desired effect (e.g., a desired therapeutic effect), e.g., the standard of care dose for the intended use of the free agent. In one embodiment, the agent are incorporated into the particles at a dose or amount of the agent that is less than the standard of care dose of the agent for a desired therapy (e.g., a dose that is less than about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, or about 0.95 that of the standard of care dose of the agent).

In some embodiments, the agent is incorporated into a particle at a dose equivalent to the dose or amount of said agent in free form to have a desired effect (e.g., a desired therapeutic effect), e.g., the standard of care dose for the intended use of the free agent. In these embodiments, the particle produces a greater therapeutic effect and/or a less adverse effect than the free agent. In certain embodiments, the particle increases the amount of the agent delivered to a tissue or cell in need thereof and reduces the amount of the agent exposed to a non-target tissue or cell, as compared to the free agent.

In some embodiments, the agent is incorporated into a particle at a dose higher than the dose or amount of said agent in free form to have a desired effect (e.g., a desired therapeutic effect), e.g., the standard of care dose for the intended use of the free agent. In some embodiments, the agent is incorporated into a particle at a dose higher than the dose or amount of said agent in free form that would produce an adverse effect by systemic administration (e.g., a reduction in blood pressure). In some embodiments, since the particle described herein releases the agent at a target site based on pH microenvironment, other non-target sites (e.g., blood vessels) with different pH would be less likely to be exposed to the agent.

In another aspect, provided are kits including a first container comprising a polymer (e.g., brush polymer, BASP) or pharmaceutical composition described herein. In certain embodiments, the kits are useful for delivering an agent (e.g., to a subject or cell). In certain embodiments, the kits are useful for treating a disease (e.g., proliferative disease, hematological disease, neurological disease, painful condition, psychiatric disorder, or metabolic disorder) in a subject in need thereof. In certain embodiments, the kits are useful for preventing a disease (e.g., proliferative disease, hematological disease, neurological disease, painful condition, psychiatric disorder, or metabolic disorder) in a subject in need thereof. In certain embodiments, the kits are useful for reducing the risk of developing a disease (e.g., proliferative disease, hematological disease, neurological disease, painful condition, psychiatric disorder, or metabolic disorder) in a subject in need thereof. In certain embodiments, the kits are useful for diagnosing a disease in a subject in need thereof.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for delivering an agent. In certain embodiments, the kits and instructions provide for treating a disease (e.g., proliferative disease, hematological disease, neurological disease, painful condition, psychiatric disorder, or metabolic disorder) in a subject in need thereof. In certain embodiments, the kits and instructions provide for preventing a disease (e.g., proliferative disease, hematological disease, neurological disease, painful condition, psychiatric disorder, or metabolic disorder) in a subject in need thereof. In certain embodiments, the kits and instructions provide for reducing the risk of developing a disease (e.g., proliferative disease, hematological disease, neurological disease, painful condition, psychiatric disorder, or metabolic disorder) in a subject in need thereof. In certain embodiments, the kits and instructions provide for inhibiting the activity (e.g., aberrant activity, such as increased activity) of a protein kinase in a subject or cell. A kit described herein may include one or more additional pharmaceutical agents described herein as a separate composition.

Methods of Using the Brush Polymers, BASPs, Compositions, and Kits

The present disclosure also provides methods of using brush polymers, BASPs, compositions, and kits. In some aspects, the present disclosure provides methods of delivering an agent to a subject in need thereof, methods of delivering an agent to a cell, methods of treating a disease in a subject in need thereof, methods of preventing a disease in a subject in need thereof, and methods of diagnosing a disease in a subject in need thereof.

In certain embodiments, the methods described herein include administering to a subject with an effective amount of the polymers described herein, or a pharmaceutical composition thereof. In certain embodiments, the methods described herein include implanting to a subject with an effective amount of the polymers described herein, or a pharmaceutical composition thereof. In certain embodiments, the methods described herein comprise treating a disease or condition in a subject in need thereof by administering to or implanting in the subject a therapeutically effective amount of: a polymer described herein; or a pharmaceutical composition thereof; wherein at least one instance of M is a therapeutic agent. In certain embodiments, the methods described herein comprise preventing a disease or condition in a subject in need thereof by administering to or implanting in the subject a prophylactically effective amount of: a polymer described herein; or a pharmaceutical composition thereof; wherein at least one instance of M is a prophylactic agent. In certain embodiments, the methods described herein comprise diagnosing a disease or condition in a subject in need thereof by administering to or implanting in the subject a diagnostically effective amount of: a polymer described herein; or a pharmaceutical composition thereof; wherein at least one instance of M is a diagnostic agent.

In certain embodiments, the disease or condition is a proliferative disease, hematological disease, neurological disease, painful condition, psychiatric disorder, metabolic disorder, or a long-term medical condition. In certain embodiments, the disease is cancer (e.g. lung cancer, large bowel cancer, pancreas cancer, biliary tract cancer, or endometrial cancer), benign neoplasm, angiogenesis, inflammatory disease, autoinflammatory disease, or autoimmune disease. In certain embodiments, the long-term medical condition is hypertension.

In some embodiments, the polymers described herein, or a pharmaceutical composition thereof, are useful in treating a cancer. In some embodiments, the polymers described herein, or a pharmaceutical composition thereof, are useful to delay the onset of, slow the progression of, or ameliorate the symptoms of cancer. In some embodiments, the polymers described herein, or a pharmaceutical composition thereof, are administered in combination with other compounds, drugs, or therapeutics to treat cancer.

In some embodiments, the polymers described herein, or a pharmaceutical composition thereof are useful for treating a cancer including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarcinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM), a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendocrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In some embodiments, the polymers described herein, or a pharmaceutical composition thereof, are useful in treating lung cancer, head-and-neck cancer, esophagus cancer, stomach cancer, breast cancer, pancreas cancer, liver cancer, kidney cancer, prostate caner, glioblastomas, metastatic melanomas, peritoneal or pleural mesotheliomas.

In some embodiments, the proliferative disease is a benign neoplasm. All types of benign neoplasms disclosed herein or known in the art are contemplated as being within the scope of the disclosure. In some embodiments, the proliferative disease is associated with angiogenesis. All types of angiogenesis disclosed herein or known in the art are contemplated as being within the scope of the disclosure. In certain embodiments, the proliferative disease is an inflammatory disease. All types of inflammatory diseases disclosed herein or known in the art are contemplated as being within the scope of the disclosure. In certain embodiments, the inflammatory disease is rheumatoid arthritis. In some embodiments, the proliferative disease is an autoinflammatory disease. All types of autoinflammatory diseases disclosed herein or known in the art are contemplated as being within the scope of the disclosure. In some embodiments, the proliferative disease is an autoimmune disease. All types of autoimmune diseases disclosed herein or known in the art are contemplated as being within the scope of the disclosure.

In some embodiments, the polymers herein, or a pharmaceutical composition thereof contain at least one instance of M useful in treating cancer. In certain embodiments, M is a therapeutic agent. In certain embodiments, the therapeutic agent is an anti-cancer agent. Anti cancer agents encompass biotherapeutic anti-cancer agents as well as chemotherapeutic agents. Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents include, but are not limited to, anti-estrogens (e.g. tamoxifen, raloxifene, and megestrol), LHRH agonists (e.g. goscrelin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonuclotide reductase inhibitors (e.g. hydroxyurea and deferoxamine), uracil analogs (e.g., 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g., mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®) sorafenib (NEXAVAR®), everolimus (AFINITOR®) alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In some embodiments, the polymers described herein, or a pharmaceutical composition thereof contain at least one instance of M useful in treating hypertension. In certain embodiments, M is a therapeutic agent. In certain embodiments, the therapeutic agent is an anti-hypertension agent. Exemplary anti-hypertension agents include, but are not limited to, amiloride, amlodipine, atenolol, azilsartan, benazepril, bendroflumethiazide, betaxolol, bisoprolol, bucindolol, bumetanide, candesartan, captopril, carteolol, carvedilol, chlorothiazide, chlorthalidone, cilnidipine, clevidipine, diltiazem, doxazosin, enalapril, epitizide, eplerenone, eprosartan, ethacrynic acid, felodipine, Fimasartan, fosinopril, furosemide, hydrochlorothiazide, indapamide, indoramin, irbesartan, isradipine, labetalol, lercanidipine, levamlodipine, lisinopril, losartan, methyclothiazide, metolazone, metoprolol, moexipril, nadolol, nebivolol, nicardipine, nifedipine, nimodipine, nisoldipine, nitrendipine, olmesartan, oxprenolol, penbutolol, perindopril, pindolol, phenoxybenzamine, phentolamine, polythiazide, prazosin, propranolol, quinapril, ramipril, spironolactone, telmisartan, terazosin, timolol, tolazoline, torsemide, trandolapril, triamterene, valsartan, and verapamil.

In certain embodiments, the polymers described herein, or a pharmaceutical composition thereof, are administered in combination with one or more additional pharmaceutical agents described herein. In certain embodiments, the additional pharmaceutical agent is an anti-cancer agent. In certain embodiments, the additional pharmaceutical agent is an anti-hypertension agent.

In certain embodiments, the methods described herein include contacting a cell with an effective amount of the polymers described herein, or a pharmaceutical composition thereof. In certain embodiments, the cell is in vitro. In certain embodiments, the cell is in vivo.

In certain embodiments, the subject is a human. In certain embodiments, the subject is a non-human mammal. In certain embodiments, the subject is an animal.

Properties and Uses of the Polymers, Compositions, and Kits

In certain aspects, a polymer as described herein is a thermosetting polymer. In certain aspects, a polymer as described herein is used to produce a thermosetting polymer. In some embodiments, a polymer as described herein is impact resistant. In certain embodiments, a polymer as described herein is abrasion resistant. In some embodiments, a polymer as described herein is corrosion resistant.

In some aspects, a polymer as described herein is suitable for the manufacture of a good (i.e., a tangible item available for purchase). In some aspects, a polymer as described herein is used to manufacture a good (i.e., a tangible item available for purchase). In certain embodiments, a polymer as described herein is suitable for the manufacture of a vehicle panel. In some embodiments, a polymer as described herein is used to manufacture a vehicle panel. In certain embodiments, a polymer as described herein is suitable for the manufacture of a resin. In some embodiments, a polymer as described herein is used to manufacture a resin. In certain embodiments, a polymer as described herein is suitable for the manufacture of a medical device. In some embodiments, a polymer as described herein is used to manufacture a medical device.

In certain aspects, a polymer (e.g., brush polymer, BASP) as described herein is degradable. In certain embodiments, a polymer degrades (e.g., ≥90%, ≥95%, ≥98%, ≥99%, or ≥99.9% degraded) in less than or equal to 1 year, 1 month, 1 week, 72 hours, 48 hours, or 24 hours. In some embodiments, ≥95% of a polymer degrades in 12 hours. In certain embodiments, ≥50% of a polymer degrades in 6 hours. In certain embodiments, a polymer is chemically degradable. In some embodiments, a polymer is chemically degradable in the presence of a fluoride source. In certain embodiments, the fluoride source is tetra(unsubstituted alkyl)-ammonium fluoride. In certain embodiments, the fluoride source is tetra(unsubstituted $C_{1-6}$ alkyl)-ammonium fluoride (e.g., TBAF). In certain embodiments, the fluoride source is a metal fluoride (e.g., alkali metal fluoride or alkaline earth metal fluoride). In some embodiments, a polymer is chemically degradable in the presence of at least 1 equivalent of fluoride source. In certain embodiments, the equivalent is relative to the amount of the second monomer. In some embodiments, a polymer is chemically degradable in the presence of excess (e.g., about 2 equivalents) of fluoride source. In certain embodiments, a polymer is chemically degradable in the presence of tetra-n-butylammonium fluoride (TBAF). In certain embodiments, a polymer is chemically degradable in the presence of acid. In certain embodiments, the acid is an aqueous solution. In certain embodiments, the acid is an inorganic acid. In certain embodiments, the acid is an organic acid. In certain embodiments, the acid has a $pK_a$ value of less than 3, less than 2, less than 1, or less than 0, under ambient conditions. In certain embodiments, the acid is HCl, HBr, HI, $HClO_4$, $HNO_3$, $H_2SO_4$, $CH_3SO_3H$, or $CF_3SO_3H$. In certain embodiments, the acid is HCl. In certain embodiments, the acid is $CF_3CO_2H$. In some embodiments, a polymer is chemically degradable in the presence of at least 1 equivalent of acid.

In some embodiments, a polymer is chemically degradable in the presence of excess (e.g., about 2 equivalents) of acid. In some embodiments, a polymer is chemically degradable in the presence of concentrated HCl. In certain embodiments, ≥50% of a polymer chemically degrades in about 6 hours. In some embodiments, ≥95% of a polymer chemically degrades in about 12 hours. In certain embodiments, the half-life of a polymer under chemical degradation is 6 hours. In certain embodiments, the half-life of the polymer in the presence of a fluoride source or acid under ambient temperature and ambient pressure is between 3 hours and 12 hours, inclusive. In some embodiments, a polymer is biologically degradable. In some embodiments, a polymer is biodegradable. In certain embodiments, a polymer is degraded by a microorganism (e.g., bacteria or fungus). In some embodiments, a polymer is degraded by a subject (e.g., a human). In certain embodiments, a polymer is degradable under non-physiological conditions. In certain embodiments, a polymer is degradable under physiological conditions. In some embodiments, the biological half-life of the polymer (e.g., the time it takes for the concentration of the polymer to halve under physiological conditions) is less than or equal to about 48 hours. In some embodiments, the biological half-life of the polymer (e.g., the time it takes for the concentration of the polymer to halve under physiological conditions) is less than or equal to about 24 hours. In some embodiments, the biological half-life of the polymer (e.g., the time it takes for the concentration of the polymer to halve under physiological conditions) is less than or equal to about 12 hours. In some embodiments, the biological half-life of the polymer (e.g., the time it takes for the concentration of the polymer to halve under physiological conditions) is less than or equal to about 2 hours.

Clauses

1. A brush polymer prepared by a method comprising polymerizing:
one or more instances of a first monomer, wherein each instance of the first monomer is independently of Formula (A1) or (A2):

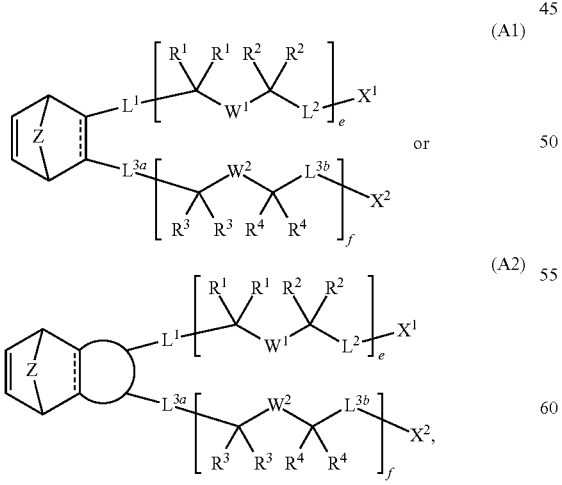

or a salt thereof; and
a second monomer, where the second monomer is of Formula (B):

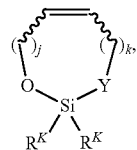

or a salt thereof;
in the presence of a metathesis catalyst;
wherein:
each instance of

is Ring B, wherein each instance of Ring B is independently a substituted or unsubstituted, monocyclic carbocyclic ring, substituted or unsubstituted, monocyclic heterocyclic ring, substituted or unsubstituted, monocyclic aryl ring, or substituted or unsubstituted, monocyclic heteroaryl ring;
each instance of Z is independently $C(R^P)_2$ or O;
each instance of $R^P$ is independently hydrogen, halogen, or substituted or unsubstituted, $C_{1-6}$ alkyl;
each instance of ==== is independently a single bond or double bond;
each instance of $L^1$, $L^2$, $L^{3a}$, and $L^{3b}$ is independently a single bond, substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or $C_{2-200}$ heteroalkynylene;
each instance of $R^1$, $R^2$, $R^3$, and $R^4$ is independently hydrogen, halogen, or substituted or unsubstituted, $C_{1-6}$ alkyl, or two instances of $R^1$ attached to the same carbon atom are taken together to form oxo, or two instances of $R^2$ attached to the same carbon atom are taken together to form oxo, or two instances of $R^3$ attached to the same carbon atom are taken together to form oxo, or two instances of $R^4$ attached to the same carbon atom are taken together to form oxo;
each instance of $W^1$ and $W^2$ is independently a single bond,

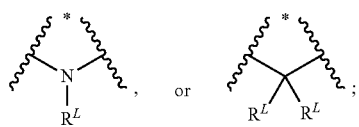

each instance of $R^L$ is independently hydrogen, a nitrogen protecting group when attached to a nitrogen atom, or $-L(M)_m$;
each instance of M is independently hydrogen or an agent;
each instance of m is independently an integer between 1 and 10, inclusive;
each instance of L is independently substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or substituted or unsubstituted, $C_{2-200}$ heteroalkynylene;

optionally one or more carbon atoms in each instance of the substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;

optionally one or more heteroatoms in each instance of the substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;

each instance of e and f is independently an integer between 0 and 10, inclusive;

each instance of $X^1$ and $X^2$ is independently hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, $-OR^C$, $-N(R^C)_2$, $-C(=O)R^C$, $-C(=O)OR^C$, $-C(=O)N(R^C)_2$, $-NR^CC(=O)R^C$, $-NR^CC(=O)OR^C$, $-NR^CC(=O)N(R^C)_2$, $-OC(=O)R^C$, $-OC(=O)OR^C$, or $-OC(=O)N(R^C)_2$;

each instance of $R^C$ is independently hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, a leaving group, an oxygen protecting group when attached to an oxygen atom, a nitrogen protecting group when attached to a nitrogen atom,

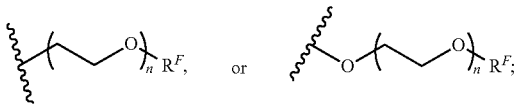

each instance of n is independently an integer between 1 and 300, inclusive; and each instance of $R^F$ is independently hydrogen, substituted or unsubstituted, $C_{1-6}$ alkyl, or an oxygen protecting group;

or

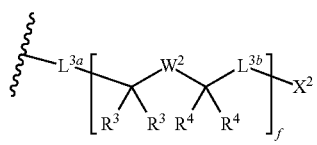

is hydrogen or absent, as valency permits;

Y is O or $C(R^Q)_2$;

each instance of $R^Q$ is independently hydrogen, halogen, or substituted or unsubstituted, $C_{1-6}$ alkyl;

each instance of $R^K$ is independently hydrogen, halogen, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or $-OR^N$;

each instance of $R^N$ is independently hydrogen, substituted or unsubstituted acyl, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or an oxygen protecting group;

j is 1, 2, or 3; and k is 0, 1, 2, or 3.

1a. A brush polymer comprising:

n2 instances of a block, wherein the each instance of the block is independently of Formula (A3) or (A4):

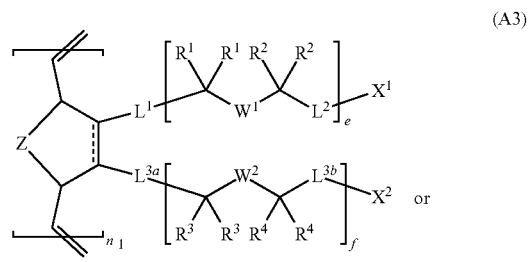

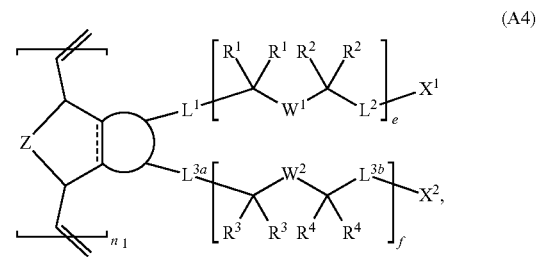

or a salt thereof; and n3 instances of a linker of the formula:

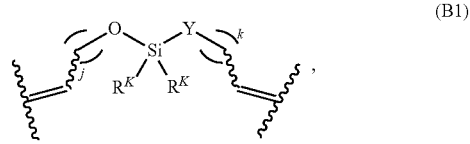

or a salt thereof;

wherein:

each instance of n1 is independently an integer between 2 and 1,000, inclusive;

n2 is an integer between 2 and 100, inclusive;

n3 is an integer between 1 and 101, inclusive;

at least two instances of the block are immediately separated by one or more instances of the linker;

each instance of

is Ring B, wherein each instance of Ring B is independently a substituted or unsubstituted, monocyclic carbocyclic ring, substituted or unsubstituted, monocyclic heterocyclic ring, substituted or unsubstituted, monocyclic aryl ring, or substituted or unsubstituted, monocyclic heteroaryl ring;

each instance of Z is independently $C(R^P)_2$ or O;

each instance of $R^P$ is independently hydrogen, halogen, or substituted or unsubstituted, $C_{1-6}$ alkyl;

each instance of ==== is independently a single bond or double bond;

each instance of $L^1$, $L^2$, $L^{3a}$, and $L^{3b}$ is independently a single bond, substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or $C_{2-200}$ heteroalkynylene;

each instance of $R^1$, $R^2$, $R^3$, and $R^4$ is independently hydrogen, halogen, or substituted or unsubstituted, $C_{1-6}$ alkyl, or two instances of $R^1$ attached to the same carbon atom are taken together to form oxo, or two instances of $R^2$ attached to the same carbon atom are taken together to form oxo, or two instances of $R^3$ attached to the same carbon atom are taken together to form oxo, or two instances of $R^4$ attached to the same carbon atom are taken together to form oxo;

each instance of $W^1$ and $W^2$ is independently a single bond,

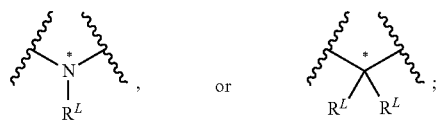

each instance of $R^L$ is independently hydrogen, a nitrogen protecting group when attached to a nitrogen atom, or -L(M)$_m$;

each instance of M is independently hydrogen or an agent;

each instance of m is independently an integer between 1 and 10, inclusive;

each instance of L is independently substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or substituted or unsubstituted, $C_{2-200}$ heteroalkynylene;

optionally one or more carbon atoms in each instance of the substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;

optionally one or more heteroatoms in each instance of the substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;

each instance of e and f is independently an integer between 0 and 10, inclusive;

each instance of $X^1$ and $X^2$ is independently hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, —$OR^C$, —$N(R^C)_2$, —$C(=O)R^C$, —$C(=O)OR^C$, —$C(=O)N(R^C)_2$, —$NR^CC(=O)R^C$, —$NR^CC(=O)OR^C$, —$NR^CC(=O)N(R^C)_2$, —$OC(=O)R^C$, —$OC(=O)OR^C$, or —$OC(=O)N(R^C)_2$;

each instance of $R^C$ is independently hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, a leaving group, an oxygen protecting group when attached to an oxygen atom, a nitrogen protecting group when attached to a nitrogen atom,

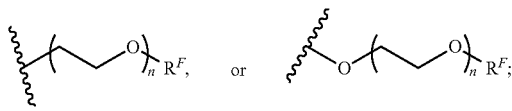

each instance of n is independently an integer between 1 and 300, inclusive; and each instance of $R^F$ is independently hydrogen, substituted or unsubstituted, $C_{1-6}$ alkyl, or an oxygen protecting group;

or

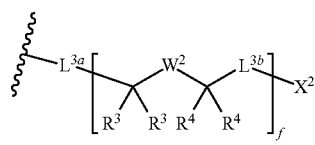

is hydrogen or absent, as valency permits;

Y is O or $C(R^Q)_2$;

each instance of $R^Q$ is independently hydrogen, halogen, or substituted or unsubstituted, $C_{1-6}$ alkyl;

each instance of $R^K$ is independently hydrogen, halogen, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or —$OR^N$;

each instance of $R^N$ is independently hydrogen, substituted or unsubstituted acyl, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or an oxygen protecting group;

j is 1, 2, or 3; and k is 0, 1, 2, or 3.

1b. The brush polymer of clause 1a, wherein at least one instance of n1 is an integer between 10 and 100, inclusive.

1c. The brush polymer of clause 1a or 1b, wherein n2 is 2.

1d. The brush polymer of any one of clauses 1a-1c, wherein n3 is 1.

1e. The brush polymer of any one of clauses 1a-1d, wherein Formula (A4) is of the formula

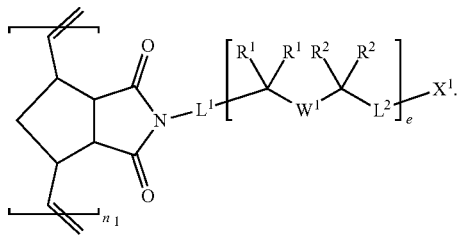

1f. The brush polymer of clause 1e, wherein Formula (A4) is of the formula:

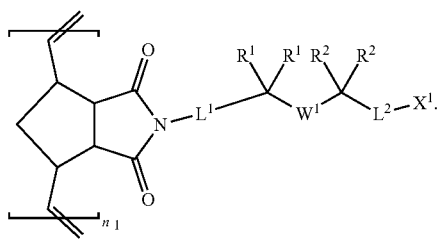

1g. The brush polymer of any one of clauses 1a-1f, wherein the linker is of the formula

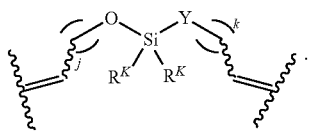

1h. The brush polymer of clause 1g, wherein the linker is of the formula

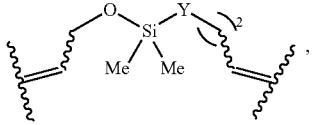

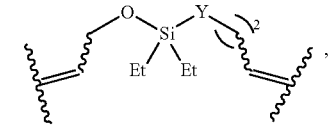

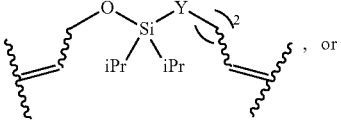, or

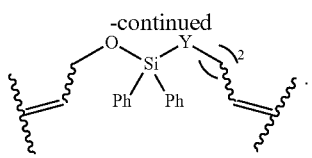

2. The brush polymer of clause 1, wherein each instance of the first monomer is of Formula (A1).

3. The brush polymer of clause 2, wherein at least one instance of the first monomer is of the formula:

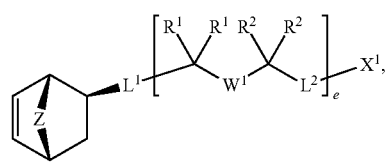

or a salt thereof.

4. The brush polymer of clause 1, wherein each instance of the first monomer is of Formula (A2).

5. The brush polymer of clause 4, wherein at least one instance of the first monomer is of the formula:

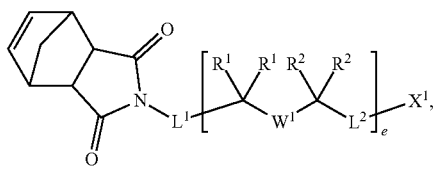

or a salt thereof.

6. The brush polymer of any one of clauses 4-5, wherein at least one instance of the first monomer is of the formula:

(A2a)
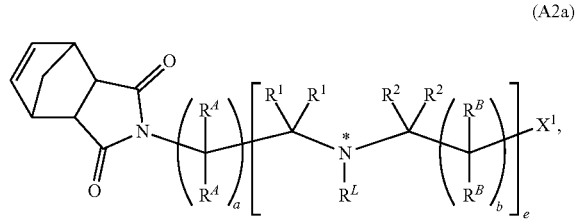

or a salt thereof, wherein:
each instance of $R^A$ is independently hydrogen, halogen, or substituted or unsubstituted, $C_{1-6}$ alkyl;
a is an integer between 1 and 20, inclusive;
each instance of $R^B$ is independently hydrogen, halogen, or substituted or unsubstituted, $C_{1-6}$ alkyl;
each instance of b is independently an integer between 1 and 20, inclusive; and
e is an integer between 1 and 10, inclusive.

7. The brush polymer of any one of clauses 4-6, wherein at least one instance of the first monomer is of the formula:

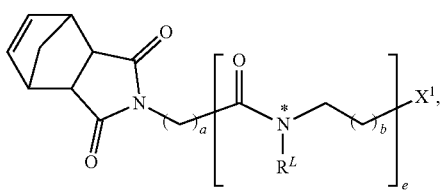

or a salt thereof, wherein e is an integer between 1 and 10, inclusive.

8. The brush polymer of any one of clauses 4-7, wherein at least one instance of the first monomer is of the formula:

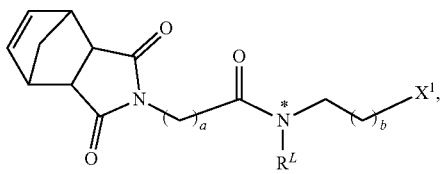

or a salt thereof.

9. The brush polymer of any one of clauses 4-8, wherein at least one instance of the first monomer is of the formula:

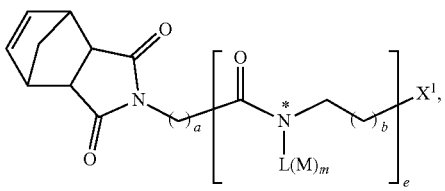

or a salt thereof, wherein:
e is an integer between 1 and 10, inclusive; and
at least one instance of -L(M)$_m$ comprises one or more instances of —C≡CH.

10. The brush polymer of any one of clauses 4-9, wherein at least one instance of the first monomer is of the formula:

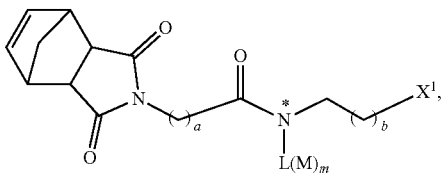

or a salt thereof, wherein -L(M)$_m$ comprises one or more instances of —C≡CH.

11. The brush polymer of any one of clauses 4-10, wherein at least one instance of the first monomer is of the formula:

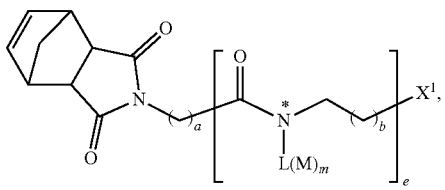

or a salt thereof, wherein:
e is an integer between 1 and 10, inclusive; and
at least one instance of M is an agent.

12. The brush polymer of any one of clauses 4-11, wherein at least one instance of the first monomer is of the formula:

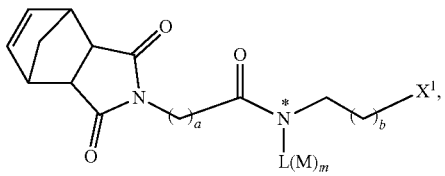

or a salt thereof, wherein at least one instance of M is an agent.

13. The brush polymer of any one of clauses 1-12, wherein at least one instance of Ring B is a substituted or unsubstituted, monocyclic heterocyclic ring.
14. The brush polymer of any one of clauses 6-13, wherein each instance of $R^A$ is hydrogen.
15. The brush polymer of any one of clauses 6-14, wherein at least one instance of a is 2, 3, 4, 5, or 6.
16. The brush polymer of any one of clauses 6-15, wherein each instance of $R^B$ is hydrogen.
17. The brush polymer of any one of clauses 6-16, wherein at least one instance of b is 1, 2, 3, 4, 5, or 6.
18. The brush polymer of any one of clauses 5-17, wherein at least one instance of

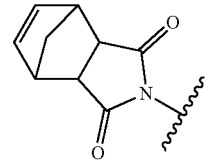 [SMILES: *N1C(=O)C2C3C=CC(C3)C2C1=O]

is

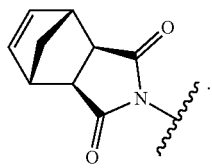 [SMILES: *N1C(=O)[C@@H]2[C@H](C1=O)[C@H]1C=C[C@@H]2C1]

19. The brush polymer of any one of clauses 1-18, wherein at least one instance of Z is C(R$^P$)$_2$.
20. The brush polymer of any one of clauses 1-19, wherein each instance of R$^P$ is hydrogen.
21. The brush polymer of any one of clauses 1-20, wherein at least one instance of ==== is a single bond.

22. The brush polymer of any one of clauses 1-21, wherein each instance of

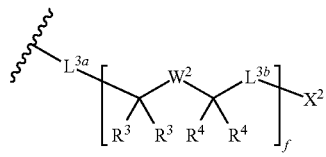

is hydrogen or absent, as valency permits.
23. The brush polymer of any one of clauses 1-22, wherein at least one instance of $L^t$ is substituted or unsubstituted, $C_{1-20}$ alkylene.
24. The brush polymer of any one of clauses 1-23, wherein at least two instances of $R^1$ attached to the same carbon atom are taken together to form oxo.
25. The brush polymer of any one of clauses 1-24, wherein at least one instance of $W^1$ is

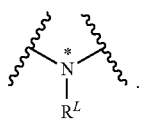

26. The brush polymer of any one of clauses 1-25, wherein at least one instance of $R^L$ is $-L(M)_m$.
27. The brush polymer of clause 26, wherein at least one instance of $-L(M)_m$ comprises one or more click-chemistry handles.
28. The brush polymer of any one of clauses 26-27, wherein at least one instance of $-L(M)_m$ comprises one or more instances of $-C\equiv CH$.
29. The brush polymer of any one of clauses 1-28, wherein at least one instance of M is an agent.
30. The brush polymer of any one of clauses 1-29, wherein at least one instance of L is substituted or unsubstituted, $C_{2-200}$ heteroalkylene, wherein:
one or more carbon atoms and/or one or more heteroatoms, of the substituted or unsubstituted, $C_{2-200}$ heteroalkylene are replaced with

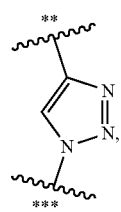

wherein the atom labeled with "*" is closer to the attachment point labeled with "" than the attachment point labeled with "*"; and
optionally one or more carbon atoms and/or one or more heteroatoms, of the substituted or unsubstituted, $C_{2-200}$ heteroalkylene are independently replaced with substituted or unsubstituted phenylene.
31. The brush polymer of any one of clauses 1-31, wherein at least one instance of L is $C_{2-50}$ heteroalkylene, wherein:
the $C_{2-50}$ heteroalkylene is unsubstituted or substituted with one or more substituents independently selected from the group consisting of halogen, unsubstituted $C_{1-6}$ alkyl, and oxo;
one or more carbon atoms and/or one or more heteroatoms, of the $C_{2-50}$ heteroalkylene are replaced with

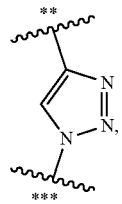 [SMILES: *c1cn(*)nn1]

wherein the atom labeled with "*" is closer to the attachment point labeled with "" than the attachment point labeled with "*"; and
optionally one or more carbon atoms and/or one or more heteroatoms, of the $C_{2-50}$ heteroalkylene are independently replaced with substituted or unsubstituted phenylene.
32. The brush polymer of any one of clauses 1-31, or a salt thereof, wherein at least one instance of L comprises an amino acid or a peptide.
33. The brush polymer of any one of clauses 1-32, or a salt thereof, wherein at least one instance of L is cleavable by ultraviolet irradiation, hydrolysis, reduction, oxidation, or contacting with an enzyme.
34. The brush polymer of any one of clauses 1-33, or a salt thereof, wherein each instance of M is hydrogen.
35. The brush polymer of any one of clauses 1-33, or a salt thereof, wherein at least one instance of M is an agent.
36. The brush polymer of any one of clauses 1-35, or a salt thereof, wherein at least one instance of m is 1.
37. The brush polymer of any one of clauses 1-36, wherein at least two instances of $R^2$ attached to the same carbon atom are each hydrogen.
38. The brush polymer of any one of clauses 1-37, wherein at least one instance of $L^2$ is substituted or unsubstituted, $C_{1-20}$ alkylene.
39. The brush polymer of any one of clauses 1-38, wherein at least one instance of e is 1.
40. The brush polymer of any one of clauses 1-39, wherein at least one instance of $X^1$ is $-OR^C$, $-N(R^C)_2$, $-C(=O)R^C$, $-C(=O)OR^C$, $-C(=O)N(R^C)_2$, $-NR^CC(=O)R^C$, $-NR^CC(=O)OR^C$, $-NR^CC(=O)N(R^C)_2$, $-OC(=O)R^C$, $-OC(=O)OR^C$, or $-OC(=O)N(R^C)_2$.
41. The brush polymer of any one of clauses 1-40, wherein at least one instance of $R^C$ is

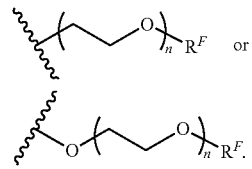

41a. The brush polymer of any one of clauses 1-40, wherein at least one instance of $R^C$ is a polystyrene radical.

42. The brush polymer of any one of clauses 1-41a, wherein the second monomer is of the formula:

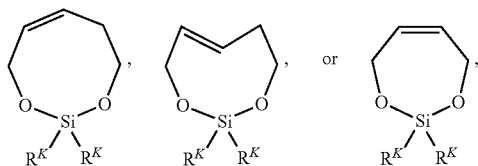

or a salt thereof.
43. The brush polymer of any one of clauses 1-42, wherein Y is O.
44. The brush polymer of any one of clauses 1-43, wherein each instance of $R^K$ is independently substituted or unsubstituted, $C_{1-6}$ alkyl, or substituted or unsubstituted phenyl.
45. The brush polymer of any one of clauses 1-44, wherein each instance of $R^K$ is unsubstituted $C_{1-3}$ alkyl or unsubstituted phenyl.
46. The brush polymer of any one of clauses 1-45, wherein:
the step of polymerizing comprises polymerizing a first instance of the first monomer, or a salt thereof; a second instance of the first monomer, or a salt thereof; and the second monomer, or a salt thereof, in the presence of the metathesis catalyst;
the first instance of the first monomer comprises a first instance of the agent;
the second instance of the first monomer comprises a second instance of the agent; and
the first and second instances of the agent are the same or different from each other.
47. The brush polymer of any one of clauses 1-46, wherein the molar ratio of the one or more instances of the first monomer to the second monomer is between 1:2 and 2:1, inclusive.
47a. The brush polymer of any one of clauses 1-46, wherein the molar ratio of the second monomer to the one or more instances of the first monomer is between 1:5 and 1:35, inclusive.
48. The brush polymer of any one of clauses 1-47a, wherein the number average polymerization degree is between 2 and 1,000, inclusive, with respect to the first monomer; and between 2 and 1,000, inclusive, with respect to the second monomer.
49. The brush polymer of any one of clauses 1-48, wherein the number average polymerization degree is between 10 and 200, inclusive, with respect to the first monomer; and between 10 and 200, inclusive, with respect to the second monomer.
50. A brush-arm star polymer (BASP) prepared by a method comprising crosslinking one or more instances of the brush polymer of any one of clauses 1-49 in the presence of:
a crosslinker of Formula (C):

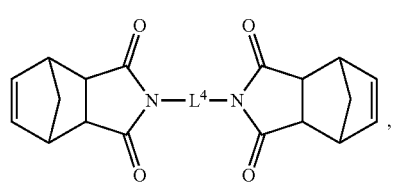

(C)

or a salt thereof; and
a metathesis catalyst;

wherein:
$L^4$ is substituted or unsubstituted, $C_{1-100}$ alkylene, substituted or unsubstituted, $C_{2-100}$ heteroalkylene, substituted or unsubstituted, $C_{2-100}$ alkenylene, substituted or unsubstituted, $C_{2-100}$ heteroalkenylene, substituted or unsubstituted, $C_{2-100}$ alkynylene, substituted or unsubstituted, $C_{2-100}$ heteroalkynylene, substituted or unsubstituted carbocyclylene, substituted or unsubstituted heterocyclylene, substituted or unsubstituted arylene, or substituted or unsubstituted heteroarylene, or a combination thereof.
51. The BASP of clause 50, wherein $L^4$ is -(substituted or unsubstituted phenylene)-(substituted or unsubstituted, $C_{2-20}$ heteroalkylene)-(substituted or unsubstituted phenylene)-.
52. The BASP of any one of clauses 50-51, wherein:
$L^4$ comprises —O—$C(R^M)_2$—O— in the backbone of $L^4$; and
each instance of $R^M$ is independently hydrogen, halogen, or substituted or unsubstituted, $C_{1-6}$ alkyl.
53. The BASP of any one of clauses 50-52, wherein:
the step of crosslinking comprises crosslinking a first and second instances of the brush polymer in the presence of the crosslinker, or a salt thereof;
the first instance of the brush polymer comprises a first instance of the agent;
the second instance of the brush polymer comprises a second instance of the agent; and
the first and second instances of the agent are the same or different from each other.
53a. The brush polymer of any one of clauses 1-49 or BASP of anyone of clauses 50-53, wherein the brush polymer or BASP is degradable.
53b. The brush polymer of any one of clauses 1-49 or BASP of anyone of clauses 50-53, wherein the brush polymer or BASP is biologically degradable (biodegradable).
53c. The brush polymer of any one of clauses 1-49 or BASP of anyone of clauses 50-53, wherein the brush polymer or BASP is chemically degradable.
53d. The brush polymer or BASP of clause 53c, wherein the brush polymer or BASP is chemically degradable in the presence of a fluoride source.
53e. The brush polymer or BASP of clause 53d, wherein the fluoride source is tetra(unsubstituted $C_{1-6}$ alkyl)-ammonium.
53f. The brush polymer or BASP of clause 53c, wherein the brush polymer or BASP is chemically degradable in the presence of an acid.
53g. The brush polymer or BASP of clause 53f, wherein the acid is HCl.
53h. The brush polymer of any one of clauses 1-49 or BASP of anyone of clauses 50-53, wherein the biological half-life of the brush polymer or BASP is less than or equal to about 48 hours.
54. A method of preparing a brush polymer of any one of clauses 1-49, the method comprises polymerizing one or more instances of the first monomer, and the second monomer in the presence of the metathesis catalyst.
55. A method of preparing a brush-arm star polymer (BASP) of any one of clauses 50-53, the method comprises crosslinking one or more instances of the brush polymer in the presence of the crosslinker and the metathesis catalyst.

56. The brush polymer of any one of clauses 1-49 and 53a-53h, BASP of any one of clauses 50-53h, or method of any one of clauses 54-55, wherein the metathesis catalyst is a ruthenium catalyst.
57. The brush polymer of any one of clauses 1-49 and 53a-53h, BASP of any one of clauses 50-53h, or method of any one of clauses 54-55, wherein the metathesis catalyst is a Grubbs catalyst.
58. A composition comprising:
a brush polymer of any one of clauses 1-49 and 53a-53h, or a brush-arm star polymer (BASP) of any one of clauses 50-53h; and
optionally an excipient.
59. The composition of clause 58, wherein the excipient is a pharmaceutically acceptable excipient.
60. The composition of clause 58, wherein the excipient is a cosmetically acceptable excipient.
61. The composition of clause 58, wherein the excipient is a nutraceutically acceptable excipient.
62. A kit comprising:
brush polymer of any one of clauses 1-49 and 53a-53h, BASP of any one of clauses 50-53h, or a composition of any one of clauses 58-61; and
instructions for using the brush polymer, BASP, or composition.
63. A method of delivering an agent to a subject in need thereof, the method comprising administering to the subject in need thereof a brush polymer of any one of clauses 1-49 and 53a-53h, BASP of any one of clauses 50-53h, or a composition of any one of clauses 58-61, wherein:
each of the brush polymer and BASP comprises at least one instance of M; and
at least one instance of M is an agent.
64. A method of delivering an agent to a cell, the method comprising contacting the cell with a brush polymer of any one of clauses 1-49 and 53a-53h, BASP of any one of clauses 50-53h, or a composition of any one of clauses 58-61, wherein:
each of the brush polymer and BASP comprises at least one instance of M; and
at least one instance of M is an agent.
65. The brush polymer, BASP, composition, kit, or method of any one of clauses 1-64, wherein at least one instance of the agent is a pharmaceutical agent.
66. The brush polymer, BASP, composition, kit, or method of any one of clauses 1-64, wherein at least one instance of the agent is a cosmetic agent.
67. The brush polymer, BASP, composition, kit, or method of any one of clauses 1-64, wherein at least one instance of the agent is a nutraceutical agent.
68. The brush polymer, BASP, composition, kit, or method of any one of clauses 1-64, wherein at least one instance of the agent is a small molecule.
69. The brush polymer, BASP, composition, kit, or method of any one of clauses 1-64, wherein at least one instance of the agent is a peptide or protein.
70. A method of treating a disease in a subject in need thereof, the method comprising administering to the subject in need thereof a therapeutically effective amount of a brush polymer of any one of clauses 1-49 and 53a-53h, BASP of any one of clauses 50-53h, or a composition of any one of clauses 58-61, wherein each of the brush polymer and BASP comprises at least one instance of the agent, wherein:
each of the brush polymer and BASP comprises at least one instance of M; and
at least one instance of M is a therapeutic agent.
71. The method of clause 70, wherein the disease is cancer.
72. The method of any one of clauses 70-71, wherein at least one instance of the agent or therapeutic agent is an anti-cancer agent.
73. The method of any one of clauses 70-72, wherein at least one instance of the agent or therapeutic agent is an anti-cancer agent selected from the group consisting of abiraterone acetate, ABVD, ABVE, ABVE-PC, AC, AC-T, ADE, ado-trastuzumab emtansine, afatinib dimaleate, aldesleukin, alemtuzumab, anastrozole, arsenic trioxide, asparaginase *Erwinia chrysanthemi*, axitinib, azacitidine, BEACOPP, belinostat, bendamustine hydrochloride, BEP, bevacizumab, bicalutamide, bleomycin, blinatumomab, bortezomib, bosutinib, brentuximab vedotin, busulfan, cabazitaxel, cabozantinib-s-malate, CAF, capecitabine, CAPDX, carboplatin, carboplatin-taxol, carfilzomibcarmustine, carmustine implant, ceritinib, cetuximab, chlorambucil, chlorambucil-prednisone, CHOP, cisplatin, clofarabine, CMF, COPP, COPP-ABV, crizotinib, CVP, cyclophosphamide, cytarabine, dabrafenib, dacarbazine, dactinomycin, dasatinib, daunorubicin hydrochloride, decitabine, degarelix, denileukin diftitox, denosumab, Dinutuximab, docetaxel, doxorubicin hydrochloride, doxorubicin hydrochloride liposome, enzalutamide, epirubicin hydrochloride, EPOCH, erlotinib hydrochloride, etoposide, etoposide phosphate, everolimus, exemestane, FEC, fludarabine phosphate, fluorouracil, FOLFIRI, FOLFIRI-BEVACIZUMAB, FOLFIRI-CETUXIMAB, FOLFIRINOX, FOLFOX, FU-LV, fulvestrant, gefitinib, gemcitabine hydrochloride, gemcitabine-cisplatin, gemcitabine-oxaliplatin, goserelin acetate, Hyper-CVAD, ibritumomab tiuxetan, ibrutinib, ICE, idelalisib, ifosfamide, imatinib mesylate, imiquimod, ipilimumab, irinotecan hydrochloride, ixabepilone, lanreotide acetate, lapatinib ditosylate, lenalidomide, lenvatinib, letrozole, leucovorin calcium, leuprolide acetate, liposomal cytarabine, lomustine, mechlorethamine hydrochloride, megestrol acetate, mercaptopurine, methotrexate, mitomycin c, mitoxantrone hydrochloride, MOPP, nelarabine, nilotinib, nivolumab, obinutuzumab, OEPA, ofatumumab, OFF, olaparib, omacetaxine mepesuccinate, OPPA, oxaliplatin, paclitaxel, paclitaxel albumin-stabilized nanoparticle formulation, PAD, palbociclib, pamidronate disodium, panitumumab, panobinostat, pazopanib hydrochloride, pegaspargase, peginterferon alfa-2b, peginterferon alfa-2b, pembrolizumab, pemetrexed disodium, pertuzumab, plerixafor, pomalidomide, ponatinib hydrochloride, pralatrexate, prednisone, procarbazine hydrochloride, radium 223 dichloride, raloxifene hydrochloride, ramucirumab, R-CHOP, recombinant HPV bivalent vaccine, recombinant human papillomavirus, nonavalent vaccine, recombinant human papillomavirus, quadrivalent vaccine, recombinant interferon alfa-2b, regorafenib, rituximab, romidepsin, ruxolitinib phosphate, siltuximab, sipuleucel-t, sorafenib tosylate, STANFORD V, sunitinib malate, TAC, tamoxifen citrate, temozolomide, temsirolimus, thalidomide, thiotepa, topotecan hydrochloride, toremifene, tositumomab and iodine I 131, tositumomab, TPF, trametinib, trastuzumab, VAMP, vandetanib, VEIP, vemurafenib, vinblastine sulfate, vincristine sulfate, vincristine sulfate liposome, vinorelbine tartrate, vismodegib, vorinostat, XELIRI, XELOX, ziv-aflibercept, and zoledronic acid.

74. A method of preventing a disease in a subject in need thereof, the method comprising administering to the subject in need thereof a prophylactically effective amount of a brush polymer of any one of clauses 1-49 and 53a-53h, BASP of any one of clauses 50-53h, or a composition of any one of clauses 58-61, wherein each of the brush polymer and BASP comprises at least one instance of the agent, wherein:

each of the brush polymer and BASP comprises at least one instance of M; and at least one instance of M is a prophylactic agent.

75. A method of diagnosing a disease in a subject in need thereof, the method comprising administering to the subject in need thereof a diagnostically effective amount of brush polymer of any one of clauses 1-49 and 53a-53h, BASP of any one of clauses 50-53h, or a composition of any one of clauses 58-61, wherein each of the brush polymer and BASP comprises at least one instance of the agent, wherein:

each of the brush polymer and BASP comprises at least one instance of M; and at least one instance of M is a diagnostic agent.

Embodiments

1. A polymer prepared by a method comprising polymerizing:
one or more instances of a first monomer, wherein each instance of the first monomer is independently of Formula (D1) or (D2):

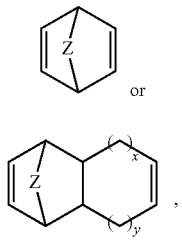

or a salt thereof; and
a second monomer, where the second monomer is of Formula (B):

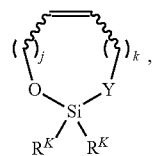

or a salt thereof;
in the presence of a metathesis catalyst;
wherein:
each instance of Z is independently $C(R^P)_2$ or O;
each instance of $R^P$ is independently hydrogen, halogen, or substituted or unsubstituted, $C_{1-6}$ alkyl;
each instance of x is independently 0, 1, or 2;
each instance of y is independently 0, 1, or 2;
Y is O or $C(R^Q)_2$;

each instance of $R^Q$ is independently hydrogen, halogen, or substituted or unsubstituted, $C_{1-6}$ alkyl;

each instance of $R^K$ is independently hydrogen, halogen, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or $-OR^N$;

each instance of $R^N$ is independently hydrogen, substituted or unsubstituted acyl, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or an oxygen protecting group;

j is 1, 2, or 3; and
k is 0, 1, 2, or 3.

1a. The polymer of embodiment 1, wherein at least one instance of Z is $C(R^P)_2$.

1b. The polymer of any one of embodiments 1-1a, wherein each instance of $R^P$ is hydrogen.

2. The polymer of any one of embodiments 1-1b, wherein each instance of the first monomer is of Formula (D1).

3. The polymer of any one of embodiments 1-2, wherein at least one instance of the first monomer is of the formula:

or a salt thereof.

4. The polymer of any one of embodiments 1-1b, wherein each instance of the first monomer is of Formula (D2).

5. The polymer of any one of embodiments 1-1b and 4, wherein at least one instance of x is 0.

6. The polymer of any one of embodiments 1-1b and 4-5, wherein at least one instance of y is 1.

7. The polymer of any one of embodiments 1-1b and 4-6, wherein at least one instance of the first monomer is of the formula:

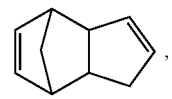

or a salt thereof.

8. The polymer of any one of embodiments 1-1b and 4-7, wherein at least one instance of the first monomer is of the formula:

or a salt thereof.

9. The polymer of any one of embodiments 1-8, wherein at least one instance of j is 1.

10. The polymer of any one of embodiments 1-9, wherein at least one instance of k is 1 or 2.

11. The polymer of any one of embodiments 1-10, wherein Y is O.

12. The polymer of any one of embodiments 1-11, wherein the second monomer is of the formula:

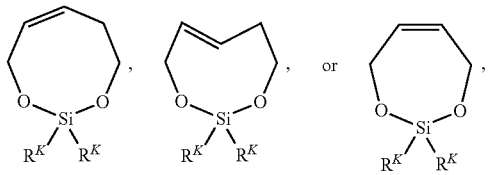

or a salt thereof.

13. The polymer of any one of embodiments 1-12, wherein each instance of $R^K$ is independently hydrogen, substituted or unsubstituted, $C_{1-6}$ alkyl, or substituted or unsubstituted phenyl.

14. The polymer of any one of embodiments 1-13, wherein each instance of $R^K$ is independently substituted or unsubstituted, $C_{1-6}$ alkyl, or substituted or unsubstituted phenyl.

15. The polymer of any one of embodiments 1-14, wherein each instance of $R^K$ is unsubstituted $C_{1-3}$ alkyl.

16. The polymer of any one of embodiments 1-14, wherein each instance of $R^K$ is unsubstituted phenyl.

17. The polymer of any one of embodiments 1-12, wherein each instance of $R^K$ is —$OR^N$.

18. The polymer of any one of embodiments 1-12, wherein one instance of $R^K$ is hydrogen, and one instance of $R^K$ is unsubstituted $C_{1-3}$ alkyl or unsubstituted phenyl.

19. The polymer of any one of embodiments 1-16, wherein the second monomer is of the formula:

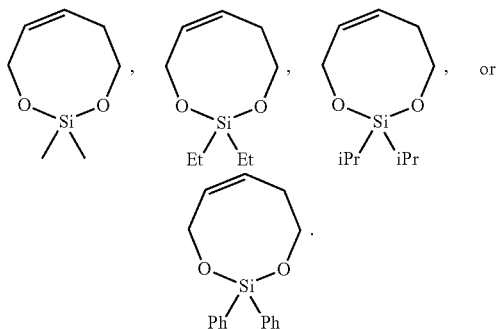

20. The polymer of any one of embodiments 1-19, wherein the molar ratio of the one or more instances of the first monomer to the second monomer is between 6:1 and 19:1, inclusive.

21. The polymer of any one of embodiments 1-20, wherein the average molecular weight of the polymer as determined by gel permeation chromatography is between 100 kDa and 10,000 kDa, inclusive.

22. The polymer of any one of embodiments 1-21, wherein the crosslink density is about 10% to 15%, inclusive.

23. The polymer of any one of embodiments 1-22, wherein the polymer is degradable.

24. The polymer of any one of embodiments 1-23, wherein the polymer is biologically degradable (biodegradable).

25. The polymer of any one of embodiments 1-23, wherein the polymer is chemically degradable.

26. The polymer of embodiment 25, wherein the polymer is chemically degradable in the presence of a fluoride source.

27. The polymer of embodiment 26, wherein the fluoride source is tetra(unsubstituted $C_{1-6}$ alkyl)-ammonium fluoride.

28. The polymer of embodiment 25, wherein the polymer is chemically degradable in the presence of an acid.

29. The polymer of embodiment 28, wherein the acid is HCl.

30. The polymer of any one of embodiments 28-29, wherein the half-life of the polymer in the presence of a fluoride source or acid under ambient temperature and ambient pressure is between 3 hours and 12 hours, inclusive.

31. The polymer of any one of embodiments 1-30, wherein the polymer is a thermosetting polymer.

32. The polymer of any one of embodiments 1-31, wherein the polymer is suitable for the manufacture of a good, a resin, a medical device, or a vehicle panel.

33. The polymer of any one of embodiments 1-32, wherein the polymer has one or more properties selected from the group consisting impact resistant, abrasion resistant, and corrosion resistant.

34. A method of preparing a polymer of any one of embodiments 1-33, the method comprises polymerizing one or more instances of the first monomer, and the second monomer in the presence of the metathesis catalyst.

35. The method of embodiment 34, further comprising exposing the polymer to a solvent.

36. The method of embodiment 34 or 35, further comprising solid-liquid phase separation.

37. The method of any one of embodiment 36, further comprising curing.

38. The method of embodiment 37, wherein the curing forms a resin.

39. The polymer or method of any one of embodiments 1-38, wherein the molar ratio between the first monomer and the metathesis catalyst is between 2000:1 and 3000:1, inclusive.

40. The polymer or method of any one of embodiments 1-39, wherein the metathesis catalyst is a ruthenium catalyst.

41. The polymer or method of any one of embodiments 1-40, wherein the metathesis catalyst is a Grubbs catalyst.

42. A composition comprising:
a polymer of any one of embodiments 1-33 and 39-41; and
optionally an excipient.

43. A kit comprising:
a polymer of any one of embodiments 1-33 and 39-41, or a composition of any one of embodiment 42; and
instructions for using the polymer, or composition.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Materials, General Methods, and Instrumentation

Figure 1A:
FIG. 1A shows an overview of ring opening metathesis polymerization (ROMP).
Figure 1B:
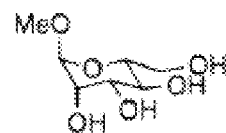
FIG. 1B shows use of surface plasmon resonance (SPR) detection for the study of polymers generated via ROMP. *Journal of the American Chemical Society*, 1998, 120, 10579.
Figure 1B:
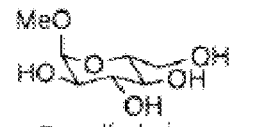
Figure 1B:
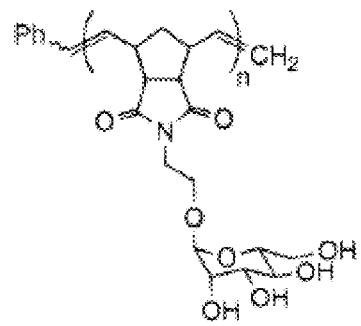
Figure 1B:
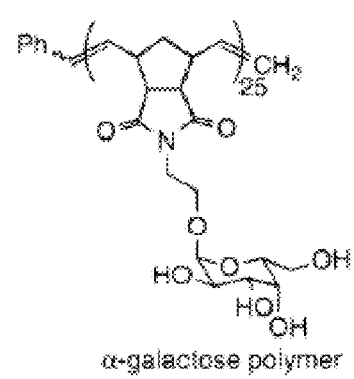
Figure 1C:
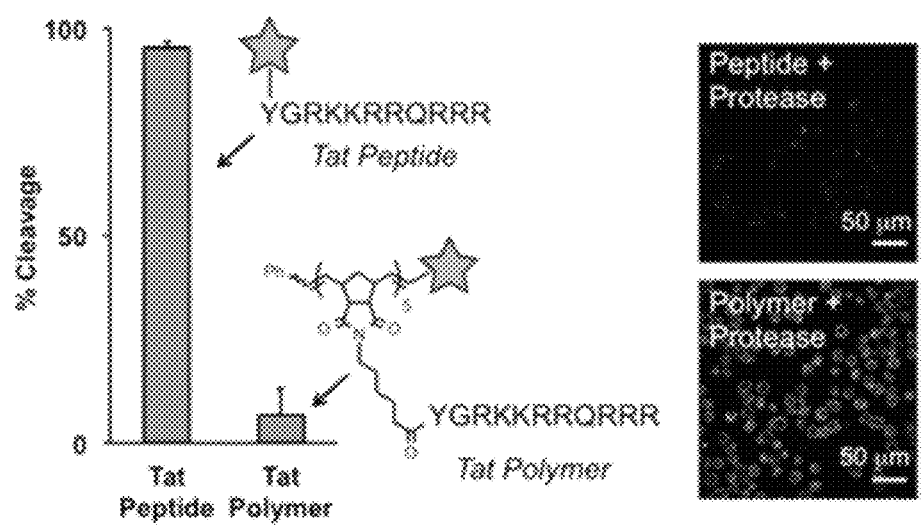
FIG. 1C shows a methodology for formulation of peptides into brush polymers. *Journal of the American Chemical Society*, 2014, 136, 15422.
Figure 2:
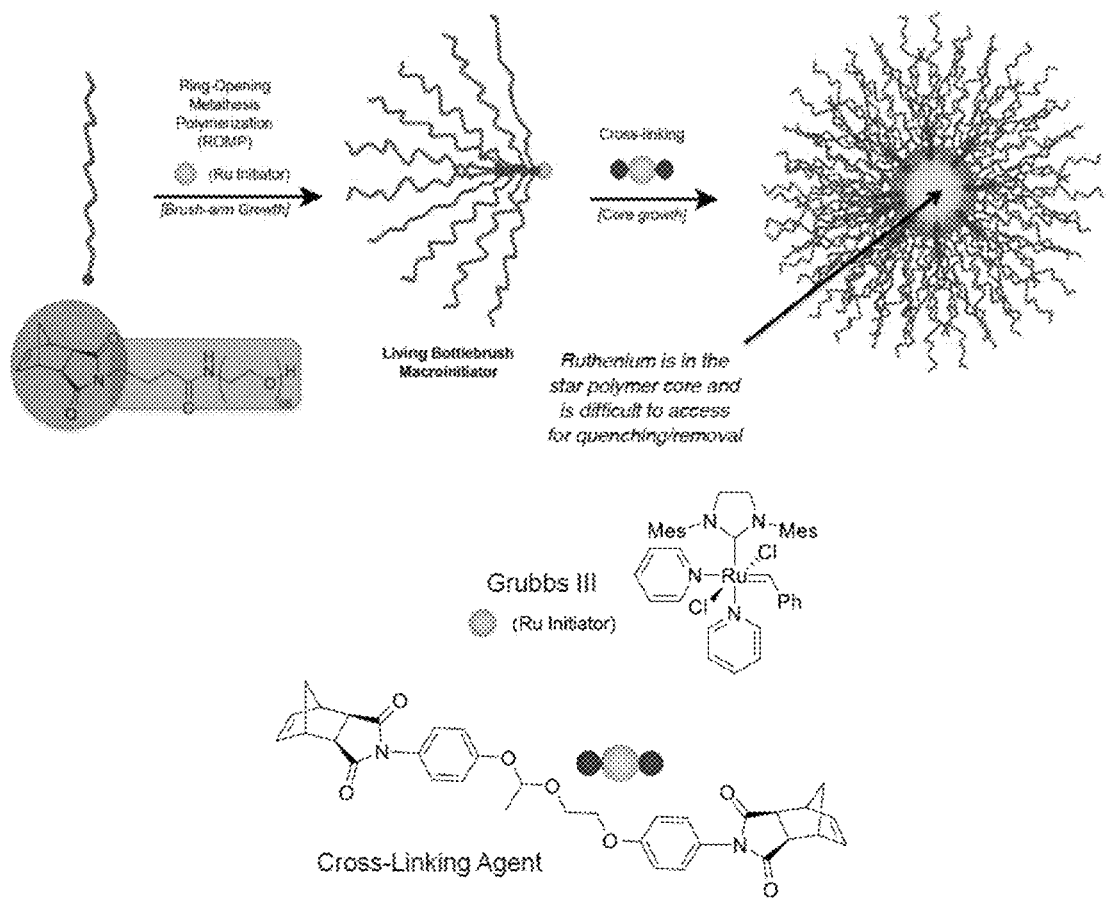
FIG. 2 shows a synthesis of brush arm star polymers (BASPs).
Figure 3A:
FIG. 3A shows a polymer resulting from ROMP that did not degrade above a pH of 4.5. *Angewandte Chemie International Edition*, 2013, 52, 5061.
Figure 3B:
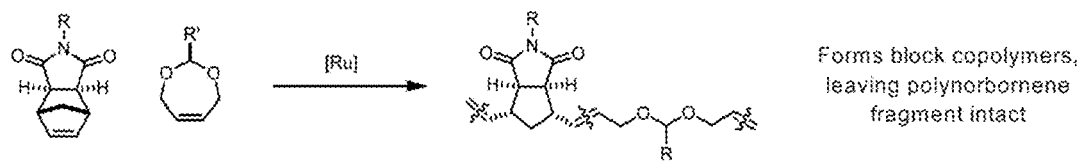
FIG. 3B shows a synthesis of a polymer via ROMP which formed block copolymers and left the polynorbornene fragment intact. *Angewandte Chemie International Edition*, 2006, 45, 8045.
Figure 3C:
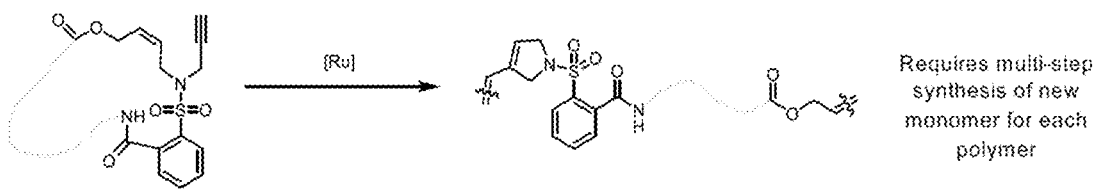
FIG. 3C shows a synthesis of a polymer via ROMP wherein a multistep synthesis was required for each monomer to generate a new polymer. *Journal of the American Chemical Society*, 2015, 137, 8038.
Figure 4A:
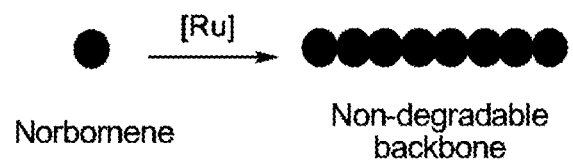
FIG. 4A shows a traditional route to generate polymers via ROMP wherein the backbone is non-degradable.
Figure 4B:
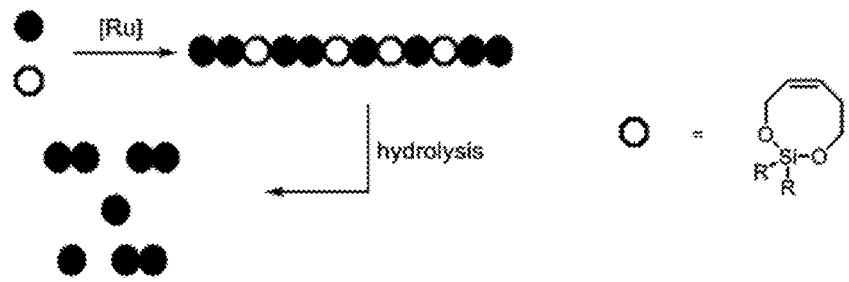
FIG. 4B shows a scheme of the approach undertaken herein where incorporation of cyclic silyl ether moieties may allow for hydrolysis to occur and degradation of the polymer.
Figure 5A:
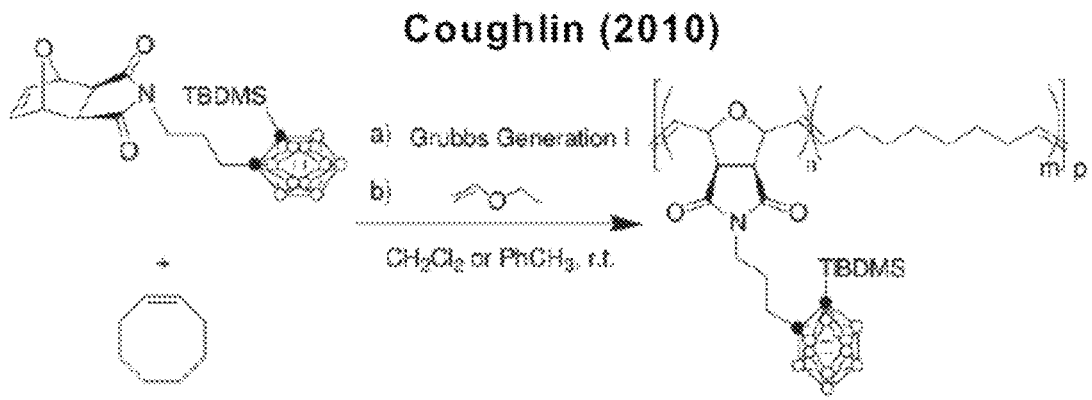
FIG. 5A shows a scheme of ring-opening metathesis copolymerization of a cyclooctene and a oxanorbornene. *Journal of Polymer Science: Part A: Polymer Chemistry*, 2010, 48, 2557.
Figure 5B:
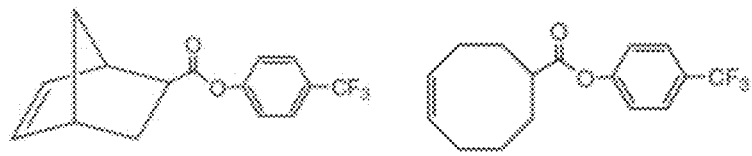
FIG. 5B shows monomers used by Leon and coworkers for ROMP and copolymerization. *Journal of Macromolecular Science,* 2011, 48, 211.
Figure 5C:
FIG. 5C shows monomers used by Endo and coworkers in ring-opening metathesis copolymerization. *Journal of Polymer Science A,* 2005, 43, 6599.
Figure 5D:
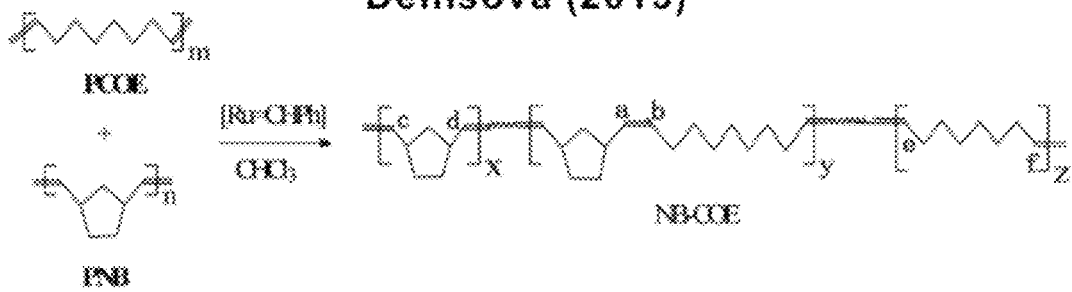
FIG. 5D shows a synthesis of norbornene-cyclooctene copolymers by cross-metathesis of polynorbornene with polyoctenamer. *RSC Advances,* 2014, 5, 316.

All reagents were purchased from commercial suppliers and used without further purification unless noted or stated otherwise. Grubbs 2$^{nd}$ Generation catalyst was purchased from Sigma-Aldrich, dissolved in dry dichloromethane, and concentrated under vacuum before use. Grubbs 3$^{rd}$ generation catalyst (referred to as G3; see FIG. 2) was generated directly from commercially available 2$^{nd}$ generation catalyst following literature procedure (Love, J. A.; Morgan, J. P.; Trnka, T. M.; Grubbs, R. H. *Angew. Chem., Int. Ed.* 2002, 41, 4035-4037).

Monomers were synthesized according to literature procedures. Small molecule norbornene monomers (such as NB1,[1] NB2,[2] NB3,[3] NB4,[4] PEG-MM,[5] PS-MM,[6] PLA-MM,[7] Cy5.5-MM,[8] Tel-MM,[9] and crosslinker AcXL[10], shown in FIGS. 7A to 7D) were prepared according to literature procedures (*International Journal of Organic Chemistry*, 2012, 2, 26. *Journal of the American Chemical Society*, 2017, 139, 17683). PEG-norbornene was synthesized according to prior literature procedure (*Journal of the American Chemical Society*, 2012, 134, 16337). Dicyclopentadiene and norbornene were distilled and stored at −20° C. until they were ready to use. Monomers were melted into a liquid by gentle heating in a water bath. The crosslinker acetal XL was prepared according to literature procedure (*ACS Macro Letters*, 2014, 3, 854-857). Column chromatography was carried out on silica gel 60F (EMD Millipore, 0.040-0.063 mm) following reported procedures. PS-MM and PLA-MM were further purified by preparative gel permeation chromatography before use. Dry tetrahydrofuran (THF) and dichloromethane (DCM) were passed through an activated alumina column prior to use. Thin-layer chromatography was performed using Baker-flex pre-coated TLC plates containing F254 indicator. Liquid chromatography mass spectrometry (LC/MS) and preparative HPLC were performed on an Agilent 1260 LC system equipped with a Zorbax SB-C18 rapid resolution HT column (LC/MS) and a Zorbax SB-C18 semi-preparative column (prep-HPLC) using a binary solvent system (MeCN and H$_2$O with 0.1% CH$_3$COOH). Recycling preparative HPLC was performed on a LaboACE system (Japan Analytical Industry) using a JAIGEL-2.5HR column. Gel permeation chromatography (GPC) analyses were performed on an Agilent 1260 Infinity setup with two Shodex KD-806M columns in tandem and a 0.025 M LiBr DMF mobile phase run at 60° C. The differential refractive index (dRI) of each compound was monitored using a Wyatt Optilab T-rEX detector. Nuclear magnetic resonance (NMR) spectra were recorded on Bruker AVANCE III-400 spectrometer, with working frequencies of 400 MHz ($^1$H). Chemical shifts are reported in ppm relative to the signals corresponding to the residual non-deuterated solvents: CDCl$_3$: δ H=7.26 ppm. Unless provided otherwise, an NMR spectrum of a polymer is an NMR spectrum of a reaction (e.g., polymerization or degradation) mixture where the polymer is a reactant, intermediate, or product. Dynamic light scattering (DLS) measurements were performed on a Wyatt Mobius DLS instrument. Samples were prepared at 1 mg/mL in pH 5.0 or pH 7.4 0.1 M sodium phosphate/citrate buffer. The solutions were passed through a 0.45 um Nylon filter into disposable polystyrene cuvettes, which were cleaned with compressed air. Measurements were made in sets of 10 acquisitions to generate an average spectrum. Hydrodynamic diameters were calculated using the DLS correlation function via a regularization fitting method (Dynamics 7.4.0.72 software package from Wyatt). Particles were kept at room temperature and measurements were made at the indicated time points.

$^1$H nuclear magnetic resonance ($^1$H-NMR) and $^{13}$C nuclear magnetic resonance ($^{13}$C-NMR) spectra were acquired at the MIT Department of Chemistry Instrumentation Facility on a Varian Mercury 300, Bruker AVANCE III DRX 400, or Varian Inova 500. Chemical shifts are reported in ppm relative to signals from the NMR solvent: for CDCl$_3$, this corresponds to 7.26 for 1H and 77.0 for $^{13}$C spectra. High-resolution mass spectrometry (HRMS) measurements were obtained on a JEOL AccuTOF system at the MIT Department of Chemistry Instrumentation Facility. MALDI-TOF analyses were performed on a Bruker microflex LRF using a 0.1% alpha-cyano-4-hydroxycinnamic acid matrix.

Gel permeation chromatography (GPC) analyses of polyethylene glycol (PEG)-containing polymers were performed on an Agilent 1260 Infinity system with dual Agilent PL1110-6500 columns and a 0.025 M LiBr in DMF mobile phase at 60° C. The differential refractive index (dRI) of each compound was monitored using a Wyatt Optilab T-rEX detector. For polymers containing primarily polystyrene (PS) or polylactic acid (PLA), GPC analysis was performed on a Tosoh EcoSEC HLC-8320 with dual TSKgel SuperH3000 columns and a chloroform mobile phase.

Dynamic light scattering (DLS) measurements were performed using a Wyatt Technology Mobius DLS instrument. Samples were prepared at 1.0 mg/mL in the requisite buffer. The solutions were filtered through a 0.2 μm nylon filter into disposable polystyrene cuvettes, which were pre-cleaned with compressed air. The solutions were immediately capped after addition of the solution to the cuvette. Measurements were made in sets of 10 acquisitions; the average hydrodynamic diameters were calculated using the DLS-correlation function via a regularization fitting method (Dynamics 7.4.0.72 software package from Wyatt).

Synthesis and Characterization

Example 0: Synthesis of Precursor TBS-Protected Alkynol

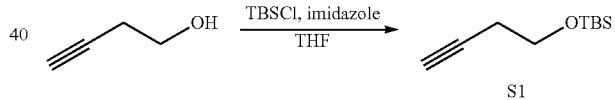

The synthesis of TBS-protected alkyne S1 was adapted from a literature protocol (Al-Shuhaib, Z. et al, *Tet. Lett.* 2013, 54, 6716-6718). 20.0 g (285 mmol) of 3-butynol, a clear liquid, was dissolved in 200 mL of dry THF in an oven-dried 1 L flask charged with stir bar. Next, 43.0 g (285 mmol, 1 eq.) of tert-butyldimethylsilyl chloride and 29.1 g (428 mmol, 1.5 eq.) of imidazole were added. The reaction was stirred for two hours at room temperature, during which time a significant amount of white precipitate formed. The mixture was filtered to remove imidazolium salt and was concentrated by rotary evaporation. The remaining residue was diluted with 200 mL of diethyl ether, washed with 200 mL of saturated ammonium chloride solution and 200 mL of saturated sodium bicarbonate solution, dried over sodium sulfate, and concentrated to yield 51.3 g (98%) of S1, which was utilized in the next step without further purification. NMR spectra matched those reported in the literature.

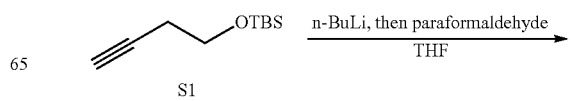

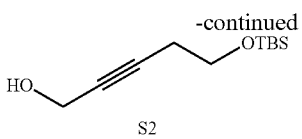

S2

The synthesis of TBS-protected diol S2 was adapted from a literature protocol (Trost, B. M.; Kainmals, C. A. *Org. Lett.* 2017, 19, 2346-2349). 48.5 g (263 mmol) of TBS butynol was dissolved in 400 mL of dry THF in an oven-dried 1 L flask charged with stir bar. The solution was placed under a dry nitrogen atmosphere and cooled to −78° C. using an acetone/dry ice bath. To the mixture was carefully added 110 mL of 2.5 M n-butyllithium in hexanes (276 mmol, 1.05 equiv.) over the course of 15 minutes. The now yellow reaction mixture was stirred for 1 h at −78° C., and then was allowed to warm to 0° C. Next, 9.5 g (316 mmol, 1.2 eq.) of paraformaldehyde was added in one portion and the reaction was allowed to stir at room temperature overnight. The solution was then quenched with the addition of 300 mL of saturated ammonium chloride and 300 mL of diethyl ether was added. The organic layer was collected and the aqueous layer was extracted with another 300 mL of diethyl ether. The organic layers were then dried over sodium sulfate and concentrated to yield a pale-yellow oil, which was purified by silica gel chromatography with 6:1 hexanes/ethyl acetate to yield 38.7 g (68%) of S2 as a clear oil. NMR spectra matched those reported in the literature.

Example 1. Preparation of Cyclic Silyl Ethers Precursors

Figure 6A:
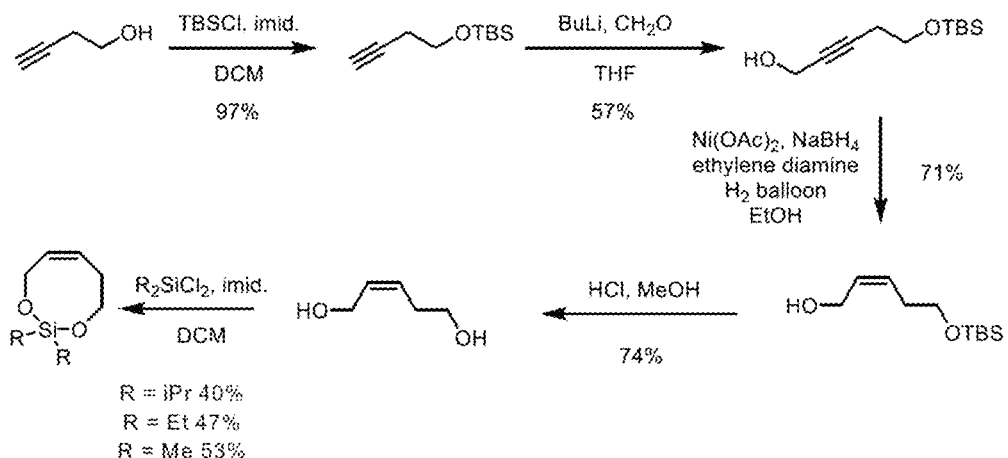
FIG. 6A shows a synthesis used to generate cyclic silyl ethers with corresponding yields.
Figure 6B:
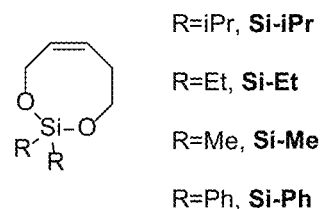
FIG. 6B shows the formulae of exemplary cyclic silyl ethers.
Figure 6C:
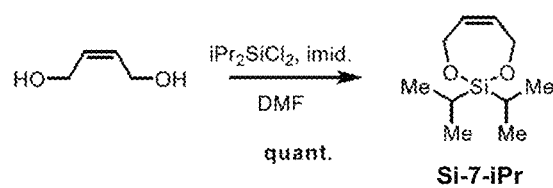
FIG. 6C shows a synthesis used to generate cyclic silyl ether Si-7-iPr.

See FIGS. 6A to 6C.

Example 1: Synthesis of TBS Diol

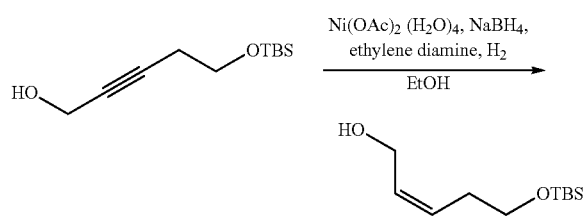

The reduction of TBS-protected alkynol was performed via an adaptation of literature procedure (Al-Shuhaib, Z. et al, Tet. Lett. 2013, 54, 6716-6718). The starting TBS-protected alkynol was prepared as described above or following literature procedure (Al-Shuhaib, Z. et al, Tet. Lett. 2013, 54, 6716-6718). To a 1 L flask charged with stir bar was added 210 mL of absolute ethanol and 3.57 (14.4 mmol, 0.13 equiv.) of nickel acetate tetrahydrate. The solution was placed under a hydrogen atmosphere using hydrogen-filled balloons. To the mixture was carefully added a suspension of 735 mg (19.5 mmol, 0.178 equiv.) of sodium borohydride in 45 mL of ethanol, turning the light teal solution a dark black color. After stirring for 30 minutes, 3 mL (3.9 g, 64.5 mmol, 0.586 equiv.) of ethylene diamine was added followed by a solution of 23.7 g (110 mmol) of TBS alkynol in 75 mL of ethanol. The reaction was stirred at room temperature and monitored via NMR. After five hours, NMR showed full conversion of starting material to product. The flask was then evacuated of hydrogen gas. The mixture was diluted with 500 mL of ethyl acetate and poured through a pad of silica to remove Ni salts. The solution was then concentrated under vacuum and purified with a short plug of silica using 4:1 hexanes/ethyl acetate to yield 12.0 g (50%) of TBS alkene diol as a clear oil. 1H NMR (400 MHz, Chloroform-d) δ 5.87-5.76 (m, 1H), 5.63-5.52 (m, 1H), δ 4.13 (t, J=5.6 Hz, 2H), 3.64 (t, J=6.1 Hz, 2H), 2.34 (q, J=6.6 Hz, 2H), 2.16 (s, 1H), 0.89 (s, 9H), 0.05 (s, 6H). 13C NMR (101 MHz, CDCl$_3$) δ 130.84, 129.36, 77.32, 77.00, 76.68, 62.21, 57.92, 30.83, 25.89, 18.36, −5.46. HRMS (DART+): Calculated for C$_{11}$H$_{25}$O$_2$Si (M+H)$^+$: 217.1623, found 217.1796. R$_f$=0.40 (4:1 hexanes/ethyl acetate, KMnO$_4$).

Example 2. Preparation of Alkene-Diol

Scheme 2: Synthesis of Alkene-Diol

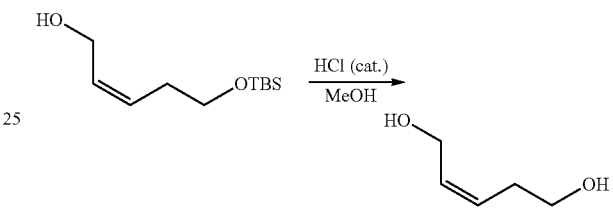

12.0 g (55.4 mmol) of TBS diol was dissolved in 200 mL of methanol containing 1% concentrated hydrochloric acid. The reaction was stirred at RT while being closely monitored by TLC. After 15 minutes, TLC showed conversion to product. The reaction was neutralized through the addition of 30% aqueous sodium hydroxide and concentrated, then purified with 2:1 hexanes/ethyl acetate to ethyl acetate to yield 4.44 g (44 mmol, 80%) of product as a clear oil. $^1$H NMR (300 MHz, Chloroform-d) δ 5.93-5.78 (m, 1H), 5.68-5.52 (m, 1H), 4.14 (d, J=7.1 Hz, 2H), 3.66 (t, J=5.9 Hz, 2H), 2.82 (s, 1H), 2.69 (s, 1H), 2.36 (dtd, J=7.5, 5.9, 1.4 Hz, 2H). $^{13}$C NMR (101 MHz, CDCl$_3$) δ 130.68, 129.03, 60.86, 57.24, 30.32. R$_f$=0.50 (ethyl acetate, KMnO$_4$).

Example 3. Preparation of Si—Me

Scheme 3: Synthesis of Si-Me

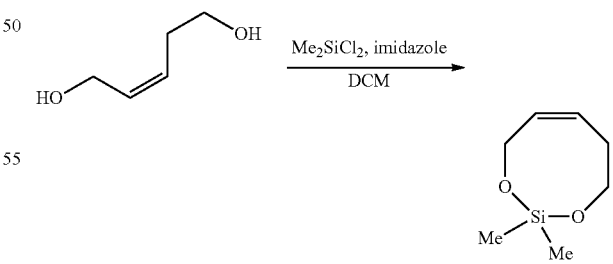

1.02 g of alkene-diol (10 mmol) and 1.36 g of imidazole (20 mmol, 2 equiv.) was dissolved in 500 mL of dry DCM in an oven-dried flask. Next, 1.22 mL of dichlorodimethylsilane (1.29 g, 10 mmol, 1 equiv.) was added dropwise over 5 minutes, during which the solution turned cloudy. The mixture was stirred for 1 hour, then filtered and concentrated. The yellow residue was then transferred into a small flask and distilled under vacuum (140° C., 10 mtorr) to yield a clear oil. The oil was further purified via column chromatography with 20:1 hexanes/ethyl acetate to yield 0.837 g (53%) of Si-Me (also referred to as MeSi, Me-Si, and SiMe) as a clear oil. $^1$H NMR (500 MHz, Chloroform-d) δ 5.88 (dt, J=11.4, 5.7 Hz, 1H), 5.74 (app. dtt, J=11.1, 8.5, 1.2 Hz, 1H), 4.31 (dd, J=5.8, 1.2 Hz, 2H), 3.88-3.81 (m, 2H), 2.49 (dt, J=8.6, 5.3 Hz, 2H), 0.14 (s, 6H). $^{13}$C NMR (101 MHz, CDCl$_3$) δ 130.87, 129.38, 60.65, 57.13, 30.15, 0.66. R$_f$=0.60 (20:1 hexanes/ethyl acetate, KMnO$_4$).

Example 4. Preparation of Si-Et

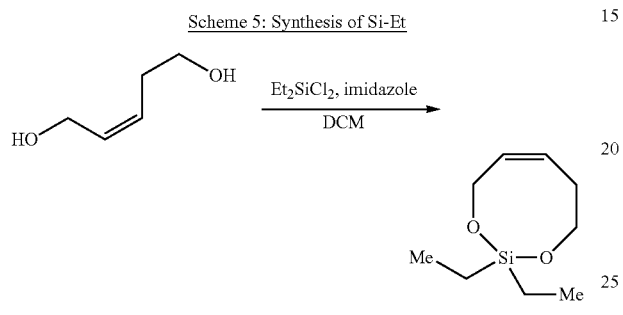

Et-Silane 1.02 g of alkene-diol (10 mmol) and 1.36 g of imidazole (20 mmol, 2 equiv.) was dissolved in 500 mL of dry DCM in an oven-dried flask. Next, 1.50 mL of dichlorodiethylsilane (1.57 g, 10 mmol, 1 equiv.) was added dropwise over 5 minutes, during which the solution turned cloudy. The mixture was stirred for 1 hour, then filtered and concentrated. The yellow residue was then transferred into a small flask and distilled under vacuum (140° C., 10 mtorr) to yield a clear oil. The oil was further purified via column chromatography with 20:1 hexanes/ethyl acetate to yield 1.15 g (62%) of EtSi (also referred to as Si-Et, SiEt, and Et-Si) as a clear oil that was kept at −20° C. $^1$H NMR (300 MHz, Chloroform-d) δ 5.97-5.83 (m, 1H), 5.74 (app. dtt, J=10.9, 8.5, 1.1 Hz, 1H), 4.35-4.26 (m, 2H), 3.90-3.81 (m, 2H), 2.55-2.42 (m, 2H), 0.97 (app. td, J=8.0, 0.6 Hz, 6H), 0.62 (app. qd, J=7.9, 0.9 Hz, 4H). $^{13}$C NMR (101 MHz, CDCl$_3$) δ 131.64, 129.15, 62.91, 59.96, 30.44, 6.27, 4.30. HRMS (DART+): Calculated for C$_9$H$_{19}$O$_2$Si (M+H)$^+$: 187.1154, found 187.1318. R$_f$=0.65 (20:1 hexanes/ethyl acetate, KMnO$_4$).

Example 5. Preparation of Si—iPr

Figure 7A:
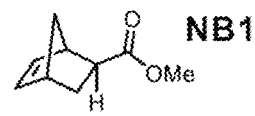
FIG. 7A shows the formula of compound NB1.
Figure 7B:
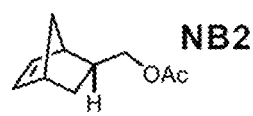
FIG. 7B shows the formula of compound NB2.
Figure 7C:
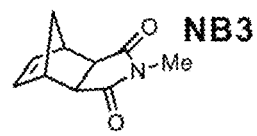
FIG. 7C shows the formula of compound NB3.
Figure 7D:
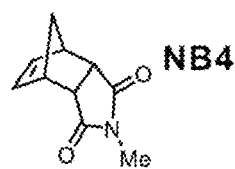
FIG. 7D shows the formula of compound NB4.
Figure 7E:
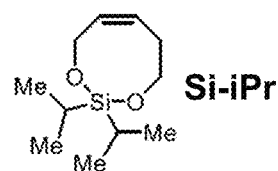
FIG. 7E shows the formula of compound Si-iPr.
Figure 8A:
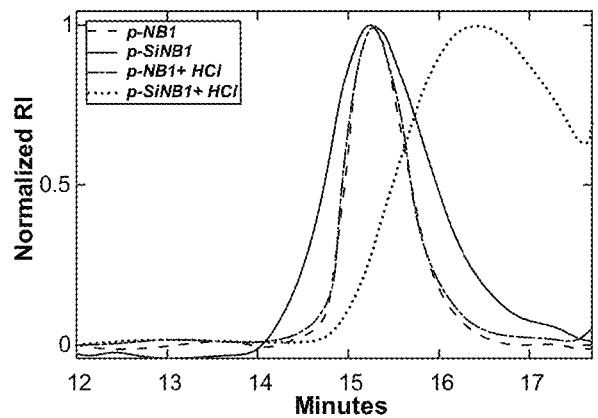
FIG. 8A shows a resulting chromatogram from gel permeation chromatography (GPC) of NB1 homopolymer (p-NB1) where the degree of polymerization (DP) was 50 and (NB1)-(Si-iPr) copolymer (p-SiNB1) where the DP was 50 and ratio (molar ratio) of monomers used was 1:1. All of the copolymers degrade under acidic conditions, whereas homopolymers of NB1-NB4 do not.
Figure 8B:
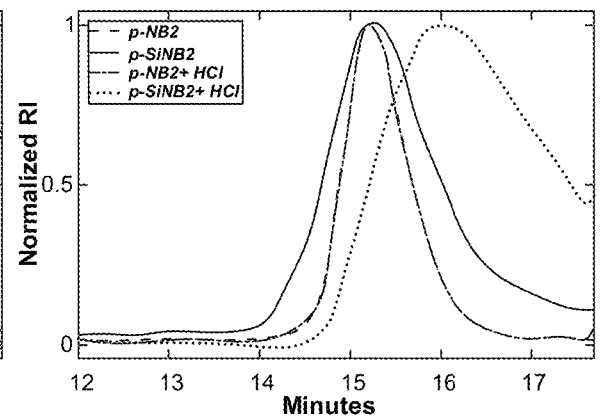
FIG. 8B shows a resulting chromatogram from GPC of NB2 homopolymer (p-NB2) and (NB2)-(Si-iPr) copolymer (p-SiNB2) with and without treatment with HCl (where the DP was 50 before further treatment and ratio of monomers used was 1:1). All of the copolymers degrade under acidic conditions, whereas homopolymers of NB1-NB4 do not.
Figure 8C:
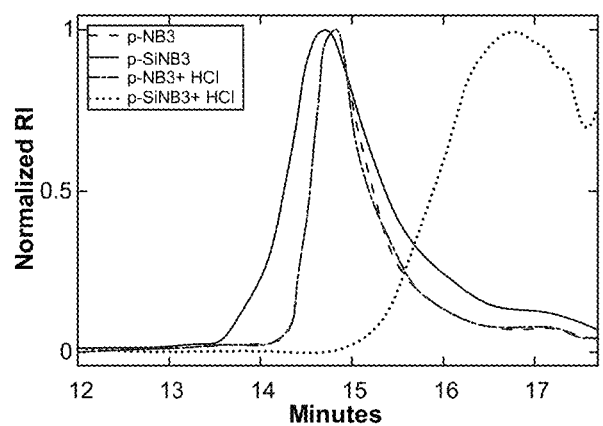
FIG. 8C shows a resulting chromatogram from GPC of NB3 homopolymer (p-NB3) and (NB3)-(Si-iPr) copolymer (p-SiNB3) with and without treatment with HCl (where the DP was 50 before further treatment and ratio of monomers used was 1:1). All of the copolymers degrade under acidic conditions, whereas homopolymers of NB1-NB4 do not.
Figure 8D:
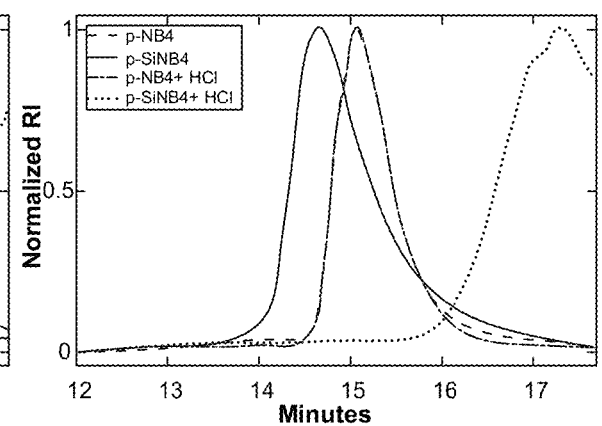
FIG. 8D shows a resulting chromatogram from GPC of NB4 homopolymer (p-NB4) and (NB4)-(Si-iPr) copolymer (p-SiNB4) with and without treatment with HCl (where the DP was 50 before further treatment and ratio of monomers used was 1:1). All of the copolymers degrade under acidic conditions, whereas homopolymers of NB1-NB4 do not.
Figure 9A:
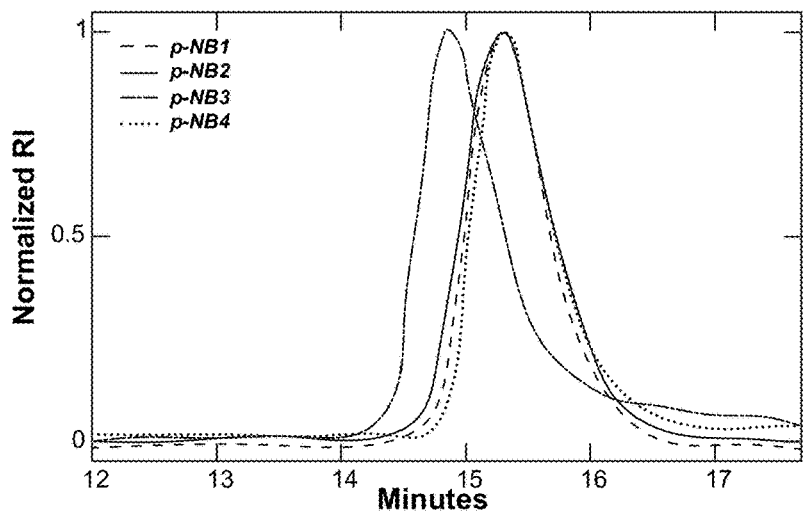
FIG. 9A shows a resulting chromatogram from GPC of four homopolymers (p-NB1, p-NB2, p-NB3, and p-NB4) where the DP was 50 for each polymer.
Figure 9B:
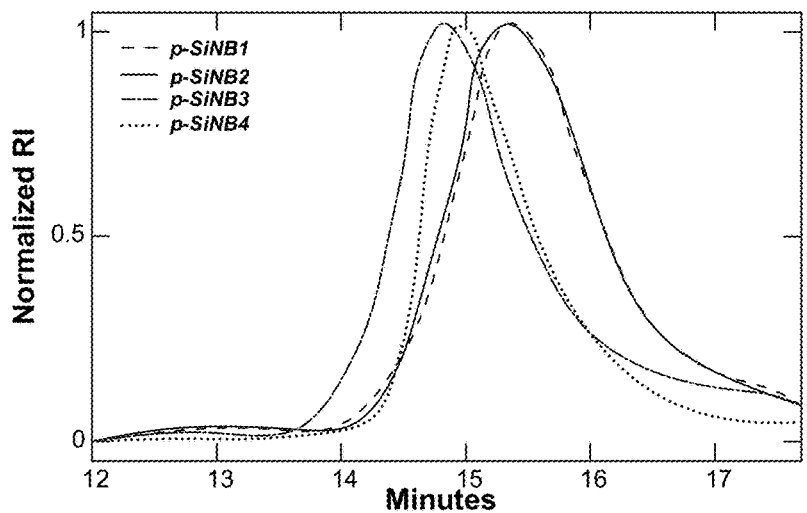
FIG. 9B shows a resulting chromatogram from GPC of four copolymers (p-SiNB1, p-SiNB2, p-SiNB3, and p-SiNB4) where the DP was 50 for each polymer and ratio of monomers used was 1:1.
Figure 9C:
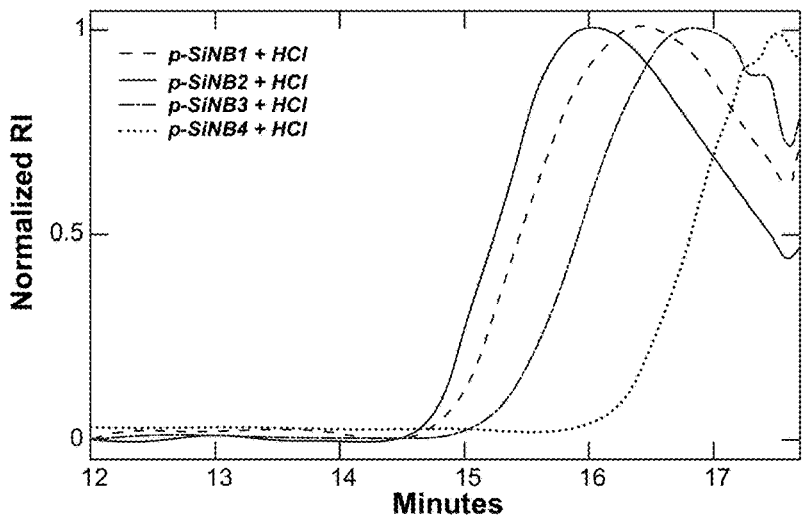
FIG. 9C shows a resulting chromatogram from GPC of four copolymers (p-SiNB1, p-SiNB2, p-SiNB3, and p-SiNB4) after treatment with HCl (where each polymer had a DP of 50 before further treatment and ratio of monomers used was 1:1).
Figure 10A:
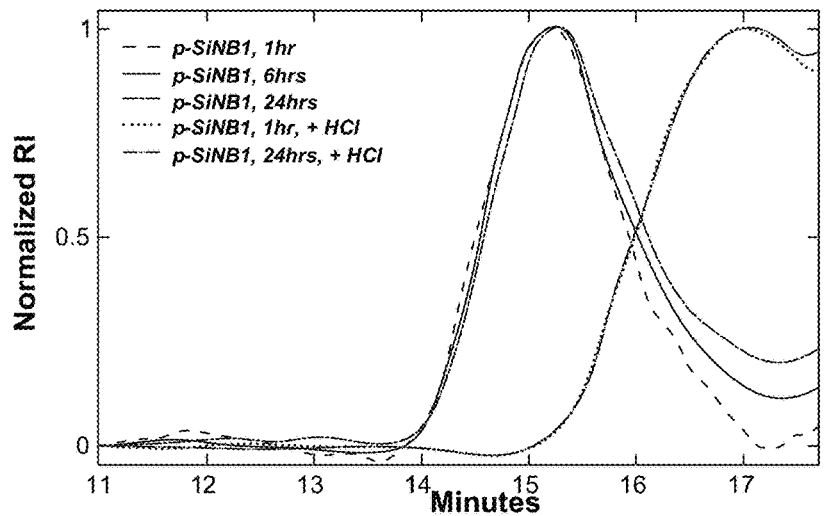
FIG. 10A shows a resulting chromatogram from GPC of p-SiNB1 at 1, 6, and 24 hours of polymerization time without HCl, and at 1 and 24 hours of polymerization time and after treatment with HCl.
Figure 10B:
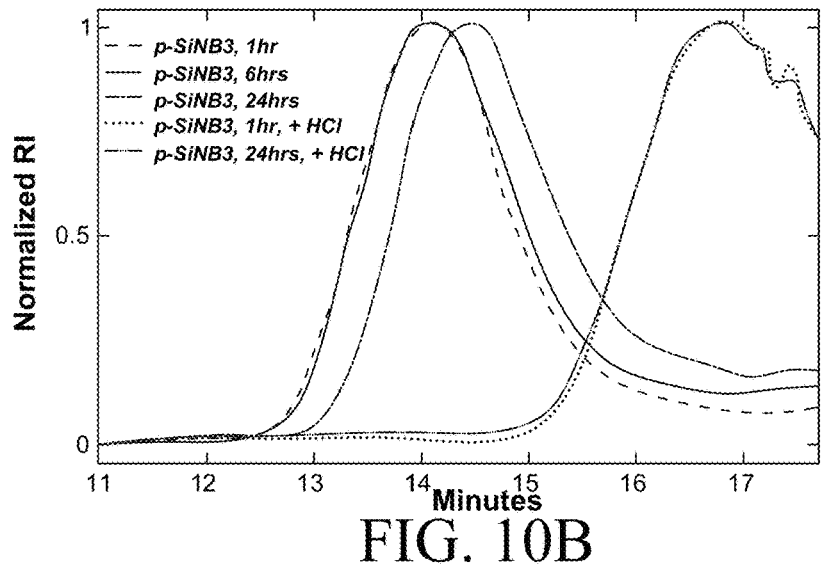
FIG. 10B shows a resulting chromatogram from GPC of p-SiNB3 at 1, 6, and 24 hours of polymerization time, and at 1 and 24 hours of polymerization time and after treatment with HCl.
Figure 10C:
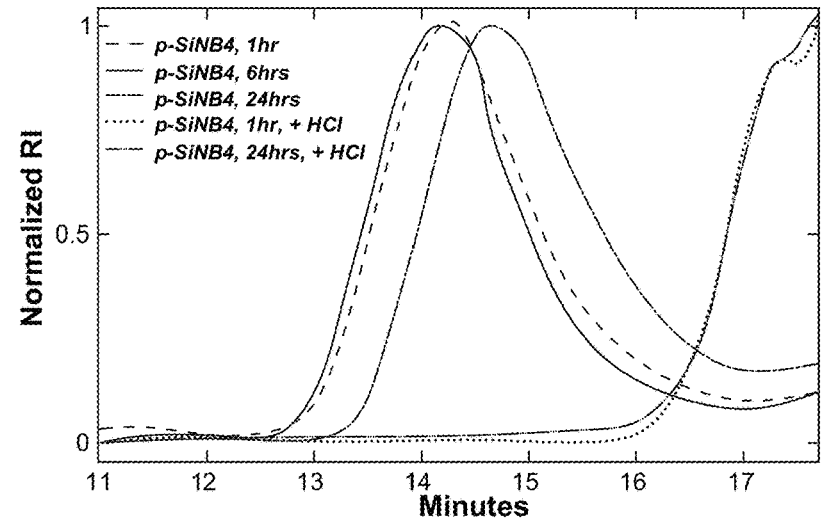
FIG. 10C shows a resulting chromatogram from GPC of p-SiNB4 at 1, 6, and 24 hours of polymerization time, and at 1 and 24 hours of polymerization time and after treatment with HCl.

See FIG. 7E.

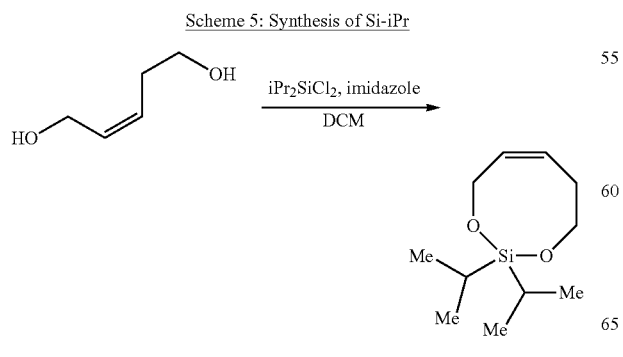

1.02 g of alkene-diol (10 mmol) and 1.36 g of imidazole (20 mmol, 2 equiv.) was dissolved in 500 mL of dry DCM in an oven-dried flask. Next, 1.50 mL of dichlorodiisopropylsilane (1.57 g, 10 mmol, 1 equiv.) was added dropwise over 5 minutes, during which the solution turned cloudy. The mixture was stirred for 3 hours, then filtered and concentrated. The yellow residue was then transferred into a small flask and distilled under vacuum (140° C., 10 mtorr) to yield a clear oil. The oil was further purified via column chromatography with 20:1 hexanes/ethyl acetate to yield 1.05 g (49%) of iPrSi (also referred to as Si-iPr, SiiPr, and iPr-Si) as a clear oil that was kept at −20° C. $^1$H NMR (400 MHz, Chloroform-d) δ 5.92 (dt, J=11.5, 6.0 Hz, 1H), 5.73 (dt, J=10.9, 8.5 Hz, 1H), 4.40-4.25 (m, 2H), 4.05-3.90 (m, 2H), 2.44 (dt, J=8.6, 5.2 Hz, 2H), 1.00 (s, 12H). $^{13}$C NMR (101 MHz, CDCl$_3$) δ 131.85, 129.38, 63.54, 60.34, 30.75, 17.43, 12.47. HRMS (DART+): Calculated for C$_{11}$H$_{23}$O$_2$Si (M+H)$^+$: 215.1467, found 215.1436. R$_f$=0.70 (20:1 hexanes/ethyl acetate, KMnO$_4$).

Example 6. Preparation of Si-Ph

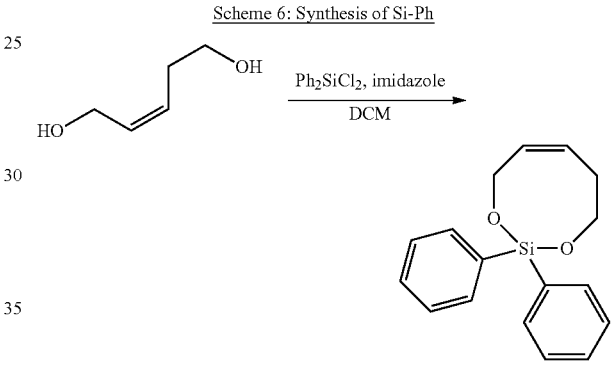

0.303 g (3 mmol) of diol and 0.408 g (6 mmol, 2 equiv.) of imidazole were dissolved in 150 mL dry DCM. Next, dichlorodiphenylsilane was added dropwise over 5 minutes, during which the solution turned cloudy. The mixture was stirred for 3 hours, then filtered and concentrated. The mixture was purified using a short column of hexanes to 10:1 hexanes/ethyl acetate. The resulting oil, which was a mixture of cyclic monomer and higher order cyclic oligomers, were purified by preparative GPC to yield 93 mg (11%) of pure Si-Ph (also referred to as PhSi, SiPh, and Ph-Si) as a clear oil that was kept at −20° C. $^1$H NMR (400 MHz, Chloroform-d) δ 7.71-7.63 (m, 4H), 7.45-7.32 (m, 4H), 5.90 (dt, J=11.0, 5.4 Hz, 1H), 5.78-5.66 (m, 1H), 4.49 (dd, J=5.4, 1.3 Hz, 2H), 4.04-3.97 (m, 2H), 2.54 (dt, J=8.6, 5.3 Hz, 2H). $^{13}$C NMR (101 MHz, CDCl$_3$) δ 134.58, 133.40, 131.80, 130.10, 128.81, 127.82, 63.42, 61.06, 30.67. HRMS (DART+): Calculated for C$_{17}$H$_{19}$O$_2$Si (M+H)$^+$: 283.1154, found 283.1138. R$_f$=0.80 (20:1 hexanes/ethyl acetate, UV, KMnO$_4$)

Example 7. Preparation of 7-iPr—Si

-continued

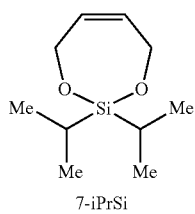

7-iPrSi 0.264 g (3 mmol) of cis-1,4-butenediol and 0.408 g (6 mmol, 2 equiv.) of imidazole were dissolved in 60 mL of dry DMF. Next, dichlorodiisopropylsilane (0.555 g, 3 mmol) was added dropwise over 5 min. The solution was stirred overnight, quenched with 150 mL H$_2$O, extracted with 2×200 mL hexanes, dried over sodium sulfate, and concentrated. The product was purified with 10:1 hexanes/ethyl acetate to yield 0.750 g (quant.) of the desired product (7-iPrSi) as a clear oil. $^1$H NMR (400 MHz, Chloroform-d) δ 5.67 (t, J=1.9 Hz, 2H), 4.50 (d, J=1.8 Hz, 4H), 1.08 (d, J=1.7 Hz, 14H). $^{13}$C NMR (101 MHz, CDCl$_3$) δ 129.83, 62.54, 17.30, 12.03. HRMS (DART+): Calculated for C$_{10}$H$_2$O$_2$Si (M+H)$^+$: 201.1310, found 201.1065. R$_f$=0.70 (20:1 hexanes/ethyl acetate, UV, KMnO$_4$).

Example 8

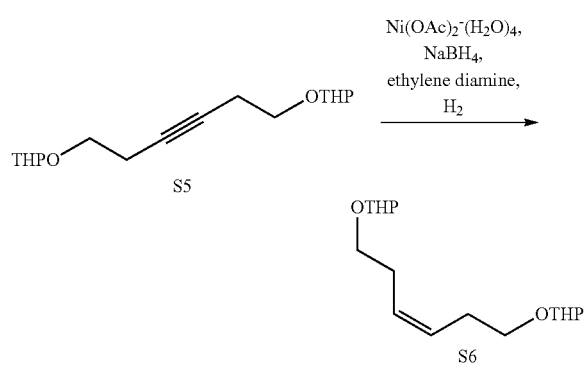

S5 was prepared according to reported procedures (O'Rourke, N. F. et al. *Org. Lett.* 2016, 18, 1250-1253). To a 300 mL flask charged with stir bar was added 40 mL of absolute ethanol and 0.714 g (2.87 mmol, 0.13 equiv.) of nickel acetate tetrahydrate. The solution was placed under a hydrogen atmosphere using a hydrogen-filled balloon. To the mixture was carefully added a suspension of 147 mg (3.89 mmol, 0.178 equiv.) of sodium borohydride in 9 mL of ethanol, turning the light teal solution a dark black color. After stirring for 30 min, 0.6 mL (0.54 g, 8.98 mmol, 0.586 equiv.) of ethylene diamine were added followed by a solution of S5 (6.20 g, 22 mmol) in 15 mL of ethanol. The reaction was stirred at room temperature and monitored by $^1$H NMR spectroscopy. After 5 h, NMR showed full conversion of starting material to product. The flask was then evacuated of hydrogen gas and placed under ambient atmosphere. The mixture was diluted with 500 mL of ethyl acetate and poured through a pad of silica to remove Ni salts. The solution was then concentrated under vacuum and purified with a short plug of silica using 4:1 hexanes/ethyl acetate to yield 3.58 g (57%) of S6 as a clear oil. $^1$H NMR (400 MHz, Chloroform-d) δ 5.51 (t, J=4.9 Hz, 2H), 4.59 (t, J=3.5 Hz, 2H), 3.87 (ddd, J=11.1, 7.6, 3.3 Hz, 2H), 3.74 (dt, J=9.3, 7.0 Hz, 2H), 3.49 (dt, J=10.7, 4.8 Hz, 2H), 3.41 (dt, J=9.5, 7.0 Hz, 2H), 2.38 (q, J=6.5 Hz, 4H), 1.83 (qd, J=7.6, 7.1, 3.4 Hz, 2H), 1.71 (ddd, J=12.3, 7.9, 4.4 Hz, 2H), 1.64-1.41 (m, 8H). $^{13}$C NMR (101 MHz, CDCl$_3$) δ 127.61, 98.63, 66.86, 62.15, 30.61, 27.97, 25.40, 19.49. HRMS (DART+): Calculated for C$_{16}$H$_{29}$O$_4$ (M+H)$^+$: 285.2065, found 285.1765. R$_f$=0.50 (10:1 hexanes/ethyl acetate, KMnO$_4$)

Example 9

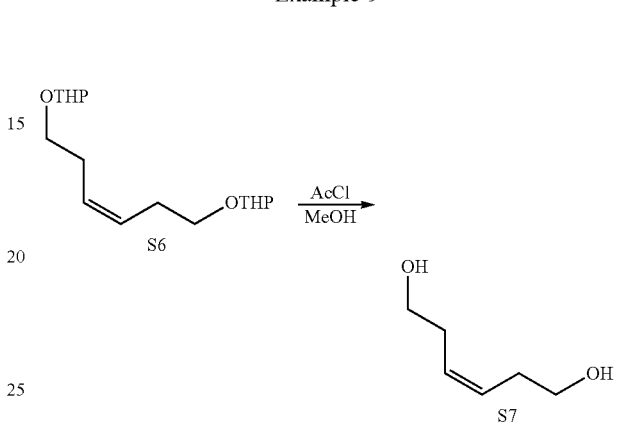

In a round bottom flask, 0.5 mL of acetyl chloride were added to 50 mL of methanol. The solution was stirred for 5 min, then 3.0 g (10.6 mmol) of S6 were added. The mixture was stirred for 15 min, after which time TLC showed full conversion to product. The mixture was then neutralized with 30% sodium hydroxide and concentrated under vacuum. The remaining residue was passed through a short silica column, starting with 1:1 hexanes/ethyl acetate and eluting the product with ethyl acetate. The solution was concentrated to yield 0.694 g (56%) of S7 as a clear oil. $^1$H NMR (400 MHz, Chloroform-d) δ 5.57 (ddd, J=6.3, 4.8, 1.3 Hz, 2H), 3.66 (t, J=5.9 Hz, 4H), 2.52 (s, 2H), 2.43-2.21 (m, 4H). $^{13}$C NMR (101 MHz, CDCl$_3$) δ 128.82, 61.57, 30.41. HRMS (DART+): Calculated for C$_6$H$_{13}$O$_2$ (M+H)$^+$: 117.09155, found 117.0778. R$_f$=0.50 (ethyl acetate, KMnO$_4$)

Example 10. Preparation of 9-iPrSi

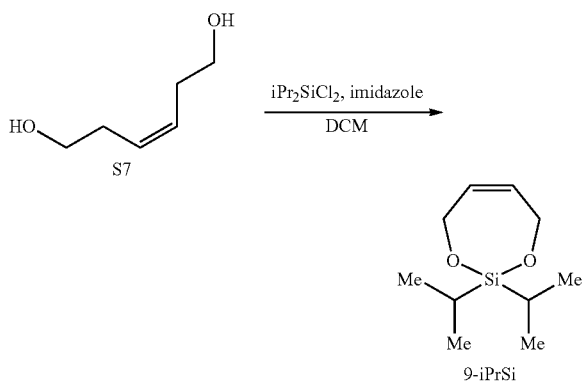

9-iPrSi

To 300 mL of dry DCM was added 0.408 g (6 mmol, 2 equiv.) of imidazole. Next, solutions of 0.348 g (3 mmol) of S7 and dichlorodiisopropylsilane (0.555 g, 3 mmol, 1 equiv.), each in 5 mL of dry DCM, were added dropwise over 5 min, during which time the solution turned cloudy. The mixture was stirred for 3 h, filtered, and concentrated. The mixture was purified using a short column of hexanes to 10:1 hexanes/ethyl acetate. The resulting oil, which was a mixture of cyclic monomer and higher order cyclic oligomers, was purified by preparative GPC (using chloroform eluent) to yield 0.244 g (36%) of 9-iPrSi as a clear oil. 41 NMR (400 MHz, Chloroform-d) δ 5.83-5.46 (m, 2H), 3.91-3.78 (m, 4H), 2.35 (qd, J=5.2, 1.7 Hz, 4H), 1.19-0.77 (m, 14H). $^{13}$C NMR (101 MHz, CDCl$_3$) δ 129.56, 62.94, 30.70, 17.68, 12.02. HRMS (DART+): Calculated for $C_{12}H_{25}O_2Si$ (M+H)$^+$: 229.1623, found 229.1391. $R_f$=0.75 (20:1 hexanes/ethyl acetate, KMnO$_4$)

Example 11. Synthesis of Cy3-MM

Cy3-MM was prepared in an analogous fashion to that reported for Cy5.5-MM. Briefly, 13.4 mg of Cy3-Azide (Lumiprobe) was added to a 2-dram vial. Next, 60 mg of an alkyne-containing macromonomer[11] were added. The combined solids were transferred into a nitrogen-filled glovebox and dissolved in 1 mL of DCM. Next, a spatula tip of copper (I) acetate was added and the solution stirred for 1 h, after which time LC-MS analysis indicated full conversion of Cy3-Azide. The mixture was then concentrated and purified by preparative HPLC using an acetonitrile-0.1% AcOH in water gradient. The desired fractions were partially concentrated by rotary evaporation until ~25% of the residual solvent remained, then 250 mL of DCM were added and the entire mixture was dried with sodium sulfate. The desired product was collected by removal of the sodium sulfate and concentration to yield Cy3-MM as a magenta solid. Calculated mass (M)$^+$: 3698.84 found 3696.08 (see FIGS. 63A-63B).

Example 12.1. General Procedure for Copolymerization of Norbornene Derivatives with Cyclic Silyl Ethers All polymerization reactions were performed inside a nitrogen-filled glovebox. To a 2 mL vial with stir bar was added 105 μL of dioxane. Next, 15 μL of 0.5 M norbornene in dioxane, 15 μL of 0.5 M cyclic silyl ether in dioxane or dioxane, and 15 μL of 0.01 M G3 catalyst in dioxane were added. The solution was stirred for 60 minutes, then quenched with a drop of ethyl vinyl ether and analyzed by gel permeation chromatography. 40 μL of this mixture was analyzed by GPC. The remainder was concentrated under vacuum at room temperature, then diluted with 100 μL fo dioxane and 10 μL of 2M HCl. The mixture was stirred for 30 minutes, then dried with Na$_2$SO$_4$ and analyzed by GPC.

Figure 11:
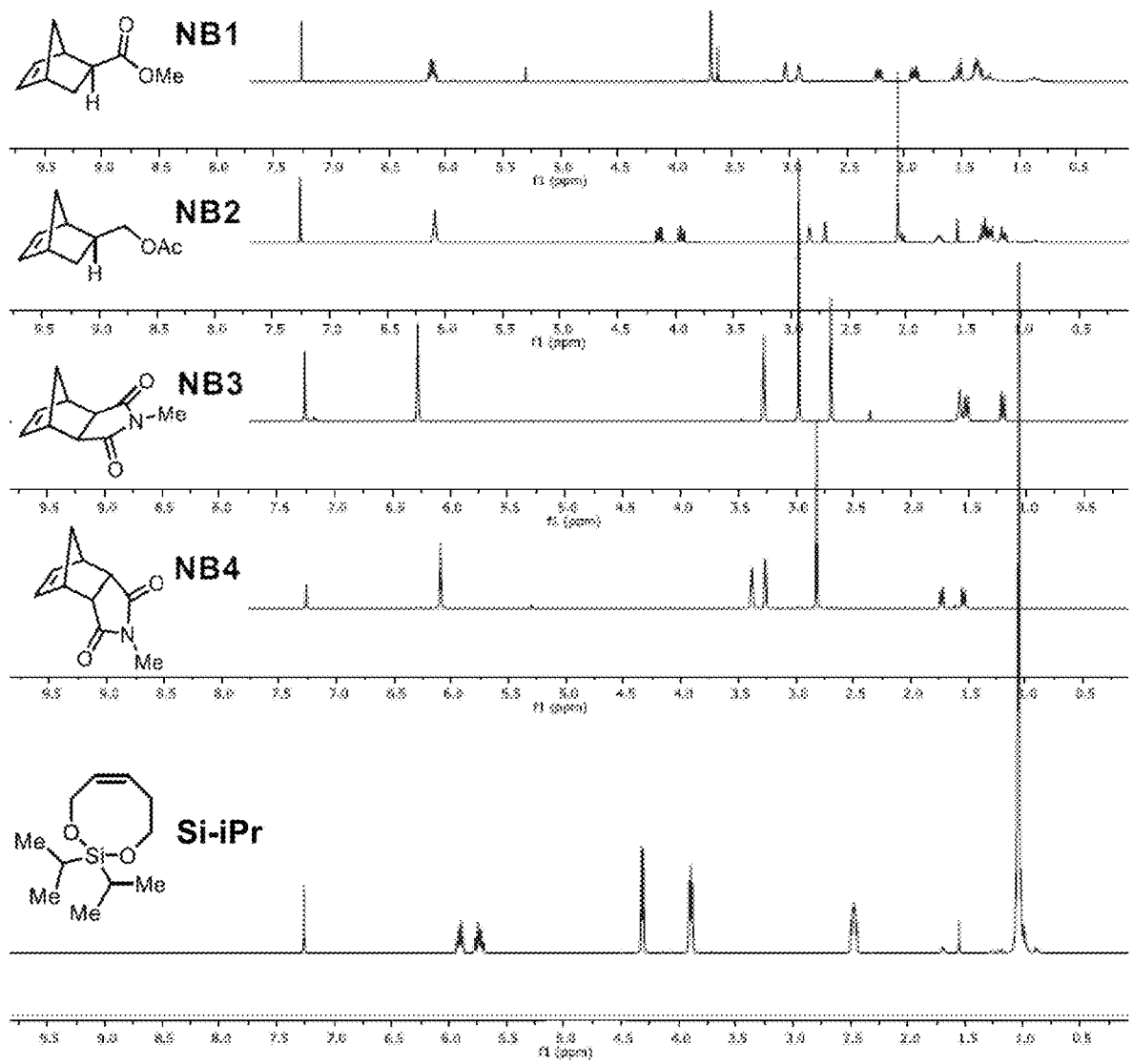
FIG. 11 shows the $^1$H NMR spectra in CDCl$_3$ of exemplary monomers.
Figure 12:
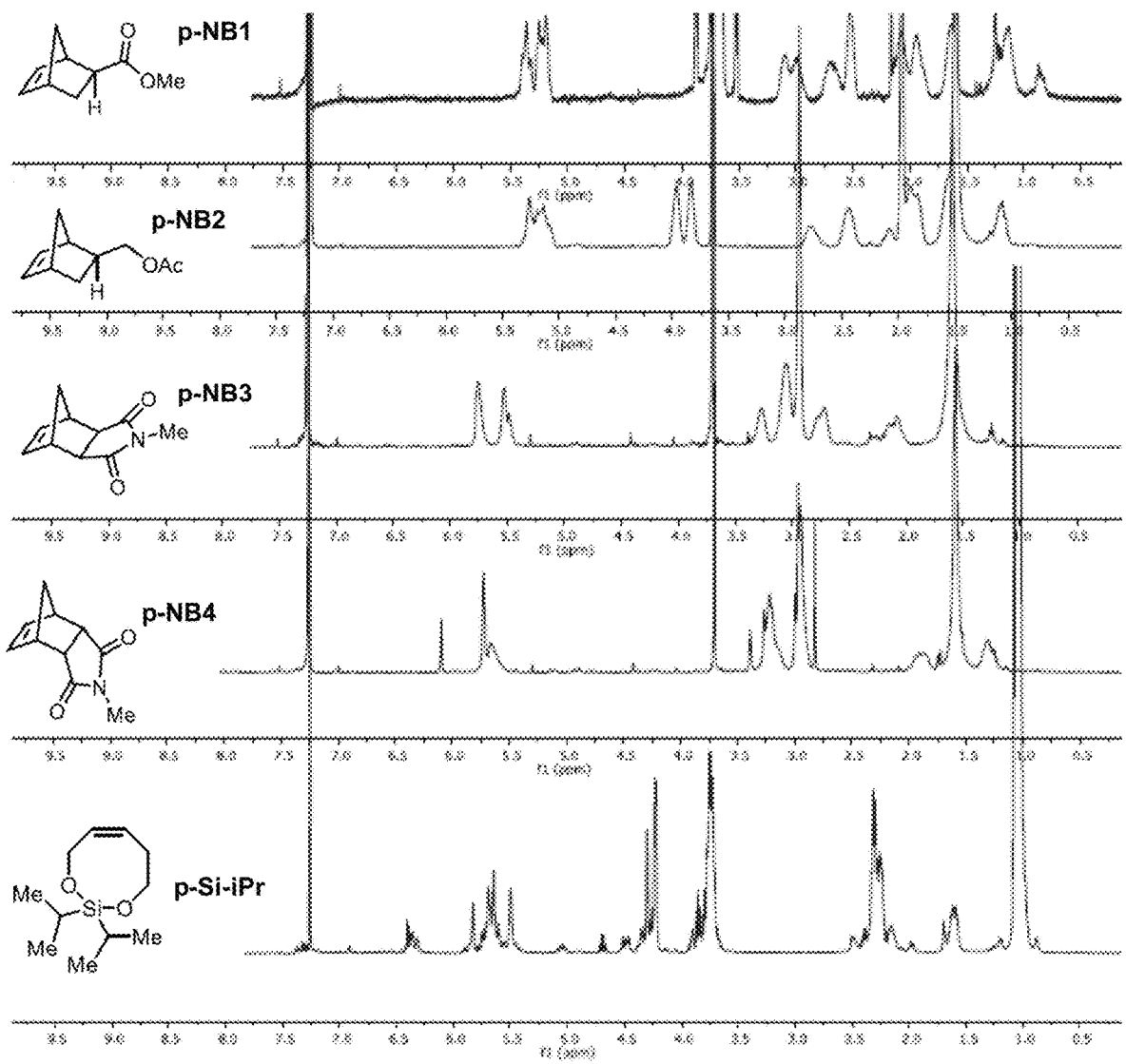
FIG. 12 shows the $^1$H NMR spectra in CDCl$_3$ of the homopolymers of exemplary monomers after 1 hour of polymerization time where each polymer had a DP of 50. Each spectrum is labeled with the formula of the monomer employed in the polymerization.
Figure 13:
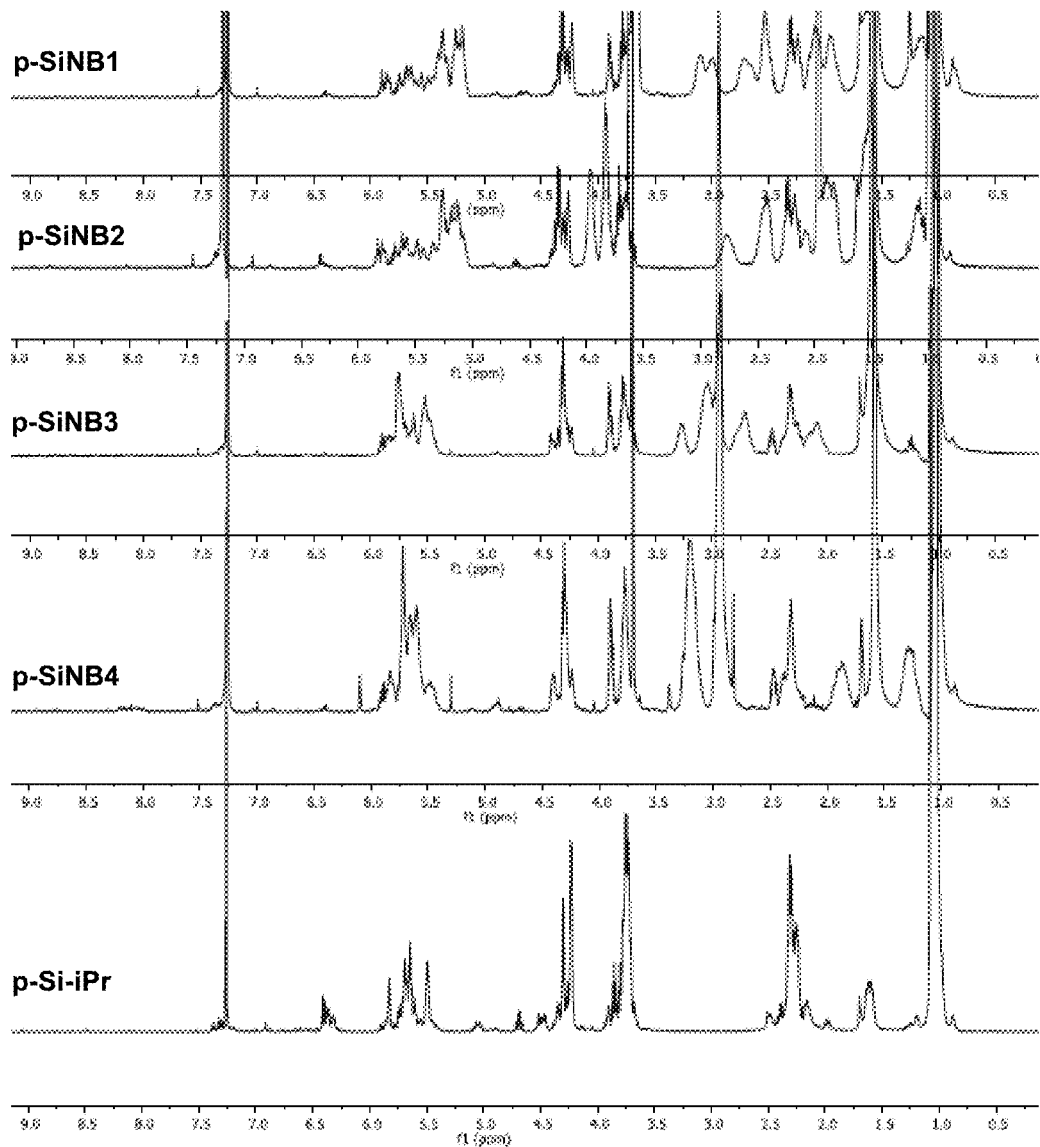
FIG. 13 shows the $^1$H NMR spectra in CDCl$_3$ of copolymers p-SiNB1, p-SiNB2, p-SiNB3, and p-SiNB4, and of homopolymer Si-iPr (p-Si-iPr) after 1 hour of polymerization time where the ratio of monomers used for each copolymer was 1:1 and each polymer had a DP of 50.
Figure 14:
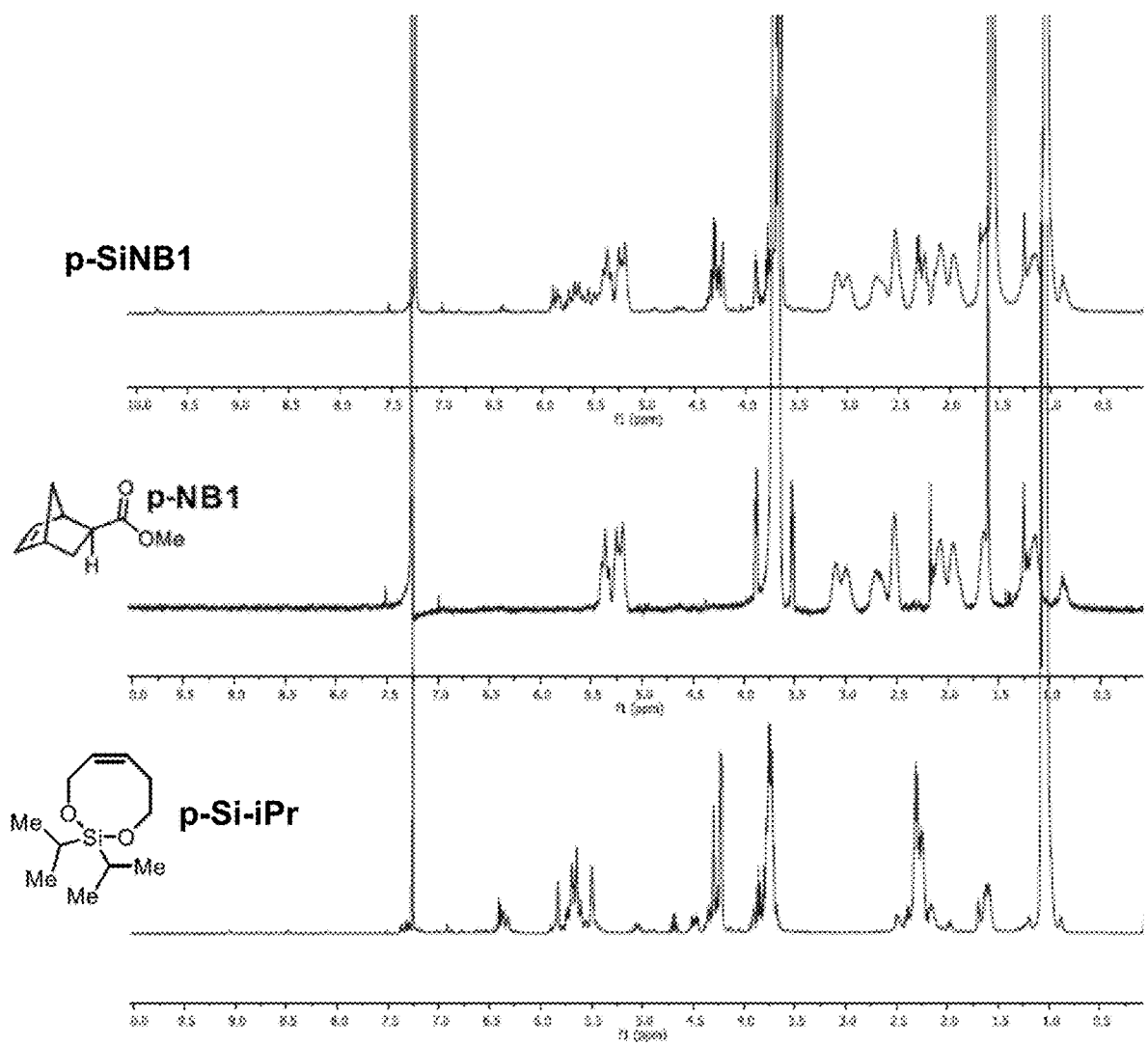
FIG. 14 shows the $^1$H NMR spectra in CDCl$_3$ of p-SiNB1 copolymer compared to homopolymers p-NB1 and p-Si-iPr after 1 hour of polymerization time where the ratio of monomers used for each copolymer was 1:1 and each polymer had a DP of 50.
Figure 15:
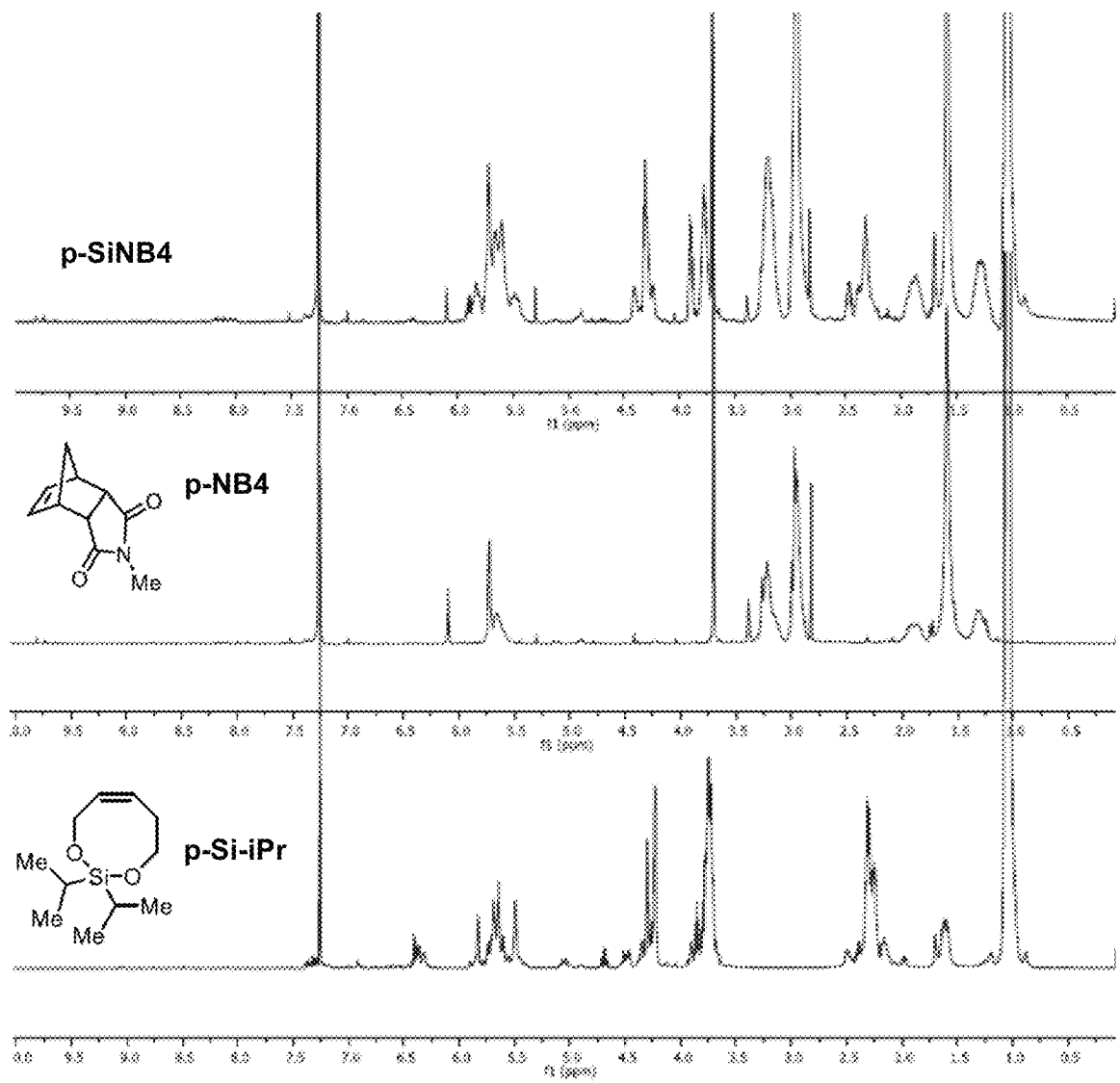
FIG. 15 shows the $^1$H NMR spectra in CDCl$_3$ of p-SiNB4 copolymer compared to homopolymers p-NB4 and p-Si-iPr after 1 hour of polymerization time where the ratio of monomers used for each copolymer was 1:1 and each polymer had a DP of 50.
Figure 16:
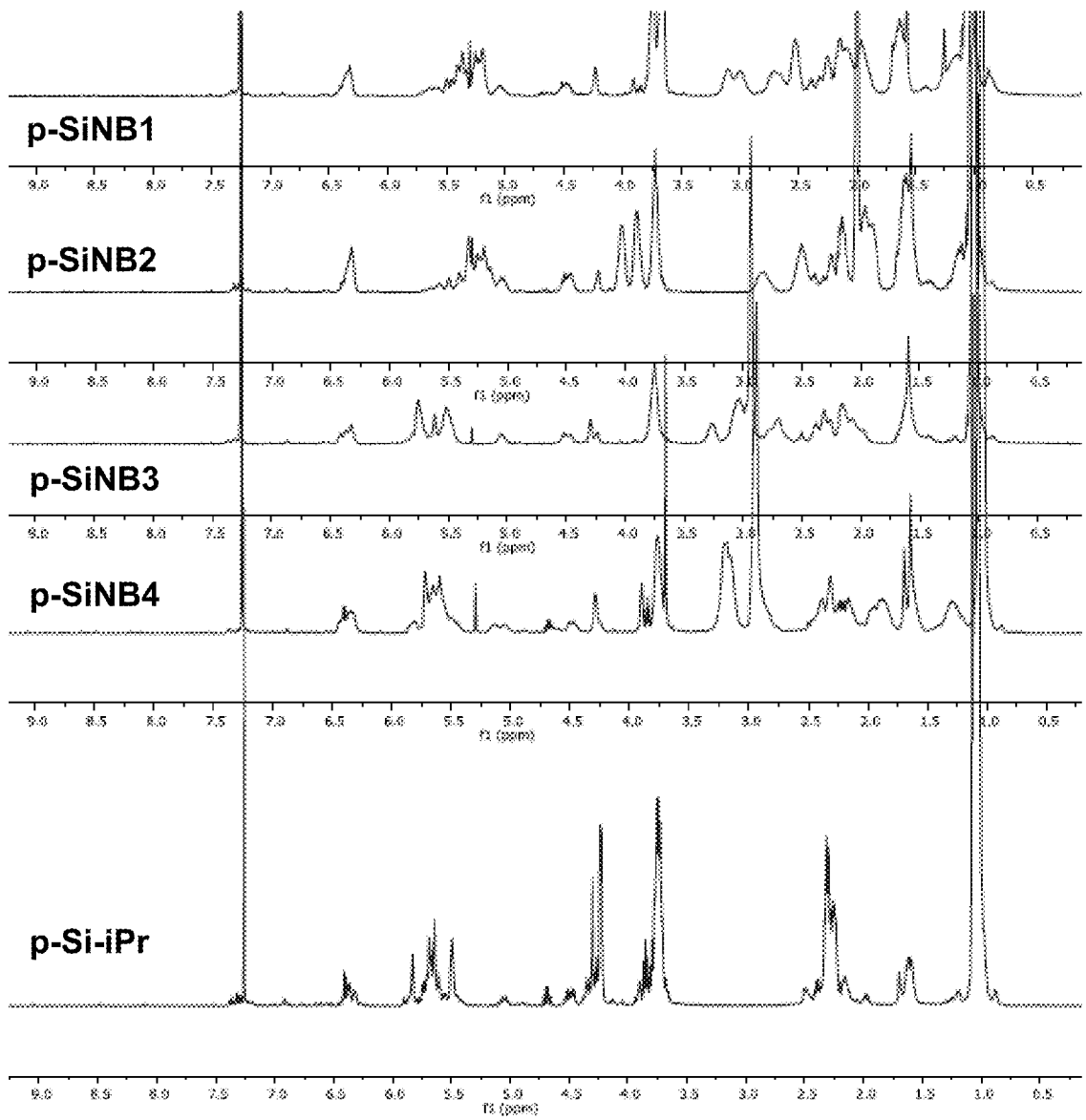
FIG. 16 shows the $^1$H NMR spectra in CDCl$_3$ of copolymers p-SiNB1, p-SiNB2, p-SiNB3, and p-SiNB4, and of homopolymer p-Si-iPr after 24 hours of polymerization time where the ratio of monomers used for each copolymer was 1:1 and each polymer had a DP of 50.
Figure 17A:
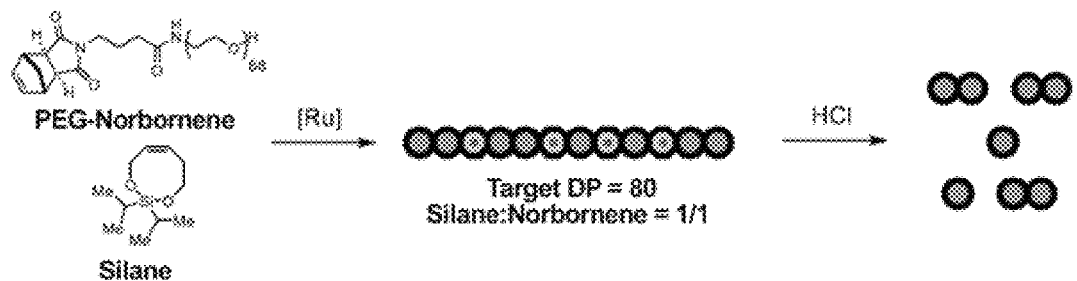
FIG. 17A shows an illustration of formation of a brush polymer and subsequent degradation after treatment with HCl. The resulting brush polymer included moieties derived from PEG-norbornene (circles), and Si(iPr)$_2$ moieties (octagons) in a 1:1 ratio, with a target degree of polymerization of 80. After treatment with HCl, some or all of the Si—O bonds were cleaved.
Figure 17B:
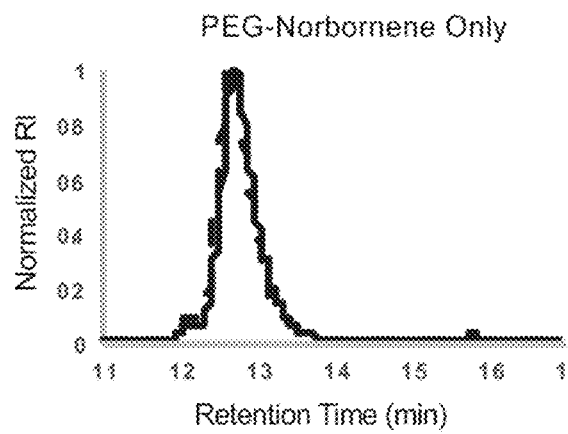
FIG. 17B shows a resulting chromatogram from GPC of a PEG-norbornene homopolymer with and without treatment of HCl (where each polymer had a DP of 30 before further treatment). Unless otherwise provided, PEG-norbornene recited in the figures is as shown in FIG. 17A.
Figure 17C:
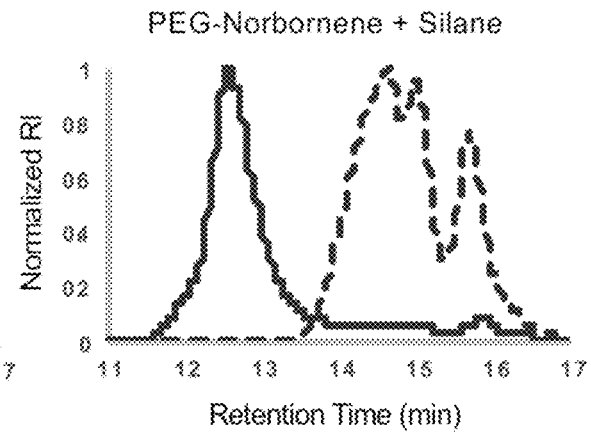
FIG. 17C shows a resulting chromatogram from GPC of a PEG-norbornene and Si-iPr copolymer with and without treatment of HCl (where each polymer had a DP of 30 before further treatment and ratio of monomers used was 1:1).
Figure 17D:
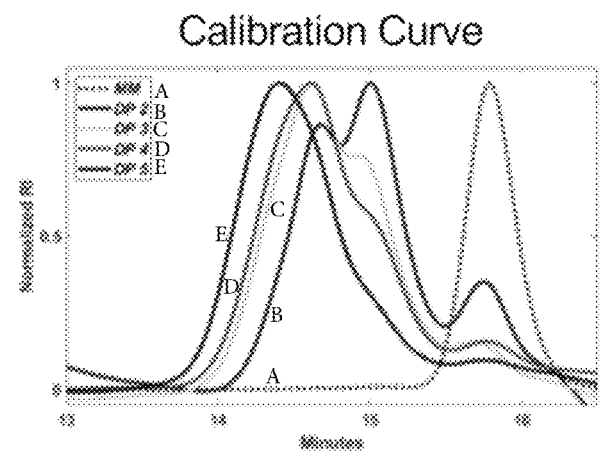
FIG. 17D shows an exemplary GPC calibration curve using a PEG-norbornene monomer (MM or macromonomer) and homopolymers of PEG-norbornene of different degrees of polymerization.
Figure 17E:
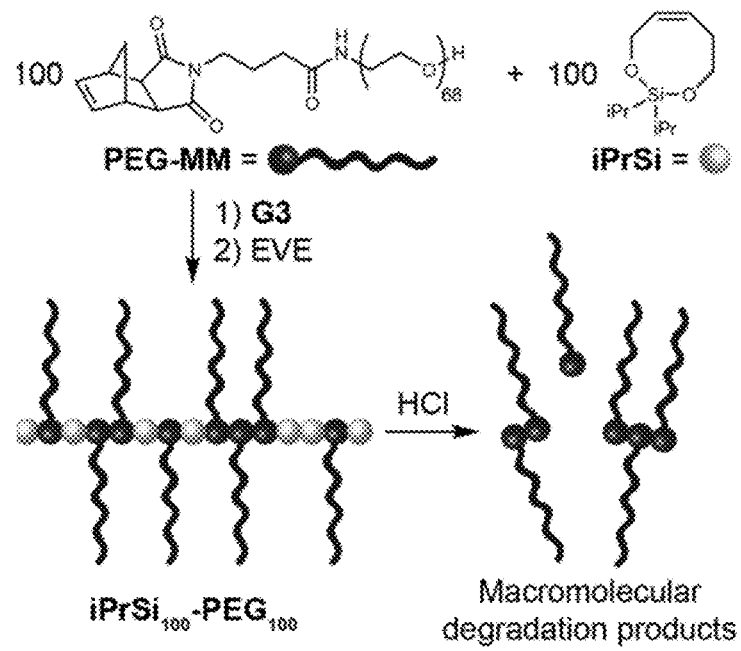
FIG. 17E shows the synthetic scheme for the synthesis of backbone-degradable PEG-based bottlebrush polymer (iPrSi$_{100}$-PEG$_{100}$) derived from copolymerization of a norbornene-terminated polyethylene glycol macromonomer (PEG-MM) with an eight-membered cyclic silyl ether monomer (iPrSi, 1:1 molar ratio of monomers). Acidic degradation cleaves the polynorbornene backbone leading to the production of oligomeric PEG-based fragments.
Figure 17F:
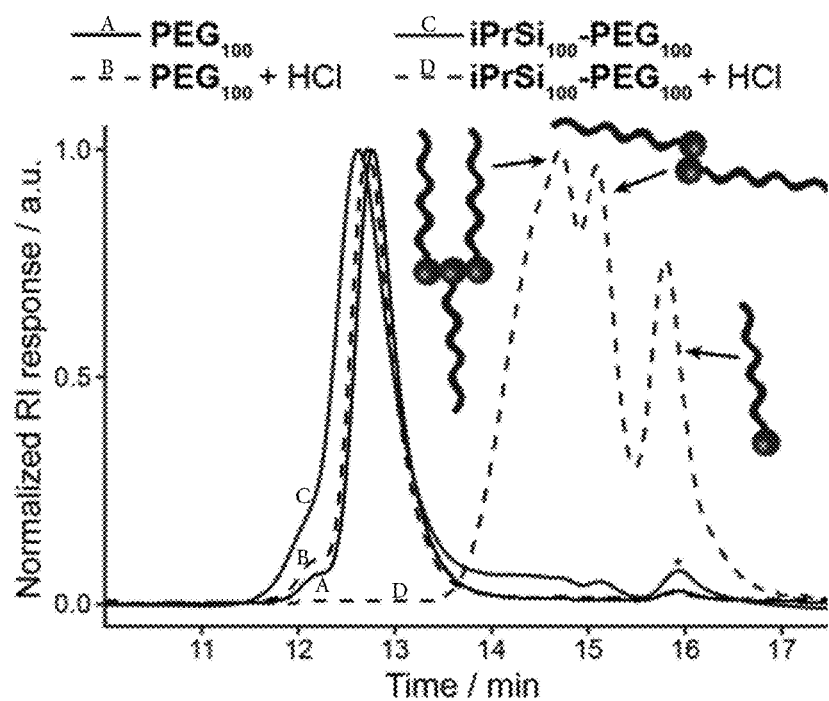
FIG. 17F shows GPC traces before and after forced hydrolysis of iPrSi$_{100}$-PEG$_{100}$ and a traditional PEG bottlebrush homopolymer (PEG$_{100}$) demonstrating that only the copolymer undergoes degradation. *indicates residual PEG-MM from the ROMP reaction.
Figure 18A:
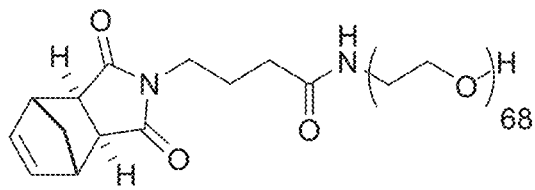
FIG. 18A shows the formula of compound Exo.
Figure 18B:
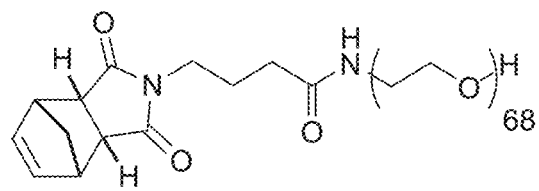
FIG. 18B shows the formula of compound Endo.
Figure 18C:
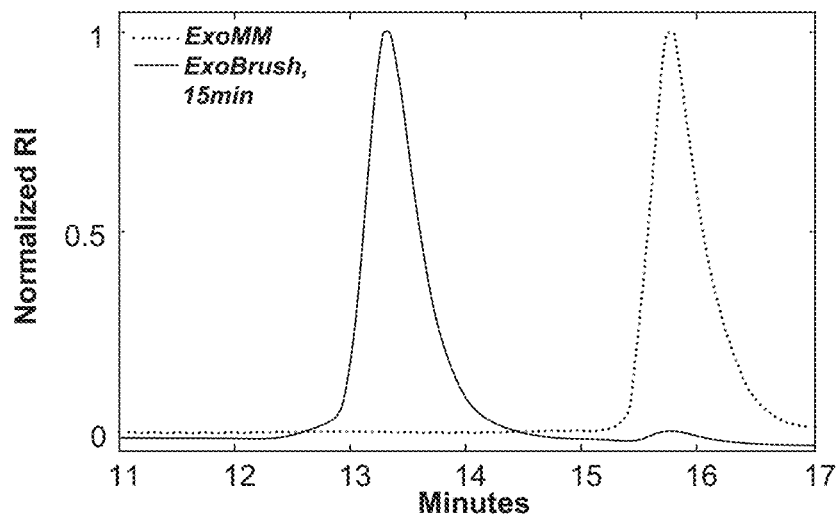
FIG. 18C shows a resulting chromatogram from GPC of compound Exo and corresponding homopolymer (ExoBrush) at 15 minutes of polymerization time where the DP was 30.
Figure 18D:
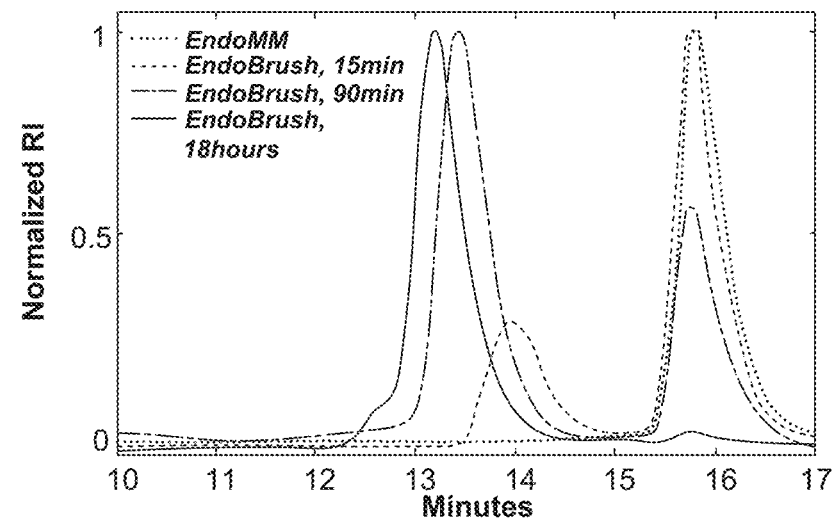
FIG. 18D shows a resulting chromatogram from GPC of compound Endo and corresponding homopolymer (EndoBrush) at varying polymerization times where the DP was 30.
Figure 19A:
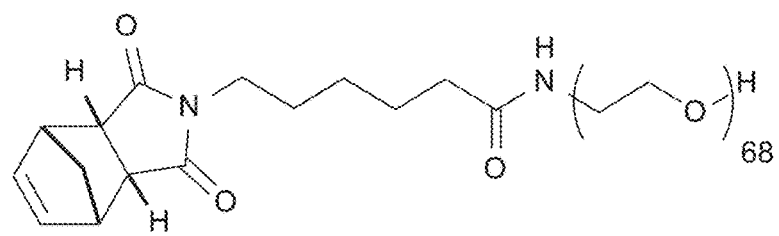
FIG. 19A shows the formula of compound 6 Endo.
Figure 19B:
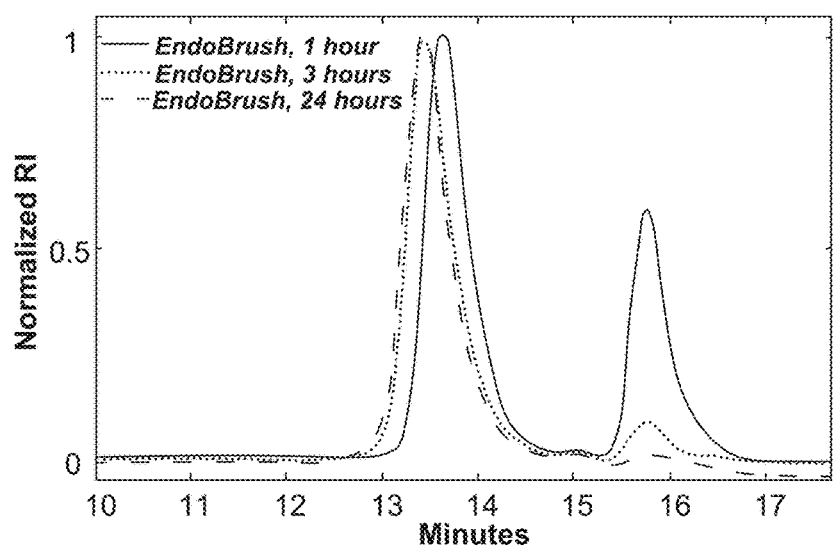
FIG. 19B shows a resulting chromatogram from GPC of the homopolymer of Endo (EndoBrush) after 1, 3, and 24 hours of polymerization time where the DP was 30.
Figure 19C:
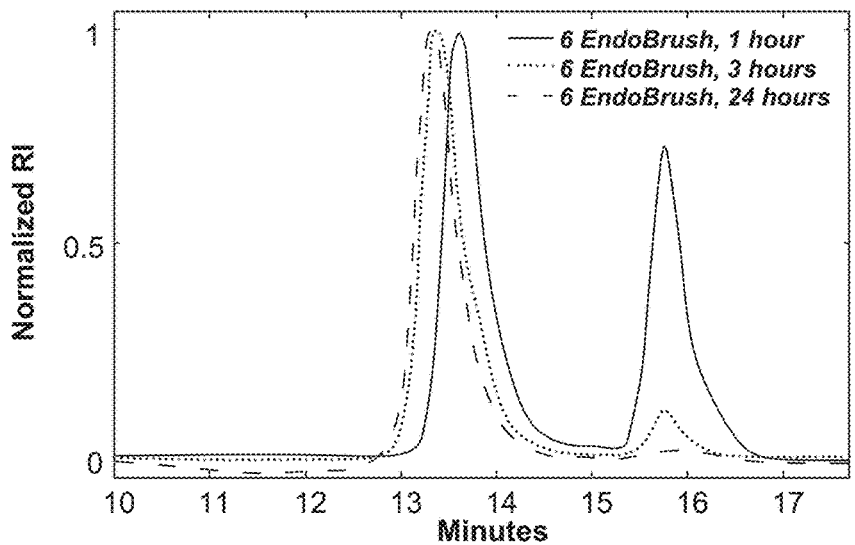
FIG. 19C shows a resulting chromatogram from GPC of the homopolymer of 6 Endo (6 EndoBrush) after 1, 3, and 24 hours of polymerization time where the DP was 30.
Figure 20:
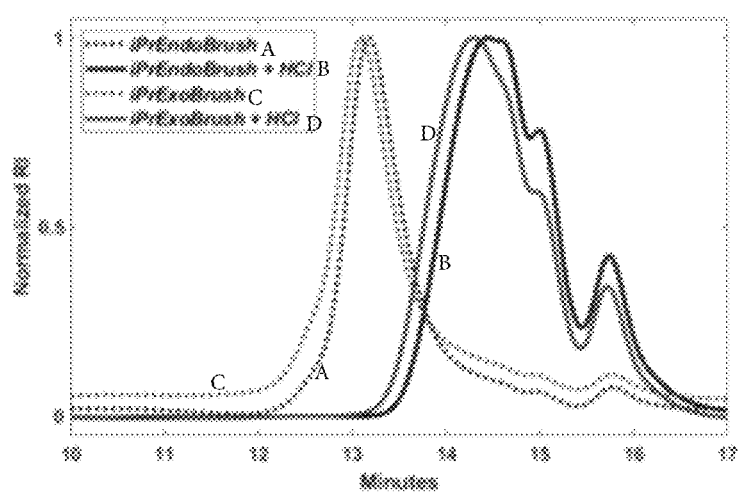
FIG. 20 shows a resulting chromatogram from GPC of (Exo)-(Si-iPr) copolymer (iPrExoBrush) or (Endo)-(Si-iPr) copolymer (iPrEndoBrush) with and without treatment with HCl (where each polymer had a DP of 30 before further treatment and ratio of monomers used was 1:1). GPC trace of BASP after aggregation, as observed by DLS, shows the presence of large quantities of residual crosslinked polymer. These results support the possible outcome that the BASP cores remain crosslinked over the course of these experiments, degrading via an 'outside-in' mechanism as the PEG fragments are shed the hydrophobic core of the particle is revealed, which eventually leads to aggregation as observed by DLS. This type of degradation mechanism stands in contrast to previous observations on the degradation of the non-silyl ether BASPs with degradable cores, which undergo 'inside-out' degradation upon cleavage of the crosslinker to its component bottlebrushes.
Figure 21A:
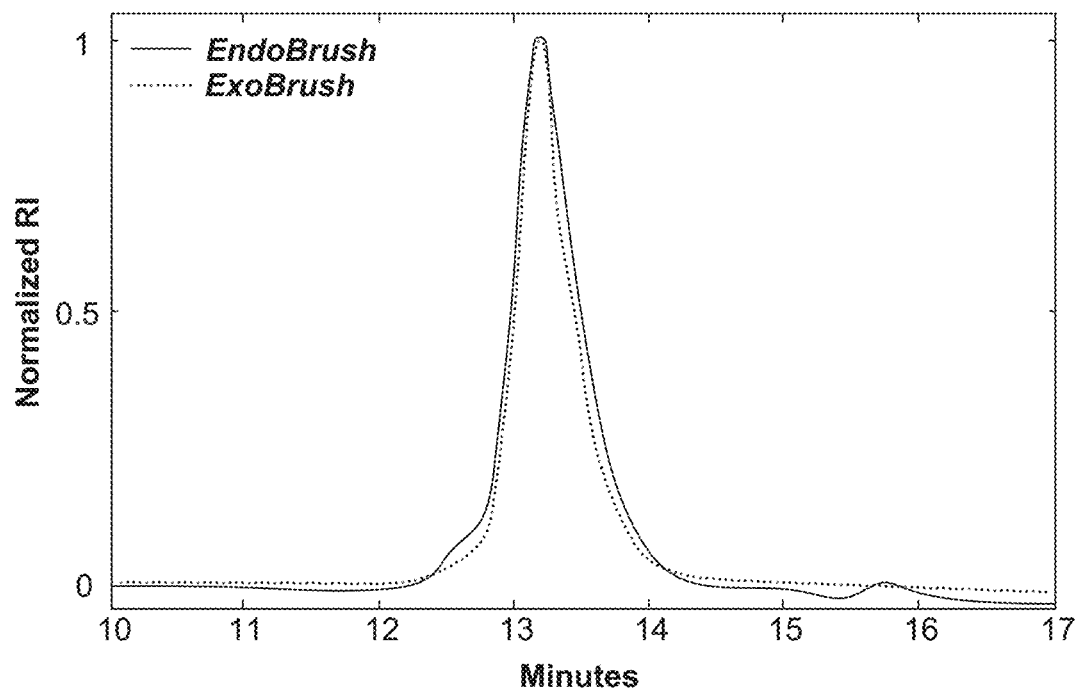
FIG. 21A shows a resulting chromatogram from GPC of homopolymers ExoBrush and EndoBrush where each polymer had a DP of 30.
Figure 21B:
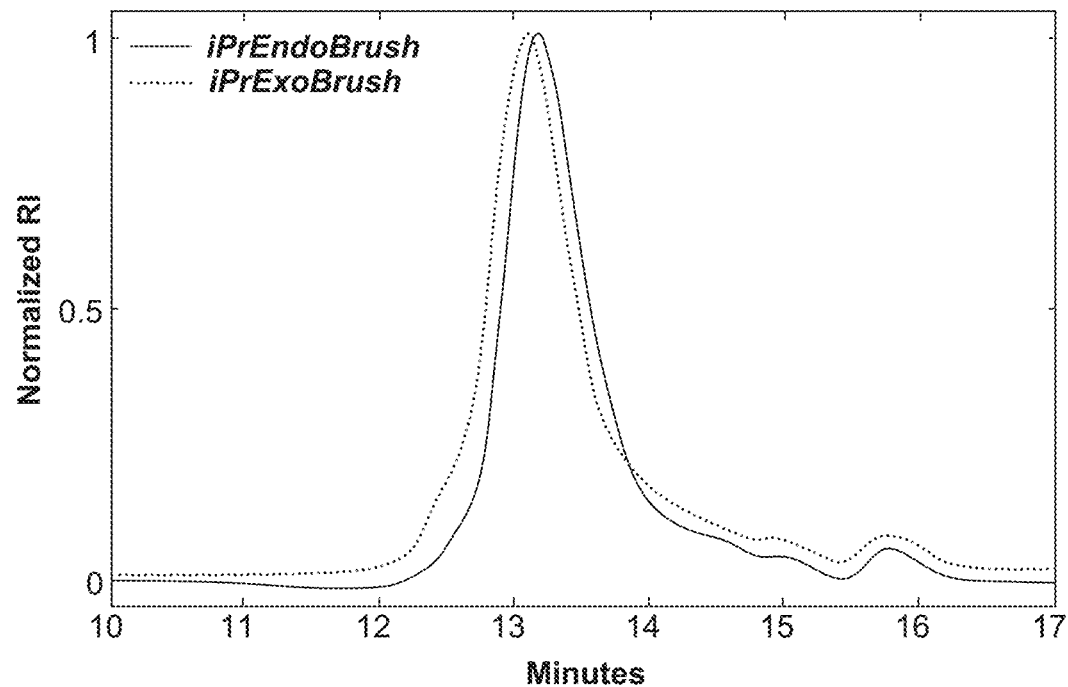
FIG. 21B shows a resulting chromatogram from GPC of copolymers iPrExoBrush and iPrEndoBrush where each polymer had a DP of 30 and ratio of monomers used was 1:1.
Figure 21C:
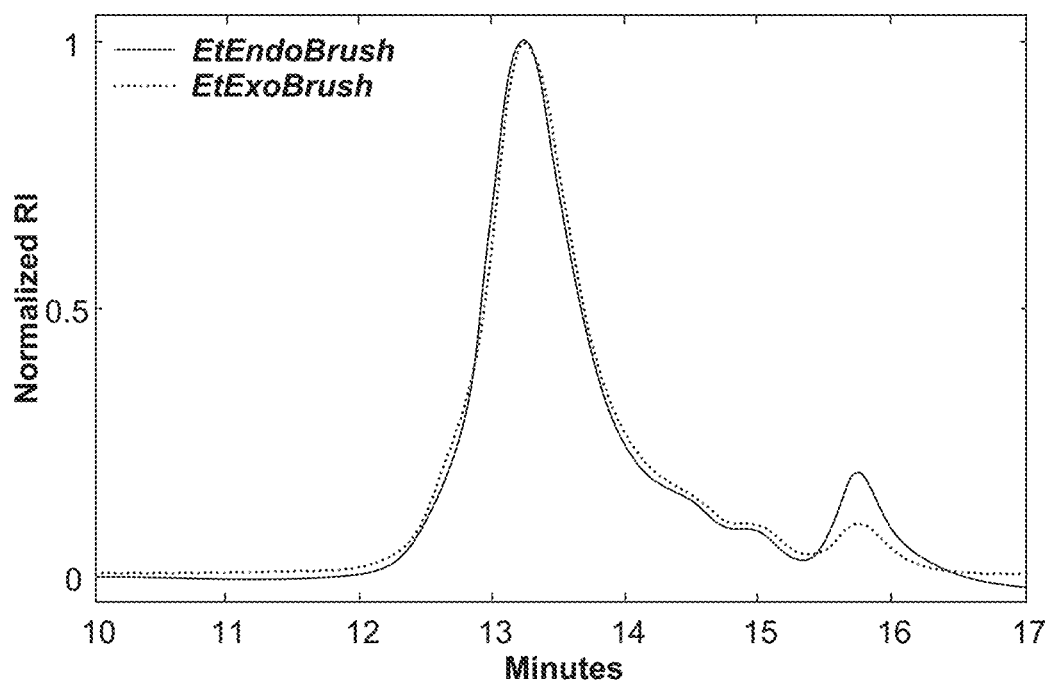
FIG. 21C shows a resulting chromatogram from GPC of (Exo)-(Si-Et) copolymer (EtExoBrush) or (Endo)-(Si-Et) copolymer (EtEndoBrush) where each polymer had a DP of 30 and ratio of monomers used was 1:1.
Figure 21D:
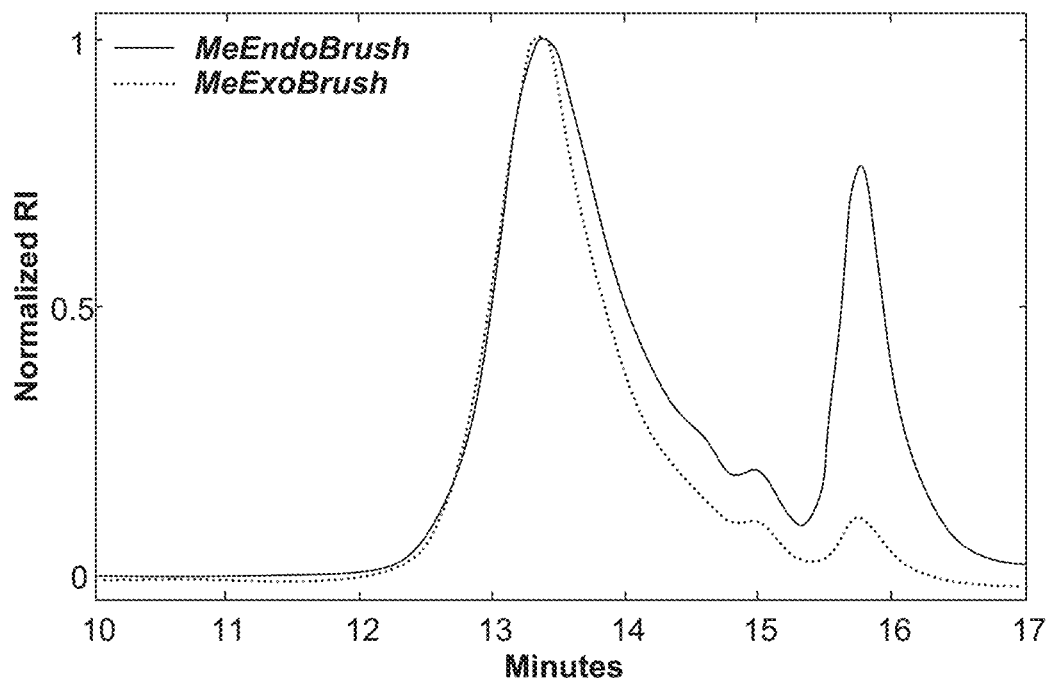
FIG. 21D shows a resulting chromatogram from GPC of (Exo)-(Si-Me) copolymer (MeExoBrush) or (Endo)-(Si-Me) copolymer (MeEndoBrush) where each polymer had a DP of 30 and ratio of monomers used was 1:1.
Figure 22A:
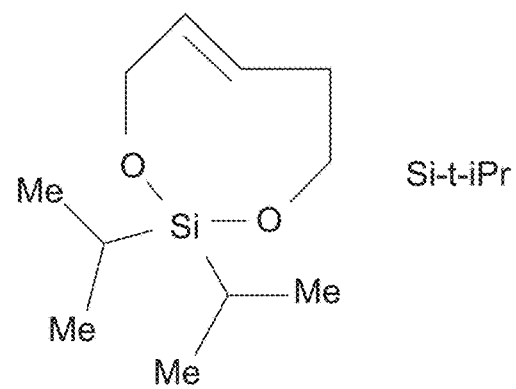
FIG. 22A shows the formula of compound Si-t-iPr.
Figure 22B:
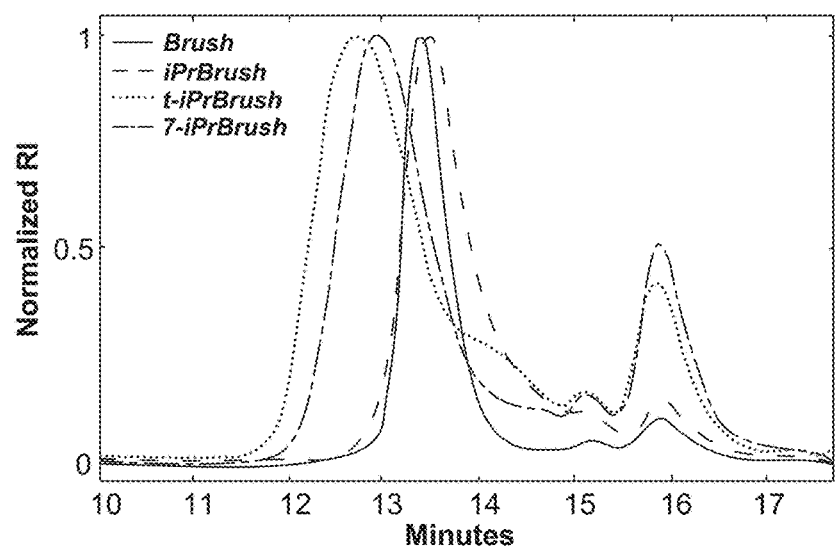
FIG. 22B shows a resulting chromatogram from GPC of the brush polymers where each polymer had a DP of 30 and ratio of monomers used was 1:1:PEG-norbornene homopolymer (Brush), (PEG-norbornene)-(Si-iPr) copolymer (iPrBrush), (PEG-norbornene)-(Si-t-iPr) copolymer (t-iPrBrush), and (PEG-norbornene)-(Si-7-iPr) copolymer (7-iPrBrush).
Figure 22C:
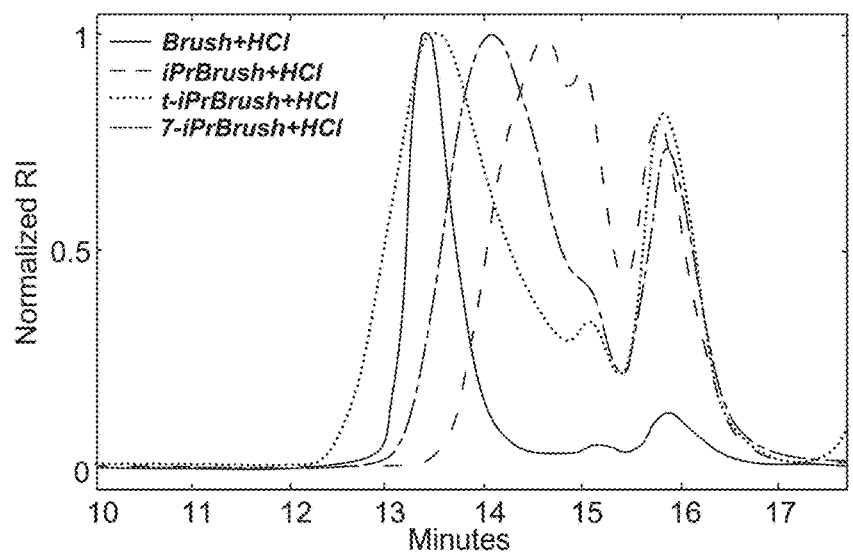
FIG. 22C shows a resulting chromatogram from GPC of the brush polymers where each polymer had a DP of 30 and ratio of monomers used was 1:1:Brush, iPrBrush, t-iPrBrush, and 7-iPrBrush after treatment with HCl.
Figure 23A:
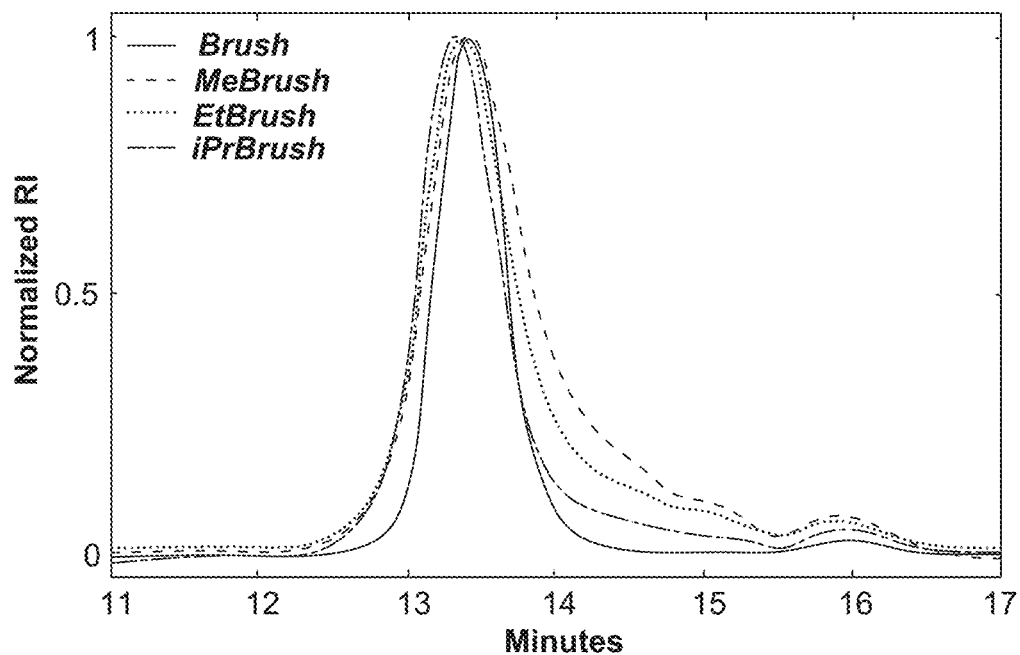
FIG. 23A shows a resulting chromatogram from GPC of the brush polymers where each polymer had a DP of 30 and ratio of monomers used was 1:1:Brush, (PEG-norbornene)-(Si-Me) copolymer (MeBrush), (PEG-norbornene)-(Si-Et) copolymer (EtBrush), and (PEG-norbornene)-(Si-iPr) copolymer (iPrBrush).
Figure 23B:
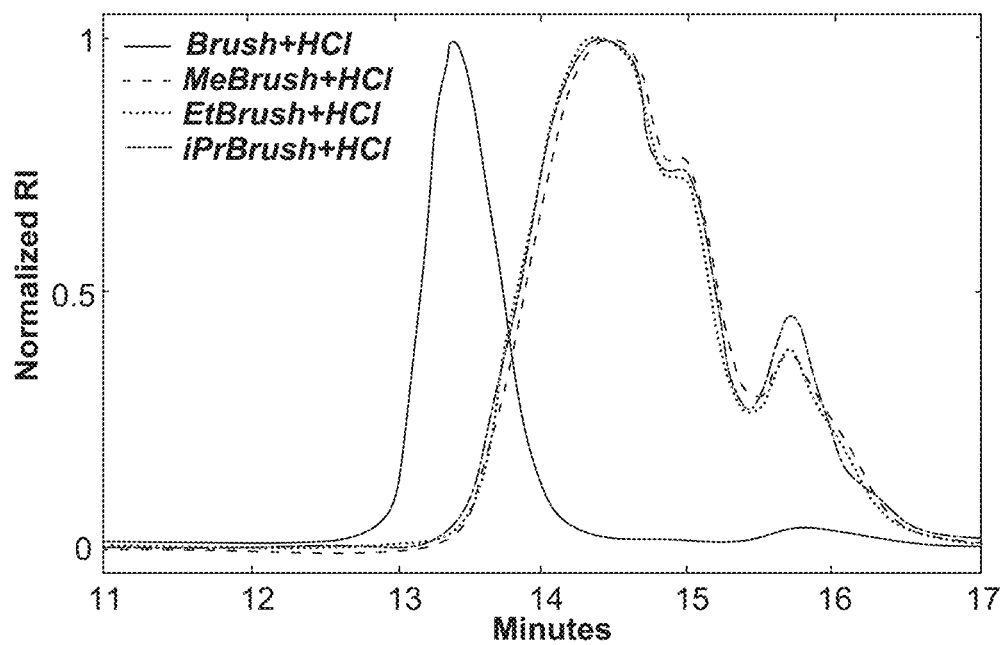
FIG. 23B shows a resulting chromatogram from GPC of exemplary brush polymers (Brush, MeBrush, EtBrush, and iPrBrush) after treatment with HCl (where each polymer had a DP of 30 before further treatment and ratio of monomers used was 1:1).
Figure 24A:
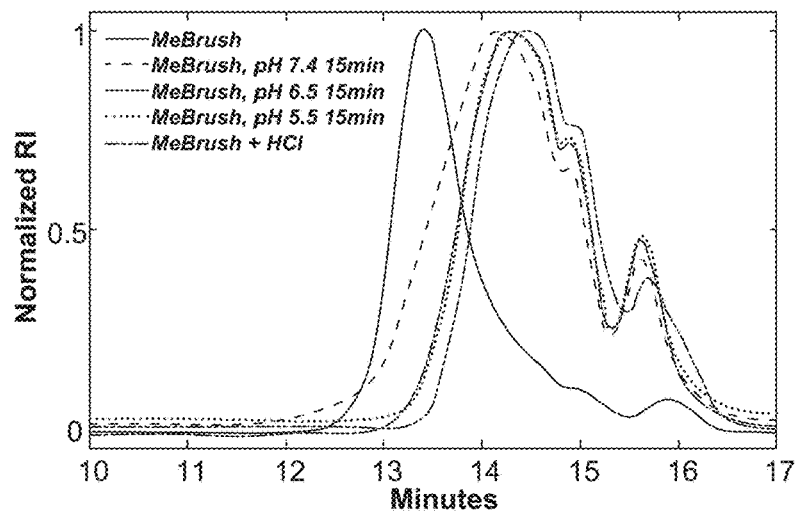
FIG. 24A shows a resulting chromatogram from GPC of brush polymer MeBrush after 15 minutes of degradation time at various pH values, or after treatment with HCl (where each polymer had a DP of 30 before further treatment and ratio of monomers used was 1:1).
Figure 24B:
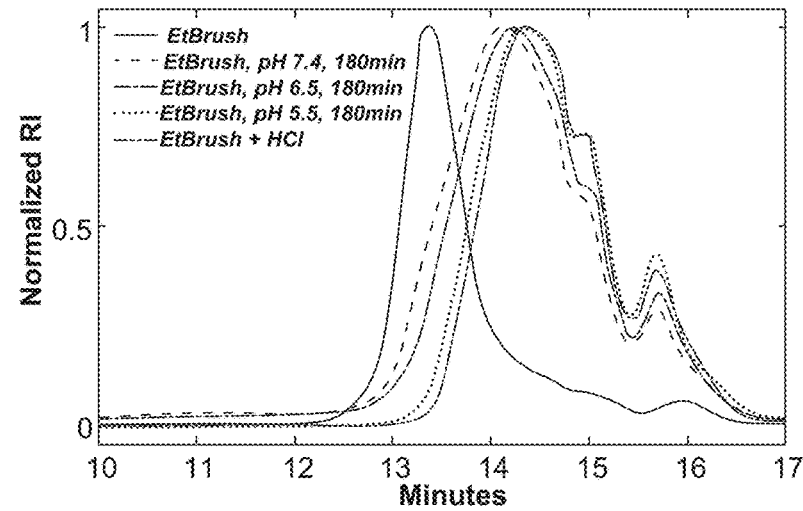
FIG. 24B shows a resulting chromatogram from GPC of brush polymer EtBrush after 180 minutes of degradation time at various pH values, or after treatment with HCl (where each polymer had a DP of 30 before further treatment and ratio of monomers used was 1:1).
Figure 24C:
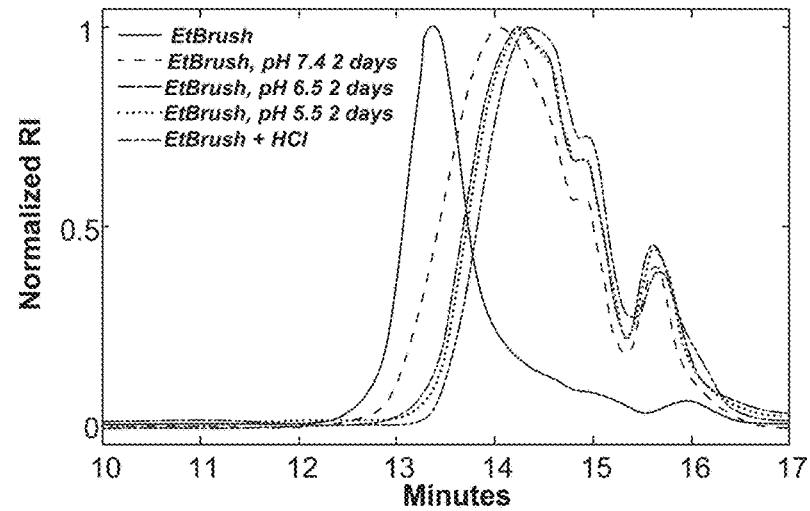
FIG. 24C shows a resulting chromatogram from GPC of brush polymer EtBrush after 2 days of degradation time at various pH values, or after treatment with HCl (where each polymer had a DP of 30 before further treatment and ratio of monomers used was 1:1).
Figure 25A:
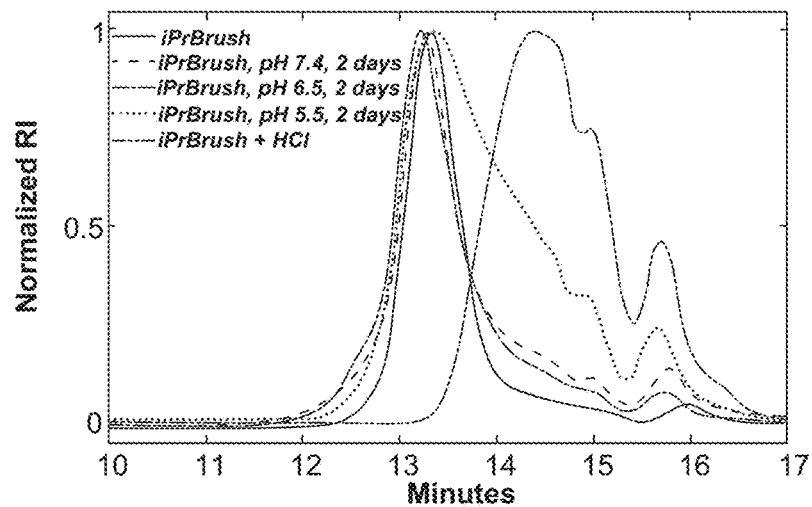
FIG. 25A shows a resulting chromatogram from GPC of brush polymer iPrBrush after 2 days of degradation time at various pH values, or after treatment with HCl (where each polymer had a DP of 30 before further treatment and ratio of monomers used was 1:1).
Figure 25B:
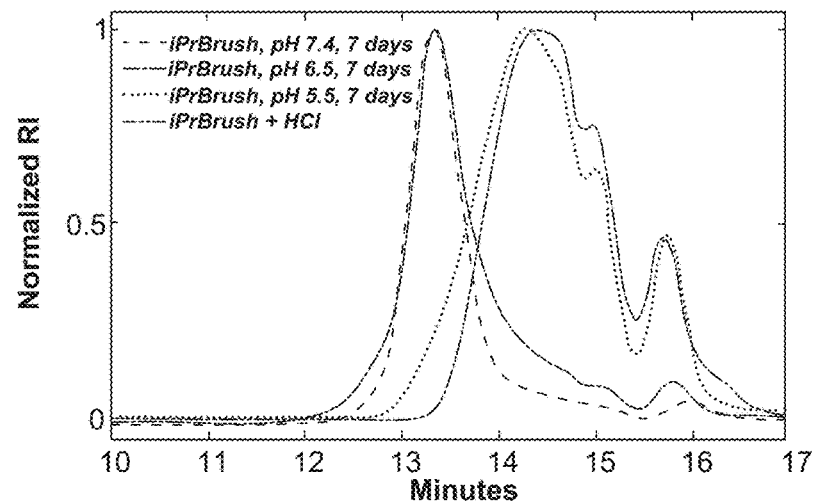
FIG. 25B shows a resulting chromatogram from GPC of brush polymer iPrBrush after 7 days of degradation time at various pH values, or after treatment with HCl (where each polymer had a DP of 30 before further treatment and ratio of monomers used was 1:1).
Figure 25C:
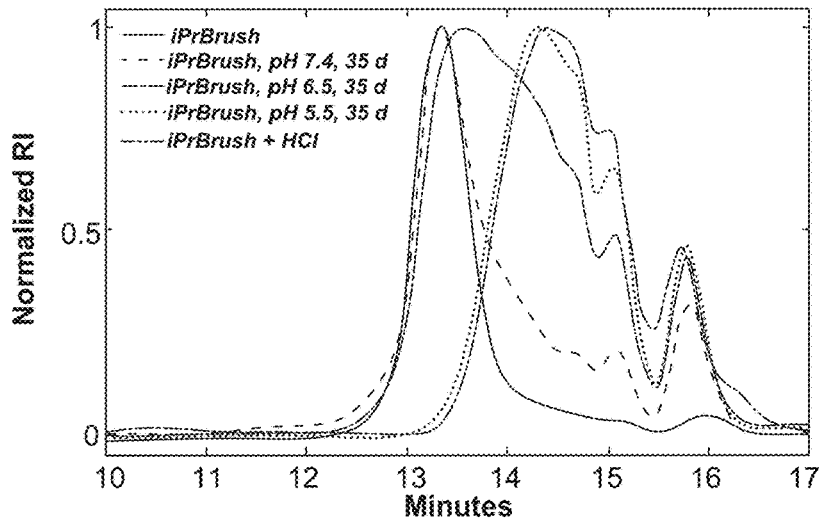
FIG. 25C shows a resulting chromatogram from GPC of brush polymer iPrBrush after 35 days of degradation time at various pH values, or after treatment with HCl.
Figure 26A:
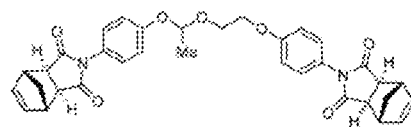
FIG. 26A shows the formula of crosslinker acetal XL, where XL means crosslinker.
Figure 26B:
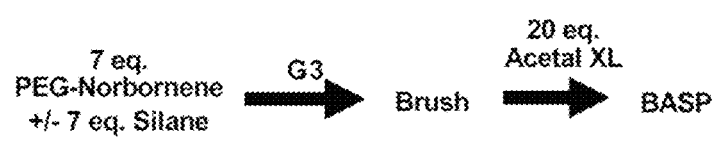
FIG. 26B shows a synthesis of a BASP using PEG-norbornene. First, a brush polymer was formed by ROMP of PEG-norbornene and a cyclic silyl ether ("Silane") using a 1:1 ratio of monomers. The brush polymers were then crosslinked via reactions with acteal XL (20 equivalents to 7 equivalents of brush) to generate the BASP.
Figure 26C:
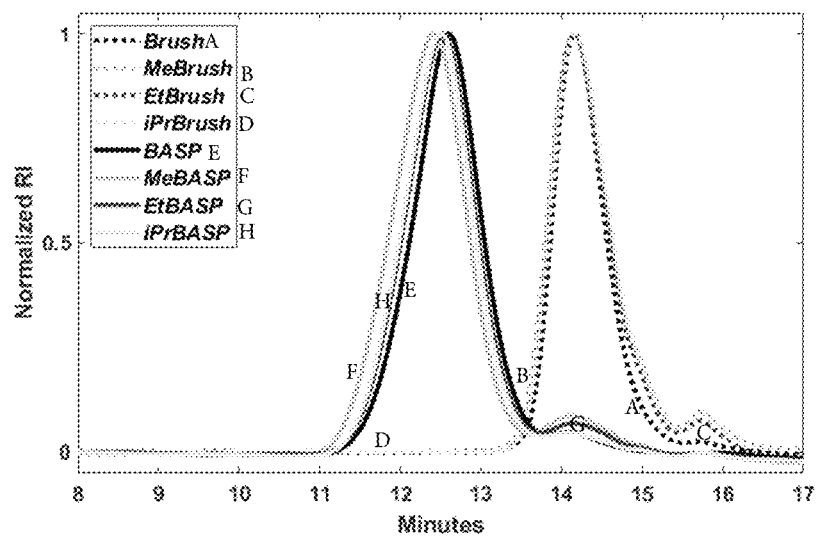
FIG. 26C shows a resulting chromatogram from GPC of various brush polymers and the corresponding BASPs generated via reaction with crosslinker acteal XL (where brush polymer Brush was used to generate BASP, brush polymer MeBrush was used to generate MeBASP, brush polymer EtBrush was used to generate EtBASP, and brush polymer iPrBrush was used to generate iPrBASP).
Figure 26D:
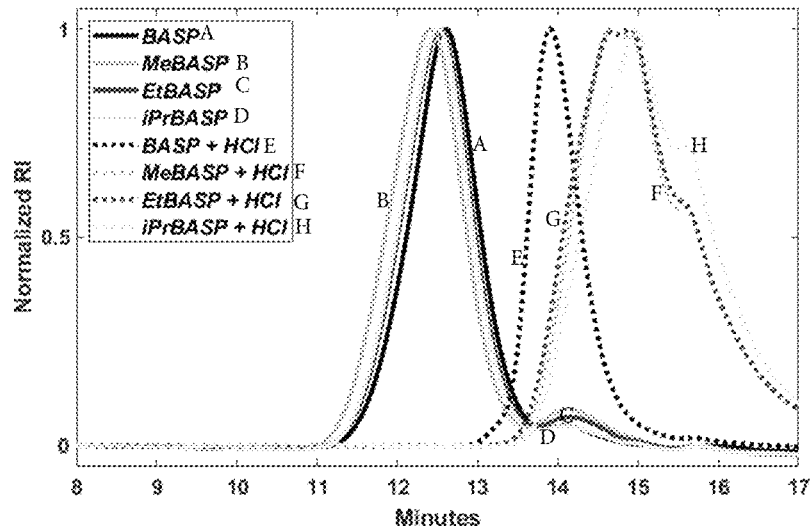
FIG. 26D shows a resulting chromatogram from GPC of BASPs: BASP, MeBASP, Et BASP, and iPrBASP with and without treatment with HCl (where the ratio of brush to crosslinker used was 7:20).
Figure 27A:
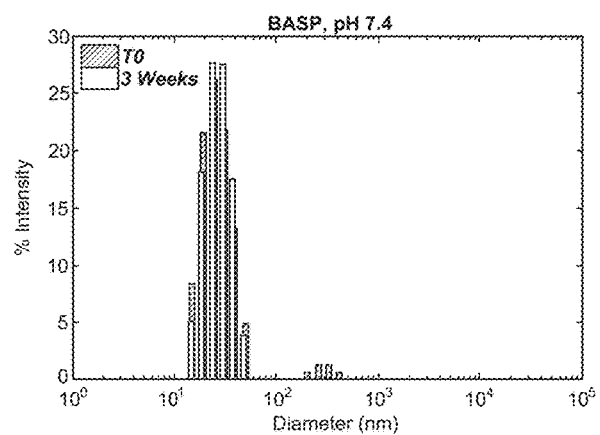
FIG. 27A shows a graph of intensity versus diameter from dynamic light scattering (DLS) at pH 7.4 of BASP at time 0 and after 3 weeks of degradation time (where the ratio of brush to crosslinker used was 7:20).
Figure 27B:
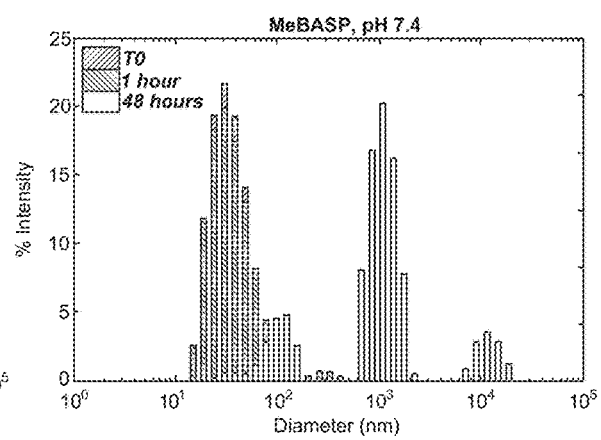
FIG. 27B shows a graph of intensity versus diameter from DSL at pH 7.4 of MeBASP at time 0, after 1 hour, and after 48 hours of degradation time (where the ratio of brush to crosslinker used was 7:20).
Figure 27C:
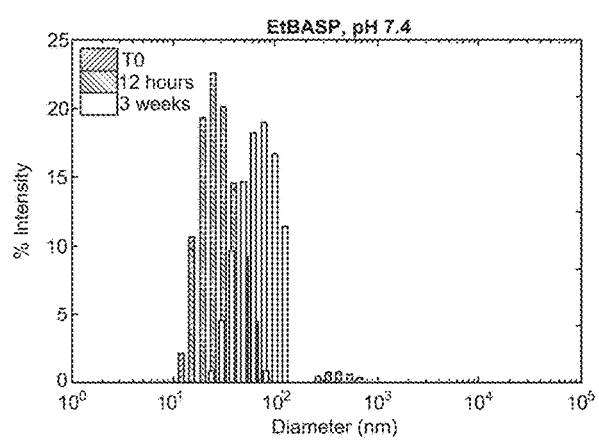
FIG. 27C shows a graph of intensity versus diameter from DSL at pH 7.4 of EtBASP at time 0, after 12 hours, and after 3 weeks of degradation time (where the ratio of brush to crosslinker used was 7:20).
Figure 27D:
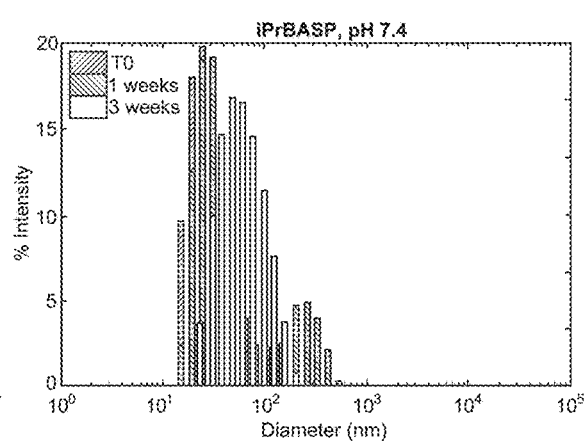
FIG. 27D shows a graph of intensity versus diameter from DSL at pH 7.4 of iPrBASP at time 0, after 1 week, and after 3 weeks of degradation time (where the ratio of brush to crosslinker used was 7:20).
Figures 28A, 28B:
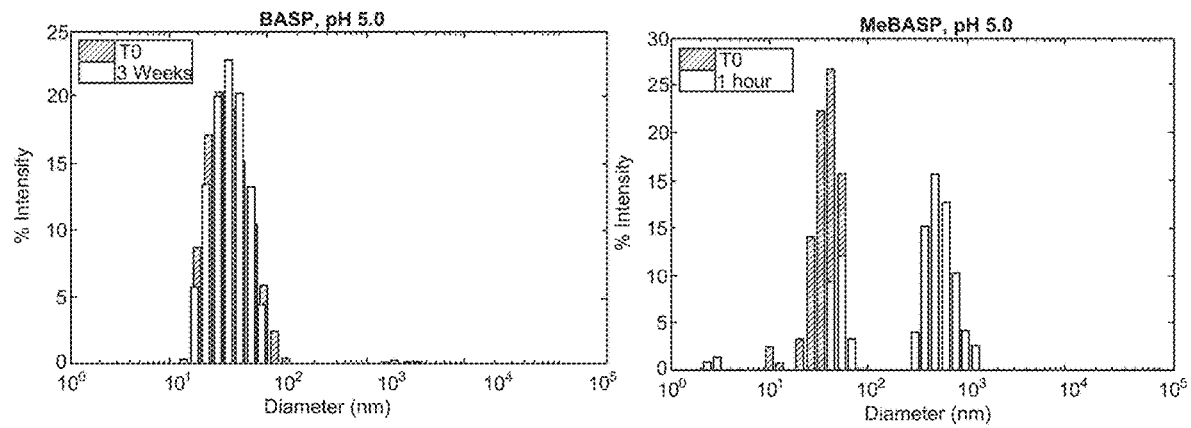
FIG. 28A shows a graph of intensity versus diameter from DSL at pH 5 of BASP at time 0 and after 3 weeks of degradation time (where the ratio of brush to crosslinker used was 7:20).
FIG. 28B shows a graph of intensity versus diameter from DSL at pH 5 of MeBASP at time 0 and after 1 hour of degradation time (where the ratio of brush to crosslinker used was 7:20).
Figures 28C, 28D:
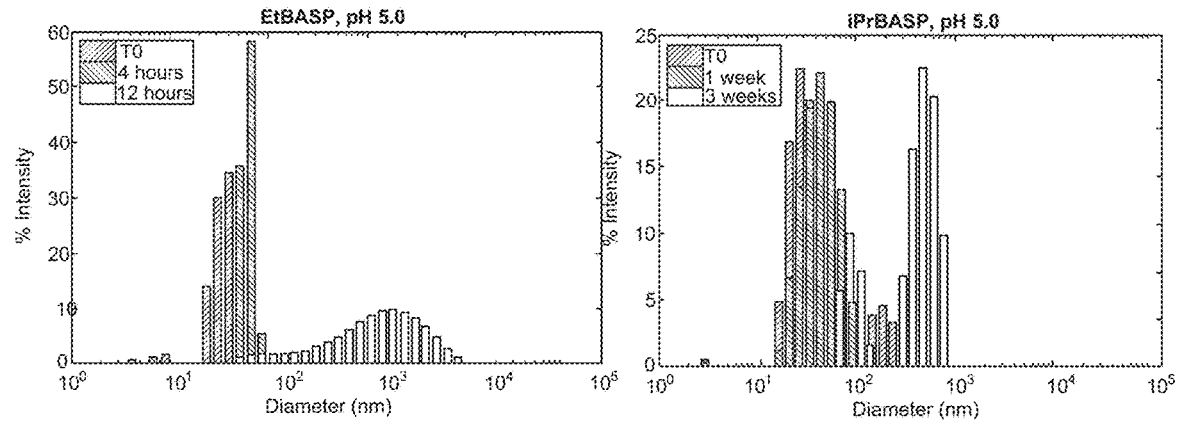
FIG. 28C shows a graph of intensity versus diameter from DSL at pH 5 of EtBASP at time 0, after 4 hours, and after 12 hours of degradation time (where the ratio of brush to crosslinker used was 7:20).
FIG. 28D shows a graph of intensity versus diameter from DSL at pH 5 of iPrBASP at time 0, after 1 week, and after 3 weeks of degradation time (where the ratio of brush to crosslinker used was 7:20).
Figure 29A:
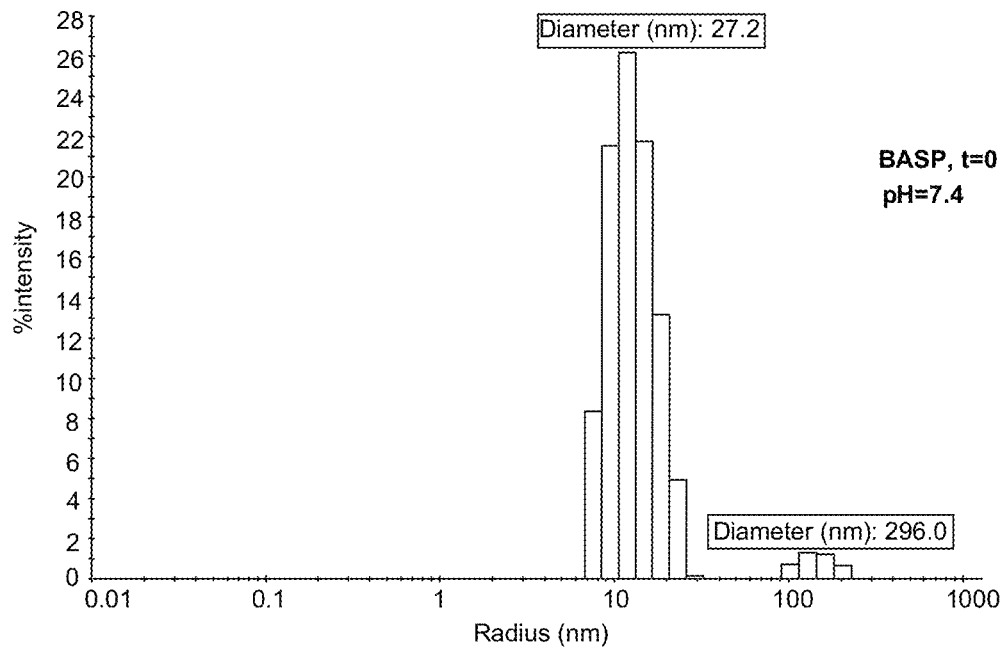
FIG. 29A shows a graph of intensity versus diameter from DSL at pH 7.4 of BASP after a degradation time of 0 (where the ratio of brush to crosslinker used was 7:20).
Figure 29B:
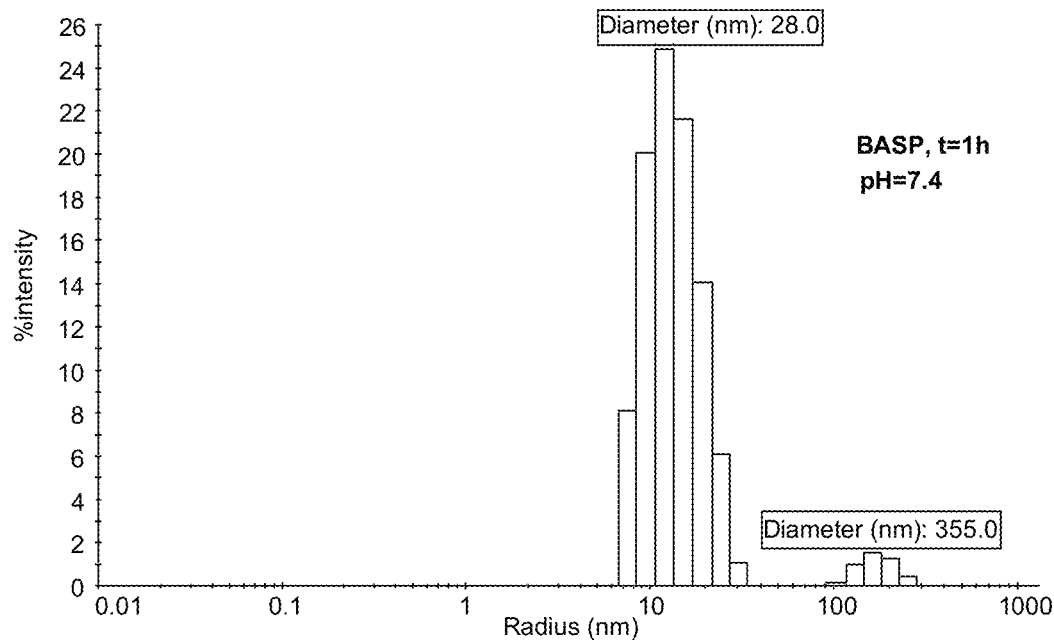
FIG. 29B shows a graph of intensity versus diameter from DSL at pH 7.4 of BASP after a degradation time of 1 hour (where the ratio of brush to crosslinker used was 7:20).
Figure 29C:
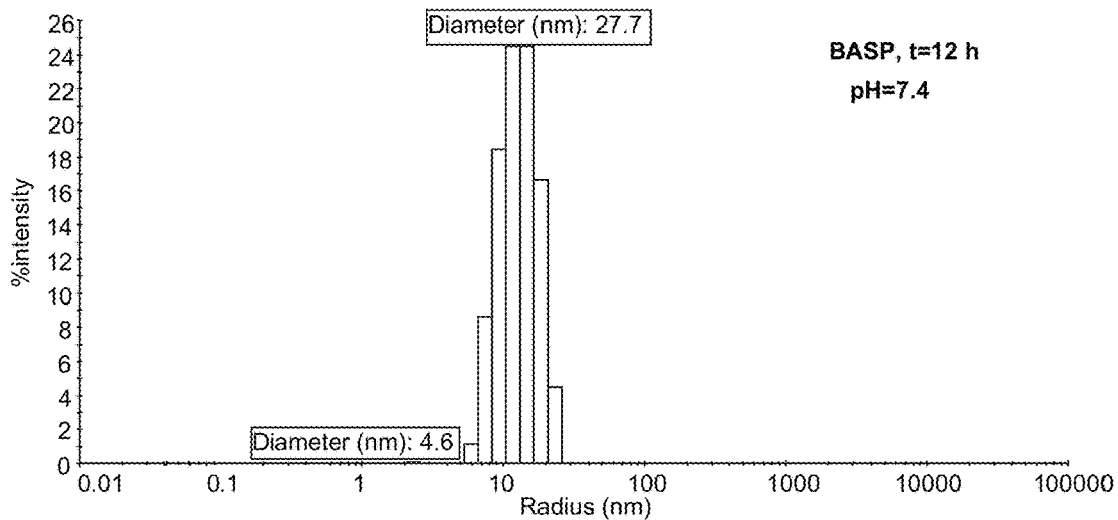
FIG. 29C shows a graph of intensity versus diameter from DSL at pH 7.4 of BASP after a degradation time of 12 hours (where the ratio of brush to crosslinker used was 7:20).
Figure 29D:
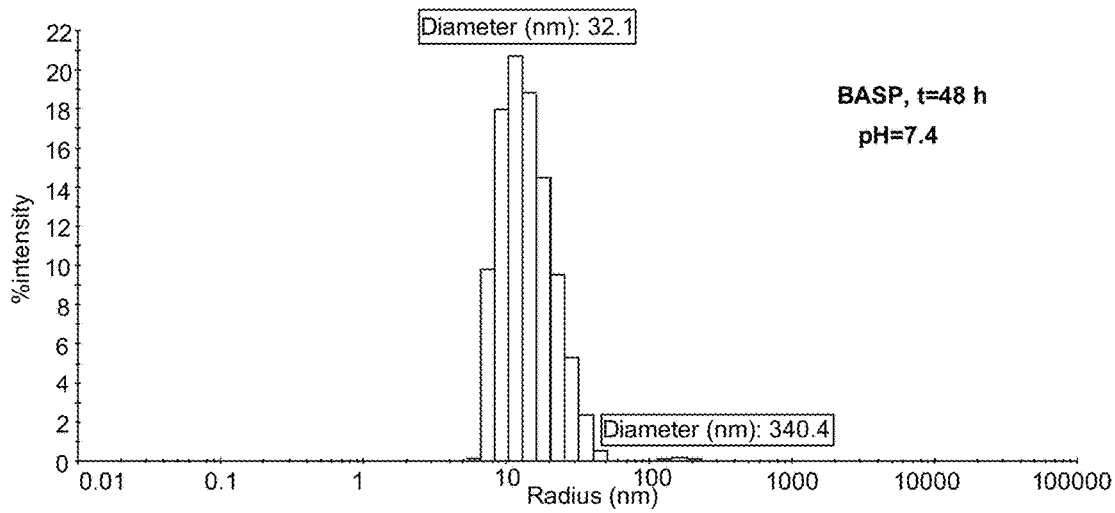
FIG. 29D shows a graph of intensity versus diameter from DSL at pH 7.4 of BASP after a degradation time of 48 hours (where the ratio of brush to crosslinker used was 7:20).
Figure 29E:
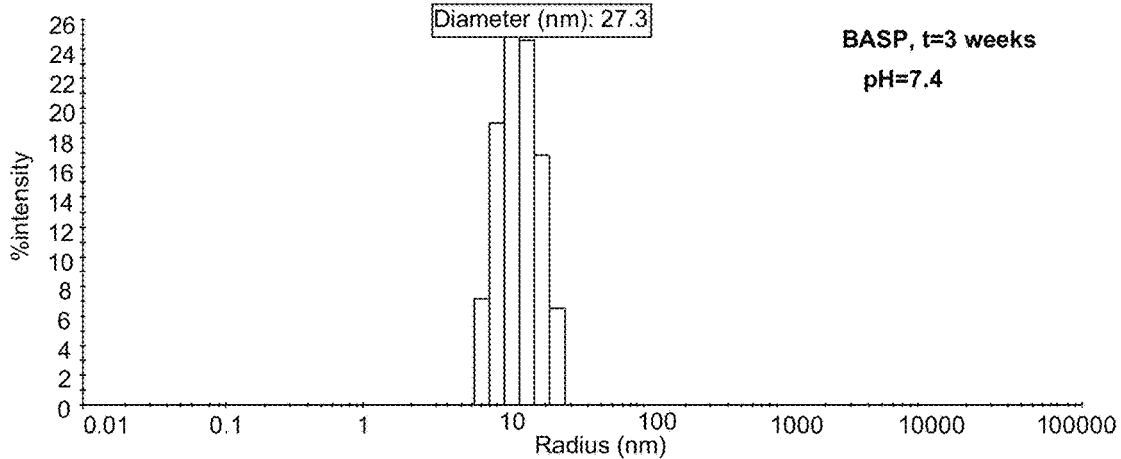
FIG. 29E shows a graph of intensity versus diameter from DSL at pH 7.4 of BASP after a degradation time of 3 weeks (where the ratio of brush to crosslinker used was 7:20).
Figure 30A:
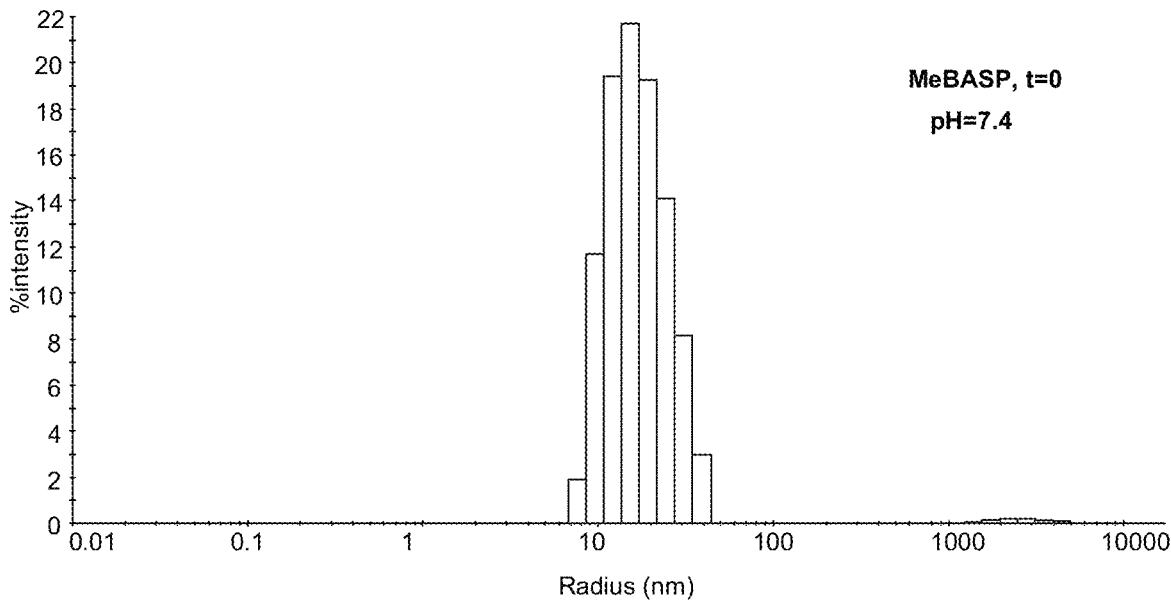
FIG. 30A shows a graph of intensity versus diameter from DSL at pH 7.4 of MeBASP after a degradation time of 0 (where the ratio of brush to crosslinker used was 7:20).
Figure 30B:
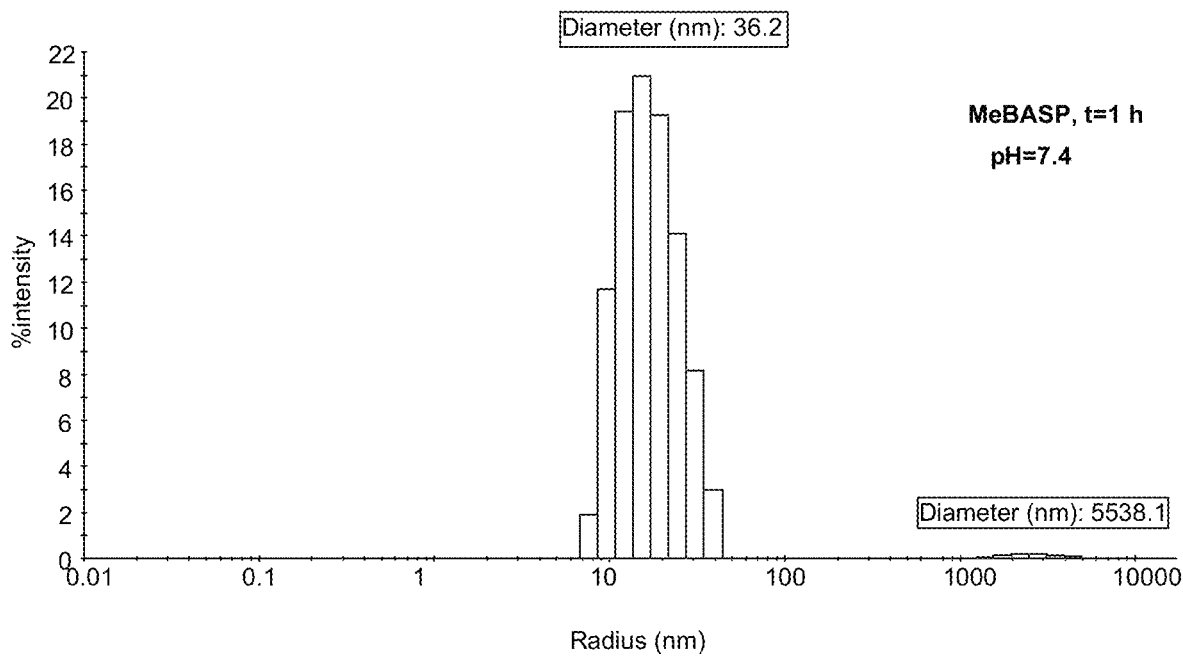
FIG. 30B shows a graph of intensity versus diameter from DSL at pH 7.4 of MeBASP after a degradation time of 1 hour (where the ratio of brush to crosslinker used was 7:20).
Figure 30C:
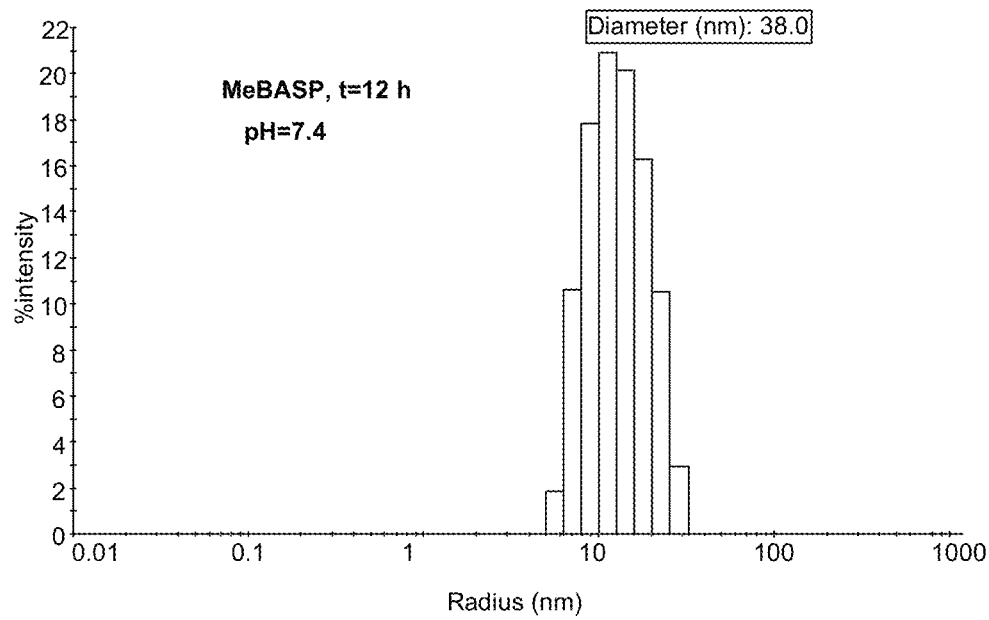
FIG. 30C shows a graph of intensity versus diameter from DSL at pH 7.4 of MeBASP after a degradation time of 12 hours (where the ratio of brush to crosslinker used was 7:20).
Figure 30D:
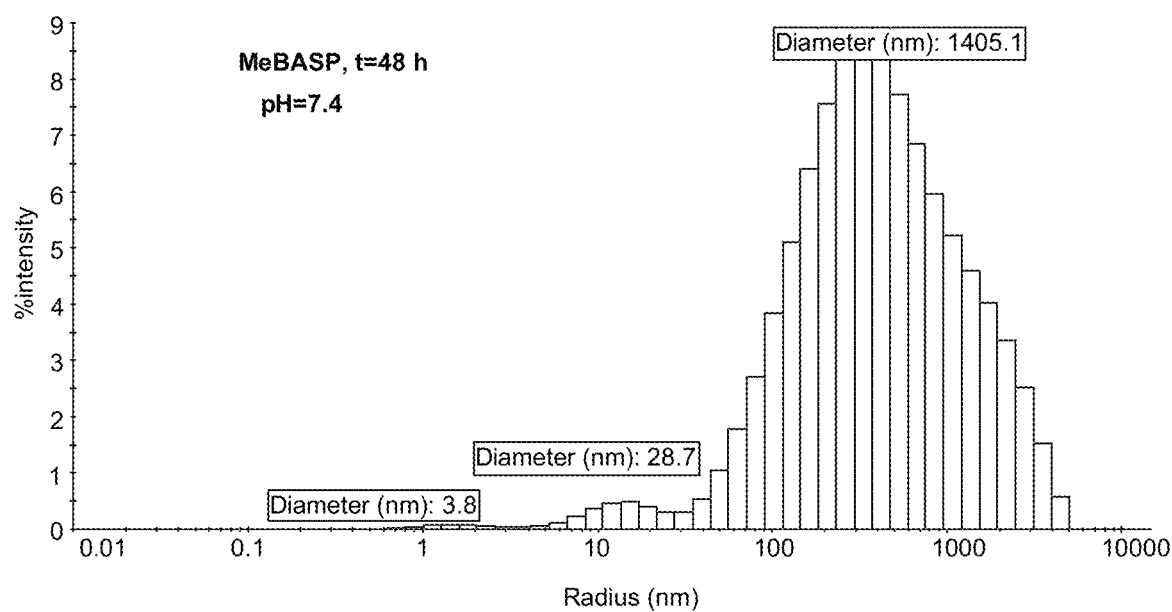
FIG. 30D shows a graph of intensity versus diameter from DSL at pH 7.4 of MeBASP after a degradation time of 48 hours (where the ratio of brush to crosslinker used was 7:20).
Figure 31A:
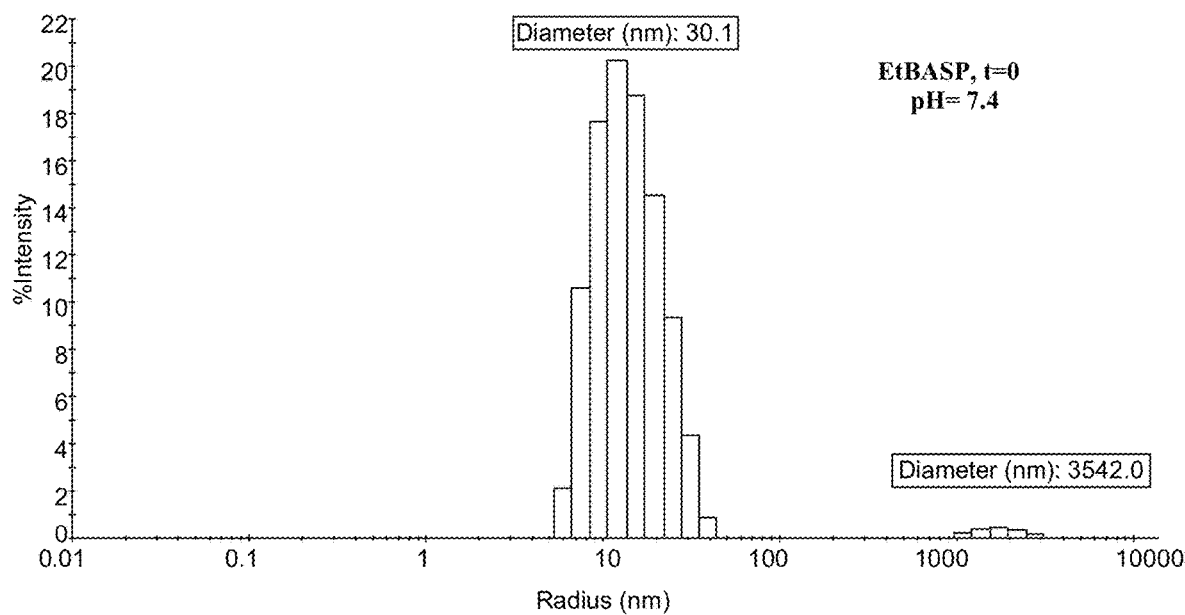
FIG. 31A shows a graph of intensity versus diameter from DSL at pH 7.4 of EtBASP after a degradation time of 0 (where the ratio of brush to crosslinker used was 7:20).
Figure 31B:
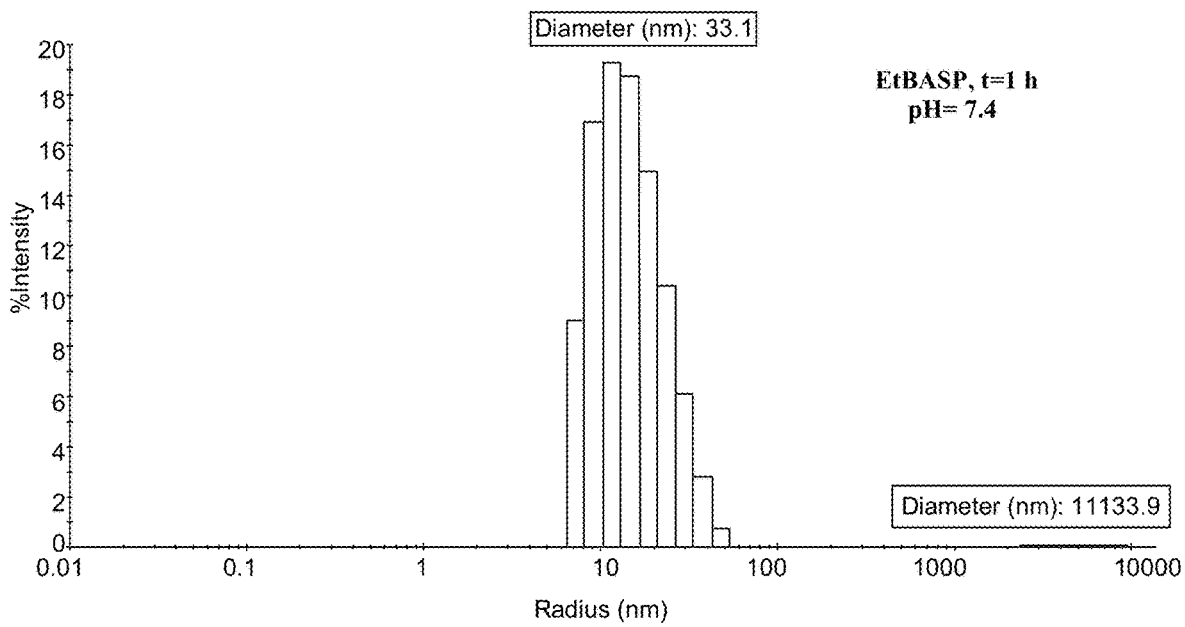
FIG. 31B shows a graph of intensity versus diameter from DSL at pH 7.4 of EtBASP after a degradation time of 1 hour (where the ratio of brush to crosslinker used was 7:20).
Figure 31C:
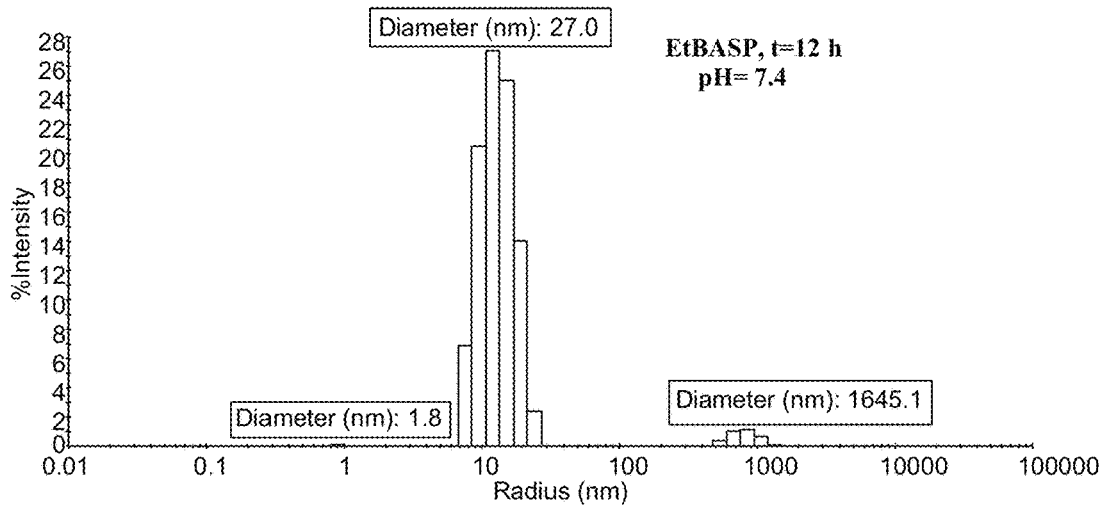
FIG. 31C shows a graph of intensity versus diameter from DSL at pH 7.4 of EtBASP after a degradation time of 12 hours (where the ratio of brush to crosslinker used was 7:20).
Figure 31D:
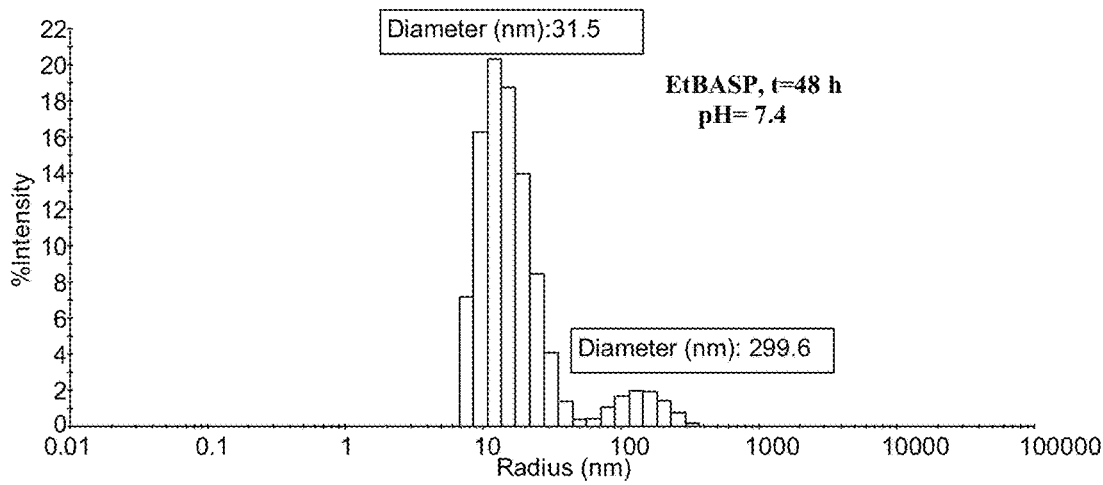
FIG. 31D shows a graph of intensity versus diameter from DSL at pH 7.4 of EtBASP after a degradation time of 48 hours (where the ratio of brush to crosslinker used was 7:20).
Figure 31E:
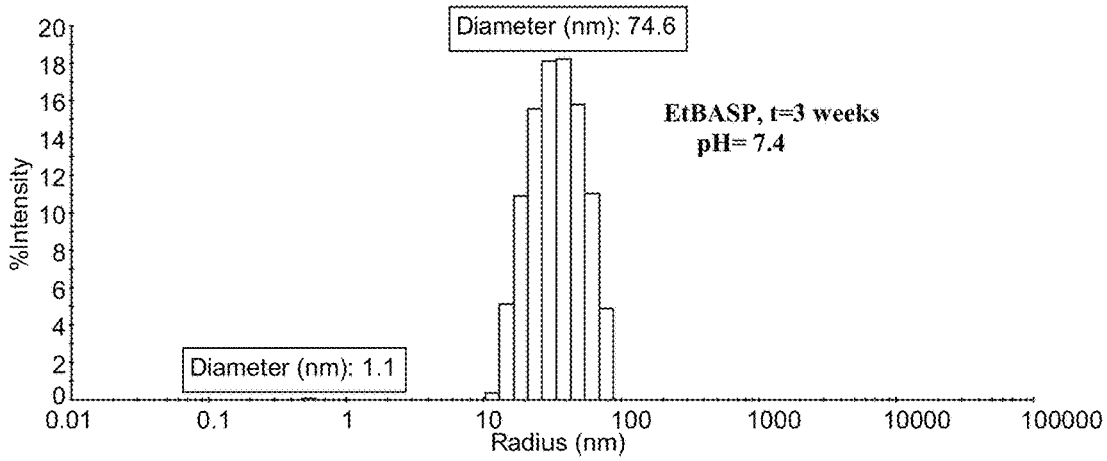
FIG. 31E shows a graph of intensity versus diameter from DSL at pH 7.4 of EtBASP after a degradation time of 3 weeks (where the ratio of brush to crosslinker used was 7:20).
Figure 32A:
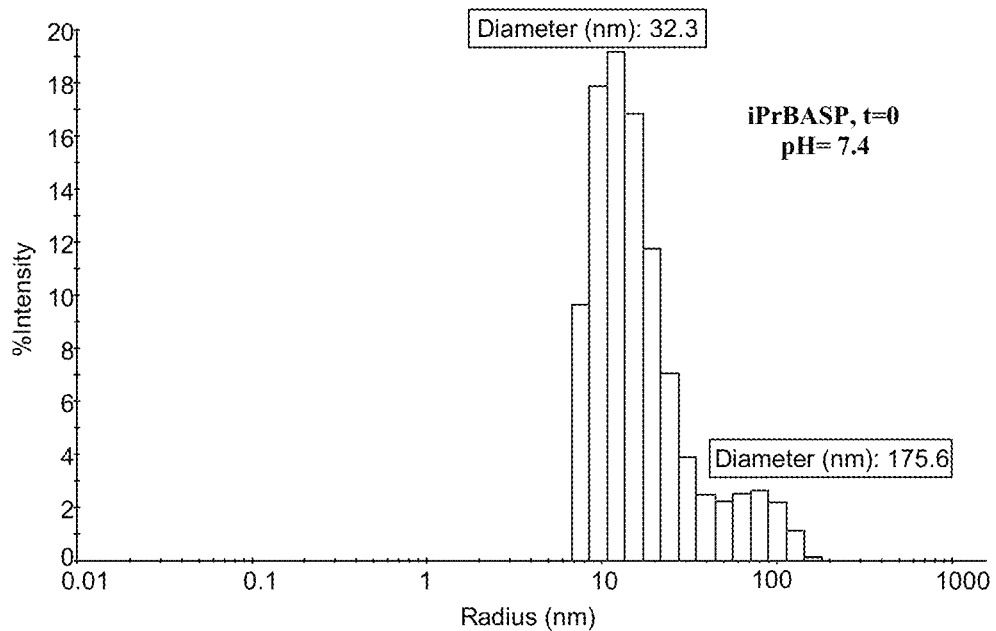
FIG. 32A shows a graph of intensity versus diameter from DSL at pH 7.4 of iPrBASP after a degradation time of 0 (where the ratio of brush to crosslinker used was 7:20).
Figure 32B:
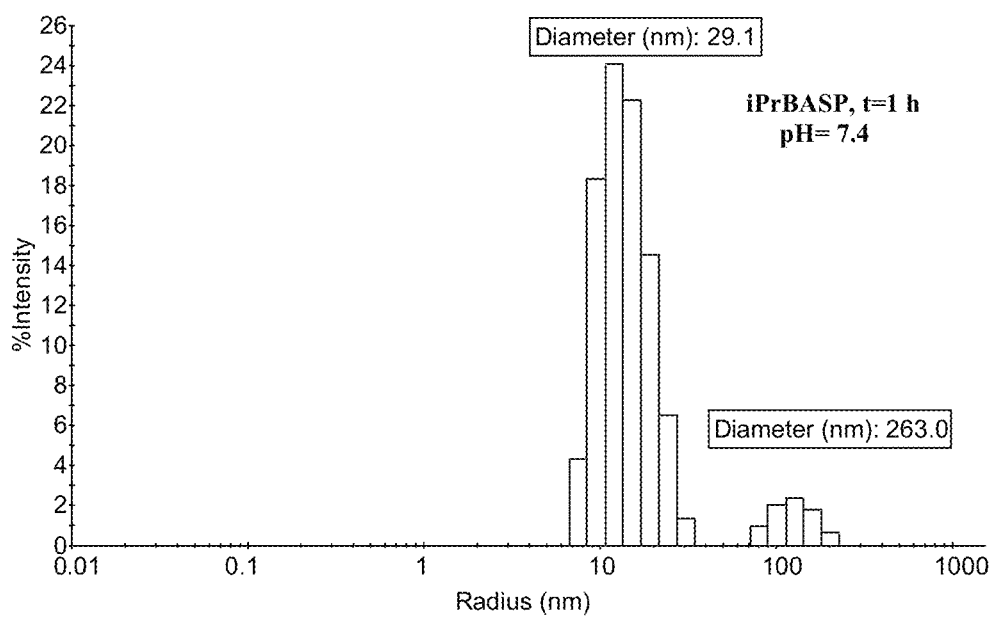
FIG. 32B shows a graph of intensity versus diameter from DSL at pH 7.4 of iPrBASP after a degradation time of 1 hour (where the ratio of brush to crosslinker used was 7:20).
Figure 32C:
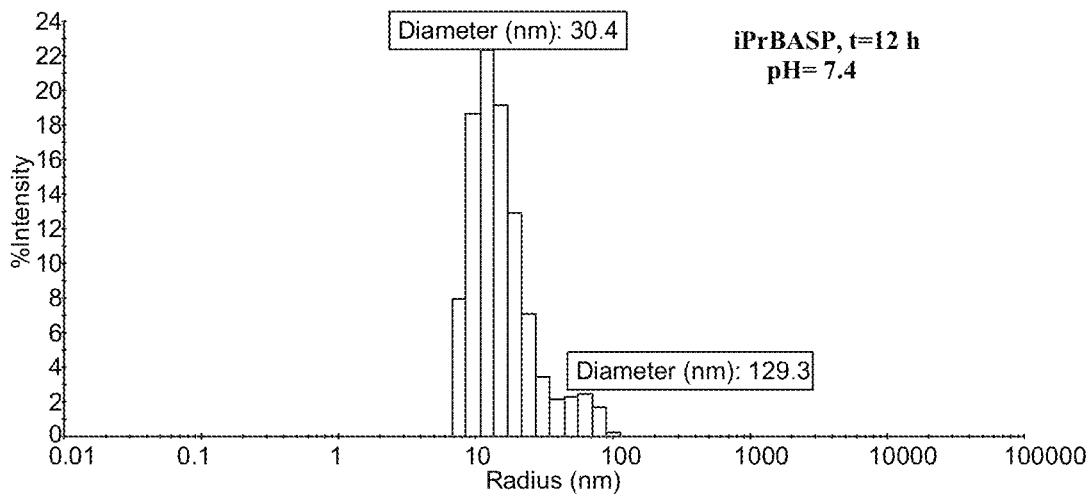
FIG. 32C shows a graph of intensity versus diameter from DSL at pH 7.4 of iPrBASP after a degradation time of 12 hours (where the ratio of brush to crosslinker used was 7:20).
Figure 32D:
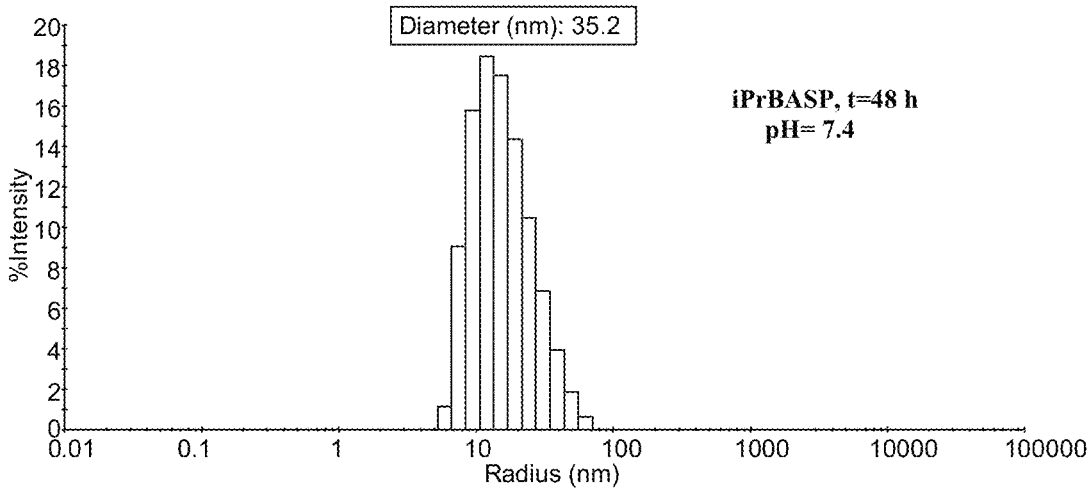
FIG. 32D shows a graph of intensity versus diameter from DSL at pH 7.4 of iPrBASP after a degradation time of 48 hours (where the ratio of brush to crosslinker used was 7:20).
Figure 32E:
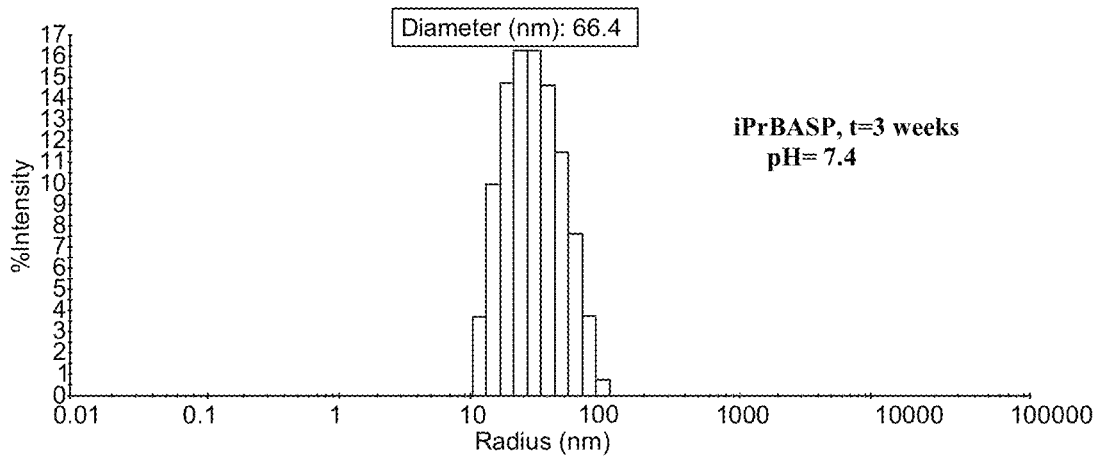
FIG. 32E shows a graph of intensity versus diameter from DSL at pH 7.4 of iPrBASP after a degradation time of 3 weeks (where the ratio of brush to crosslinker used was 7:20).
Figure 33A:
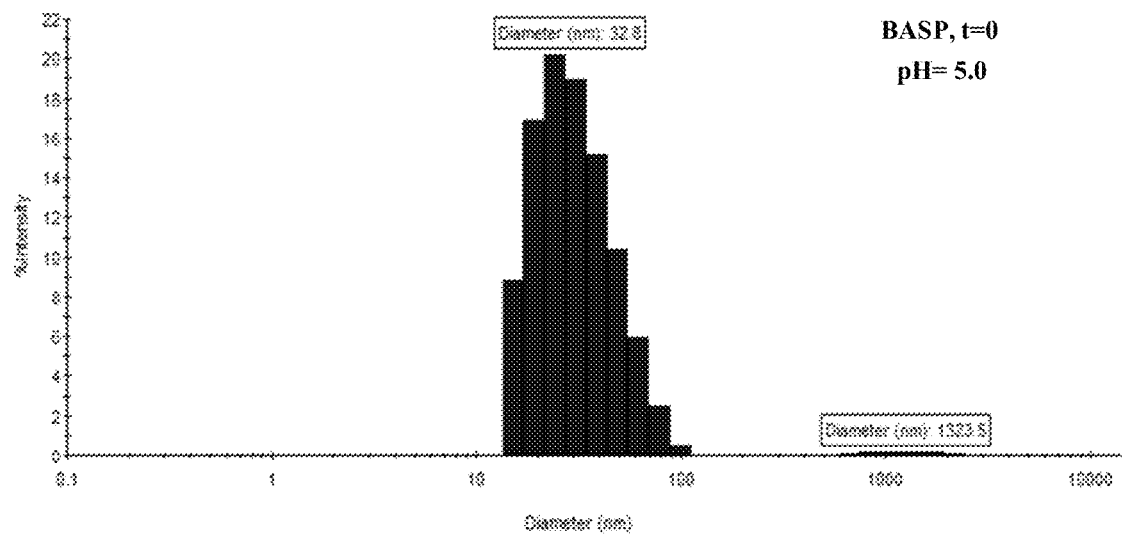
FIG. 33A shows a graph of intensity versus diameter from DSL at pH 5.0 of BASP after a degradation time of 0 (where the ratio of brush to crosslinker used was 7:20).
Figure 33B:
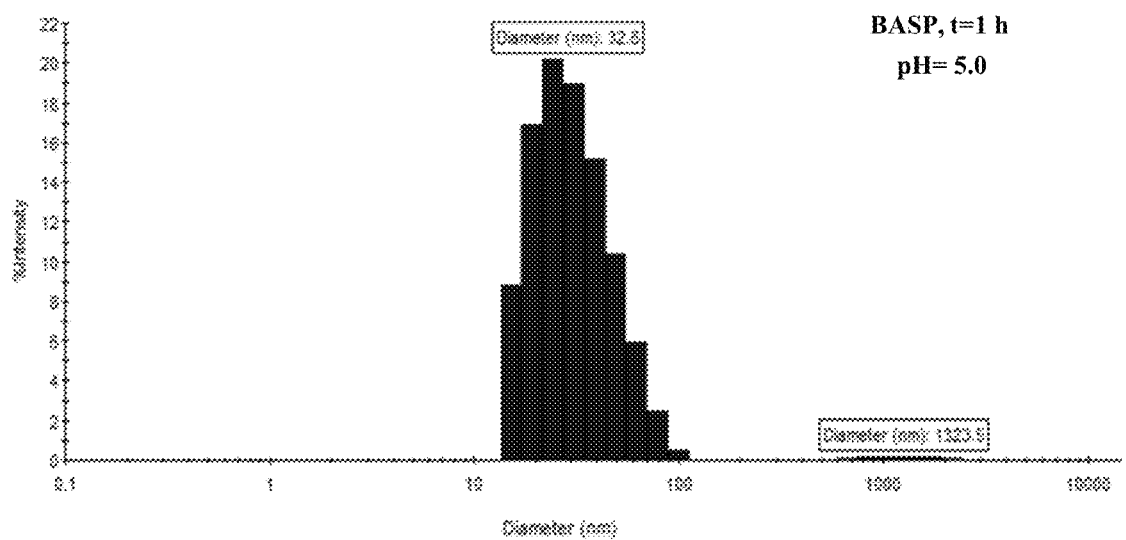
FIG. 33B shows a graph of intensity versus diameter from DSL at pH 5.0 of BASP after a degradation time of 1 hour (where the ratio of brush to crosslinker used was 7:20).
Figure 33C:
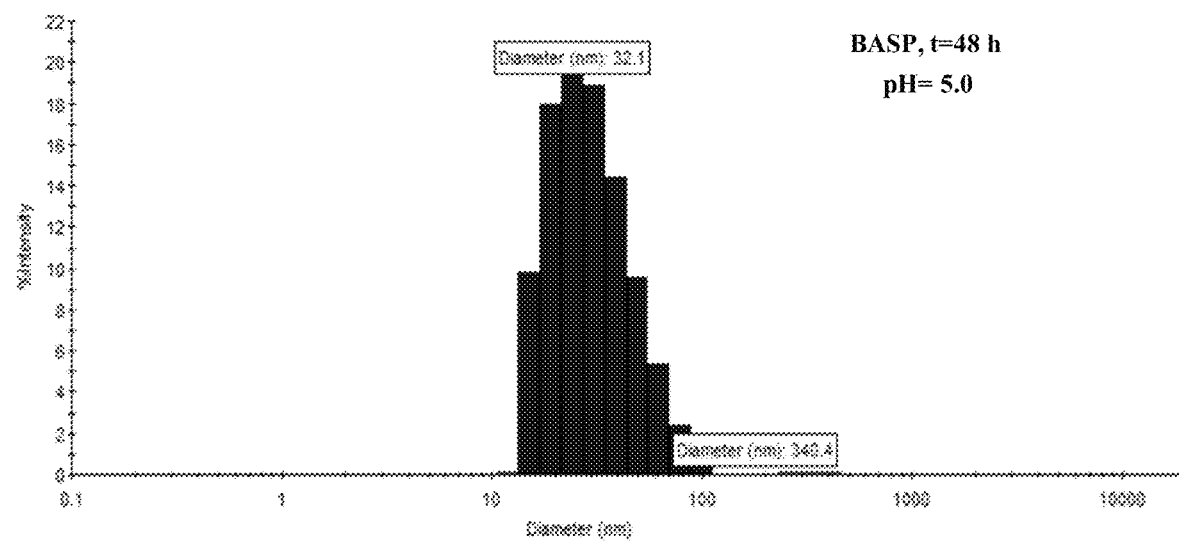
FIG. 33C shows a graph of intensity versus diameter from DSL at pH 5.0 of BASP after a degradation time of 48 hours (where the ratio of brush to crosslinker used was 7:20).
Figure 33D:
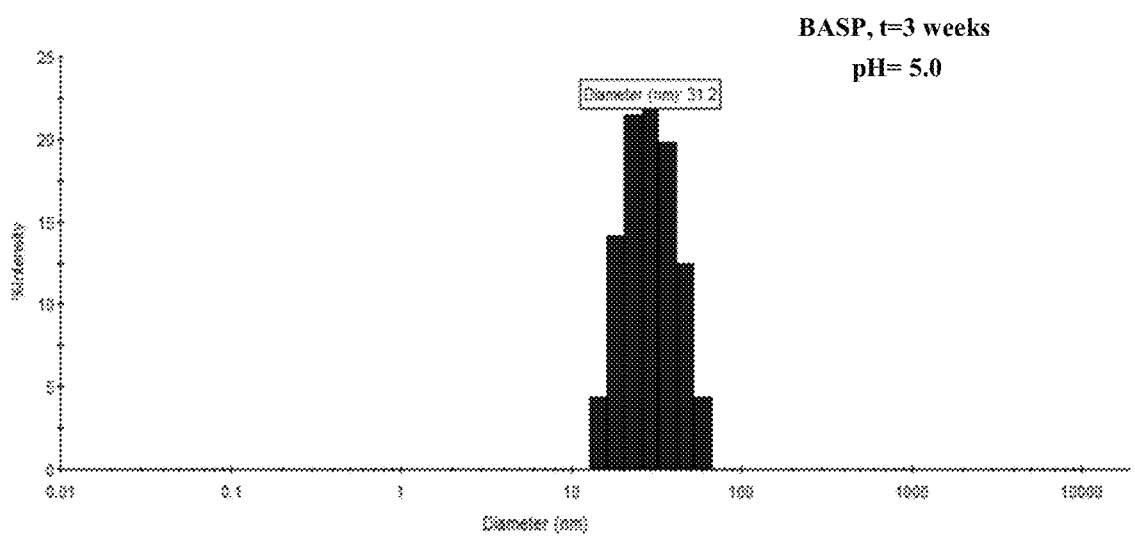
FIG. 33D shows a graph of intensity versus diameter from DSL at pH 5.0 of BASP after a degradation time of 3 weeks (where the ratio of brush to crosslinker used was 7:20).
Figure 34A:
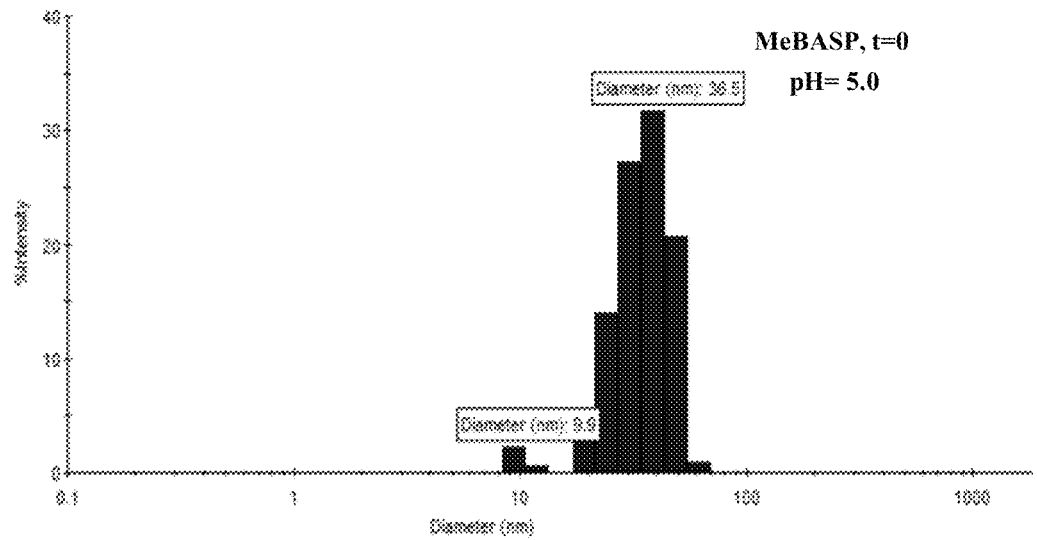
FIG. 34A shows a graph of intensity versus diameter from DSL at pH 5.0 of MeBASP after a degradation time of 0 (where the ratio of brush to crosslinker used was 7:20).
Figure 34B:
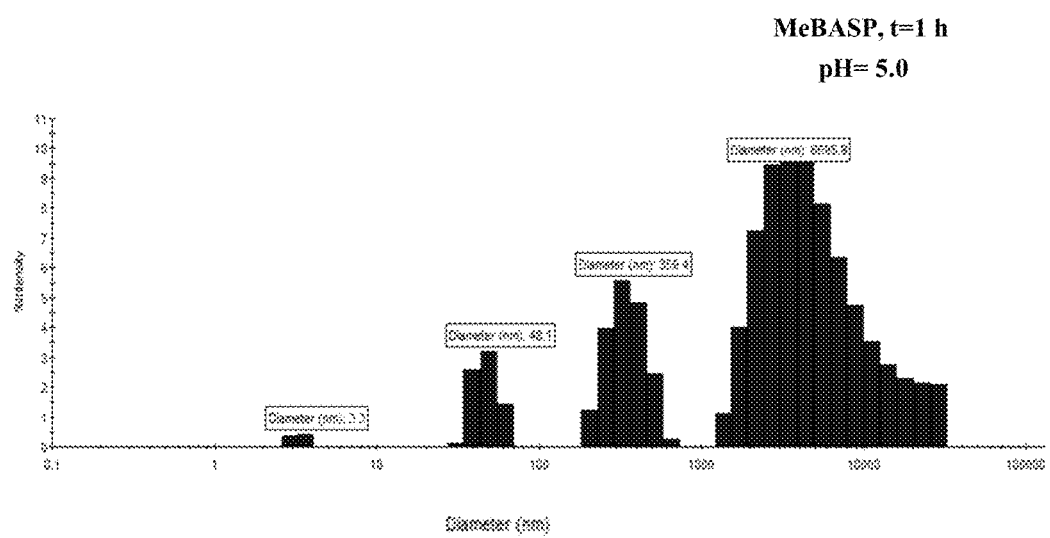
FIG. 34B shows a graph of intensity versus diameter from DSL at pH 5.0 of MeBASP after a degradation time of 1 hour (where the ratio of brush to crosslinker used was 7:20).
Figure 35A:
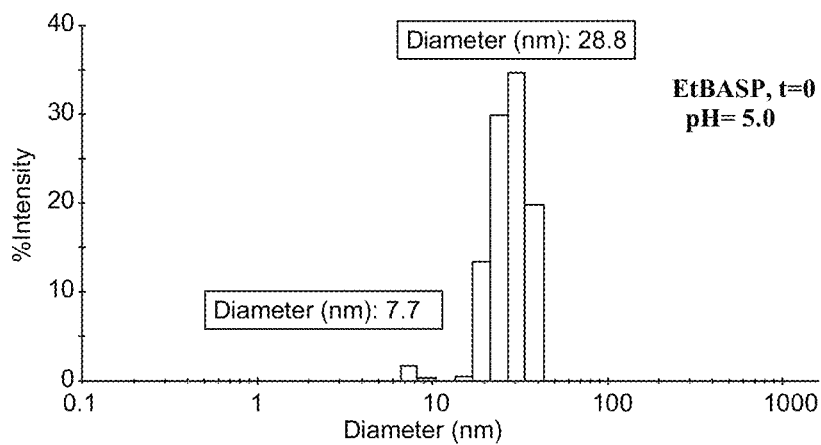
FIG. 35A shows a graph of intensity versus diameter from DSL at pH 5.0 of EtBASP after a degradation time of 0 (where the ratio of brush to crosslinker used was 7:20).
Figure 35B:
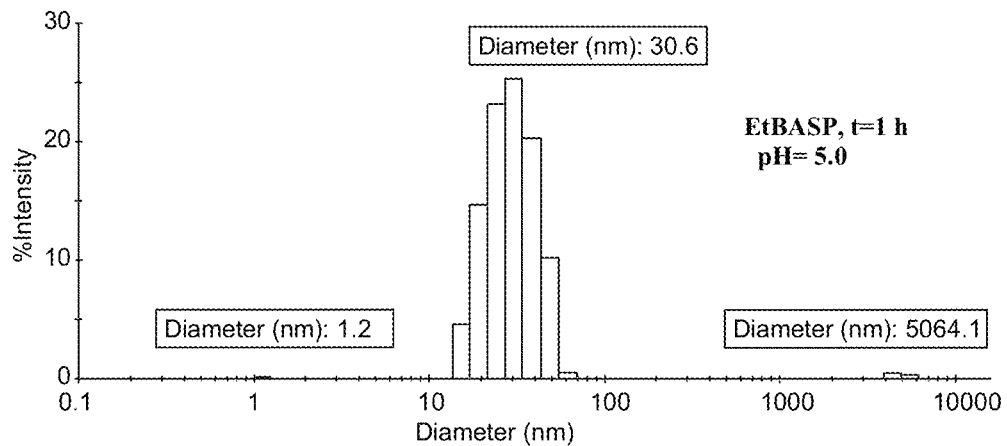
FIG. 35B shows a graph of intensity versus diameter from DSL at pH 5.0 of EtBASP after a degradation time of 1 hour (where the ratio of brush to crosslinker used was 7:20).
Figure 35C:
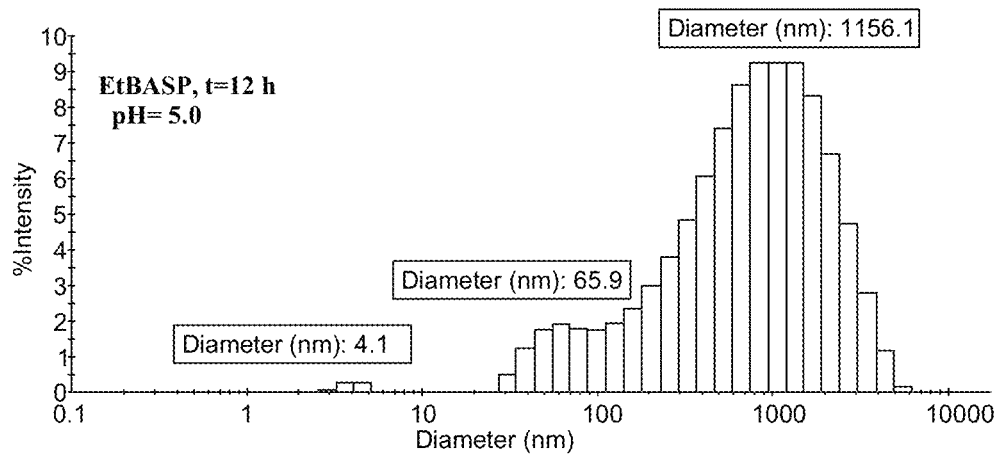
FIG. 35C shows a graph of intensity versus diameter from DSL at pH 5.0 of EtBASP after a degradation time of 12 hours (where the ratio of brush to crosslinker used was 7:20).
Figure 36A:
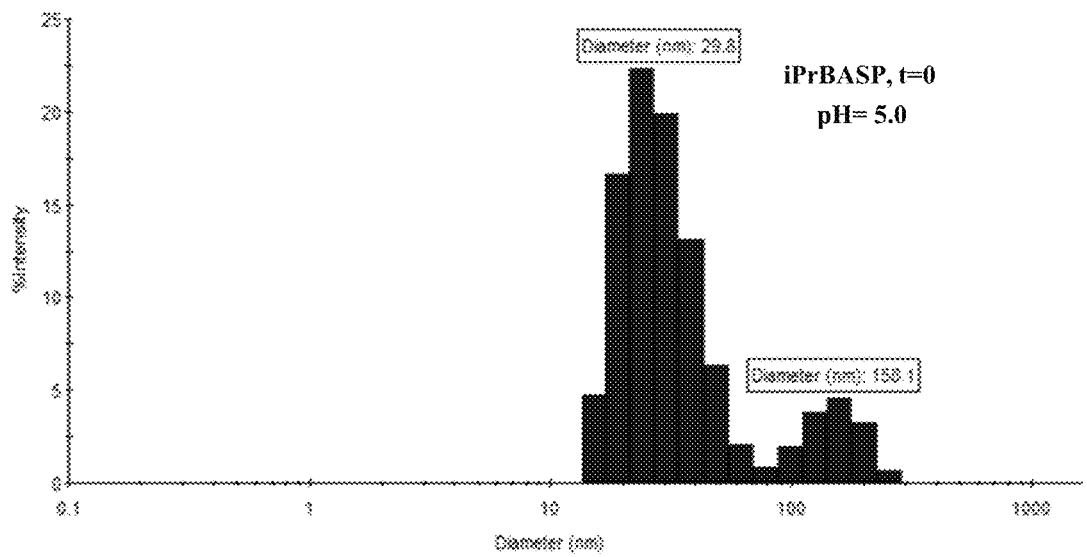
FIG. 36A shows a graph of intensity versus diameter from DSL at pH 5.0 of iPrBASP after a degradation time of 0 (where the ratio of brush to crosslinker used was 7:20).
Figure 36B:
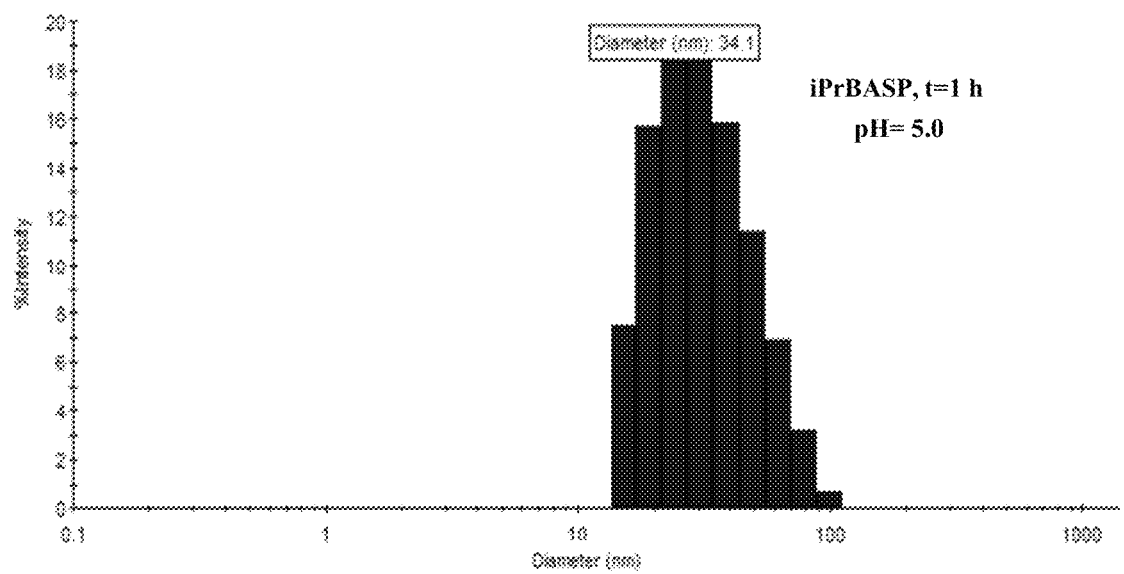
FIG. 36B shows a graph of intensity versus diameter from DSL at pH 5.0 of iPrBASP after a degradation time of 1 hour (where the ratio of brush to crosslinker used was 7:20).
Figure 36C:
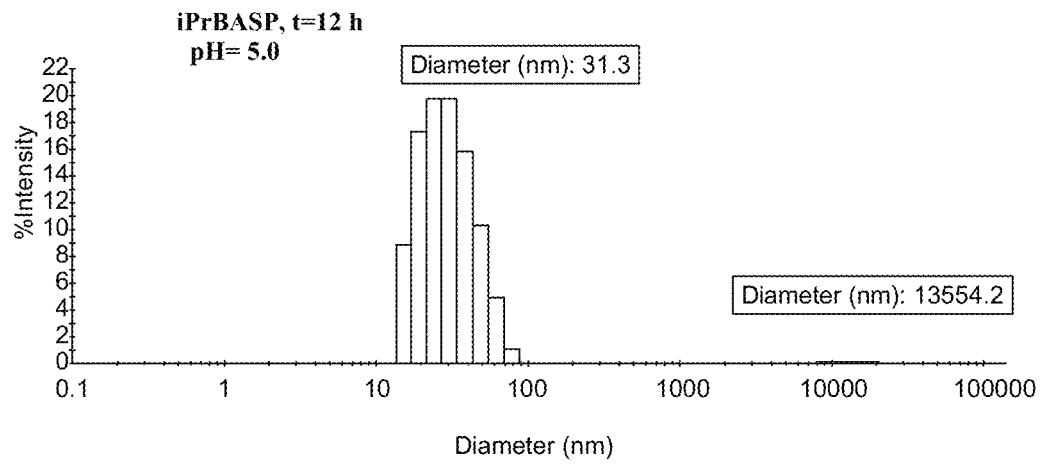
FIG. 36C shows a graph of intensity versus diameter from DSL at pH 5.0 of iPrBASP after a degradation time of 12 hours (where the ratio of brush to crosslinker used was 7:20).
Figure 36D:
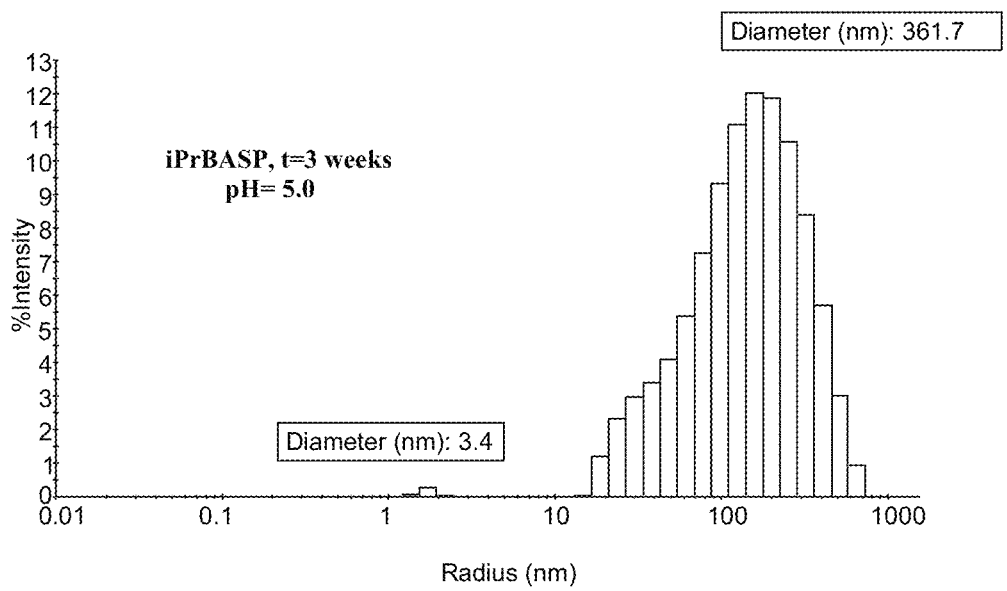
FIG. 36D shows a graph of intensity versus diameter from DSL at pH 5.0 of iPrBASP after a degradation time of 3 weeks (where the ratio of brush to crosslinker used was 7:20).

Exemplary polymerization reactions for the generation of homopolymers and copolymers and their resulting GPC chromatograms are shown in FIGS. 8A to 10 C. Each homopolymer and corresponding copolymer varied in their retention time and/or peak shape. $^1$H NMR spectra corresponding to the reaction mixture of polymerization reactions with exemplary monomers appear in FIGS. 11 to 16. Upon polymerization of the monomers shown in FIG. 11, peak broadening as well as appearance of new peaks were observed in the spectra of the corresponding homopolymers (FIG. 12). Polymerization of the norbornene monomers with Si-iPr resulted in spectra containing additional and unique peaks (FIG. 13) compared to those seen in either of the corresponding homopolymers. Both FIGS. 14 and 15 show that in either case the copolymer had unique peaks compared to the corresponding homopolymers. FIG. 16 shows the polymerization reactions after 24 hours where peak broadening as well as the appearance of new peaks were observed compared to the spectra of the corresponding homopolymers. The appearance of new peaks or change in peak shape was indicative of the presence of a new species.

Example 12.2. Linear Copolymer Synthesis

NB1-NB4 and the requisite silyl ether monomers were transferred into a water- and air-free glovebox under N$_2$ atmosphere and dissolved in dioxane to form a 0.5 M solution. A pre-measured amount of Grubbs' 3$^{rd}$ generation bispyridyl catalyst in a vial was diluted with dioxane to form a freshly prepared 0.01 M stock solution.

Inside the glovebox, to a 0.5-dram vial containing a stir bar were added 105 μL of dioxane, 15 μL of 0.5 M norbornene stock, and 15 μL of 0.5 M silyl ether stock (or dioxane for polynorbornene homopolymers). Finally, 15 μL of the catalyst solution were added to generate polymers with a target DP of 50 for each monomer. The mixture was stirred for 30 min, removed from the glovebox, quenched with a drop of ethyl vinyl ether (EVE), and analyzed by DMF GPC.

Example 13.1. Preparation of Brush Polymers

All polymerization reactions were performed inside a nitrogen-filled glovebox. 50 mg of PEG-norbornene was dissolved in 198 μL of dioxane and the solution transferred into a 2 mL vial with stir bar. Next, 15.4 μL of 1 M cyclic silyl ether in dioxane was added (or dioxane for non-degradable brushes). Finally, 25.7 μL of 0.02 M G3 in dioxane was added. The reaction immediately turned from a green to orange color as the reaction initiated. The reaction was allowed to proceed for 30 minutes, then quenched with a drop of ethyl vinyl ether. This solution was used directly for stability experiments. For biological experiments, the material was dialyzed against 1 L of water for 6 hours using a 8K MWCO membrane filter, then lyophilized.

Exemplary polymerization reactions for the generation of brush polymers and their resulting GPC chromatograms are shown in FIGS. 17A to 26 D, 38 A to 38 C, and 40A to 40C.

Example 13.2. Bottlebrush Copolymer Synthesis

Bottlebrush polymers were synthesized using 200 mg of PEG-MM in 800 μL of dioxane. 200 μL of solution were added into each of four one-dram vials, followed by 30 μL of 0.5 M silyl ether in dioxane or 30 μL of dioxane. Finally, 75 μL of 0.02 M Grubbs' 3$^{rd}$ generation catalyst in dioxane were added to target a DP of 30 for each monomer. The mixture was stirred for 30 min, quenched with a drop of EVE, and analyzed by GPC. The reaction mixtures were used directly for the degradation experiments described in the following section.

Drug-conjugated, PLA, and PS bottlebrush copolymers were synthesized in an analogous fashion.

Example 14.1. Preparation of BASPs

All polymerization reactions were performed inside a nitrogen-filled glovebox. 100 mg of PEG-norbornene was dissolved in 396 μL of dioxane and the solution transferred into a 4 mL vial with stir bar. Next, 30.8 μL of 1 M cyclic silyl ether in dioxane was added (or 30.8 μL dioxane for non-degradable brushes). Finally, 220 μL of 0.02 M G3 in dioxane was added. The reaction immediately turned from a green to orange color as the reaction initiated. The reaction was allowed to proceed for 30 minutes to ensure full formation of brush. Unless provided otherwise, the DP of the brush described in Example 9 was the same as the DP of the brush described in other Examples.

Next, to this mixture was added 4×35.6 µL of 0.1 M AcXL over 15 minutes. The crosslinking reaction was allowed to proceed for 90 minutes. The reaction was removed from the glovebox and quenched with a drop of ethyl vinyl ether. This solution was used directly for stability experiments. For biological experiments, the material was dialyzed against 1 L of water for 6 hours using a 8K MWCO membrane filter, then lyophilized.

Exemplary polymerization reactions for the generation of BASPs and their resulting GPC chromatograms of are shown in FIGS. 26A to 26D.

Example 14.2. Brush Arm Star Polymer Synthesis 50 mg of PEG-MM were dissolved in 199 µL of dioxane in a glovebox. Next, 40 µL of PEG-MINI solution were added to each of four one-dram vials loaded with stir bars. Next, 6.2 µL of 0.5 M silyl ether or dioxane were added. 22.1 µL of 0.02 M Grubbs' $3^{rd}$ generation catalyst in dioxane were added and the solution was stirred for 15 min. Next, 88.4 µL total of 0.1 M AcXL in dioxane were added in four portions over 15 min. The solutions were allowed to crosslink for 90 min, removed from the glovebox, and quenched with EVE and analyzed by GPC. The solutions were concentrated under vacuum before dissolution in 100 µL dioxane for degradation experiments.

Example 15. Linear Block Copolymer Synthesis

In a $N_2$ glovebox, 80 µL of dioxane were added to a 0.5-dram vial with a stir bar. 10 µL of a 1M solution of NB4 in dioxane were added, followed by 10 µL of a freshly prepared solution of 0.02 M Grubbs' $3^{rd}$ generation catalyst in dioxane for a target DP of 50. The solution was stirred for 30 min. Next, 17.5 µL of a 4:3 mixture of 1 M NB4 and 1 M iPrSi were added to introduce another 50 units of each monomer onto the polymer. The solution was stirred for another 2 h, taken out of the glovebox, quenched with a drop of EVE, concentrated under vacuum, and redissolved in 100 µL dioxane before degradation experiments. A sample was taken for analysis by DMF GPC.

Example 16. Bottlebrush Block Copolymer Synthesis

In a $N_2$ glovebox, 100 mg of PEG-MM and 100 mg of PS-MM were each dissolved into 400 µL of dioxane. 106 µL of PEG-MM solution were added to a 0.5-dram vial. To the solution were added 12.8 µL of 0.02 M Grubbs' $3^{rd}$ generation catalyst in dioxane. The solution was stirred for 30 min for a target DP of 30 for the PEG block. Next, a mixture of 106 µL of PS-MM stock and 6 µL of 1M iPrSi stock in dioxane was added in one portion for a target DP of 30 for the PS block. The solution was stirred for another 2 h, removed from the glovebox, and quenched with a drop of EVE. The solution was then concentrated under vacuum and diluted in 200 µL of dioxane before use in degradation experiments. A sample was taken for analysis by GPC.

Example 17. Block Copolymer Synthesis with Degradable Linkers

In a glovebox, 100 mg of PEG-MM were dissolved in 400 µL of dioxane. 106 µL of solution were added to each of two vials. Next, 12.5 µL of freshly prepared 0.02 M Grubbs' $3^{rd}$ generation catalyst in dioxane were added. The mixture was stirred for 1 h. Next, a combination of 20 µL of 1M NB3 and 10 µL of iPrSi were combined. 7.5 µL of this solution were added to one of the vials, while 5 of NB3 were added to the other. The solution was stirred for 30 min. Finally, 300 mg of PS-MM in 300 µL of dioxane were added. The solution was stirred for 6 h, quenched with EVE, and characterized by GPC. The solution was then concentrated under vacuum before use in degradation experiments.

TABLE 1

Reference table with polymer samples presented in the main text and their target DPs.

| Sample Name | Target DP | Theoretical $M_n$ | Observed $M_n$ | $M_w/M_n$ |
|---|---|---|---|---|
| $PEG_{100}$ | 100 PEG-MM | $3.23 \times 10^5$ | $3.69 \times 10^5$ | 1.05 |
| $iPrSi_{100}PEG_{100}$ | 100 PEG-MM/100 iPrSi | $3.41 \times 10^5$ | $3.25 \times 10^5$ | 1.14 |
| $NB1_{50}$ | 50 NB1 | $7.60 \times 10^3$ | $8.28 \times 10^5$ | 1.02 |
| $iPrSi_{50}NB1_{50}$ | 50 NB1/50 iPrSi | $1.85 \times 10^4$ | $8.93 \times 10^3$ | 1.14 |
| $NB2_{50}$ | 50 NB2 | $8.30 \times 10^3$ | $9.53 \times 10^3$ | 1.02 |
| $iPrSi_{50}NB2_{50}$ | 50 NB2/50 iPrSi | $1.90 \times 10^4$ | $9.97 \times 10_3$ | 1.13 |
| $NB3_{50}$ | 50 NB3 | $8.85 \times 10^3$ | $1.07 \times 10^4$ | 1.01 |
| $iPrSi_{50}NB3_{50}$ | 50 NB3/50 iPrSi | $1.96 \times 10^4$ | $1.12 \times 10^4$ | 1.11 |
| $NB4_{50}$ | 50 NB4 | $8.85 \times 10^3$ | $7.64 \times 10^3$ | 1.02 |
| $iPrSi_{50}NB4_{50}$ | 50 NB4/50 iPrSi | $1.96 \times 10^4$ | $1.08 \times 10_4$ | 1.09 |
| $PEG_{30}$ | 30 PEG-MM | $9.69 \times 10^4$ | $1.02 \times 10^5$ | 1.02 |
| $MeSi_{30}PEG_{30}$ | 30 PEG-MM/30 MeSi | $1.02 \times 10^5$ | $1.22 \times 10^5$ | 1.24 |
| $EtSi_{30}PEG_{30}$ | 30 PEG-MM/30 EtSi | $1.03 \times 10^5$ | $1.30 \times 10^5$ | 1.14 |
| $PhSi_{30}PEG_{30}$ | 30 PEG-MM/30 PhSi | $1.05 \times 10^5$ | $1.28 \times 10^5$ | 1.17 |
| $iPrSi_{30}PEG_{30}$ | 30 PEG-MM/30 iPrSi | $1.03 \times 10^5$ | $1.27 \times 10^5$ | 1.15 |
| BASP | 7 PEG-MM, 20 AcXL | — | $7.87 \times 10^5$ | 1.30 |
| MeSi-BASP | 7 PEG-MM, 7 MeSi, 20 AcXL | — | $1.28 \times 10^6$ | 1.40 |
| EtSi-BASP | 7 PEG-MM, 7 EtSi, 20 AcXL | — | $9.58 \times 10^5$ | 1.31 |
| iPrSi-BASP | 7 PEG-MM, 7 PhSi, 20 AcXL | — | $9.54 \times 10^5$ | 1.32 |

Example 18. Degradation with HCl

Unless provided otherwise, HCl degradation experiments of the polymers were performed according to the method described in Example 18.

Polymers were degraded using the following HCl degradation conditions: To a solution of 50 uL of crude polymer in dioxane was added 10 uL of 2M HCl. The mixture was then stirred for 30 minutes, then dried/neutralized with the addition of sodium sulfate. After allowing the material to sit for 10 minutes, the combined solids were taken up in 1 mL of DMF with 0.025 M LiBr and the mixture analyzed via gel permeation chromatography (GPC).

Figure 37:
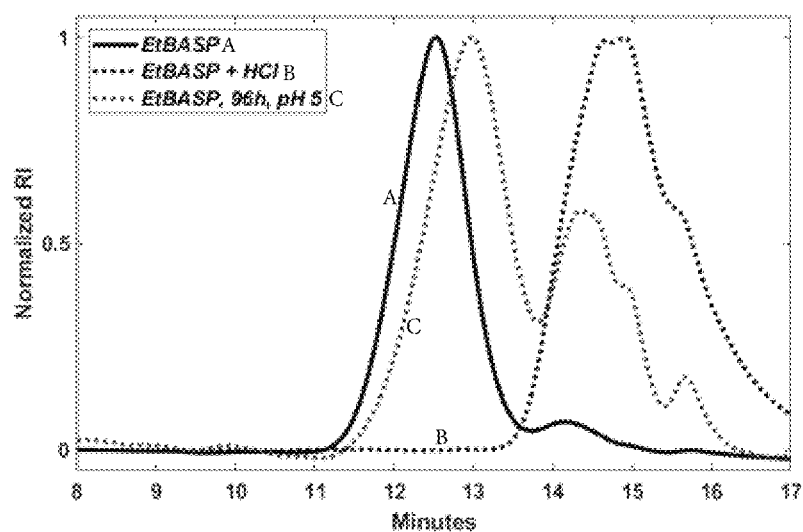
FIG. 37 shows a resulting chromatogram from GPC of EtBASP, EtBASP after treatment with HCl, and EtBASP after treatment at pH 5 after 96 hours of degradation time (where the ratio of brush to crosslinker used was 7:20).
Figure 38A:
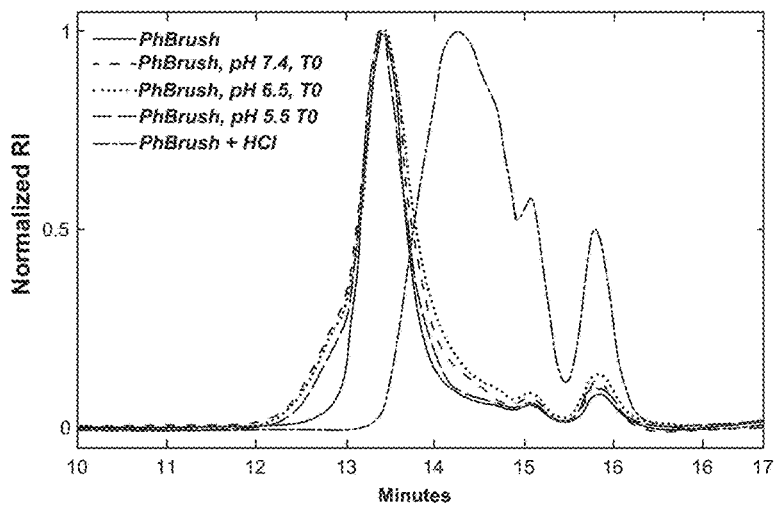
FIG. 38A shows a resulting chromatogram from GPC of PhBrush after no degradation at various pH, or after treatment with HCl (where each polymer had a DP of 30 before further treatment and ratio of monomers used was 1:1).
Figure 38B:
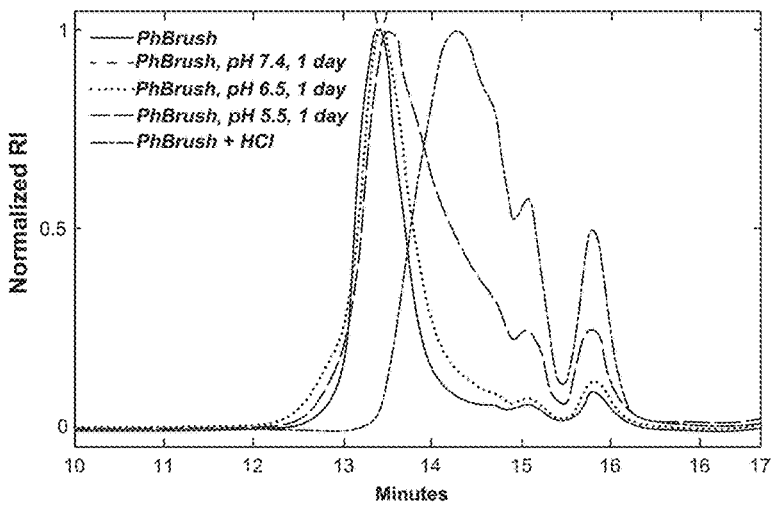
FIG. 38B shows a resulting chromatogram from GPC of PhBrush after 1 day of degradation time at various pH, or after treatment with HCl (where each polymer had a DP of 30 before further treatment and ratio of monomers used was 1:1).
Figure 38C:
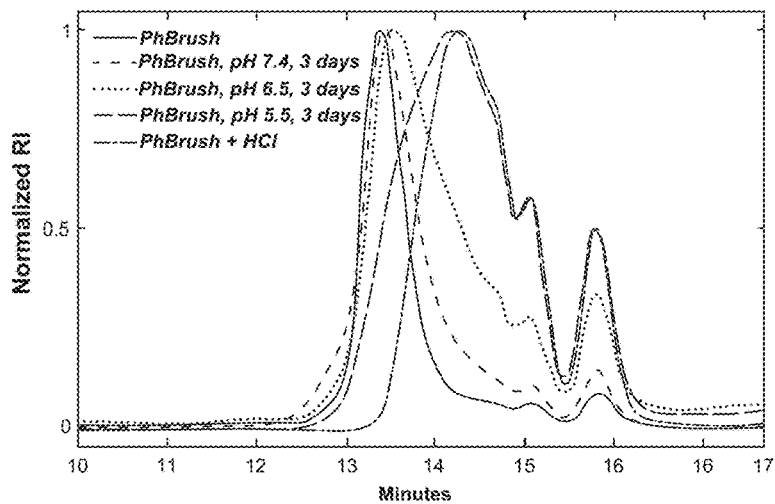
FIG. 38C shows a resulting chromatogram from GPC of PhBrush after 3 days of degradation time at various pH, or after treatment with HCl (where each polymer had a DP of 30 before further treatment and ratio of monomers used was 1:1).

The resulting GPC chromatograms of exemplary polymers treated with HCl appear in FIGS. 8 A to 8D, 9C, and 10A to 10C. The resulting GPC chromatograms of exemplary brush polymers treated with HCl appear in FIGS. 17 C, 20, 22C, 23B, and 24A to 25 C. The resulting GPC chromatograms of exemplary BASPs treated with HCl appear in FIGS. 26D and 37. Dynamic light scattering results from exemplary BASPs and after degradation are shown in FIGS. 27A to 36D.

Example 19. Polymer Degradation and Characterization of Degradation Products Acidic Hydrolysis of Linear Copolymers To force degradation of the material, the polymerization solution was concentrated in a vacuum chamber at room temperature to remove residual EVE and diluted in 100 μL of dioxane. To the solution were added 10 μL of 2M HCl. The mixture was stirred for 30 minutes. Excess sodium sulfate was added and the mixture was allowed to sit for 5 min. Finally, the mixture was extracted with DCM, filtered with a 0.2 μm nylon filter, concentrated, and analyzed by GPC.

Gel permeation chromatography (GPC) analyses were performed on an Agilent 1260 Infinity system with a 0.025 M LiBr in DMF mobile phase at 60° C. The differential refractive index (dRI) of each compound was monitored using a Wyatt Optilab T-rEX detector.

Example 20. Acidic Hydrolysis of Bottlebrush Polymers and Star Polymers

30 μL of the polymer mixture were concentrated under vacuum to remove EVE and taken up in 100 μL of dioxane. 10 μL of 2M HCl were added and the mixture was stirred for 30 min. Excess sodium sulfate was added and the reaction mixture was allowed to sit for 5 min. Finally, the mixture was suspended in DCM, filtered with a 0.2 μm Nylon filter, concentrated under vacuum, and analyzed by GPC.

Example 21. Degradation of Bottlebrush Polymers Under Buffered Conditions

200 μL of each crude reaction mixture, prepared as described above, were placed in a vial containing 10 mL of the requisite buffer. The solution was incubated at 37° C. for the indicated times. The pH 5.5, 6.5, and 7.4 solutions were prepared using mixtures of 0.2 M $Na_2HPO_4$ and 0.1 M citric acid.

At set timepoints, 1 mL of the material was flash frozen into liquid $N_2$ and lyophilized; the resulting material was extracted with DCM, filtered, and concentrated under vacuum. The residue was dissolved in DMF with 0.025 M LiBr and analyzed by gel permeation chromatography. A similar approach was used for the brush-arm star polymer samples as well, where samples from the dynamic light scattering experiments were flash frozen, lyophilized, and extracted before characterization by DMF GPC.

To assess the size of the degradation fragments, PEG-MM was polymerized at target DP values of 2, 3, or 4 and analyzed by DMF GPC.

Example 22. Characterization of Bottlebrush Polymer Degradation Fragments

To further confirm the nature of the degradation fragments, short polymer fragments were individually synthesized by combining PEG-MINI and G3 catalyst in a 2:1 molar ratio. This reaction generated an oligomer mixture with an average DP of 2 that contained macromonomer as well as oligomers of DP=3 and larger.

Example 23. Quantification of Bottlebrush Polymer Degradation

The area under the curve of each GPC trace (see FIG. 65) after a specific retention time (13.75 minutes, A) was determined for all samples. This value was divided by the total integrated value under each peak ($A_o$) to yield a ratio R. The cutoff retention time was chosen to minimize R in the intact bottlebrush polymer while maximizing this value for the fully-degraded sample.

To convert the R value into a percent degradation, this value was normalized using the $A/A_o$ derived from the fully-intact (0 min, $R_{initial}$) and fully degraded (after HCl treatment, $R_{final}$) bottlebrush polymers, which were set at 0 and 100% degradation, respectively on a linear scale. In this case, degradation refers to the fraction of silyl ether linkages that are degraded within the polymer. This normalization was performed separately for each type of bottlebrush polymer. R was then calculated from each timepoint using the corresponding GPC traces and converted to a percent degradation using our normalization procedure.

Specifically, percentage degradation for each timepoint is calculated by:

$$\text{Percent degradation} = (R - R_{initial})/(R_{final} - R_{initial}) \times 100\%$$

Example 24. Degradation of Non-PEG Containing Bottlebrush Polymers

For the PS and PLA-based bottlebrush polymers, 15 μL of the crude ROMP reaction mixture were diluted with 15 μL of dioxane. Next, 7 of 1M tetrabutylammonium fluoride in THE were added. The solution was incubated for 15 min before being diluted with 1 mL of chloroform, filtered through a 0.2 μm Teflon filter (A ChemTek), and analyzed by chloroform GPC.

GPC analysis was performed in a Tosoh EcoSEC HLC-8320 with dual TSKgel SuperH3000 columns and a chloroform mobile phase.

Example 25. Characterization of Brush Arm Star Polymer Degradation

Solutions of brush-arm star polymers in dioxane were diluted to 1.0 mg/mL in the requisite buffer. Dynamic light scattering (DLS) measurements were performed using a Wyatt Technology Mobius DLS instrument. The solutions were filtered through a 0.2 μm Nylon filter (A ChemTek) into disposable polystyrene cuvettes, which were pre-cleaned with compressed air. The solutions were immediately capped after addition of the solution to the cuvette. Measurements were made in sets of 10 acquisitions; the average hydrodynamic diameters were calculated using the DLS-correlation function via a regularization fitting method (Dynamics 7.4.0.72 software package from Wyatt). The cuvettes were sealed with parafilm and stored at room temperature between measurements.

For GPC analysis, a sample was flash frozen and lyophilized. Afterwards the polymer was extracted with DCM, filtered with a 0.2 μm Nylon filter, concentrated under gentle vacuum, and analyzed by GPC.

Example 26. Degradation of Block Copolymers

To 30 μL of the polymer mixture were added 10 μL of 2 M HCl. The mixture was stirred for 30 min. Excess sodium sulfate was added and the reaction mixtures allowed to sit for five minutes. Finally, the mixture was suspended in DCM, filtered with a 0.2 μm Nylon filter, concentrated under vacuum, and analyzed by GPC.

Example 27. Linker Degradation of Bottlebrush Copolymers

The concentrated polymer reaction mixture was redissolved in 200 μL of dioxane. 20 μL of this solution were diluted with 80 μL of dioxane. 10 μL of 2 M HCl were added and the solution was allowed to sit for 30 min. Excess sodium sulfate was added and, after 5 min, the mixture was extracted with DCM, filtered with a 0.2 μm nylon filter, concentrated, and analyzed by GPC to assess degradation.

To study the potential impact of polymer degradation toward generating responsive materials, 20 μL of sample were diluted in 1 mL of dioxane. A solution in 10 mL of MeOH was prepared. 1 mL of each solution was transferred to a vial and 10 μL of 2 M HCl were added and the solutions were monitored over time visually. Pictures were acquired with a smartphone camera.

Example 28. Reaction Optimization and Characterization

Silyl Ether Screening for Bottlebrush Copolymer Synthesis

To assess the role of silyl ether ring size on bottlebrush copolymer synthesis, solutions of 0.5 M silyl ether (7-iPrSi, iPrSi, and 9-iPrSi) were added to PEG-MM before polymerization at a 1:1 molar ratio. Bottlebrush polymers with a target DP of 30 for each monomer were synthesized and degraded in an analogous manner to that described above.

To assess how excess of silyl ether impacts polymerization efficiency, different volumes of iPrSi stock were added in order to generate mixtures of 1:3 or 1:5 molar ratios of PEG-MM/iPrSi before the addition of G3 catalyst.

Example 29. Probing Backbone Accessibility to Chain Transfer Reactions

To assess chain-transfer upon prolonged reaction times, the reaction mixtures were quenched at the designated timepoints (beyond 30 min) by removal from the glovebox and the addition of a drop of EVE. Copolymer characterization by GPC before and after degradation were performed following the protocol described above.

To further study the susceptibility of the polymer backbone to chain-transfer, samples of polymer were removed from a glovebox and quenched with EVE. The solutions were then concentrated under vacuum to remove residual EVE. The mixtures were then taken up in 100 μL of dioxane. To the mixtures were added 10 μL of cis-octene and 10 μL of 0.02 M Grubbs' $2^{nd}$ generation catalyst. After incubation for 1 h, the solutions were quenched with EVE and characterized by GPC.

Example 30. Computational Chemistry

Calculations were performed using a combination of Avogadro 1.2.0 and ORCA 4.1. Structures were optimized by first using molecular mechanics (UFF) and a systematic rotor search followed by further geometry optimization with B3LYP/6-31G(d). Strain energies were calculated by comparing the heats of formation of the cyclic monomer and ethylene and the corresponding ring-opened product derived from a homodesmotic ring-opening metathesis reaction.

Example 31. In Vitro Experiments

Dye-Labeled Bottlebrush Polymer Synthesis for In Vitro Experiments

Bottlebrush polymer was synthesized using 400 mg of PEG-MM and 4 mg of Cy3-MM in 1600 μL of dioxane. 425 μL of the resulting solution were added into each of four vials, followed by 60 μL of 0.5 M silyl ether in dioxane or 60 μL of dioxane. Finally, 50 μL of 0.02 M G3 in dioxane were added to yield a target DP of 30. The mixture was stirred for 30 min and quenched with a drop of EVE. Polymers were concentrated under vacuum at room temperature, then diluted to a concentration of 10 mg/mL immediately before uptake and toxicity experiments.

Example 32. In Vitro Polymer Uptake Assayed by Flow Cytometry

OVCAR8 cells were plated at 100,000 cells/well overnight in 100 μL DMEM+10% FBS in a 96 well plate. Next, 7.5 μL of 10 mg/mL of bottlebrush were added and the cells were incubated for 1, 3, or 12 h. The cells were washed with 2×150 μL PBS and suspended by treatment with 100 μL of trypsin at 37° C. After 15 min, the cells were transferred into a Thermo-Fisher 97-well cell trainer and transferred into a V-bottom plate by centrifugation at 1300 RPM for 5 min. The supernatant was removed and the cells were resuspended in 150 μL of PBS and analyzed by flow cytometry.

Jurkat cells were grown to confluency and then diluted to 500,000 cells/mL in RPMI with 10% FBS. 150 μL of cells were added to each of 6×9 wells in a 150 μL V-bottom plate. To the solutions were added 7.5 μL of bottlebrush polymer solution in PBS or nothing to cells. Incubation was performed for 1, 4, or 12 h at 37° C. The cells were then washed by centrifugation at 1300 rpm for 5 min, removal of the supernatant, and resuspension in 150 μL PBS. This wash step was repeated once more before analysis of the cells by flow cytometry. An analogous approach was taken with OVCAR8 cells. Flow cytometry experiments were performed at the Flow Cytometry Core as a part of the Koch institute for Integrative Cancer Research at MIT on a BD LSR II and analyzed with FlowJo 10.4.2. Statistical significance was assessed through two-sample Student's t tests.

Example 33. In Vitro Polymer Toxicity Assayed by Flow Cytometry

OVCAR8 cells were plated at 10,000 cells per well in 100 μL of DMEM in a 96-well tissue-culture treated polystyrene plate (VWR) and allowed to adhere overnight. The media was then replaced with media containing solutions of bottlebrush polymer at a concentration of 1 mg/mL and the cells were incubated for another 36 h. The cells were then washed with PBS and assayed for viability using DAPI staining for 30 min, washing with PBS, and characterization via flow cytometry. As a positive control, cells were treated with 100 µL of EtOH immediately before washing and DAPI staining. An analogous approach was used to assay Jurkat cell viability.

Example 34. In Vitro Polymer Uptake Assayed by Confocal Microscopy

OVCAR8 cells were plated at 100,000 cells/well overnight in 200 µL DMEM+10% FBS in a Nunc Lab-Tek Chambered Coverglass. Next, 7.5 µL of 10 mg/mL of bottlebrush polymer were added and the cells were incubated for 12 h. Finally, the cells were stained with LysoTracker Far Red at 50 nM for 30 min and Hoescht 33342 at 5 µg/mL for 10 min before washing with PBS. Cells were imaged on a Nikon MR confocal microscope at the Koch Institute Microscopy Core.

Example 35. In Vivo Experiments

Animal Usage

All experiments involving animals were reviewed and approved by the MIT Committee for Animal Care (CAC). BALB/c mice (female, 8-12 weeks old, Taconic) were used for in vivo toxicity, pharmacokinetic, and biodistribution studies (n=3-4). All animals received an alfalfa-free diet (TestDiet) for two weeks prior to the start of these studies to minimize residual auto-fluorescence.

Example 36. Dye-Labeled Bottlebrush Synthesis for In Vivo Experiments

Bottlebrush polymer was synthesized in an analogous fashion to polymers used in in vitro experiments, except Cy5.5-MM was used in place of Cy3-MM. Polymers were dialyzed for five h before lyophilization and storage at 4° C. Lyophilized polymer was diluted in 5% glucose solution to a final concentration of 25 mg/mL and filtered through a sterile 0.2 µm nylon filter immediately before use.

Example 37. Pharmacokinetic Studies

Bottlebrush polymers were dissolved in 5% glucose solution and filtered through a sterile 0.2 µm nylon filter. Solutions were prepared fresh before each set of injections. 200 µL of solution were administered via tail vein injection at different timepoints (5 mg per animal). Animals were euthanized and blood was collected via cardiac puncture into a heparin-coated tube (Sarstedt). Blood samples were stored at 4° C. immediately following collection. 100 µL of sample from each mouse was added to a 96-well plate and characterized by fluorescence imaging (IVIS, Cy 5.5, $\lambda_{ex}/\lambda_{em}$=675/720 nm, Xenogen). Statistical significance was assessed through two-sample Student's t tests.

Example 38. Biodistribution Studies

For biodistribution studies, organs were harvested from each mouse following blood collection and imaged by fluorescence imaging for whole organ images (IVIS, Cy 5.5, $\lambda_{ex}/\lambda_{em}$=675/720 nm, Xenogen).

To quantify the amount of polymer in each sample, the samples were then homogenized by diluting each sample 5x w/v with PBS buffer (VWR) in a 5 mL Eppendorf tube. This dilution step was chosen to standardize the amount of tissue present in each homogenate. Two 3.5 mm UFO stainless steel beads were added to each tube and the sample was homogenized twice for two minutes at "Speed 16" on a Next Advance Bullet Blender Gold homogenizer at 4° C. The homogenates were then transferred into a smaller Eppendorf tube and stored at 4° C. until analysis. 100 µL of each homogenate solution was added to each well of a black 96-well polystyrene plate and the mixtures were characterized by fluorescence imaging (IVIS, Cy 5.5, $\lambda_{ex}/\lambda_{em}$=675/720 nm, Xenogen). A vehicle only control was used for background correction and fluorescence was normalized by the weight of tissue being measured. Statistical significance was assessed through two-sample Student's t tests.

Example 39. Blood Chemistry Analysis

Serum was isolated from freshly acquired blood using a VACUETTE serum clot activator tube (Greiner) and a full blood chemistry panel analysis performed by the Charles River Laboratories. Blood samples were collected 10 w after treatment by cardiac puncture before harvesting the organs of the mice for biodistribution studies.

TABLE 2

Blood chemistry results from mice treated with $PEG_{30}$, $iPrSi_{30}PEG_{30}$, or $PhSi_{30}PEG_{30}$ bottlebrush polymers as compared to untreated controls. Blood samples were collected 10 weeks after treatment.

| Assay | Units | Control Mouse | 10 WK $PEG_{30}$ Brush | 10 WK $iPrSi_{30}PEG_{30}$ Brush | 10 WK $PhSi_{30}PEG_{30}$ Brush |
|---|---|---|---|---|---|
| CHOL | mg/dL | 99 | 126 | 124 | 107 |
| TRIG | mg/dL | 86 | 262 | 195 | 194 |
| ALT | U/L | 26 | 20 | 22 | 25 |
| AST | U/L | 162 | 82 | 108 | 121 |
| ALP | U/L | 81 | 76 | 82 | 69 |
| GLU | mg/dL | 103 | 293 | 224 | 290 |
| PROS | mg/dL | 9.2 | 7.7 | 8.4 | 11.3 |
| Ca | mg/dL | 9.1 | 10.8 | 10.3 | 10.9 |
| TP | g/dL | 5.1 | 5.7 | 5.6 | 5.5 |
| ALB | g/dL | 3.0 | 3.2 | 3.2 | 3.2 |
| GLOB | g/dL | 2.1 | 2.5 | 2.4 | 2.3 |
| A/G | — | 1.4 | 1.3 | 1.3 | 1.4 |
| BUN | mg/dL | 14 | 15 | 13 | 15 |
| CREAT | mg/dL | 0.2 | 0.1 | 0.1 | 0.2 |
| TBIL | mg/dL | 0.30 | 0.33 | 0.35 | 0.32 |
| Na | mEq/L | 151 | — | 150 | 150 |
| K | mEq/L | 9.4 | — | 9.0 | 10.0 |
| Cl | mEq/L | 113 | — | 112 | 113 |
| Na/K | — | — | 16.06 | — | 16.67 | 15.00 |

Note:
a mild elevation in blood glucose levels was observed for all three bottlebrush samples.

Example 40. Histology and Pathology

Organs were fixed in 30% formalin overnight and stored in ethanol. Samples were processed for histology at the Hope Tang Histology Facility at the Koch institute for Integrative Cancer Research at MIT. Organ samples were collected from mice at the 6 w timepoint before tissue homogenization for biodistribution studies.

Example 41. MTT Assay

OVCAR8 cells were seeded at 10,000 cells/well in a 96-well tissue-culture treated polystyrene plate and allowed to grow for 24 hours in order to attach to the substrate. To the cells were added BASP from a 10 mg/mL stock in media. The BASP was further diluted through serial dilutions. The cells were incubated for 48 hours with BASP, then media was removed, the cells washed with PBS, and viability was measured via MTT assay. Data was normalized to the viability of untreated cells, as measured by MTT. Measurements were performed in triplicate.

Figure 39:
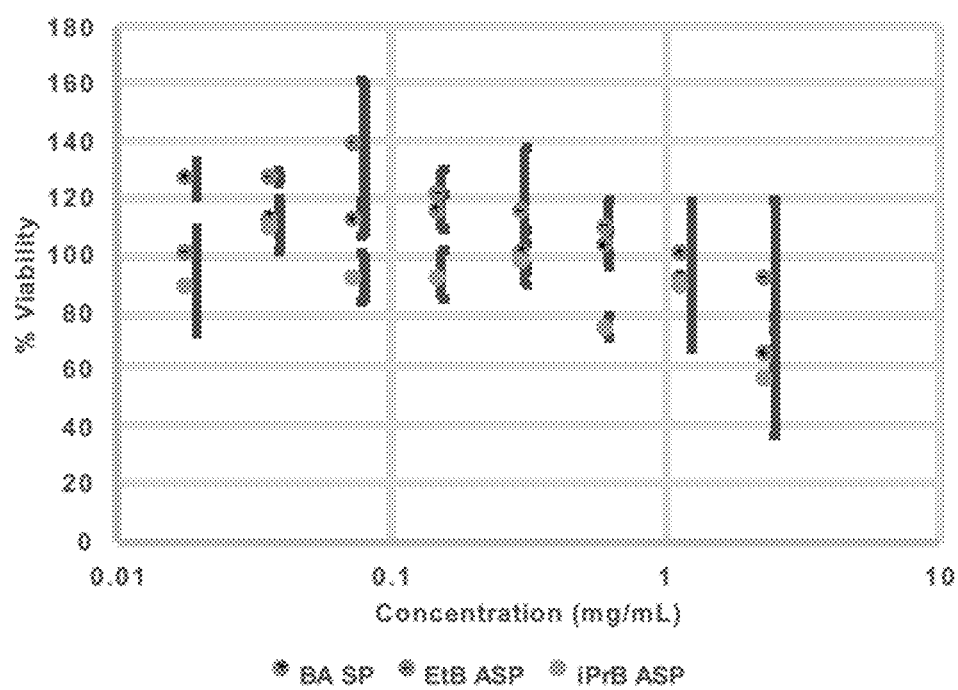
FIG. 39 demonstrates the cytotoxic profile of brush polymers.
Figure 40A:
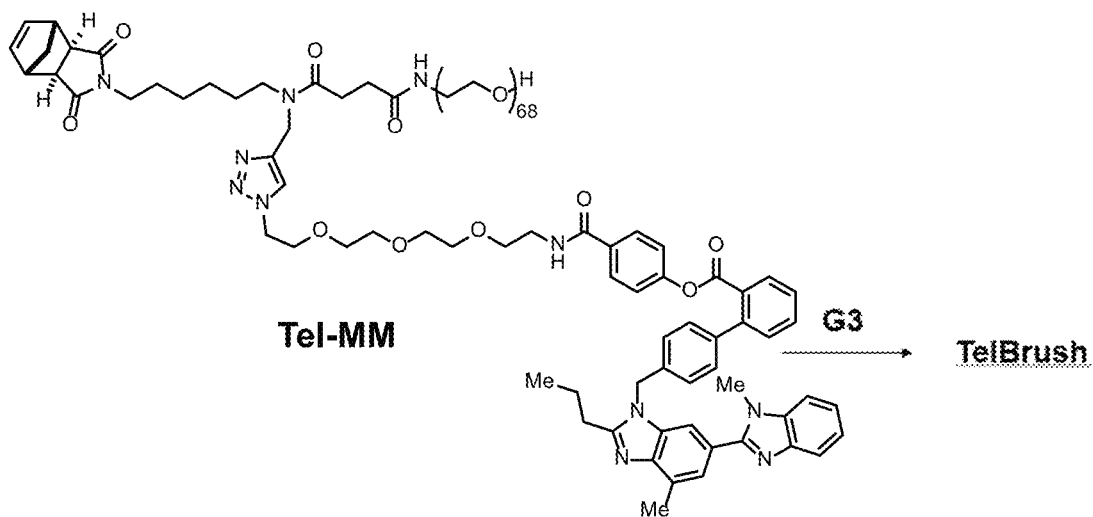
FIG. 40A shows the formula of compound Tel-MM, the telmisartin (Tel) loaded PEG-norbornene monomer. Grubbs $3^{rd}$ generation catalyst was used to ring open polymerize Tel-MM generating a brush polymer (TelBrush).
Figure 40B:
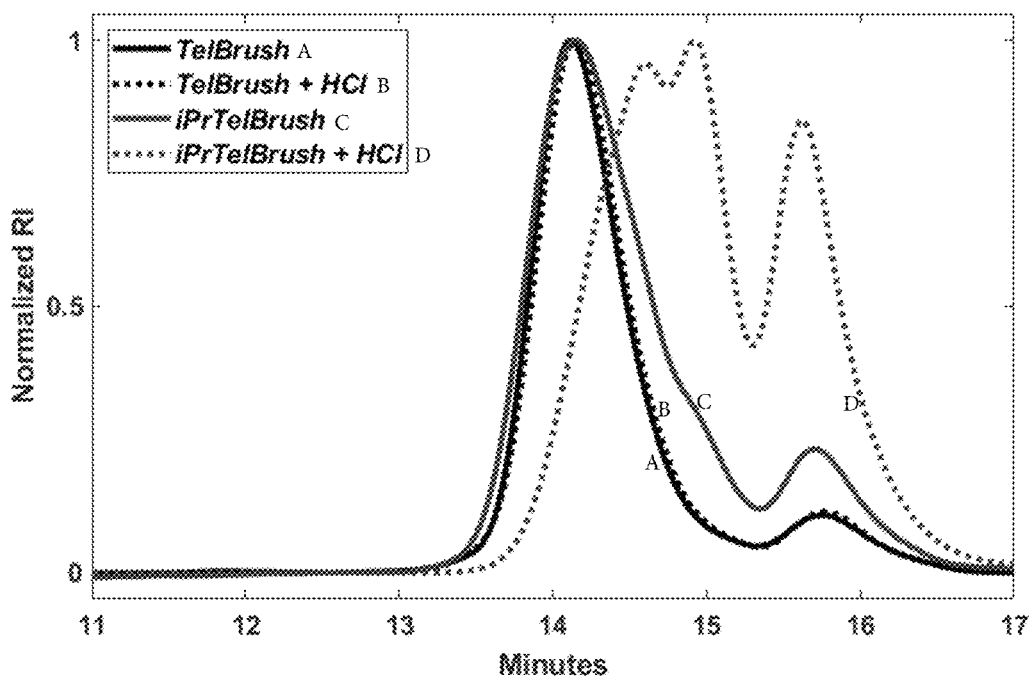
FIG. 40B shows a resulting chromatogram from GPC of brush polymers TelBrush and iPrBrush with and without treatment with HCl (where each polymer had a DP of 30 before further treatment and ratio of monomers used was 1:1). GPC traces of copolymers (target DP=10 macromonomer units) using a branched telmisartan-conjugated macromonomer and their subsequent degradation under acidic conditions are shown. The star corresponds to unreacted monomer in the solid GPC traces (prior to degradation).
Figure 41A:
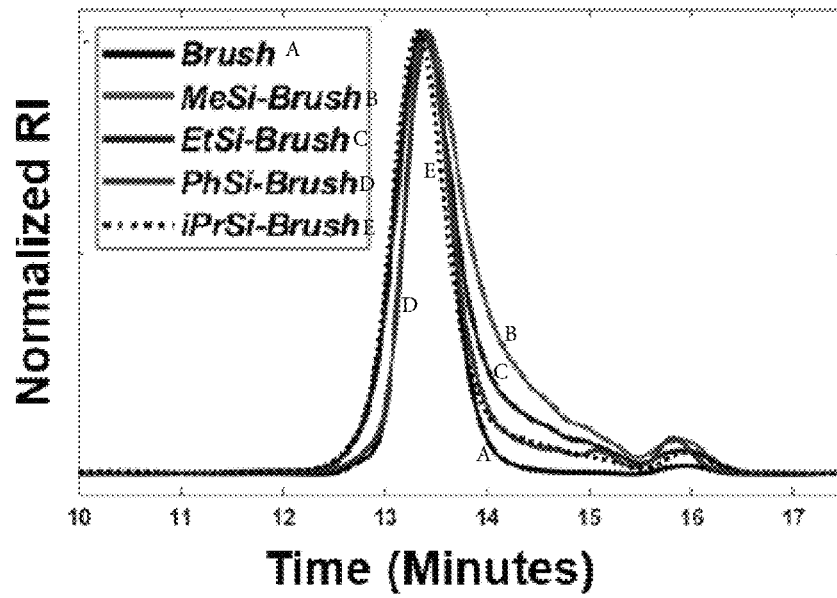
FIG. 41A shows a resulting chromatogram from GPC of Brush, MeBrush, EtBrush, iPrBrush, and PhBrush as synthesized. GPC traces show the successful formation of bottlebrush copolymers using the four different silyl ether monomers and PEG-MINI.
Figure 41B:
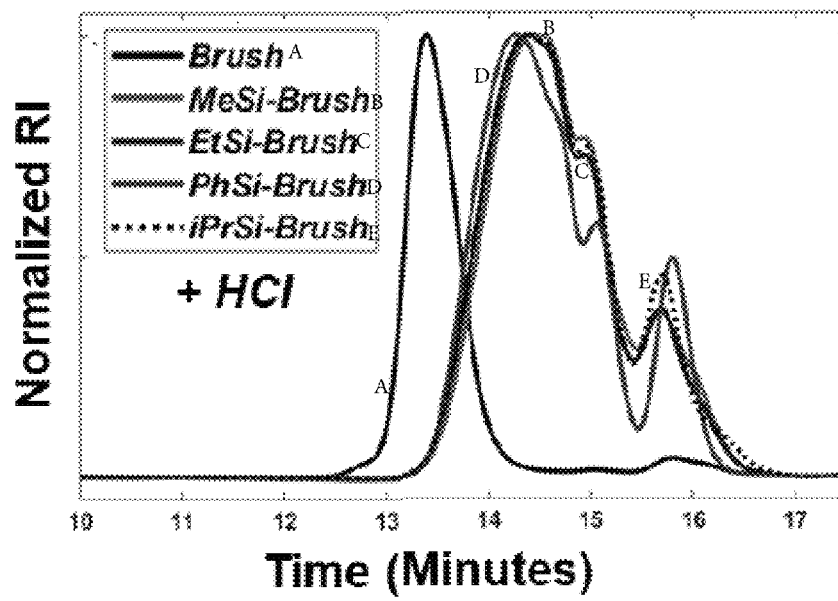
FIG. 41B shows a resulting chromatogram from GPC of Brush, MeBrush, EtBrush, iPrBrush, and PhBrush after treatment with HCl. GPC traces show the degradation products of all four copolymers. The traditional bottlebrush homopolymer PEG30 is not degradable under these conditions.

The MTT assay shown in FIG. 39 demonstrated that copolymerization with cyclic silyl ether monomer did not substantively change the cytotoxic profile of the resulting brush polymers.

Detailed Description of Examples 42-65

Polymers comprising pDCPD doped with different levels of iPrSi were prepared. Finely powdered Grubbs' $2^{nd}$ generation catalyst into mixtures of dicyclopentadiene (DCPD) and iPrSi (0, 5, 10, or 15% v/v). These solutions were prepared at a catalyst concentration of 2 mg/mL, which corresponds to a monomer to catalyst ratio of between 2000-3000 to 1, depending on the amount of silyl ether utilized. 200 μL of the mixtures were added to 2 mL vials and cured the materials at 120° C. for 15 minutes, followed by sample removal and further curing at 120° C. All the samples showed qualitatively similar mechanical and optical properties, and no dramatic difference in curing times between the materials was observed (FIG. 66B).

These samples were exposed to an excess quantity of TBAF (tetrabutylammonium fluoride) in THF, which cleaves the silyl ether functionalities within the material. Upon re examination of the solutions after 12 hours, it was observed that samples containing 10 or 15% iPrSi had dissolved into soluble fragments. In contrast, undoped pDCPD remained fully intact, consistent with the expected chemical resistance of this crosslinked material to cleavage by fluoride (FIG. 66C). While 5% iPrSi sample remained intact, the material appeared noticeably swollen; here, full cleavage of the silyl ether groups was confirmed by ICP-OES (FIG. 67). These results suggest that the incorporation of the silyl ether monomer enables full dissolution of pDCPD at some threshold level of cleavable units along the material backbone. Only a relatively small amount of this monomer appeared to be needed in order to endow the material with this property. The degradation of silyl ether doped pDCPD is time-dependent (FIG. 68). Only surface-erosion at intermediate timepoints was observed, suggesting that fluoride-mediated cleavage may be limited by the rate of diffusion of fluoride into the material.

The relationship between the introduction of different amounts of cleavage sites along the pDCPD polymer backbone and the properties of the material was explored. A series of samples containing either 0, 2.5, 5, 7.5, or 10% iPrSi were prepared and treated to the TBAF conditions described above (FIG. 69A). Here, full dissolution of the material appeared between 7.5 and 10% doping under these conditions, suggesting that the threshold for network disassembly lies within this range, while samples containing 2.5% and 5% iPrSi showed noticeable swelling. As a control, samples which were exposed only to THF without TBAF remained intact.

The mechanical properties of the TBAF-treated or THF-swollen materials were studied by oscillatory rheology (FIG. 69B, FIG. 70). The samples containing silyl ether monomer and swollen only with THF showed similar mechanical properties. All materials showed a modulus of greater than $10^5$ Pa when fully swollen in THF, consistent with their highly crosslinked nature. The comparable mechanical properties across all these samples suggests that small amounts of iPrSi (which at 5% corresponds to just one monomer per thirty DCPD monomers) have minimal impact on crosslinking efficiency in pDCPD. In contrast to the THF-swollen samples, TBAF-treated samples show a silyl ether-dependent softening of the material, consistent with chemical cleavage of elastically active chains. While the parent pDCPD remained unchanged, the 5% material showed a nearly 100-fold decrease in modulus as compared to the untreated material. The mass of the residual material was quantified, which likewise showed a loss of material in a silyl ether dependent fashion (FIG. 69B). There was a significant loss of mass in the 5% sample, which showed only a 30% of the residual mass of the parent material after silyl ether cleavage and sample drying. Quantification of the mass of this material, both before and after swelling in THF, enabled a quantification of material swelling ratio (FIG. 69C). These analyses enabled an initial quantification of elastically active chains in our materials using a Flory-Rehner equation. For these three samples, the concentration of elastically active chains were identified at $2.49 \times 10^{-3}$ mol/cm$^3$, $4.47 \times 10^{-4}$ mol/cm$^3$, and $2.74 \times 10^{-5}$ mol/cm$^3$ for 0, 2.5, and 5% iPrSi doped pDCPD, respectively.

A small amount of solid material remained in vial even after TBAF treatment (for example, see FIGS. 66A, 67A). When dogbone-shaped sample was dissolved in TBAF, it was found that the undissolved material is derived from the surface of the original sample, suggesting that the surface of the material appears to be resistant to silyl-ether mediated cleavage (FIG. 71). While the undissolved material makes up a negligible fraction of the initial mass (FIG. 69C), suggesting that almost all of the material dissolves into solution, it was decided to further characterize the nature of this material. One hypothesis is that this region may lack silyl ether groups, which may result from phase separation at the monomer-air or monomer-mold interface during polymerization. To evaluate this, the amount of silicon present in the material was quantified by X-ray photoelectron spectroscopy (XPS), which enables elemental characterization within the first few atomic layers of a sample. Using this technique, it was determined that silicon was present on both the surface and interior of the 10% iPrSi-doped pDCPD, showing that silyl ether functional groups are present on the material surface (FIG. 72). The potential for phase separation of iPrSi and DCPD during polymerization in the material was analyzed by small-angle X-ray scattering (SAXS). For materials up to 25% incorporation of iPrSi, virtually no difference in SAXS scattering pattern was observed, suggesting that the silyl ether group remains evenly and randomly incorporated within the material (FIG. 73). Therefore, as the silyl ether functionalities still appear to be present on the material surface, it was proposed that this phenomenon may instead be due to additional crosslinking reactions that occur only at the material surface.

The presence of hydrolytically labile silyl ether groups on the material surface, confirmed by XPS, may enable etching of the material surface under forcing conditions. The material was exposed to 2M NaOH for 30 minutes and the properties of the material were evaluated over time. Under these conditions, no apparent change in the bulk material was observed, but surface characterization of the material by AFM confirmed etching on the nanoscale (FIG. 74). Contact angle measurements were performed on the samples and it was found that all materials showed similar contact angles. Treatment of the material with sodium hydroxide resulted in a decrease in contact angle that depended on the amount of silyl ether monomer in the material, consistent with the increased density of hydrophilic hydroxyl groups on the material surface (FIG. 75). Finally, characterization of the material by FTIR confirmed the presence of silyl ether functionalities in the material, and cleavage resulted in loss of some of the silyl ether functionalities, consistent with hydrolysis under these conditions (FIG. 76 to 77).

The dissolution of the material into soluble fragments enables further opportunities for high-resolution characterization techniques of the parent pDCPD resin. Samples that contained 10, 20, 33, or 50% iPrSi were prepared and treated using 2 molar equivalents of TBAF in THE relative to silyl ether for 12 hours, which was sufficient for complete dissolution of all four samples (FIG. 78). Solvent was removed under rotary evaporation and directly analyzed the resulting solids by gel-permeation chromatography (GPC). GPC analysis showed that higher levels of silyl ether monomer incorporation resulted in lower molecular weight fragments, as expected (FIG. 79A, FIGS. 80A, 80B, 81A, and 81B). Excitingly, all fragments showed earlier than expected retention times as would be expected from the linear polymer, fully consistent with the interchain crosslinking expected in the parent pDCPD. Notably, the molecular weight of the 10% fragment, at 30 kDa, is significantly larger than what would be expected for a linear polymer of pDCPD that contains 10% v/v iPrSi (2.1 kDa, or roughly one silyl ether monomer per 16 DCPD monomers), suggesting that the fragments characterized by GPC consists of on average at least 15 different crosslinked pDCPD linear chains.

The fragments were next characterized by solution phase NMR. A dose dependent change in the relative ratios of the pDCPD backbone and the fragments that were derived from silyl ether monomer was observed (FIG. 79B, FIGS. 82, 83, 84A and 84B). Comparison of the NMR spectra to that of linear pDCPD, prepared by molybdenum-catalyzed ROMP, showed marked differences in NMR spectra (FIGS. 85A, 85B, 86A, 86B). The ability to generate high-resolution NMR spectra of this material opened the door to more detailed experimental characterization. Systematic analysis of the resulting fragments by solution-phase NMR was carried our. Historically, NMR characterization these materials have been limited to solid state techniques, which suffers from lack of resolution. As the soluble fragments from the silyl ether doped pDCPD are amenable to solution-phase characterization techniques, it was posisble gain insight on the properties of pDCPD indirectly by analyzing these fragments. Diffusion spectroscopy (DOSY) analysis of the pDCPD fragments showed further showed a clear trend between particle diameter and the amount of iPrSi doped into pDCPD (FIGS. 87-91). From this analysis, it was estimated a particle diameter of 3.7 nm for fragments derived from 10% iPrSi doped pDCPD.

A full 2-D characterization of the fragments derived from pDCPD was performed, including COSY, HSQC, HMBC, and NOESY (FIGS. 92-95), enabling a full assignment of all observed peaks. From this, alongside literature precedent on the analysis of linear pDCPD from $^{13}$C spectra, it was possible to determine a crosslink density of ~12% in these fragments, consistent with the observations from both the Flory-Rehnert analysis and GPC analysis. The high resolution NMR spectra further allowed further characterization of the material with high resolution. These spectra enabled the identification of the presence of an E to Z ratio of the backbone olefins of 1.5 to 1 and confirmed early work showing a 3:2 ratio of aliphatic to olefin carbons in the fragments derived from the bulk material (FIG. 79C). Overall, the ability to dissolve pDCPD into soluble fragments enables the characterization of the bulk material with unprecedented resolution.

The it was sought to confirm that the incorporation of the silyl monomer would have minimal impact on the highly favorable mechanical properties of pDCPD. It was found that pDCPD and pDCPD containing 10% iPrSi showed nearly identical mechanical properties, both in terms of overall modulus and in terms of elongation to break (FIG. 96A, 96B, 96C, FIG. 97). Increasing the amount of iPrSi in the material to 20% still maintained most of the mechanical properties of pDCPD, while differences were observed at 33 and 50% incorporation. Interestingly, samples containing 33% iPrSi showed considerable resistance to breaking under tensile stress, enabling elongation of over 300%. It was independently confirmed on bulk samples through nanoindentation analysis (FIG. 96E). Indentation of the samples at both 300 and 1000 nm resulted in measured reduced moduli that were fully consistent with the mechanical measurements performed on the bulk samples. No statistically different mechanical properties were observed for samples containing 0 to 20% iPrSi, as also observed from the tensile testing measurements. Interestingly, it was found up to 2-3× higher reduced moduli for the samples when at indentation depths of 300 nm instead of 1000 nm. This implies the presence of a two-phase mechanical regime in the materials, with a mechanically tough yet thin layer present at the material surface. This observation further supports the hypothesis on the presence of a more highly crosslinked layer near the material surface of the samples.

The materials, pDCPD and iPrSi doped pDCPD, were characterized by thermal gravimetric analysis, which showed nearly identical decomposition temperatures (FIG. 98). Therefore, while the incorporation of large quantities of iPrSi can endow pDCPD with new properties, small amounts (<20% v/v) have a minimal impact on the bulk properties of the material while endowing the material with full degradability.

The incorporation of degradable crosslinkers has been proposed as another strategy to generate tough yet degradable resins. It was hypothesized that such an approach may fail since this does not prevent the formation of crosslinks derived from the original DCPD monomer. To evaluate this directly, a crosslinker monomer was synthesized by the reaction of diisopropyldichlorosilane and cyclooctenol. pDCPD containing 20% v/v of this crosslinker was generated and the resulting material subjected to TBAF following the same protocol used before (FIG. 99A). Under these conditions, no dissolution of this silane-containing material was observed, suggesting that the introduction of cleavage points along the polynorbornene backbone, uniquely enabled by iPrSi, is important for bulk material dissolution. Rheological measurements were performed on the THF-swollen or TBAF-treated samples (FIGS. 99B to 100). The cleavage of the material resulted in some loss of material crosslinking, as evidenced by the loss of mechanical strength in the swollen material, but both samples remain mechanically robust, with a modulus of $10^5$ Pa or greater It was noted that the number of silyl ether groups in this material was identical to the number found in 10% iPrSi doped pDCPD, which readily degrades into soluble fragments under identical conditions.

It was hypothesized that alternative silyl ether monomers containing more labile substituents might enable more rapid degradation. Initial studies were performed looking at the rate of degradation between iPrSi containing materials and EtSi containing materials (FIG. 102A). These two monomers differ by the type of substitution on the silicon atom, which leads to differences in stability to both fluoride and acid. Consistent with the hypothesis, more rapid cleavage of the EtSi containing monomer was observed under aqueous conditions, suggesting that hydrolytic stability of the material can be tuned by modification of dopant substituents (FIGS. 102B and 102C). Moreover, this demonstrates the generality of the approach for preparing degradable pDCPD through doping of these degradable monomers, opening the door to many applications for tuning the properties of the final materials for a desired application. The ability to degrade materials using acidic conditions further opens the door to mild and inexpensive strategies for the dissolution and reprocessing of the material fragments. Initial studies suggest that some organic solvent is necessary to fully swell the polymer network may be important for degradation.

Example 42. Synthesis of Cyclooctene-Functionalized Silyl Ether

Scheme 42: Synthesis of SiXL

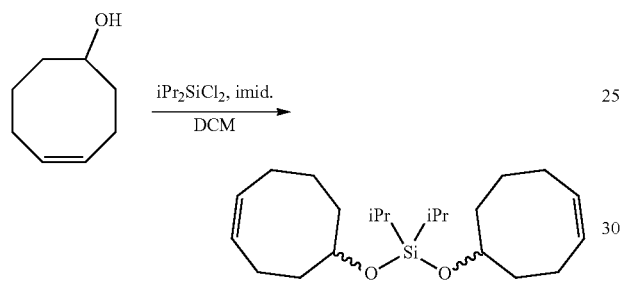

5-Hydroxy-1-cyclooctene (2 mmol, 0.252 g) was dissolved in 4 mL of dry dichloromethane. Imidazole (2 mmol, 1 equiv., 0.136 g) was then added and the solution cooled to 0° C. Finally, dichlorodiisopropylsilane (1 mmol, 0.5 equiv., 0.185 g, 0.180 mL) was then added dropwise. A white precipitate formed. The solution was then stirred at RT for 30 minutes. The solids were removed by filtration and the resulting solution as concentrated. The material was then concentrated by purified by column chromatography using 20:1 hexanes/ethyl acetate to yield 0.218 (60%) of diastereomeric products as a clear oil.

$^1$H NMR (400 MHz, Chloroform-d) δ 5.68 (dt, J=10.6, 7.5 Hz, 1H), 5.57 (dt, J=10.5, 7.9 Hz, 1H), 4.00 (td, J=8.6, 4.2 Hz, 1H), 2.47-2.30 (m, 1H), 2.21 (dtd, J=13.0, 8.4, 4.1 Hz, 1H), 2.17-2.05 (m, 1H), 1.99 (dtd, J=14.1, 6.9, 3.6 Hz, 1H), 1.92-1.55 (m, 5H), 1.44 (dtd, J=14.0, 9.7, 9.1, 3.9 Hz, 1H), 1.02 (dd, J=7.1, 1.6 Hz, 7H), 0.99-0.81 (m, 1H). $^{13}$C NMR (101 MHz, CDCl$_3$) δ 130.23, 129.24, 77.32, 77.00, 76.68, 72.67, 72.49, 72.47, 37.80, 36.32, 36.30, 25.76, 25.75, 25.04, 22.64, 22.63, 17.48, 17.44, 17.17, 12.59, 12.56, 12.55, 12.45, 12.18. HRMS (DART): Calculated for C$_{22}$H$_{41}$O$_2$Si (M+H)$^+$365.2875, found 365.2779.

Example 43. General Procedure for Copolymerization of DCPD Derivatives with Cyclic Silyl Ethers See FIGS. 66, 101, and 99

Scheme 43: The Stucture of Monomers and Protocol for Synthesizing Degradable pDCPD

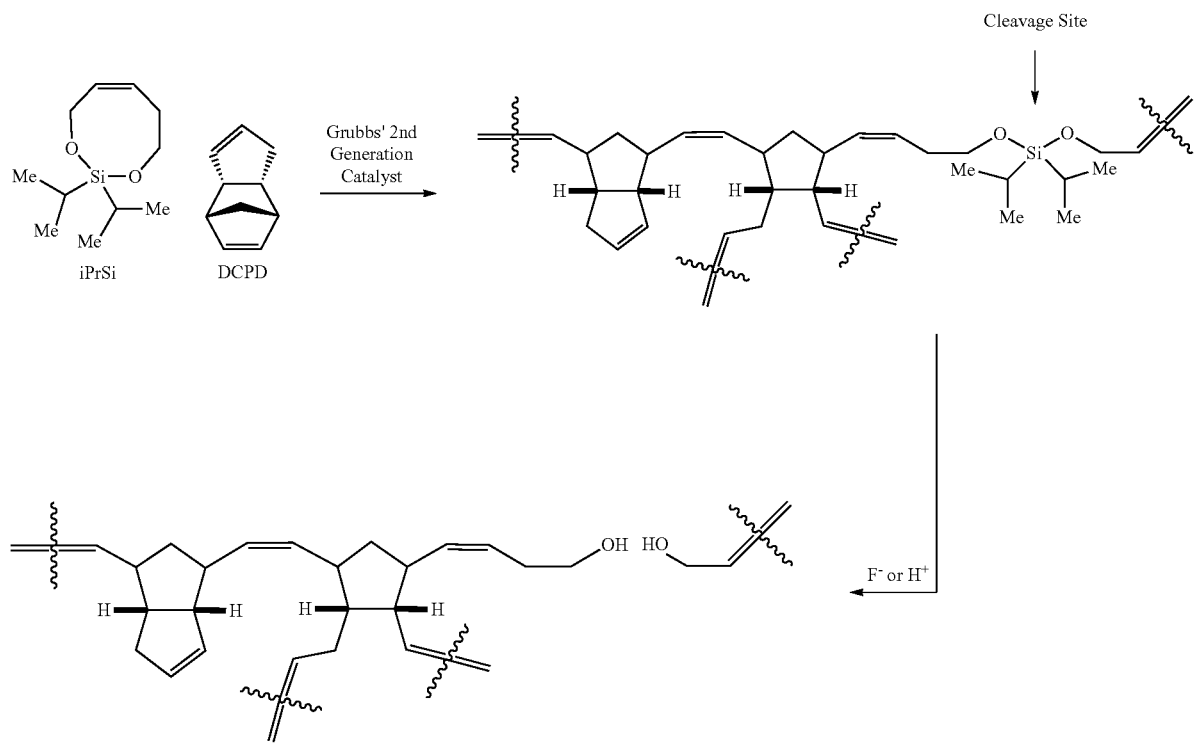

Degradable pDCPD was generated by dissolving finely powdered Grubbs' $2^{nd}$ generation catalyst into DCPD with or without different levels of iPrSi at a concentration of 2 mg of catalyst per mL of monomer. 200 uL of the mixture was added to 2 mL vials. The reaction was prepared by heating it to 110° C. for 15 minutes, removing from the vial, and further curing at 110° C. for 30 minutes. As shown in FIG. 66B, all materials qualitatively showed similar mechanical and optical properties, and no dramatic difference in curing times between the materials was observed.

The material was then soaked in a solution of 0.5 M TBAF in THF to study the degradation. The material fully dissolved upon a 12 hour incubation. In contrast, pDCPD itself remained intact, although there was some swelling of the material under these conditions as demonstrated in FIG. 66C. A series of samples with 5% (29.1 iPrSi:1 DCPD), 10% (14.2 iPrSi:1 DCPD), or 15% iPrSi (8.9 iPrSi:1 DCPD) v/v were synthesized to assess the amount of silane required to generate pDCPD. Material that contained only 5% iPrSi remained fully intact in TBAF, whereas those containing 10% or 15% of iPrSi degraded under TBAF. Under these conditions, only a very small amount of remaining insoluble material was still present after a 12 hour incubation in TBAF. The 5% iPrSi sample remained intact, but was softer.

Additional conditions for dissolving the material by cleavage of the silane functionalities are suitable for full material degradation. Specifically, softening of pDCPD occurred in THF containing 15% concentrated HCl (FIG. 101).

The potential impact of cross-linking density was assessed by synthesizing a crosslinker monomer (SiXL) by the reaction of diisopropyldichlorosilane and cyclooctenol as demonstrated in FIG. 99A. pDCPD containing 20% v/v of SiXL (10.7 SiXL:1 DCPD) was generated (FIG. 99B) and the resulting material subjected to TBAF (FIG. 99C). Under these conditions, no dissolution of this silane-containing material was observed, suggesting that the introduction of cleavage points along the polynorbornene backbone, uniquely enabled by iPrSi, was important in the generation of degradable pDCPD. This was consistent with the notion that there is no net change in the number of crosslinks within the material upon cleaving the silyl ethers when a crosslinker is added. In contrast, by introducing cleavable points along the polynorbornene backbone, this decreased the number of crosslinks in the material upon silyl ether cleavage, enabling the dissolution of the material into soluble fragments.

Overall, the combination of understanding network topology allowed for the generation of materials that combine both high mechanical toughness with degradability under mild conditions. Many other types of monomers, designed to copolymerize efficiently with DCPD and other norbornenes, are under investigation to enable further elaboration of these materials that satisfy the need for both high functional performance alongside biodegradability.

Example 44. Resin Precursor Preparation

Dicyclopentadiene and iPrSi were mixed in the desired ratio. Next, finely powdered Grubbs $2^{nd}$ generation catalyst was dissolved into this mixture at a catalyst concentration of 2 mg/mL We found that the use of finely powdered catalyst, generated by dissolving the Grubbs catalyst in dichloromethane, evaporation of solvent under vacuum, and scraping the material with a spatula, enabled rapid and full dissolution of the catalyst in DCPD/iPrSi mixtures. The solution remained liquid at room temperature at silyl ether concentrations of 10% or higher, while we observed solidification at 5% or lower concentrations. In these cases, the solidified monomer mixture was melted by gentle heating in a water bath. The homogenous pink mixture was used within five minutes to prepare resin of the desired format.

Example 45. Resin Synthesis (Pellets)

200 µL of mixture added to a 2 mL flat-bottom screw thread glass vials (VWR, Part No. 46610-772, 12×32 mm). The vials were then heated at 120° C. for 15 minutes, during which the pink solution turned into a yellow solid as the solution polymerized and crosslinked to form pDCPD. The vials were then removed from the oven, cooled to room temperature, and broken with a hammer to release the sample. The collected pDCPD samples were then cured for another 30 minutes at 120° C., then stored at room temperature until further use.

Example 46. Resin Synthesis (Flat Sheets)

50 µL of monomer mixture was sandwiched between two glass slides (VWR, Part No. 16004-422), with additional slides used as a spacer between the top and bottom surface. The material was then cured at 120° C. for 15 minutes, during which the pink solution turned into a yellow solid as the solution polymerized and crosslinked to form pDCPD. The sample was then removed from the oven, cooled to room temperature, and the glass slides removed to yield the free resin. The collected pDCPD samples were then cured for another 30 minutes at 120° C., then stored at room temperature under vacuum until further use.

Example 47. Tensile Testing Experiments

See FIGS. 96A, 96B, 96C, 96D, and 96E

Dogbones were prepared using silicone molds containing a modified 1BB format with larger grips. Silicone molds were prepared from Smooth-On Mold Max 60 poured over aluminum dogbones, cut to the 1BB format, and placed in an aluminum tin. The silicone was cured following manufacturer instructions. 900 µL of pDCPD mixture was added to each mold and the samples were then cured at 110° C. for 1 hour. The dogbones were then removed from the mold and kept at room temperature until use.

Tensile testing was performed on an 8848 MicroTester (Instron) with an extension rate of 1 mm/s using a 1 kN load cell.

Example 48. FTIR Measurements

See FIGS. 76 and 77 pDCPD samples were prepared between two glass slides to provide perfectly smooth surfaces. The samples were then characterized on a Thermo Nicolet 6700 FT-IR Spectrometer with under attenuated total reflectance mode with a ZnSe crystal.

For NaOH etched samples, material was soaked in 10 mL of 2 M NaOH for 1 hour in a 20 mL vial, then washed thoroughly with ddH$_2$O before dried under vacuum. The samples were then characterized again by FTIR.

Example 49. Contact Angle Measurements

See FIGS. 75A and 75B

Contact angle measurements were performed on a Model 500 Contact Angle Goniometer (ramé-hart, Succasunna, N.J.) on the smooth bottom surface of the pDCPD pellets. For each measurement, 10 µL of water was added to the sample surface and water was added at a rate of 15 µL/min.

For etched samples, the pellets were placed in 2 M NaOH for 30 minutes before washing with water to remove excess NaOH and drying under high vacuum.

Example 50. Surface Roughness Measurements by AFM

See FIG. 74

Surface roughness measurements were performed on a Cypher S AFM (Asylum) fitted with an AC160-TS silicon tip. Flat samples were suitable for characterization by AFM were prepared by sandwiching the monomer solution between two glass slides using other glass slides as shims. The samples were cured at 110° C. for 30 minutes.

For surface etching, samples were etched with 2M NaOH for 30 minutes, before washing 3× with water and lyophilization.

Experiments were performed at the MIT Department of Materials Science and Engineering NanoMechanical Technology Laboratory.

Example 51. Surface Mechanical Measurements by Nanoindentation

See FIG. 96E

Mechanical testing was performed on a TriboIndenter (Hysitron) using a Berkovich diamond tip. Indentations were performed using a 10 s approach, 10 s static, and 10 s departure. Indentation depths of 300 and 1000 nm were performed.

Experiments were performed at the MIT Department of Materials Science and Engineering NanoMechanical Technology Laboratory.

Example 52. Surface Silicon Quantification by XPS

See FIGS. 72A and 72B

10% iPrSi-doped pDCPD was prepared following standard protocol. Cross sections of the material were acquired by cutting the pellets with a razor blade. XPS measurements were performed on a PHI VersaProbe II XPS. High energy resolution spectra were charge corrected to place the principal C1s peak at 284.8 eV.

Experiments were performed at the MIT Department of Materials Science and Engineering NanoMechanical Technology Laboratory.

Example 53. Silicon Quantification by ICP-OES

See FIG. 67 pDCPD samples were digested in a 37% $HNO_3$ solution in a 2 mL glass vial, then diluted 50-100× into a solution of 1% $HNO_3$. As a reference, iPrSi monomer was similarly digested using nitric acid treatment before elemental analysis.

Example 54. Quantification of Polymer Mass (Time)

A 200 mg sample of iPrSi doped pDCPD was covered with 5 mL of THF containing 188 uL of 1M TBAF (2 equivalents). At a certain timepoint, the solution was removed and the material was washed with 3×5 mL THF. The solid was allowed to sit in 10 mL THF for 1 hour, then washed again and allowed to sit in 10 mL THF for another 24 hours. The solvent was then removed under vacuum for 48 hours and the mass of the residual solid was measured.

Example 55. Quantification of Polymer Mass (Amount of Si Doping)

200 mg samples of pDCPD containing 0, 2.5, 5, 7.5, or 10% pDCPD was covered with 10 mL of 0.5 M TBAF. The solution was allowed to sit for 24 hours, then the solution was removed and the residual solid was washed with 3×5 mL THF and allowed to sit in 10 mL THF for 24 hours. The THF was removed and another 10 mL of THF was added. After another 24 hours, the THF was removed and residual solvent removed by storing the materials in a vacuum oven for 48 hours. The mass of remaining solids were measured and compared to the initial mass of the pDCPD samples.

Example 56. Swelling Ratio Measurements

See FIG. 69C

Samples of pDCPD were swollen in THF for at least 24 hours. The materials were gently dried with a Kimwipe to remove excess solvent and the mass of the swollen material measured. The resulting solids were then dried under vacuum oven for 24 hours to remove any residual solvent and the mass of the resulting dried material measured. The swelling ratio is reported as the ratio of the mass of the swollen material to that of the dried material.

Example 57. Rheological Measurements

Samples of pDCPD containing 0, 2.5, or 5% pDCPD were treated with TBAF to cleave the silyl ether functionalities and washed with THF to remove residual TBAF and silyl fluoride byproducts. Afterwards, samples were washed with THF and allowed to fully swell.

Frequency sweep rheology experiments were performed on a TA Instruments Discovery Hybrid Rheometer HR-2 rheometer. A parallel-plate geometry (radius=8 mm) was used and coupled with a bottom plate, with the typical gap of 5.00 mm between the two plates. Frequency sweep experiments were performed from 0.1 to 100 rad/s at 1.0% strain. Experiments were performed at 25° C. and measurements were performed immediately and completed within five minutes to minimize solvent evaporation.

Example 58. Comparison of EtSi vs. iPrSi Doped pDCPD

See FIGS. 102A, 102B, 102C, and 102D

10% EtSi doped pDCPD was prepared in an analogous manner to that of iPrSi doped pDCPD to generate ~200 mg pellets. For dissolution experiments, the material was placed into a 20 mL vial and 10 mL of 15% conc. HCl in THF or 0.5 M TBAF was added. The resulting mixtures were then monitored over time.

Example 59. Synthesis of Linear pDCPD 1 g of DCPD was transferred into a nitrogen-filled glovebox and dissolved in 4 mL of toluene. Next, a pill of XiMo Schrock's catalyst (Strem, CAS No. 139220-25-0) was added and the mixture allowed to stir for 24 hours. The remaining material was collected and the soluble fractions were precipitated in methanol and concentrated under vacuum to yield the polymer as a white solid.

Example 60. Isolation of Dissolved Material for Solution-State Characterization 200 uL pellets of doped pDCPD, prepared by earlier protocol, was placed in 5 mL of THF. Next, sufficient amounts of TBAF were added for 2 equivalents relative to silyl ether monomer. The material was allowed to sit for 12 hours, after which time all of the materials had fully dissolved. The fragments were then concentrated under vacuum and the resulting fragments were characterized by NMR and GPC without further purification.

To remove tetrabutylammonium salts, which interfered with DOSY and 2D NMR analysis, the material was incubated with an excess of Dowex resin and calcium carbonate and filtered following literature protocol.

Example 61. Gel Permeation Chromatography

See FIG. 81

The dissolved fragments were dissolved in $CHCl_3$ at a concentration of 2 mg/mL. The material was then filtered through a 0.2 μm Teflon filter before analysis. GPC analysis was performed on a Tosoh EcoSEC HLC-8320 with dual TSKgel SuperH3000 columns and a chloroform mobile phase. Molecular weight calculations were performed using linear polystyrene standards.

Example 62. Thermogravimetric Analysis

Thermogravimetric analysis was performed on ~2-3 mg samples of pDCPD. Analyses were performed on a Mettler-Toledo TGA/DSC 2 STAR system equipped with a Gas Controller GC 200 Star System. Analyses were performed under a constant stream of nitrogen gas at a temperature ramp of 15° C./minute.

Example 63. Small Angle X-Ray Scattering (SAXS) Experiments

See FIG. 73

SAXS experiments were performed at the Advanced Photon Source (APS) of Argonne National Laboratory (Sector 12 beamline). X-rays of wavelength 0.89 Å (14 keV) were used, and the system was calibrated using silver behenate as the standard. For all samples, the exposure time was 0.5 s. 2D scattering data were recorded and were converted to 1D plots by radial averaging and subtraction of background scattering.

Example 64. Preparation of Poly-Dicyclopentadiene Nanoparticles

FIGS. 103, 104A, 104B, 105, and 106 describe a strategy for generating poly-dicyclopentatdiene nanoparticles, as well as the characterization of the nanoparticles via $^1H$ NMR, $^{13}C$ NMR, SEM, and TEM.

200 uL pellets of doped pDCPD, prepared by earlier protocol, was placed in 5 mL of THF. Next, sufficient amounts of TBAF were added for 2 equivalents relative to silyl ether monomer, with an overall volume of 10 mL. For 10% pDCPD, the cleavage solution consisted of 190 uL of 1M TBAF in THF diluted into 9.8 mL of THF. The material was allowed to sit for 12 hours, after which time all of the materials had fully dissolved.

For SEM measurements, the solution was further diluted with THF and dropcast onto the sample stage (FIG. 106).

For TEM measurements, the solution was further diluted with THF and dropcast onto a TEM grid and stained with ruthenium tetraoxide vapor (FIG. 105).

For NMR experiments, to remove tetrabutylammonium salts from the TBAF, the material was incubated with an excess of Dowex resin and calcium carbonate and filtered. The solvent was removed and the mixture was rediluted in deuterated solvent and subjected to NMR analysis (FIGS. 104A and 104B).

Example 65

In order to study how iPrSi doped pDCPD might behave when used in real-world applications, samples were exposed to both moisture and irradiation under a model of environmentally relevant conditions and monitored the total carbon content released from the material. The results indicated that iPrSi doped pDCPD, although showing the potential for full degradability, remained fully intact under environmentally relevant conditions. An initial technoeconomic analysis suggested that the silyl ether monomer can be manufactured inexpensively on scale, opening the door to the broader implementation of our approach for generating tough yet degradable materials.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A polymer prepared by a method comprising polymerizing:
   one or more instances of a first monomer, or a salt thereof; and
   a second monomer, wherein the second monomer is a compound of Formula (B):

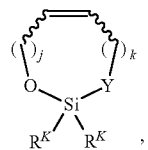

(B)

or a salt thereof, wherein any two instances of the first monomer are the same as or different from each other, and the second monomer is the same as or different from any instance of the first monomer;
in the presence of a metathesis catalyst;
wherein:
Y is O or $C(R^Q)_2$;
each instance of e is independently hydrogen, halogen, or substituted or unsubstituted, $C_{1-6}$ alkyl;
each instance of $R^K$ is independently hydrogen, halogen, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or $-OR^N$;
each instance of $R^N$ is independently hydrogen, substituted or unsubstituted acyl, substituted or unsubstituted, $C_{1-10}$ alkyl, substituted or unsubstituted carbocyclyl, substituted or unsubstituted heterocyclyl, substituted or unsubstituted aryl, substituted or unsubstituted heteroaryl, or an oxygen protecting group;
j is 1, 2, or 3; and
k is 0, 1, 2, or 3.

2. The polymer of claim 1, wherein each instance of the first monomer is independently of Formula (A1) or (A2):

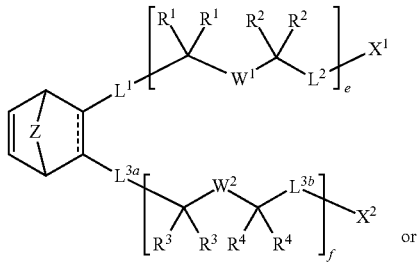

(A1)

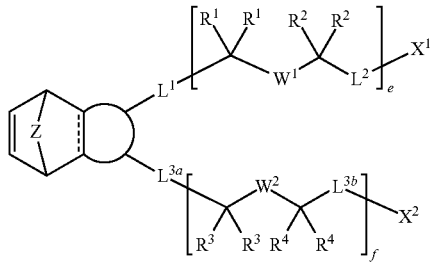

(A2)

or a salt thereof;
wherein:
each instance of

is Ring B, wherein each instance of Ring B is independently a substituted or unsubstituted, monocyclic carbocyclic ring, substituted or unsubstituted, monocyclic heterocyclic ring, substituted or unsubstituted, monocyclic aryl ring, or substituted or unsubstituted, monocyclic heteroaryl ring;

each instance of Z is independently $C(R^P)_2$ or O;

each instance of $R^P$ is independently hydrogen, halogen, or substituted or unsubstituted, $C_{1-6}$ alkyl;

each instance of ==== is independently a single bond or double bond;

each instance of $L^1$, $L^2$, $L^{3a}$, and $L^{3b}$ is independently a single bond, substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or substituted or unsubstituted $C_{2-200}$ heteroalkynylene;

each instance of $R^1$, $R^2$, $R^3$, and $R^4$ is independently hydrogen, halogen, or substituted or unsubstituted, $C_{1-6}$ alkyl, or two instances of $R^1$ attached to the same carbon atom are taken together to form oxo, or two instances of $R^2$ attached to the same carbon atom are taken together to form oxo, or two instances of $R^3$ attached to the same carbon atom are taken together to form oxo, or two instances of $R^4$ attached to the same carbon atom are taken together to form oxo;

each instance of $W^1$ and $W^2$ is independently a single bond,

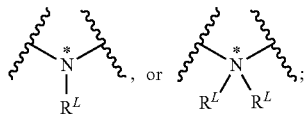, or 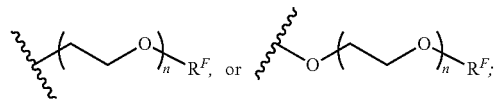

each instance of $R^L$ is independently hydrogen, a nitrogen protecting group when attached to a nitrogen atom, or $-L(M)_m$;

each instance of M is independently hydrogen or an agent;

each instance of m is independently an integer between 1 and 10, inclusive;

each instance of L is independently substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or substituted or unsubstituted, $C_{2-200}$ heteroalkynylene;

optionally one or more carbon atoms in each instance of the substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;

optionally one or more heteroatoms in each instance of the substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;

each instance of e and f is independently an integer between 0 and 10, inclusive;

each instance of $X^1$ and $X^2$ is independently hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, $-OR^C$, $-N(R^C)_2$, $-C(=O)R^C$, $-C(=O)OR^C$, $-C(=O)N(R^C)_2$, $-NR^CC(=O)R^C$, $-NR^CC(=O)OR^C$, $-NR^CC(=O)N(R^C)_2$, $-OC(=O)R^C$, $-OC(=O)OR^C$, or $-OC(=O)N(R^C)_2$;

each instance of $R^C$ is independently hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, a leaving group, an oxygen protecting group when attached to an oxygen atom, a nitrogen protecting group when attached to a nitrogen atom, each instance of n is independently an integer between 1 and 300, inclusive; and each instance of $R^F$ is independently hydrogen, substituted or unsubstituted, $C_{1-6}$ alkyl, or an oxygen protecting group; or

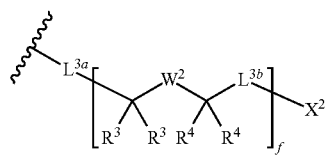

is hydrogen or absent, as valency permits.

3. A method of preparing the polymer of claim 1, the method comprises polymerizing one or more instances of the first monomer, and the second monomer in the presence of the metathesis catalyst.

4. A method of delivering an agent to a subject in need thereof, the method comprising administering to the subject in need thereof the polymer of claim 2, wherein:
the polymer comprises at least one instance of an agent, wherein each instance of the agent is independently a therapeutic agent, prophylactic agent, or diagnostic agent.

5. A method of delivering an agent to a cell, the method comprising contacting the cell with the polymer of claim 2, wherein:
the polymer comprises at least one instance of an agent, wherein each instance of the agent is independently a therapeutic agent, prophylactic agent, or diagnostic agent.

6. A method of treating cancer in a subject in need thereof, the method comprising administering to the subject in need thereof a therapeutically effective amount of the polymer of claim 2, wherein the polymer comprises at least one instance of a therapeutic agent, wherein:
at least one instance of the therapeutic agent is an anti-cancer agent.

7. A method of preventing cancer in a subject in need thereof, the method comprising administering to the subject in need thereof a prophylactically effective amount of the polymer of claim 2, wherein the polymer comprises at least one instance of a prophylactic agent, wherein:
at least one instance of the prophylactic agent is an anti-cancer agent.

8. A method of diagnosing cancer in a subject in need thereof, the method comprising administering to the subject in need thereof a diagnostically effective amount of the polymer of claim 2, wherein the polymer comprises at least one instance of a diagnostic agent, wherein:
at least one instance of the diagnostic agent is an imaging agent or contrast agent.

9. A composition comprising:
the polymer of claim 1; and
optionally an excipient.

10. A kit comprising:
the polymer of claim 1; and
instructions for using the polymer.

11. The polymer of claim 1, wherein at least one instance of the first monomer is of Formula (A') or (A"):

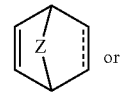  (A')

or

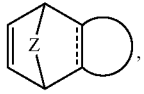  (A"), or salt thereof, wherein
each instance of

is Ring B, wherein each instance of Ring B is independently a substituted or unsubstituted, monocyclic carbocyclic ring, substituted or unsubstituted, monocyclic heterocyclic ring, substituted or unsubstituted, monocyclic aryl ring, or substituted or unsubstituted, monocyclic heteroaryl ring;

each instance of Z is independently $C(R^P)_2$ or O;

each instance of $R^P$ is independently hydrogen, halogen, or substituted or unsubstituted, $C_{1-6}$ alkyl; and each instance of ----- is independently a single bond or double bond.

12. The polymer of claim 11, wherein each instance of the first monomer is independently of Formula (D1) or (D2):

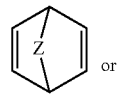  (D1)

or

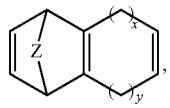  (D2), or a salt thereof, wherein:
each instance of x is independently 0, 1, or 2; and
each instance of y is independently 0, 1, or 2.

13. The polymer of claim 12, wherein at least one instance of Z is $CH_2$.

14. The polymer of claim 1, wherein at least one instance of the first monomer is of the formula:

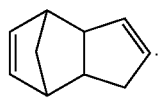

15. The polymer of claim 1, wherein each instance of the first monomer is of the formula:

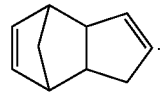

16. The polymer of claim 2, wherein at least one instance of the first monomer is of the formula:

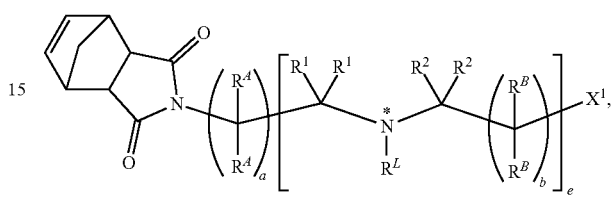  (A2a)

or a salt thereof, wherein:
each instance of $R^A$ is independently hydrogen, halogen, or substituted or unsubstituted, $C_{1-6}$ alkyl;
a is an integer between 1 and 20, inclusive;
each instance of $R^B$ is independently hydrogen, halogen, or substituted or unsubstituted, $C_{1-6}$ alkyl;
each instance of b is independently an integer between 1 and 20, inclusive; and
e is an integer between 1 and 10, inclusive.

17. The polymer of claim 16, wherein at least one instance of the first monomer is of the formula:

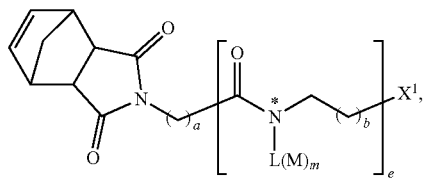

or a salt thereof, wherein:
e is an integer between 1 and 10, inclusive; and
at least one instance of $-L(M)_m$ comprises one or more instances of —C≡CH.

18. The polymer of claim 16, wherein at least one instance of the first monomer is of the formula:

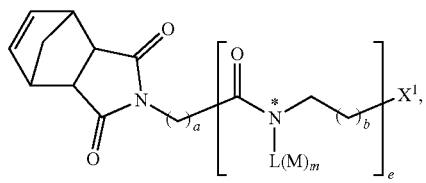

or a salt thereof, wherein:
e is an integer between 1 and 10, inclusive; and
at least one instance of M is a therapeutic agent, prophylactic agent, or diagnostic agent.

19. The polymer of claim 18, wherein at least one instance of L is $C_{2-50}$ heteroalkylene, wherein:
the $C_{2-50}$ heteroalkylene is unsubstituted or substituted with one or more substituents independently selected from the group consisting of halogen, unsubstituted $C_{1-6}$ alkyl, and oxo;

one or more carbon atoms and/or one or more heteroatoms of the $C_{2-50}$ heteroalkylene are replaced with

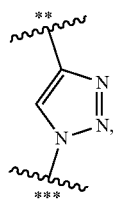

wherein the atom labeled with "*" is closer to the attachment point labeled with "" than the attachment point labeled with "*"; and optionally one or more carbon atoms and/or one or more heteroatoms of the $C_{2-50}$ heteroalkylene are independently replaced with substituted or unsubstituted phenylene.

20. The polymer of claim 18, wherein at least one instance of L is of the formula:

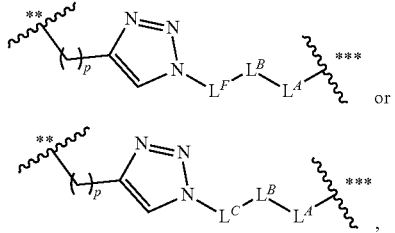

wherein:
each instance of p is independently an integer from 1 to 10, inclusive;
each instance of $L^F$ is independently substituted or unsubstituted, $C_{2-180}$ heteroalkylene;
each instance of $L^C$ is independently substituted or unsubstituted, $C_{1-180}$ alkylene;
each instance of $-L^B-L^A-$ is independently $-C(=O)O-$ or $-OC(=O)-$; and
the nitrogen atom labeled with "*" is closer to the attachment point labeled with "" than the attachment point labeled with "*".

21. The polymer of claim 18, wherein at least one instance of $X^1$ is $-C(=O)N(R^C)_2$.

22. The polymer of claim 21, wherein at least one instance of $R^C$ is

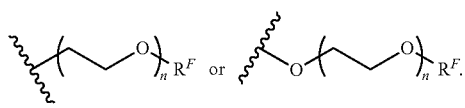

23. The polymer of claim 1, wherein Y is O.

24. The polymer of claim 1, wherein j is 1 and k is 1, j is 1 and k is 2, or j is 2 and k is 2.

25. The polymer of claim 1, wherein the second monomer is of the formula:

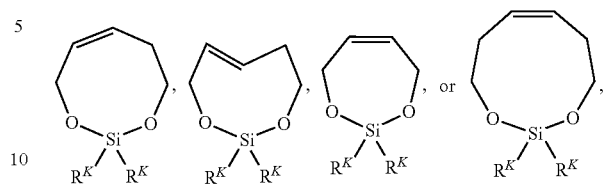

or a salt thereof.

26. The polymer of claim 1, wherein each instance of $R^K$ is independently hydrogen, substituted or unsubstituted, $C_{1-6}$ alkyl, or substituted or unsubstituted phenyl.

27. The polymer of claim 1, wherein each instance of $R^K$ is unsubstituted $C_{1-3}$ alkyl.

28. The polymer of claim 15, wherein each instance of $R^K$ is unsubstituted $C_{1-3}$ alkyl.

29. The polymer of claim 1, wherein the second monomer is of the formula:

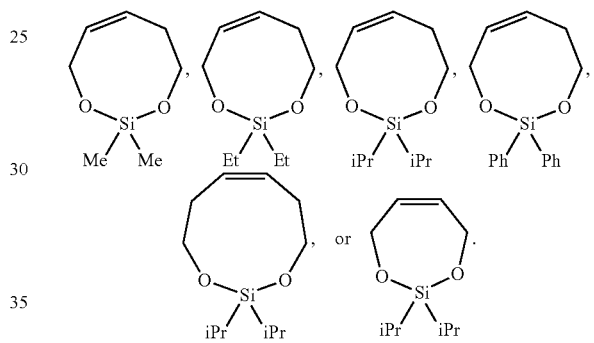

30. The polymer of claim 15, wherein the second monomer is of the formula:

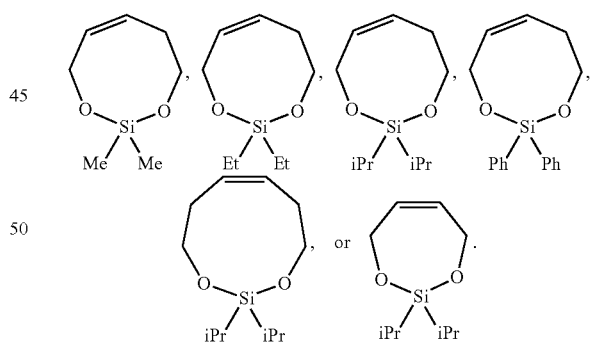

31. The polymer of claim 1, wherein the second monomer is of the formula:

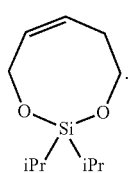

32. The polymer of claim 15, wherein the second monomer is of the formula:
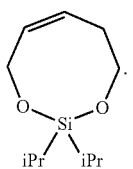
33. The method of claim 4, wherein at least one instance of the agent is an imaging agent or contrast agent.
34. The method of claim 4, wherein at least one instance of the agent is an anti-cancer agent.
35. The method of claim 4, wherein the subject is a human.
* * * * *

UNITED STATES PATENT AND TRADEMARK OFFICE
CERTIFICATE OF CORRECTION

| | | |
|---|---|---|
| PATENT NO. | : 11,897,905 B2 | Page 1 of 1 |
| APPLICATION NO. | : 17/204462 | |
| DATED | : February 13, 2024 | |
| INVENTOR(S) | : Jeremiah A. Johnson et al. | |

It is certified that error appears in the above-identified patent and that said Letters Patent is hereby corrected as shown below:

In the Specification

At Column 1, Lines 18-19, please change the sentence:
"This invention was made with Government support under Grant No. R01 CA220468 awarded by the National Institutes of Health."
To:
-- This invention was made with Government support under CA220468 awarded by the National Institutes of Health. --.

In the Claims

In Claim 16, at Column 178, Line 25, the text:
"R B"
Should be replaced with:
-- $R^B$ --.

Signed and Sealed this
Third Day of December, 2024

*Katherine Kelly Vidal*
Katherine Kelly Vidal
*Director of the United States Patent and Trademark Office*